US011976072B2

(12) United States Patent
Codelli et al.

(10) Patent No.: US 11,976,072 B2
(45) Date of Patent: May 7, 2024

(54) DIACYLGLYCEROL KINASE MODULATING COMPOUNDS

(71) Applicant: Gilead Sciences, Inc., Foster City, CA (US)

(72) Inventors: Julian A. Codelli, Mountlake Terrace, WA (US); Michael Graupe, Pacifica, CA (US); Juan A. Guerrero, Clayton, CA (US); Stephen D. Holmbo, Kirkland, WA (US); Tetsuya Kobayashi, Pleasanton, CA (US); Yasamin Moazami, Seattle, WA (US); Leena B. Patel, Seattle, WA (US); Heath A. Weaver, Seattle, WA (US); Jie Xu, Foster City, CA (US); Suet C. Yeung, Redmond, WA (US); QingMing Zhu, Walnut Creek, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 17/845,534

(22) Filed: Jun. 21, 2022

(65) Prior Publication Data
US 2023/0060354 A1 Mar. 2, 2023

Related U.S. Application Data

(60) Provisional application No. 63/213,906, filed on Jun. 23, 2021.

(51) Int. Cl.
*C07D 487/04* (2006.01)
*A61P 31/18* (2006.01)
*A61P 31/20* (2006.01)
*A61P 35/00* (2006.01)
*A61P 35/04* (2006.01)
*C07D 519/00* (2006.01)

(52) U.S. Cl.
CPC ......... *C07D 487/04* (2013.01); *C07D 519/00* (2013.01)

(58) Field of Classification Search
CPC ..... C07D 487/04; C07D 519/00; A61P 31/18; A61P 31/20; A61P 35/00; A61P 35/04
See application file for complete search history.

(56) References Cited

U.S. PATENT DOCUMENTS

| | | | |
|---|---|---|---|
| 2021/0188845 A1 | 6/2021 | Gentles et al. | |
| 2022/0315603 A1 | 10/2022 | Watanabe et al. | |
| 2022/0324866 A1* | 10/2022 | Sawa | A61K 31/704 |
| 2023/0046340 A1 | 2/2023 | Codelli et al. | |
| 2023/0060004 A1 | 2/2023 | Graupe et al. | |
| 2023/0116253 A1 | 4/2023 | Codelli et al. | |

FOREIGN PATENT DOCUMENTS

| | | |
|---|---|---|
| WO | WO-2007114239 A1 | 10/2007 |
| WO | WO-2019005883 A1 | 1/2019 |
| WO | WO-2020006016 A1 | 1/2020 |
| WO | WO-2020006018 A1 | 1/2020 |
| WO | WO-2021041588 A1 | 3/2021 |
| WO | WO-2021105115 A1 | 6/2021 |
| WO | WO-2021105116 A1 | 6/2021 |
| WO | WO-2021105117 A1 | 6/2021 |
| WO | WO-2021127554 A1 | 6/2021 |
| WO | WO-2021130638 A1 | 7/2021 |
| WO | WO-2021132422 A1 | 7/2021 |
| WO | WO-2021133748 A1 | 7/2021 |
| WO | WO-2021133749 A1 | 7/2021 |
| WO | WO-2021133750 A1 | 7/2021 |
| WO | WO-2021133751 A1 | 7/2021 |
| WO | WO-2021133752 A1 | 7/2021 |
| WO | WO-2021214019 A1 | 10/2021 |
| WO | WO-2021214020 A1 | 10/2021 |
| WO | WO-2021258010 A1 | 12/2021 |
| WO | WO-2022133083 A1 | 6/2022 |
| WO | WO-2022271650 A1 | 12/2022 |
| WO | WO-2022271659 A1 | 12/2022 |
| WO | WO-2022271677 A1 | 12/2022 |

OTHER PUBLICATIONS

Avila-Florez et al., "Predominant contribution of DGKξ over DGKα in the control of PKC/PDK-1-regulated functions in T cells", Immunol. Cell. Biol., 2017, 95, 549-563.
Carrasco et al., "Diacylglycerol, when simplicity becomes complex", Trends Biochem. Sci., 2007, 32(1), 27-36.
Deng et al., "Synthesis and Anticonvulsant Activity of 5-Substituted-[1,2,4]triazolo[4,3-alquinazolines]" Youji Huazu/Chinese Journal of Organic Chemistry, 2011, 31(12), 2082-2087.
Dominguez et al., "Diacylglycerol kinase a is a critical signaling node and novel therapeutic target in glioblastoma and other cancers", Cancer Discov., 2013, 3(7), 782-797.
Hayashi et al., "Screening of subtype-specific activator and inhibitors for diacylglycerol kinase", Journal of Biochemistry, 2019, 165(6), 517-522.
Joshi et al., "Diacylglycerol kinases: regulated controllers of T cell activation, function, and development", Int. J. Mol. Sci., 2013, 14, 6649-6673.
Jung et al., "CRISPR/Cas9-Mediated Knockout of DGK Improves Antitumor Activities of Human T Cells", Cancer Res., 2018, 78, 4692-4703.
Merida et al., "Diacylglycerol kinases in cancer", Adv. Biol. Regul., 2017, 63, 22-31.
Riese et al., "Enhanced effector responses in activated CD8+ T cells deficient in diacylglycerol kinases", Cancer Res., 2013, 73, 3566-3577.
Sakane et al., "Diacylglycerol Kinases as Emerging Potential Drug Targets for a Variety of Diseases: An Update", Front. Cell Dev. Biol., Apr. 2016, 82.
Spranger et al., "Impact of oncogenic pathways on evasion of antitumour immune responses", Nat. Rev. Cancer., 2018, 18, 139-147.

(Continued)

*Primary Examiner* — Sun Jae Yoo

(57) ABSTRACT

The present disclosure provides diacylglycerol kinase modulating compounds, and pharmaceutical compositions thereof, for treating cancer, including solid tumors, and viral infections, such as HIV or hepatitis B virus infection. The compounds can be used alone or in combination with other agents.

19 Claims, No Drawings

(56) References Cited

OTHER PUBLICATIONS

Torres-Ayuso et al., "Diacylglycerol kinase a promotes 3D cancer cell growth and limits drug sensitivity through functional interaction with Src", Oncotarget, May 2014, 9710-9726.
Velnati et al., "Identification of a novel DGK[alpha] inhibitor for XLP-1 therapy by virtual screening", European Journal of Medicinal Chemistry, 2019, 164, 378-390.
Zha et al., "T cell anergy is reversed by active Ras and is regulated by diacylglycerol kinase-alpha", Nat. Immunol., Jul. 2006, 1166-1173.
De Fusco et al., "Fragment-Based Design of a Potent MAT2a Inhibitor and in Vivo Evaluation in an MTAP Null Xenograft Model", J Med Chem., 2021, 64(10), 6814-6826.
Intl. Search Report-Written Opinion, dated Oct. 20, 2022, for Intl. Appl. No. PCT/US2022/034321, 16 pages.

* cited by examiner

DIACYLGLYCEROL KINASE MODULATING COMPOUNDS

CROSS REFERENCE TO RELATED APPLICATIONS

This application claims priority to U.S. Provisional Application No. 63/213,906, filed Jun. 23, 2021, which is incorporated herein in its entireties for all purposes.

FIELD

The present disclosure relates to compounds that modulate diacylglycerol kinase. The present disclosure also relates to processes and intermediates for the preparation of such compounds, methods of using such compounds and pharmaceutical compositions comprising the compounds described herein.

BACKGROUND

Diacylglycerol (DAG) is known as a second messenger of signaling molecule and takes an important role in cellular proliferation, differentiation and/or metabolism (Carrasco, S., Merida, I. Trends Biochem. Sci. 2007, 32, 27-36.) Intracellular concentration and localization of DAG is strictly controlled, and diacylglycerol kinase (DGK) is one of enzymes controlling them. DGK is an enzyme that synthesizes a phosphatidic acid (PA) by transferring a phosphoryl group to DAG. Ten human isozymes ($\alpha$, $\beta$, $\gamma$, $\delta$, $\epsilon$, $\zeta$, $\eta$, $\theta$, $\iota$, $\kappa$) are known (Joshi, R. P., Koretzky, G. A. Int. J. Mol. Sci., 2013, 14, 6649-6673.) Each isozyme is believed to localize and associate with different proteins and/or with different cell types. DGK is reported to be involved in pathogenesis of multiple diseases including cancers, immune diseases, neurodegenerative diseases, and diabetes (Sakane, F., et al. Front. Cell Dev. Biol., 2016, 4, 82.)

DGK$\alpha$ has been a target of research, including research into possible cancer treatment. For example, an inhibitory activity on proliferation of glioblastoma cells was reported as a result of knockdown caused by RNA-interference targeting DGK$\alpha$ (Dominguez, C. L., et al. Cancer Discov., 2013, 782-797.) An inhibitory effect was also reported on a human colon carcinoma cell line in three-dimensional cell culture, and the knockdown of DGK$\alpha$ was further reported to inhibit tumor proliferation in a mouse model (Torres-Ayuso, P., et al. Oncotarget, 2014, 5, 9710-9726.) Inhibition of DGK$\alpha$ has been disclosed in WO 2007/114239. Accordingly, a compound with an inhibitory activity on DGK$\alpha$ may be useful for therapeutics, such as treating a cancer in which DGK$\alpha$ is involved in its proliferation.

In recent years, cancer immunotherapy has attracted attention as a potential cancer treatment. An immune checkpoint inhibitor such as anti-CTLA-4 (Cytotoxic T lymphocyte antigen 4) antibody, anti-PD-1 (Programmed death receptor 1) antibody, anti-PD-L1 (Programmed death ligand 1) antibody etc. could be administered and an antitumor immune response can be potentiated in a patient. Some immune checkpoint inhibitors have been already approved as a medicine for antitumor therapy. However, the antitumor effects are often limited to a few patients. Further, some patients become resistant to the inhibitors (Spranger, S., Gajewski, T. F., Nat. Rev. Cancer, 2018, 18, 139-147.)

DGK$\alpha$ is expressed in a T-cell, mediating a signaling of T-cell receptor (TCR) and is believed to play a role in T-cell activation (Joshi et al. as above and Merida, I. et al., Adv. Biol. Regul., 2017, 63, 22-31.) When a T-cell is under a condition of immunological unresponsiveness such as anergy, expression of DGK$\alpha$ can be increased, and an overexpression of DGK$\alpha$ has been reported to induce a condition of anergy (Zha, Y. et al., Nat. Immunol., 2006, 7, 1166-1173.) Further, activation of a T-cell has been reported as a result of knockdown of DGK$\alpha$ in the T-cell by means of RNA-interference (Avila-Flores, A., et al. Immunol. Cell. Biol., 2017, 95, 549-563.) Accordingly, a compound with an activity to control DGK$\alpha$ may be useful for preventing and/or treating diseases related to a T-cell, such as immunologic or inflammatory diseases.

Recently CAR (Chimeric Antigen Receptor) T cell therapy has also attracted attention as a promising immune cancer therapy. It has been reported that DGK$\alpha$-deficient CAR T cells have high effector function and anti-tumor effect on a solid cancer (Riese, M. J. et al. Cancer Res., 2013, 73, 3566-3577; Jung, I. Y., et al. Cancer Res., 2018, 78, 4692-4703.) Hence, use of a compound having inhibitory effect on DGK$\alpha$ may be complementary with CAR T cell therapy.

However, there remains a need for DGK$\alpha$ inhibitors, for example, with desirable pharmaceutical and therapeutic properties.

BRIEF SUMMARY

In one embodiment, the present disclosure provides a compound of Formula (I):

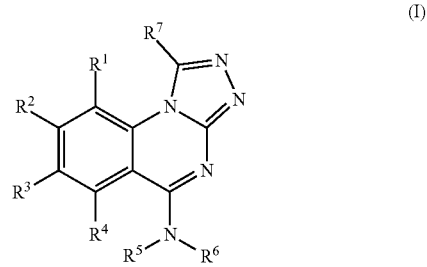

or a pharmaceutically acceptable salt thereof, wherein
  $R^1$ is hydrogen, $C_{1-6}$ alkyl, or halogen;
  $R^2$ is hydrogen $C_{1-6}$ alkyl, or halogen;
  $R^3$ is hydrogen, $C_{1-6}$ alkyl, halogen, or —CN;
  $R^4$ is hydrogen, $C_{1-6}$ alkyl, or halogen;

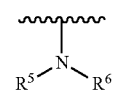

is

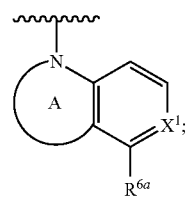

$X^1$ is N or CH;
  Ring A is a 6 to 8 membered heterocycloalkyl optionally having one additional heteroatom N or O, wherein Ring A is optionally substituted with 1 or 2 $R^{6g}$, each $R^{6g}$ is independently $C_{1-6}$ alkyl, halogen, $C_{1-6}$ haloalkyl, —OH, or $C_{1-6}$ alkoxy;

$R^{6a}$ is $C_{2-6}$ alkynyl substituted with 1 or 2 $R^{6j}$;

$R^{6a}$ is $C_{2-6}$ alkynyl substituted with 1 or 2 $R^{6j}$;

each $R^{6j}$ is independently —C(O)N($R^{6j3}$)($R^{6j4}$), —N($R^{6j1}$)C(O)$R^{6j2}$, —N($R^{6j1}$)S(O)$_2$($R^{6j2}$), $C_{3-10}$ cycloalkyl substituted with 1 or 2 $R^{6p}$ which can be the same or different;

$R^{6j1}$ is hydrogen or $C_{1-6}$ alkyl;

$R^{6j2}$ is $C_{3-10}$ cycloalkyl substituted with $C_{1-6}$ haloalkyl, or heteroaryl substituted with 1 to 3 $R^{6j2a}$ which can be the same or different;

each $R^{6j2a}$ is independently $C_{1-6}$ alkyl or $C_{1-6}$ haloalkyl;

$R^{6j3}$ is hydrogen or $C_{1-6}$ alkyl;

$R^{6j4}$ is $C_{3-10}$ cycloalkyl substituted with $C_{1-6}$ haloalkyl; or $R^{6j3}$ and $R^{6j4}$ together with the N to which they are attached form a 5 to 7 membered heterocycloalkyl optionally having one additional heteroatom N or O, the heterocycloalkyl is optionally substituted with 1 to 4 $R^{6j3a}$ which can be the same or different;

each $R^{6j3a}$ is independently halogen or $C_{1-6}$ alkyl;

each $R^{6p}$ is —N($R^{6p1}$)C(O)$R^{6p2}$ or heteroaryl substituted with $C_{1-6}$ alkyl;

$R^{6p1}$ is hydrogen or $C_{1-6}$ alkyl;

$R^{6p2}$ is $C_{3-10}$ cycloalkyl substituted with $C_{1-6}$ haloalkyl;

$R^7$ is hydrogen or $C_{1-6}$ alkyl; and each heteroaryl is a 5 to 6 membered ring having 1 to 2 heteroatoms each independently N or O.

In one embodiment, the present disclosure provides a compound as shown in Table 1, or a pharmaceutically acceptable salt thereof.

In another embodiment, the present disclosure provides a method of treating cancer in a subject in need thereof comprises administering to the subject a therapeutically effective amount of a compound of the present disclosure, or a pharmaceutically acceptable salt thereof, or a pharmaceutical composition of the present disclosure.

In another embodiment, the present disclosure provides a method of treating an HIV or a hepatitis B virus infection in a subject in need thereof comprises administering to the subject a therapeutically effective amount of a compound of the present disclosure, or a pharmaceutically acceptable salt thereof, or a pharmaceutical composition of the present disclosure.

DETAILED DESCRIPTION

I. Definitions

"Alkyl" is a linear or branched saturated monovalent hydrocarbon. For example, an alkyl group can have 1 to 18 carbon atoms (i.e., $C_{1-18}$ alkyl) or 1 to 8 carbon atoms (i.e., $C_{1-8}$ alkyl) or 1 to 6 carbon atoms (i.e., $C_{1-6}$ alkyl) or 1 to 4 carbon atoms (i.e., $C_{1-4}$ alkyl). Examples of alkyl groups include, but are not limited to, methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl (i-Bu, i-butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), and 3,3-dimethyl-2-butyl (—CH(CH$_3$)C(CH$_3$)$_3$). Other alkyl groups include heptyl, octyl, nonyl, decyl, undecyl, dodecyl, pentadcyl, hexadecyl, heptadecyl and octadecyl.

"Alkynyl" refers to either a straight chain or branched hydrocarbon having at least 2 carbon atoms and at least one triple bond. Alkynyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Examples of alkynyl groups include, but are not limited to, acetylenyl, propynyl, 1-butynyl, 2-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl. Alkynyl groups can be substituted or unsubstituted.

"Alkoxy" refers to an alkyl group having an oxygen atom that connects the alkyl group to the point of attachment: alkyl-O—. As for alkyl group, alkoxy groups can have any suitable number of carbon atoms, such as $C_{1-6}$. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. The alkoxy groups can be further substituted with a variety of substituents described within. Alkoxy groups can be substituted or unsubstituted.

"Halo" or "halogen" as used herein refers to fluoro (—F), chloro (—Cl), bromo (—Br) and iodo (—I).

"Haloalkyl" as used herein refers to an alkyl as defined herein, wherein one or more hydrogen atoms of the alkyl are independently replaced by a halo substituent, which may be the same or different. For example, $C_{1-4}$ haloalkyl is a $C_{1-4}$ alkyl wherein one or more of the hydrogen atoms of the $C_{1-4}$ alkyl have been replaced by a halo substituent. Examples of haloalkyl groups include but are not limited to fluoromethyl, fluorochloromethyl, difluoromethyl, difluorochloromethyl, trifluoromethyl, 1,1,1-trifluoroethyl and pentafluoroethyl.

"Cycloalkyl" refers to a single saturated or partially unsaturated all carbon ring having 3 to 20 annular carbon atoms (i.e., $C_{3-20}$ cycloalkyl), for example from 3 to 12 annular atoms, for example from 3 to 10 annular atoms, or 3 to 8 annular atoms, or 3 to 6 annular atoms, or 3 to 5 annular atoms, or 3 to 4 annular atoms. The term "cycloalkyl" also includes multiple condensed, saturated and partially unsaturated all carbon ring systems (e.g., ring systems comprising 2, 3 or 4 carbocyclic rings). Accordingly, cycloalkyl includes multicyclic carbocyles such as a bicyclic carbocycles (e.g., bicyclic carbocycles having 6 to 12 annular carbon atoms such as bicyclo[3.1.0]hexane and bicyclo[2.1.1]hexane), and polycyclic carbocycles (e.g., tricyclic and tetracyclic carbocycles with up to 20 annular carbon atoms). The rings of a multiple condensed ring system can be connected to each other via fused, spiro and bridged bonds when allowed by valency requirements. Non-limiting examples of monocyclic cycloalkyl include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl and 1-cyclohex-3-enyl.

"Heterocyclyl" or "heterocycle" or "heterocycloalkyl" as used herein refers to a single saturated or partially unsaturated non-aromatic ring or a multiple ring system having at least one heteroatom in the ring (i.e., at least one annular heteroatom selected from oxygen, nitrogen, and sulfur) wherein the multiple ring system includes at least non-aromatic ring containing at least one heteroatom. The multiple ring system can also include other aromatic rings and non-aromatic rings. Unless otherwise specified, a heterocyclyl group has from 3 to 20 annular atoms, for example from 3 to 12 annular atoms, for example from 3 to 10 annular atoms, or 3 to 8 annular atoms, or 3 to 6 annular atoms, or 3 to 5 annular atoms, or 4 to 6 annular atoms, or 4 to 5 annular atoms. Thus, the term includes single saturated or partially unsaturated rings (e.g., 3, 4, 5, 6 or 7-membered rings) having from 1 to 6 annular carbon atoms and from 1 to 3 annular heteroatoms selected from the group consisting of oxygen, nitrogen and sulfur in the ring. The heteroatoms can optionally be oxidized to form —N(—OH)—, =N(—O⁻)—, —S(=O)— or —S(=O)₂—. The rings of the multiple condensed ring (e.g. bicyclic heterocyclyl) system can be connected to each other via fused, spiro and bridged bonds when allowed by valency requirements. Heterocycles include, but are not limited to, azetidine, aziridine, imidazolidine, morpholine, oxirane (epoxide), oxetane, thietane, piperazine, piperidine, pyrazolidine, piperidine, pyrrolidine, pyrrolidinone, tetrahydrofuran, tetrahydrothiophene, dihydropyridine, tetrahydropyridine, quinuclidine, 2-oxa-6-azaspiro[3.3]heptan-6-yl, 6-oxa-1-azaspiro[3.3]heptan-1-yl, 2-thia-6-azaspiro[3.3]heptan-6-yl, 2,6-diazaspiro[3.3]heptan-2-yl, 2-azabicyclo[3.1.0]hexan-2-yl, 3-azabicyclo[3.1.0]hexanyl, 2-azabicyclo[2.1.1]hexanyl, 2-azabicyclo[2.2.1]heptan-2-yl, 4-azaspiro[2.4]heptanyl, 5-azaspiro[2.4]heptanyl, and the like.

Heterocycloalkyl rings also include 9 to 15 membered fused ring heterocycloalkyls having 2, 3, or more rings wherein at least one ring is an aryl ring and at least one ring is a non-aromatic ring containing at least one heteroatom. Representative fused bicyclic heterocycloalkyls include, but are not limited to, indoline (dihydroindole), isoindoline (dihydroisoindole), indazoline (dihydroindazole), benzo[d]imidazole, dihydroquinoline, dihydroisoquinoline, dihydrobenzofuran, dihydroisobenzofuran, benzo[d][1,3]dioxol, dihydrobenzo[b]dioxine, dihydrobenzo[d]oxazole, dihydrobenzo[b]thiophene, dihydroisobenzo[c]thiophene, dihydrobenzo[d]thiazole, dihydrobenzo[c]isothiazole, and benzo[b][1,4]thiazine, as shown in the structures below:

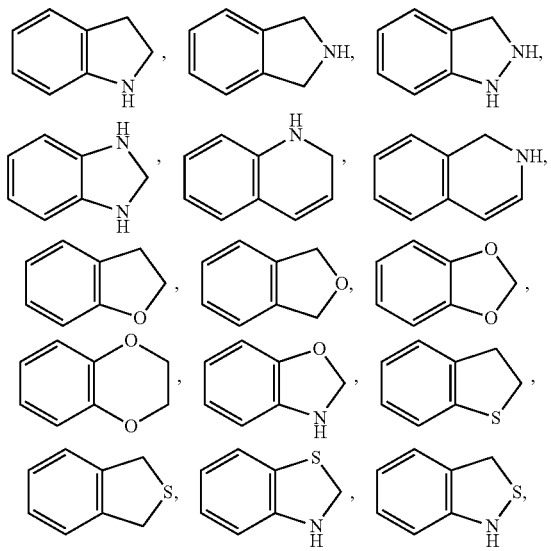

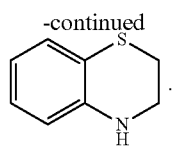

Fused bicyclic heterocycloalkyls can also be represented by the following structure:

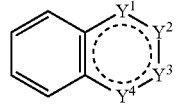

wherein Y¹, Y², Y³ and Y⁴ are each independently absent, —CH₂—, —NH—, —O— or —S—, at least one of Y¹, Y², Y³ and Y⁴ is —NH—, —O— or —S—, and the dashed circle represents a saturated or partially unsaturated non-aromatic ring. The fused bicyclic heterocycloalkyls are optionally substituted.

"Aryl" as used herein refers to a single all carbon aromatic ring or a multiple condensed all carbon ring system wherein at least one of the rings is aromatic. For example, in some embodiments, an aryl group has 6 to 20 carbon atoms, 6 to 14 carbon atoms, or 6 to 12 carbon atoms. Aryl includes a phenyl radical. Aryl also includes multiple condensed ring systems (e.g., ring systems comprising 2, 3 or 4 rings) having 9 to 20 carbon atoms, e.g., 9 to 16 carbon atoms, in which at least one ring is aromatic and wherein the other rings may be aromatic or not aromatic (i.e., carbocycle). Such multiple condensed ring systems are optionally substituted with one or more (e.g., 1, 2 or 3) oxo groups on any carbocycle portion of the multiple condensed ring system. The rings of the multiple condensed ring system can be connected to each other via fused, spiro and bridged bonds when allowed by valency requirements. It is also to be understood that when reference is made to a certain atom-range membered aryl (e.g., 6-10 membered aryl), the atom range is for the total ring atoms of the aryl. For example, a 6-membered aryl would include phenyl and a 10-membered aryl would include naphthyl and 1,2,3,4-tetrahydronaphthyl. Non-limiting examples of aryl groups include, but are not limited to, phenyl, indenyl, naphthyl, 1,2,3,4-tetrahydronaphthyl, anthracenyl, and the like.

"Heteroaryl" as used herein refers to a single aromatic ring that has at least one atom other than carbon in the ring, wherein the atom is selected from the group consisting of oxygen, nitrogen and sulfur; "heteroaryl" also includes multiple condensed ring systems that have at least one such aromatic ring, which multiple condensed ring systems are further described below. Thus, "heteroaryl" includes single aromatic rings of from 1 to 6 carbon atoms and 1-4 heteroatoms selected from the group consisting of oxygen, nitrogen and sulfur. The sulfur and nitrogen atoms may also be present in an oxidized form provided the ring is aromatic. Exemplary heteroaryl ring systems include but are not limited to pyridyl, pyrimidinyl, oxazolyl or furyl. "Heteroaryl" also includes multiple condensed ring systems (e.g., ring systems comprising 2, 3 or 4 rings) wherein a heteroaryl group, as defined above, is condensed with one or more rings selected from heteroaryls (to form for example 1,8-naphthyridinyl), heterocycles, (to form for example 1,2,3,4-tetrahydro-1,8-naphthyridinyl), carbocycles (to form for example 5,6,7,8-tetrahydroquinolyl) and aryls (to form for example indazolyl) to form the multiple condensed ring system. Thus, a heteroaryl (a single aromatic ring or multiple condensed ring system) has 1-20 carbon atoms and 1-6 heteroatoms within the heteroaryl ring. Such multiple condensed ring systems may be optionally substituted with one or more (e.g., 1, 2, 3 or 4) oxo groups on the carbocycle or heterocycle portions of the condensed ring. The rings of the multiple condensed ring system can be connected to each other via fused, spiro and bridged bonds when allowed by valency requirements. It is to be understood that the individual rings of the multiple condensed ring system may be connected in any order relative to one another. It is to be understood that the point of attachment for a heteroaryl or heteroaryl multiple condensed ring system can be at any suitable atom of the heteroaryl or heteroaryl multiple condensed ring system including a carbon atom and a heteroatom (e.g., a nitrogen). It also to be understood that when a reference is made to a certain atom-range membered heteroaryl (e.g., a 5 to 10 membered heteroaryl), the atom range is for the total ring atoms of the heteroaryl and includes carbon atoms and heteroatoms. For example, a 5-membered heteroaryl would include a thiazolyl and a 10-membered heteroaryl would include a quinolinyl. Exemplary heteroaryls include but are not limited to pyridyl, pyrrolyl, pyrazinyl, pyrimidinyl, pyridazinyl, pyrazolyl, thienyl, indolyl, imidazolyl, oxazolyl, isoxazolyl, thiazolyl, furyl, oxadiazolyl, thiadiazolyl, quinolyl, isoquinolyl, benzothiazolyl, benzoxazolyl, indazolyl, quinoxalyl, quinazolyl, 5,6,7,8-tetrahydroisoquinolinyl benzofuranyl, benzimidazolyl, thianaphthenyl, pyrrolo[2,3-b]pyridinyl, quinazolinyl-4(3H)-one, and triazolyl.

A "compound of the present disclosure" includes compounds disclosed herein, for example a compound of the present disclosure includes compounds of Formula (I) and compounds shown in Table 1.

"Composition" as used herein is intended to encompass a product comprising the specified ingredients in the specified amounts, as well as any product, which results, directly or indirectly, from combination of the specified ingredients in the specified amounts. By "pharmaceutically acceptable" it is meant the carrier, diluent or excipient must be compatible with the other ingredients of the formulation and deleterious to the recipient thereof.

"Pharmaceutically effective amount" refers to an amount of a compound of the present disclosure in a formulation or combination thereof, that provides the desired therapeutic or pharmaceutical result.

"Pharmaceutically acceptable excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Treatment" or "treat" or "treating" as used herein refers to an approach for obtaining beneficial or desired results. For purposes of the present disclosure, beneficial or desired results include, but are not limited to, alleviation of a symptom and/or diminishment of the extent of a symptom and/or preventing a worsening of a symptom associated with a disease or condition. In some embodiments, "treatment" or "treating" includes one or more of the following: a) inhibiting the disease or condition (e.g., decreasing one or more symptoms resulting from the disease or condition, and/or diminishing the extent of the disease or condition); b) slowing or arresting the development of one or more symptoms associated with the disease or condition (e.g., stabilizing the disease or condition, delaying the worsening or progression of the disease or condition); and c) relieving the disease or condition, e.g., causing the regression of clinical symptoms, ameliorating the disease state, delaying the progression of the disease, increasing the quality of life, and/or prolonging survival.

"Therapeutically effective amount" or "effective amount" as used herein refers to an amount that is effective to elicit the desired biological or medical response, including the amount of a compound that, when administered to a subject for treating a disease, is sufficient to effect such treatment for the disease. The effective amount can vary depending on the compound, the disease, and its severity and the age, weight, etc., of the subject to be treated. The effective amount can include a range of amounts. As is understood in the art, an effective amount may be in one or more doses, i.e., a single dose or multiple doses may be required to achieve the desired treatment endpoint. An effective amount may be considered in the context of administering one or more therapeutic agents, and a single agent may be considered to be given in an effective amount if, in conjunction with one or more other agents, a desirable or beneficial result may be or is achieved. Suitable doses of any co-administered compounds may optionally be lowered due to the combined action (e.g., additive or synergistic effects) of the compounds.

"Administering" refers to oral administration, administration as a suppository, topical contact, parenteral, intravenous, intraperitoneal, intramuscular, intralesional, intranasal or subcutaneous administration, intrathecal administration, or the implantation of a slow-release device e.g., a mini-osmotic pump, to the subject. The administration can be carried out according to a schedule specifying frequency of administration, dose for administration, and other factors.

"Co-administration" as used herein refers to administration of unit dosages of the compounds disclosed herein before or after administration of unit dosages of one or more additional therapeutic agents, for example, administration of the compound disclosed herein within seconds, minutes, or hours of the administration of one or more additional therapeutic agents. For example, in some embodiments, a unit dose of a compound of the present disclosure is administered first, followed within seconds or minutes by administration of a unit dose of one or more additional therapeutic agents. Alternatively, in other embodiments, a unit dose of one or more additional therapeutic agents is administered first, followed by administration of a unit dose of a compound of the present disclosure within seconds or minutes. In some embodiments, a unit dose of a compound of the present disclosure is administered first, followed, after a period of hours (e.g., 1-12 hours), by administration of a unit dose of one or more additional therapeutic agents. In other embodiments, a unit dose of one or more additional therapeutic agents is administered first, followed, after a period of hours (e.g., 1-12 hours), by administration of a unit dose of a compound of the present disclosure. Co-administration of a compound disclosed herein with one or more additional therapeutic agents generally refers to simultaneous or sequential administration of a compound disclosed herein and one or more additional therapeutic agents, such that therapeutically effective amounts of each agent are present in the body of the patient.

"Subject" refers to animals such as mammals, including, but not limited to, primates (e.g., humans), cows, sheep, goats, horses, dogs, cats, rabbits, rats, mice and the like. In some embodiments, the subject is a human.

"Disease" or "condition" refer to a state of being or health status of a patient or subject capable of being treated with a compound, pharmaceutical composition, or method provided herein. The disease may be an autoimmune, inflammatory, cancer, infectious (e.g., a viral infection), metabolic, developmental, cardiovascular, liver, intestinal, endocrine, neurological, or other disease. In some embodiments, the disease is cancer (e.g. lung cancer, ovarian cancer, osteosarcoma, bladder cancer, cervical cancer, liver cancer, kidney cancer, skin cancer (e.g., Merkel cell carcinoma), testicular cancer, leukemia, lymphoma, head and neck cancer, colorectal cancer, prostate cancer, pancreatic cancer, melanoma, breast cancer, neuroblastoma).

"Cancer" refers to all types of cancer, neoplasm or malignant tumors found in mammals, including leukemias, lymphomas, melanomas, neuroendocrine tumors, carcinomas and sarcomas. Exemplary cancers that may be treated with a compound, pharmaceutical composition, or method provided herein include lymphoma, sarcoma, bladder cancer, bone cancer, brain tumor, cervical cancer, colon cancer, esophageal cancer, gastric cancer, head and neck cancer, kidney cancer, myeloma, thyroid cancer, leukemia, prostate cancer, breast cancer (e.g. triple negative, ER positive, ER negative, chemotherapy resistant, herceptin resistant, HER2 positive, doxorubicin resistant, tamoxifen resistant, ductal carcinoma, lobular carcinoma, primary, metastatic), ovarian cancer, pancreatic cancer, liver cancer (e.g. hepatocellular carcinoma), lung cancer (e.g. non-small cell lung carcinoma, squamous cell lung carcinoma, adenocarcinoma, large cell lung carcinoma, small cell lung carcinoma, carcinoid, sarcoma), glioblastoma multiforme, glioma, melanoma, prostate cancer, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma.

Additional examples include, cancer of the thyroid, endocrine system, brain, breast, cervix, colon, head & neck, esophagus, liver, kidney, lung, non-small cell lung, melanoma, mesothelioma, ovary, sarcoma, stomach, uterus or Medulloblastoma, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, Paget's Disease of the Nipple, Phyllodes Tumors, Lobular Carcinoma, Ductal Carcinoma, cancer of the pancreatic stellate cells, cancer of the hepatic stellate cells, or prostate cancer.

"Leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound, pharmaceutical composition, or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocyte leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

"Sarcoma" generally refers to a tumor which is made up of a substance like the embryonic connective tissue and is generally composed of closely packed cells embedded in a fibrillar or homogeneous substance. Sarcomas that may be treated with a compound, pharmaceutical composition, or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

"Melanoma" is taken to mean a tumor arising from the melanocytic system of the skin and other organs. Melanomas that may be treated with a compound, pharmaceutical composition, or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

"Carcinoma" refers to a malignant new growth made up of epithelial cells tending to infiltrate the surrounding tissues and give rise to metastases. Exemplary carcinomas that may be treated with a compound, pharmaceutical composition, or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basal oid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, ductal carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lobular carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tubular carcinoma, tuberous carcinoma, verrucous carcinoma, or carcinoma villosum.

"Metastasis," "metastatic," and "metastatic cancer" can be used interchangeably and refer to the spread of a proliferative disease or disorder, e.g., cancer, from one organ or another non-adjacent organ or body part. Cancer occurs at an originating site, e.g., breast, which site is referred to as a primary tumor, e.g., primary breast cancer. Some cancer cells in the primary tumor or originating site acquire the ability to penetrate and infiltrate surrounding normal tissue in the local area and/or the ability to penetrate the walls of the lymphatic system or vascular system circulating through the system to other sites and tissues in the body. A second clinically detectable tumor formed from cancer cells of a primary tumor is referred to as a metastatic or secondary tumor. When cancer cells metastasize, the metastatic tumor and its cells are presumed to be similar to those of the original tumor. Thus, if lung cancer metastasizes to the breast, the secondary tumor at the site of the breast consists of abnormal lung cells and not abnormal breast cells. The secondary tumor in the breast is referred to a metastatic lung cancer. Thus, the phrase metastatic cancer refers to a disease in which a subject has or had a primary tumor and has one or more secondary tumors. The phrases non-metastatic cancer or subjects with cancer that is not metastatic refers to diseases in which subjects have a primary tumor but not one or more secondary tumors. For example, metastatic lung cancer refers to a disease in a subject with or with a history of a primary lung tumor and with one or more secondary tumors at a second location or multiple locations, e.g., in the breast.

"Associated" or "associated with" in the context of a substance or substance activity or function associated with a disease (e.g., diabetes, cancer (e.g. prostate cancer, renal cancer, metastatic cancer, melanoma, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma)) means that the disease (e.g. lung cancer, ovarian cancer, osteosarcoma, bladder cancer, cervical cancer, liver cancer, kidney cancer, skin cancer (e.g., Merkel cell carcinoma), testicular cancer, leukemia, lymphoma, head and neck cancer, colorectal cancer, prostate cancer, pancreatic cancer, melanoma, breast cancer, neuroblastoma) is caused by (in whole or in part), or a symptom of the disease is caused by (in whole or in part) the substance or substance activity or function.

Provided are also pharmaceutically acceptable salts, hydrates, solvates, tautomeric forms, polymorphs, and prodrugs of the compounds described herein. "Pharmaceutically acceptable" or "physiologically acceptable" refer to compounds, salts, compositions, dosage forms and other materials which are useful in preparing a pharmaceutical composition that is suitable for veterinary or human pharmaceutical use.

The compounds of the present disclosure as described herein may be prepared and/or formulated as pharmaceutically acceptable salts or when appropriate as a free base. Pharmaceutically acceptable salts are non-toxic salts of a free base form of a compound that possesses the desired pharmacological activity of the free base. These salts may be derived from inorganic or organic acids or bases. Examples of a pharmaceutically acceptable salt of the compound of Formula (I) of the present disclosure include an inorganic acid salt such as hydrochloride, sulfate, carbonate, and phosphate etc., and an organic acid salt such as fumarate, maleate, methanesulfonate, and p-toluenesulfonate etc. Further salts with an alkaline metal such as sodium, potassium etc., with an alkaline earth metal such as magnesium or calcium etc., with an organic amine such as a lower alkyl amine, or a lower alcoholamine, with a basic amino acid such as lysine, arginine, ornithine, or an ammonium salt is also included. For example, a compound that contains a basic nitrogen may be prepared as a pharmaceutically acceptable salt by contacting the compound with an inorganic or organic acid. Non-limiting examples of pharmaceutically acceptable salts include sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, γ-hydroxybutyrates, glycolates, tartrates, and mandelates. Lists of other suitable pharmaceutically acceptable salts are found in Remington: The Science and Practice of Pharmacy, $21^{st}$ Edition, Lippincott Wiliams and Wilkins, Philadelphia, Pa., 2006.

Examples of "pharmaceutically acceptable salts" of the compounds disclosed herein also include salts derived from an appropriate base, such as an alkali metal (for example, sodium, potassium), an alkaline earth metal (for example, magnesium), ammonium and $NX_4^+$ (wherein X is $C_1$-$C_4$ alkyl). Also included are base addition salts, such as sodium or potassium salts.

Provided are also compounds described herein or pharmaceutically acceptable salts, isomers, or a mixture thereof, in which from 1 to n hydrogen atoms attached to a carbon atom may be replaced by a deuterium atom or D, in which n is the number of hydrogen atoms in the molecule. As known in the art, the deuterium atom is a non-radioactive isotope of the hydrogen atom. Such compounds may increase resistance to metabolism, and thus may be useful for increasing the half-life of the compounds described herein or pharmaceutically acceptable salts, isomer, or a mixture thereof when administered to a mammal. See, e.g., Foster, "Deuterium Isotope Effects in Studies of Drug Metabolism", Trends Pharmacol. Sci., 5(12):524-527 (1984). Such compounds are synthesized by means well known in the art, for example by employing starting materials in which one or more hydrogen atoms have been replaced by deuterium.

Examples of isotopes that can be incorporated into the disclosed compounds also include isotopes of hydrogen, carbon, nitrogen, oxygen, phosphorous, fluorine, chlorine, and iodine, such as $^2H$, $^3H$, C, $^{13}C$, $^{14}C$, $^{13}N$, $^{15}N$, $^{15}O$, $^{17}O$, $^{18}O$, $^{31}P$, $^{32}P$ $^{35}S$, $^{18}F$, $^{36}Cl$, $^{123}I$ and 125I, respectively. Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of Formula (I) and compounds shown in Table 1 can generally be prepared by conventional techniques known to those skilled in the art or by processes analogous to those described in the Examples as set out below using an appropriate isotopically-labeled reagent in place of the non-labeled reagent previously employed.

The compounds of the embodiments disclosed herein, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present disclosure is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included. Where compounds are represented in their chiral form, it is understood that the embodiment encompasses, but is not limited to, the specific diastereornerically or enantiomerically enriched form, Where chirality is not specified but is present, it is understood that the embodiment is directed to either the specific diastereornerically or enantiomerically enriched form; or a racemic or scalemic mixture of such compound(s). As used herein, "scalemic mixture" is a mixture of stereoisomers at a ratio other than 1:1.

"Racemates" refers to a mixture of enantiomers. The mixture can comprise equal or unequal amounts of each enantiomer.

"Stereoisomer" and "stereoisomers" refer to compounds that differ in the chirality of one or more stereocenters. Stereoisomers include enantiomers and diastereomers. The compounds may exist in stereoisomeric form if they possess one or more asymmetric centers or a double bond with asymmetric substitution and, therefore, can be produced as individual stereoisomers or as mixtures. Unless otherwise indicated, the description is intended to include individual stereoisomers as well as mixtures. The methods for the determination of stereochemistry and the separation of stereoisomers are well-known in the art (see, e.g., Chapter 4 of Advanced Organic Chemistry, 4th ed., J. March, John Wiley and Sons, New York, 1992).

"Tautomer" refers to alternate forms of a compound that differ in the position of a proton, such as enol-keto and imine-enamine tautomers, or the tautomeric forms of heteroaryl groups containing a ring atom attached to both a ring —NH— and a ring =N— such as pyrazoles, imidazoles, benzimidazoles, triazoles, and tetrazoles.

Unless defined otherwise, all technical and scientific terms used herein have the same meaning as commonly understood by one of ordinary skill in the art. A dash at the front or end of a chemical group is a matter of convenience; chemical groups may be depicted with or without one or more dashes without losing their ordinary meaning. A wavy line drawn through a line in a structure indicates a point of attachment of a group. A dashed line indicates an optional bond. Unless chemically or structurally required, no directionality is indicated or implied by the order in which a chemical group is written or the point at which it is attached to the remainder of the molecule. For instance, the group "—$SO_2CH_2$—" is equivalent to "—$CH_2SO_2$—" and both may be connected in either direction. Similarly, an "arylalkyl" group, for example, may be attached to the remainder of the molecule at either an aryl or an alkyl portion of the group. A prefix such as "$C_{u-v}$" or ($C_u$-$C_v$) indicates that the following group has from u to v carbon atoms. For example, "$C_{1-6}$alkyl" and "$C_1$-$C_6$ alkyl" both indicate that the alkyl group has from 1 to 6 carbon atoms.

"Solvate" as used herein refers to the result of the interaction of a solvent and a compound. Solvates of salts of the compounds described herein are also provided. Hydrates of the compounds described herein are also provided.

"Prodrug" as used herein refers to a derivative of a drug that upon administration to the human body is converted to the parent drug according to some chemical or enzymatic pathway.

II. Compounds

The present disclosure provides compounds of Formula (I) and compounds as shown in Table 1, and pharmaceutically acceptable salts thereof.

In some embodiments, the compound has the structure of Formula (I):

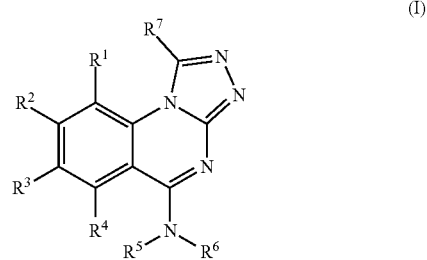

or a pharmaceutically acceptable salt thereof.

In some embodiments, the compound of Formula (I), or or a pharmaceutically acceptable salt thereof, is the compound wherein $R^1$ is hydrogen, $C_{1-6}$ alkyl, or halogen;
$R^2$ is hydrogen $C_{1-6}$ alkyl, or halogen;
$R^3$ is hydrogen, $C_{1-6}$ alkyl, halogen, or —CN;
$R^4$ is hydrogen, $C_{1-6}$ alkyl, or halogen;

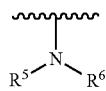

is

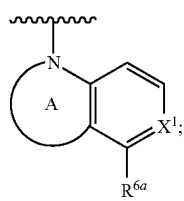

$X^1$ is N or CH;
Ring A is a 6 to 8 membered heterocycloalkyl optionally having one additional heteroatom N or O, wherein Ring A is optionally substituted with 1 or 2 $R^{6g}$, each $R^{6g}$ is independently $C_{1-6}$ alkyl, halogen, $C_{1-6}$ haloalkyl, —OH, or alkoxy;
$R^{6a}$ is $C_{2-6}$ alkynyl substituted with 1 or 2 $R^{6j}$;
each $R^{6j}$ is independently —C(O)N($R^{6j3}$)($R^{6j4}$), —N($R^{6j1}$)C(O)$R^{6j2}$, —N($R^{6j1}$)S(O)$_2$($R^{6j2}$), $C_{3-10}$ cycloalkyl substituted with 1 or 2 $R^{6p}$ which can be the same or different;
$R^{6j1}$ is hydrogen or $C_{1-6}$ alkyl;
$R^{6j2}$ is $C_{3-10}$ cycloalkyl substituted with $C_{1-6}$ haloalkyl, or heteroaryl substituted with 1 to 3 $R^{6j2a}$ which can be the same or different;
each $R^{6j2a}$ is independently $C_{1-6}$ alkyl or $C_{1-6}$ haloalkyl;
$R^{6j3}$ is hydrogen or $C_{1-6}$ alkyl;
$R^{6j4}$ is $C_{3-10}$ cycloalkyl substituted with $C_{1-6}$ haloalkyl;
or $R^{6j3}$ and $R^{6j4}$ together with the N to which they are attached form a 5 to 7 membered heterocycloalkyl optionally having one additional heteroatom N or O, the heterocycloalkyl is optionally substituted with 1 to 4 $R^{6j3a}$ which can be the same or different;
each $R^{6j3a}$ is independently halogen or $C_{1-6}$ alkyl;
each $R^{6p}$ is —N($R^{6p1}$)C(O)$R^{6p2}$ or heteroaryl substituted with $C_{1-6}$ alkyl;
$R^{6p1}$ is hydrogen or $C_{1-6}$ alkyl;
$R^{6p2}$ is $C_{3-10}$ cycloalkyl substituted with $C_{1-6}$ haloalkyl;
$R^7$ is hydrogen or $C_{1-6}$ alkyl; and
each heteroaryl is a 5 to 6 membered ring having 1 to 2 heteroatoms each independently N or O.

In some embodiments, Ring A is unsubstituted. In some embodiments, Ring A is substituted with 1 or 2 $R^{6g}$, each $R^{6g}$ is independently $C_{1-6}$ alkyl, halogen, $C_{1-6}$ haloalkyl, —OH, or $C_{1-6}$ alkoxy. In some embodiments, Ring A is substituted with $C_{1-6}$ alkyl. In some embodiments, Ring A is substituted with —OH.

In some embodiments, the present disclosure provides a compound of Formula (I), or a pharmaceutically acceptable salt thereof, wherein

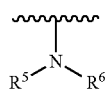

is

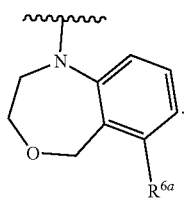

In some embodiments,

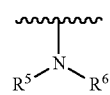

is

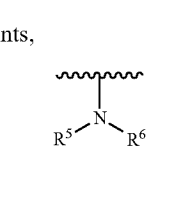

In some embodiments,

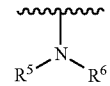

is

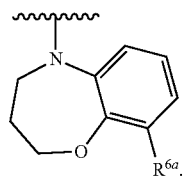

In some embodiments,

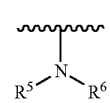

is

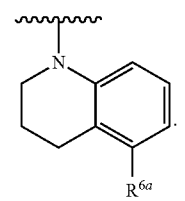

In some embodiments, the present disclosure provides a compound of Formula (I), or a pharmaceutically acceptable salt thereof, wherein R

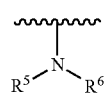
is
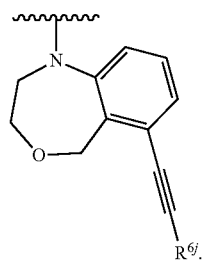
In some embodiments,
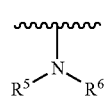
is
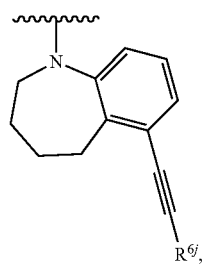
In some embodiments,
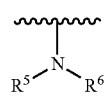
is
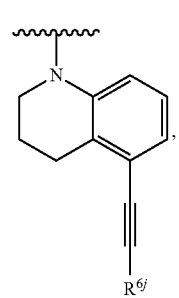
In some embodiments,
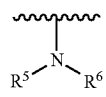
is
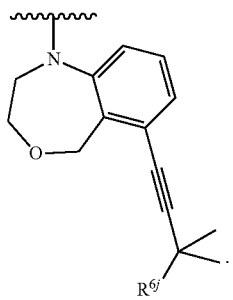
In some embodiments,
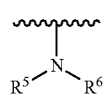
is
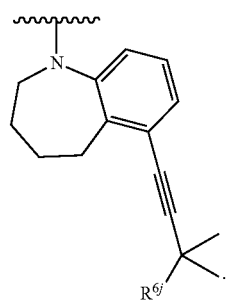
In some embodiments,
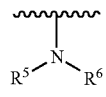
is
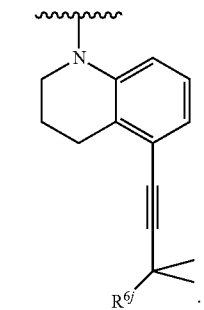

In some embodiments,

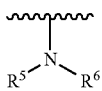

is

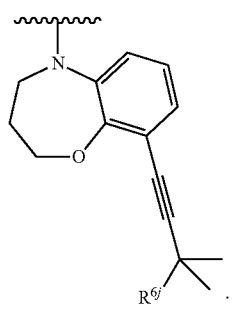

In some embodiments,

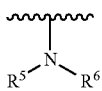

is

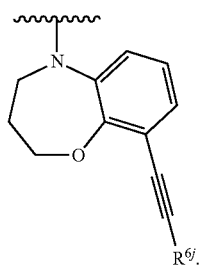

In some embodiments, the present disclosure provides a compound of Formula (I), or a pharmaceutically acceptable salt thereof, wherein $R^{6j}$ is —NHC(O)$R^{6j2}$, $R^{6j2}$ is cyclopropyl substituted with $C_{1-3}$ haloalkyl. In some embodiments, $R^{6j}$ is —NHC(O)$R^{6j2}$; $R^{6j2}$ is 5 or 6 membered heteroaryl substituted 1 to 3 $R^{6j2a}$; and each $R^{6j2a}$ is independently $C_{1-3}$ alkyl or $C_{1-3}$ haloalkyl.

In some embodiments, the present disclosure provides a compound of Formula (I), or a pharmaceutically acceptable salt thereof, wherein $R^{6j}$ is —C(O)N($R^{6j3}$)($R^{6j4}$); $R^{6j3}$ is hydrogen; and $R^{6j4}$ is cyclopropyl substituted with $C_{1-3}$ haloalkyl. In some embodiments, $R^{6j}$ is —C(O)N($R^{6j3}$)($R^{6j4}$); $R^{6j3}$ and $R^{6j4}$ together with the N to which they are attached form piperidinyl or morpholinyl, wherein the piperidinyl or morpholinyl is optionally substituted with 1 to 3 $R^{6j3a}$ which can be the same or different; each $R^{6j3a}$ is independently —F or $C_{1-3}$ alkyl. In some embodiments, $R^{6j3}$ and $R^{6j4}$ together with the N to which they are attached form piperidinyl or morpholinyl, wherein the piperidinyl or morpholinyl is substituted with 1 to 3 $R^{6j3a}$; each $R^{6j3a}$ is independently —F or $C_{1-3}$ alkyl.

In some embodiments, the present disclosure provides a compound of Formula (I), or a pharmaceutically acceptable salt thereof, wherein $R^{6j}$ is cyclopropyl substituted with —NHC(O)$R^{6p2}$, $R^{6p2}$ is cyclopropyl substituted with $C_{1-3}$ haloalkyl. In some embodiments, $R^{6j}$ is cyclopropyl substituted with —NHC(O)$R^{6p2}$, wherein $R^{6p2}$ is 5 to 6 membered heteroaryl having 1 to 2 heteroatoms each independently N or O, the heteroaryl is substituted with $C_{1-6}$ alkyl.

In some embodiments, the present disclosure provides a compound of Formula (I), or a pharmaceutically acceptable salt thereof, wherein $R^{6j}$ is —NHS(O)$_2$($R^{6j2}$). In some embodiments, $R^{6j2}$ is $C_{3-10}$ cycloalkyl substituted with $C_{1-6}$ haloalkyl. In some embodiments, $R^{6j2}$ is heteroaryl substituted with 1 to 3 $R^{6j2a}$ which can be the same or different.

In some embodiments, the present disclosure provides a compound of Formula (I), or a pharmaceutically acceptable salt thereof, wherein each $R^{6j}$ is

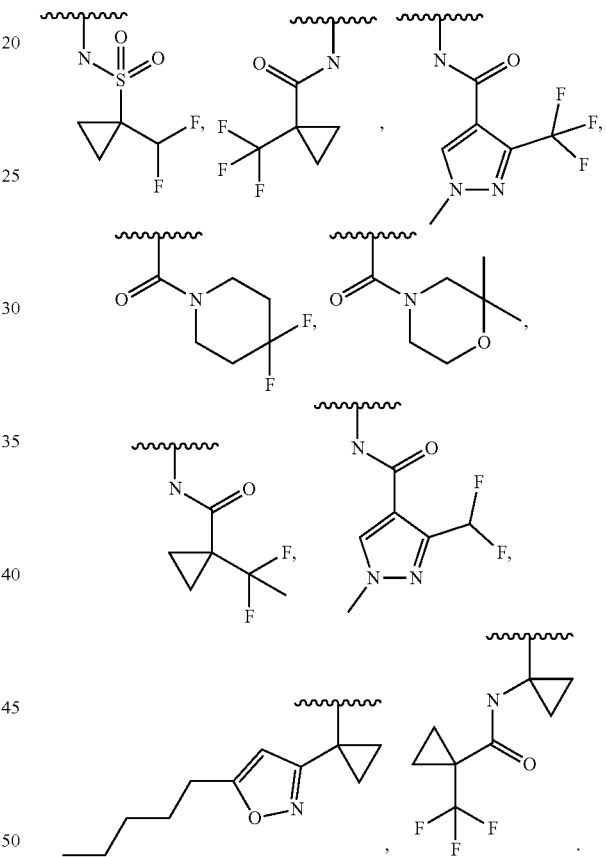

In some embodiments, $R^{6j}$ is

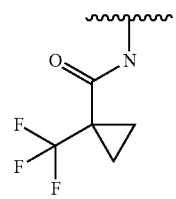

In some embodiments, the present disclosure provides a compound of Formula (I), or a pharmaceutically acceptable salt thereof, wherein

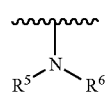

is

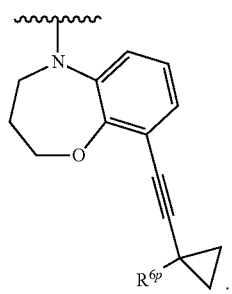

In some embodiments,

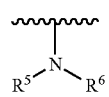

is

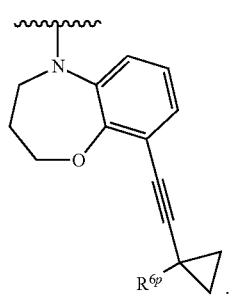

in some embodiments,

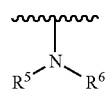

is

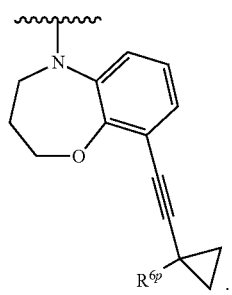

In some embodiments,

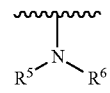

is

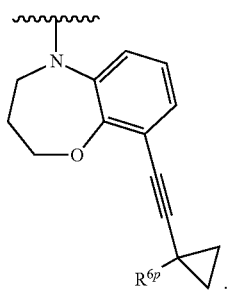

In some embodiments, $R^{6p}$ is —N($R^{6p1}$)C(O)$R^{6p2}$, $R^{6p1}$ is hydrogen or $C_{1-6}$ alkyl; and $R^{6p2}$ is $C_{3-10}$ cycloalkyl substituted with $C_{1-6}$ haloalkyl. In some embodiments, $R^{6p1}$ is hydrogen. In some embodiments, $R^{6p2}$ is cyclopropyl substituted with $C_{1-6}$ haloalkyl. In some embodiments, $R^{6p}$ is 5 or 6 membered heteroaryl substituted with $C_{1-6}$ alkyl.

In some embodiments, the present disclosure provides a compound of Formula (I), or a pharmaceutically acceptable salt thereof, wherein

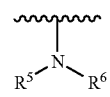

is

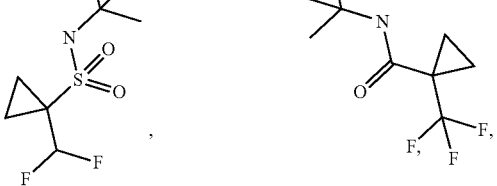

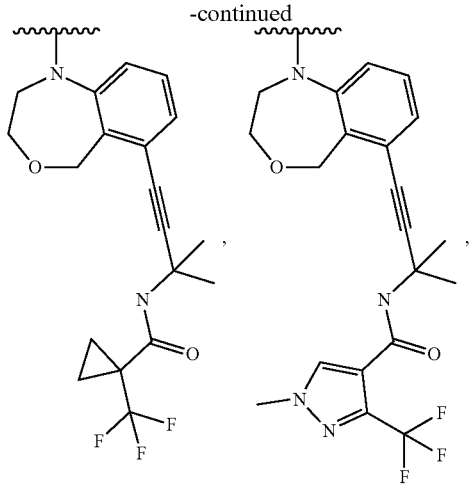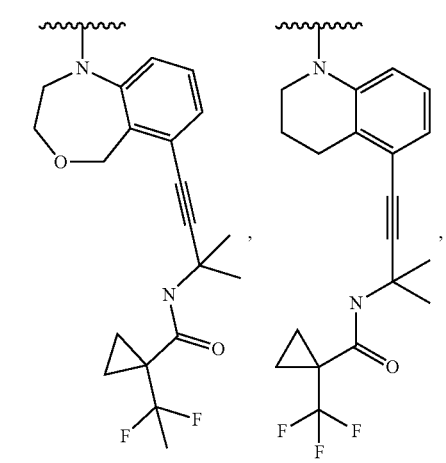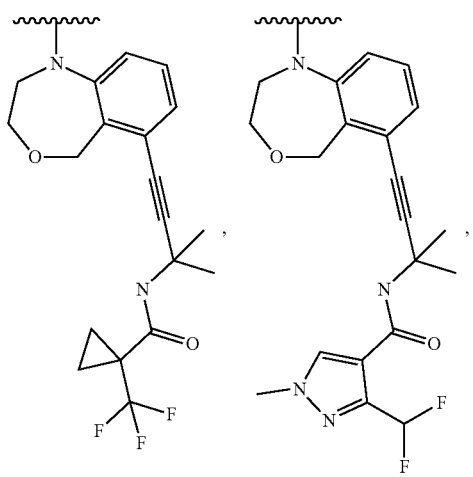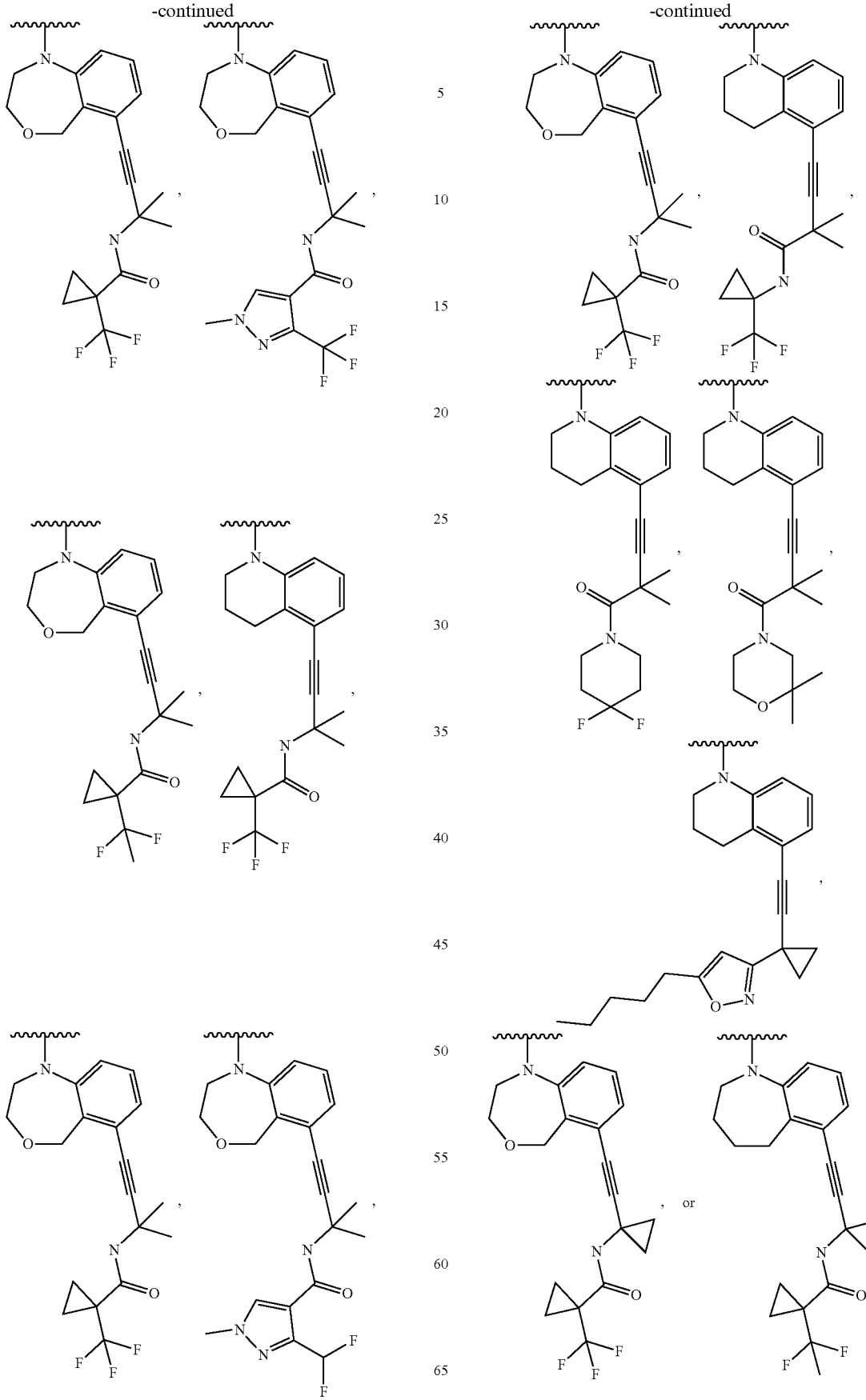

In some embodiments, the present disclosure provides a compound of Formula (I), or a pharmaceutically acceptable salt thereof, wherein

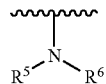

is

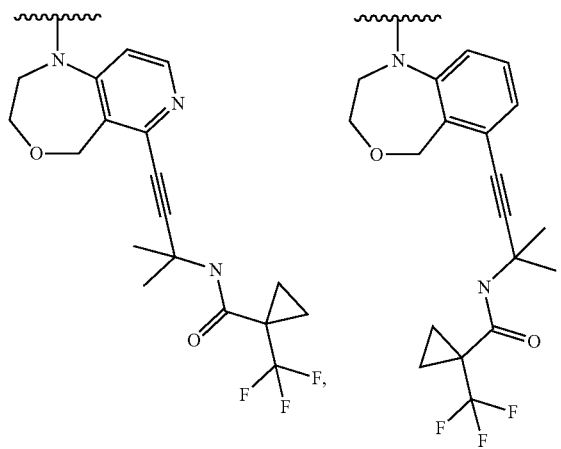

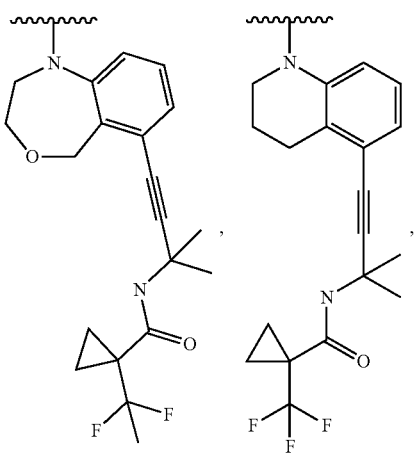

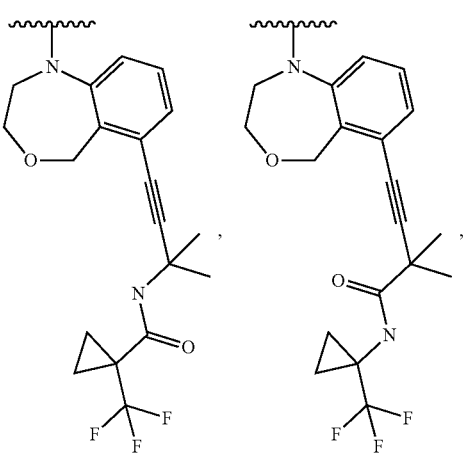

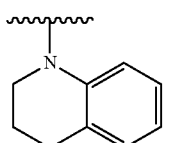

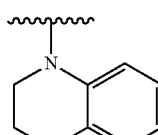

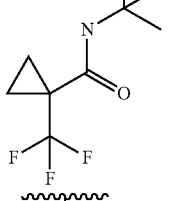

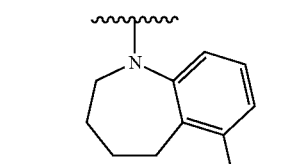

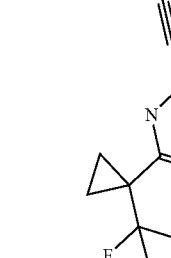

In some embodiments, the present disclosure provides a compound of Formula (I), or a pharmaceutically acceptable salt thereof, wherein $R^1$ is hydrogen, —CH$_3$, —F, or —Cl. In some embodiments, $R^1$ is hydrogen.

In some embodiments, the present disclosure provides a compound of Formula (I), or a pharmaceutically acceptable salt thereof, wherein $R^2$ is hydrogen, —F, or —Cl. In some embodiments, $R^2$ is hydrogen.

In some embodiments, the present disclosure provides a compound of Formula (I), or a pharmaceutically acceptable salt thereof, wherein $R^3$ is hydrogen, —F, or —CN. In some embodiments, $R^3$ is hydrogen. In some embodiments, $R^3$ is —F.

In some embodiments, the present disclosure provides a compound of Formula (I), or a pharmaceutically acceptable salt thereof, wherein $R^4$ is hydrogen, —CH$_3$, —F, or —Cl. In some embodiments, $R^4$ is hydrogen. In some embodiments, $R^4$ is —Cl. In some embodiments, $R^4$ is —F.

In some embodiments, the present disclosure provides a compound of Formula (I), or a pharmaceutically acceptable salt thereof, wherein $R^7$ is hydrogen. In some embodiments, $R^7$ is —CH$_3$. In some embodiments, $R^7$ is —C$_2$H$_5$.

In some embodiments, the present disclosure provides a compound having a structure as shown in Table 1, or a pharmaceutically acceptable salt thereof. In some embodiments, the present disclosure provides a compound having a structure as shown in Table 1.

One of skill in the art is aware that when a group is substituted with two or more substituents, the two or more substituents may be the same or different unless explicitly stated otherwise.

One of skill in the art is aware that each and every embodiment of a group (e.g., $R^1$) disclosed herein may be combined with any other embodiment of each of the remaining groups (e.g., $R^2$, $R^3$, $R^4$, $R^5$, $R^6$, $R^7$ etc.) to generate a complete compound of Formula (I), or any Formula described herein or a pharmaceutically acceptable salt, each of which is deemed within the ambit of the present disclosure.

TABLE 1

Compounds and characterization of the compounds

| EXAMPLE | STRUCTURE | LC/MS | NMR |
| --- | --- | --- | --- |
| 1 | 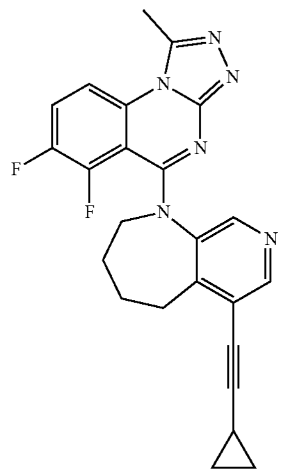 [SMILES: Cc1nnc2nc(N3CCCCc4c(C#CC5CC5)cncc43)c3c(F)c(F)ccc3n12] | 431.29 | 1H NMR (400 MHz, DMSO-d6) δ 8.39 (s, 1H), 8.23-8.12 (m, 1H), 8.12-7.98 (m, 1H), 7.89 (s, 1H), 4.0-4.4 (br, s, 2H), 3.18 (s, 2H), 2.99 (s, 3H), 2.02-1.71 (m, 4H), 1.67 (tt, J = 8.2, 5.0 Hz, 1H), 0.97 (dt, J = 8.2, 3.2 Hz, 2H), 0.89-0.77 (m, 2H). |
| 2 | 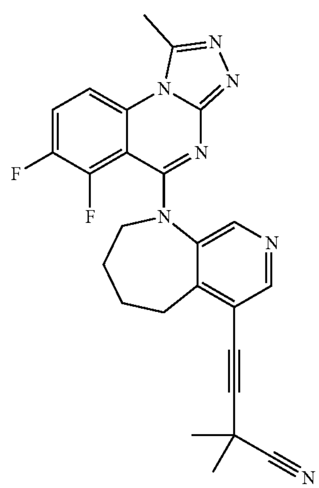 [SMILES: Cc1nnc2nc(N3CCCCc4c(C#CC(C)(C)C#N)cncc43)c3c(F)c(F)ccc3n12] | 458.319 | 1H NMR (400 MHz, DMSO-d6) δ 8.40 (s, 1H), 8.24-8.13 (m, 1H), 8.06 (q, J = 9.1 Hz, 1H), 7.93 (s, 1H), 4.0-4.4 (br, s, 2H), 3.22 (s, 2H), 2.99 (s, 3H), 2.02-1.65 (m, 4H), 1.53 (s, 6H). |
| 3 | 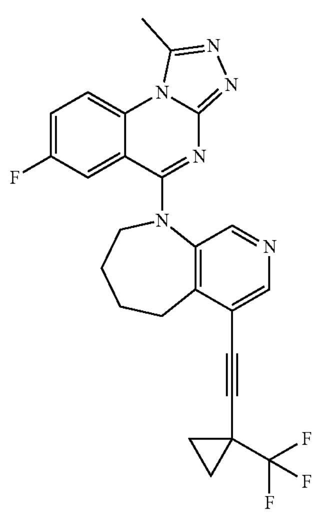 [SMILES: Cc1nnc2nc(N3CCCCc4c(C#CC5(C(F)(F)F)CC5)cncc43)c3cc(F)ccc3n12] | 481.331 | 1H NMR (400 MHz, DMSO-d6) δ 8.62 (s, 1H), 8.42 (dd, J = 9.5, 4.7 Hz, 1H), 8.16 (s, 1H), 7.87 (ddd, J = 9.4, 7.6, 2.9 Hz, 1H), 6.65 (dd, J = 10.0, 2.9 Hz, 1H), 4.22 (s, 2H), 3.25 (t, J = 6.0 Hz, 2H), 3.02 (s, 3H), 2.04-1.69 (m, 4H), 1.61-1.39 (m, 4H). |

TABLE 1-continued

Compounds and characterization of the compounds

| EXAMPLE | STRUCTURE | LC/MS | NMR |
|---|---|---|---|
| 4 | 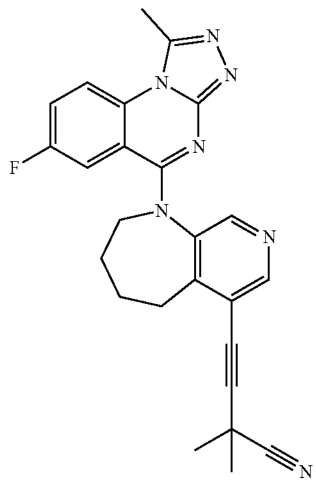 [SMILES: Cc1nnc2nc(N3CCCCc4c(C#CC(C)(C)C#N)cncc43)c3cc(F)ccc3n12] | 440.376 | 1H NMR (400 MHz, DMSO-d6) δ 8.64 (s, 1H), 8.39 (dd, J = 9.5, 4.7 Hz, 1H), 8.15 (s, 1H), 7.84 (ddd, J = 9.3, 7.7, 2.9 Hz, 1H), 6.65 (dd, J = 10.0, 2.9 Hz, 1H), 4.22 (s, 2H), 3.26 (s, 2H), 3.01 (s, 3H), 2.00-1.75 (m, 10H). |
| 5 | 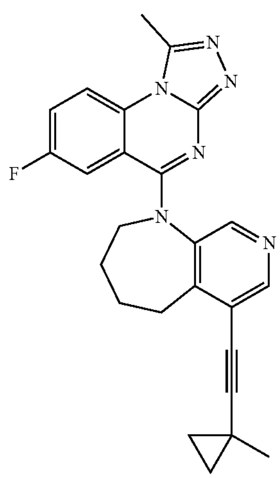 | 427.325 | 1H NMR (400 MHz, DMSO-d6) δ 8.56 (s, 1H), 8.42 (dd, J = 9.5, 4.8 Hz, 1H), 8.10 (s, 1H), 7.88 (ddd, J = 9.4, 7.6, 2.9 Hz, 1H), 6.62 (dd, J = 10.1, 2.9 Hz, 1H), 4.22 (s, 2H), 3.22 (s, 2H), 3.02 (s, 3H), 2.02-1.66 (m, 4H), 1.39 (s, 3H), 1.06 (q, J = 4.0 Hz, 2H), 0.94-0.79 (m, 2H). |
| 6 | 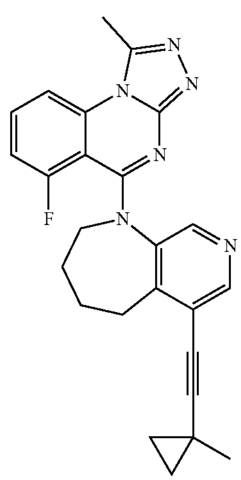 [SMILES: Cc1nnc2nc(N3CCCCc4c(C#CC5(C)CC5)cncc43)c3c(F)cccc3n12] | 427.331 | 1H NMR (400 MHz, DMSO-d6) δ 8.39 (s, 1H), 8.26-8.13 (m, 1H), 8.00 (td, J = 8.4, 5.5 Hz, 1H), 7.90 (s, 1H), 7.39-7.21 (m, 1H), 4.22 (s, 2H), 3.19 (s, 2H), 3.02 (s, 3H), 2.05-1.58 (m, 4H), 1.38 (s, 3H), 1.04 (q, J = 4.0 Hz, 2H), 0.91-0.70 (m, 2H). |

TABLE 1-continued

Compounds and characterization of the compounds

| EXAMPLE | STRUCTURE | LC/MS | NMR |
|---|---|---|---|
| 7 | 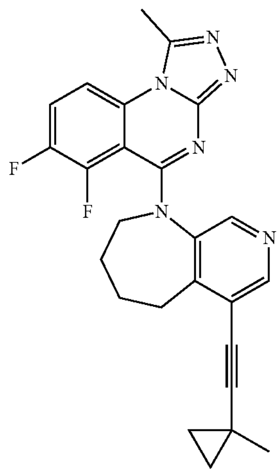 [SMILES: Cc1nnc2nc(N3CCCCc4c(C#CC5(C)CC5)cncc43)c3c(F)c(F)ccc3n12] | 445.302 | 1H NMR (400 MHz, DMSO-d6) δ 8.40 (s, 1H), 8.19 (ddd, J = 9.8, 4.2, 1.4 Hz, 1H), 8.09 (td, J = 9.5, 8.0 Hz, 1H), 7.92 (s, 1H), 4.22 (br, s, 2H), 3.18 (s, 2H), 3.00 (s, 3H), 1.97-1.58 (m, 4H), 1.38 (s, 3H), 1.05 (q, J = 4.0 Hz, 2H), 0.89-0.70 (m, 2H). |
| 8 | 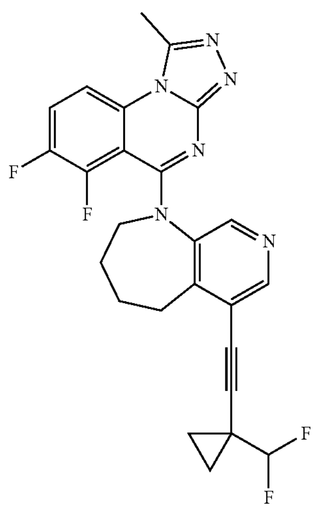 [SMILES: Cc1nnc2nc(N3CCCCc4c(C#CC5(C(F)F)CC5)cncc43)c3c(F)c(F)ccc3n12] | 481.316 | 1H NMR (400 MHz, DMSO-d6) δ 8.45 (s, 1H), 8.20 (ddd, J = 9.6, 4.1, 1.4 Hz, 1H), 8.10 (td, J = 9.5, 8.0 Hz, 1H), 7.98 (s, 1H), 5.84 (t, J = 55.5 Hz, 1H), 4.22 (s, 2H), 3.21 (s, 2H), 3.01 (s, 3H), 2.02-1.61 (m, 4H), 1.31 (s, 4H). |
| 9 | 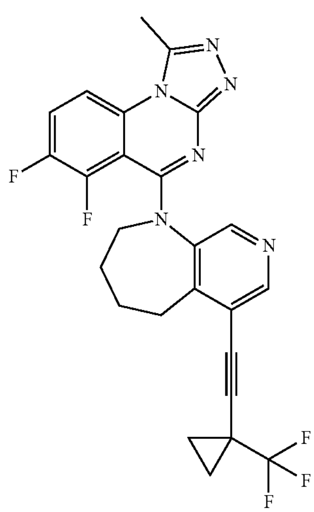 [SMILES: Cc1nnc2nc(N3CCCCc4c(C#CC5(C(F)(F)F)CC5)cncc43)c3c(F)c(F)ccc3n12] | 499.311 | 1H NMR (400 MHz, DMSO-d6) δ 8.47 (s, 1H), 8.18 (ddd, J = 9.6, 4.2, 1.4 Hz, 1H), 8.08 (td, J = 9.5, 8.0 Hz, 1H), 7.99 (s, 1H), 4.22 (br, s, 2H), 3.20 (s, 2H), 3.00 (s, 3H), 2.01-1.64 (m, 4H), 1.56-1.43 (m, 4H). |

TABLE 1-continued

Compounds and characterization of the compounds

| EXAMPLE | STRUCTURE | LC/MS | NMR |
|---|---|---|---|
| 10 | 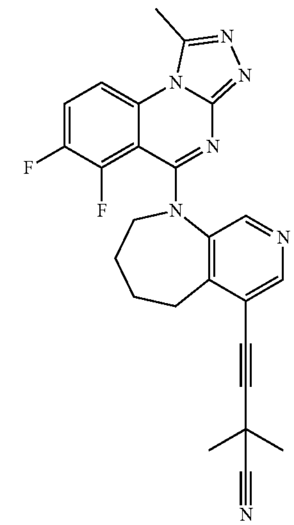 [SMILES: Cc1nnc2nc(N3CCCCc4c(C#CC(C)(C)C#N)cncc43)c3c(F)c(F)ccc3n12] | 444.1 | 1H NMR (400 MHz, DMSO-d6) δ 8.41-8.13 (m, 3H), 8.05 (td, J = 8.4, 5.5 Hz, 1H), 7.46 (dd, J = 12.1, 8.2 Hz, 1H), 3.94 (s, 2H), 3.01 (s, 3H), 2.96 (s, 2H), 2.06 (s, 2H), 1.79 (s, 4H). |
| 11 | 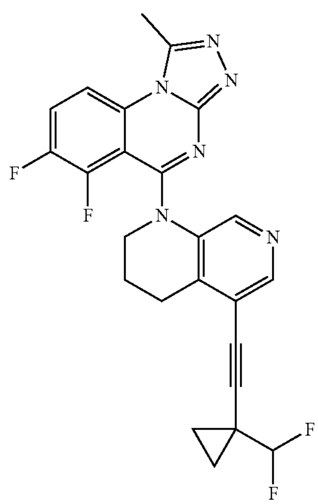 [SMILES: Cc1nnc2nc(N3CCCc4c(C#CC5(C(F)F)CC5)cncc43)c3c(F)c(F)ccc3n12] | 467.2 | 1H NMR (400 MHz, DMSO-d6) δ 8.33-8.04 (m, 4H), 5.83 (t, J = 55.5 Hz, 1H), 3.93 (s, 2H), 3.01 (s, 3H), 2.95 (s, 2H), 2.05 (s, 2H), 1.30 (q, J = 2.9 Hz, 4H). |
| 12 | 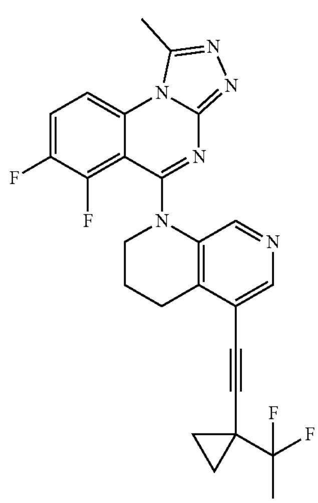 [SMILES: Cc1nnc2nc(N3CCCc4c(C#CC5(C(C)(F)F)CC5)cncc43)c3c(F)c(F)ccc3n12] | 481.2 | 1H NMR (400 MHz, DMSO-d6) δ 8.31 (s, 1H), 8.27 (s, 1H), 8.26-8.12 (m, 2H), 3.94 (s, 2H), 3.02 (s, 3H), 2.97 (d, J = 7.1 Hz, 2H), 2.05 (s, 2H), 1.88 (t, J = 18.4 Hz, 3H), 1.38-1.15 (m, 4H). |

TABLE 1-continued
Compounds and characterization of the compounds
| EXAMPLE | STRUCTURE | LC/MS | NMR |
|---|---|---|---|
| 13 | 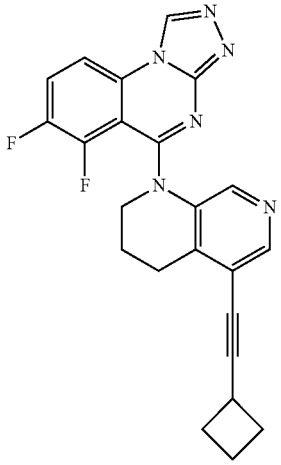 [SMILES: Fc1ccc2c(c(N3CCCc4c(C#CC5CCC5)cncc43)nc3nncn32)c1F] | 417.1 | 1H NMR (400 MHz, DMSO-d6) δ 9.84 (s, 1H), 8.43-8.17 (m, 4H), 3.91 (d, J = 6.5 Hz, 2H), 3.40 (p, J = 8.4 Hz, 1H), 2.97 (s, 2H), 2.38 (dtd, J = 11.7, 8.5, 3.7 Hz, 2H), 2.20 (pd, J = 9.0, 2.5 Hz, 2H), 2.11-1.79 (m, 4H). |
| 14 | 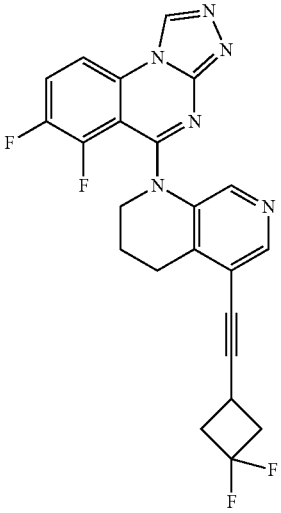 [SMILES: Fc1ccc2c(c(N3CCCc4c(C#CC5CC(F)(F)C5)cncc43)nc3nncn32)c1F] | 453.1 | 1H NMR (400 MHz, DMSO-d6) δ 9.83 (s, 1H), 8.45-8.17 (m, 4H), 3.91 (s, 2H), 3.37 (dtt, J = 9.1, 7.0, 4.7 Hz, 1H), 3.11 (tt, J = 13.3, 9.4 Hz, 2H), 2.97 (s, 2H), 2.80 (qdd, J = 14.0, 6.8, 3.6 Hz, 2H), 2.04 (s, 2H). |
| 15 | 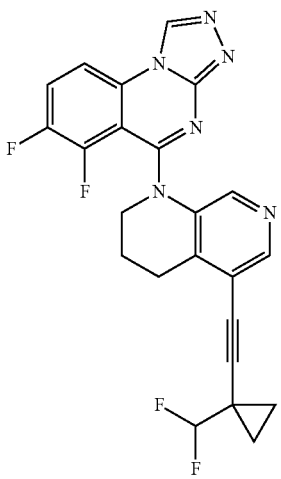 | 453.1 | 1H NMR (400 MHz, DMSO-d6) δ 9.82 (s, 1H), 8.35 (dd, J = 9.5, 3.7 Hz, 1H), 8.28-8.14 (m, 3H), 5.83 (t, J = 55.5 Hz, 1H), 3.91 (s, 2H), 2.94 (s, 2H), 2.04 (s, 2H), 1.29 (q, J = 2.8 Hz, 4H). |

TABLE 1-continued

Compounds and characterization of the compounds

| EXAMPLE | STRUCTURE | LC/MS | NMR |
|---|---|---|---|
| 16 | 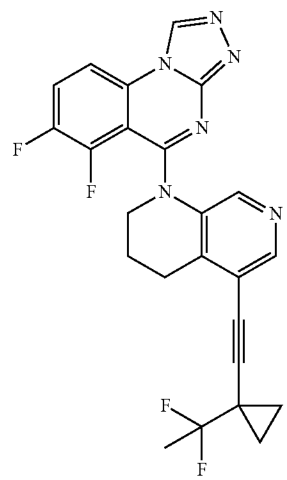 | 467.1 | 1H NMR (400 MHz, DMSO-d6) δ 9.84 (s, 1H), 8.45-8.12 (m, 4H), 3.91 (s, 2H), 2.95 (d, J = 6.9 Hz, 2H), 2.04 (s, 2H), 1.88 (t, J = 18.5 Hz, 3H), 1.42-1.10 (m, 4H). |
| 17 | 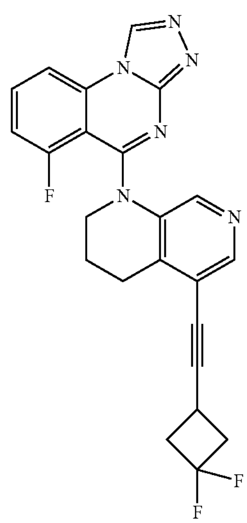 | 435.1 | 1H NMR (400 MHz, DMSO-d6) δ 9.86 (s, 1H), 8.38-8.18 (m, 3H), 8.09 (td, J = 8.3, 5.2 Hz, 1H), 7.45 (dd, J = 12.1, 8.2 Hz, 1H), 3.94 (s, 2H), 3.37 (dqt, J = 9.2, 7.0, 2.2 Hz, 1H), 3.11 (tt, J = 13.3, 9.5 Hz, 2H), 2.97 (d, J = 6.7 Hz, 2H), 2.80 (tdd, J = 14.0, 12.2, 6.9 Hz, 2H), 2.06 (d, J = 8.8 Hz, 2H). |
| 18 | 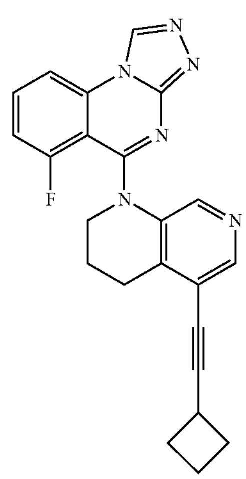 [SMILES: Fc1cccc2c1c(N1CCCc3c(C#CC4CCC4)cncc31)nc1nncn12] | 399.1 | 1H NMR (400 MHz, DMSO-d6) δ 9.87 (s, 1H), 8.29 (dd, J = 14.9, 8.2 Hz, 3H), 8.10 (td, J = 8.3, 5.2 Hz, 1H), 7.46 (dd, J = 12.1, 8.2 Hz, 1H), 3.94 (s, 2H), 3.40 (p, J = 8.4 Hz, 1H), 2.98 (t, J = 6.7 Hz, 2H), 2.46-2.31 (m, 2H), 2.20 (dq, J = 11.5, 9.1 Hz, 2H), 1.82-2, 12 (m, 4H). |

TABLE 1-continued

Compounds and characterization of the compounds

| EXAMPLE | STRUCTURE | LC/MS | NMR |
|---|---|---|---|
| 19 | 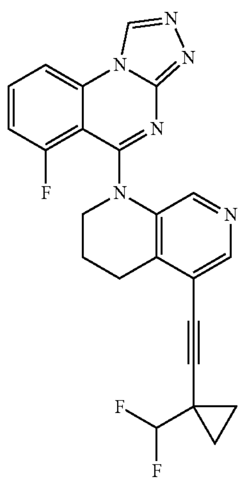 [SMILES: Fc1cccc2c1c(N1CCCc3c(C#CC4(C(F)F)CC4)cncc31)nc1nncn12] | 435.1 | 1H NMR (400 MHz, DMSO-d6) δ 9.88 (s, 1H), 8.43-8.19 (m, 3H), 8.10 (td, J = 8.3, 5.1 Hz, 1H), 7.46 (dd, J = 12.1, 8.2 Hz, 1H), 5.83 (t, J = 55.5 Hz, 1H), 3.95 (s, 2H), 2.96 (t, J = 6.7 Hz, 2H), 2.07 (d, J = 6.6 Hz, 2H), 1.30 (q, J = 2.9 Hz, 4H). |
| 20 | 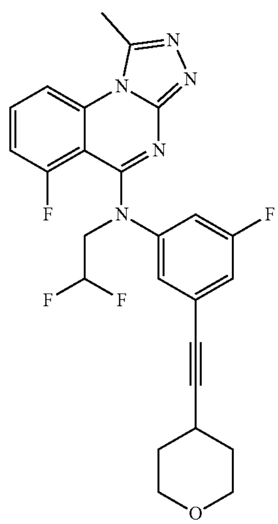 [SMILES: Cc1nnc2nc(N(CC(F)F)c3cc(F)cc(C#CC4CCOCC4)c3)c3c(F)cccc3n12] | 484.373 | 1H NMR (400 MHz, DMSO-d6) δ 8.14 (d, J = 8.5 Hz, 1H), 7.93 (td, J = 8.4, 5.4 Hz, 1H), 7.25 (dd, J = 12.0, 8.2 Hz, 1H), 7.08-7.00 (m, 2H), 6.96 (dt, J = 8.9, 1.8 Hz, 1H), 6.52 (tt, J = 55.8, 3.9 Hz, 1H), 4.76-4.41 (m, 2H), 3.77 (dt, J = 11.5, 4.3 Hz, 2H), 3.41 (ddd, J = 11.7, 9.2, 2.7 Hz, 2H), 2.99 (s, 3H), 2.84 (tt, J = 8.9, 4.1 Hz, 1H), 1.79 (dq, J = 12.4, 3.9 Hz, 2H), 1.56 (ddt, J = 13.9, 9.3, 4.7 Hz, 2H). |
| 21 | 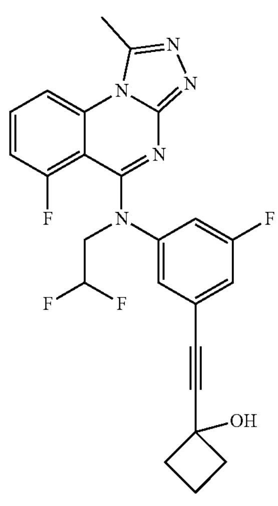 [SMILES: Cc1nnc2nc(N(CC(F)F)c3cc(F)cc(C#CC4(O)CCC4)c3)c3c(F)cccc3n12] | 470.276 | 1H NMR (400 MHz, DMSO-d6) δ 8.14 (d, J = 8.6 Hz, 1H), 7.94 (td, J = 8.4, 5.4 Hz, 1H), 7.26 (dd, J = 12.0, 8.2 Hz, 1H), 7.16-7.02 (m, 2H), 6.98 (dt, J = 8.8, 1.8 Hz, 1H), 6.53 (tt, J = 55.8, 3.8 Hz, 1H), 5.87 (s, 1H), 4.62 (td, J = 14.9, 3.7 Hz, 2H), 2.99 (s, 3H), 2.41-2.27 (m, 2H), 2.17 (qd, J = 9.1, 2.7 Hz, 2H), 1.86-1.62 (m, 2H). |

TABLE 1-continued

Compounds and characterization of the compounds

| EXAMPLE | STRUCTURE | LC/MS | NMR |
|---|---|---|---|
| 22 | 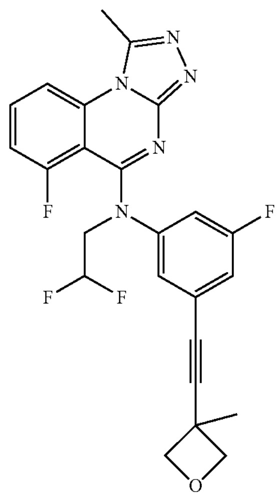 [SMILES: Cc1nnc2nc(N(CC(F)F)c3cc(F)cc(C#CC4(C)COC4)c3)c3c(F)cccc3n12] | 470.292 | 1H NMR (400 MHz, DMSO-d6) δ 8.14 (d, J = 8.5 Hz, 1H), 7.94 (td, J = 8.4, 5.4 Hz, 1H), 7.26 (dd, J = 12.0, 8.2 Hz, 1H), 7.12 (t, J = 1.6 Hz, 1H), 7.06 (dt, J = 10.9, 2.3 Hz, 1H), 7.00 (dt, J = 9.0, 1.6 Hz, 1H), 6.72-6.32 (m, 1H), 4.70 (d, J = 5.5 Hz, 2H), 4.61 (dd, J = 16.2, 12.5 Hz, 2H), 4.39 (d, J = 5.5 Hz, 2H), 2.99 (s, 3H), 1.59 (s, 3H) |
| 23 | 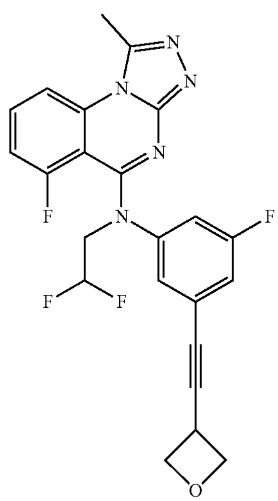 [SMILES: Cc1nnc2nc(N(CC(F)F)c3cc(F)cc(C#CC4COC4)c3)c3c(F)cccc3n12] | 456.289 | 1H NMR (400 MHz, DMSO-d6) δ 8.14 (d, J = 8.5 Hz, 1H), 7.93 (td, J = 8.4, 5.4 Hz, 1H), 7.26 (dd, J = 12.0, 8.2 Hz, 1H), 7.09 (td, J = 5.6, 5.0, 2.4 Hz, 2H), 7.00 (dt, J = 8.8, 1.8 Hz, 1H), 6.53 (tt, J = 55.7, 3.8 Hz, 1H), 4.75 (dd, J = 8.5, 5.4 Hz, 2H), 4.68-4.50 (m, 4H), 4.09 (tt, J = 8.5, 7.1 Hz, 1H), 2.99 (s, 3H). |
| 24 | 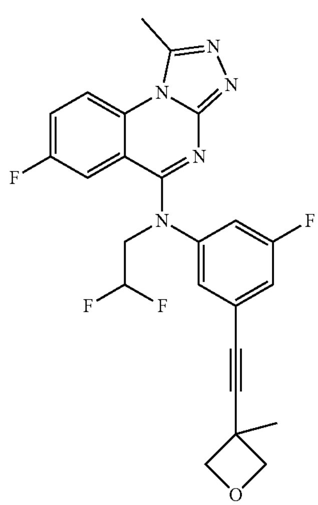 [SMILES: Cc1nnc2nc(N(CC(F)F)c3cc(F)cc(C#CC4(C)COC4)c3)c3cc(F)ccc3n12] | 470.269 | 1H NMR (400 MHz, DMSO-d6) δ 8.33 (dd, J = 9.4, 4.7 Hz, 1H), 7.80 (ddd, J = 9.3, 7.9, 2.9 Hz, 1H), 7.25 (dp, J = 6.1, 2.2 Hz, 2H), 7.20-7.13 (m, 1H), 7.09 (dd, J = 9.7, 2.9 Hz, 1H), 6.56 (tt, J = 55.9, 4.0 Hz, 1H), 4.71 (d, J = 5.5 Hz, 2H), 4.56 (td, J = 14.5, 3.9 Hz, 2H), 4.40 (d, J = 5.5 Hz, 2H), 2.98 (s, 3H), 1.60 (s, 3H). |

TABLE 1-continued

Compounds and characterization of the compounds

| EXAMPLE | STRUCTURE | LC/MS | NMR |
| --- | --- | --- | --- |
| 25 | 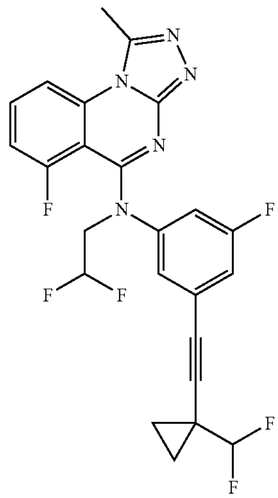 [SMILES: Cc1nnc2nc(N(CC(F)F)c3cc(F)cc(C#CC4(C(F)F)CC4)c3)c3c(F)cccc3n12] | 490.1 | 1H NMR (400 MHz, DMSO-d6) δ 8.18 (d, J = 8.6 Hz, 1H), 7.98 (td, J = 8.4, 5.4 Hz, 1H), 7.30 (dd, J = 12.0, 8.2 Hz, 1H), 7.21-7.08 (m, 2H), 7.04 (dt, J = 8.8, 1.7 Hz, 1H), 6.73-6.30 (m, 1H), 5.74 (t, J = 55.5 Hz, 1H), 4.75-4.54 (m, 2H), 3.02 (s, 3H), 1.30-1.07 (m, 4H). |
| 26 | 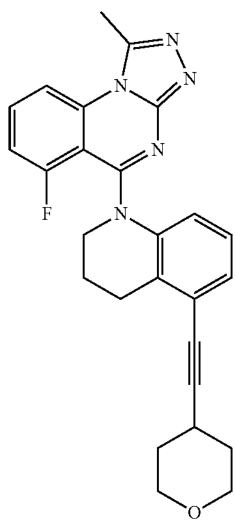 [SMILES: Cc1nnc2nc(N3CCCc4c(C#CC5CCOCC5)cccc43)c3c(F)cccc3n12] | 442.2 | 1H NMR (400 MHz, DMSO-d6) δ 8.11 (d, J = 8.6 Hz, 1H), 7.92 (td, J = 8.4, 5.4 Hz, 1H), 7.29 (dd, J = 11.9, 8.2 Hz, 1H), 7.04 (dd, J = 7.6, 1.1 Hz, 1H), 6.87 (t, J = 7.9 Hz, 1H), 6.69 (dd, J = 8.0, 1.1 Hz, 1H), 3.62-4.13 (m, 4H), 3.50 (ddd, J = 11.6, 8.7, 2.9 Hz, 2H), 2.73-3.12 (m, 6H), 2.28-1.80 (m, 4H), 1.65 (dtd, J = 12.7, 8.7, 3.7 Hz, 2H). |
| 27 | 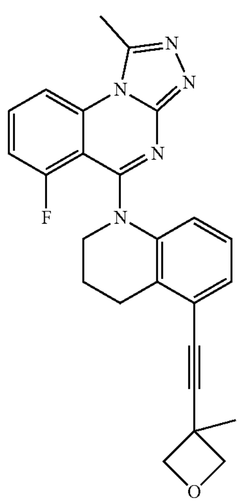 [SMILES: Cc1nnc2nc(N3CCCc4c(C#CC5(C)COC5)cccc43)c3c(F)cccc3n12] | 428.287 | 1H NMR (400 MHz, DMSO-d6) δ 8.12 (d, J = 8.5 Hz, 1H), 7.93 (td, J = 8.3, 5.4 Hz, 1H), 7.29 (dd, J = 12.0, 8.2 Hz, 1H), 7.07 (dd, J = 7.6, 1.0 Hz, 1H), 6.89 (t, J = 7.9 Hz, 1H), 6.72 (d, J = 8.1 Hz, 1H), 4.79 (d, J = 5.4 Hz, 2H), 4.48 (d, J = 5.5 Hz, 2H), 3.86 (d, J = 88.8 Hz, 2H), 2.72-3.13 (m, 5H), 2.01 (dd, J = 94.6, 38.2 Hz, 2H), 1.68 (s, 3H). |

TABLE 1-continued

Compounds and characterization of the compounds

| EXAMPLE | STRUCTURE | LC/MS | NMR |
|---|---|---|---|
| 28 | 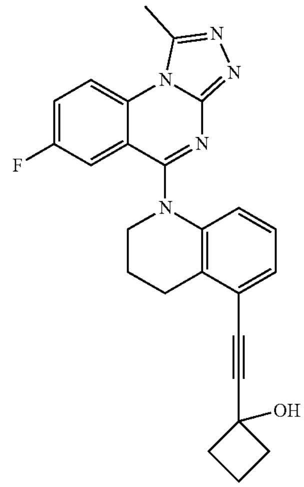 [SMILES: Cc1nnc2nc(N3CCCc4c(C#CC5(O)CCC5)cccc43)c3cc(F)ccc3n12] | 428.267 | 1H NMR (400 MHz, DMSO-d6) δ 8.32 (dd, J = 9.4, 4.6 Hz, 1H), 7.80 (ddd, J = 9.3, 8.0, 2.9 Hz, 1H), 7.42 (dd, J = 9.6, 2.9 Hz, 1H), 7.09 (dd, J = 7.6, 1.1 Hz, 1H), 6.94 (t, J = 7.9 Hz, 1H), 6.68 (dd, J = 8.2, 1.1 Hz, 1H), 5.92 (s, 1H), 3.90 (t, J = 6.1 Hz, 2H), 3.01 (t, J = 6.7 Hz, 2H), 2.97 (s, 3H), 2.47-2.36 (m, 2H), 2.26 (qd, J = 9.2, 2.6 Hz, 2H), 2.10 (p, J = 6.4 Hz, 2H), 1.82 (tdd, J = 9.3, 6.9, 3.8 Hz, 2H). |
| 29 | 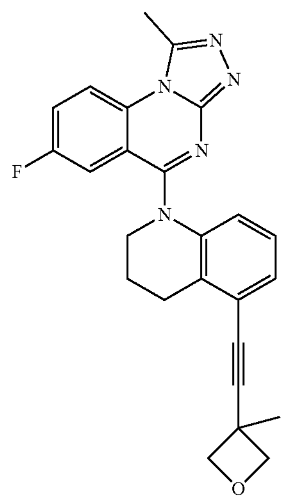 [SMILES: Cc1nnc2nc(N3CCCc4c(C#CC5(C)COC5)cccc43)c3cc(F)ccc3n12] | 428.262 | 1H NMR (400 MHz, DMSO-d6) δ 8.32 (dd, J = 9.4, 4.6 Hz, 1H), 7.80 (ddd, J = 9.3, 8.0, 3.0 Hz, 1H), 7.41 (dd, J = 9.5, 2.9 Hz, 1H), 7.10 (dd, J = 7.6, 1.1 Hz, 1H), 6.94 (t, J = 7.9 Hz, 1H), 6.69 (dd, J = 8.2, 1.1 Hz, 1H), 4.80 (d, J = 5.4 Hz, 2H), 4.49 (d, J = 5.4 Hz, 2H), 3.89 (t, J = 6.1 Hz, 2H), 2.8-3.2 (m, 5H), 2.10 (t, J = 6.4 Hz, 2H), 1.69 (s, 3H). |
| 30 | 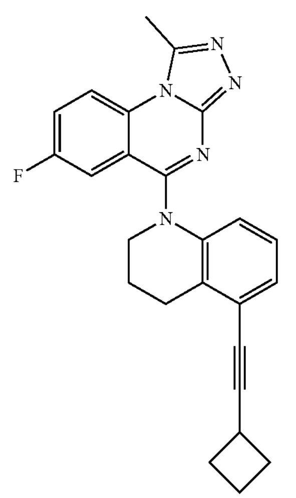 [SMILES: Cc1nnc2nc(N3CCCc4c(C#CC5CCC5)cccc43)c3cc(F)ccc3n12] | 412.296 | 1H NMR (400 MHz, DMSO-d6) δ 8.36 (dd, J = 9.5, 4.6 Hz, 1H), 7.84 (t, J = 7.2 Hz, 1H), 7.40 (dd, J = 9.6, 2.9 Hz, 1H), 7.12 (d, J = 7.5 Hz, 1H), 6.95 (t, J = 7.9 Hz, 1H), 6.73 (d, J = 8.1 Hz, 1H), 3.94 (t, J = 6.3 Hz, 2H), 3.36 (t, J = 8.4 Hz, 1H), 2.99 (s, 5H), 2.39-2.30 (m, 2H), 2.23-2.15 (m, 2H), 2.15-2.05 (m, 2H), 1.96 (dq, J = 17.3, 8.8 Hz, 2H). |

TABLE 1-continued

Compounds and characterization of the compounds

| EXAMPLE | STRUCTURE | LC/MS | NMR |
|---|---|---|---|
| 31 | 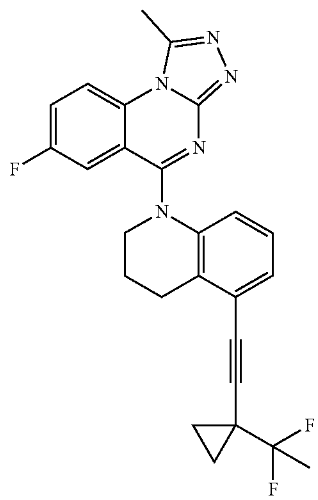 [SMILES: Cc1nnc2nc(N3CCCc4c(C#CC5(C(C)(F)F)CC5)cccc43)c3cc(F)ccc3n12] | 462.39 | 1H NMR (400 MHz, DMSO-d6) δ 8.40 (dd, J = 9.4, 4.6 Hz, 1H), 7.89 (ddd, J = 9.4, 7.8, 2.9 Hz, 1H), 7.45 (dd, J = 9.6, 2.9 Hz, 1H), 7.20 (dd, J = 7.7, 1.1 Hz, 1H), 7.00 (t, J = 7.9 Hz, 1H), 6.83 (d, J = 8.2 Hz, 1H), 3.99 (t, J = 6.2 Hz, 2H), 3.00 (d, J = 9.4 Hz, 5H), 2.11 (p, J = 6.4 Hz, 2H), 1.88 (t, J = 18.4 Hz, 3H), 1.38-1.09 (m, 4H). |
| 32 | 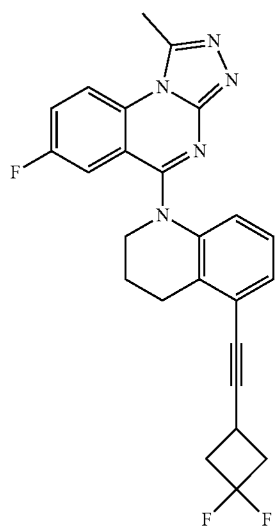 [SMILES: Cc1nnc2nc(N3CCCc4c(C#CC5CC(F)(F)C5)cccc43)c3cc(F)ccc3n12] | 448.335 | 1H NMR (400 MHz, DMSO-d6) δ 8.39 (dd, J = 9.4, 4.6 Hz, 1H), 7.95-7.82 (m, 1H), 7.42 (dd, J = 9.6, 2.9 Hz, 1H), 7.21 (d, J = 7.5 Hz, 1H), 7.00 (t, J = 7.9 Hz, 1H), 6.83 (d, J = 8.1 Hz, 1H), 3.99 (t, J = 6.2 Hz, 2H), 3.33 (dtt, J = 9.2, 6.9, 2.3 Hz, 1H), 3.20-3.04 (m, 2H), 3.01 (s, 5H), 2.87-2.62 (m, 2H), 2.11 (p, J = 6.6 Hz, 2H). |
| 33 | 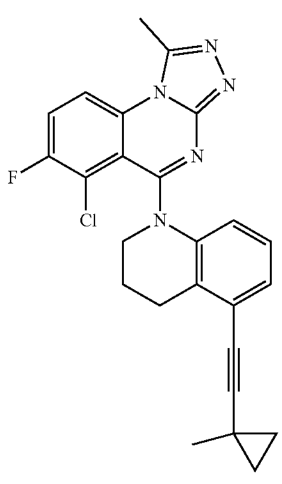 [SMILES: Cc1nnc2nc(N3CCCc4c(C#CC5(C)CC5)cccc43)c3c(Cl)c(F)ccc3n12] | 446.1 | 1H NMR (400 MHz, DMSO-d6) δ 8.38 (dd, J = 9.5, 4.5 Hz, 1H), 8.07 (dd, J = 9.4, 8.4 Hz, 1H), 7.07 (dd, J = 7.7, 1.1 Hz, 1H), 6.86 (t, J = 7.9 Hz, 1H), 6.56 (dd, J = 8.3, 1.1 Hz, 1H), 4.16 (ddd, J = 12.3, 7.3, 4.9 Hz, 1H), 3.72 (ddd, J = 12.1, 7.3, 4.6 Hz, 1H), 3.03 (dd, J = 8.2, 5.5 Hz, 1H), 3.01 (s, 3H), 2.84 (dt, J = 17.1, 7.1 Hz, 1H), 2.25 (ddt, J = 13.5, 11.5, 6.5 Hz, 1H), 1.94 (dq, J = 13.3, 6.8 Hz, 1H), 1.35 (s, 3H), 0.98 (q, J = 3.9 Hz, 2H), 0.82-0.74 (m, 2H). |

TABLE 1-continued

Compounds and characterization of the compounds

| EXAMPLE | STRUCTURE | LC/MS | NMR |
|---|---|---|---|
| 34 | 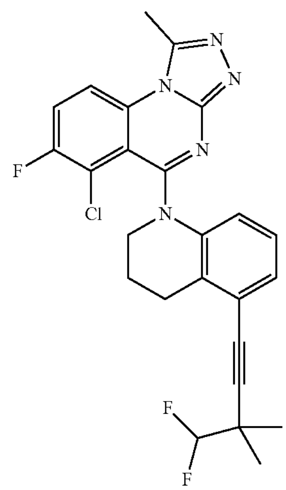 [SMILES: Cc1nnc2nc(N3CCCc4c(C#CC5(C(F)F)CC5)cccc43)c3c(Cl)c(F)ccc3n12] | 484.1 | 1H NMR (400 MHz, DMSO-d6) δ 8.39 (dd, J = 9.5, 4.5 Hz, 1H), 8.08 (dd, J = 9.4, 8.4 Hz, 1H), 7.11 (dd, J = 7.6, 1.1 Hz, 1H), 6.90 (t, J = 7.9 Hz, 1H), 6.63 (dd, J = 8.2, 1.1 Hz, 1H), 6.08 (t, J = 56.4 Hz, 1H), 4.16 (ddd, J = 12.2, 7.3, 4.7 Hz, 1H), 3.73 (ddd, J = 12.1, 7.5, 4.4 Hz, 1H), 3.05 (dd, J = 11.8, 5.2 Hz, 1H), 3.01 (s, 3H), 2.88 (dt, J = 17.1, 6.9 Hz, 1H), 2.26 (ddd, J = 12.8, 7.1, 4.9 Hz, 1H), 1.96 (ddt, J = 13.5, 11.2, 6.9 Hz, 1H), 1.37 (d, J = 1.3 Hz, 6H). |
| 35 | 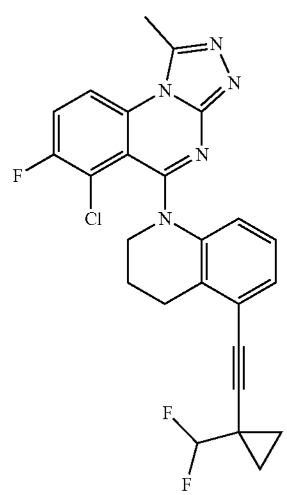 | 482.1 | 1H NMR (400 MHz, DMSO-d6) δ 8.39 (dd, J = 9.5, 4.5 Hz, 1H), 8.08 (dd, J = 9.4, 8.5 Hz, 1H), 7.12 (dd, J = 7.6, 1.1 Hz, 1H), 6.89 (t, J = 7.9 Hz, 1H), 6.62 (dd, J = 8.2, 1.1 Hz, 1H), 5.81 (t, J = 55.6 Hz, 1H), 4.15 (ddd, J = 12.3, 7.4, 4.9 Hz, 1H), 3.74 (ddd, J = 12.1, 7.3, 4.5 Hz, 1H), 3.10-3.02 (m, 1H), 3.01 (s, 3H), 2.87 (dt, J = 17.1, 7.0 Hz, 1H), 2.26 (ddd, J = 12.7, 7.1, 5.0 Hz, 1H), 1.95 (dq, J = 12.2, 6.6, 6.1 Hz, 1H), 1.29-1.19 (m, 4H). |
| 36 | 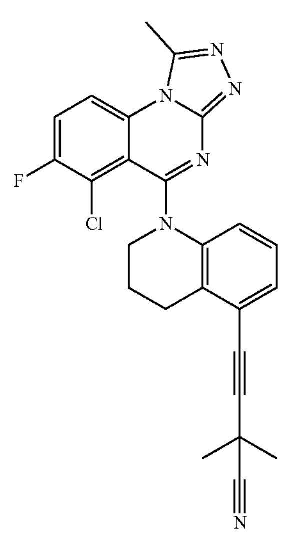 [SMILES: Cc1nnc2nc(N3CCCc4c(C#CC(C)(C)C#N)cccc43)c3c(Cl)c(F)ccc3n12] | 459.1 | 1H NMR (400 MHz, DMSO-d6) δ 8.39 (dd, J = 9.5, 4.5 Hz, 1H), 8.09 (dd, J = 9.5, 8.4 Hz, 1H), 7.18 (dd, J = 7.6, 1.1 Hz, 1H), 6.93 (t, J = 7.9 Hz, 1H), 6.68 (dd, J = 8.3, 1.1 Hz, 1H), 4.16 (ddd, J = 12.3, 7.4, 4.8 Hz, 1H), 3.75 (ddd, J = 12.1, 7.4, 4.4 Hz, 1H), 3.10-3.02 (m, 1H), 3.01 (s, 3H), 2.91 (dt, J = 17.2, 7.0 Hz, 1H), 2.26 (tq, J = 11.3, 6.3, 5.6 Hz, 1H), 2.02-1.90 (m, 1H), 1.77 (s, 6H). |

TABLE 1-continued

Compounds and characterization of the compounds

| EXAMPLE | STRUCTURE | LC/MS | NMR |
|---|---|---|---|
| 37 | 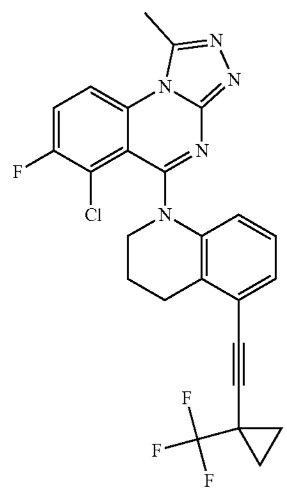 [SMILES: Cc1nnc2nc(N3CCCc4c(C#CC5(C(F)(F)F)CC5)cccc43)c3c(Cl)c(F)ccc3n12] | 500.1 | 1H NMR (400 MHz, DMSO-d6) δ 8.39 (dd, J = 9.5, 4.5 Hz, 1H), 8.08 (dd, J = 9.4, 8.4 Hz, 1H), 7.15 (dd, J = 7.6, 1.1 Hz, 1H), 6.91 (t, J = 7.9 Hz, 1H), 6.66 (dd, J = 8.3, 1.1 Hz, 1H), 4.15 (ddd, J = 12.2, 7.4, 4.8 Hz, 1H), 3.74 (ddd, J = 12.1, 7.4, 4.4 Hz, 1H), 3.07 (dt, J = 17.1, 6.3 Hz, 1H), 3.01 (s, 3H), 2.87 (dt, J = 17.1, 7.1 Hz, 1H), 2.25 (ddt, J = 13.7, 11.5, 6.5 Hz, 1H), 1.96 (ddd, J = 13.6, 11.5, 6.6 Hz, 1H), 1.52-1.37 (m, 4H). |
| 38 | 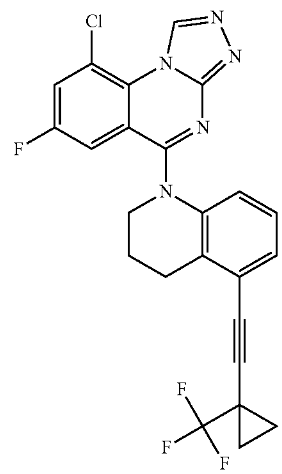 [SMILES: Fc1cc(Cl)c2c(c1)c(N1CCCc3c(C#CC4(C(F)(F)F)CC4)cccc31)nc1nncn12] | 486.1 | 1H NMR (400 MHz, DMSO-d6) δ 10.11 (s, 1H), 8.21 (dd, J = 8.1, 2.8 Hz, 1H), 7.53 (dd, J = 9.0, 2.8 Hz, 1H), 7.14 (dd, J = 7.6, 1.1 Hz, 1H), 6.96 (t, J = 7.9 Hz, 1H), 6.83 (dd, J = 8.3, 1.1 Hz, 1H), 3.91 (t, J = 6.1 Hz, 2H), 2.98 (t, J = 6.7 Hz, 2H), 2.17-2.03 (m, 2H), 1.55-1.34 (m, 4H). |
| 39 | 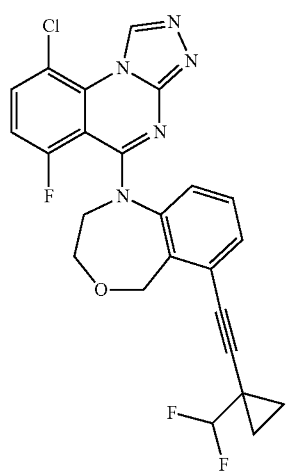 [SMILES: Fc1ccc(Cl)c2c1c(N1CCOCc3c(C#CC4(C(F)F)CC4)cccc31)nc1nncn12] | 484.1 | 1H NMR (400 MHz, DMSO-d6) δ 10.13 (s, 1H), 8.06 (dd, J = 9.0, 4.9 Hz, 1H), 7.29-7.17 (m, 2H), 7.00 (t, J = 7.9 Hz, 1H), 6.88 (dd, J = 8.0, 1.2 Hz, 1H), 5.81 (t, J = 55.5 Hz, 1H), 4.93 (s, 4H), 4.00 (s, 2H), 1.26 (tt, J = 4.1, 1.9 Hz, 4H). |

US 11,976,072 B2

TABLE 1-continued

Compounds and characterization of the compounds

| EXAMPLE | STRUCTURE | LC/MS | NMR |
|---|---|---|---|
| 40 | 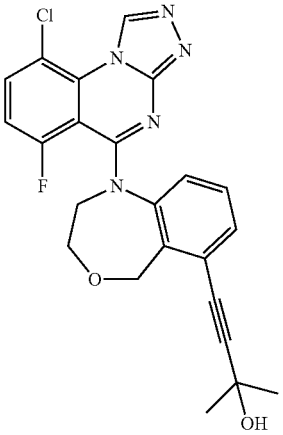 [SMILES: CC(C)(O)C#Cc1cccc2c1COCCN2c1nc2nncn2c2c(Cl)ccc(F)c12] | 452.093 | 1H NMR (400 MHz, DMSO-d6) δ 10.11 (s, 1H), 8.06 (dd, J = 9.0, 4.9 Hz, 1H), 7.27-7.17 (m, 2H), 6.99 (t, J = 7.9 Hz, 1H), 6.86 (dd, J = 8.0, 1.1 Hz, 1H), 5.17 (s, 4H), 3.99 (s, 2H), 1.51 (s, 6H). |
| 41 | 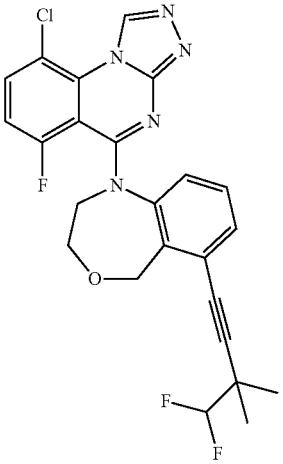 [SMILES: CC(C)(C#Cc1cccc2c1COCCN2c1nc2nncn2c2c(Cl)ccc(F)c12)C(F)F] | 486.1 | 1H NMR (400 MHz, DMSO-d6) δ 10.09 (s, 1H), 8.04 (dd, J = 9.0, 4.9 Hz, 1H), 7.29-7.13 (m, 2H), 6.99 (t, J = 7.9 Hz, 1H), 6.87 (dd, J = 8.0, 1.1 Hz, 1H), 6.10 (t, J = 56.4 Hz, 1H), 4.97 (s, 4H), 3.99 (s, 2H), 1.37 (d, J = 1.2 Hz, 6H). |
| 42 | 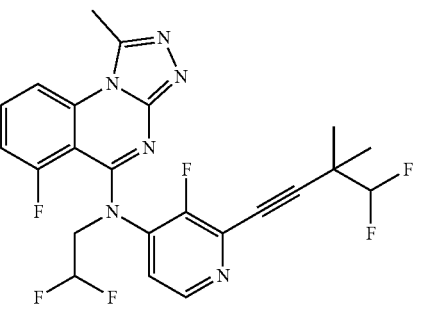 [SMILES: Cc1nnc2nc(N(CC(F)F)c3ccnc(C#CC(C)(C)C(F)F)c3F)c3c(F)cccc3n12] | 493.151 | 1H NMR (400 MHz, DMSO-d6) δ 8.21 (d, J = 8.6 Hz, 1H), 8.12 (d, J = 5.3 Hz, 1H), 8.00 (td, J = 8.4, 5.6 Hz, 1H), 7.36 (ddd, J = 12.3, 8.3, 0.8 Hz, 1H), 7.22 (dd, J = 6.7, 5.3 Hz, 1H), 6.55 (tt, J = 55.8, 4.2 Hz, 1H), 6.10 (t, J = 56.2 Hz, 1H), 4.54 (td, J = 13.9, 4.1 Hz, 2H), 3.03 (s, 3H), 1.37 (d, J = 1.0 Hz, 6H). |
| 43 | 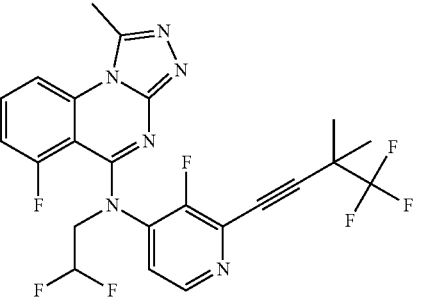 [SMILES: Cc1nnc2nc(N(CC(F)F)c3ccnc(C#CC(C)(C)C(F)(F)F)c3F)c3c(F)cccc3n12] | 511.1 | 1H NMR (400 MHz, DMSO-d6) δ 8.21 (d, J = 8.6 Hz, 1H), 8.14 (d, J = 5.3 Hz, 1H), 8.01 (td, J = 8.5, 5.6 Hz, 1H), 7.36 (ddd, J = 12.4, 8.3, 0.8 Hz, 1H), 7.26 (dd, J = 6.7, 5.3 Hz, 1H), 6.55 (tt, J = 55.8, 4.1 Hz, 1H), 4.55 (td, J = 13.9, 4.1 Hz, 2H), 3.03 (s, 3H), 1.54 (s, 6H). |

TABLE 1-continued

Compounds and characterization of the compounds

| EXAMPLE | STRUCTURE | LC/MS | NMR |
|---|---|---|---|
| 44 | 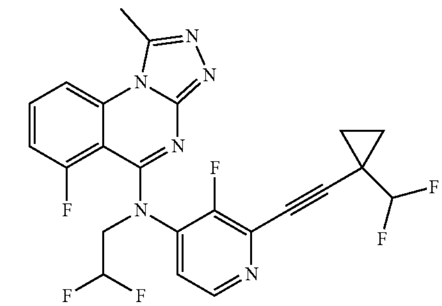 [SMILES: Cc1nnc2nc(N(CC(F)F)c3ccnc(C#CC4(C(F)F)CC4)c3F)c3c(F)cccc3n12] | 491.1 | 1H NMR (400 MHz, DMSO-d6) δ 8.20 (d, J = 8.6 Hz, 1H), 8.12 (d, J = 5.4 Hz, 1H), 8.00 (td, J = 8.4, 5.6 Hz, 1H), 7.35 (ddd, J = 12.4, 8.3, 0.9 Hz, 1H), 7.23 (dd, J = 6.7, 5.3 Hz, 1H), 6.55 (tt, J = 55.9, 4.1 Hz, 1H), 5.81 (t, J = 55.3 Hz, 1H), 4.55 (td, J = 14.0, 4.1 Hz, 2H), 3.03 (s, 3H), 1.34-1.25 (m, 4H). |
| 45 | 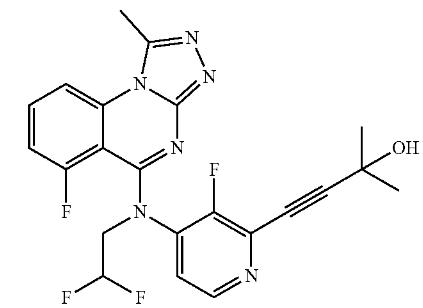 [SMILES: Cc1nnc2nc(N(CC(F)F)c3ccnc(C#CC(C)(C)O)c3F)c3c(F)cccc3n12] | 459.1 | 1H NMR (400 MHz, DMSO-d6) δ 8.21 (d, J = 8.6 Hz, 1H), 8.13 (d, J = 5.4 Hz, 1H), 8.00 (td, J = 8.4, 5.6 Hz, 1H), 7.36 (ddd, J = 12.3, 8.3, 0.9 Hz, 1H), 7.22 (dd, J = 6.6, 5.4 Hz, 1H), 6.55 (tt, J = 55.9, 4.1 Hz, 1H), 4.60-4.50 (m, 2H), 3.03 (s, 3H), 1.48 (s, 6H). |
| 46 | 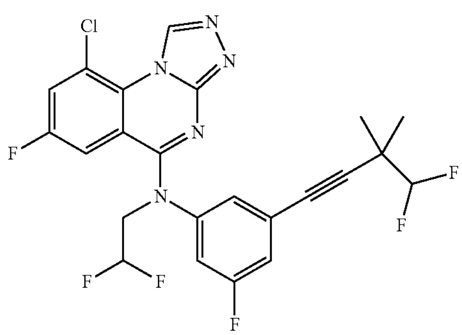 [SMILES: CC(C)(C#Cc1cc(F)cc(N(CC(F)F)c2nc3nncn3c3c(Cl)cc(F)cc23)c1)C(F)F] | 512.1 | 1H NMR (400 MHz, DMSO-d6) δ 10.12 (s, 1H), 8.19 (dd, J = 8.1, 2.8 Hz, 1H), 7.33-7.22 (m, 2H), 7.17 (dd, J = 9.1, 2.8 Hz, 1H), 7.14-7.07 (m, 1H), 6.73-6.38 (m, 1H), 6.02 (t, J = 56.3 Hz, 1H), 4.58 (td, J = 14.5, 4.0 Hz, 2H), 1.31 (s, 6H). |
| 47 | 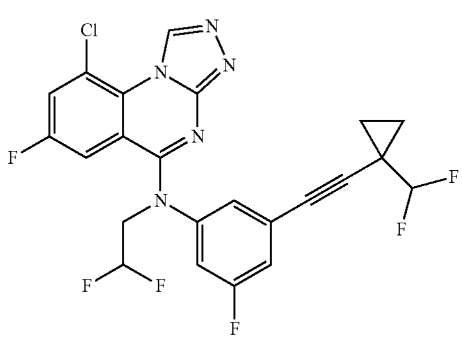 [SMILES: Fc1cc(C#CC2(C(F)F)CC2)cc(N(CC(F)F)c2nc3nncn3c3c(Cl)cc(F)cc23)c1] | 510.1 | 1H NMR (400 MHz, DMSO-d6) δ 10.13 (s, 1H), 8.20 (dd, J = 8.0, 2.8 Hz, 1H), 7.28 (d, J = 12.2 Hz, 2H), 7.16 (td, J = 9.6, 2.6 Hz, 2H), 6.55 (tt, J = 55.8, 3.9 Hz, 1H), 5.75 (t, J = 55.5 Hz, 1H), 4.58 (td, J = 14.4, 4.0 Hz, 2H), 1.20 (dt, J = 9.8, 3.0 Hz, 4H). |

TABLE 1-continued

Compounds and characterization of the compounds

| EXAMPLE | STRUCTURE | LC/MS | NMR |
|---|---|---|---|
| 48 | 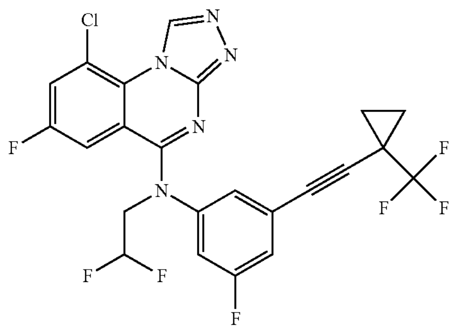 [SMILES: Fc1cc(C#CC2(C(F)(F)F)CC2)cc(N(CC(F)F)c2nc3nncn3c3c(Cl)cc(F)cc23)c1] | 528 | 1H NMR (400 MHz, DMSO-d6) δ 10.14 (s, 1H), 8.21 (dd, J = 8.1, 2.8 Hz, 1H), 7.37-7.25 (m, 2H), 7.19 (ddd, J = 9.1, 6.8, 2.2 Hz, 2H), 6.55 (tt, J = 55.9, 4.0 Hz, 1H), 4.58 (td, J = 14.4, 4.0 Hz, 2H), 1.47-1.35 (m, 4H). |
| 49 | 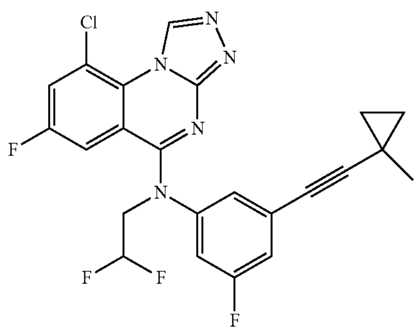 [SMILES: CC1(C#Cc2cc(F)cc(N(CC(F)F)c3nc4nncn4c4c(Cl)cc(F)cc34)c2)CC1] | 474.1 | 1H NMR (400 MHz, DMSO-d6) δ 10.13 (s, 1H), 8.21 (dd, J = 8.1, 2.8 Hz, 1H), 7.23 (dd, J = 9.0, 2.0 Hz, 2H), 7.16 (dd, J = 9.1, 2.8 Hz, 1H), 7.08 (dt, J = 9.6, 1.7 Hz, 1H), 6.54 (tt, J = 55.8, 4.1 Hz, 1H), 4.56 (td, J = 14.5, 4.1 Hz, 2H), 1.28 (s, 3H), 0.93 (q, J = 4.1 Hz, 2H), 0.74 (q, J = 4.1 Hz, 2H). |
| 50 | 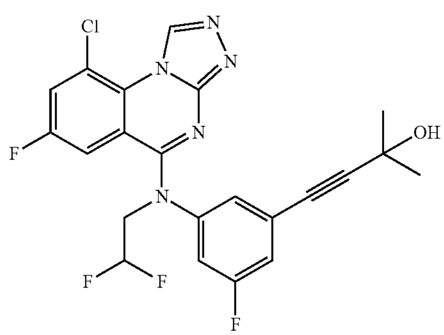 [SMILES: CC(C)(O)C#Cc1cc(F)cc(N(CC(F)F)c2nc3nncn3c3c(Cl)cc(F)cc23)c1] | 478.1 | 1H NMR (400 MHz, DMSO-d6) δ 10.14 (s, 1H), 8.21 (dd, J = 8.1, 2.8 Hz, 1H), 7.32-7.23 (m, 2H), 7.17 (dd, J = 9.1, 2.9 Hz, 1H), 7.11 (dt, J = 9.3, 1.7 Hz, 1H), 6.55 (tt, J = 55.9, 4.0 Hz, 1H), 4.58 (td, J = 14.4, 4.0 Hz, 2H), 1.43 (s, 6H). |
| 51 | 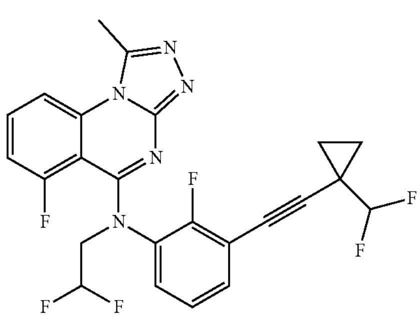 [SMILES: Cc1nnc2nc(N(CC(F)F)c3cccc(C#CC4(C(F)F)CC4)c3F)c3c(F)cccc3n12] | 490.1 | 1H NMR (400 MHz, DMSO-d6) δ 8.17 (d, J = 8.6 Hz, 1H), 7.97 (td, J = 8.4, 5.5 Hz, 1H), 7.43-7.34 (m, 1H), 7.30 (dd, J = 12.1, 8.3 Hz, 1H), 7.19 (td, J = 8.0, 1.6 Hz, 1H), 7.01 (t, J = 7.9 Hz, 1H), 6.56 (tt, J = 56.0, 4.2 Hz, 1H), 5.79 (t, J = 55.5 Hz, 1H), 4.44 (td, J = 13.7, 4.2 Hz, 2H), 3.01 (s, 3H), 1.25 (dt, J = 10.2, 2.7 Hz, 4H). |

TABLE 1-continued

Compounds and characterization of the compounds

| EXAMPLE | STRUCTURE | LC/MS | NMR |
|---|---|---|---|
| 52 | 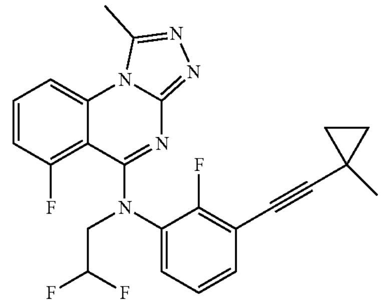 [SMILES: Cc1nnc2nc(N(CC(F)F)c3cccc(C#CC4(C)CC4)c3F)c3c(F)cccc3n12] | 454.2 | 1H NMR (400 MHz, DMSO-d6) δ 8.17 (d, J = 8.6 Hz, 1H), 7.97 (td, J = 8.4, 5.5 Hz, 1H), 7.31 (td, J = 8.8, 2.3 Hz, 2H), 7.13 (td, J = 8.0, 1.6 Hz, 1H), 6.98 (t, J = 7.9 Hz, 1H), 6.56 (tt, J = 55.9, 4.2 Hz, 1H), 4.44 (td, J = 13.7, 4.2 Hz, 2H), 3.02 (s, 3H), 1.33 (s, 3H), 0.97 (q, J = 4.0 Hz, 2H), 0.79 (q, J = 4.1 Hz, 2H). |
| 53 | 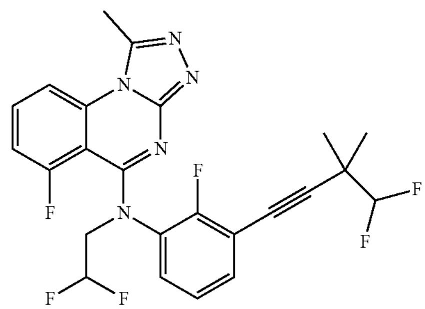 [SMILES: Cc1nnc2nc(N(CC(F)F)c3cccc(C#CC(C)(C)C(F)F)c3F)c3c(F)cccc3n12] | 492.1 | 1H NMR (400 MHz, DMSO-d6) δ 8.17 (d, J = 8.6 Hz, 1H), 7.97 (td, J = 8.4, 5.5 Hz, 1H), 7.39-7.28 (m, 2H), 7.17 (td, J = 8.0, 1.6 Hz, 1H), 7.00 (t, J = 7.9 Hz, 1H), 6.56 (tt, J = 56.0, 4.2 Hz, 1H), 6.08 (t, J = 56.3 Hz, 1H), 4.44 (td, J = 13.7, 4.2 Hz, 2H), 3.01 (s, 3H), 1.35 (s, 6H). |
| 54 | 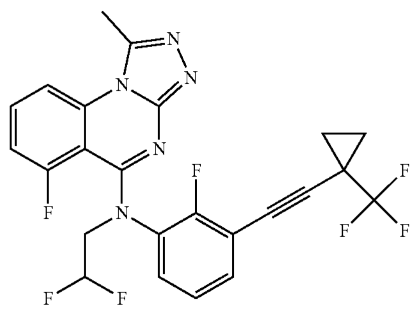 [SMILES: Cc1nnc2nc(N(CC(F)F)c3cccc(C#CC4(C(F)(F)F)CC4)c3F)c3c(F)cccc3n12] | 508.101 | 1H NMR (400 MHz, DMSO-d6) δ 8.15 (d, J = 8.6 Hz, 1H), 7.95 (td, J = 8.4, 5.5 Hz, 1H), 7.39 (ddd, J = 7.8, 6.3, 1.6 Hz, 1H), 7.28 (dd, J = 12.2, 8.3 Hz, 1H), 7.20 (td, J = 8.0, 1.6 Hz, 1H), 7.01 (t, J = 7.9 Hz, 1H), 6.56 (tt, J = 56.1, 4.2 Hz, 1H), 4.42 (td, J = 13.7, 4.2 Hz, 2H), 3.00 (s, 3H), 1.57-1.36 (m, 4H). |
| 55 | 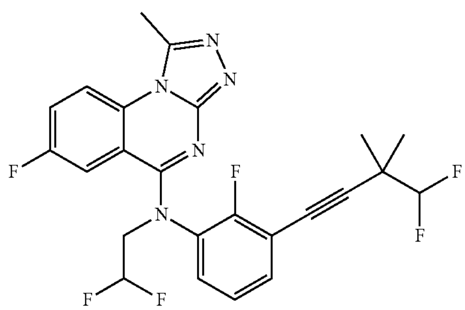 [SMILES: Cc1nnc2nc(N(CC(F)F)c3cccc(C#CC(C)(C)C(F)F)c3F)c3cc(F)ccc3n12] | 492.174 | 1H NMR (400 MHz, DMSO-d6) δ 8.41 (dd, J = 9.4, 4.7 Hz, 1H), 7.88 (ddd, J = 9.4, 7.7, 2.9 Hz, 1H), 7.69 (td, J = 7.9, 1.7 Hz, 1H), 7.53 (ddd, J = 8.0, 6.5, 1.6 Hz, 1H), 7.35 (t, J = 8.0 Hz, 1H), 6.99 (dd, J = 10.0, 2.9 Hz, 1H), 6.76-6.42 (m, 1H), 6.02 (t, J = 56.3 Hz, 1H), 4.50 (td, J = 13.9, 4.2 Hz, 2H), 3.01 (s, 3H), 1.29 (d, J = 1.1 Hz, 6H). |
| 56 | 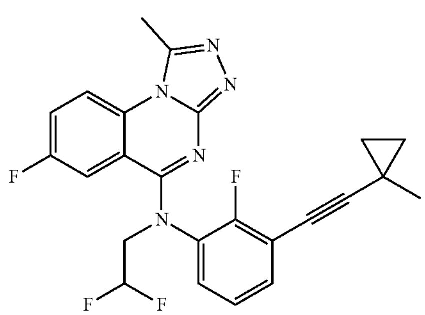 [SMILES: Cc1nnc2nc(N(CC(F)F)c3cccc(C#CC4(C)CC4)c3F)c3cc(F)ccc3n12] | 454.2 | 1H NMR (400 MHz, DMSO-d6) δ 8.40 (dd, J = 9.4, 4.7 Hz, 1H), 7.87 (ddd, J = 9.9, 7.8, 2.8 Hz, 1H), 7.62 (td, J = 7.8, 1.6 Hz, 1H), 7.53-7.44 (m, 1H), 7.31 (t, J = 7.9 Hz, 1H), 6.97 (dd, J = 10.0, 2.9 Hz, 1H), 6.59 (tt, J = 55.9, 4.2 Hz, 1H), 4.49 (td, J = 13.9, 4.2 Hz, 2H), 3.00 (s, 3H), 1.27 (s, 3H), 0.92 (q, J = 4.0 Hz, 2H), 0.75 (q, J = 4.1 Hz, 2H). |

TABLE 1-continued

Compounds and characterization of the compounds

| EXAMPLE | STRUCTURE | LC/MS | NMR |
|---|---|---|---|
| 57 | 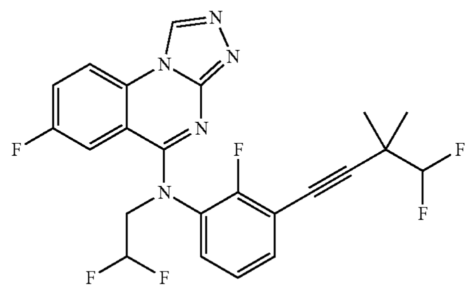 [SMILES: CC(C)(C#Cc1cccc(N(CC(F)F)c2nc3nncn3c3ccc(F)cc23)c1F)C(F)F] | 478.1 | 1H NMR (400 MHz, DMSO-d6) δ 9.81 (s, 1H), 8.53 (dd, J = 9.2, 4.9 Hz, 1H), 7.95 (ddd, J = 9.1, 7.9, 2.8 Hz, 1H), 7.68 (td, J = 7.9, 1.6 Hz, 1H), 7.54 (ddd, J = 8.0, 6.5, 1.6 Hz, 1H), 7.34 (t, J = 8.0 Hz, 1H), 6.85 (dd, J = 10.2, 2.7 Hz, 1H), 6.77-6.42 (m, 1H), 6.03 (t, J = 56.3 Hz, 1H), 4.49 (td, J = 13.9, 4.2 Hz, 2H), 1.30 (d, J = 1.3 Hz, 6H). |
| 58 | 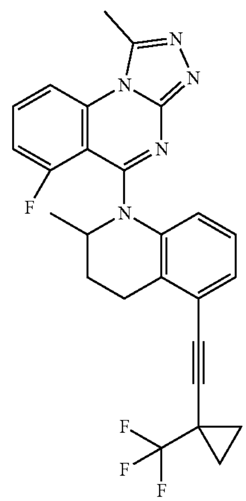 [SMILES: Cc1nnc2nc(N3c4cccc(C#CC5(C(F)(F)F)CC5)c4CCC3C)c3c(F)cccc3n12] | 480.1 | 1H NMR (400 MHz, DMSO-d6) δ 8.18 (d, J = 8.6 Hz, 1H), 8.00 (td, J = 8.4, 5.3 Hz, 1H), 7.36-7.26 (m, 1H), 7.18 (d, J = 7.5 Hz, 1H), 6.91 (t, J = 7.9 Hz, 1H), 6.75 (d, J = 8.1 Hz, 1H), 5.03-4.87 (m, 1H), 3.05-2.85 (m, 5H), 2.53-2.36 (m, 1H; obscured by residual solvent peak), 1.97-1.85 (m, 1H), 1.52-1.41 (m, 4H), 1.27 (d, J = 6.5 Hz, 3H). |
| 59 | 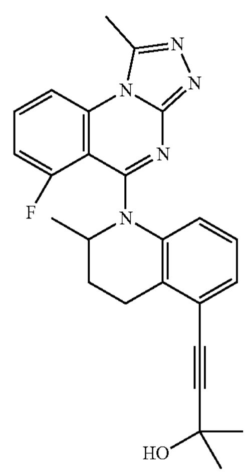 [SMILES: Cc1nnc2nc(N3c4cccc(C#CC(C)(C)O)c4CCC3C)c3c(F)cccc3n12] | 430.1 | 1H NMR (400 MHz, DMSO-d6) δ 8.17 (d, J = 8.6 Hz, 1H), 8.00 (td, J = 8.4, 5.3 Hz, 1H), 7.35-7.26 (m, 1H), 7.14 (d, J = 7.5 Hz, 1H), 6.90 (t, J = 7.9 Hz, 1H), 6.71 (d, J = 8.1 Hz, 1H), 5.04-4.88 (m, 1H), 3.06-2.83 (m, 5H), 2.55-2.38 (m, 1H; obscured by residual solvent peak), 1.95-1.80 (m, 1H), 1.52 (s, 6H), 1.26 (d, J = 6.5 Hz, 3H). |
| 60 | 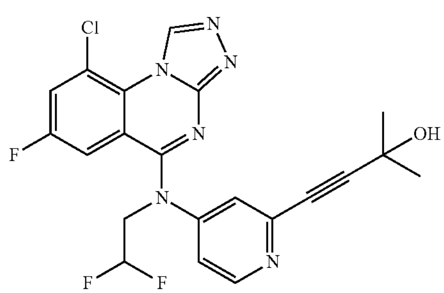 [SMILES: CC(C)(O)C#Cc1cc(N(CC(F)F)c2nc3nncn3c3c(Cl)cc(F)cc23)ccn1] | 461.19 | 1H NMR (400 MHz, Methanol-d4) δ 10.37 (s, 1H), 8.36 (d, J = 6.7 Hz, 1H), 8.19 (dd, J = 8.0, 2.8 Hz, 1H), 7.61 (dd, J = 8.0, 2.7 Hz, 1H), 7.48 (d, J = 2.5 Hz, 1H), 7.32 (d, J = 6.8 Hz, 1H), 6.69-6.22 (m, 2H), 4.75 (td, J = 14.6, 3.4 Hz, 2H), 1.56 (s, 6H). |

TABLE 1-continued

Compounds and characterization of the compounds

| EXAMPLE | STRUCTURE | LC/MS | NMR |
|---|---|---|---|
| 61 | 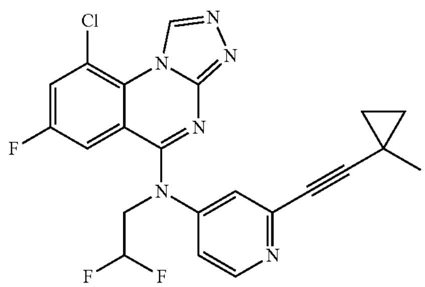 [SMILES: CC1(C#Cc2cc(N(CC(F)F)c3nc4nncn4c4c(Cl)cc(F)cc34)ccn2)CC1] | 457.16 | 1H NMR (400 MHz, Methanol-d4) δ 10.38 (s, 1H), 8.30 (d, J = 6.8 Hz, 1H), 8.20 (dd, J = 8.0, 2.8 Hz, 1H), 7.64 (dd, J = 8.0, 2.8 Hz, 1H), 7.42 (d, J = 2.6 Hz, 1H), 7.30 (d, J = 5.8 Hz, 1H), 6.64-6.28 (m, 3H), 4.74 (td, J = 14.7, 3.5 Hz, 2H), 1.36 (s, 3H), 1.10 (q, J = 4.2 Hz, 2H), 0.86 (q, J = 4.3 Hz, 2H). |
| 62 | 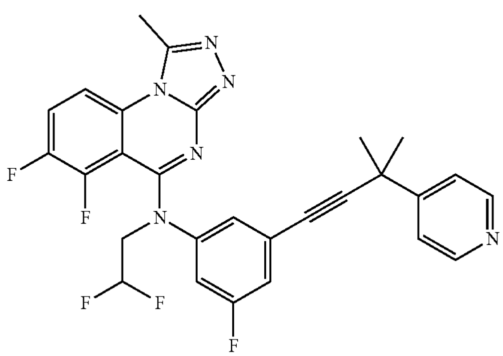 [SMILES: Cc1nnc2nc(N(CC(F)F)c3cc(F)cc(C#CC(C)(C)c4ccncc4)c3)c3c(F)c(F)ccc3n12] | 437.2 | 1H NMR (400 MHz, DMSO-d6) δ 8.83 (d, J = 5.8 Hz, 2H), 8.26-8.16 (m, 1H), 8.13-8.03 (m, 3H), 7.45-7.37 (m, 1H), 7.28 (t, J = 1.6 Hz, 1H), 7.17 (ddt, J = 10.6, 9.2, 2.2 Hz, 2H), 6.55 (tt, J = 55.8, 3.8 Hz, 1H), 4.66 (td, J = 14.7, 3.8 Hz, 2H), 3.02 (s, 3H), 1.69 (s, 6H). |
| 63 | 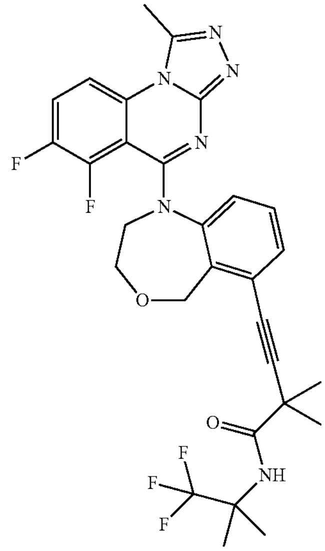 [SMILES: Cc1nnc2nc(N3CCOCc4c(C#CC(C)(C)C(=O)NC(C)(C)C(F)(F)F)cccc43)c3c(F)c(F)ccc3n12] | 587.3 | 1H NMR (400 MHz, Methanol-d4) δ 8.27 (d, J = 7.9 Hz, 1H), 8.03 (q, J = 8.9 Hz, 1H), 7.47 (d, J = 7.7 Hz, 1H), 7.14 (t, J = 7.9 Hz, 1H), 6.90 (d, J = 8.0 Hz, 1H), 4.17 (s, 2H), 3.81-3.68 (m, 2H), 3.11 (s, 3H), 2.18 (s, 2H), 1.72-1.52 (m, 12H). |

TABLE 1-continued

Compounds and characterization of the compounds

| EXAMPLE | STRUCTURE | LC/MS | NMR |
|---|---|---|---|
| 64 | 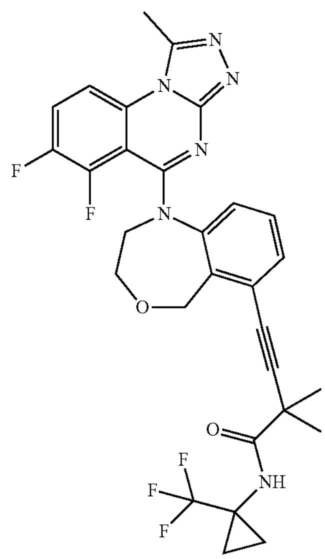 [SMILES: Cc1nnc2nc(N3CCOCc4c(C#CC(C)(C)C(=O)NC5(C(F)(F)F)CC5)cccc43)c3c(F)c(F)ccc3n12] | 585.22 | 1H NMR (400 MHz, Methanol-d4) δ 8.71 (s, 1H), 8.27 (d, J = 8.6 Hz, 1H), 8.02 (q, J = 8.8 Hz, 1H), 7.47 (d, J = 7.8 Hz, 1H), 7.11 (t, J = 7.8 Hz, 1H), 6.87 (d, J = 7.9 Hz, 1H), 4.17 (s, 2H), 3.10 (s, 3H), 1.61 (d, J = 19.4 Hz, 6H), 1.34 (dt, J = 8.2, 5.7 Hz, 2H), 1.23-1.05 (m, 2H). |
| 65 | 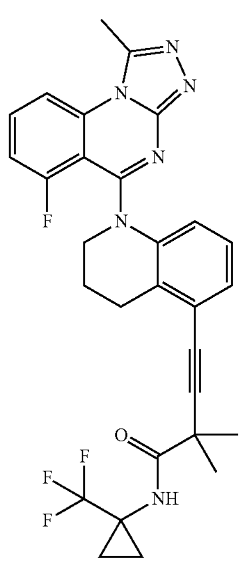 [SMILES: Cc1nnc2nc(N3CCCc4c(C#CC(C)(C)C(=O)NC5(C(F)(F)F)CC5)cccc43)c3c(F)cccc3n12] | 551.32 | 1H NMR (400 MHz, Methanol-d4) δ 8.63 (s, 1H), 8.25 (d, J = 8.6 Hz, 1H), 8.13-8.00 (m, 1H), 7.31 (q, J = 7.7, 6.4 Hz, 1H), 7.02-6.90 (m, 1H), 6.86 (d, J = 8.2 Hz, 1H), 3.14-2.77 (m, 6H), 1.68-1.44 (m, 2H), 1.44-1.26 (m, 2H), 1.15 (s, 2H). |

TABLE 1-continued

Compounds and characterization of the compounds

| EXAMPLE | STRUCTURE | LC/MS | NMR |
|---|---|---|---|
| 66 | 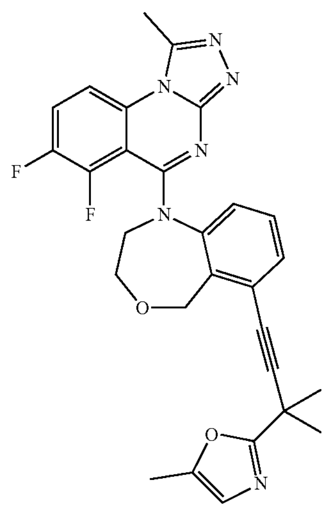 [SMILES: Cc1cnc(C(C)(C)C#Cc2cccc3c2COCCN3c2nc3nnc(C)n3c3ccc(F)c(F)c23)o1] | 515.17 | 1H NMR (400 MHz, Methanol-d4) δ 8.26 (dd, J = 10.4, 3.2 Hz, 1H), 8.01 (q, J = 9.0 Hz, 1H), 7.47-7.37 (m, 1H), 7.10 (td, J = 7.9, 1.5 Hz, 1H), 6.85 (d, J = 7.9 Hz, 1H), 6.79 (q, J = 1.2 Hz, 1H), 5.47 (s, 2H), 4.16 (s, 2H), 3.76-3.40 (m, 2H), 3.10 (s, 3H), 2.39 (d, J = 1.2 Hz, 3H), 1.81 (s, 6H). |
| 67 | 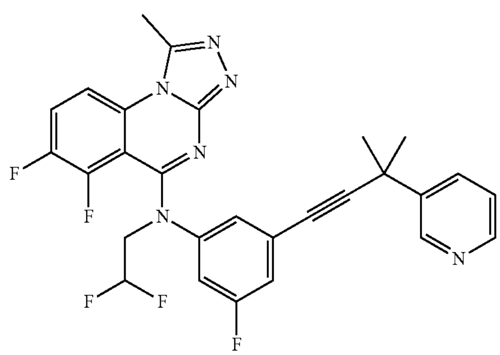 [SMILES: Cc1nnc2nc(N(CC(F)F)c3cc(F)cc(C#CC(C)(C)c4cccnc4)c3)c3c(F)c(F)ccc3n12] | 437.21 | 1H NMR (400 MHz, Methanol-d4) δ 9.03 (d, J = 2.3 Hz, 1H), 8.73 (d, J = 5.6 Hz, 2H), 8.26 (d, J = 8.1 Hz, 1H), 8.09-7.85 (m, 2H), 7.26 (s, 1H), 7.21-7.01 (m, 2H), 6.51 (tt, J = 55.9, 4.0 Hz, 1H), 4.67 (td, J = 13.8, 4.1 Hz, 2H), 3.10 (s, 3H), 1.78 (s, 6H). |
| 68 | 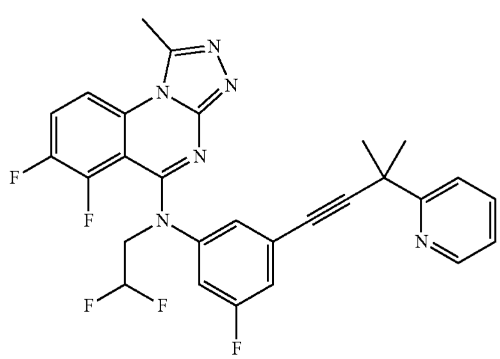 [SMILES: Cc1nnc2nc(N(CC(F)F)c3cc(F)cc(C#CC(C)(C)c4ccccn4)c3)c3c(F)c(F)ccc3n12] | 437.15 | 1H NMR (400 MHz, Methanol-d4) δ 8.58 (d, J = 5.3 Hz, 1H), 8.27 (d, J = 8.6 Hz, 1H), 8.02 (q, J = 9.0 Hz, 2H), 7.89 (d, J = 8.1 Hz, 1H), 7.47 (s, 1H), 7.21 (s, 1H), 7.13 (t, J = 10.9 Hz, 2H), 6.67-6.30 (m, 1H), 4.68 (d, J = 4.0 Hz, 2H), 3.11 (s, 3H), 1.73 (s, 6H). |

TABLE 1-continued

Compounds and characterization of the compounds

| EXAMPLE | STRUCTURE | LC/MS | NMR |
|---|---|---|---|
| 69 | 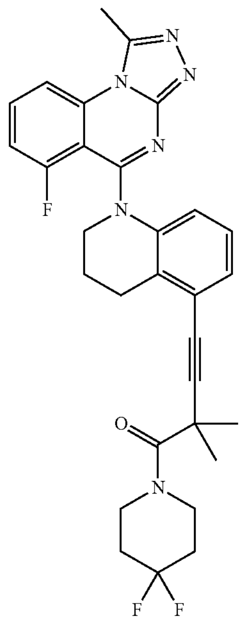 [SMILES: Cc1nnc2nc(N3CCCc4c(C#CC(C)(C)C(=O)N5CCC(F)(F)CC5)cccc43)c3c(F)cccc3n12] | 547.29 | 1H NMR (400 MHz, Methanol-d4) δ 8.26 (d, J = 8.6 Hz, 1H), 8.08 (td, J = 8.5, 5.4 Hz, 1H), 7.38-7.24 (m, 2H), 6.99 (t, J = 7.9 Hz, 1H), 6.89 (d, J = 8.1 Hz, 1H), 4.39-3.74 (m, 4H), 3.11 (s, 5H), 2.38-1.96 (m, 4H), 1.65 (s, 6H), 1.42-1.33 (m, 2H). |
| 70 | 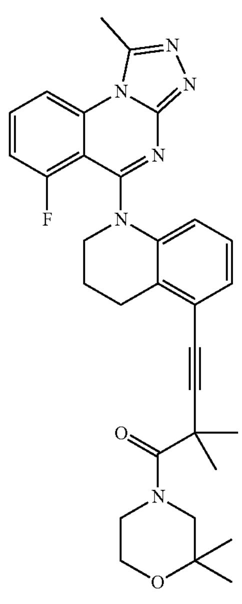 [SMILES: Cc1nnc2nc(N3CCCc4c(C#CC(C)(C)C(=O)N5CCOC(C)(C)C5)cccc43)c3c(F)cccc3n12] | 541.27 | 1H NMR (400 MHz, Methanol-d4) δ 8.26 (d, J = 8.6 Hz, 1H), 8.08 (td, J = 8.5, 5.4 Hz, 1H), 7.39-7.23 (m, 2H), 6.98 (t, J = 7.9 Hz, 1H), 6.89 (d, J = 8.1 Hz, 1H), 4.05 (s, 6H), 3.81 (t, J = 4.9 Hz, 2H), 3.11 (s, 2H), 2.21 (s, 3H), 1.65 (s, 3H), 1.24 (s, 4H). |

TABLE 1-continued

Compounds and characterization of the compounds

| EXAMPLE | STRUCTURE | LC/MS | NMR |
|---|---|---|---|
| 71 | 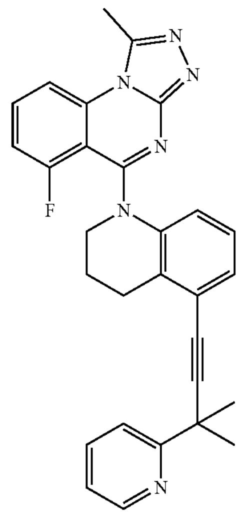 [SMILES: Cc1nnc2nc(N3CCCc4c(C#CC(C)(C)c5ccccn5)cccc43)c3c(F)cccc3n12] | 477.15 | 1H NMR (400 MHz, Methanol-d4) δ (t, J = 6.1 Hz, 2H), 7.40-7.31 (m, 1H), 7.05 (d, J = 7.8 Hz, 1H), 6.94 (ddd, J = 23.9, 16.2, 8.1 Hz, 2H), 6.72 (d, J = 8.0 Hz, 1H), 3.90 (q, J = 6.3 Hz, 1H), 3.77 (p, J = 6.9 Hz, 1H), 3.11 (s, 3H), 2.80 (t, J = 6.6 Hz, 2H), 2.22 (s, 2H), 1.83 (s, 6H). |
| 72 | 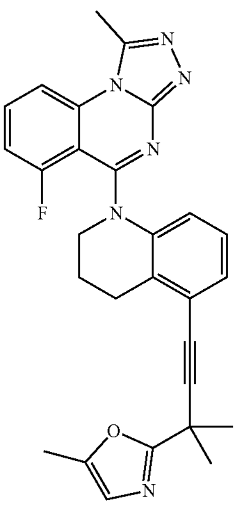 [SMILES: Cc1cnc(C(C)(C)C#Cc2cccc3c2CCCN3c2nc3nnc(C)n3c3cccc(F)c23)o1] | 481.19 | 1H NMR (400 MHz, Methanol-d4) δ 8.24 (d, J = 8.6 Hz, 1H), 8.06 (td, J = 8.5, 5.4 Hz, 1H), 7.37-7.22 (m, 2H), 6.95 (t, J = 7.9 Hz, 1H), 6.85 (d, J = 8.0 Hz, 1H), 6.79 (d, J = 1.4 Hz, 1H), 4.41-3.97 (m, 2H), 3.10 (s, 5H), 2.39 (d, J = 1.2 Hz, 3H), 2.20 (s, 2H), 1.80 (s, 6H). |
| 73 | 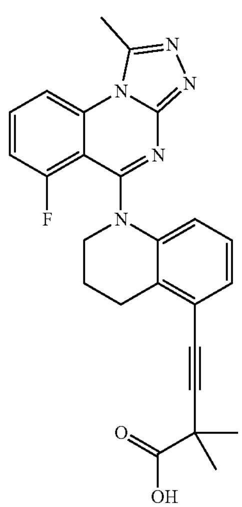 [SMILES: Cc1nnc2nc(N3CCCc4c(C#CC(C)(C)C(=O)O)cccc43)c3c(F)cccc3n12] | 444.16 | 1H NMR (400 MHz, Methanol-d4) δ 8.24 (d, J = 8.6 Hz, 1H), 8.04 (td, J = 8.5, 5.4 Hz, 1H), 7.40 (dd, J = 7.8, 1.2 Hz, 1H), 7.28 (dd, J = 11.5, 8.3 Hz, 1H), 7.06 (t, J = 7.9 Hz, 1H), 6.93 (d, J = 8.1 Hz, 1H), 4.26-4.02 (m, 2H), 3.10 (s, 3H), 2.19 (s, 2H), 1.97-1.76 (m, 2H), 1.46 (s, 6H). |

TABLE 1-continued

Compounds and characterization of the compounds

| EXAMPLE | STRUCTURE | LC/MS | NMR |
|---|---|---|---|
| 74 | 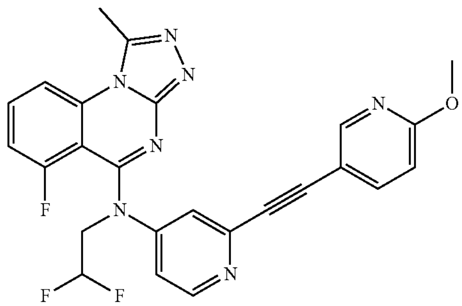 [SMILES: COc1ccc(C#Cc2cc(N(CC(F)F)c3nc4nnc(C)n4c4cccc(F)c34)ccn2)cn1] | 490.14 | 1H NMR (400 MHz, Methanol-d4) δ 8.48-8.32 (m, 3H), 8.16 (td, J = 8.5, 5.5 Hz, 1H), 7.84 (dd, J = 8.7, 2.3 Hz, 1H), 7.62 (s, 1H), 7.47 (dd, J = 12.0, 8.3 Hz, 1H), 7.36 (d, J = 7.0 Hz, 1H), 6.88 (dd, J = 8.7, 0.8 Hz, 1H), 6.46 (tt, J = 54.9, 3.5 Hz, 1H), 4.85-4.64 (m, 2H), 3.98 (s, 3H), 3.20 (s, 3H). |
| 75 | 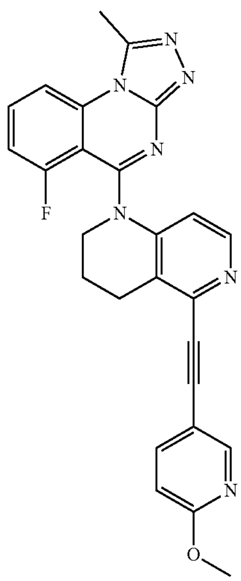 [SMILES: COc1ccc(C#Cc2nccc3c2CCCN3c2nc3nnc(C)n3c3cccc(F)c23)cn1] | 466.172 | 1H NMR (400 MHz, Methanol-d4) δ 8.56 (d, J = 2.4 Hz, 1H), 8.41 (d, J = 8.7 Hz, 1H), 8.20-8.12 (m, 1H), 8.02-7.93 (m, 2H), 7.54 (dd, J = 12.0, 8.3 Hz, 1H), 6.95 (d, J = 8.7 Hz, 1H), 6.87 (d, J = 7.0 Hz, 1H), 4.08 (s, 2H), 4.01 (d, J = 3.5 Hz, 3H), 3.22 (d, J = 22.5 Hz, 5H), 2.35 (s, 2H). |
| 76 | 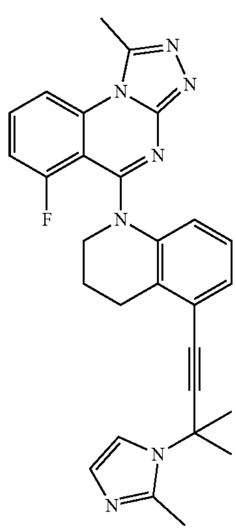 [SMILES: Cc1nccn1C(C)(C)C#Cc1cccc2c1CCCN2c1nc2nnc(C)n2c2cccc(F)c12] | 479.91 | 1H NMR (400 MHz, Methanol-d4) δ 8.27 (d, J = 8.6 Hz, 1H), 8.14-8.01 (m, 1H), 7.83 (d, J = 2.3 Hz, 1H), 7.54 (d, J = 2.3 Hz, 1H), 7.41-7.23 (m, 2H), 7.08-6.90 (m, 2H), 4.19 (s, 2H), 3.11 (s, 5H), 3.04 (s, 3H), 2.16 (s, 8H). |

TABLE 1-continued

Compounds and characterization of the compounds

| EXAMPLE | STRUCTURE | LC/MS | NMR |
|---|---|---|---|
| 77 | 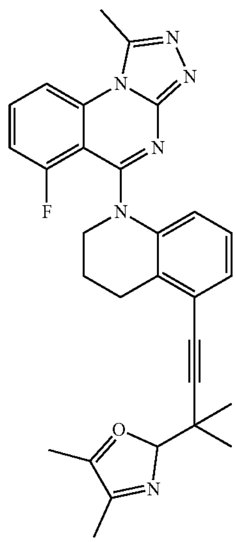 | 495.2 | 1H NMR (400 MHz, Methanol-d4) δ 8.26 (d, J = 8.6 Hz, 1H), 8.09 (td, J = 8.5, 5.4 Hz, 1H), 7.37-7.27 (m, 2H), 6.96 (t, J = 7.9 Hz, 1H), 6.91-6.85 (m, 1H), 4.12 (q, J = 7.1 Hz, 2H), 3.11 (s, 4H), 2.59 (q, J = 6.8 Hz, 1H), 2.30 (q, J = 1.0 Hz, 2H), 2.11 (q, J = 0.9 Hz, 2H), 2.05 (s, 6H). |
| 78 | 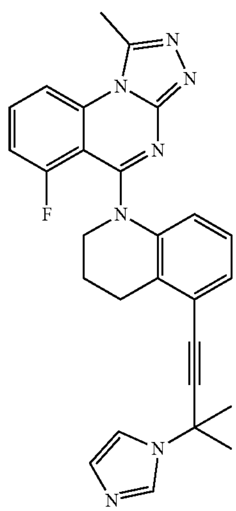 [SMILES: Cc1nnc2nc(N3CCCc4c(C#CC(C)(C)n5ccnc5)cccc43)c3c(F)cccc3n12] | 465.94 | 1H NMR (400 MHz, Methanol-d4) δ 9.32 (t, J = 1.5 Hz, 1H), 8.26 (d, J = 8.6 Hz, 1H), 8.13-8.01 (m, 2H), 7.71 (t, J = 1.8 Hz, 1H), 7.43-7.39 (m, 1H), 7.31 (ddd, J = 11.6, 8.4, 0.9 Hz, 1H), 7.11-6.88 (m, 2H), 4.18 (s, 2H), 3.11 (s, 5H), 2.26 (d, J = 28.6 Hz, 2H), 2.14 (s, 6H). |
| 79 | 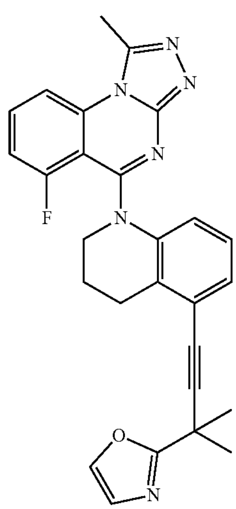 [SMILES: Cc1nnc2nc(N3CCCc4c(C#CC(C)(C)c5ncco5)cccc43)c3c(F)cccc3n12] | 467.2 | 1H NMR (400 MHz, Methanol-d4) δ 8.26 (dd, J = 8.5, 2.6 Hz, 1H), 8.15-8.03 (m, 1H), 7.95 (d, J = 0.9 Hz, 1H), 7.40-7.25 (m, 2H), 7.19 (d, J = 0.9 Hz, 1H), 7.02-6.86 (m, 2H), 4.18 (d, J = 38.1 Hz, 2H), 3.11 (d, J = 3.2 Hz, 5H), 2.21 (s, 2H), 1.83 (s, 6H). |

TABLE 1-continued

Compounds and characterization of the compounds

| EXAMPLE | STRUCTURE | LC/MS | NMR |
|---|---|---|---|
| 80 | 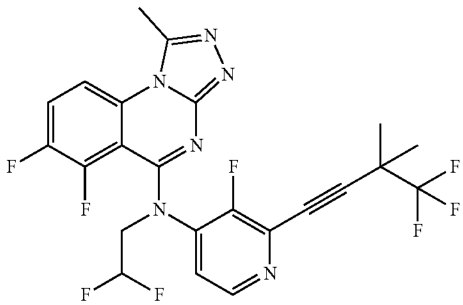 [SMILES: Cc1nnc2nc(N(CC(F)F)c3ccnc(C#CC(C)(C)C(F)(F)F)c3F)c3c(F)c(F)ccc3n12] | 529.21 | 1H NMR (400 MHz, Methanol-d4) δ 8.31 (d, J = 8.5 Hz, 1H), 8.19 (d, J = 5.4 Hz, 1H), 8.03 (q, J = 9.0 Hz, 1H), 7.24 (t, J = 6.0 Hz, 1H), 6.78-6.40 (m, 1H), 4.62 (td, J = 13.3, 4.2 Hz, 2H), 3.12 (s, 3H), 1.59 (s, 6H). |
| 81 | 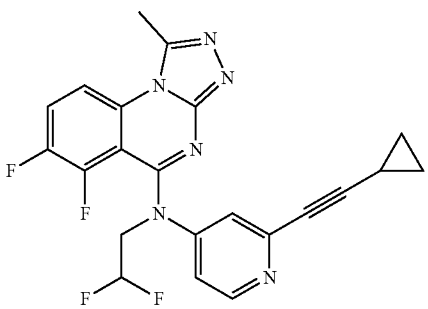 [SMILES: Cc1nnc2nc(N(CC(F)F)c3ccnc(C#CC4CC4)c3)c3c(F)c(F)ccc3n12] | 441.13 | 1H NMR (400 MHz, Methanol-d4) δ 8.41 (d, J = 10.3 Hz, 1H), 8.31 (t, J = 8.8 Hz, 1H), 8.15 (dt, J = 18.0, 10.0 Hz, 1H), 7.47 (s, 1H), 7.35 (s, 1H), 6.67-6.25 (m, 1H), 4.79 (d, J = 14.4 Hz, 2H), 3.28-3.09 (m, 3H), 1.72-1.53 (m, 1H), 1.19-0.81 (m, 4H). |
| 82 | 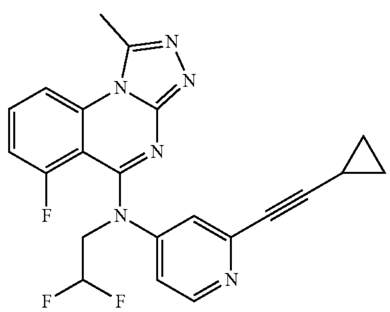 [SMILES: Cc1nnc2nc(N(CC(F)F)c3ccnc(C#CC4CC4)c3)c3c(F)cccc3n12] | 423.15 | 1H NMR (400 MHz, Methanol-d4) δ 8.40 (d, J = 8.6 Hz, 1H), 8.27 (d, J = 7.1 Hz, 1H), 8.16 (td, J = 8.5, 5.6 Hz, 1H), 7.55-7.38 (m, 2H), 7.32 (s, 1H), 6.42 (tt, J = 54.7, 3.5 Hz, 1H), 4.75 (t, J = 14.7 Hz, 2H), 3.20 (s, 3H), 1.61 (td, J = 8.5, 4.3 Hz, 1H), 1.14-0.79 (m, 4H). |
| 83 | 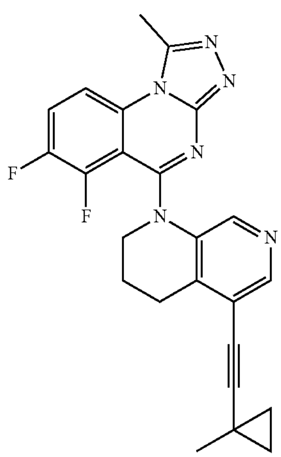 | 431.19 | 1H NMR (400 MHz, Methanol-d4) δ 8.28-8.07 (m, 1H), 7.96 (s, 1H), 7.55 (d, J = 34.8 Hz, 2H), 4.00 (s, 2H), 3.05 (s, 2H), 2.15-2.0 (m, 5H), 1.41 (s, 3H), 0.93 (d, J = 101.9 Hz, 4H). |

TABLE 1-continued

Compounds and characterization of the compounds

| EXAMPLE | STRUCTURE | LC/MS | NMR |
|---|---|---|---|
| 84 | 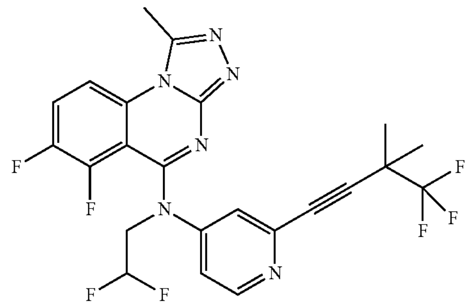 [SMILES: Cc1nnc2nc(N(CC(F)F)c3ccnc(C#CC(C)(C)C(F)(F)F)c3)c3c(F)c(F)ccc3n12] | 511.19 | 1H NMR (400 MHz, Methanol-d4) δ 8.35-8.17 (m, 2H), 8.01 (td, J = 9.5, 8.0 Hz, 1H), 7.31 (d, J = 2.5 Hz, 1H), 7.06 (dd, J = 5.9, 2.5 Hz, 1H), 6.66-6.22 (m, 1H), 4.81-4.56 (m, 2H), 3.12 (s, 3H), 1.53 (s, 6H). |
| 85 | 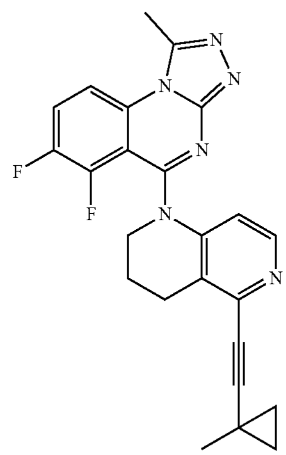 | 431.23 | 1H NMR (400 MHz, Methanol-d4) δ 8.29 (ddd, J = 9.6, 3.9, 1.9 Hz, 1H), 8.03 (td, J = 9.6, 8.1 Hz, 1H), 7.85 (d, J = 6.0 Hz, 1H), 6.62 (d, J = 6.0 Hz, 1H), 4.03 (d, J = 48.7 Hz, 2H), 3.12 (s, 3H), 3.03 (dd, J = 7.6, 5.2 Hz, 2H), 2.26 (d, J = 33.3 Hz, 2H), 1.45 (s, 3H), 1.13 (q, J = 4.1 Hz, 2H), 0.96-0.78 (m, 2H) |
| 86 | 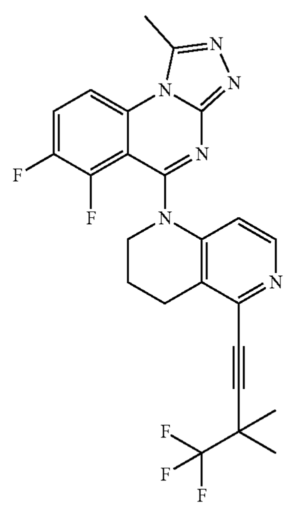 | 487.23 | 1H NMR (400 MHz, Methanol-d4) δ 8.28 (ddd, J = 9.6, 3.9, 1.9 Hz, 1H), 8.02 (td, J = 9.5, 8.0 Hz, 1H), 7.90 (d, J = 5.8 Hz, 1H), 6.66 (d, J = 5.8 Hz, 1H), 4.03 (d, J = 46.0 Hz, 2H), 3.11 (s, 3H), 3.09-2.97 (m, 2H), 2.26 (d, J = 35.6 Hz, 2H), 1.62 (s, 6H). |
| 87 | 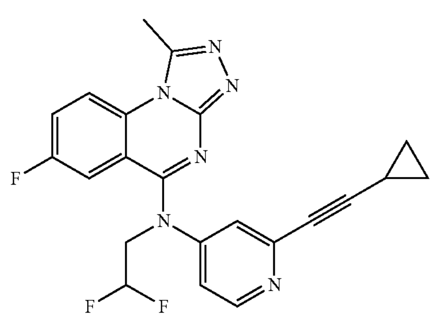 [SMILES: Cc1nnc2nc(N(CC(F)F)c3ccnc(C#CC4CC4)c3)c3cc(F)ccc3n12] | 423.2 | 1H NMR (400 MHz, Methanol-d4) δ 8.47 (dd, J = 9.4, 4.4 Hz, 1H), 8.29 (d, J = 5.8 Hz, 1H), 7.84-7.73 (m, 1H), 7.29 (dd, J = 9.0, 2.9 Hz, 1H), 7.19 (d, J = 2.4 Hz, 1H), 7.07 (dd, J = 5.8, 2.5 Hz, 1H), 4.68 (td, J = 14.5, 3.5 Hz, 1H), 3.12 (s, 2H), 1.49 (ddd, J = 13.3, 8.5, 4.9 Hz, 1H), 1.00-0.67 (m, 4H). |

TABLE 1-continued

Compounds and characterization of the compounds

| EXAMPLE | STRUCTURE | LC/MS | NMR |
|---|---|---|---|
| 88 | 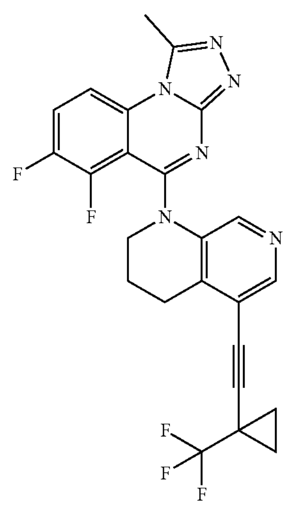 | 485.21 | 1H NMR (400 MHz, Methanol-d4) δ 8.20 (d, J = 3.6 Hz, 1H), 8.07 (s, 1H), 7.98 (q, J = 9.1 Hz, 1H), 7.67 (ddd, J = 13.6, 10.4, 7.5 Hz, 1H), 4.02 (s, 2H), 3.07 (s, 3H), 2.17 (s, 2H), 1.96 (s, 2H), 1.57-1.34 (m, 4H). |
| 89 | 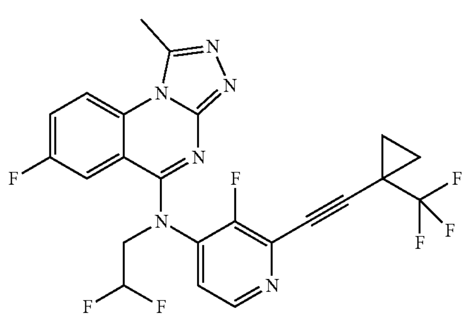 [SMILES: Cc1nnc2nc(N(CC(F)F)c3ccnc(C#CC4(C(F)(F)F)CC4)c3F)c3cc(F)ccc3n12] | 509.22 | 1H NMR (400 MHz, Methanol-d4) δ 8.55 (dd, J = 9.4, 4.4 Hz, 1H), 8.44 (d, J = 5.3 Hz, 1H), 7.89 (ddd, J = 9.9, 7.5, 2.7 Hz, 1H), 7.64 (t, J = 5.7 Hz, 1H), 7.25 (dd, J = 9.2, 2.7 Hz, 1H), 6.81-6.35 (m, 1H), 4.65 (td, J = 13.5, 4.1 Hz, 2H), 3.13 (s, 2H), 1.53-1.31 (m, 4H). |
| 90 | 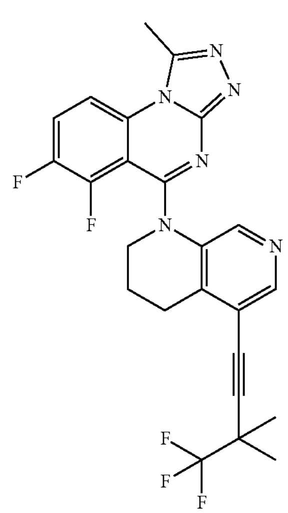 | 487.25 | 1H NMR (400 MHz, Methanol-d4) δ 8.51-8.27 (m, 3H), 8.14 (td, J = 9.5, 8.0 Hz, 1H), 4.27-4.05 (m, 2H), 3.16-3.08 (m, 5H), 2.22 (s, 2H), 1.62 (s, 6H). |

TABLE 1-continued

Compounds and characterization of the compounds

| EXAMPLE | STRUCTURE | LC/MS | NMR |
|---|---|---|---|
| 91 | 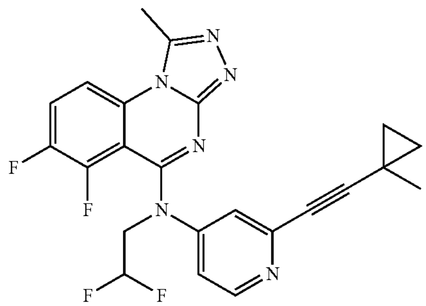 | 455.3 | 1H NMR (400 MHz, Methanol-d4) δ 8.40 (ddd, J = 9.5, 3.8, 1.8 Hz, 1H), 8.29 (d, J = 7.0 Hz, 1H), 8.13 (td, J = 9.5, 8.1 Hz, 1H), 7.47 (s, 1H), 7.33 (d, J = 6.6 Hz, 1H), 6.61-6.10 (m, 1H), 4.76 (t, J = 14.7 Hz, 2H), 3.18 (s, 3H), 1.37 (s, 3H), 1.12 (q, J = 4.3 Hz, 2H), 0.88 (q, J = 4.3 Hz, 2H). |
| 92 | 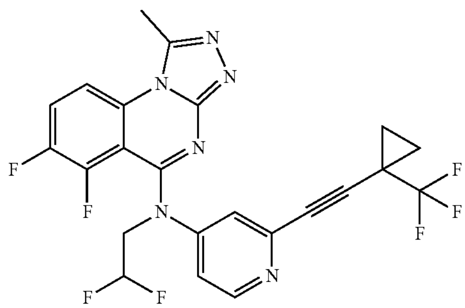 [SMILES: Cc1nnc2nc(N(CC(F)F)c3ccnc(C#CC4(C(F)(F)F)CC4)c3)c3c(F)c(F)ccc3n12] | 509.2 | 1H NMR (400 MHz, Methanol-d4) δ 8.45-8.30 (m, 2H), 8.13 (td, J = 9.6, 8.2 Hz, 1H), 7.58 (d, J = 2.7 Hz, 1H), 7.37 (dd, J = 6.9, 2.7 Hz, 1H), 6.44 (tt, J = 54.9, 3.5 Hz, 1H), 4.77 (td, J = 14.7, 3.4 Hz, 2H), 3.18 (s, 3H), 1.60-1.37 (m, 4H). |
| 93 | 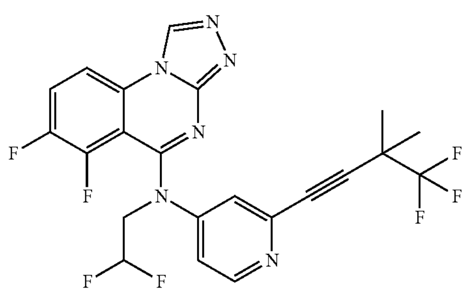 [SMILES: CC(C)(C#Cc1cc(N(CC(F)F)c2nc3nncn3c3ccc(F)c(F)c23)ccn1)C(F)(F)F] | 497.2 | 1H NMR (400 MHz, Methanol-d4) δ 9.82 (s, 1H), 8.35 (dd, J = 10.3, 5.1 Hz, 2H), 8.12 (td, J = 9.5, 7.9 Hz, 1H), 7.54 (d, J = 2.6 Hz, 1H), 7.29 (dd, J = 6.5, 2.6 Hz, 1H), 6.46 (tt, J = 55.1, 3.6 Hz, 1H), 4.78 (td, J = 14.5, 3.5 Hz, 2H), 1.56 (s, 6H). |
| 94 | 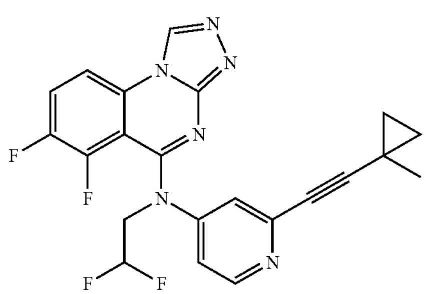 [SMILES: CC1(C#Cc2cc(N(CC(F)F)c3nc4nncn4c4ccc(F)c(F)c34)ccn2)CC1] | 441.18 | 1H NMR (400 MHz, Methanol-d4) δ 9.85 (s, 1H), 8.38 (d, J = 9.6 Hz, 1H), 8.29 (d, J = 6.7 Hz, 1H), 8.15 (q, J = 9.1 Hz, 1H), 7.45 (s, 1H), 7.30 (s, 1H), 6.67-6.18 (m, 1H), 4.75 (d, J = 14.1 Hz, 2H), 1.37 (s, 3H), 1.11 (d, J = 2.7 Hz, 2H), 0.86 (q, J = 4.2 Hz, 2H). |
| 95 | 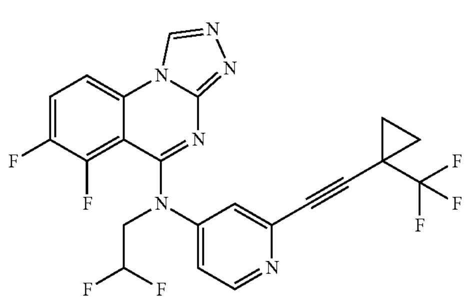 [SMILES: Fc1ccc2c(c(N(CC(F)F)c3ccnc(C#CC4(C(F)(F)F)CC4)c3)nc3nncn32)c1F] | 495.15 | 1H NMR (400 MHz, Methanol-d4) δ 9.81 (s, 1H), 8.34 (t, J = 7.1 Hz, 2H), 8.12 (q, J = 9.0 Hz, 1H), 7.51 (s, 1H), 7.35-7.22 (m, 1H), 6.67-6.18 (m, 1H), 4.84-4.64 (m, 2H), 1.56-1.32 (m, 4H). |

TABLE 1-continued

Compounds and characterization of the compounds

| EXAMPLE | STRUCTURE | LC/MS | NMR |
|---|---|---|---|
| 96 | 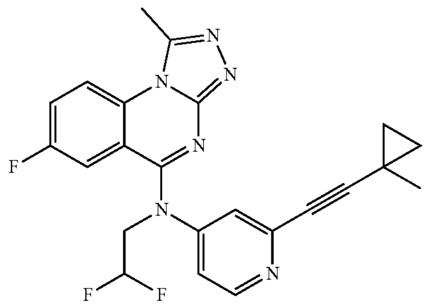 [SMILES: Cc1nnc2nc(N(CC(F)F)c3ccnc(C#CC4(C)CC4)c3)c3cc(F)ccc3n12] | 437.21 | 1H NMR (400 MHz, Methanol-d4) δ 8.59 (dd, J = 9.4, 4.3 Hz, 1H), 8.29 (d, J = 7.0 Hz, 1H), 7.94 (ddd, J = 9.5, 7.9, 2.9 Hz, 1H), 7.60 (dd, J = 8.5, 2.8 Hz, 1H), 7.42 (d, J = 2.7 Hz, 1H), 7.29 (d, J = 5.2 Hz, 1H), 6.60-6.24 (m, 1H), 4.75 (d, J = 3.3 Hz, 2H), 3.18 (s, 3H), 1.36 (s, 3H), 1.10 (q, J = 4.2 Hz, 2H), 0.93-0.80 (m, 2H). |
| 97 | 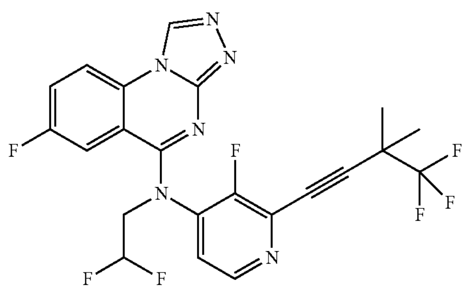 [SMILES: CC(C)(C#Cc1nccc(N(CC(F)F)c2nc3nncn3c3ccc(F)cc23)c1F)C(F)(F)F] | 497.18 | 1H NMR (400 MHz, Methanol-d4) δ 9.72 (s, 1H), 8.49 (dd, J = 9.6, 4.7 Hz, 1H), 8.43 (d, J = 5.3 Hz, 1H), 7.87 (td, J 8.9, 8.5, 2.6 Hz, 1H), 7.61 (t, J = 5.8 Hz, 1H), 7.17 (dd, J = 9.3, 2.7 Hz, 1H), 6.61 (t, J = 56.0 Hz, 1H), 4.64 (td, J = 13.3, 4.1 Hz, 2H), 1.53 (s, 6H). |
| 98 | 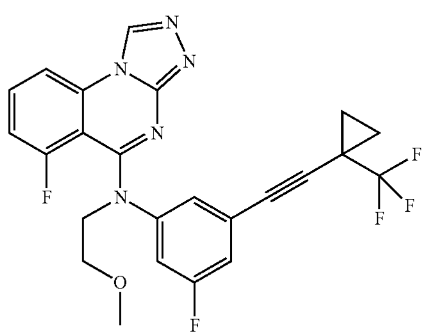 [SMILES: COCCN(c1cc(F)cc(C#CC2(C(F)(F)F)CC2)c1)c1nc2nncn2c2cccc(F)c12] | 488.14 | 1H NMR (400 MHz, Methanol-d4) δ 9.60 (s, 1H), 8.17 (d, J = 8.3 Hz, 1H), 8.01 (td, J = 8.3, 5.0 Hz, 1H), 7.27-7.13 (m, 2H), 7.05 (dd, J = 9.0, 1.9 Hz, 1H), 4.47 (t, J = 5.4 Hz, 2H), 3.81 (t, J 5.4 Hz, 2H), 3.37 (s, 3H), 1.48-1.16 (m, 4H). |
| 99 | 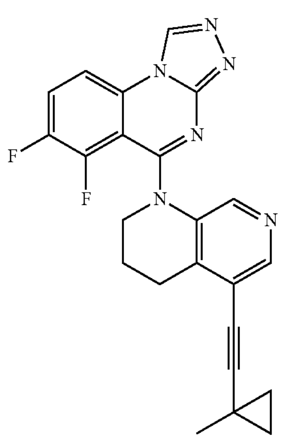 [SMILES: CC1(C#Cc2cncc3c2CCCN3c2nc3nncn3c3ccc(F)c(F)c23)CC1] | 417.19 | 1H NMR (400 MHz, Methanol-d4) δ 9.66 (s, 1H), 8.27 (s, 2H), 8.09 (q, J = 9.2 Hz, 2H), 4.08 (s, 2H), 3.10 (s, 2H), 2.18 (s, 2H), 1.43 (s, 3H), 1.11 (q, J = 4.3 Hz, 2H), 0.93-0.77 (m, 2H). |

TABLE 1-continued

Compounds and characterization of the compounds

| EXAMPLE | STRUCTURE | LC/MS | NMR |
|---|---|---|---|
| 100 | 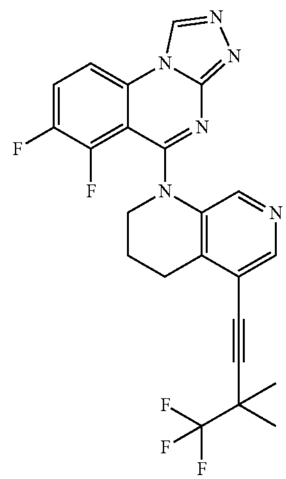 [SMILES: CC(C)(C#Cc1cncc2c1CCCN2c1nc2nncn2c2ccc(F)c(F)c12)C(F)(F)F] | 473.2 | 1H NMR (400 MHz, Methanol-d4) δ 9.69 (s, 1H), 8.35 (d, J = 7.8 Hz, 1H), 8.29 (dd, J = 9.3, 2.9 Hz, 1H), 8.12 (q, J = 9.1 Hz, 2H), 4.13 (s, 2H), 3.11 (t, J = 6.7 Hz, 2H), 2.21 (s, 2H), 1.62 (s, 6H). |
| 101 | 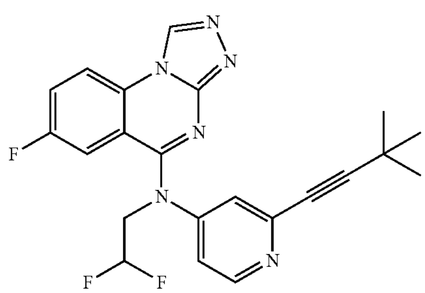 [SMILES: CC(C)(C)C#Cc1cc(N(CC(F)F)c2nc3nncn3c3ccc(F)cc23)ccn1] | 425.17 | 1H NMR (400 MHz, Methanol-d4) δ 9.84 (s, 1H), 8.56 (dd, J = 9.2, 4.4 Hz, 1H), 8.31 (d, J = 6.8 Hz, 1H), 7.94 (ddd, J = 9.2, 8.0, 2.7 Hz, 1H), 7.53 (dd, J = 8.7, 2.7 Hz, 1H), 7.48 (d, J = 2.7 Hz, 1H), 7.30 (dd, J = 6.7, 2.7 Hz, 1H), 6.46 (tt, J = 55.0, 3.4 Hz, 1H), 4.74 (dd, J = 14.7, 3.5 Hz, 2H), 1.34 (s, 9H). |
| 102 | 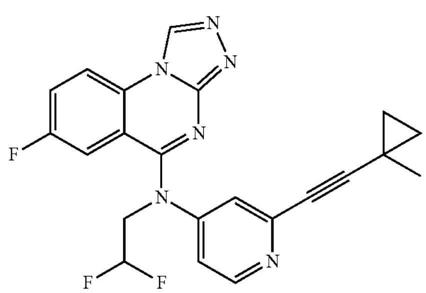 [SMILES: CC1(C#Cc2cc(N(CC(F)F)c3nc4nncn4c4ccc(F)cc34)ccn2)CC1] | 423.21 | 1H NMR (400 MHz, Methanol-d4) δ 9.83 (s, 1H), 8.56 (dd, J = 9.2, 4.3 Hz, 1H), 8.29 (d, J = 6.8 Hz, 1H), 7.93 (ddd, J = 9.1, 8.0, 2.7 Hz, 1H), 7.52 (dd, J = 8.7, 2.7 Hz, 1H), 7.43 (d, J = 2.7 Hz, 1H), 7.28 (dd, J = 6.9, 2.7 Hz, 1H), 6.45 (tt, J = 55.1, 3.4 Hz, 1H), 4.73 (dd, J = 14.6, 3.5 Hz, 2H), 1.36 (s, 3H), 1.10 (q, J = 4.2 Hz, 2H), 0.90-0.78 (m, 2H). |
| 103 | 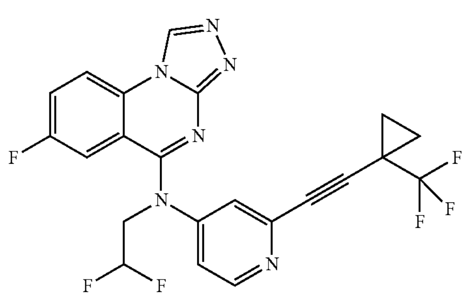 [SMILES: Fc1ccc2c(c1)c(N(CC(F)F)c1ccnc(C#CC3(C(F)(F)F)CC3)c1)nc1nncn12] | 495.15 | 1H NMR (400 MHz, Methanol-d4) δ 9.81 (s, 1H), 8.34 (t, J = 7.1 Hz, 2H), 8.12 (q, J = 9.0 Hz, 1H), 7.51 (s, 1H), 7.35-7.22 (m, 1H), 6.67-6.18 (m, 1H), 4.84-4.64 (m, 2H), 1.56-1.32 (m, 4H). |

TABLE 1-continued

Compounds and characterization of the compounds

| EXAMPLE | STRUCTURE | LC/MS | NMR |
|---|---|---|---|
| 104 | 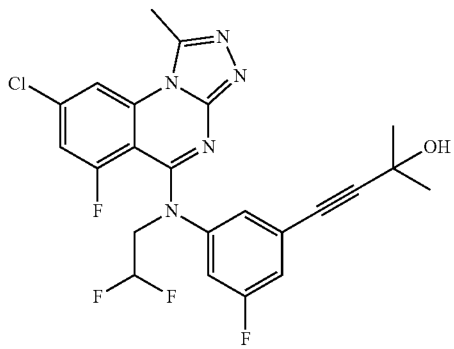 [SMILES: Cc1nnc2nc(N(CC(F)F)c3cc(F)cc(C#CC(C)(C)O)c3)c3c(F)cc(Cl)cc3n12] | 492.13 | 1H NMR (400 MHz, Methanol-d4) δ 8.21 (d, J = 6.1 Hz, 1H), 7.48 (d, J = 11.5 Hz, 1H), 7.20-7.02 (m, 3H), 6.47 (dd, J = 57.4, 53.7 Hz, 1H), 4.77-4.56 (m, 2H), 3.13 (s, 3H), 1.52 (t, J = 2.0 Hz, 6H). |
| 105 | 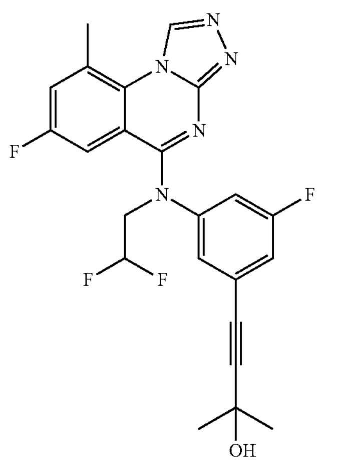 [SMILES: Cc1cc(F)cc2c(N(CC(F)F)c3cc(F)cc(C#CC(C)(C)O)c3)nc3nncn3c12] | 458.154 | 1H NMR (400 MHz, Methanol-d4) δ 9.72 (s, 1H), 7.85-7.66 (m, 1H), 7.35-7.13 (m, 3H), 7.06 (dd, J = 9.5, 2.8 Hz, 1H), 6.75-6.28 (m, 1H), 4.63 (td, J = 13.5, 4.1 Hz, 2H), 2.99 (s, 3H), 1.53 (s, 6H). |
| 106 | 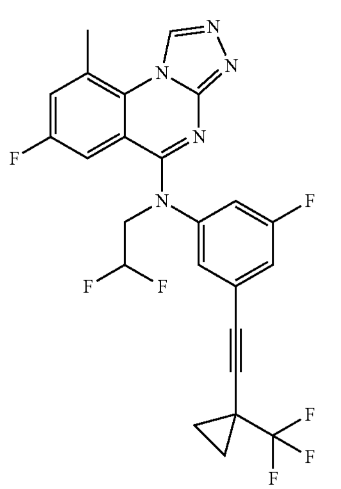 [SMILES: Cc1cc(F)cc2c(N(CC(F)F)c3cc(F)cc(C#CC4(C(F)(F)F)CC4)c3)nc3nncn3c12] | 508.224 | 1H NMR (400 MHz, Methanol-d4) δ 9.73 (s, 1H), 7.75 (dd, J = 8.6, 2.8 Hz, 1H), 7.40-7.16 (m, 3H), 7.06 (dd, J = 9.4, 2.8 Hz, 1H), 6.53 (tt, J = 55.9, 4.1 Hz, 1H), 4.64 (td, J = 13.6, 4.1 Hz, 2H), 3.00 (s, 3H), 1.52-1.21 (m, 4H). |

TABLE 1-continued
Compounds and characterization of the compounds
| EXAMPLE | STRUCTURE | LC/MS | NMR |
|---|---|---|---|
| 107 | 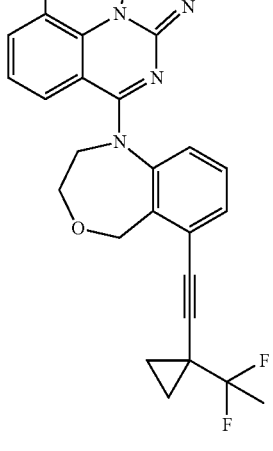 | 460.284 | 1H NMR (400 MHz, Methanol-d4) δ 9.67 (s, 1H), 7.86-7.72 (m, 1H), 7.50 (dd, J = 7.8, 1.1 Hz, 1H), 7.35-7.12 (m, 3H), 6.96 (dd, J = 8.0, 1.1 Hz, 1H), 5.08 (b, 2H), 4.16 (b, 2H), 3.39-3.26 (m, 2H), 2.97 (s, 3H), 1.91 (t, J = 17.9 Hz, 3H), 1.42-1.26 (m, 2H), 1.25-1.05 (m, 2H). |
| 108 | 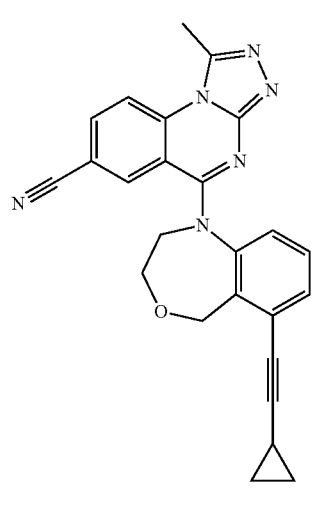 [SMILES: Cc1nnc2nc(N3CCOCc4c(C#CC5CC5)cccc43)c3cc(C#N)ccc3n12] | 421.293 | 1H NMR (400 MHz, Methanol-d4) δ 8.50 (d, J = 8.9 Hz, 1H), 8.20 (d, J = 8.8 Hz, 1H), 7.54 (d, J = 7.8 Hz, 1H), 7.43 (d, J = 1.6 Hz, 1H), 7.25 (t, J = 7.9 Hz, 1H), 6.98 (d, J = 7.9 Hz, 1H), 5.21 (b, 2H), 4.15 (s, 2H), 3.36-3.26 (m, 2H), 3.10 (s, 3H), 1.62 (tt, J = 8.5, 5.0 Hz, 1H), 1.11-0.94 (m, 2H), 0.94-0.77 (m, 2H). |
| 109 | 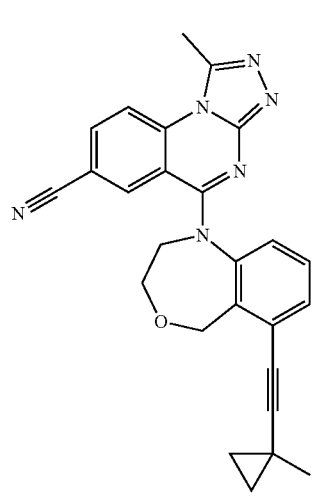 [SMILES: Cc1nnc2nc(N3CCOCc4c(C#CC5(C)CC5)cccc43)c3cc(C#N)ccc3n12] | 435.297 | 1H NMR (400 MHz, Methanol-d4) δ 8.51 (d, J = 8.9 Hz, 1H), 8.20 (d, J = 8.8 Hz, 1H), 7.53 (d, J = 7.8 Hz, 1H), 7.43 (d, J = 1.7 Hz, 1H), 7.26 (t, J = 7.9 Hz, 1H), 6.98 (d, J = 7.9 Hz, 1H), 5.21 (b, 2H), 4.15 (s, 2H), 3.37-3.27 (m, 2H), 3.10 (s, 3H), 1.44 (s, 3H), 1.09 (q, J = 4.1 Hz, 2H), 0.92-0.74 (m, 2H). |

TABLE 1-continued
Compounds and characterization of the compounds
| EXAMPLE | STRUCTURE | LC/MS | NMR |
|---|---|---|---|
| 110 | 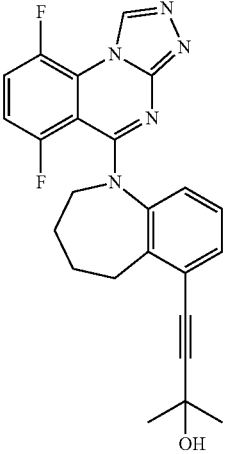 [SMILES: CC(C)(O)C#Cc1cccc2c1CCCCN2c1nc2nncn2c2c(F)ccc(F)c12] | 434.31 | 1H NMR (400 MHz, Methanol-d4) δ 9.38 (d, J = 2.6 Hz, 1H), 7.87 (td, J = 9.9, 3.7 Hz, 1H), 7.43-7.28 (m, 1H), 7.23-7.06 (m, 1H), 6.97 (t, J = 7.8 Hz, 1H), 6.75 (d, J = 7.9 Hz, 1H), 3.43-3.24 (m, 2H), 2.15-1.73 (m, 6H), 1.63 (s, 6H). |
| 111 | 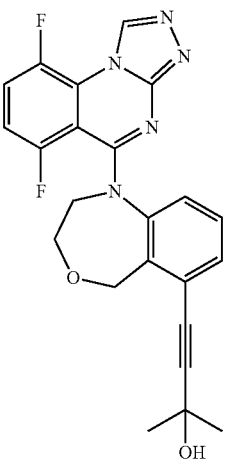 [SMILES: CC(C)(O)C#Cc1cccc2c1COCCN2c1nc2nncn2c2c(F)ccc(F)c12] | 436.288 | 1H NMR (400 MHz, Methanol-d4) δ 9.46 (d, J = 2.6 Hz, 1H), 7.93 (ddd, J = 10.5, 9.3, 3.9 Hz, 1H), 7.38 (dd, J = 7.9, 1.2 Hz, 1H), 7.21 (ddd, J = 11.2, 9.3, 4.0 Hz, 1H), 7.07 (t, J = 7.9 Hz, 1H), 6.85 (d, J = 8.0 Hz, 1H), 4.99-4.84 (m, 2H), 4.15 (b, 2H), 3.37-3.25 (m, 2H), 1.64 (s, 6H). |
| 112 | 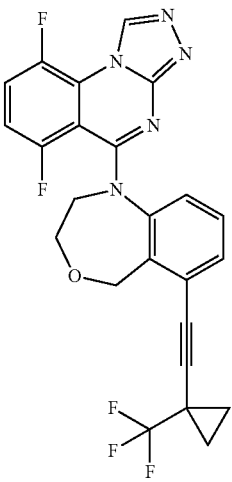 [SMILES: Fc1ccc(F)c2c1c(N1CCOCc3c(C#CC4(C(F)(F)F)CC4)cccc31)nc1nncn12] | 486.314 | 1H NMR (400 MHz, Methanol-d4) δ 9.46 (d, J = 2.6 Hz, 1H), 7.92 (td, J = 9.9, 3.8 Hz, 1H), 7.39 (d, J = 7.8 Hz, 1H), 7.30-7.15 (m, 1H), 7.08 (t, J = 7.9 Hz, 1H), 6.87 (d, J = 7.9 Hz, 1H), 5.01-4.82 (m, 2H), 4.14 (s, 2H), 3.39-3.27 (m, 2H), 1.63-1.29 (m, 4H). |

TABLE 1-continued
Compounds and characterization of the compounds
| EXAMPLE | STRUCTURE | LC/MS | NMR |
|---|---|---|---|
| 113 | 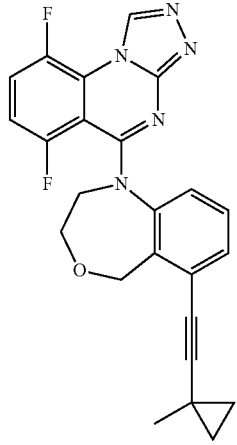 [SMILES: CC1(C#Cc2cccc3c2COCCN3c2nc3nncn3c3c(F)ccc(F)c23)CC1] | 432.329 | 1H NMR (400 MHz, Methanol-d4) δ 9.45 (d, J = 2.7 Hz, 1H), 7.92 (ddd, J = 10.6, 9.3, 3.9 Hz, 1H), 7.31 (dd, J = 7.8, 1.2 Hz, 1H), 7.21 (ddd, J = 11.3, 9.3, 4.0 Hz, 1H), 7.02 (t, J = 7.9 Hz, 1H), 6.84-6.66 (m, 1H), 4.93-4.76 (m, 2H), 4.13 (s, 2H), 3.39-3.27 (m, 2H), 1.42 (s, 3H), 1.10-0.99 (m, 2H), 0.93-0.63 (m, 2H). |
| 114 | 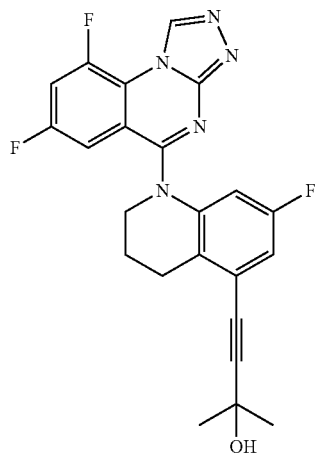 [SMILES: CC(C)(O)C#Cc1cc(F)cc2c1CCCN2c1nc2nncn2c2c(F)cc(F)cc12] | 438.284 | 1H NMR (400 MHz, Methanol-d4) δ 9.49 (d, J = 2.8 Hz, 1H), 7.93 (ddd, J = 11.1, 8.2, 2.6 Hz, 1H), 7.27 (dt, J = 9.4, 2.0 Hz, 1H), 7.06 (dd, J = 8.9, 2.5 Hz, 1H), 6.80 (dd, J = 10.0, 2.6 Hz, 1H), 4.17 (t, J = 6.4 Hz, 2H), 3.09 (t, J = 6.6 Hz, 2H), 2.28-2.15 (m, 2H), 1.64 (s, 6H). |
| 115 | 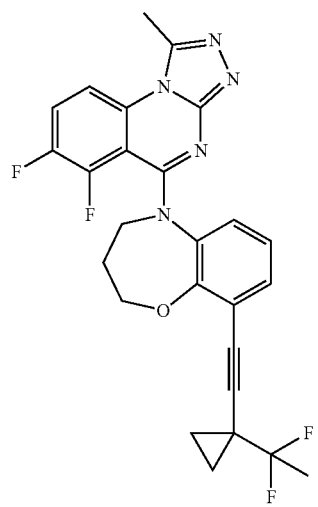 [SMILES: Cc1nnc2nc(N3CCCOc4c(C#CC5(C(C)(F)F)CC5)cccc43)c3c(F)c(F)ccc3n12] | 496.289 | 1H NMR (400 MHz, Methanol-d4) δ 8.24 (ddd, J = 9.6, 3.9, 1.8 Hz, 1H), 8.00 (td, J = 9.5, 7.9 Hz, 1H), 7.36 (dd, J = 7.2, 2.1 Hz, 1H), 6.88-6.72 (m, 2H), 4.46 (s, 2H), 3.39-3.29 (m, 2H), 3.09 (s, 3H), 2.30 (t, J = 5.7 Hz, 2H), 1.95 (t, J = 18.0 Hz, 3H), 1.42-1.26 (m, 2H), 1.21-1.09 (m, 2H). |

TABLE 1-continued

Compounds and characterization of the compounds

| EXAMPLE | STRUCTURE | LC/MS | NMR |
|---|---|---|---|
| 116 | 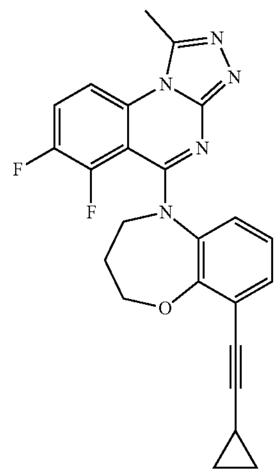 [SMILES: Cc1nnc2nc(N3CCCOc4c(C#CC5CC5)cccc43)c3c(F)c(F)ccc3n12] | 432.273 | 1H NMR (400 MHz, Methanol-d4) δ 8.21 (ddd, J = 9.4, 3.9, 1.9 Hz, 1H), 8.05-7.86 (m, 1H), 7.31 (dd, J = 7.7, 1.8 Hz, 1H), 6.87-6.61 (m, 2H), 4.42 (s, 2H), 3.38-3.19 (m, 2H), 3.07 (s, 3H), 2.25 (d, J = 5.8 Hz, 2H), 1.61-1.48 (m, 1H), 1.02-0.89 (m, 2H), 0.89-0.74 (m, 2H). |
| 117 | 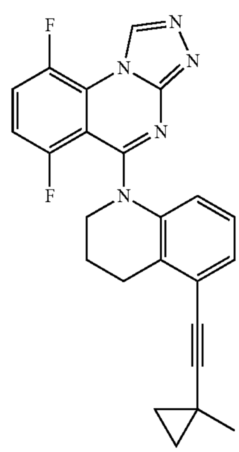 [SMILES: CC1(C#Cc2cccc3c2CCCN3c2nc3nncn3c3c(F)ccc(F)c23)CC1] | 416.341 | 1H NMR (400 MHz, Methanol-d4) δ 9.42 (s, 1H), 7.93 (td, J = 10.0, 3.8 Hz, 1H), 7.39-7.06 (m, 2H), 7.02-6.72 (m, 2H), 4.42-4.00 (m, 2H), 3.15-2.95 (b, 2H), 2.18 (b, 2H), 1.41 (s, 3H), 1.07-0.97 (m, 2H), 0.95-0.70 (m, 2H). |
| 118 | 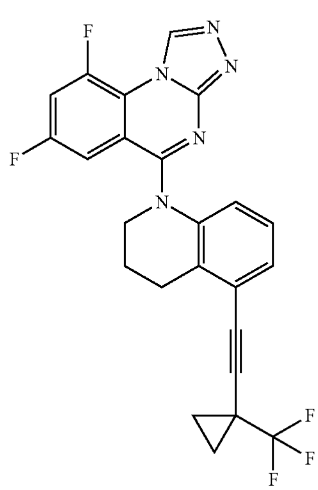 [SMILES: Fc1cc(F)c2c(c1)c(N1CCCc3c(C#CC4(C(F)(F)F)CC4)cccc31)nc1nncn12] | 470.358 | 1H NMR (400 MHz, Methanol-d4) δ 9.46 (d, J = 2.7 Hz, 1H), 7.89 (ddd, J = 11.1, 8.2, 2.6 Hz, 1H), 7.44-7.29 (m, 1H), 7.18-7.02 (m, 2H), 6.97 (d, J = 8.1 Hz, 1H), 4.21 (t, J = 6.6 Hz, 2H), 3.11 (t, J = 6.6 Hz, 2H), 2.22 (p, J = 6.6 Hz, 2H), 1.58-1.32 (m, 4H). |

TABLE 1-continued

Compounds and characterization of the compounds

| EXAMPLE | STRUCTURE | LC/MS | NMR |
|---|---|---|---|
| 119 | 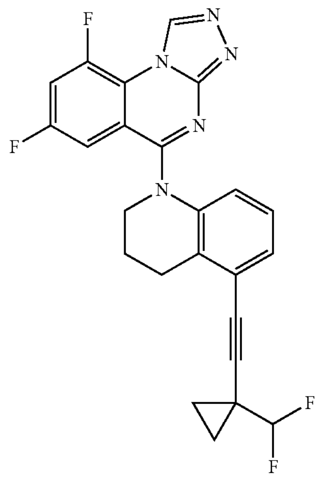 [SMILES: Fc1cc(F)c2c(c1)c(N1CCCc3c(C#CC4(C(F)F)CC4)cccc31)nc1nncn12] | 452.347 | 1H NMR (400 MHz, Methanol-d4) δ 9.46 (d, J = 2.7 Hz, 1H), 7.89 (ddd, J = 11.2, 8.2, 2.6 Hz, 1H), 7.36 (d, J = 7.8 Hz, 1H), 7.20-6.99 (m, 2H), 6.94 (d, J = 8.1 Hz, 1H), 5.74 (t, J = 56.5 Hz, 1H), 4.21 (t, J = 6.6 Hz, 2H), 3.12 (t, J = 6.6 Hz, 2H), 2.30-2.15 (m, 2H), 1.33-1.16 (m, 4H). |
| 120 | 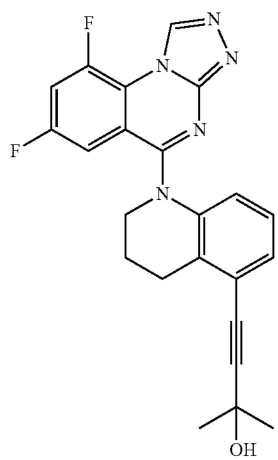 [SMILES: CC(C)(O)C#Cc1cccc2c1CCCN2c1nc2nncn2c2c(F)cc(F)cc12] | 420.327 | 1H NMR (400 MHz, Methanol-d4) δ 9.45 (d, J = 2.6 Hz, 1H), 7.88 (t, J = 9.8 Hz, 1H), 7.35 (d, J = 7.6 Hz, 1H), 7.07 (t, J = 8.3 Hz, 2H), 6.93 (d, J = 8.2 Hz, 1H), 4.26-4.13 (m, 2H), 3.24-3.06 (m, 2H), 2.22 (t, J = 6.6 Hz, 2H), 1.64 (s, 6H). |
| 121 | 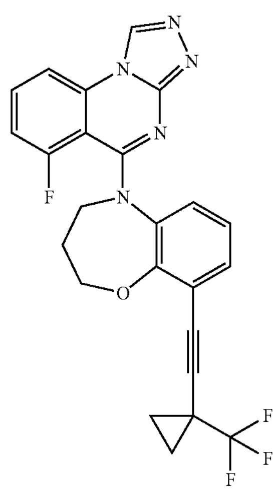 [SMILES: Fc1cccc2c1c(N1CCCOc3c(C#CC4(C(F)(F)F)CC4)cccc31)nc1nncn12] | 468.376 | 1H NMR (400 MHz, Methanol-d4) δ 9.61 (s, 1H), 8.15 (d, J = 8.3 Hz, 1H), 8.01 (td, J = 8.3, 5.0 Hz, 1H), 7.35 (dd, J = 7.1, 2.2 Hz, 1H), 7.29-7.07 (m, 1H), 6.93-6.68 (m, 2H), 4.45 (s, 2H), 3.39-3.27 (m, 2H), 2.27 (q, J = 5.8 Hz, 2H), 1.56-1.25 (m, 4H). |

TABLE 1-continued

Compounds and characterization of the compounds

| EXAMPLE | STRUCTURE | LC/MS | NMR |
|---|---|---|---|
| 122 | 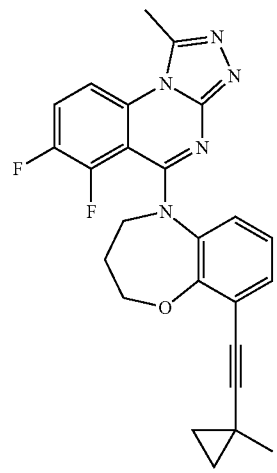 [SMILES: Cc1nnc2nc(N3CCCOc4c(C#CC5(C)CC5)cccc43)c3c(F)c(F)ccc3n12] | 446.32 | 1H NMR (400 MHz, Methanol-d4) δ 8.22 (d, J = 9.4 Hz, 1H), 7.98 (q, J = 9.0 Hz, 1H), 7.31 (dd, J = 7.7, 1.7 Hz, 1H), 6.84-6.65 (m, 2H), 4.42 (s, 2H), 3.36-3.28 (m, 2H), 3.08 (s, 3H), 2.26 (s, 2H), 1.41 (s, 3H), 1.05 (q, J = 4.1 Hz, 2H), 0.86-0.68 (m, 2H). |
| 123 | 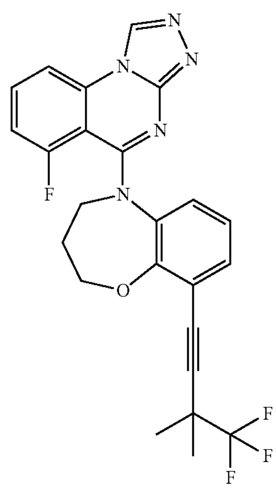 [SMILES: CC(C)(C#Cc1cccc2c1OCCCN2c1nc2nncn2c2cccc(F)c12)C(F)(F)F] | 470.354 | 1H NMR (400 MHz, Methanol-d4) δ 9.60 (t, J = 2.1 Hz, 1H), 8.21-8.07 (m, 1H), 8.00 (tt, J = 8.7, 3.4 Hz, 1H), 7.32 (q, J = 3.3 Hz, 1H), 7.20 (t, J = 10.2 Hz, 1H), 6.80 (t, J = 3.7 Hz, 2H), 4.44 (s, 2H), 3.38-3.23 (m, 2H), 2.28 (d, J = 7.1 Hz, 2H), 1.66-1.50 (m, 6H). |
| 124 | 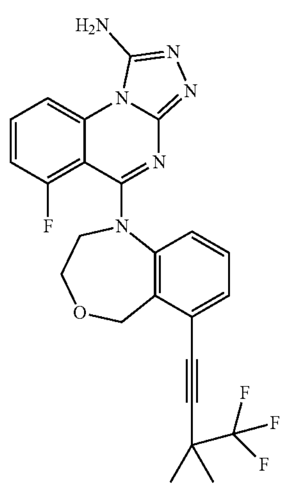 [SMILES: CC(C)(C#Cc1cccc2c1COCCN2c1nc2nnc(N)n2c2cccc(F)c12)C(F)(F)F] | 485.1 | 1H NMR (400 MHz, DMSO-d6) δ 8.27 (d, J = 8.5 Hz, 1H), 7.94 (td, J = 8.5, 5.5 Hz, 1H), 7.50 (s, 2H), 7.34 (dd, J = 7.7, 1.2 Hz, 1H), 7.25 (dd, J = 12.2, 8.3 Hz, 1H), 7.09 (t, J = 7.9 Hz, 1H), 6.99 (dd, J = 8.0, 1.2 Hz, 1H), 4.57 (d, J = 445.6 Hz, 6H), 1.55 (s, 6H). |

TABLE 1-continued

Compounds and characterization of the compounds

| EXAMPLE | STRUCTURE | LC/MS | NMR |
|---|---|---|---|
| 125 | 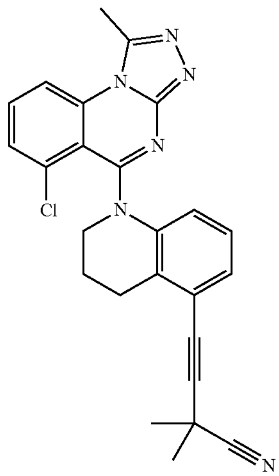 [SMILES: Cc1nnc2nc(N3CCCc4c(C#CC(C)(C)C#N)cccc43)c3c(Cl)cccc3n12] | 441.1 | 1H NMR (400 MHz, DMSO-d6) δ 8.47-8.23 (m, 1H), 7.94 (t, J = 8.3 Hz, 1H), 7.64 (dd, J = 8.0, 0.9 Hz, 1H), 7.16 (d, J = 7.7 Hz, 1H), 6.91 (t, J = 7.9 Hz, 1H), 6.64 (d, J = 8.2 Hz, 1H), 4.27-4.02 (m, 1H), 3.72 (ddd, J = 12.1, 7.4, 4.5 Hz, 1H), 3.01 (s, 4H), 2.95-2.79 (m, 1H), 2.34-2.22 (m, 1H), 1.96 (dt, J = 12.9, 6.2 Hz, 1H), 1.76 (s, 6H). |
| 126 | 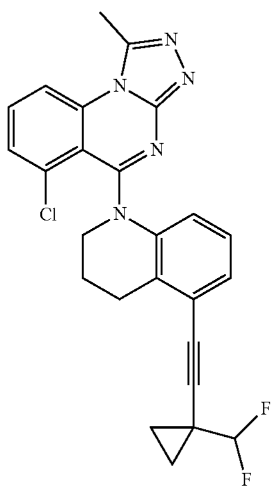 [SMILES: Cc1nnc2nc(N3CCCc4c(C#CC5(C(F)F)CC5)cccc43)c3c(Cl)cccc3n12] | 464.1 | 1H NMR (400 MHz, DMSO-d6) δ 8.34 (dd, J = 8.7, 1.0 Hz, 1H), 7.94 (t, J = 8.2 Hz, 1H), 7.66-7.60 (m, 1H), 7.12 (dd, J = 7.6, 1.1 Hz, 1H), 6.87 (t, J = 7.9 Hz, 1H), 6.60 (d, J = 8.2 Hz, 1H), 5.80 (t, J = 55.6 Hz, 1H), 4.20 (dd, J = 12.5, 6.5 Hz, 1H), 3.71 (ddd, J = 12.2, 7.3, 4.6 Hz, 1H), 3.01 (s, 4H), 2.85 (dt, J = 17.1, 7.1 Hz, 1H), 2.32-2.11 (m, 1H), 1.95 (dq, J = 13.0, 6.7 Hz, 1H), 1.35-1.14 (m, 4H). |
| 127 | 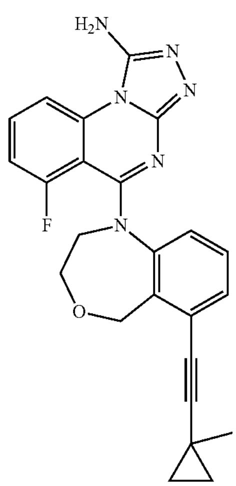 [SMILES: CC1(C#Cc2cccc3c2COCCN3c2nc3nnc(N)n3c3cccc(F)c23)CC1] | 429.2 | 1H NMR (400 MHz, DMSO-d6) δ 8.27 (d, J = 8.6 Hz, 1H), 8.08-7.79 (m, 1H), 7.37 (s, 2H), 7.31-7.15 (m, 2H), 7.01 (t, J = 7.9 Hz, 1H), 6.86 (d, J = 7.9 Hz, 1H), 5.14 (s, 3H), 4.00 (s, 3H), 1.36 (s, 3H), 1.00 (q, J = 4.0 Hz, 2H), 0.86-0.72 (m, 2H). |

TABLE 1-continued

Compounds and characterization of the compounds

| EXAMPLE | STRUCTURE | LC/MS | NMR |
|---|---|---|---|
| 128 | 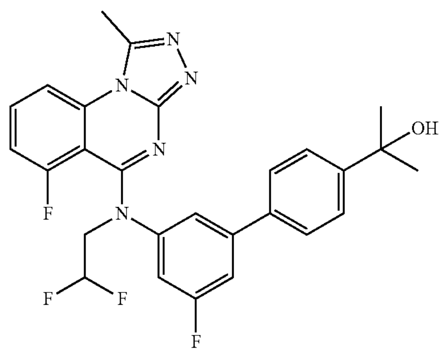 [SMILES: Cc1nnc2nc(N(CC(F)F)c3cc(F)cc(-c4ccc(C(C)(C)O)cc4)c3)c3c(F)cccc3n12] | 510.1 | 1H NMR (400 MHz, DMSO-d6) δ 8.18 (d, J = 8.6 Hz, 1H), 7.96 (td, J = 8.4, 5.3 Hz, 1H), 7.58-7.36 (m, 4H), 7.36-7.20 (m, 3H), 7.12 (dt, J = 10.4, 2.2 Hz, 1H), 6.57 (t, J = 55.6 Hz, 1H), 4.74 (t, J = 13.9 Hz, 2H), 3.02 (s, 3H), 1.41 (s, 6H). |
| 129 | 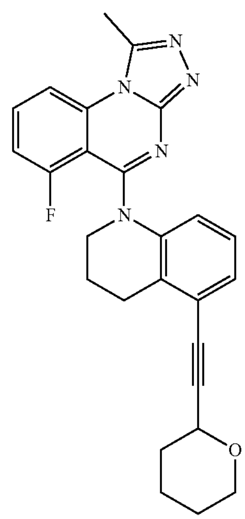 [SMILES: Cc1nnc2nc(N3CCCc4c(C#CC5CCCCO5)cccc43)c3c(F)cccc3n12] | 442.2 | 1H NMR (400 MHz, DMSO-d6) δ 8.17 (d, J = 8.7 Hz, 1H), 8.00 (td, J = 8.4, 5.4 Hz, 1H), 7.37 (dd, J = 11.9, 8.2 Hz, 1H), 7.16 (d, J = 7.5 Hz, 1H), 6.95 (t, J = 7.8 Hz, 1H), 6.85 (d, J = 8.2 Hz, 1H), 4.63 (dd, J = 7.2, 3.4 Hz, 1H), 4.13 (s, 2H), 3.91 (dt, J = 10.5, 4.8 Hz, 1H), 3.55 (dt, J = 11.2, 5.7 Hz, 1H), 3.00 (s, 3H), 2.91 (m, 2H), 2.05 (s, 2H), 1.87 (s, 2H), 1.69 (s, 2H), 1.53 (t, J = 5.6 Hz, 2H). |
| 130 | 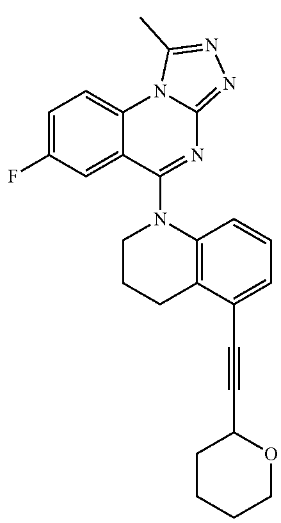 [SMILES: Cc1nnc2nc(N3CCCc4c(C#CC5CCCCO5)cccc43)c3cc(F)ccc3n12] | 442.2 | 1H NMR (400 MHz, DMSO-d6) δ 8.38 (dd, J = 9.4, 4.5 Hz, 1H), 7.87 (td, J = 9.6, 8.7, 3.0 Hz, 1H), 7.45 (dd, J = 9.6, 2.9 Hz, 1H), 7.20 (d, J = 7.5 Hz, 1H), 7.01 (t, J = 7.9 Hz, 1H), 6.83 (d, J = 8.3 Hz, 1H), 4.65 (dd, J = 7.2, 3.3 Hz, 1H), 3.95 (dt, J = 21.9, 6.0 Hz, 3H), 3.56 (dt, J = 11.1, 5.6 Hz, 1H), 3.01 (s, 5H), 2.18-1.99 (m, 2H), 1.89 (q, J = 16.0, 12.4 Hz, 2H), 1.68 (dd, J = 19.4, 10.8 Hz, 2H), 1.53 (t, J = 5.5 Hz, 2H). |

TABLE 1-continued

Compounds and characterization of the compounds

| EXAMPLE | STRUCTURE | LC/MS | NMR |
|---|---|---|---|
| 131 | 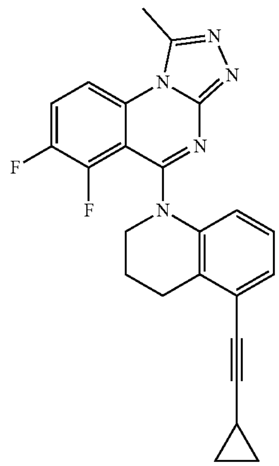 [SMILES: Cc1nnc2nc(N3CCCc4c(C#CC5CC5)cccc43)c3c(F)c(F)ccc3n12] | 416.1 | 1H NMR (400 MHz, DMSO-d6) δ 8.20-7.99 (m, 2H), 7.07 (d, J = 7.5 Hz, 1H), 6.90 (t, J = 7.9 Hz, 1H), 6.76 (d, J = 8.2 Hz, 1H), 3.98 (m, 2H), 2.97 (s, 3H), 2.12 (s, 2H), 1.61 (tt, J = 8.3, 5.0 Hz, 1H), 1.02-0.88 (m, 2H), 0.85-0.72 (m, 2H). |
| 132 | 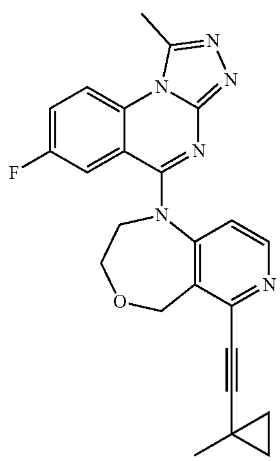 [SMILES: Cc1nnc2nc(N3CCOCc4c3ccnc4C#CC3(C)CC3)c3cc(F)ccc3n12] | 429.31 | 1H NMR (400 MHz, Methanol-d4) δ 8.54 (dd, J = 9.4, 4.4 Hz, 1H), 8.17 (d, J = 6.0 Hz, 1H), 7.88 (m, 1H), 7.29 (dd, J = 9.0, 2.8 Hz, 1H), 6.95 (d, J = 6.1 Hz, 1H), 5.27 (s, 2H), 4.56 (br, 2H), 4.14 (t, J = 4.9 Hz, 2H), 3.15 (s, 3H), 1.48 (s, 3H), 1.22 (q, J = 4.2 Hz, 2H), 0.94 (q, J = 4.3 Hz, 2H). |
| 133 | 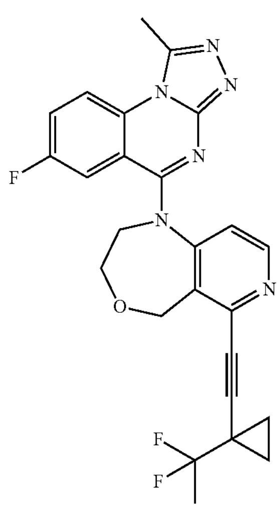 [SMILES: Cc1nnc2nc(N3CCOCc4c3ccnc4C#CC3(C(C)(F)F)CC3)c3cc(F)ccc3n12] | 479.34 | 1H NMR (400 MHz, Methanol-d4) δ 8.53 (dd, J = 9.4, 4.4 Hz, 1H), 8.23 (d, J = 5.6 Hz, 1H), 7.85 (m, 1H), 7.19 (dd, J = 9.1, 2.8 Hz, 1H), 6.95 (d, J = 5.6 Hz, 1H), 5.28 (s, 2H), 4.51 (s, 2H), 4.14 (t, J = 4.7 Hz, 2H), 3.14 (s, 3H), 1.95 (t, J = 18.0 Hz, 3H), 1.47-1.37 (m, 2H), 1.32 (m, 2H). |

TABLE 1-continued

Compounds and characterization of the compounds

| EXAMPLE | STRUCTURE | LC/MS | NMR |
|---|---|---|---|
| 134 | 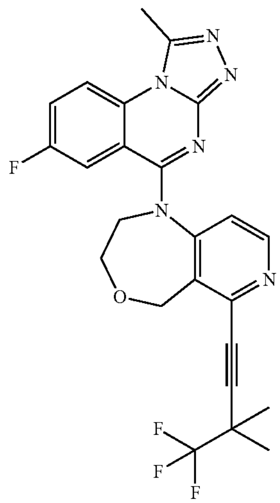 [SMILES: Cc1nnc2nc(N3CCOCc4c3ccnc4C#CC(C)(C)C(F)(F)F)c3cc(F)ccc3n12] | 485.38 | 1H NMR (400 MHz, Methanol-d4) δ 8.52 (dd, J = 9.5, 4.5 Hz, 1H), 8.27 (d, J = 5.6 Hz, 1H), 7.85 (m, 1H), 7.16 (dd, J = 9.1, 2.9 Hz, 1H), 6.97 (d, J = 5.5 Hz, 1H), 5.28 (s, 2H), 4.49 (s, 2H), 4.13 (t, J = 4.7 Hz, 2H), 3.14 (s, 3H), 1.65 (s, 6H). |
| 135 | 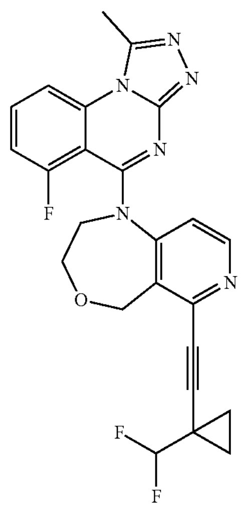 [SMILES: Cc1nnc2nc(N3CCOCc4c3ccnc4C#CC3(C(F)F)CC3)c3c(F)cccc3n12] | 465.36 | 1H NMR (400 MHz, Methanol-d4) δ 8.28 (dd, J = 8.6, 0.9 Hz, 1H), 8.11 (d, J = 5.7 Hz, 1H), 8.05 (td, J = 8.5, 5.5 Hz, 1H), 7.29 (m, 1H), 6.84 (d, J = 5.7 Hz, 1H), 5.77 (t, J = 56.2 Hz, 1H), 5.20 (br, 2H), 4.37 (br, 2H), 4.13 (t, J = 4.6 Hz, 2H), 3.13 (s, 3H), 1.36 (m, 4H). |
| 136 | 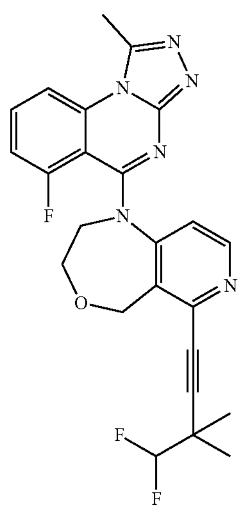 [SMILES: Cc1nnc2nc(N3CCOCc4c3ccnc4C#CC(C)(C)C(F)F)c3c(F)cccc3n12] | 467.38 | 1H NMR (400 MHz, Methanol-d4) δ 8.32 (d, J = 8.6 Hz, 1H), 8.15 (dd, J = 5.7, 0.9 Hz, 1H), 8.13-8.03 (m, 1H), 7.32 (dd, J = 12.2, 8.4 Hz, 1H), 6.90 (dd, J = 5.8, 2.4 Hz, 1H), 5.92 (t, J = 56.4 Hz, 1H), 5.21 (br, 2H), 4.43 (br, 2H), 4.14 (t, J = 4.5 Hz, 2H), 3.15 (s, 3H), 1.49 (s, 6H). |

… TABLE 1-continued
Compounds and characterization of the compounds
| EXAMPLE | STRUCTURE | LC/MS | NMR |
|---|---|---|---|
| 137 | 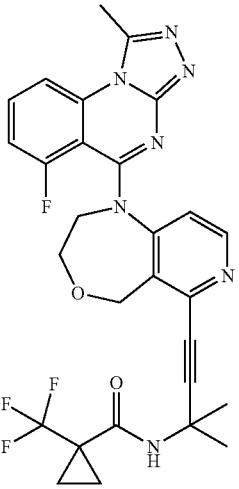 [SMILES: Cc1nnc2nc(N3CCOCc4c3ccnc4C#CC(C)(C)NC(=O)C3(C(F)(F)F)CC3)c3c(F)cccc3n12] | 568.37 | 1H NMR (400 MHz, Methanol-d4) δ 8.35 (d, J = 8.6 Hz, 1H), 8.26 (d, J = 6.5 Hz, 1H), 8.11 (td, J = 8.5, 5.5 Hz, 1H), 7.38 (dd, J = 12.2, 8.3 Hz, 1H), 7.17 (d, J = 6.4 Hz, 1H), 4.97 (br, 2H), 4.64 (m, 2H), 4.13 (m, 2H), 3.17 (s, 3H), 1.54 (s, 6H), 1.46-1.40 (m, 2H), 1.40-1.34 (m, 2H). |
| 138 | 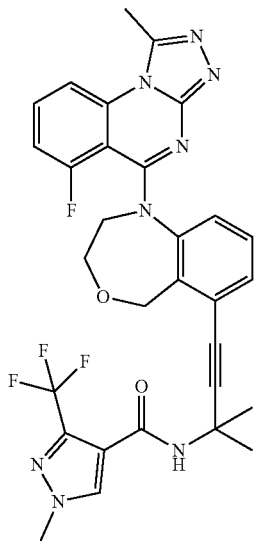 [SMILES: Cc1nnc2nc(N3CCOCc4c(C#CC(C)(C)NC(=O)c5cn(C)nc5C(F)(F)F)cccc43)c3c(F)cccc3n12] | 607.41 | 1H NMR (400 MHz, Methanol-d4) δ 8.17-8.06 (m, 2H), 7.87 (td, J = 8.4, 5.4 Hz, 1H), 7.27 (dd, J = 7.8, 1.1 Hz, 1H), 7.06 (dd, J = 12.0, 8.3 Hz, 1H), 6.96 (t, J = 7.9 Hz, 1H), 6.60 (dd, J = 8.0, 1.1 Hz, 1H), 5.19 (br, 4H), 4.07 (m, 2H), 3.98 (s, 3H), 3.05 (s, 3H), 1.80 (s, 6H). |
| 139 | 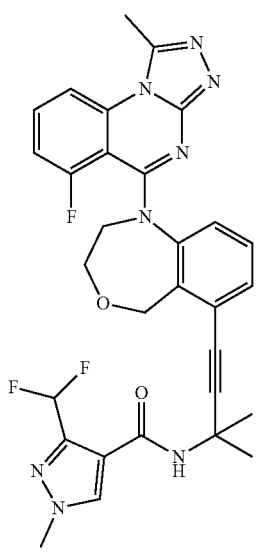 [SMILES: Cc1nnc2nc(N3CCOCc4c(C#CC(C)(C)NC(=O)c5cn(C)nc5C(F)F)cccc43)c3c(F)cccc3n12] | 589.37 | 1H NMR (400 MHz, Methanol-d4) δ 8.17 (d, J = 1.5 Hz, 1H), 8.13 (d, J = 8.5 Hz, 1H), 7.87 (td, J = 8.4, 5.4 Hz, 1H), 7.42-7.19 (m, 2H), 7.13-7.02 (m, 1H), 6.96 (t, J = 7.9 Hz, 1H), 6.60 (dd, J = 8.0, 1.0 Hz, 1H), 5.51 (s, 4H), 4.07 (t, J = 4.4 Hz, 2H), 3.97 (s, 3H), 3.05 (s, 3H), 1.81 (s, 6H). |

TABLE 1-continued
Compounds and characterization of the compounds
| EXAMPLE | STRUCTURE | LC/MS | NMR |
|---|---|---|---|
| 140 | 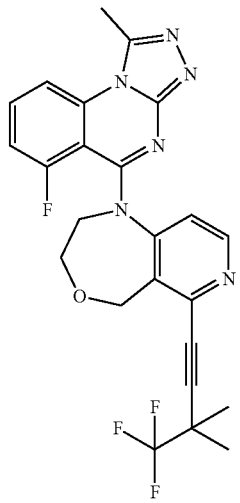 [SMILES: Cc1nnc2nc(N3CCOCc4c3ccnc4C#CC(C)(C)C(F)(F)F)c3c(F)cccc3n12] | 485.32 | 1H NMR (400 MHz, Methanol-d4) δ 8.28 (d, J = 8.6 Hz, 1H), 8.16 (d, J = 5.6 Hz, 1H), 8.07 (td, J = 8.5, 5.5 Hz, 1H), 7.29 (dd, J = 12.1, 8.3 Hz, 1H), 6.85 (d, J = 5.5 Hz, 1H), 5.18 (br, 2H), 4.90 (br, 2H), 4.14 (s, 2H), 3.14 (s, 3H), 1.63 (s, 6H). |
| 141 | 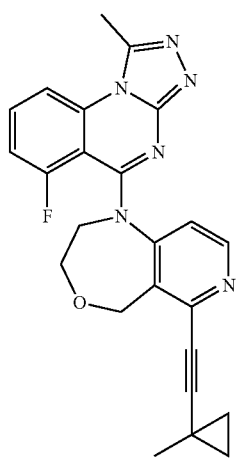 [SMILES: Cc1nnc2nc(N3CCOCc4c3ccnc4C#CC3(C)CC3)c3c(F)cccc3n12] | 429.33 | 1H NMR (400 MHz, Methanol-d4) δ 8.34 (dd, J = 8.7, 0.9 Hz, 1H), 8.17-8.06 (m, 2H), 7.36 (m, 1H), 6.97 (d, J = 6.1 Hz, 1H), 5.19 (s, 2H), 4.53 (br, 2H), 4.20-4.06 (m, 2H), 3.16 (s, 3H), 1.48 (s, 3H), 1.21 (q, J = 4.2 Hz, 2H), 0.99-0.87 (m, 2H). |
| 142 | 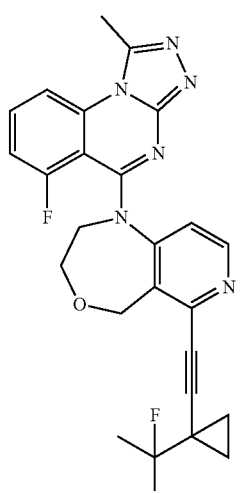 | 479.32 | 1H NMR (400 MHz, Methanol-d4) δ 8.29 (d, J = 8.6 Hz, 1H), 8.14 (d, J = 5.7 Hz, 1H), 8.08 (td, J = 8.5, 5.4 Hz, 1H), 7.30 (m, 1H), 6.86 (d, J = 5.7 Hz, 1H), 5.19 (s, 2H), 4.35-4.78 (br, 2H), 4.35 (m, 2H), 4.14 (t, J = 4.6 Hz, 2H), 3.14 (s, 3H), 1.93 (t, J = 18.0 Hz, 3H), 1.45-1.36 (m, 2H), 1.30 (m, 2H). |

TABLE 1-continued

Compounds and characterization of the compounds

| EXAMPLE | STRUCTURE | LC/MS | NMR |
|---|---|---|---|
| 143 | 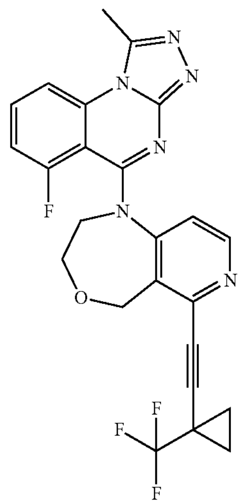 [SMILES: Cc1nnc2nc(N3CCOCc4c3ccnc4C#CC3(C(C)(F)F)CC3)c3c(F)cccc3n12] | 483.33 | 1H NMR (400 MHz, Methanol-d4) δ 8.28 (d, J = 8.6 Hz, 1H), 8.14 (d, J = 5.5 Hz, 1H), 8.06 (td, J = 8.4, 5.4 Hz, 1H), 7.28 (m, 1H), 6.84 (d, J = 5.5 Hz, 1H), 5.18 (br, 2H), 4.40 (br, 2H), 4.13 (t, J = 4.5 Hz, 2H), 3.14 (s, 3H), 1.60-1.53 (m, 2H), 1.49 (tt, J = 6.1, 3.0 Hz, 2H). |
| 144 | 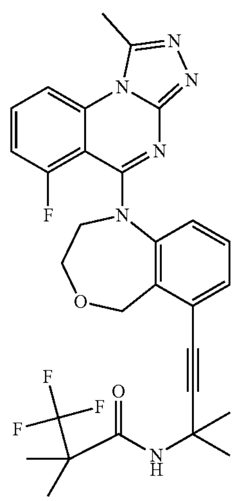 [SMILES: Cc1nnc2nc(N3CCOCc4c(C#CC(C)(C)NC(=O)C(C)(C)C(F)(F)F)cccc43)c3c(F)cccc3n12] | 569.38 | 1H NMR (400 MHz, Methanol-d4) δ 8.23 (d, J = 8.6 Hz, 1H), 8.02 (td, J = 8.5, 5.4 Hz, 1H), 7.51 (s, 1H), 7.36 (dd, J = 7.8, 1.2 Hz, 1H), 7.21 (dd, J = 11.8, 8.4 Hz, 1H), 7.03 (t, J = 7.9 Hz, 1H), 6.78 (dd, J = 8.0, 1.1 Hz, 1H), 5.37 (br, 2H), 4.87 (br, 1H), 4.14 (s, 2H), 3.10 (s, 3H), 1.75 (s, 6H), 1.48 (s, 6H). |
| 145 | 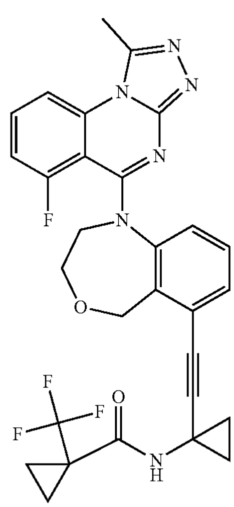 [SMILES: Cc1nnc2nc(N3CCOCc4c(C#CC5(NC(=O)C6(C(F)(F)F)CC6)CC5)cccc43)c3c(F)cccc3n12] | 565.37 | 1H NMR (400 MHz, Methanol-d4) δ 8.12 (d, J = 8.5 Hz, 1H), 7.87 (m, 1H), 7.43 (d, J = 7.9 Hz, 1H), 7.05 (dd, J = 12.0, 8.3 Hz, 1H), 6.98 (td, J = 8.0, 7.5, 4.7 Hz, 1H), 6.47 (d, J = 7.8 Hz, 1H), 5.03 (br, 2H), 4.88 (br, 2H, ) 4.08 (m, 2H), 3.05 (s, 3H), 1.66 (q, J = 4.9 Hz, 2H), 1.56 (d, J = 18.1 Hz, 2H), 1.53-1.46 (m, 2H), 1.36-1.27 (m, 2H). |

TABLE 1-continued

Compounds and characterization of the compounds

| EXAMPLE | STRUCTURE | LC/MS | NMR |
|---|---|---|---|
| 146 | 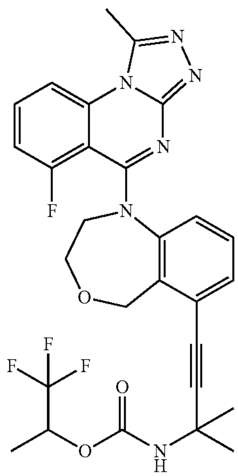 [SMILES: Cc1nnc2nc(N3CCOCc4c(C#CC(C)(C)NC(=O)OC(C)C(F)(F)F)cccc43)c3c(F)cccc3n12] | 571.34 | 1H NMR (400 MHz, Methanol-d4) δ 8.24 (d, J = 8.6 Hz, 1H), 8.03 (td, J = 8.5, 5.3 Hz, 1H), 7.37 (dd, J = 7.8, 1.0 Hz, 1H), 7.22 (dd, J = 11.8, 8.3 Hz, 1H), 7.04 (t, J = 7.9 Hz, 1H), 6.80 (dd, J = 8.0, 1.1 Hz, 1H), 5.37 (br, 2H), 5.32 (q, J = 6.7 Hz, 1H), 5.05 (br, 2H), 4.15 (s, 2H), 3.10 (s, 3H), 1.71 (s, 6H), 1.44 (d, J = 6.6 Hz, 3H). |
| 147 | 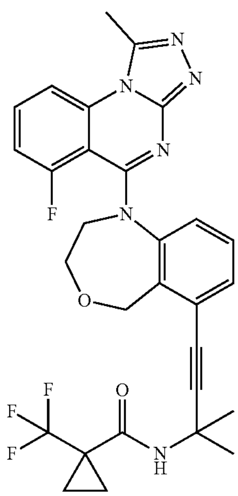 [SMILES: Cc1nnc2nc(N3CCOCc4c(C#CC(C)(C)NC(=O)C5(C(F)(F)F)CC5)cccc43)c3c(F)cccc3n12] | 567.35 | 1H NMR (400 MHz, Methanol-d4) δ 8.24 (d, J = 8.6 Hz, 1H), 8.03 (td, J = 8.5, 5.3 Hz, 1H), 7.37 (dd, J = 7.8, 1.0 Hz, 1H), 7.21 (dd, J = 11.8, 8.3 Hz, 1H), 7.04 (t, J = 7.9 Hz, 1H), 6.82 (d, J = 7.9 Hz, 1H), 5.51 (br, 2H), 4.98 (br, 2H), 4.32-4.05 (m, 2H), 3.10 (s, 3H), 1.74 (s, 6H), 1.36-1.27 (m, 4H). |
| 148 | 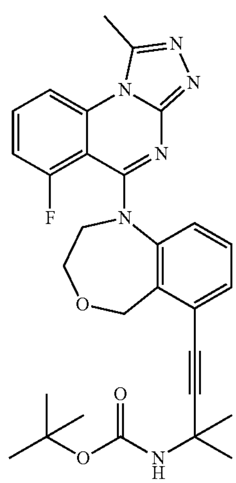 [SMILES: Cc1nnc2nc(N3CCOCc4c(C#CC(C)(C)NC(=O)OC(C)(C)C)cccc43)c3c(F)cccc3n12] | 531.24 | 1H NMR (400 MHz, CDCl3/Methanol-d4) δ 8.10 (d, J = 8.5 Hz, 1H), 7.87 (td, J = 8.4, 5.4 Hz, 1H), 7.26 (dd, J = 7.8, 1.1 Hz, 1H), 7.04 (m, 1H), 6.95 (t, J = 7.9 Hz, 1H), 6.54 (dd, J = 8.1, 1.1 Hz, 1H), 5.32 (br, 2H), 4.07 (s, 2H), 3.37 (s, 2H), 3.06 (s, 3H), 1.67 (s, 6H), 1.51 (s, 9H). |

TABLE 1-continued

Compounds and characterization of the compounds

| EXAMPLE | STRUCTURE | LC/MS | NMR |
|---|---|---|---|
| 149 | 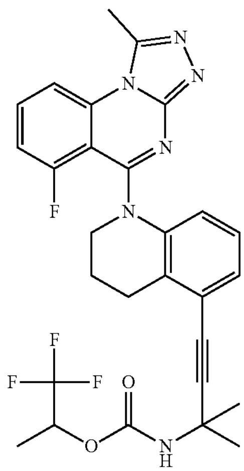 [SMILES: Cc1nnc2nc(N3CCCc4c(C#CC(C)(C)NC(=O)OC(C)C(F)(F)F)cccc43)c3c(F)cccc3n12] | 555.39 | 1H NMR (400 MHz, Methanol-d4) δ 8.25 (d, J = 8.6 Hz, 1H), 8.08 (td, J = 8.5, 5.4 Hz, 1H), 7.32 (m, 1H), 7.27 (dd, J = 7.6, 1.2 Hz, 1H), 6.95 (t, J = 7.9 Hz, 1H), 6.86 (dd, J = 8.1, 1.2 Hz, 1H), 5.30 (m, 1H), 4.20 (m, 2H), 3.10 (m, 5H), 2.19 (m, 2H), 1.71 (s, 6H), 1.43 (d, J = 6.6 Hz, 3H). |
| 150 | 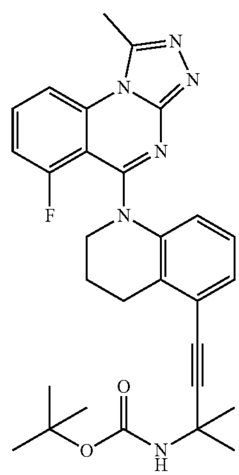 [SMILES: Cc1nnc2nc(N3CCCc4c(C#CC(C)(C)NC(=O)OC(C)(C)C)cccc43)c3c(F)cccc3n12] | 515.27 | 1H NMR (400 MHz, CDCl3/Methanol-d4) δ 8.08 (dd, J = 8.5, 3.7 Hz, 1H), 7.90 (td, J = 8.4, 5.2 Hz, 1H), 7.13 (m, 2H), 6.83 (t, J = 7.9 Hz, 1H), 6.54 (dt, J = 8.2, 1.4 Hz, 1H), 4.11 (q, J = 7.1 Hz, 2H), 3.05 (m, 5H), 2.15 (m, 2H), 1.67 (s, 6H), 1.49 (s, 9H). |
| 151 | 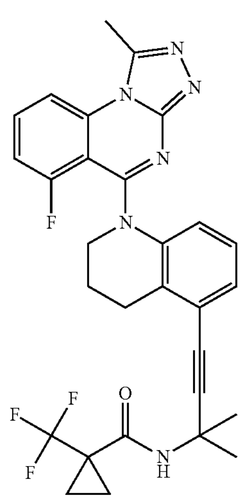 [SMILES: Cc1nnc2nc(N3CCCc4c(C#CC(C)(C)NC(=O)C5(C(F)(F)F)CC5)cccc43)c3c(F)cccc3n12] | 551.35 | 1H NMR (400 MHz, Methanol-d4) δ 8.25 (d, J = 8.6 Hz, 1H), 8.08 (td, J = 8.4, 5.4 Hz, 1H), 7.32 (dd, J = 11.5, 8.3 Hz, 1H), 7.26 (dd, J = 7.6, 1.2 Hz, 1H), 6.94 (t, J = 7.9 Hz, 1H), 6.87 (dd, J = 8.2, 1.2 Hz, 1H), 4.49-3.89 (m, 2H), 3.10 (m, 5H), 2.19 (m, 2H), 1.74 (s, 6H), 1.36-1.26 (m, 4H). |

TABLE 1-continued

Compounds and characterization of the compounds

| EXAMPLE | STRUCTURE | LC/MS | NMR |
|---|---|---|---|
| 152 | 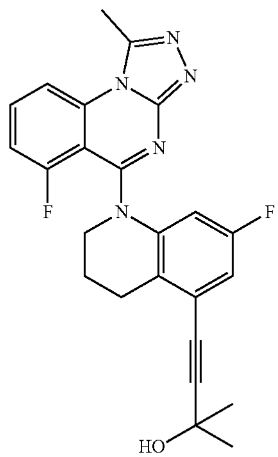 [SMILES: Cc1nnc2nc(N3CCCc4c(C#CC(C)(C)O)cc(F)cc43)c3c(F)cccc3n12] | 434.3 | 1H NMR (400 MHz, Methanol-d4) δ 8.29 (d, J = 8.6 Hz, 1H), 8.11 (td, J = 8.4, 5.3 Hz, 1H), 7.40 (dd, J = 11.6, 8.3 Hz, 1H), 6.99 (dd, J = 8.9, 2.5 Hz, 1H), 6.74 (dd, J = 10.1, 2.6 Hz, 1H), 4.16 (m, 2H), 3.12 (s, 3H), 3.04 m, 2H), 2.19 (m, 2H), 1.63 (s, 6H). |
| 153 | 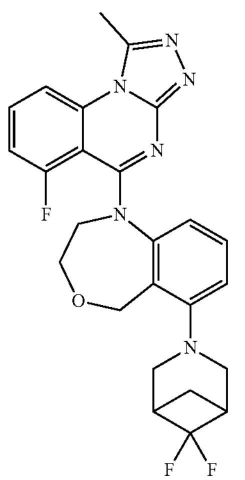 [SMILES: Cc1nnc2nc(N3CCOCc4c(N5CC6CC(C5)C6(F)F)cccc43)c3c(F)cccc3n12] | 481.2 | 1H NMR (400 MHz, DMSO-d6) δ 8.15 (d, J = 8.6 Hz, 1H), 8.00-7.90 (m, 1H), 7.26 (dd, J = 12.0, 8.2 Hz, 1H), 7.11 (d, J = 8.1 Hz, 1H), 6.98 (t, J = 8.0 Hz, 1H), 6.48 (d, J = 7.9 Hz, 1H), 5.52-4.49 (m, 4H), 4.02 (br s, 4H), 3.00 (s, 3H), 2.98-2.91 (m, 2H), 2.24 (dd, J = 17.5, 9.2 Hz, 1H), 1.96-1.83 (m, 1H). One methylene peak from the benzoxazepine is obstructed by the broad water signal |
| 154 | 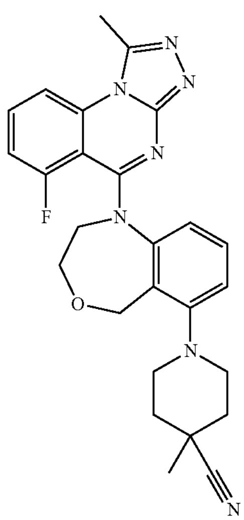 [SMILES: Cc1nnc2nc(N3CCOCc4c(N5CCC(C)(C#N)CC5)cccc43)c3c(F)cccc3n12] | 472.2 | 1H NMR (400 MHz, DMSO-d6) δ 8.16 (d, J = 8.6 Hz, 1H), 8.00-7.92 (m, 1H), 7.26 (dd, J = 12.0, 8.3 Hz, 1H), 7.03-6.95 (m, 2H), 6.53-6.46 (m, 1H), 4.03 (s, 4H), 3.28 (br s, 4H), 3.01 (s, 3H), 2.88 (br s, 2H), 2.10-1.94 (m, 2H), 1.90-1.73 (m, 2H), 1.45 (s, 3H). |

TABLE 1-continued

Compounds and characterization of the compounds

| EXAMPLE | STRUCTURE | LC/MS | NMR |
| --- | --- | --- | --- |
| 155 | 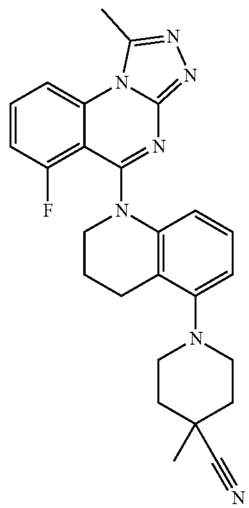 [SMILES: Cc1nnc2nc(N3CCCc4c(N5CCC(C)(C#N)CC5)cccc43)c3c(F)cccc3n12] | 456.2 | 1H NMR (400 MHz, DMSO-d6) δ 8.18 (d, J = 8.6 Hz, 1H), 8.07-7.95 (m, 1H), 7.36 (dd, J = 11.6, 8.3 Hz, 1H), 7.00-6.88 (m, 2H), 6.57 (dd, J = 7.0, 2.0 Hz, 1H), 3.99 (br s, 2H), 3.23-3.06 (m, 2H), 3.02 (s, 3H), 2.92-2.78 (m, 2H), 2.03 (d, J = 12.6 Hz, 2H), 1.79 (t, J = 12.0 Hz, 2H), 1.45 (s, 3H). Two methylene peaks from the tetrahydroquinoline are broad and hidden under other peaks (between 3.2-2.6 ppm and 2.3-1.55 ppm) |
| 156 | 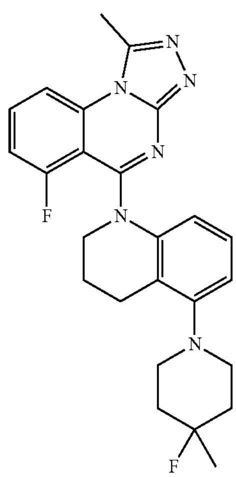 [SMILES: Cc1nnc2nc(N3CCCc4c(N5CCC(C)(F)CC5)cccc43)c3c(F)cccc3n12] | 449.2 | 1H NMR (400 MHz, DMSO-d6) δ 8.17 (d, J = 8.6 Hz, 1H), 8.05-7.94 (m, 1H), 7.35 (dd, J = 11.6, 8.3 Hz, 1H), 6.95-6.86 (m, 2H), 6.57-6.47 (m, 1H), 3.99 (s, 2H), 3.13-2.70 (m, 9H), 2.28-1.65 (m, 6H), 1.42 (d, J = 21.6 Hz, 3H). |
| 157 | 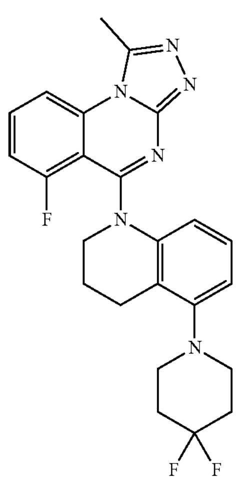 [SMILES: Cc1nnc2nc(N3CCCc4c(N5CCC(F)(F)CC5)cccc43)c3c(F)cccc3n12] | 453.1 | 1H NMR (400 MHz, DMSO-d6) δ 8.17 (d, J = 8.6 Hz, 1H), 8.04-7.96 (m, 1H), 7.35 (dd, J = 11.7, 8.3 Hz, 1H), 6.95-6.89 (m, 2H), 6.56 (dd, J = 5.3, 3.8 Hz, 1H), 3.98 (br s, 2H), 3.26-2.58 (m, 9H), 2.32-1.68 (m, 6H). |

TABLE 1-continued
Compounds and characterization of the compounds
| EXAMPLE | STRUCTURE | LC/MS | NMR |
|---|---|---|---|
| 158 | 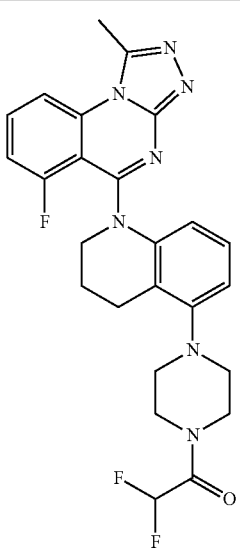 [SMILES: Cc1nnc2nc(N3CCCc4c(N5CCN(C(=O)C(F)F)CC5)cccc43)c3c(F)cccc3n12] | 496.2 | 1H NMR (400 MHz, DMSO-d6) δ 8.18 (d, J = 8.6 Hz, 1H), 8.05-7.93 (m, 1H), 7.36 (dd, J = 11.7, 8.2 Hz, 1H), 6.96-6.66 (m, 3H), 6.58 (dd, J = 7.7, 1.2 Hz, 1H), 5.08 (br s, 2H), 3.99 (br s, 2H), 3.71 (s, 4H), 3.01 (s, 3H), 2.95 (s, 4H), 2.00 (br s, 2H). |
| 159 | 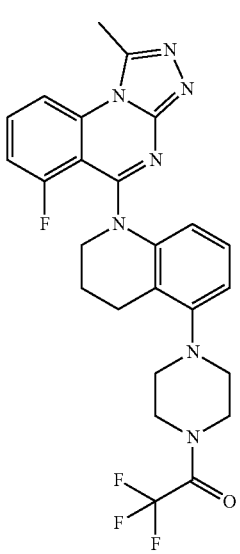 [SMILES: Cc1nnc2nc(N3CCCc4c(N5CCN(C(=O)C(F)(F)F)CC5)cccc43)c3c(F)cccc3n12] | 514.1 | 1H NMR (400 MHz, DMSO-d6) δ 8.17 (d, J = 8.6 Hz, 1H), 8.04-7.95 (m, 1H), 7.35 (dd, J = 11.7, 8.3 Hz, 1H), 6.97-6.86 (m, 2H), 6.58 (dd, J = 7.5, 1.4 Hz, 1H), 4.85 (br s, 2H), 3.98 (br s, 2H), 3.77 (s, 4H), 3.01 (s, 7H), 2.03 (br s, 2H). |

… TABLE 1-continued
Compounds and characterization of the compounds
| EXAMPLE | STRUCTURE | LC/MS | NMR |
|---|---|---|---|
| 160 | 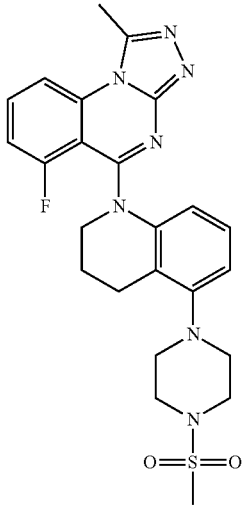 [SMILES: Cc1nnc2nc(N3CCCc4c(N5CCN(S(C)(=O)=O)CC5)cccc43)c3c(F)cccc3n12] | 496.1 | 1H NMR (400 MHz, DMSO-d6) δ 8.17 (d, J = 8.6 Hz, 1H), 8.03-7.95 (m, 1H), 7.36 (dd, J = 11.7, 8.2 Hz, 1H), 6.97-6.87 (m, 2H), 6.56 (dd, J = 7.2, 1.8 Hz, 1H), 3.98 (br s, 2H), 3.32 (s, 4H), 3.16-2.72 (m, 12H), 2.03 (br s, 2H). |
| 161 | 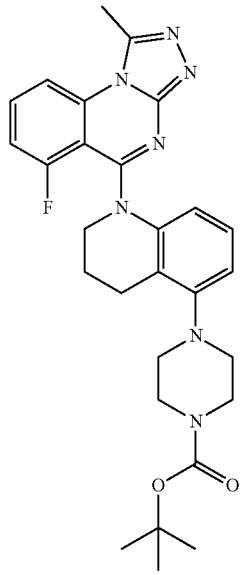 [SMILES: Cc1nnc2nc(N3CCCc4c(N5CCN(C(=O)OC(C)(C)C)CC5)cccc43)c3c(F)cccc3n12] | 518.2 | 1H NMR (400 MHz, DMSO-d6) δ 8.08 (d, J = 8.5 Hz, 1H), 7.92-7.84 (m, 1H), 7.23 (dd, J = 11.8, 8.2 Hz, 1H), 6.85 (t, J = 8.0 Hz, 1H), 6.75 (d, J = 7.9 Hz, 1H), 6.38 (d, J = 7.9 Hz, 1H), 3.85 (br s, 2H), 3.51 (s, 4H), 3.15-2.69 (m, 9H), 2.21 (br s, 1H), 1.74 (br s, 1H), 1.44 (s, 9H). |
| 162 | 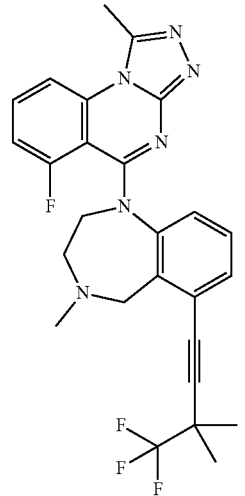 [SMILES: Cc1nnc2nc(N3CCN(C)Cc4c(C#CC(C)(C)C(F)(F)F)cccc43)c3c(F)cccc3n12] | 497.2 | 1H NMR (400 MHz, DMSO-d6) δ 8.14 (d, J = 8.4 Hz, 1H), 7.92 (td, J = 8.4, 5.5 Hz, 1H), 7.41 (d, J = 7.7 Hz, 1H), 7.27-7.17 (m, 2H), 6.95 (d, J = 8.1 Hz, 1H), 4.71 (br s, 2H), 2.99 (br s, 5H), 1.60 (s, 6H). One methylene peak and N—CH3 peak overlap with water signal. |

TABLE 1-continued

Compounds and characterization of the compounds

| EXAMPLE | STRUCTURE | LC/MS | NMR |
|---|---|---|---|
| 163 | 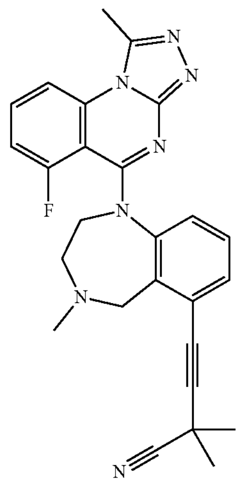 [SMILES: Cc1nnc2nc(N3CCN(C)Cc4c(C#CC(C)(C)C#N)cccc43)c3c(F)cccc3n12] | 454.2 | 1H NMR (400 MHz, DMSO-d6) δ 8.14 (d, J = 8.5 Hz, 1H), 7.92 (td, J = 8.4, 5.5 Hz, 1H), 7.45 (d, J = 7.7 Hz, 1H), 7.27-7.16 (m, 2H), 6.96 (d, J = 8.0 Hz, 1H), 4.73 (br s, 2H), 2.99 (br s, 5H), 1.82 (s, 6H). One methylene peak and N—CH3 peak obscured by water signal. |
| 164 | 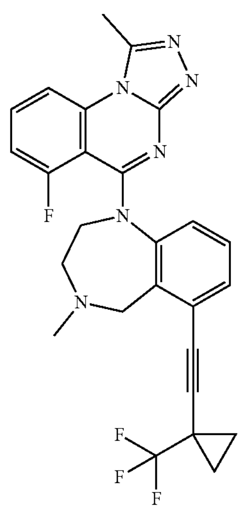 | 495.2 | 1H NMR (400 MHz, DMSO-d6) δ 8.14 (d, J = 8.5 Hz, 1H), 7.92 (td, J = 8.4, 5.6 Hz, 1H), 7.42 (d, J = 7.7 Hz, 1H), 7.26-7.16 (m, 2H), 6.94 (d, J = 8.0 Hz, 1H), 4.71 (br s, 3H), 3.74 (br s, 2H), 2.99 (br s, 5H), 1.55 (s, 4H). One methylene peak overlaps with water signal. |
| 165 | 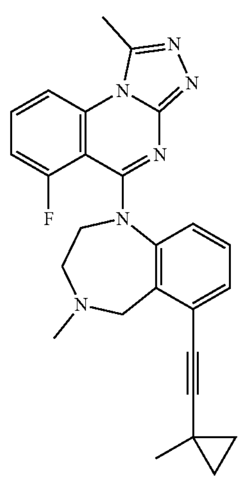 [SMILES: Cc1nnc2nc(N3CCN(C)Cc4c(C#CC5(C)CC5)cccc43)c3c(F)cccc3n12] | 441.2 | 1H NMR (400 MHz, DMSO-d6) δ 8.13 (d, J = 8.6 Hz, 1H), 7.92 (td, J = 8.4, 5.5 Hz, 1H), 7.32 (d, J = 7.7 Hz, 1H), 7.21 (dd, J = 12.4, 8.3 Hz, 1H), 7.15 (t, J = 7.9 Hz, 1H), 6.83 (d, J = 8.0 Hz, 1H), 4.74-4.63 (m, 2H), 3.70 (br s, 3H), 2.99 (br s, 5H), 1.40 (s, 3H), 1.12-1.04 (m, 2H), 0.89-0.81 (m, 2H). One methylene peak is obstructed by the water signal. |

TABLE 1-continued

Compounds and characterization of the compounds

| EXAMPLE | STRUCTURE | LC/MS | NMR |
|---|---|---|---|
| 166 | 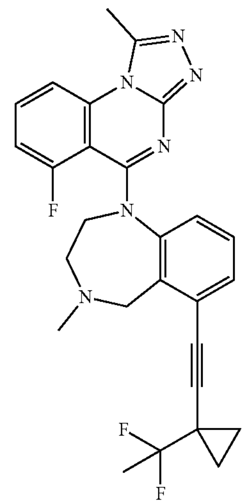 [SMILES: Cc1nnc2nc(N3CCN(C)Cc4c(C#CC5(C(C)(F)F)CC5)cccc43)c3c(F)cccc3n12] | 491.2 | 1H NMR (400 MHz, DMSO-d6) δ 8.14 (d, J = 8.5 Hz, 1H), 7.92 (td, J = 8.4, 5.5 Hz, 1H), 7.39 (d, J = 7.7 Hz, 1H), 7.25-7.14 (m, 2H), 6.89 (d, J = 8.1 Hz, 1H), 4.71 (s, 2H), 2.99 (s, 3H), 1.87 (t, J = 18.5 Hz, 3H), 1.37-1.31 (m, 2H), 1.31-1.25 (m, 2H). Two methylene peaks and the N—CH3 peak are obstructed by the water signal. |
| 167 | 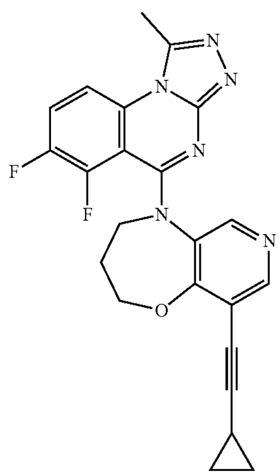 [SMILES: Cc1nnc2nc(N3CCCOc4c(C#CC5CC5)cncc43)c3c(F)c(F)ccc3n12] | 433.1 | 1H NMR (400 MHz, DMSO-d6) δ 8.32 (s, 1H), 8.19 (ddd, J = 9.5, 4.2, 1.4 Hz, 1H), 8.15-8.05 (m, 1H), 7.90 (s, 1H), 4.72 (br s, 2H), 4.23 (br s, 2H), 3.00 (s, 3H), 2.36-2.21 (m, 2H), 1.63 (tt, J = 8.2, 5.0 Hz, 1H), 1.00-0.90 (m, 2H), 0.84-0.74 (m, 2H). |
| 168 | 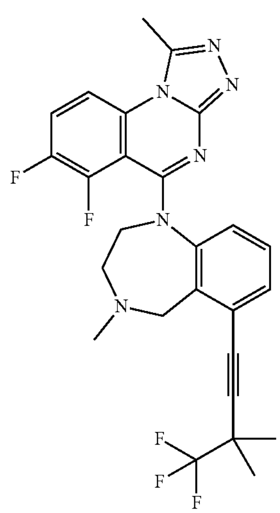 [SMILES: Cc1nnc2nc(N3CCN(C)Cc4c(C#CC(C)(C)C(F)(F)F)cccc43)c3c(F)c(F)ccc3n12] | 515.2 | 1H NMR (400 MHz, DMSO-d6) δ 8.16 (dd, J = 9.9, 4.0 Hz, 1H), 8.09-7.99 (m, 1H), 7.43 (d, J = 7.8 Hz, 1H), 7.24 (t, J = 7.9 Hz, 1H), 6.99 (d, J = 8.0 Hz, 1H), 4.71 (s, 2H), 2.98 (s, 3H), 1.60 (s, 6H). Two methylene signals and the N—CH3 signal overlap with the water peak. |

TABLE 1-continued

Compounds and characterization of the compounds

| EXAMPLE | STRUCTURE | LC/MS | NMR |
|---|---|---|---|
| 169 | 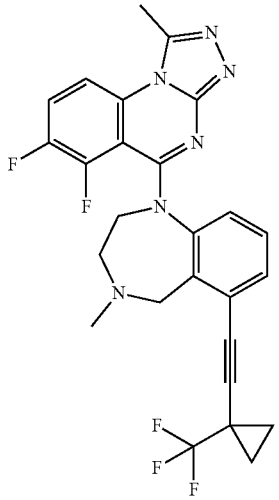 | 513.1 | 1H NMR (400 MHz, DMSO-d6) δ 8.19-8.11 (m, 1H), 8.04 (q, J = 9.2 Hz, 1H), 7.43 (d, J = 7.7 Hz, 1H), 7.23 (t, J = 7.9 Hz, 1H), 6.98 (d, J = 8.1 Hz, 1H), 4.71 (s, 2H), 2.98 (s, 4H), 1.55 (s, 4H). Two methylenes and N—CH3 overlap with the water signal. |
| 170 | 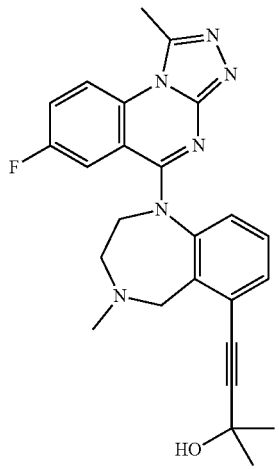 [SMILES: Cc1nnc2nc(N3CCN(C)Cc4c(C#CC(C)(C)O)cccc43)c3cc(F)ccc3n12] | 445.2 | 1H NMR (400 MHz, DMSO-d6) δ 8.34 (dd, J = 9.4, 4.7 Hz, 1H), 7.82-7.74 (m, 1H), 7.46 (dd, J = 7.7, 1.2 Hz, 1H), 7.30 (t, J = 7.9 Hz, 1H), 7.01 (dd, J = 8.0, 1.2 Hz, 1H), 6.88 (dd, J = 9.9, 2.9 Hz, 1H), 4.89 (s, 2H), 3.73 (s, 3H), 3.51 (s, 2H), 2.99 (s, 3H), 2.94 (s, 2H), 1.57 (s, 6H). |
| 171 | 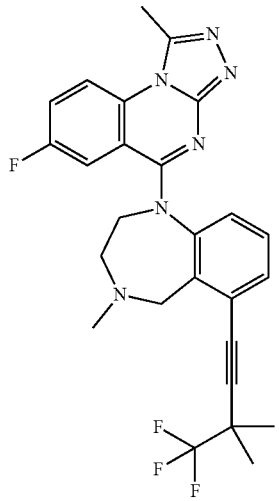 | 497.2 | 1H NMR (400 MHz, DMSO-d6) δ 8.33 (dd, J = 9.5, 4.7 Hz, 1H), 7.83-7.71 (m, 1H), 7.51 (dd, J = 7.7, 1.1 Hz, 1H), 7.31 (t, J = 7.9 Hz, 1H), 7.04 (dd, J = 8.2, 1.1 Hz, 1H), 6.92 (d, J = 9.6 Hz, 1H), 4.83 (s, 2H), 3.72 (s, 2H), 2.98 (s, 3H), 2.92 (s, 2H), 1.61 (s, 6H). N—CH3 peak is obscured by the water peak. |

TABLE 1-continued

Compounds and characterization of the compounds

| EXAMPLE | STRUCTURE | LC/MS | NMR |
|---|---|---|---|
| 172 | 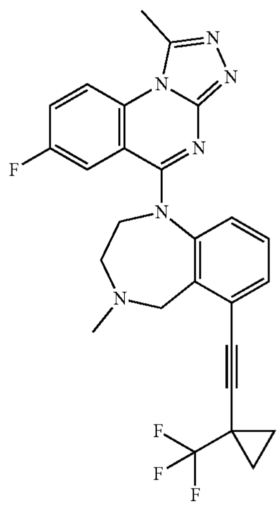 [SMILES: Cc1nnc2nc(N3CCN(C)Cc4c(C#CC5(C(F)(F)F)CC5)cccc43)c3cc(F)ccc3n12] | 495.2 | 1H NMR (400 MHz, DMSO-d6) δ 8.33 (dd, J = 9.4, 4.7 Hz, 1H), 7.82-7.73 (m, 1H), 7.52 (dd, J = 7.7, 1.1 Hz, 1H), 7.31 (t, J = 7.9 Hz, 1H), 7.04 (dd, J = 8.1, 1.1 Hz, 1H), 6.89 (dd, J = 9.7, 2.9 Hz, 1H), 4.83 (s, 2H), 2.98 (s, 3H), 2.91 (s, 2H), 1.59-1.52 (m, 4H). One methylene peak and the N—CH3 peak are obscured by the water peak. |
| 173 | 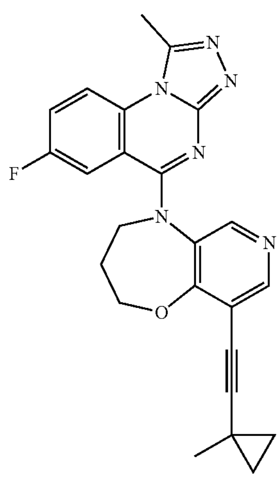 [SMILES: Cc1nnc2nc(N3CCCOc4c(C#CC5(C)CC5)cncc43)c3cc(F)ccc3n12] | 429.2 | 1H NMR (400 MHz, DMSO-d6) δ 8.48-8.36 (m, 2H), 7.98 (s, 1H), 7.93-7.85 (m, 1H), 7.04 (dd, J = 9.9, 2.9 Hz, 1H), 4.72-4.67 (m, 2H), 4.29 (s, 2H), 3.02 (s, 3H), 2.32-2.22 (m, 2H), 1.36 (s, 3H), 1.05-0.97 (m, 2H), 0.85-0.78 (m, 2H). |
| 174 | 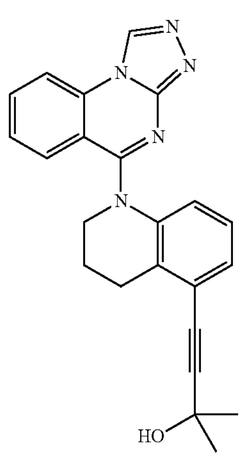 [SMILES: CC(C)(O)C#Cc1cccc2c1CCCN2c1nc2nncn2c2ccccc12] | 384.2 | 1H NMR (400 MHz, DMSO-d6) δ 9.88 (s, 1H), 8.42 (d, J = 8.2 Hz, 1H), 7.98 (ddd, J = 8.5, 7.2, 1.3 Hz, 1H), 7.63 (dd, J = 8.4, 1.3 Hz, 1H), 7.48 (ddd, J = 8.4, 7.2, 1.1 Hz, 1H), 7.16 (dd, J = 7.5, 1.2 Hz, 1H), 6.99 (t, J = 7.9 Hz, 1H), 6.87 (d, J = 8.1 Hz, 1H), 4.01 (t, J = 6.4 Hz, 2H), 3.00 (t, J = 6.7 Hz, 2H), 2.17-2.04 (m, 2H), 1.52 (s, 6H). |

TABLE 1-continued

Compounds and characterization of the compounds

| EXAMPLE | STRUCTURE | LC/MS | NMR |
|---|---|---|---|
| 175 | 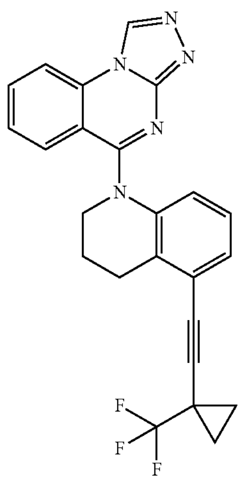 [SMILES: FC(F)(F)C1(C#Cc2cccc3c2CCCN3c2nc3nncn3c3ccccc23)CC1] | 434.1 | 1H NMR (400 MHz, DMSO-d6) δ 9.87 (s, 1H), 8.42 (d, J = 8.2 Hz, 1H), 7.98 (ddd, J = 8.5, 7.2, 1.3 Hz, 1H), 7.66 (dd, J = 8.3, 1.3 Hz, 1H), 7.48 (ddd, J = 8.4, 7.2, 1.1 Hz, 1H), 7.21 (dd, J = 7.5, 1.2 Hz, 1H), 7.00 (t, J = 7.9 Hz, 1H), 6.91 (d, J = 8.1 Hz, 1H), 4.00 (t, J = 6.3 Hz, 2H), 2.98 (t, J = 6.7 Hz, 2H), 2.17-2.05 (m, 2H), 1.53-1.47 (m, 2H), 1.47-1.39 (m, 2H). |
| 176 | 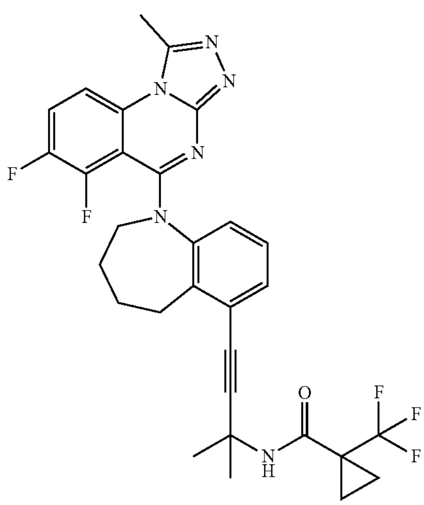 [SMILES: Cc1nnc2nc(N3CCCCc4c(C#CC(C)(C)NC(=O)C5(C(F)(F)F)CC5)cccc43)c3c(F)c(F)ccc3n12] | 583.4 | 1H NMR (400 MHz, Methanol-d4) δ 8.28-8.09 (m, 1H), 7.95 (q, J = 9.0 Hz, 1H), 7.87 (br s, 1H), 7.39 (dd, J = 7.8, 1.2 Hz, 1H), 6.98 (t, J = 7.9 Hz, 1H), 6.73 (dd, J = 7.9, 1.2 Hz, 1H), 5.06 (br s, 1H), 4.10-3.36 (m, 3H), 3.05 (s, 3H), 2.27-1.80 (m, 4H), 1.72 (s, 6H), 1.33-1.17 (m, 4H). |
| 177 | 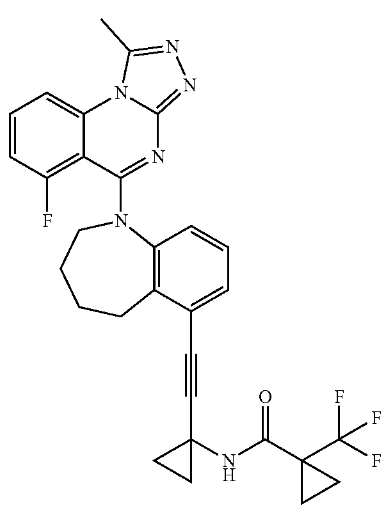 [SMILES: Cc1nnc2nc(N3CCCCc4c(C#CC5(NC(=O)C6(C(F)(F)F)CC6)CC5)cccc43)c3c(F)cccc3n12] | 563.41 | 1H NMR (400 MHz, Methanol-d4) δ 8.17 (d, J = 8.6 Hz, 1H), 7.97 (td, J = 8.5, 5.4 Hz, 1H), 7.31 (dd, J = 7.8, 1.2 Hz, 1H), 7.20-7.04 (m, 1H), 6.92 (t, J = 7.9 Hz, 1H), 6.69 (dd, J = 7.9, 1.2 Hz, 1H), 5.14 (s, 1H), 3.81-3.64 (m, 1H), 3.62-3.35 (m, 2H), 3.06 (s, 3H), 2.22-1.52 (m, 4H), 1.46-1.10 (m, 8H). |

TABLE 1-continued

Compounds and characterization of the compounds

| EXAMPLE | STRUCTURE | LC/MS | NMR |
|---|---|---|---|
| 178 | 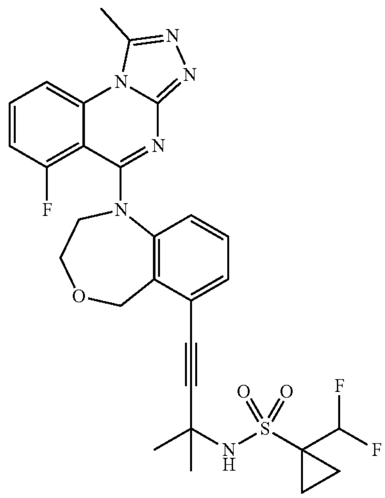 [SMILES: Cc1nnc2nc(N3CCOCc4c(C#CC(C)(C)NS(=O)(=O)C5(C(F)F)CC5)cccc43)c3c(F)cccc3n12] | 459.13 | 1H NMR (400 MHz, Methanol-d4) δ 8.25 (d, J = 8.6 Hz, 1H), 8.03 (td, J = 8.4, 5.4 Hz, 1H), 7.52 (d, J = 7.7 Hz, 1H), 7.19 (dd, J = 11.9, 8.3 Hz, 1H), 7.13 (t, J = 7.9 Hz, 1H), 6.94 (d, J = 7.9 Hz, 1H), 5.17 (br s, 4H), 4.16 (br s, 2H), 3.10 (s, 3H), 3.07 (s, 6H), 1.87 (s, 6H). |
| 179 | 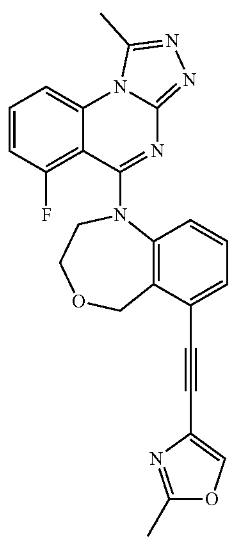 [SMILES: Cc1nc(C#Cc2cccc3c2COCCN3c2nc3nnc(C)n3c3cccc(F)c23)co1] | 455.36 | 1H NMR (400 MHz, Methanol-d4) δ 8.22 (d, J = 8.6 Hz, 1H), 8.17 (br s, 1H, NH), 8.00 (td, J = 8.5, 5.4 Hz, 1H), 7.47 (d, J = 7.8 Hz, 1H), 7.20 (dd, J = 11.9, 8.3 Hz, 1H), 7.09 (t, J = 7.9 Hz, 1H), 6.84 (d, J = 8.0 Hz, 1H), 5.21 (br s, 4H), 4.14 (br s, 2H), 3.09 (s, 3H), 2.51 (s, 3H). |
| 180 | 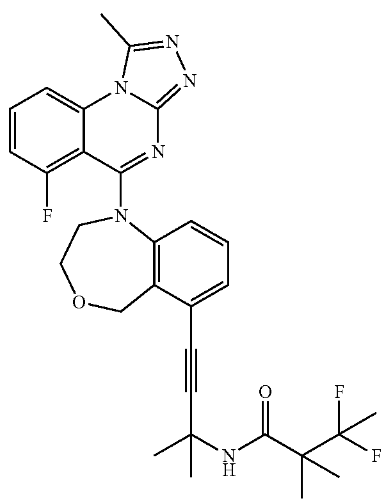 [SMILES: Cc1nnc2nc(N3CCOCc4c(C#CC(C)(C)NC(=O)C(C)(C)C(C)(F)F)cccc43)c3c(F)cccc3n12] | 565.33 | 1H NMR (400 MHz, Methanol-d4) δ 8.23 (d, J = 8.6 Hz, 1H), 8.03 (td, J = 8.5, 5.3 Hz, 1H), 7.36 (dd, J = 7.8, 1.1 Hz, 1H), 7.21 (dd, J = 11.8, 8.3 Hz, 1H), 7.14 (br s, 1H, NH), 7.02 (t, J = 7.9 Hz, 1H), 6.84-6.75 (m, 1H), 5.52 (br s, 4H), 4.13 (br s, 2H), 3.09 (s, 3H), 1.72 (s, 6H), 1.66 (t, J = 19.3 Hz, 3H), 1.35 (s, 6H). |

TABLE 1-continued

Compounds and characterization of the compounds

| EXAMPLE | STRUCTURE | LC/MS | NMR |
|---------|-----------|-------|-----|
| 181 | 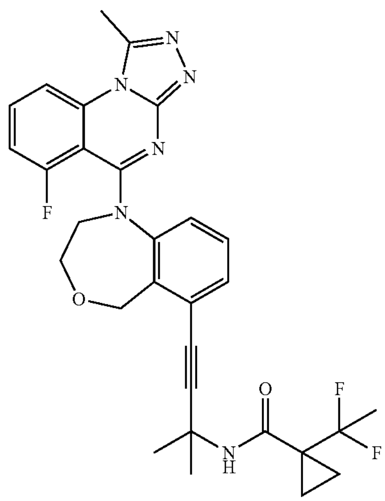 [SMILES: Cc1nnc2nc(N3CCOCc4c(C#CC(C)(C)NC(=O)C5(C(C)(F)F)CC5)cccc43)c3c(F)cccc3n12] | 563.39 | 1H NMR (400 MHz, Methanol-d4) δ 8.23 (d, J = 8.6 Hz, 1H), 8.03 (td, J = 8.5, 5.4 Hz, 1H), 7.71 (br s, 1H, NH), 7.36 (dd, J = 7.8, 1.1 Hz, 1H), 7.21 (dd, J = 11.8, 8.3 Hz, 1H), 7.03 (t, J = 7.9 Hz, 1H), 6.80 (dd, J = 8.0, 1.1 Hz, 1H), 5.49 (br s, 4H), 4.13 (br s, 2H), 3.09 (s, 3H), 1.78 (t, J = 18.5 Hz, 3H), 1.71 (s, 6H), 1.10 (s, 4H). |
| 182 | 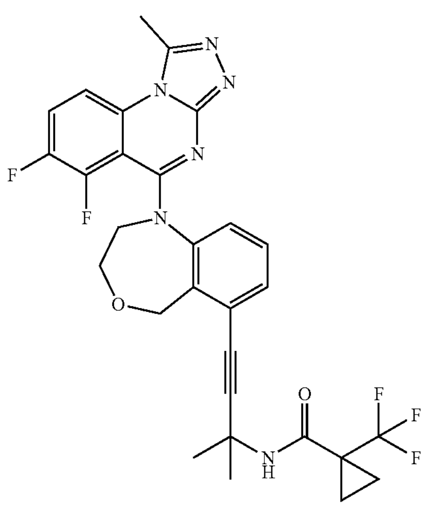 [SMILES: Cc1nnc2nc(N3CCOCc4c(C#CC(C)(C)NC(=O)C5(C(F)(F)F)CC5)cccc43)c3c(F)c(F)ccc3n12] | 585.36 | 1H NMR (400 MHz, Methanol-d4) δ 8.25 (ddd, J = 9.6, 3.9, 1.8 Hz, 1H), 8.10-7.95 (m, 1H), 7.89 (br s, 1H, NH), 7.59-7.31 (m, 1H), 7.07 (t, J = 7.9 Hz, 1H), 6.88-6.68 (m, 1H), 5.50 (br s, 4H), 4.14 (br s, 2H), 3.08 (s, 3H), 1.73 (br s, 6H), 1.38-1.19 (m, 4H). |
| 183 | 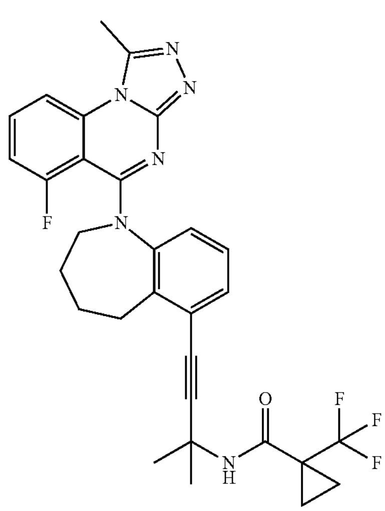 [SMILES: Cc1nnc2nc(N3CCCCc4c(C#CC(C)(C)NC(=O)C5(C(F)(F)F)CC5)cccc43)c3c(F)cccc3n12] | 565.37 | 1H NMR (400 MHz, Methanol-d4) δ 8.17 (d, J = 8.6 Hz, 1H), 7.97 (td, J = 8.5, 5.3 Hz, 1H), 7.85 (br s, 1H, NH), 7.35 (dd, J = 7.8, 1.2 Hz, 1H), 7.20-7.05 (m, 1H), 6.93 (t, J = 7.9 Hz, 1H), 6.70 (dd, J = 7.9, 1.2 Hz, 1H), 5.13 (s, 1H), 3.70-3.35 (m, 2H), 3.06 (s, 3H), 2.24-1.77 (m, 5H), 1.72 (s, 6H), 1.28 (ddt, J = 8.4, 2.8, 1.3 Hz, 4H). |

TABLE 1-continued

Compounds and characterization of the compounds

| EXAMPLE | STRUCTURE | LC/MS | NMR |
|---|---|---|---|
| 184 | 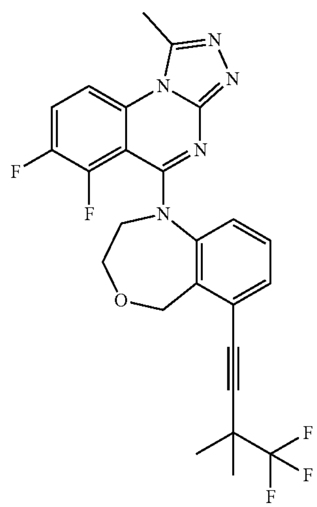 [SMILES: Cc1nnc2nc(N3CCOCc4c(C#CC(C)(C)C(F)(F)F)cccc43)c3c(F)c(F)ccc3n12] | 498.37 | 1H NMR (400 MHz, Methanol-d4) δ 8.26 (ddd, J = 9.6, 3.9, 1.9 Hz, 1H), 8.02 (td, J = 9.4, 8.0 Hz, 1H), 7.41 (dd, J = 7.9, 1.2 Hz, 1H), 7.09 (t, J = 7.9 Hz, 1H), 6.86 (dd, J = 8.0, 1.1 Hz, 1H), 5.44 (br s, 4H), 4.15 (br s, 2H), 3.09 (s, 3H), 1.82 (t, J = 18.7 Hz, 3H), 1.48 (s, 6H). |
| 185 | 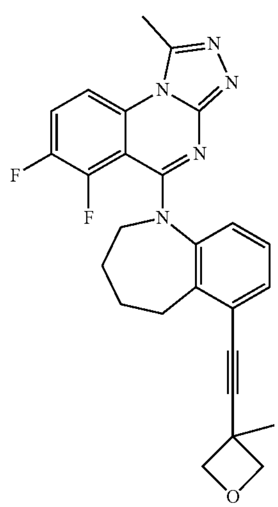 [SMILES: Cc1nnc2nc(N3CCCCc4c(C#CC5(C)COC5)cccc43)c3c(F)c(F)ccc3n12] | 460.3 | 1H NMR (400 MHz, Methanol-d4) δ 8.08 (ddd, J = 9.5, 4.0, 1.8 Hz, 1H), 7.78 (td, J = 9.5, 8.0 Hz, 1H), 7.29 (dd, J = 7.8, 1.2 Hz, 1H), 6.90 (t, J = 7.8 Hz, 1H), 6.55 (d, J = 7.8 Hz, 1H), 4.93 (d, J = 5.5 Hz, 2H), 4.55 (d, J = 5.5 Hz, 2H), 3.33 (br s, 2H), 3.01 (s, 3H), 1.90 (br s, 4H), 1.75 (s, 3H), 1.29 (br s, 2H). |
| 186 | 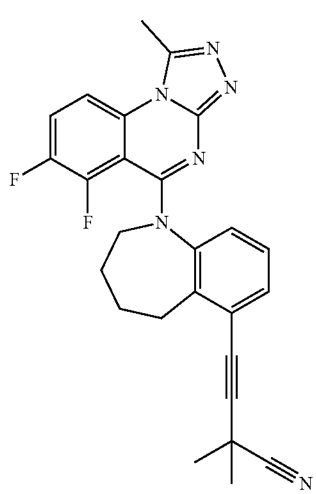 [SMILES: Cc1nnc2nc(N3CCCCc4c(C#CC(C)(C)C#N)cccc43)c3c(F)c(F)ccc3n12] | 457.32 | 1H NMR (400 MHz, Methanol-d4) δ 8.21 (ddd, J = 9.5, 3.9, 1.8 Hz, 1H), 7.96 (td, J = 9.4, 8.0 Hz, 1H), 7.46 (dd, J = 7.9, 1.2 Hz, 1H), 7.04 (t, J = 7.9 Hz, 1H), 6.82 (dd, J = 8.0, 1.2 Hz, 1H), 5.11 (br s, 1H), 3.48 (br s, 3H), 3.06 (s, 3H), 1.97 (brs, 4H), 1.81 (s, 6H). |

TABLE 1-continued

Compounds and characterization of the compounds

| EXAMPLE | STRUCTURE | LC/MS | NMR |
| --- | --- | --- | --- |
| 187 | 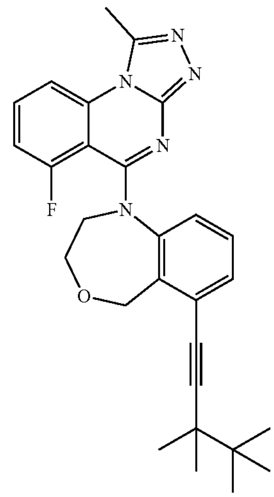 [SMILES: Cc1nnc2nc(N3CCOCc4c(C#CC(C)(C)C(C)(C)C)cccc43)c3c(F)cccc3n12] | 480.2 | 1H NMR (400 MHz, Methanol-d4) δ 8.24 (d, J = 8.6 Hz, 1H), 8.03 (td, J = 8.5, 5.3 Hz, 1H), 7.37 (d, J = 7.7 Hz, 1H), 7.23 (dd, J = 11.9, 8.3 Hz, 1H), 7.05 (t, J = 7.9 Hz, 1H), 6.83 (d, J = 7.9 Hz, 1H), 5.46 (br s, 4H), 4.14 (br s, 2H), 3.09 (s, 3H), 1.81 (t, J = 18.7 Hz, 3H), 1.48 (s, 6H). |
| 188 | 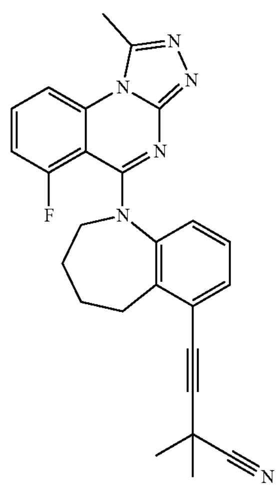 [SMILES: Cc1nnc2nc(N3CCCCc4c(C#CC(C)(C)C#N)cccc43)c3c(F)cccc3n12] | 439.36 | 1H NMR (400 MHz, Methanol-d4) δ 8.19 (d, J = 8.6 Hz, 1H), 7.98 (ddd, J = 8.5, 6.9, 4.2 Hz, 1H), 7.42 (dd, J = 7.8, 1.2 Hz, 1H), 7.18 (dd, J = 11.8, 8.0 Hz, 1H), 6.99 (t, J = 7.9 Hz, 1H), 6.82-6.73 (m, 1H), 5.16 (br s, 1H), 3.63-3.36 (m, 2H), 3.15 (br s, 1H), 3.07 (s, 3H), 2.29-0.83 (m, 4H), 1.80 (s, 6H). |
| 189 | 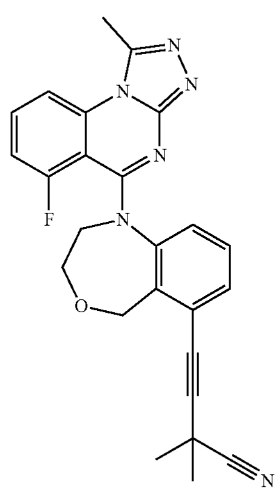 [SMILES: Cc1nnc2nc(N3CCOCc4c(C#CC(C)(C)C#N)cccc43)c3c(F)cccc3n12] | 441.35 | 1H NMR (400 MHz, Methanol-d4) δ 8.24 (d, J = 8.6 Hz, 1H), 8.04 (td, J = 8.5, 5.3 Hz, 1H), 7.43 (d, J = 7.8 Hz, 1H), 7.22 (dd, J = 11.9, 8.3 Hz, 1H), 7.09 (t, J = 7.9 Hz, 1H), 6.88 (d, J = 7.9 Hz, 1H), 5.34 (br s, 4H), 4.15 (br s, 2H), 3.09 (s, 3H), 1.81 (s, 6H). |

TABLE 1-continued

Compounds and characterization of the compounds

| EXAMPLE | STRUCTURE | LC/MS | NMR |
|---|---|---|---|
| 190 | 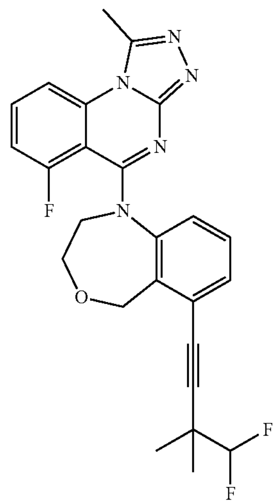 [SMILES: Cc1nnc2nc(N3CCOCc4c(C#CC(C)(C)C(F)F)cccc43)c3c(F)cccc3n12] | 466.32 | 1H NMR (400 MHz, Methanol-d4) δ 8.24 (d, J = 8.6 Hz, 1H), 8.03 (td, J = 8.5, 5.4 Hz, 1H), 7.38 (dd, J = 7.8, 1.1 Hz, 1H), 7.22 (dd, J = 11.8, 8.3 Hz, 1H), 7.05 (t, J = 7.9 Hz, 1H), 6.83 (dd, J = 8.0, 1.1 Hz, 1H), 5.84 (t, J = 56.7 Hz, 1H), 5.46 (br s, 4H), 4.14 (br s, 2H), 3.09 (s, 3H), 1.42 (d, J = 1.2 Hz, 6H). |
| 191 | 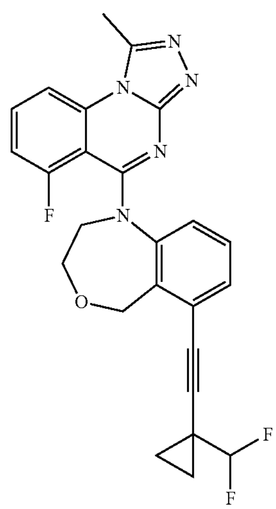 [SMILES: Cc1nnc2nc(N3CCOCc4c(C#CC5(C(F)F)CC5)cccc43)c3c(F)cccc3n12] | 464.36 | 1H NMR (400 MHz, Methanol-d4) δ 8.23 (d, J = 8.6 Hz, 1H), 8.03 (td, J = 8.5, 5.3 Hz, 1H), 7.38 (dd, J = 7.8, 1.1 Hz, 1H), 7.22 (dd, J = 11.8, 8.3 Hz, 1H), 7.04 (t, J = 7.9 Hz, 1H), 6.82 (d, J = 7.9 Hz, 1H), 5.71 (t, J = 56.4 Hz, 1H), 5.48 (br s, 4H), 4.14 (br s, 2H), 3.09 (s, 3H), 1.34-1.16 (m, 4H). |
| 192 | 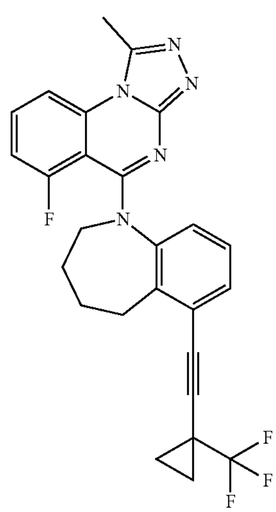 [SMILES: Cc1nnc2nc(N3CCCCc4c(C#CC5(C(F)(F)F)CC5)cccc43)c3c(F)cccc3n12] | 480.37 | 1H NMR (400 MHz, Methanol-d4) δ 8.18 (d, J = 8.6 Hz, 1H), 7.98 (td, J = 8.4, 5.3 Hz, 1H), 7.38 (dd, J = 7.7, 1.2 Hz, 1H), 7.17 (dd, J = 11.7, 8.3 Hz, 1H), 6.97 (t, J = 7.9 Hz, 1H), 6.80-6.69 (m, 1H), 5.15 (s, 1H), 3.68-3.36 (m, 3H), 3.06 (s, 3H), 2.25-1.56 (m, 4H), 1.52-1.42 (m, 2H), 1.36 (d, J = 6.2 Hz, 2H). |

TABLE 1-continued

Compounds and characterization of the compounds

| EXAMPLE | STRUCTURE | LC/MS | NMR |
|---|---|---|---|
| 193 | 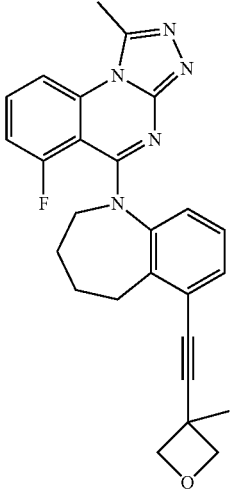 [SMILES: Cc1nnc2nc(N3CCCCc4c(C#CC5(C)COC5)cccc43)c3c(F)cccc3n12] | 442.3 | 1H NMR (400 MHz, Methanol-d4) δ 8.07 (d, J = 8.5 Hz, 1H), 7.81 (td, J = 8.4, 5.4 Hz, 1H), 7.25 (dd, J = 7.8, 1.2 Hz, 1H), 7.00 (dd, J = 11.8, 8.3 Hz, 1H), 6.86 (t, J = 7.8 Hz, 1H), 6.51 (dd, J = 7.9, 1.1 Hz, 1H), 5.49 (s, 2H), 4.91 (d, J = 5.4 Hz, 2H), 4.56 (d, J = 5.5 Hz, 2H), 3.02 (s, 3H), 1.97-1.77 (m, 4H), 1.75 (s, 3H). |
| 194 | 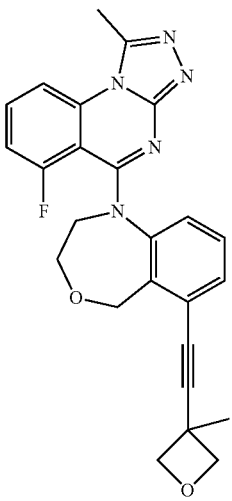 [SMILES: Cc1nnc2nc(N3CCOCc4c(C#CC5(C)COC5)cccc43)c3c(F)cccc3n12] | 444.28 | 1H NMR (400 MHz, Methanol-d4) δ 8.13 (d, J = 8.6 Hz, 1H), 7.87 (td, J = 8.4, 5.4 Hz, 1H), 7.27 (dd, J = 7.8, 1.1 Hz, 1H), 7.06 (ddd, J = 12.0, 8.3, 0.9 Hz, 1H), 6.98 (t, J = 7.9 Hz, 1H), 6.62 (dd, J = 8.0, 1.1 Hz, 1H), 5.17 (br s, 4H), 4.93 (d, J = 5.5 Hz, 2H), 4.55 (d, J = 5.5 Hz, 2H), 4.07 (br s, 2H), 3.04 (s, 3H), 1.75 (s, 3H). |
| 195 | 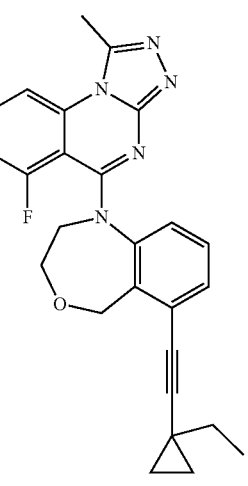 | 442.36 | 1H NMR (400 MHz, Methanol-d4) δ 8.23 (d, J = 8.6 Hz, 1H), 8.03 (td, J = 8.5, 5.4 Hz, 1H), 7.32 (dd, J = 7.8, 1.2 Hz, 1H), 7.28-7.16 (m, 1H), 7.00 (t, J = 7.9 Hz, 1H), 6.75 (dd, J = 8.0, 1.1 Hz, 1H), 5.50 (s, 4H), 4.14 (s, 2H), 3.09 (s, 3H), 1.52 (q, J = 7.3 Hz, 2H), 1.19 (t, J = 7.4 Hz, 3H), 1.06-0.94 (m, 2H), 0.84-0.71 (m, 2H). |

TABLE 1-continued

Compounds and characterization of the compounds

| EXAMPLE | STRUCTURE | LC/MS | NMR |
|---|---|---|---|
| 196 | 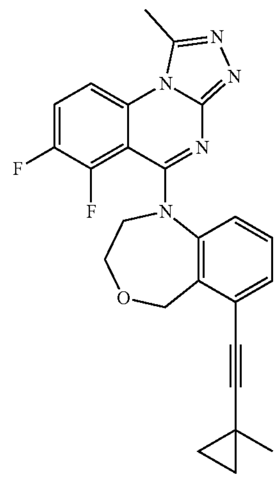 [SMILES: Cc1nnc2nc(N3CCOCc4c(C#CC5(C)CC5)cccc43)c3c(F)c(F)ccc3n12] | 446.31 | 1H NMR (400 MHz, Methanol-d4) δ 8.24 (d, J = 8.7 Hz, 1H), 8.00 (q, J = 9.0 Hz, 1H), 7.35 (d, J = 7.8 Hz, 1H), 7.04 (t, J = 7.9 Hz, 1H), 6.78 (d, J = 7.9 Hz, 1H), 5.44 (br s, 4H), 4.14 (br s, 2H), 3.08 (s, 3H), 1.41 (s, 3H), 1.05 (q, J = 4.1 Hz, 2H), 0.82-0.72 (m, 2H). |
| 197 | 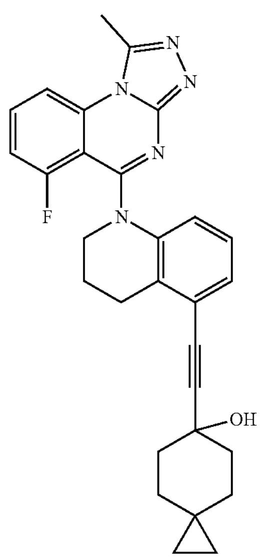 [SMILES: Cc1nnc2nc(N3CCCc4c(C#CC5(O)CCC6(CC5)CC6)cccc43)c3c(F)cccc3n12] | 482.4 | 1H NMR (400 MHz, Methanol-d4) δ 8.24 (d, J = 8.6 Hz, 1H), 8.07 (td, J = 8.5, 5.4 Hz, 1H), 7.40-7.26 (m, 2H), 6.96 (t, J = 7.9 Hz, 1H), 6.87 (d, J = 8.1 Hz, 1H), 4.20 (br s, 2H), 3.15 (br s, 2H), 3.09 (s, 3H), 2.21 (br s, 2H), 2.10-1.97 (m, 2H), 1.85 (d, J = 9.6 Hz, 4H), 1.27 (s, 2H), 0.50-0.20 (m, 4H). |
| 198 | 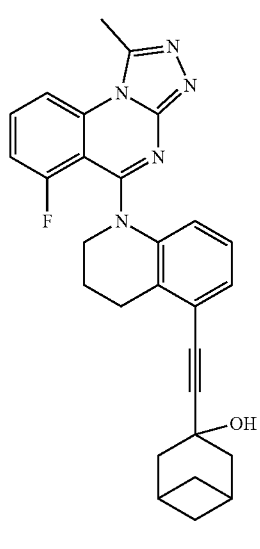 [SMILES: Cc1nnc2nc(N3CCCc4c(C#CC5(O)CC6CC(C6)C5)cccc43)c3c(F)cccc3n12] | 468.38 | 1H NMR (400 MHz, Methanol-d4) δ 8.24 (d, J = 8.6 Hz, 1H), 8.07 (td, J = 8.5, 5.3 Hz, 1H), 7.38-7.22 (m, 2H), 6.94 (t, J = 7.9 Hz, 1H), 6.85 (d, J = 6.7 Hz, 1H), 4.19 (br s, 2H), 3.09 (br s, 2H), 3.09 (s, 3H), 2.69-2.53 (m, 4H), 2.48-2.12 (m, 4H), 1.49 (dd, J = 5.9, 2.6 Hz, 2H). |

TABLE 1-continued

Compounds and characterization of the compounds

| EXAMPLE | STRUCTURE | LC/MS | NMR |
|---|---|---|---|
| 199 | 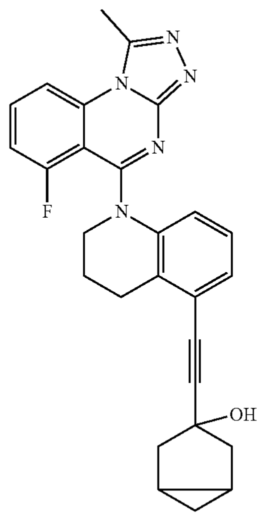 [SMILES: Cc1nnc2nc(N3CCCc4c(C#CC5(O)CC6CC6C5)cccc43)c3c(F)cccc3n12] | 454.38 | 1H NMR (400 MHz, Methanol-d4) δ 8.24 (d, J = 8.6 Hz, 1H), 8.06 (td, J = 8.5, 5.3 Hz, 1H), 7.31 (dd, J = 11.5, 8.3 Hz, 1H), 7.25 (d, J = 7.5 Hz, 1H), 6.93 (t, J = 8.0 Hz, 1H), 6.85 (d, J = 8.1 Hz, 1H), 4.17 (br s, 2H), 3.09 (s, 3H), 3.08 (br s, 2H), 2.46 (dd, J = 14.0, 3.6 Hz, 2H), 2.17 ( ), br s, 2H), 2.17 (d, J = 13.9 Hz, 2H), 1.43 (dt, J = 8.0, 3.9 Hz, 2H), 0.83 (q, J = 4.1 Hz, 1H), 0.49 (td, J = 8.3, 4.5 Hz, 1H). |
| 200 | 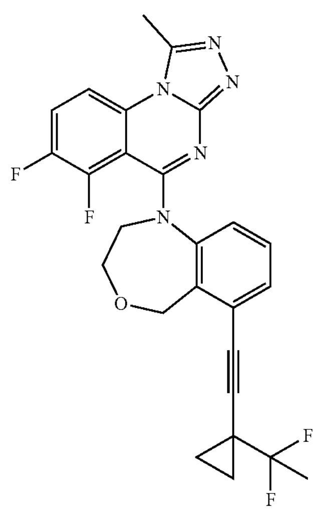 [SMILES: Cc1nnc2nc(N3CCOCc4c(C#CC5(C(C)(F)F)CC5)cccc43)c3c(F)c(F)ccc3n12] | 496.28 | 1H NMR (400 MHz, Methanol-d4) δ 8.25 (ddd, J = 9.6, 3.9, 1.9 Hz, 1H), 8.01 (td, J = 9.4, 8.0 Hz, 1H), 7.41 (dd, J = 7.8, 1.1 Hz, 1H), 7.08 (t, J = 7.9 Hz, 1H), 6.85 (dd, J = 8.0, 1.2 Hz, 1H), 5.37 (br s, 4H), 4.15 (br s, 2H), 3.09 (s, 3H), 1.89 (t, J = 18.0 Hz, 3H), 1.36-1.27 (m, 2H), 1.22-1.11 (m, 2H). |
| 201 | 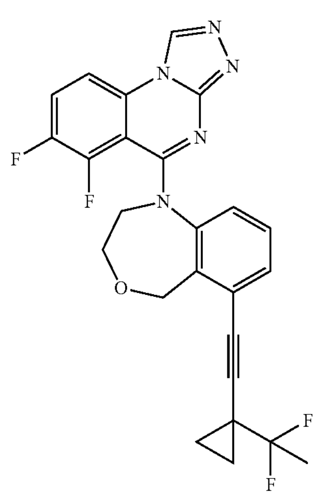 | 482.31 | 1H NMR (400 MHz, Methanol-d4) δ 9.67 (s, 1H), 8.24 (ddd, J = 9.4, 4.0, 1.8 Hz, 1H), 8.05 (td, J = 9.4, 7.7 Hz, 1H), 7.41 (dd, J = 7.9, 1.2 Hz, 1H), 7.10 (t, J = 7.9 Hz, 1H), 6.88 (dd, J = 8.0, 1.2 Hz, 1H), 4.97 (br s, 4H), 4.15 (br s, 2H), 1.89 (t, J = 18.0 Hz, 3H), 1.35-1.28 (m, 2H), 1.22-1.14 (m, 2H). |

TABLE 1-continued
Compounds and characterization of the compounds
| EXAMPLE | STRUCTURE | LC/MS | NMR |
|---|---|---|---|
| 202 | 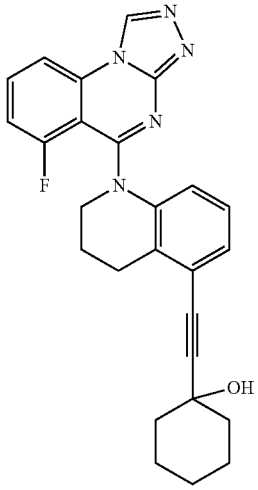 [SMILES: OC1(C#Cc2cccc3c2CCCN3c2nc3nncn3c3cccc(F)c23)CCCCC1] | 442.36 | 1H NMR (400 MHz, Methanol-d4) δ 9.63 (s, 1H), 8.20 (d, J = 8.3 Hz, 1H), 8.07 (td, J = 8.3, 5.1 Hz, 1H), 7.38-7.22 (m, 2H), 6.96 (t, J = 7.8 Hz, 1H), 6.91 (dd, J = 8.3, 1.3 Hz, 1H), 4.21 (br s, 2H), 3.11 (br s, 2H), 2.20 (br s, 2H), 1.87-1.64 (m, 4H). |
| 203 | 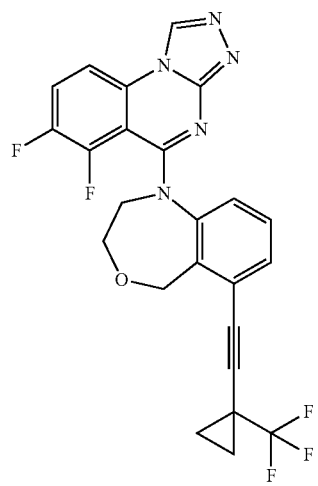 | 486.29 | 1H NMR (400 MHz, Methanol-d4) δ 9.66 (s, 1H), 8.24 (ddd, J = 9.3, 4.0, 1.8 Hz, 1H), 8.04 (td, J = 9.4, 7.7 Hz, 1H), 7.43 (dd, J = 7.8, 1.2 Hz, 1H), 7.11 (t, J = 7.9 Hz, 1H), 6.91 (dd, J = 8.0, 1.2 Hz, 1H), 4.96 (br s, 4H), 4.14 (br s, 2H), 1.56-1.34 (m, 4H). |
| 204 | 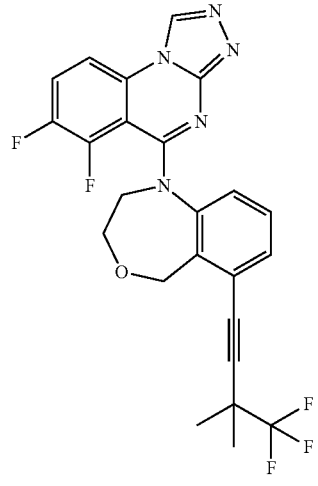 | 488.33 | 1H NMR (400 MHz, Methanol-d4) δ 9.66 (s, 1H), 8.24 (ddd, J = 9.3, 4.0, 1.8 Hz, 1H), 8.05 (td, J = 9.4, 7.7 Hz, 1H), 7.43 (dd, J = 7.9, 1.2 Hz, 1H), 7.12 (t, J = 7.9 Hz, 1H), 6.92 (dd, J = 8.0, 1.2 Hz, 1H), 5.17 (br s, 4H), 4.15 (br s, 2H), 1.61-1.55 (m, 6H). |

TABLE 1-continued

Compounds and characterization of the compounds

| EXAMPLE | STRUCTURE | LC/MS | NMR |
|---|---|---|---|
| 205 | 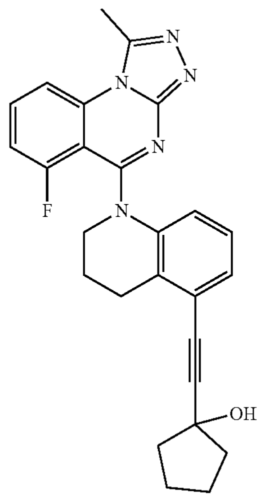 [SMILES: Cc1nnc2nc(N3CCCc4c(C#CC5(O)CCCC5)cccc43)c3c(F)cccc3n12] | 442.3 | 1H NMR (400 MHz, Methanol-d4) δ 8.24 (d, J = 8.6 Hz, 1H), 8.07 (td, J = 8.5, 5.3 Hz, 1H), 7.40-7.22 (m, 2H), 7.04-6.90 (m, 1H), 6.89-6.83 (m, 1H), 4.30 (br s, 2H), 3.15-3.00 (br s, 2H), 3.09 (s, 3H), 2.68-2.44 (m, 2H), 2.20 (br s, 2H), 2.12-1.74 (m, 6H). |
| 206 | 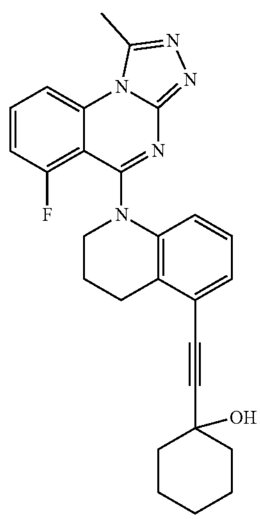 [SMILES: Cc1nnc2nc(N3CCCc4c(C#CC5(O)CCCCC5)cccc43)c3c(F)cccc3n12] | 456.37 | 1H NMR (400 MHz, Methanol-d4) δ 8.24 (d, J = 8.6 Hz, 1H), 8.07 (td, J = 8.4, 5.4 Hz, 1H), 7.40-7.25 (m, 2H), 6.95 (t, J = 7.9 Hz, 1H), 6.92-6.82 (m, 1H), 4.19 (s, 2H), 3.09 (d, J = 2.6 Hz, 3H), 2.27 (d, J = 54.0 Hz, 2H), 2.03 (d, J = 6.9 Hz, 2H), 1.89-1.55 (m, 7H), 1.34 (s, 1H). |
| 207 | 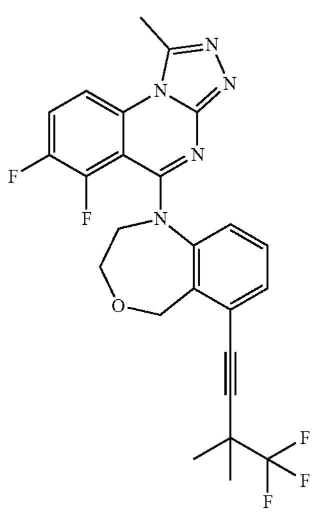 [SMILES: Cc1nnc2nc(N3CCOCc4c(C#CC(C)(C)C(F)(F)F)cccc43)c3c(F)c(F)ccc3n12] | 502.33 | 1H NMR (400 MHz, Methanol-d4) δ 8.26 (ddd, J = 9.5, 3.9, 1.8 Hz, 1H), 8.02 (td, J = 9.4, 8.0 Hz, 1H), 7.43 (dd, J = 7.8, 1.2 Hz, 1H), 7.11 (t, J = 7.9 Hz, 1H), 6.89 (dd, J = 7.9, 1.1 Hz, 1H), 5.33 (br s, 4H), 4.15 (br s, 2H), 3.09 (s, 3H), 1.59 (s, 6H). |

TABLE 1-continued

Compounds and characterization of the compounds

| EXAMPLE | STRUCTURE | LC/MS | NMR |
|---|---|---|---|
| 208 | 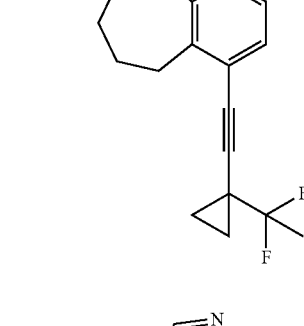 | 480.37 | 1H NMR (400 MHz, Methanol-d4) δ 9.58 (s, 1H), 8.18 (ddd, J = 9.3, 4.1, 1.8 Hz, 1H), 8.00 (td, J = 9.4, 7.6 Hz, 1H), 7.41 (dd, J = 7.9, 1.2 Hz, 1H), 7.01 (t, J = 7.9 Hz, 1H), 6.80 (dd, J = 7.9, 1.2 Hz, 1H), 5.28-4.94 (m, 1H), 3.50 (br s, 2H), 3.25 (s, 3H), 3.15 (br s, 1H), 2.22-1.69 (m, 4H), 1.89 (t, J = 16.0 Hz, 3H), 1.38-1.23 (m, 2H), 1.16 (qd, J = 3.9, 1.9 Hz, 2H). |
| 209 | 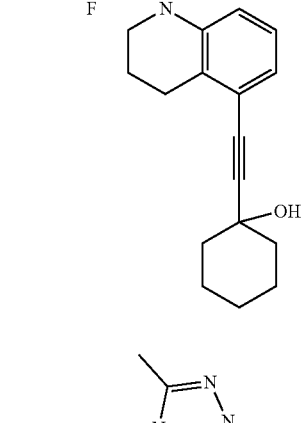 | 460.36 | 1H NMR (400 MHz, Methanol-d4) δ 9.64 (s, 1H), 8.31-8.18 (m, 1H), 8.07 (q, J = 9.1 Hz, 1H), 7.32 (dd, J = 7.7, 1.2 Hz, 1H), 7.00 (t, J = 7.9 Hz, 1H), 6.92 (d, J = 8.1 Hz, 1H), 4.20 (s, 2H), 3.11 (s, 2H), 2.21 (s, 3H), 2.09-1.98 (m, 2H), 1.86-1.57 (m, 7H), 1.43-1.24 (m, 1H). |
| 210 | 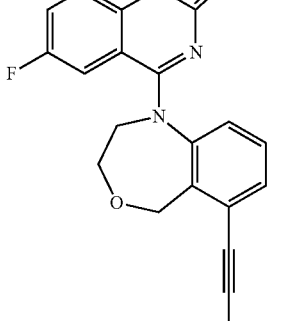 | 484.34 | 1H NMR (400 MHz, Methanol-d4) δ 8.47 (dd, J = 9.4, 4.6 Hz, 1H), 7.80 (ddd, J = 9.9, 7.3, 2.8 Hz, 1H), 7.60 (dd, J = 7.8, 1.2 Hz, 1H), 7.33 (t, J = 7.9 Hz, 1H), 7.13 (dd, J = 8.0, 1.2 Hz, 1H), 6.80 (dd, J = 10.1, 2.8 Hz, 1H), 5.60 (br s, 1H), 5.30 (br s, 2H), 4.15 (br s, 2H), 3.48 (br s, 1H), 3.09 (s, 3H), 1.60 (s, 6H). |

TABLE 1-continued
Compounds and characterization of the compounds
| EXAMPLE | STRUCTURE | LC/MS | NMR |
|---|---|---|---|
| 211 | 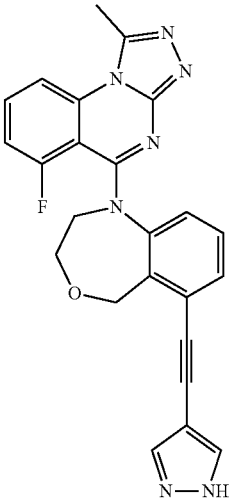 [SMILES: Cc1nnc2nc(N3CCOCc4c(C#Cc5cn[nH]c5)cccc43)c3c(F)cccc3n12] | 440.1 | 1H NMR (400 MHz, DMSO-d6) δ 8.15 (d, J = 8.6 Hz, 1H), 8.05-7.90 (m, 3H), 7.35 (d, J = 7.7 Hz, 1H), 7.25 (dd, J = 13.4, 9.2 Hz, 1H), 7.05 (t, J = 7.9 Hz, 1H), 6.80 (d, J = 7.8 Hz, 1H), 5.28-4.96 (m, 4H), 4.11-4.01 (m, 2H),   3.00 (s, 3H)." |
| 212 | 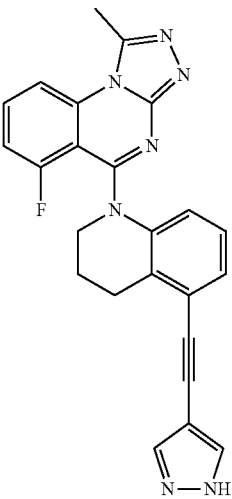 [SMILES: Cc1nnc2nc(N3CCCc4c(C#Cc5cn[nH]c5)cccc43)c3c(F)cccc3n12] | 424.1 | 1H NMR (400 MHz, DMSO-d6) δ 8.19 (d, J = 8.2 Hz, 1H), 8.07-7.91 (m, 3H), 7.45-7.34 (m, 1H), 7.23 (d, J = 8.0 Hz, 1H), 7.00-6.92 (m, 1H), 6.85 (d, J = 8.2 Hz, 1H), 4.22-3.61 (m, 4H),   3.01 (s, 3H), 2.24-1.96 (m, 2H)." |

TABLE 1-continued

Compounds and characterization of the compounds

| EXAMPLE | STRUCTURE | LC/MS | NMR |
|---|---|---|---|
| 213 | 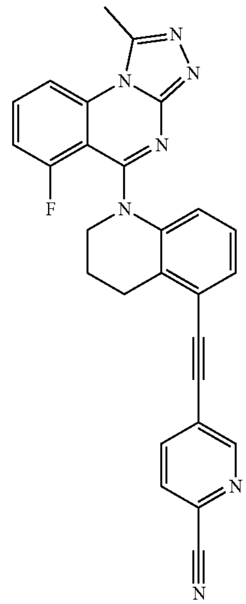 [SMILES: Cc1nnc2nc(N3CCCc4c(C#Cc5ccc(C#N)nc5)cccc43)c3c(F)cccc3n12] | 460.1 | 1H NMR (400 MHz, DMSO-d6) δ 8.99 (d, J = 2.1 Hz, 1H), 8.30 (dd, J = 8.0, 2.2 Hz, 1H), 8.17 (dd, J = 18.2, 8.4 Hz, 2H), 8.02 (td, J = 8.4, 5.4 Hz, 1H), 7.43-7.38 (m, 1H), 7.36 (d, J = 7.9 Hz, 1H), 7.05 (t, J = 7.9 Hz, 1H), 6.96 (d, J = 8.1 Hz, 1H), 4.05-3.91 (m, 2H), 3.09 (d, J = 15.4 Hz, 2H), 3.01 (s, 3H), 2.16-2.00 (m, 2H). |
| 214 | 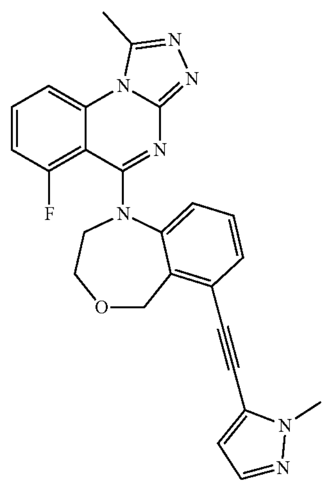 [SMILES: Cc1nnc2nc(N3CCOCc4c(C#Cc5ccnn5C)cccc43)c3c(F)cccc3n12] | 454.2 | 1H NMR (400 MHz, DMSO-d6) δ 8.16 (d, J = 8.6 Hz, 1H), 7.99-7.92 (m, 1H), 7.56 (d, J = 2.0 Hz, 1H), 7.49 (d, J = 7.5 Hz, 1H), 7.27 (dd, J = 12.1, 8.3 Hz, 1H), 7.13 (t, J = 7.9 Hz, 1H), 6.91 (d, J = 8.0 Hz, 1H), 6.72 (d, J = 2.0 Hz, 1H), 5.27-4.97 (m, 4H), 4.09-4.02 (m, 2H), 3.99 (s, 3H), 3.01 (s, 3H). |
| 215 | 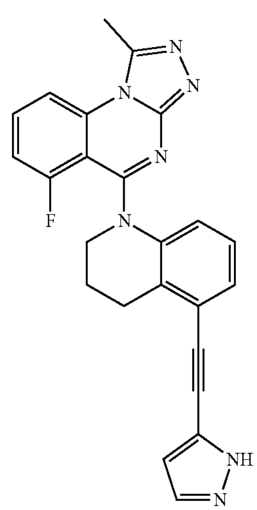 [SMILES: Cc1nnc2nc(N3CCCc4c(C#Cc5ccn[nH]5)cccc43)c3c(F)cccc3n12] | 424.1 | 1H NMR (400 MHz, DMSO-d6) δ 8.20 (d, J = 8.6 Hz, 1H), 8.03 (td, J = 8.4, 5.5 Hz, 1H), 7.81 (s, 1H), 7.41 (dd, J = 11.7, 8.3 Hz, 1H), 7.29 (d, J = 7.5 Hz, 1H), 7.02 (t, J = 7.9 Hz, 1H), 6.91 (d, J = 8.1 Hz, 1H), 6.60 (d, J = 2.2 Hz, 1H), 4.20-3.72 (m, 4H), 3.02 (s, 3H), 2.21-2.00 (m, 2H). |

TABLE 1-continued

Compounds and characterization of the compounds

| EXAMPLE | STRUCTURE | LC/MS | NMR |
| --- | --- | --- | --- |
| 216 | 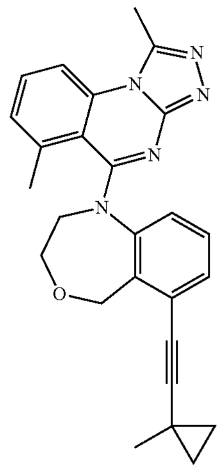 [SMILES: Cc1cccc2c1c(N1CCOCc3c(C#CC4(C)CC4)cccc31)nc1nnc(C)n12] | 424.2 | 1H NMR (400 MHz, DMSO-d6) δ 8.17 (d, J = 8.4 Hz, 1H), 7.81 (t, J = 8.0 Hz, 1H), 7.29 (d, J = 7.4 Hz, 1H), 7.19 (d, J = 7.9 Hz, 1H), 6.90 (t, J = 8.5 Hz, 1H), 6.46-6.38 (m, 1H), 5.26 (d, J = 14.1 Hz, 1H), 5.15-5.02 (m, 1H), 4.87 (d, J = 21.1 Hz, 1H), 4.10-3.99 (m, 2H), 3.54  -3.34 (m, 1H), 3.00 (s, 3H), 2.29 (s, 3H), 1.35 (s, 3H), 0.99 (q, J = 4.0 Hz, 2H), 0.80 (q, J = 4.1 Hz, 2H)." |
| 217 | 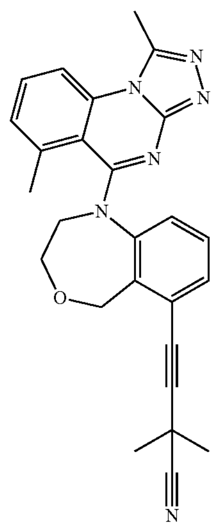 [SMILES: Cc1cccc2c1c(N1CCOCc3c(C#CC(C)(C)C#N)cccc31)nc1nnc(C)n12] | 437.1 | 1H NMR (400 MHz, DMSO-d6) δ 8.17 (d, J = 8.4 Hz, 1H), 7.80 (t, J = 9.2 Hz, 1H), 7.28 (t, J = 7.1 Hz, 2H), 6.99-6.92 (m, 1H), 6.55-6.45 (m, 1H), 5.28 (d, J = 17.2 Hz, 1H), 5.10-5.00 (m, 1H), 4.91-4.86 (m, 1H), 4.05 (d, J = 13.6 Hz, 3H), 3.00 (s, 3H), 2.33 (s, 3H), 1.77 (s, 6H). |
| 218 | 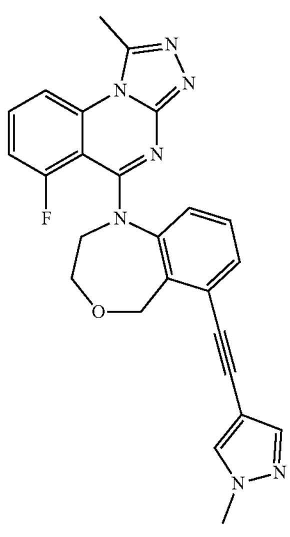 [SMILES: Cc1nnc2nc(N3CCOCc4c(C#Cc5cnn(C)c5)cccc43)c3c(F)cccc3n12] | 454.1 | 1H NMR (400 MHz, DMSO-d6) δ 8.14 (d, J = 9.6 Hz, 2H), 7.93 (dt, J = 8.6, 4.2 Hz, 1H), 7.76 (s, 1H), 7.33 (d, J = 7.7 Hz, 1H), 7.24 (dd, J = 12.5, 8.1 Hz, 1H), 7.04 (d, J = 7.8 Hz, 1H), 6.79 (d, J = 7.6 Hz, 1H), 5.28 (d, J = 17.2 Hz, 1H), 5.10-5.00 (m, 1H), 4.91-4.86 (m, 1H), 4.05-4.01 (m, J = 13.6 Hz, 3H), 3.00 (s, 3H). |

TABLE 1-continued

Compounds and characterization of the compounds

| EXAMPLE | STRUCTURE | LC/MS | NMR |
|---|---|---|---|
| 219 | 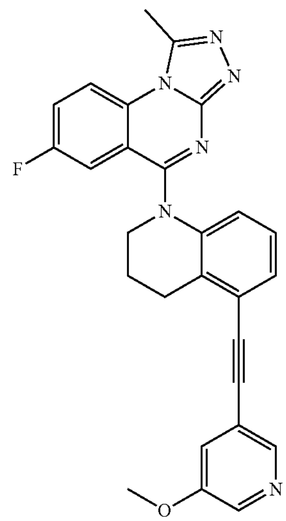 [SMILES: COc1cncc(C#Cc2cccc3c2CCCN3c2nc3nnc(C)n3c3ccc(F)cc23)c1] | 465.1 | 1H NMR (400 MHz, DMSO-d6) δ 8.41 (d, J = 1.5 Hz, 1H), 8.39-8.34 (m, 2H), 7.89-7.83 (m, 1H), 7.63 (dd, J = 2.8, 1.7 Hz, 1H), 7.48 (dd, J = 9.5, 2.9 Hz, 1H), 7.32 (d, J = 7.6 Hz, 1H), 7.06 (t, J = 7.9 Hz, 1H), 6.85 (d, J = 8.3 Hz, 1H), 3.97 (t, J = 6.1 Hz, 3H), 3.90 (s, 3H), 3.14 (t, J = 6.6 Hz, 2H), 3.00 (s, 3H), 2.14 (p, J = 6.5 Hz, 2H). |
| 220 | 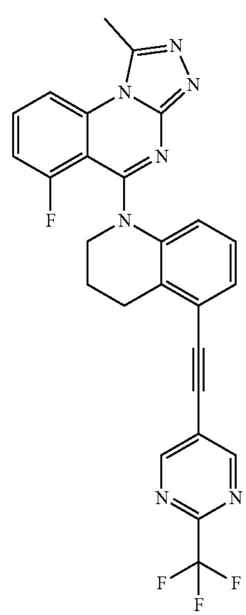 [SMILES: Cc1nnc2nc(N3CCCc4c(C#Cc5cnc(C(F)(F)F)nc5)cccc43)c3c(F)cccc3n12] | 504.1 | 1H NMR (400 MHz, DMSO-d6) δ 9.33 (s, 2H), 8.18 (d, J = 8.6 Hz, 1H), 8.02 (dt, J = 7.8, 4.0 Hz, 1H), 7.42-7.34 (m, 2H), 7.07 (d, J = 8.0 Hz, 1H), 6.97 (d, J = 8.1 Hz, 1H), 5.28-5.20 (m, 1H), 5.10-5.00 (m, 1H), 4.91-4.86 (m, 1H), 4.12-3.71 (m, 3H), 3.01 (s, 3H). |

TABLE 1-continued
Compounds and characterization of the compounds
| EXAMPLE | STRUCTURE | LC/MS | NMR |
|---|---|---|---|
| 221 | 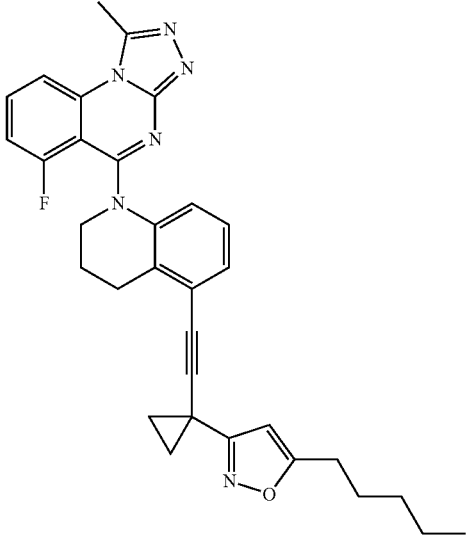 [SMILES: CCCCCc1cc(C2(C#Cc3cccc4c3CCCN4c3nc4nnc(C)n4c4cccc(F)c34)CC2)no1] | 535.2 | 1H NMR (400 MHz, DMSO-d6) δ 8.17 (d, J = 8.6 Hz, 1H), 8.00 (td, J = 8.3, 5.4 Hz, 1H), 7.37 (dd, J = 11.7, 8.4 Hz, 1H), 7.16 (d, J = 7.4 Hz, 1H), 6.93 (t, J = 7.9 Hz, 1H), 6.82 (d, J = 8.1 Hz, 1H), 6.30 (s, 1H), 3.99-3.58 (m, 6H), 3.01-2.99 (m, 3H), 2.72 (t, J = 7.5 Hz, 2H), 1.65-1.51 (m, 6H), 1.33-1.28 (m, 4H), 0.88 (t, J = 6.9 Hz, 3H). |
| 222 | 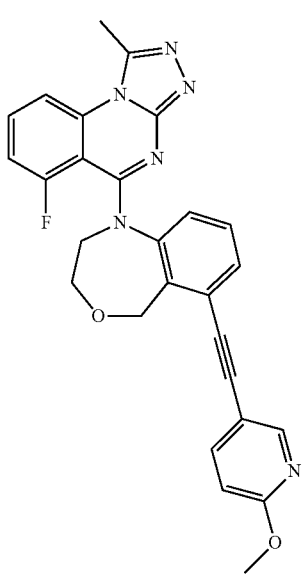 [SMILES: COc1ccc(C#Cc2cccc3c2COCCN3c2nc3nnc(C)n3c3cccc(F)c23)cn1] | 481.1 | 1H NMR (400 MHz, DMSO-d6) δ 8.49-8.44 (m, 1H), 8.16 (d, J = 8.6 Hz, 1H), 7.99-7.90 (m, 2H), 7.44 (d, J = 7.8 Hz, 1H), 7.27 (dd, J = 12.1, 8.3 Hz, 1H), 7.10 (t, J = 7.8 Hz, 1H), 6.94 (d, J = 8.6 Hz, 1H), 6.87 (d, J = 7.8 Hz, 1H), 5.28-5.20 (m, 1H), 5.10-5.00 (m, 1H), 4.91-4.86 (m, 2H), 4.11-3.96 (m, 2H), 3.92 (s, 3H), 3.01 (s, 3H). |

TABLE 1-continued

Compounds and characterization of the compounds

| EXAMPLE | STRUCTURE | LC/MS | NMR |
|---|---|---|---|
| 223 | 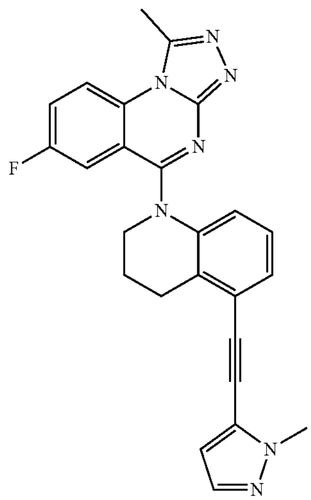 [SMILES: Cc1nnc2nc(N3CCCc4c(C#Cc5ccnn5C)cccc43)c3cc(F)ccc3n12] | 438.1 | 1H NMR (400 MHz, DMSO-d6) δ 8.38 (dd, J = 9.5, 4.5 Hz, 1H), 7.92-7.83 (m, 1H), 7.56-7.51 (m, 2H), 7.34 (d, J = 8.1 Hz, 1H), 7.07 (t, J = 7.9 Hz, 1H), 6.87 (d, J = 7.8 Hz, 1H), 6.68 (d, J = 2.0 Hz, 1H), 4.00 (s, 3H), 3.99-3.96 (m, 2H), 3.10 (d, J = 6.7 Hz, 2H), 3.01 (s, 3H), 2.18-2.09 (m, 2H). |
| 224 | 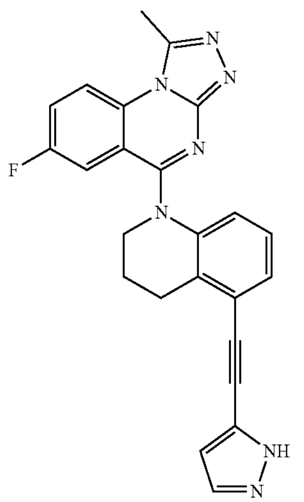 [SMILES: Cc1nnc2nc(N3CCCc4c(C#Cc5ccn[nH]5)cccc43)c3cc(F)ccc3n12] | 424.1 | 1H NMR (400 MHz, DMSO-d6) δ 8.40 (dd, J = 9.2, 4.1 Hz, 1H), 7.92-7.85 (m, 1H), 7.81 (s, 1H), 7.48 (d, J = 11.1 Hz, 1H), 7.32 (d, J = 7.4 Hz, 1H), 7.06 (t, J = 7.8 Hz, 1H), 6.89 (d, J = 8.0 Hz, 1H), 6.61 (s, 1H), 4.02 (t, J = 5.1 Hz, 2H), 3.10 (t, J = 5.9 Hz, 2H), 3.02 (s, 3H), 2.18-2.07 (m, 2H). |
| 225 | 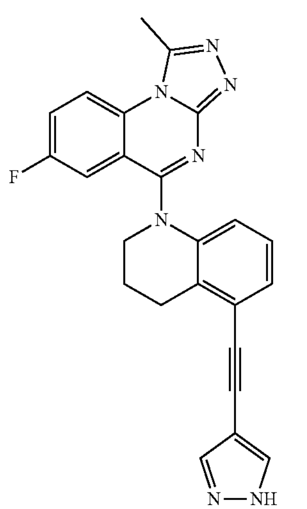 [SMILES: Cc1nnc2nc(N3CCCc4c(C#Cc5cn[nH]c5)cccc43)c3cc(F)ccc3n12] | 424.1 | 1H NMR (400 MHz, DMSO-d6) δ 8.39 (dd, J = 9.5, 4.6 Hz, 1H), 8.02-7.84 (m, 3H), 7.44 (dd, J = 9.6, 2.8 Hz, 1H), 7.26 (d, J = 7.4 Hz, 1H), 7.03 (t, J = 7.9 Hz, 1H), 6.82 (d, J = 8.3 Hz, 1H), 4.00 (t, J = 6.1 Hz, 2H), 3.07 (t, J = 6.6 Hz, 2H), 3.01 (s, 3H), 2.16-2.08 (m, 2H). |

TABLE 1-continued

Compounds and characterization of the compounds

| EXAMPLE | STRUCTURE | LC/MS | NMR |
|---|---|---|---|
| 226 | 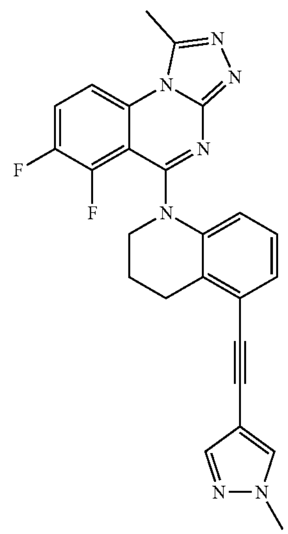 [SMILES: Cc1nnc2nc(N3CCCc4c(C#Cc5cnn(C)c5)cccc43)c3c(F)c(F)ccc3n12] | 456.2 | 1H NMR (400 MHz, DMSO-d6) δ 8.16 (dd, J = 9.3, 3.7 Hz, 1H), 8.11 (s, 1H), 8.10-8.04 (m, 1H), 7.72 (s, 1H), 7.19 (d, J = 7.5 Hz, 1H), 6.97 (t, J = 7.9 Hz, 1H), 6.84-6.80 (m, 1H), 3.87 (s, 3H), 2.98 (s, 3H). |
| 227 | 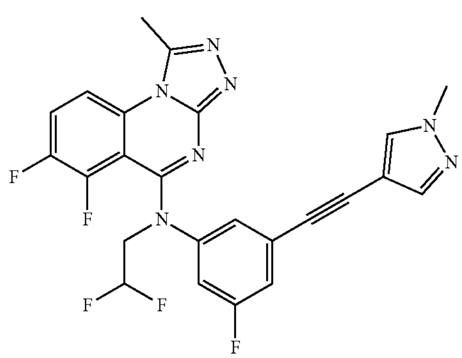 [SMILES: Cc1nnc2nc(N(CC(F)F)c3cc(F)cc(C#Cc4cnn(C)c4)c3)c3c(F)c(F)ccc3n12] | 498.1 | 1H NMR (400 MHz, DMSO-d6) δ 8.18 (dd, J = 9.4, 3.5 Hz, 1H), 8.09 (q, J = 9.5 Hz, 1H), 8.04 (s, 1H), 7.65 (s, 1H), 7.21 (s, 1H), 7.13 (dd, J = 24.7, 9.4 Hz, 2H), 6.54 (tt, J = 55.6, 3.5 Hz, 1H), 4.66 (t, J = 13.3 Hz, 2H), 3.84 (s, 3H), 3.01 (s, 3H). |
| 228 | 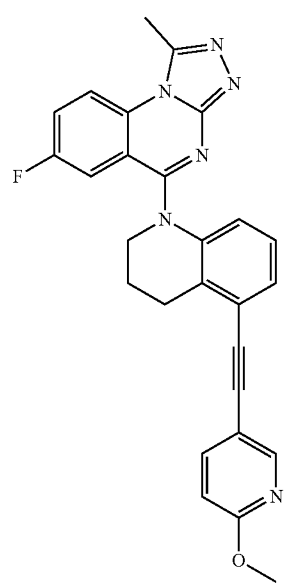 [SMILES: COc1ccc(C#Cc2cccc3c2CCCN3c2nc3nnc(C)n3c3ccc(F)cc23)cn1] | 465.2 | 1H NMR (400 MHz, DMSO-d6) δ 8.46 (d, J = 2.4 Hz, 1H), 8.39 (dd, J = 9.3, 4.6 Hz, 1H), 7.93 (d, J = 2.4 Hz, 1H), 7.87 (dd, J = 8.5, 5.8 Hz, 1H), 7.49-7.44 (m, 1H), 7.31 (d, J = 7.6 Hz, 1H), 7.05 (t, J = 7.9 Hz, 1H), 6.93 (d, J = 8.6 Hz, 1H), 6.85 (d, J = 8.2 Hz, 1H), 3.99 (t, J = 6.0 Hz, 2H), 3.91 (s, 3H), 3.11 (t, J = 6.6 Hz, 2H), 3.01 (s, 3H), 2.19-2.09 (m, 2H). |

TABLE 1-continued

Compounds and characterization of the compounds

| EXAMPLE | STRUCTURE | LC/MS | NMR |
|---|---|---|---|
| 229 | 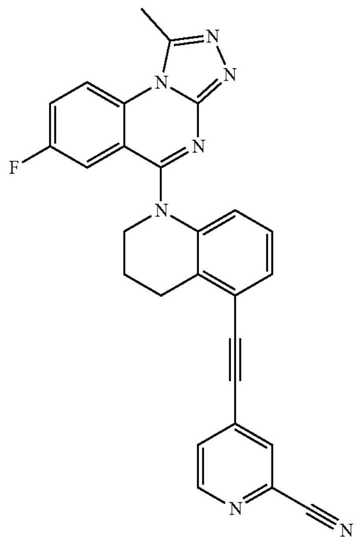 [SMILES: Cc1nnc2nc(N3CCCc4c(C#Cc5ccnc(C#N)c5)cccc43)c3cc(F)ccc3n12] | 460.2 | 1H NMR (400 MHz, DMSO-d6) δ 8.83 (d, J = 5.8 Hz, 1H), 8.40 (dd, J = 9.3, 4.6 Hz, 1H), 8.34 (s, 1H), 7.94 (dd, J = 5.1, 1.6 Hz, 1H), 7.91-7.85 (m, 1H), 7.51 (dd, J = 9.5, 2.9 Hz, 1H), 7.41-7.36 (m, 1H), 7.11 (t, J = 7.9 Hz, 1H), 6.96 (d, J = 8.2 Hz, 1H), 4.01 (t, J = 6.0 Hz, 2H), 3.18-3.12 (m, 2H), 3.02 (s, 3H), 2.15 (p, J = 8.5, 7.6 Hz, 2H). |
| 230 | 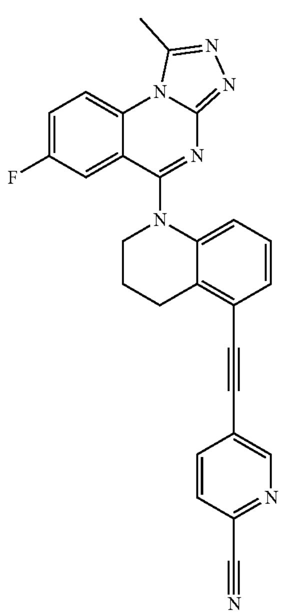 [SMILES: Cc1nnc2nc(N3CCCc4c(C#Cc5ccc(C#N)nc5)cccc43)c3cc(F)ccc3n12] | 460.1 | 1H NMR (400 MHz, DMSO-d6) δ 9.00-8.97 (m, 1H), 8.40 (dd, J = 9.3, 4.5 Hz, 1H), 8.31 (dd, J = 8.1, 2.0 Hz, 1H), 8.15 (d, J = 8.1 Hz, 1H), 7.94-7.85 (m, 1H), 7.50 (dd, J = 9.6, 2.8 Hz, 1H), 7.40 (d, J = 7.5 Hz, 1H), 7.11 (t, J = 7.8 Hz, 1H), 6.95 (d, J = 8.2 Hz, 1H), 4.01 (t, J = 6.0 Hz, 2H), 3.15 (t, J = 6.5 Hz, 2H), 3.02 (s, 3H), 2.14 (q, J = 5.5, 4.9 Hz, 2H). |

TABLE 1-continued

Compounds and characterization of the compounds

| EXAMPLE | STRUCTURE | LC/MS | NMR |
|---|---|---|---|
| 231 | 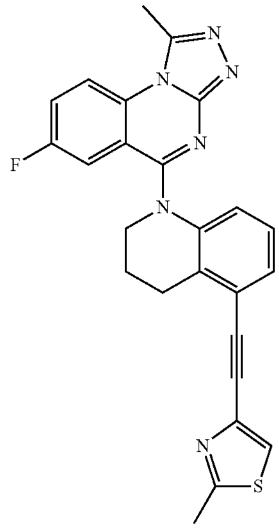 [SMILES: Cc1nc(C#Cc2cccc3c2CCCN3c2nc3nnc(C)n3c3ccc(F)cc23)cs1] | 455.1 | 1H NMR (400 MHz, DMSO-d6) δ 8.41-8.36 (m, 1H), 7.98 (s, 1H), 7.87 (td, J = 8.0, 2.9 Hz, 1H), 7.48 (dd, J = 9.6, 2.3 Hz, 1H), 7.31 (d, J = 7.6 Hz, 1H), 7.06 (t, J = 8.0 Hz, 1H), 6.86 (d, J = 8.2 Hz, 1H), 3.99 (t, J = 5.0 Hz, 2H), 3.10 (t, J = 6.6 Hz, 2H), 3.01 (s, 3H), 2.70 (s, 3H), 2.17-2.09 (m, 2H). |
| 232 | 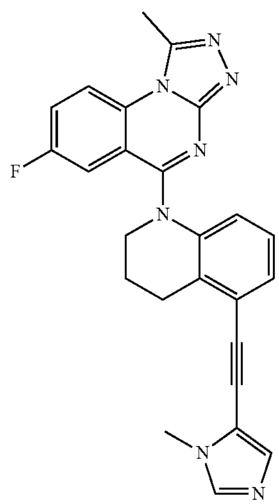 [SMILES: Cc1nnc2nc(N3CCCc4c(C#Cc5cncn5C)cccc43)c3cc(F)ccc3n12] | 438.2 | 1H NMR (400 MHz, DMSO-d6) δ 8.73 (s, 1H), 8.38 (dd, J = 9.3, 4.7 Hz, 1H), 7.92 (s, 1H), 7.90-7.83 (m, 1H), 7.55-7.49 (m, 1H), 7.34 (d, J = 7.5 Hz, 1H), 7.09 (d, J = 8.1 Hz, 1H), 6.89 (d, J = 8.4 Hz, 1H), 3.99-3.95 (m, 3H), 3.89 (s, 3H), 3.10 (t, J = 6.6 Hz, 2H), 3.01 (s, 3H), 2.19-2.09 (m, 2H). |
| 233 | 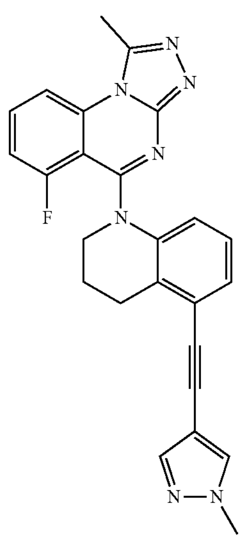 [SMILES: Cc1nnc2nc(N3CCCc4c(C#Cc5cnn(C)c5)cccc43)c3c(F)cccc3n12] | 438.2 | 1H NMR (400 MHz, DMSO-d6) δ 8.17 (d, J = 8.6 Hz, 1H), 8.12 (s, 1H), 8.04-7.96 (m, 1H), 7.72 (s, 1H), 7.41-7.33 (m, 1H), 7.19 (d, J = 7.5 Hz, 1H), 6.96 (t, J = 6.4 Hz, 1H), 6.82 (d, J = 8.2 Hz, 1H), 4.24-4.19 (m, 2H), 3.87 (s, 3H), 3.76-3.67 (m, 2H), 3.00 (s, 3H), 2.95-2.93 (m, 2H) |

TABLE 1-continued

Compounds and characterization of the compounds

| EXAMPLE | STRUCTURE | LC/MS | NMR |
|---|---|---|---|
| 234 | 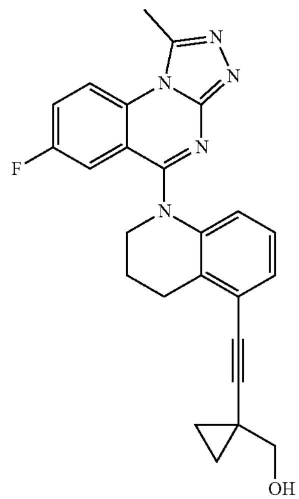 [SMILES: Cc1nnc2nc(N3CCCc4c(C#CC5(CO)CC5)cccc43)c3cc(F)ccc3n12] | 428.2 | 1H NMR (400 MHz, DMSO-d6) δ 8.36-8.31 (m, 1H), 7.85-7.80 (m, 1H), 7.40-7.36 (m, 1H), 7.08 (d, J = 1.8 Hz, 1H), 6.94 (d, J = 8.6 Hz, 1H), 6.69 (d, J = 10.8 Hz, 1H), 3.92 (t, J = 6.6 Hz, 2H), 3.49 (s, 3H), 2.98 (s, 3H), 2.96 (d, J = 9.1 Hz, 2H), 2.12-2.04 (m, 2H), 0.92 (s, 4H). |
| 235 | 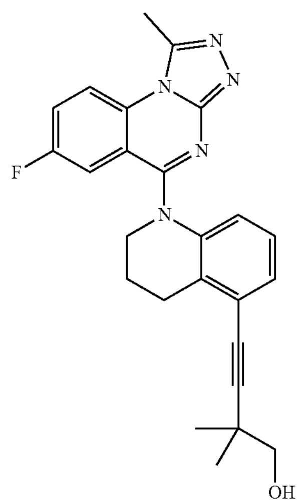 [SMILES: Cc1nnc2nc(N3CCCc4c(C#CC(C)(C)CO)cccc43)c3cc(F)ccc3n12] | 430.2 | 1H NMR (400 MHz, DMSO-d6) δ 8.39 (dd, J = 9.4, 4.6 Hz, 1H), 7.91-7.85 (m, 1H), 7.43-7.37 (m, 1H), 7.16 (d, J = 7.5 Hz, 1H), 6.98 (t, J = 7.9 Hz, 1H), 6.79 (d, J = 8.2 Hz, 1H), 3.99 (t, J = 6.1 Hz, 2H), 3.41 (s, 2H), 3.02 (s, 3H), 2.99 (d, J = 6.7 Hz, 2H), 2.17-2.03 (m, 2H), 1.26 (s, 6H). |
| 236 | 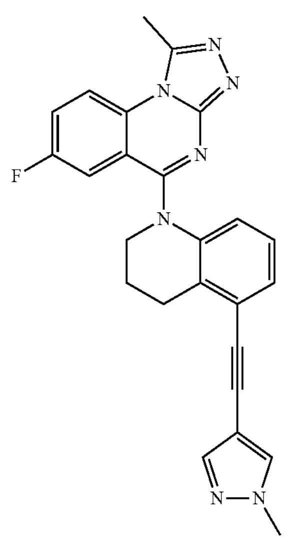 [SMILES: Cc1nnc2nc(N3CCCc4c(C#Cc5cnn(C)c5)cccc43)c3cc(F)ccc3n12] | 438.1 | 1H NMR (400 MHz, DMSO-d6) δ 8.36 (dd, J = 9.4, 4.7 Hz, 1H), 8.12 (s, 1H), 7.88-7.81 (m, 1H), 7.73 (s, 1H), 7.44 (dd, J = 9.5, 2.6 Hz, 1H), 7.20 (d, J = 7.3 Hz, 1H), 7.00 (t, J = 7.7 Hz, 1H), 6.76 (d, J = 8.4 Hz, 1H), 3.95 (t, J = 6.3 Hz, 2H), 3.88 (s, 3H), 3.05 (t, J = 6.5 Hz, 2H), 2.99 (s, 3H), 2.16-2.07 (m, 2H). |

TABLE 1-continued

Compounds and characterization of the compounds

| EXAMPLE | STRUCTURE | LC/MS | NMR |
|---|---|---|---|
| 237 | 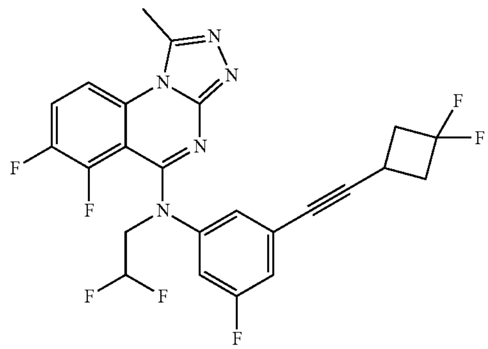 [SMILES: Cc1nnc2nc(N(CC(F)F)c3cc(F)cc(C#CC4CC(F)(F)C4)c3)c3c(F)c(F)ccc3n12] | 508.1 | "1H NMR (400 MHz, DMSO-d6) δ 8.17 (dd, J = 9.8, 3.7 Hz, 1H), 8.08 (q, J = 9.4 Hz, 1H), 7.17-7.11 (m, 2H), 7.04 (d, J = 8.7 Hz, 1H), 6.68-6.36 (m, 1H), 4.63 (t, J = 15.9 Hz, 2H), 3.27-3.16 (m, 1H), 3.06 –  2.94 (m, 1H), 3.00 (s, 3H), 2.78-2.64 (m, 2H)." |
| 238 | 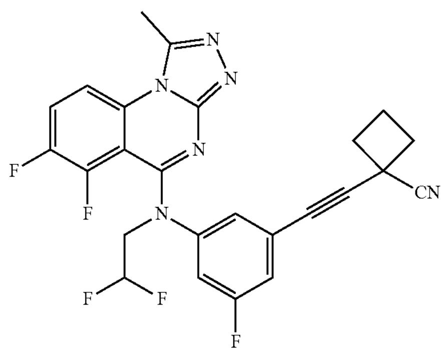 [SMILES: Cc1nnc2nc(N(CC(F)F)c3cc(F)cc(C#CC4(C#N)CCC4)c3)c3c(F)c(F)ccc3n12] | 488.1 | 1H NMR (400 MHz, DMSO-d6) δ 8.17 (dd, J = 9.6, 3.6 Hz, 1H), 8.09 (t, J = 8.7 Hz, 1H), 7.18-7.10 (m, 2H), 7.06-7.00 (m, 1H), 6.69-6.38 (m, 1H), 4.70-4.58 (m, 2H), 3.00 (s, 3H), 2.38-2.30 (m, 2H), 2.22-2.13 (m, 2H), 1.82-1.66 (m, 2H). |
| 239 | 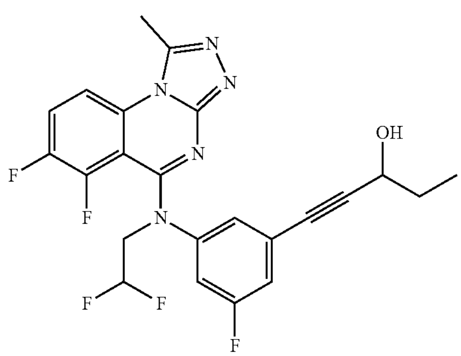 [SMILES: CCC(O)C#Cc1cc(F)cc(N(CC(F)F)c2nc3nnc(C)n3c3ccc(F)c(F)c23)c1] | 476.1 | 1H NMR (400 MHz, DMSO-d6) δ 8.18 (dd, J = 9.6, 3.4 Hz, 1H), 8.09 (q, J = 9.3 Hz, 1H), 7.15 (d, J = 12.3 Hz, 2H), 7.04-6.98 (m, 1H), 6.68-6.36 (m, 1H), 4.70-4.59 (m, 2H), 4.33 (t, J = 6.5 Hz, 1H), 3.01 (s, 3H), 1.62 (p, J = 7.2 Hz, 2H), 0.93 (t, J = 7.4 Hz, 3H). |
| 240 | 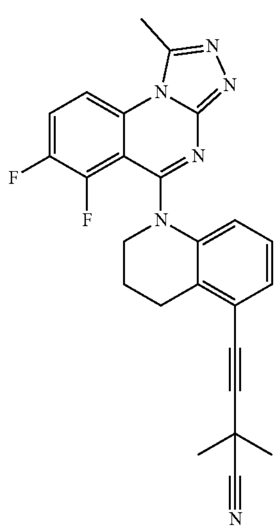 [SMILES: Cc1nnc2nc(N3CCCc4c(C#CC(C)(C)C#N)cccc43)c3c(F)c(F)ccc3n12] | 443.1 | 1H NMR (400 MHz, DMSO-d6) δ 8.20-8.16 (m, 1H), 8.14-8.07 (m, 1H), 7.20 (d, J = 7.2 Hz, 1H), 7.00 (t, J = 7.9 Hz, 1H), 6.92 (d, J = 8.0 Hz, 1H), 4.02-3.86 (m, 2H), 2.99 (s, 3H), 2.94-2.84 (m, 2H), 2.18-2.02 (m, 2H), 1.77 (s, 6H). |

TABLE 1-continued
Compounds and characterization of the compounds
| EXAMPLE | STRUCTURE | LC/MS | NMR |
|---|---|---|---|
| 241 | 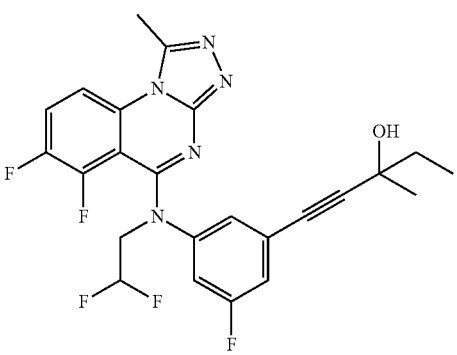 [SMILES: CCC(C)(O)C#Cc1cc(F)cc(N(CC(F)F)c2nc3nnc(C)n3c3ccc(F)c(F)c23)c1] | 490.1 | 1H NMR (400 MHz, DMSO-d6) δ 8.21-8.03 (m, 2H), 7.16-7.08 (m, 2H), 6.99 (d, J = 9.1 Hz, 1H), 6.53 (tt, J = 56.1, 3.4 Hz, 1H), 4.64 (t, J = 14.7 Hz, 2H), 3.01 (s, 3H), 1.67-1.56 (m, 2H), 1.38 (s, 3H), 0.96 (t, J = 7.4 Hz, 3H). |
| 242 | 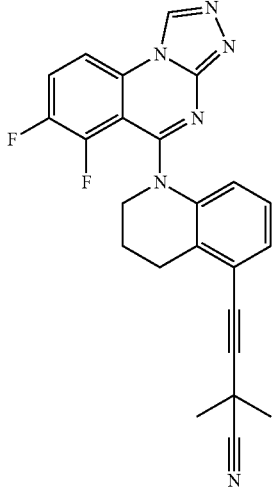 [SMILES: CC(C)(C#N)C#Cc1cccc2c1CCCN2c1nc2nncn2c2ccc(F)c(F)c12] | 429.1 | 1H NMR (400 MHz, DMSO-d6) δ 9.81 (s, 1H), 8.30 (d, J = 3.5 Hz, 1H), 8.20 (q, J = 9.4 Hz, 1H), 7.20-7.15 (m, 1H), 6.99 (q, J = 8.1 Hz, 2H), 4.02-3.82 (m, 2H), 3.01-2.87 (m, 2H), 2.15-2.03 (m, 2H), 1.77 (s, 6H). |
| 243 | 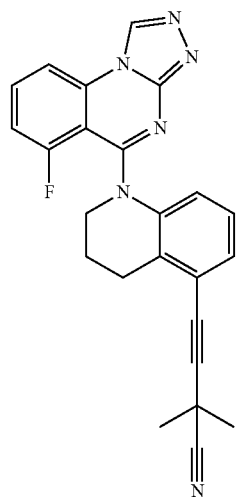 [SMILES: CC(C)(C#N)C#Cc1cccc2c1CCCN2c1nc2nncn2c2cccc(F)c12] | 411.1 | 1H NMR (400 MHz, DMSO-d6) δ 9.80 (s, 1H), 8.25 (d, J = 8.3 Hz, 1H), 8.04 (d, J = 5.3 Hz, 1H), 7.35-7.28 (m, 1H), 7.17 (d, J = 7.1 Hz, 1H), 6.94 (dd, J = 12.5, 7.3 Hz, 3H), 4.01-3.87 (m, 2H), 2.99-2.89 (m, 2H), 2.12-2.03 (m, 2H), 1.77 (s, 6H). |

TABLE 1-continued

Compounds and characterization of the compounds

| EXAMPLE | STRUCTURE | LC/MS | NMR |
|---|---|---|---|
| 244 | 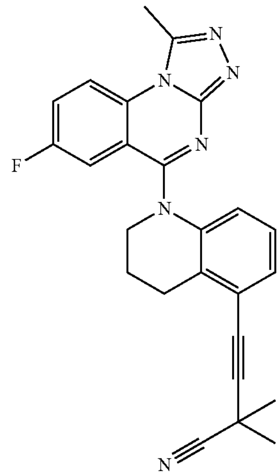 [SMILES: Cc1nnc2nc(N3CCCc4c(C#CC(C)(C)C#N)cccc43)c3cc(F)ccc3n12] | 425.2 | 1H NMR (400 MHz, DMSO-d6) δ 8.43-8.37 (m, 1H), 7.90 (td, J = 9.5, 8.7, 2.9 Hz, 1H), 7.46 (dd, J = 9.6, 2.9 Hz, 1H), 7.26 (d, J = 7.5 Hz, 1H), 7.04 (t, J = 7.9 Hz, 1H), 6.90 (d, J = 8.1 Hz, 1H), 4.00 (t, J = 6.1 Hz, 2H), 3.02-2.99 (m, 5H), 2.12 (p, J = 6.5 Hz, 2H), 1.78 (s, 6H). |
| 245 | 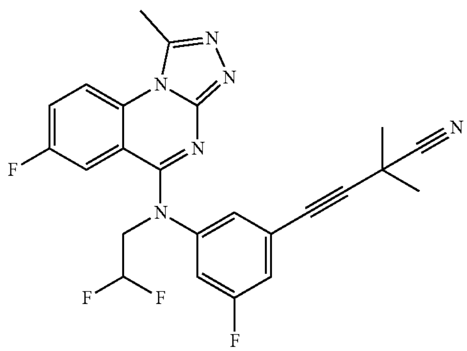 [SMILES: Cc1nnc2nc(N(CC(F)F)c3cc(F)cc(C#CC(C)(C)C#N)c3)c3cc(F)ccc3n12] | 467.2 | 1H NMR (400 MHz, DMSO-d6) δ 8.40 (dd, J = 9.4, 4.6 Hz, 1H), 7.87 (td, J = 9.5, 8.7, 2.9 Hz, 1H), 7.42-7.36 (m, 2H), 7.31 (d, J = 10.0 Hz, 1H), 7.09 (dd, J = 9.7, 2.9 Hz, 1H), 6.56 (tt, J = 55.7, 3.8 Hz, 1H), 4.61 (td, J = 14.3, 3.7 Hz, 2H), 3.03 (s, 3H), 1.70 (s, 6H). |
| 246 | 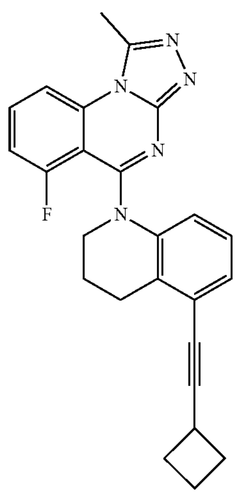 [SMILES: Cc1nnc2nc(N3CCCc4c(C#CC5CCC5)cccc43)c3c(F)cccc3n12] | 412.2 | 1H NMR (400 MHz, DMSO-d6) δ 8.14 (d, J = 8.7 Hz, 1H), 7.97 (td, J = 8.8, 5.5 Hz, 1H), 7.33 (dd, J = 12.0, 8.2 Hz, 1H), 7.07 (d, J = 7.3 Hz, 1H), 6.92-6.85 (m, 1H), 6.74 (d, J = 8.6 Hz, 1H), 4.01-3.87 (m, 2H), 2.98 (s, 3H), 2.95-2.90 (m, 2H), 2.38-2.32 (m, 2H), 2.16 (d, J = 8.7 Hz, 2H), 2.02-1.88 (m, 2H). |

Also falling within the scope herein are the in vivo metabolic products of the compounds described herein, to the extent such products are novel and unobvious over the prior art. Such products may result for example from the oxidation, reduction, hydrolysis, amidation, esterification and the like of the administered compound, primarily due to enzymatic processes. Accordingly, included are novel and unobvious compounds produced by a process comprising contacting a compound with a mammal for a period of time sufficient to yield a metabolic product thereof. Such products typically are identified by preparing a radiolabelled (e.g. $^{14}C$ or $^{3}H$) compound, administering it parenterally in a detectable dose (e.g. greater than about 0.5 mg/kg) to an animal such as rat, mouse, guinea pig, monkey, or to man, allowing sufficient time for metabolism to occur (typically from about 30 seconds to about 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g. by MS or NMR analysis. In general, analysis of metabolites is done in the same way as conventional drug metabolism studies well-known to those skilled in the art.

In some embodiments, a compound of the present disclosure has selectivity for DGKα over one or more of the other DGK isoforms, e.g., β, γ, δ, ε, ζ, η, θ, ι, and/or κ. Selectivity can be measured by relative values in corresponding biochemical assays, e.g., activity to inhibit a DGK isoform. In some embodiments, the compound comprises an activity against DGKβ, DGKγ, DGKδ, DGKε, DGKζ, DGKη, DGKθ, DGKι, and/or DGKκ, wherein the $IC_{50}$ is greater than about 30 μM in a biochemical assay.

In some embodiments, a compound of the present disclosure has selectivity for DGKα of at least about 1.2, about 1.5, about 2, about 3, about 4, about 5, about 6, about 7, about 8, about 9, about 10, about 15, about 20, about 30, about 40, about 50, about 60, about 70, about 80, about 90, about 100, about 200, about 300, about 400, about 500, about 1000, about 2000, about 3000, about 4000, about 5000, or about 10000-fold or more over one or more, e.g., 2, 3, 4, 5, 6, 7, 8, or 9 or more, other DGK isoforms including DGKβ, DGKγ, DGKδ, DGKε, DGKζ, DGKη, DGKθ, DGKι, and/or DGKκ. In some embodiments, the compound has selectivity for DGKα of at least about 1.2, about 1.5, about 2, about 3, about 4, about 5, about 6, about 7, about 8, about 9, about 10, about 15, about 20, about 30, about 40, about 50, about 60, about 70, about 80, about 90, about 100, about 200, about 300, about 400, about 500, about 1000, about 2000, about 3000, about 4000, about 5000, or about 10000-fold or more over DGKβ and/or DGKγ. In some embodiments, the compound has selectivity for DGKα of at least about 1.2, about 1.5, about 2, about 3, about 4, about 5, about 6, about 7, about 8, about 9, about 10, about 15, about 20, about 30, about 40, about 50, about 60, about 70, about 80, about 90, about 100, about 200, about 300, about 400, about 500, about 1000, about 2000, about 3000, about 4000, about 5000, or about 10000-fold or more over DGKβ. In some embodiments, the compound has selectivity for DGKα of at least about 1.2, about 1.5, about 2, about 3, about 4, about 5, about 6, about 7, about 8, about 9, about 10, about 15, about 20, about 30, about 40, about 50, about 60, about 70, about 80, about 90, about 100, about 200, about 300, about 400, about 500, about 1000, about 2000, about 3000, about 4000, about 5000, or about 10000-fold or more over DGKγ. In some embodiments, the compound has selectivity for DGKα of at least about 1.2, about 1.5, about 2, about 3, about 4, about 5, about 6, about 7, about 8, about 9, about 10, about 15, about 20, about 30, about 40, about 50, about 60, about 70, about 80, about 90, about 100, about 200, about 300, about 400, about 500, about 1000, about 2000, about 3000, about 4000, about 5000, or about 10000-fold or more over DGKδ. In some embodiments, the compound has selectivity for DGKα of at least about 1.2, about 1.5, about 2, about 3, about 4, about 5, about 6, about 7, about 8, about 9, about 10, about 15, about 20, about 30, about 40, about 50, about 60, about 70, about 80, about 90, about 100, about 200, about 300, about 400, about 500, about 1000, about 2000, about 3000, about 4000, about 5000, or about 10000-fold or more over DGKε. In some embodiments, the compound has selectivity for DGKα of at least about 1.2, about 1.5, about 2, about 3, about 4, about 5, about 6, about 7, about 8, about 9, about 10, about 15, about 20, about 30, about 40, about 50, about 60, about 70, about 80, about 90, about 100, about 200, about 300, about 400, about 500, about 1000, about 2000, about 3000, about 4000, about 5000, or about 10000-fold or more over DGKζ. In some embodiments, the compound has selectivity for DGKα of at least about 1.2, about 1.5, about 2, about 3, about 4, about 5, about 6, about 7, about 8, about 9, about 10, about 15, about 20, about 30, about 40, about 50, about 60, about 70, about 80, about 90, about 100, about 200, about 300, about 400, about 500, about 1000, about 2000, about 3000, about 4000, about 5000, or about 10000-fold or more over DGKη. In some embodiments, the compound has selectivity for DGKα of at least about 1.2, about 1.5, about 2, about 3, about 4, about 5, about 6, about 7, about 8, about 9, about 10, about 15, about 20, about 30, about 40, about 50, about 60, about 70, about 80, about 90, about 100, about 200, about 300, about 400, about 500, about 1000, about 2000, about 3000, about 4000, about 5000, or about 10000-fold or more over DGKθ. In some embodiments, the compound has selectivity for DGKα of at least about 1.2, about 1.5, about 2, about 3, about 4, about 5, about 6, about 7, about 8, about 9, about 10, about 15, about 20, about 30, about 40, about 50, about 60, about 70, about 80, about 90, about 100, about 200, about 300, about 400, about 500, about 1000, about 2000, about 3000, about 4000, about 5000, or about 10000-fold or more over DGKι. In some embodiments, the compound has selectivity for DGKα of at least about 1.2, about 1.5, about 2, about 3, about 4, about 5, about 6, about 7, about 8, about 9, about 10, about 15, about 20, about 30, about 40, about 50, about 60, about 70, about 80, about 90, about 100, about 200, about 300, about 400, about 500, about 1000, about 2000, about 3000, about 4000, about 5000, or about 10000-fold or more over DGKκ.

III. Pharmaceutical Formulations

In some embodiments, the present disclosure provides a pharmaceutical formulation comprising a pharmaceutically effective amount of a compound of the present disclosure, or a pharmaceutically acceptable salt thereof, and a pharmaceutically acceptable carrier or excipient. Also provided herein is a pharmaceutical formulation comprising a pharmaceutically effective amount of a compound of Formula (I), a compound shown in Table 1, or a pharmaceutically acceptable salt, solvate, and/or ester thereof, and a pharmaceutically acceptable carrier or excipient.

In some embodiments, the pharmaceutical composition further comprises one or more additional therapeutic agents. Any suitable additional therapeutic agent or combination therapy can be used with the compounds of Formula (I), a compound shown in Table 1, or a pharmaceutically acceptable salt thereof, such as the agents and therapies described within.

In some embodiments, the pharmaceutical composition comprises a compound of Formula (I), a compound shown in Table 1, and an additional therapeutic agent, wherein the additional therapeutic agent is an anticancer agent. In some embodiments, the pharmaceutical composition is the pharmaceutical composition wherein the additional therapeutic agent is independently an anti-neoplastic agent, nivolumab, pembrolizumab, atezolizumab, ipilimumab, chemotherapy, radiation therapy, or resection therapy. In some embodiments, the pharmaceutical composition is the pharmaceutical composition wherein the additional therapeutic agent is independently rituxan, doxorubicin, gemcitabine, nivolumab, pembrolizumab, artezolizumab, nivolumab, pembrolizumab, atezolizumab, or ipilimumab. In some embodiments, the pharmaceutical composition is the pharmaceutical composition wherein the additional therapeutic agent is a PD-1/PD-L1 inhibitor. In some embodiments, the pharmaceutical composition is the pharmaceutical composition wherein the additional therapeutic agent is a vaccine.

In some embodiments, the pharmaceutical composition is the pharmaceutical composition wherein the additional therapeutic agent comprises one or more populations of immune cells, such as natural killer (NK) cells, NK-T cells, T cells, cytokine-induced killer (CIK) cells, macrophage (MAC) cells, tumor infiltrating lymphocytes (TILs) and dendritic cell (DCs).

In some embodiments, the pharmaceutical composition is the pharmaceutical composition wherein the additional therapeutic agent comprises one or more chimeric antigen receptors (CARs).

In some embodiments, the pharmaceutical composition is the pharmaceutical composition wherein the additional therapeutic agent comprises an immunotherapy, an immunostimulatory therapy, a cytokine therapy, a chemokine therapy, a cellular therapy, a gene therapy, or combinations thereof.

In some embodiments, the pharmaceutical composition comprises a compound of Formula (I), a compound shown in Table 1, and an additional therapeutic agent, wherein the additional therapeutic agent is an agent effective against a viral infection. In some embodiments, the viral infection is HIV. In some embodiments, the viral infection is hepatitis B virus. In some embodiments, the pharmaceutical composition comprises a compound of Formula (I), a compound shown in Table 1, and an additional therapeutic agent, wherein additional therapeutic agent comprises a vaccine.

In some embodiments, the pharmaceutical composition is for use in treating a cancer.

In some embodiments, the pharmaceutical composition is for use in treating an HIV or hepatitis B infection.

In some embodiments, compounds disclosed herein are formulated with conventional carriers and excipients, which can be selected in accord with ordinary practice. Tablets can contain excipients, glidants, fillers, binders and the like. Aqueous formulations can be prepared in sterile form, and can be isotonic, for instance when intended for delivery by other than oral administration. In some embodiments, formulations can optionally contain excipients such as those set forth in the "Handbook of Pharmaceutical Excipients" (1986). Excipients can include, for example, ascorbic acid and other antioxidants, chelating agents such as EDTA, carbohydrates such as dextran, hydroxyalkylcellulose, hydroxyalkylmethylcellulose, stearic acid and the like. The pH of the formulations ranges from about 3 to about 11, for example from about 7 to about 10.

In some embodiments, the compounds disclosed herein are administered alone. In some embodiments, compounds disclosed herein are administered in pharmaceutical formulations. In some embodiments a formulation, for veterinary and/or for human use, comprises at least one compound of Formula (I), a compound shown in Table 1, or a pharmaceutically acceptable salt, solvate, and/or ester thereof, together with one or more acceptable carriers and optionally other therapeutic ingredients, such as those additional therapeutic ingredients discussed herein. In some embodiments, carrier(s) are "acceptable" in the sense of being compatible with the other ingredients of the formulation and physiologically innocuous to the recipient thereof.

In some embodiments, formulations of the disclosure include those suitable for the foregoing administration routes. In some embodiments, formulations are presented in unit dosage form. Formulations may be prepared by methods known in the art of pharmacy. Techniques and formulations can be found, for example, in Remington's Pharmaceutical Sciences (Mack Publishing Co., Easton, PA). Such methods include, for instance, a step of bringing into association the active ingredient with a carrier comprising one or more accessory ingredients. In some embodiments, formulations are prepared by bringing into association the active ingredient with liquid carriers or finely divided solid carriers or both, and then, in some embodiments, shaping the product.

Formulations suitable for oral administration may be presented as discrete units such as capsules, cachets or tablets each containing a predetermined amount of active ingredient, such as a compound of Formula (I), a compound shown in Table 1, or a pharmaceutically acceptable salt, solvate, and/or ester thereof; as a powder or granules; as a solution or a suspension in an aqueous or non-aqueous liquid; or as an oil-in-water liquid emulsion or a water-in-oil liquid emulsion. In some embodiments, an active ingredient is administered as a bolus, electuary or paste.

A tablet can be made, for example, by compression or molding, optionally with one or more accessory ingredients. Compressed tablets may be prepared, for example, by compressing in a suitable machine the active ingredient in a free-flowing form such as a powder or granules, optionally mixed with a binder, lubricant, inert diluent, preservative, surface active or dispersing agent. Molded tablets may be made, for instance, by molding in a suitable machine a mixture of the powdered active ingredient moistened with an inert liquid diluent. The tablets may optionally be coated or scored. In some embodiments, tablets are formulated so as to provide slow or controlled release of the active ingredient therefrom.

For infections of the eye or other external tissues e.g. mouth and skin, the formulations can be applied as a topical ointment or cream containing a compound of Formula (I), a compound shown in Table 1, in an amount of, for example, about 0.075 to about 20% w/w (including active ingredient(s) in a range between about 0.1% and about 20% in increments of about 0.1% w/w such as about 0.6% w/w, about 0.7% w/w, etc.), such as about 0.2 to about 15% w/w and such as about 0.5 to about 10% w/w. When formulated in an ointment, a compound of Formula (I), a compound shown in Table 1, may be employed with either a paraffinic or a water-miscible ointment base. Alternatively, a compound of Formula (I), a compound shown in Table 1, may be formulated in a cream with an oil-in-water cream base.

If desired, the aqueous phase of the cream base may include, for example, at least about 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may in some embodiments include a compound which enhances absorption or penetration of the active ingredient through the skin or other affected areas. Examples of such dermal penetration enhancers include dimethyl sulfoxide and related analogs.

The oily phase of the emulsions may be constituted from known ingredients in a known manner. While the phase may comprise merely an emulsifier (otherwise known as an emulgent), it can comprise, for example, a mixture of at least one emulsifier with a fat or an oil or with both a fat and an oil. In some embodiments, a hydrophilic emulsifier is included together with a lipophilic emulsifier which acts as a stabilizer. In some embodiments, an emulsion includes both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation include, for instance, Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired properties. The cream can be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used. These may be used alone or in combination depending on the properties required. Alternatively, high melting point lipids such as white soft paraffin and/or liquid paraffin or other mineral oils can be used.

In some embodiments, pharmaceutical formulations herein comprise a combination together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, solutions, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions contain the active materials in admixture with excipients suitable for the manufacture of aqueous suspensions. Such excipients include a suspending agent, such as sodium carboxymethylcellulose, methylcellulose, hydroxypropyl methylcelluose, sodium alginate, polyvinylpyrrolidone, gum tragacanth and gum acacia, and dispersing or wetting agents such as a naturally-occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions may also be in the form of oil-in-water emulsions. The oily phase may be a vegetable oil, such as olive oil or *arachis* oil, a mineral oil, such as liquid paraffin, or a mixture of these. Suitable emulsifying agents include naturally-occurring gums, such as gum acacia and gum tragacanth, naturally-occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions may be in the form of a sterile injectable or intravenous preparations, such as a sterile injectable aqueous or oleaginous suspension. Such suspensions may be formulated according to the known art using those suitable dispersing or wetting agents and suspending agents which have been mentioned above. Sterile injectable or intravenous preparations may also include a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form can vary depending upon the host treated and the particular mode of administration. For example, a time-release formulation intended for oral administration to humans may contain about 1 to about 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to about 500 µg of the active ingredient per milliliter of solution in order that infusion of a suitable volume at a rate of about 30 mL/hr can occur.

Formulations suitable for topical administration to the eye also include eye drops wherein the active ingredient is dissolved or suspended in a suitable carrier, especially an aqueous solvent for the active ingredient. The active ingredient can be present in such formulations in a concentration of about 0.5 to about 20%, such as about 0.5 to about 10%, for example about 1.5% w/w.

Formulations suitable for topical administration in the mouth include, for example, lozenges comprising the active ingredient in a flavored basis, such as sucrose and acacia or tragacanth; pastilles comprising the active ingredient in an inert basis, such as gelatin and glycerin, or sucrose and acacia; and mouthwashes comprising the active ingredient in a suitable liquid carrier.

Formulations for rectal administration may be presented as a suppository with a suitable base comprising, for example, cocoa butter or a salicylate.

Formulations suitable for intrapulmonary or nasal administration have a particle size, for example, in the range of about 0.1 to about 500 microns, such as about 0.5, about 1, about 30, or about 35, etc., which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment of cancer as described below.

In some embodiments, an inhalable composition comprises a compound of Formula (I), a compound shown in Table 1, or a pharmaceutically acceptable salt thereof. In some embodiments, the inhalable composition is suitable for treating cancer. In some embodiments, pharmaceutically acceptable salts are inorganic acid salts including hydrochloride, hydrobromide, sulfate or phosphate salts. For example, such salts may cause less pulmonary irritation relative to other salts. In some embodiments, an inhalable composition is delivered to the endobronchial space in an aerosol comprising particles with a mass median aerodynamic diameter (MMAD) between about 1 and about 5 µm. In some embodiments, the compound of Formula (I), a compound shown in Table 1, is formulated for aerosol delivery using a nebulizer, pressurized metered dose inhaler (pMDI), or dry powder inhaler (DPI).

Non-limiting examples of nebulizers include atomizing, jet, ultrasonic, pressurized, vibrating porous plate, or equivalent nebulizers including those nebulizers utilizing adaptive aerosol delivery technology (Denyer, *J Aerosol medicine Pulmonary Drug Delivery* 2010, 23 Supp 1, S1-S10). A jet nebulizer utilizes air pressure to break a liquid solution into aerosol droplets. An ultrasonic nebulizer works by a piezoelectric crystal that shears a liquid into small aerosol droplets. A pressurized nebulization system forces solution under pressure through small pores to generate aerosol droplets. A vibrating porous plate device utilizes rapid vibration to shear a stream of liquid into appropriate droplet sizes.

In some embodiments, a formulation for nebulization is delivered to the endobronchial space in an aerosol comprising particles with a MMAD predominantly between about 1 µm and about 5 µm using a nebulizer able to aerosolize the formulation of the compound of Formula (I), a compound shown in Table 1, into particles of the required MMAD. To be optimally therapeutically effective and to avoid upper respiratory and systemic side effects, the majority of aerosolized particles should not have a MMAD greater than about 5 µm. If an aerosol contains a large number of particles with a MMAD larger than about 5 µm, the particles are deposited in the upper airways decreasing the amount of drug delivered to the site of inflammation and bronchoconstriction in the lower respiratory tract. If the MMAD of the aerosol is smaller than about 1 µm, then the particles can in some cases remain suspended in the inhaled air and may be subsequently exhaled during expiration.

When formulated and delivered according to methods herein, the aerosol formulation for nebulization delivers a therapeutically efficacious dose of the compound of Formula (I), a compound shown in Table 1, to a therapeutic target, such as the site of a cancer. The amount of drug administered can be adjusted to reflect the efficiency of the delivery of a therapeutically efficacious dose of the compound of Formula (I), or a compound shown in Table 1. In some embodiments, a combination of the aqueous aerosol formulation with the atomizing, jet, pressurized, vibrating porous plate, or ultrasonic nebulizer permits, depending on the nebulizer, from about 20 to about 90%, such as about 70% delivery of the administered dose of the compound of Formula (I), or a compound shown in Table 1 into the airways. In some embodiments, from about 30 to about 50% of the active compound is delivered. For example, from about 70 to about 90% of the active compound can be delivered.

In some embodiments, a compound of Formula (I), a compound shown in Table 1, or a pharmaceutically acceptable salt thereof, is delivered as a dry inhalable powder. The compounds are administered endobronchially as a dry powder formulation to efficaciously deliver fine particles of compound into the endobronchial space using dry powder or metered dose inhalers. For delivery by DPI, the compound of Formula (I), or a compound shown in Table 1 is processed into particles with, predominantly, MMAD between about 1 µm and about 5 µm by milling spray drying, critical fluid processing, or precipitation from solution. Media milling, jet milling and spray-drying devices and procedures capable of producing the particle sizes with a MMAD between about 1 µm and about 5 µm are well known in the art. In some embodiments, excipients are added to the compound of Formula (I), or a compound shown in Table 1 before processing into particles of the required sizes. In some embodiments, excipients are blended with the particles of the required size to aid in dispersion of the drug particles, for example by using lactose as an excipient.

Particle size determinations are made using devices well known in the art. For example a multi-stage Anderson cascade impactor or other suitable method such as those specifically cited within the US Pharmacopoeia Chapter 601 as characterizing devices for aerosols within metered-dose and dry powder inhalers.

In some embodiments, a compound of Formula (I), or a compound shown in Table 1 can be delivered as a dry powder using a device such as a dry powder inhaler or other dry powder dispersion devices. Non-limiting examples of dry powder inhalers and devices include those disclosed in U.S. Pat. Nos. 5,458,135; 5,740,794; 5,775,320; 5,785,049; 3,906,950; 4,013,075; 4,069,819; 4,995,385; 5,522,385; 4,668,218; 4,667,668; 4,805,811 and 5,388,572. There are two major designs of dry powder inhalers. One design is a metering device in which a reservoir for the drug is place within the device and the patient adds a dose of the drug into the inhalation chamber. The second design is a factory-metered device in which each individual dose has been manufactured in a separate container. Both systems depend on the formulation of the drug into small particles of MMAD from about 1 µm to about 5 µm and often involve co-formulation with larger excipient particles such as, but not limited to, lactose. Drug powder is placed in the inhalation chamber (either by device metering or by breakage of a factory-metered dosage) and the inspiratory flow of the patient accelerates the powder out of the device and into the oral cavity. Non-laminar flow characteristics of the powder path cause the excipient-drug aggregates to decompose, and the mass of the large excipient particles causes their impaction at the back of the throat, while the smaller drug particles are deposited deep in the lungs. In some embodiments, a compound of Formula (I), or a compound shown in Table 1 or a pharmaceutically acceptable salt thereof, is delivered as a dry powder using either type of dry powder inhaler as described herein, wherein the MMAD of the dry powder, exclusive of any excipients, is predominantly in the range of about 1 µm to about 5 µm.

In some embodiments, a compound of Formula (I), a compound shown in Table 1 is delivered as a dry powder using a metered dose inhaler. Non-limiting examples of metered dose inhalers and devices include those disclosed in U.S. Pat. Nos. 5,261,538; 5,544,647; 5,622,163; 4,955,371; 3,565,070; 3,361,306 and 6,116,234. In some embodiments, a compound of Formula (I), a compound shown in Table 1, or a pharmaceutically acceptable salt thereof, is delivered as a dry powder using a metered dose inhaler wherein the MMAD of the dry powder, exclusive of any excipients, is predominantly in the range of about 1 to about 5 µm.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Unit dosage formulations include those containing a daily dose or unit daily sub-dose, as herein above recited, or an appropriate fraction thereof, of the active ingredient.

It should be understood that in addition to the ingredients particularly mentioned above the formulations may include other agents conventional in the art having regard to the type of formulation in question, for example those suitable for oral administration may include flavoring agents.

Further provided are veterinary compositions comprising at least one active ingredient as above defined together with a veterinary carrier therefor.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds herein are used to provide controlled release pharmaceutical formulations containing as active ingredient one or more of the compounds ("controlled release formulations") in which the release of the active ingredient is controlled and regulated to allow less frequency dosing or to improve the pharmacokinetic or toxicity profile of a given active ingredient.

Effective dose of active ingredient depends at least on the nature of the condition being treated, toxicity, the method of delivery, and the pharmaceutical formulation, and can be determined by the clinician using conventional dose escalation studies. It can be expected to be from about 0.0001 to about 100 mg/kg body weight per day; typically, from about 0.01 to about 10 mg/kg body weight per day; more typically, from about 0.01 to about 5 mg/kg body weight per day; most typically, from about 0.05 to about 0.5 mg/kg body weight per day. For example, the daily candidate dose for an adult human of about 70 kg body weight can range from about 1 mg to about 1000 mg, such as between about 5 mg and about 500 mg, and may take the form of single or multiple doses.

IV. Routes of Administration

One or more of the compounds of Formula (I) or a compound shown in Table 1 (herein referred to as the active ingredients) are administered by any route appropriate to the condition to be treated. Suitable routes include oral, rectal, nasal, pulmonary, topical (including buccal and sublingual), vaginal and parenteral (including subcutaneous, intramuscular, intravenous, intradermal, intrathecal and epidural), and the like. It will be appreciated that the route may vary with for example the condition of the recipient. An advantage of the compounds herein is that they are orally bioavailable and can be dosed orally.

The compounds of the present disclosure (also referred to herein as the active ingredients), can be administered by any route appropriate to the condition to be treated. Suitable routes include oral, rectal, nasal, topical (including buccal and sublingual), transdermal, vaginal and parenteral (including subcutaneous, intramuscular, intravenous, intradermal, intrathecal and epidural), and the like. It will be appreciated that the route may vary with for example the condition of the recipient. An advantage of certain compounds disclosed herein is that they are orally bioavailable and can be dosed orally.

A compound of the present disclosure may be administered to an individual in accordance with an effective dosing regimen for a desired period of time or duration, such as at least about one month, at least about 2 months, at least about 3 months, at least about 6 months, or at least about 12 months or longer. In some embodiments, the compound is administered on a daily or intermittent schedule for the duration of the individual's life.

The dosage or dosing frequency of a compound of the present disclosure may be adjusted over the course of the treatment, based on the judgment of the administering physician.

The compound may be administered to an individual (e.g., a human) in an effective amount. In some embodiments, the compound is administered once daily.

The compound can be administered by any useful route and means, such as by oral or parenteral (e.g., intravenous) administration. Therapeutically effective amounts of the compound may include from about 0.00001 mg/kg body weight per day to about 10 mg/kg body weight per day, such as from about 0.0001 mg/kg body weight per day to about 10 mg/kg body weight per day, or such as from about 0.001 mg/kg body weight per day to about 1 mg/kg body weight per day, or such as from about 0.01 mg/kg body weight per day to about 1 mg/kg body weight per day, or such as from about 0.05 mg/kg body weight per day to about 0.5 mg/kg body weight per day, or such as from about 0.3 mg to about 30 mg per day, or such as from about 30 mg to about 300 mg per day.

A compound of the present disclosure may be combined with one or more additional therapeutic agents in any dosage amount of the compound of the present disclosure (e.g., from about 1 mg to about 1000 mg of compound). Therapeutically effective amounts may include from about 1 mg per dose to about 1000 mg per dose, such as from about 50 mg per dose to about 500 mg per dose, or such as from about 100 mg per dose to about 400 mg per dose, or such as from about 150 mg per dose to about 350 mg per dose, or such as from about 200 mg per dose to about 300 mg per dose. Other therapeutically effective amounts of the compound of the present disclosure are about 100, about 125, about 150, about 175, about 200, about 225, about 250, about 275, about 300, about 325, about 350, about 375, about 400, about 425, about 450, about 475, or about 500 mg per dose. Other therapeutically effective amounts of the compound of the present disclosure are about 100 mg per dose, or about 125, about 150, about 175, about 200, about 225, about 250, about 275, about 300, about 325, about 350, about 375, about 400, about 425, about 450, or about 500 mg per dose. A single dose can be administered hourly, daily, or weekly. For example, a single dose can be administered once about every 1 hour, about 2, about 3, about 4, about 6, about 8, about 12, about 16 or once about every 24 hours. A single dose can also be administered once about every 1 day, about 2, about 3, about 4, about 5, about 6, or once about every 7 days. A single dose can also be administered once about every 1 week, about 2, about 3, or once about every 4 weeks. In some embodiments, a single dose can be administered once about every week. A single dose can also be administered once about every month.

Other therapeutically effective amounts of the compound of the present disclosure are about 20, about 25, about 30, about 35, about 40, about 45, about 50, about 55, about 60, about 65, about 70, about 75, about 80, about 85, about 90, about 95, or about 100 mg per dose.

The frequency of dosage of the compound of the present disclosure can be determined by the needs of the individual patient and can be, for example, once per day or twice, or more times, per day. Administration of the compound continues for as long as necessary to treat the disease or condition. For example, a compound can be administered to a human having cancer for a period of from about 20 days to about 180 days or, for example, for a period of from about 20 days to about 90 days or, for example, for a period of from about 30 days to about 60 days.

Administration can be intermittent, with a period of several or more days during which a patient receives a daily dose of the compound of the present disclosure followed by a period of several or more days during which a patient does not receive a daily dose of the compound. For example, a patient can receive a dose of the compound every other day, or three times per week. Again by way of example, a patient can receive a dose of the compound each day for a period of from about 1 to about 14 days, followed by a period of about 7 to about 21 days during which the patient does not receive a dose of the compound, followed by a subsequent period (e.g., from about 1 to about 14 days) during which the patient again receives a daily dose of the compound. Alternating periods of administration of the compound, followed by non-administration of the compound, can be repeated as clinically required to treat the patient.

In some embodiments, pharmaceutical compositions comprising a compound of the present disclosure, or a pharmaceutically acceptable salt thereof, in combination with one or more (e.g., one, two, three, four, one or two, one to three, or one to four) additional therapeutic agents, and a pharmaceutically acceptable excipient are provided.

In some embodiments, kits comprising a compound of the present disclosure, or a pharmaceutically acceptable salt thereof, in combination with one or more (e.g., one, two, three, four, one or two, one to three, or one to four) additional therapeutic agents are provided.

In some embodiments, a compound of the present disclosure, or a pharmaceutically acceptable salt thereof, is combined with one, two, three, four or more additional therapeutic agents. In some embodiments, a compound of the present disclosure, or a pharmaceutically acceptable salt thereof, is combined with two additional therapeutic agents. In some embodiments, a compound of the present disclosure, or a pharmaceutically acceptable salt thereof, is combined with three additional therapeutic agents. In some embodiments, a compound of the present disclosure, or a pharmaceutically acceptable salt thereof, is combined with four additional therapeutic agents. The one, two, three, four or more additional therapeutic agents can be different therapeutic agents selected from the same class of therapeutic agents, and/or they can be selected from different classes of therapeutic agents.

In some embodiments, when a compound of the present disclosure is combined with one or more additional therapeutic agents as described herein, the components of the composition are administered as a simultaneous or sequential regimen. When administered sequentially, the combination may be administered in two or more administrations.

In some embodiments, a compound of the present disclosure is combined with one or more additional therapeutic agents in a unitary dosage form for simultaneous administration to a patient, for example as a solid dosage form for oral administration.

In some embodiments, a compound of the present disclosure is co-administered with one or more additional therapeutic agents.

In order to prolong the effect of a compound of the present disclosure, it is often desirable to slow the absorption of a compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending a compound in an oil vehicle. Injectable depot forms are made by forming microencapsule matrices of a compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping a compound in liposomes or microemulsions that are compatible with body tissues.

V. Combination Therapy

The compounds of the present disclosure and compositions provided herein are also used in combination with other active therapeutic agents. The other active therapeutic agents may be anti-cancer or antiviral, e.g., anti-HIV or anti-hepatitis B virus, agents as appropriate.

A. Combination Therapies

1. Cancer

In some embodiments, a compound as described herein, is combined with one or more additional therapeutic agents, e.g., an inhibitory immune checkpoint blocker or inhibitor, a stimulatory immune checkpoint stimulator, agonist or activator, a chemotherapeutic agent, an anti-cancer agent, a radiotherapeutic agent, an anti-neoplastic agent, an anti-proliferation agent, an anti-angiogenic agent, an anti-inflammatory agent, an immunotherapeutic agent, a therapeutic antigen-binding molecule (mono- and multi-specific antibodies and fragments thereof in any format (e.g., including without limitation DARTs®, Duobodies®, BiTEs®, BiKEs, TriKEs, XmAbs®, TandAbs®, scFvs, Fabs, Fab derivatives), bi-specific antibodies, non-immunoglobulin antibody mimetics (e.g., including without limitation adnectins, affibody molecules, affilins, affimers, affitins, alphabodies, anticalins, peptide aptamers, armadillo repeat proteins (ARMs), atrimers, avimers, designed ankyrin repeat proteins (DARPins®), fynomers, knottins, Kunitz domain peptides, monobodies, and nanoCLAMPs), antibody-drug conjugates (ADC), antibody-peptide conjugate), an oncolytic virus, a gene modifier or editor, a cell comprising a chimeric antigen receptor (CAR), e.g., including a T-cell immunotherapeutic agent, an NK-cell immunotherapeutic agent, or a macrophage immunotherapeutic agent, a cell comprising an engineered T-cell receptor (TCR-T), or any combination thereof.

Illustrative Targets

In some embodiments, the one or more additional therapeutic agents include, without limitation, an inhibitor, agonist, antagonist, ligand, modulator, stimulator, blocker, activator or suppressor of a target (e.g., polypeptide or polynucleotide) including without limitation: Abelson murine leukemia viral oncogene homolog 1 gene (ABL, such as ABL1), Acetyl-CoA carboxylase (such as ACC1/2), activated CDC kinase (ACK, such as ACK1), Adenosine deaminase, adenosine receptor (such as A2BR, A2aR, A3aR), Adenylate cyclase, ADP ribosyl cyclase-1, adrenocorticotropic hormone receptor (ACTH), Aerolysin, AKT1 gene, Alk-5 protein kinase, Alkaline phosphatase, Alpha 1 adrenoceptor, Alpha 2 adrenoceptor, Alpha-ketoglutarate dehydrogenase (KGDH), Aminopeptidase N, AMP activated protein kinase, anaplastic lymphoma kinase (ALK, such as ALK1), Androgen receptor, Angiopoietin (such as ligand-1, ligand-2), Angiotensinogen (AGT) gene, murine thymoma viral oncogene homolog 1 (AKT) protein kinase (such as AKT1, AKT2, AKT3), apolipoprotein A-I (APOA1) gene, Apoptosis inducing factor, apoptosis protein (such as 1, 2), apoptosis signal-regulating kinase (ASK, such as ASK1), Arginase (I), Arginine deiminase, Aromatase, Asteroid homolog 1 (ASTE1) gene, ataxia telangiectasia and Rad 3 related (ATR) serine/threonine protein kinase, Aurora protein kinase (such as 1, 2), Axl tyrosine kinase receptor, 4-1BB ligand (CD137L), Baculoviral IAP repeat containing 5 (BIRC5) gene, Basigin, B-cell lymphoma 2 (BCL2) gene, Bcl2 binding component 3, Bcl2 protein, BCL2L11 gene, BCR (breakpoint cluster region) protein and gene, Beta adrenoceptor, Beta-catenin, B-lymphocyte antigen CD19, B-lymphocyte antigen CD20, B-lymphocyte cell adhesion molecule, B-lymphocyte stimulator ligand, Bone morphogenetic protein-10 ligand, Bone morphogenetic protein-9 ligand modulator, Brachyury protein, Bradykinin receptor, B-Raf proto-oncogene (BRAF), Brc-Abl tyrosine kinase, Bromodomain and external domain (BET) bromodomain containing protein (such as BRD2, BRD3, BRD4), Bruton's tyrosine kinase (BTK), Calmodulin, calmodulin-dependent protein kinase (CaMK, such as CAMKII), Cancer testis antigen 2, Cancer testis antigen NY-ESO-1, cancer/testis antigen 1B (CTAG1) gene, Cannabinoid receptor (such as CB1, CB2), Carbonic anhydrase, casein kinase (CK, such as CKI, CKII), Caspase (such as caspase-3, caspase-7, Caspase-9), caspase 8 apoptosis-related cysteine peptidase CASP8-FADD-like regulator, Caspase recruitment domain protein-15, Cathepsin G, CCR5 gene, CDK-activating kinase (CAK), Checkpoint kinase (such as CHK1, CHK2), chemokine (C-C motif) receptor (such as CCR2, CCR4, CCR5, CCR8), chemokine (C-X-C motif) receptor (such as CXCR1, CXCR2, CXCR3 and CXCR4), Chemokine CC21 ligand, Cholecystokinin CCK2 receptor, Chorionic gonadotropin, c-Kit (tyrosine-protein kinase Kit or CD117), CISH (Cytokine-inducible SH2-containing protein), Claudin (such as 6, 18), cluster of differentiation (CD) such as CD4, CD27, CD29, CD30, CD33, CD37, CD40, CD40 ligand receptor, CD40 ligand, CD40LG gene, CD44, CD45, CD47, CD49b, CD51, CD52, CD55, CD58, CD66e (CEACAM6), CD70 gene, CD74, CD79, CD79b, CD79B gene, CD80, CD95, CD99, CD117, CD122, CDw123, CD134, CDw137, CD158a, CD158b1, CD158b2, CD223, CD276 antigen; clusterin (CLU) gene, Clusterin, c-Met (hepatocyte growth factor receptor (HGFR)), Complement C3, Connective tissue growth factor, COP9 signalosome subunit 5, CSF-1 (colony-stimulating factor 1 receptor), CSF2 gene, CTLA-4 (cytotoxic T-lymphocyte protein 4) receptor, C-type lectin domain protein 9A (CLEC9A), Cyclin D1, Cyclin G1, cyclin-dependent kinases (CDK, such as CDK1, CDK12, CDK1B, CDK2-9), cyclooxygenase (such as COX1, COX2), CYP2B1 gene, Cysteine palmitoyltransferase porcupine, Cytochrome P450 11B2, Cytochrome P450 17, cytochrome P450 17A1, Cytochrome P450 2D6, cytochrome P450 3A4, Cytochrome P450 reductase, cytokine signalling-1, cytokine signalling-3, Cytoplasmic isocitrate dehydrogenase, Cytosine deaminase, cytosine DNA methyltransferase, cytotoxic T-lymphocyte protein-4, DDR2 gene, DEAD-box helicase 6 (DDX6), Death receptor 5 (DR5, TRATLR2), Death receptor 4 (DR4, TRAILR1), Delta-like protein ligand (such as 3, 4), Deoxyribonuclease, Deubiquitinating enzymes (DUBs), Dickkopf-1 ligand, dihydrofolate reductase (DHFR), Dihydropyrimidine dehydrogenase, Dipeptidyl peptidase IV, discoidin domain receptor (DDR, such as DDR1), Diacylglycerol kinase zeta (DGKZ), DNA binding protein (such as HU-beta), DNA dependent protein kinase, DNA gyrase, DNA methyltransferase, DNA polymerase (such as alpha), DNA primase, dUTP pyrophosphatase, L-dopachrome tautomerase, E3 ubiquitin-protein ligase (such as RNF128, CBL-B), echinoderm microtubule like protein 4, EGFR tyrosine kinase receptor, Elastase, Elongation factor 1 alpha 2, Elongation factor 2, Endoglin, Endonuclease, endoplasmic reticulum aminopeptidase (ERAP, such as ERAP 1, ERAP2), Endoplasmin, Endosialin, Endostatin, endothelin (such as ET-A, ET-B), Enhancer of zeste homolog 2 (EZH2), Ephrin (EPH) tyrosine kinase (such as Epha3, Ephb4), Ephrin B2 ligand, epidermal growth factor, epidermal growth factor receptors (EGFR), epidermal growth factor receptor (EGFR) gene, Epigen, Epithelial cell adhesion molecule (EpCAM), Erb-b2 (v-erb-b2 avian erythroblastic leukemia viral oncogene homolog 2) tyrosine kinase receptor, Erb-b3 tyrosine kinase receptor, Erb-b4 tyrosine kinase receptor, E-selectin, Estradiol 17 beta dehydrogenase, Estrogen receptor (such as alpha, beta), Estrogen related receptor, Eukaryotic translation initiation factor 5A (EIF5A) gene, Exportin 1, Extracellular signal related kinase (such as 1, 2), Extracellular signal-regulated kinases (ERK), Hypoxia-inducible factor prolyl hydroxylase (HIF-PH or EGLN), Factor (such as Xa, VIIa), farnesoid x receptor (FXR), Fas ligand, Fatty acid synthase (FASN), Ferritin, FGF-2 ligand, FGF-5 ligand, fibroblast growth factor (FGF, such as FGF1, FGF2, FGF4), Fibronectin, focal adhesion kinase (FAK, such as FAK2), folate hydrolase prostate-specific membrane antigen 1 (FOLH1), Folate receptor (such as alpha), Folate, Folate transporter 1, FYN tyrosine kinase, paired basic amino acid cleaving enzyme (FURIN), Beta-glucuronidase, Galactosyltransferase, Galectin-3, Ganglioside GD2, Glucocorticoid, glucocorticoid-induced TNFR-related protein GITR receptor, Glutamate carboxypeptidase II, glutaminase, Glutathione S-transferase P, glycogen synthase kinase (GSK, such as 3-beta), Glypican 3 (GPC3), gonadotropin-releasing hormone (GNRH), Granulocyte macrophage colony stimulating factor (GM-CSF) receptor, Granulocyte-colony stimulating factor (GCSF) ligand, growth factor receptor-bound protein 2 (GRB2), Grp78 (78 kDa glucose-regulated protein) calcium binding protein, molecular chaperone groEL2 gene, Heme oxygenase 1 (HO1), Heme oxygenase 2 (HO2), Heat shock protein (such as 27, 70, 90 alpha, beta), Heat shock protein gene, Heat stable enterotoxin receptor, Hedgehog protein, Heparanase, Hepatocyte growth factor, HERV-H LTR associating protein 2, Hexose kinase, Histamine H2 receptor, Histone methyltransferase (DOTIL), histone deacetylase (HDAC, such as 1, 2, 3, 6, 10, 11), Histone H1, Histone H3, HLA class I antigen (A-2 alpha), HLA class II antigen, HLA class I antigen alpha G (HLA-G), Non-classical HLA, Homeobox protein NANOG, HSPB1 gene, Human leukocyte antigen (HLA), Human papillomavirus (such as E6, E7) protein, Hyaluronic acid, Hyaluronidase, Hypoxia inducible factor-1 alpha (HIF1α), Imprinted Maternally Expressed Transcript (H19) gene, mitogen-activated protein kinase 1 (MAP4K1), tyrosine-protein kinase HCK, I-Kappa-B kinase (IKK, such as IKKbe), IL-1 alpha, IL-1 beta, IL-12, IL-12 gene, IL-15, IL-17, IL-2 gene, IL-2 receptor alpha subunit, IL-2, IL-3 receptor, IL-4, IL-6, IL-7, IL-8, immunoglobulin (such as G, G1, G2, K, M), Immunoglobulin Fc receptor, Immunoglobulin gamma Fc receptor (such as I, III, IIIA), indoleamine 2,3-dioxygenase (IDO, such as IDO1 and IDO2), indoleamine pyrrole 2,3-dioxygenase 1 inhibitor, insulin receptor, Insulin-like growth factor (such as 1, 2), Integrin alpha-4/beta-1, integrin alpha-4/beta-7, Integrin alpha-5/beta-1, Integrin alpha-V/beta-3, Integrin alpha-V/beta-5, Integrin alpha-V/beta-6, Intercellular adhesion molecule 1 (ICAM-1), interferon (such as alpha, alpha 2, beta, gamma), Interferon inducible protein absent in melanoma 2 (AIM2), interferon type I receptor, Interleukin 1 ligand, Interleukin 13 receptor alpha 2, interleukin 2 ligand, interleukin-1 receptor-associated kinase 4 (IRAK4), Interleukin-2, Interleukin-29 ligand, Interleukin 35 (IL-35), isocitrate dehydrogenase (such as IDH1, IDH2), Janus kinase (JAK, such as JAK1, JAK2), Jun N terminal kinase, kallikrein-related peptidase 3 (KLK3) gene, Killer cell Ig like receptor, Kinase insert domain receptor (KDR), Kinesin-like protein KIF11, Kirsten rat sarcoma viral oncogene homolog (KRAS) gene, Kisspeptin (KiSS-1) receptor, KIT gene, v-kit Hardy-Zuckerman 4 feline sarcoma viral oncogene homolog (KIT) tyrosine kinase, lactoferrin, Lanosterol-14 demethylase, LDL receptor related protein-1, Leukocyte immunoglobulin-like receptor subfamily B member 1 (ILT2), Leukocyte immunoglobulin-like receptor subfamily B member 2 (ILT4), Leukotriene A4 hydrolase, Listeriolysin, L-Selectin, Luteinizing hormone receptor, Lyase, lymphocyte activation gene 3 protein (LAG-3), Lymphocyte antigen 75, Lymphocyte function antigen-3 receptor, lymphocyte-specific protein tyrosine kinase (LCK), Lymphotactin, Lyn (Lck/Yes novel) tyrosine kinase, lysine demethylases (such as KDM1, KDM2, KDM4, KDM5, KDM6, A/B/C/D), Lysophosphatidate-1 receptor, lysosomal-associated membrane protein family (LAMP) gene, Lysyl oxidase homolog 2, lysyl oxidase protein (LOX), 5-Lipoxygenase (5-LOX), Hematopoietic Progenitor Kinase 1 (HPK1), Hepatocyte growth factor receptor (MET) gene, macrophage colony-stimulating factor (MCSF) ligand, Macrophage migration inhibitory fact, MAGEC1 gene, MAGEC2 gene, Major vault protein, MAPK-activated protein kinase (such as MK2), Mas-related G-protein coupled receptor, matrix metalloprotease (MMP, such as MMP2, MMP9), Mcl-1 differentiation protein, Mdm2 p53-binding protein, Mdm4 protein, Melan-A (MART-1) melanoma antigen, Melanocyte protein Pmel 17, melanocyte stimulating hormone ligand, melanoma antigen family A3 (MAGEA3) gene, Melanoma associated antigen (such as 1, 2, 3, 6), Membrane copper amine oxidase, Mesothelin, MET tyrosine kinase, Metabotropic glutamate receptor 1, Metalloreductase STEAPI (six transmembrane epithelial antigen of the prostate 1), Metastin, methionine aminopeptidase-2, Methyltransferase, Mitochondrial 3 ketoacyl CoA thiolase, mitogen-activate protein kinase (MAPK), mitogen-activated protein kinase (MEK, such as MEK1, MEK2), mTOR (mechanistic target of rapamycin (serine/threonine kinase), mTOR complex (such as 1,2), mucin (such as 1, 5A, 16), mut T homolog (MTH, such as MTH1), Myc proto-oncogene protein, myeloid cell leukemia 1 (MCL1) gene, myristoylated alanine-rich protein kinase C substrate (MARCKS) protein, NAD ADP ribosyltransferase, natriuretic peptide receptor C, Neural cell adhesion molecule 1, Neurokinin 1 (NK1) receptor, Neurokinin receptor, Neuropilin 2, NF kappa B activating protein, NIMA-related kinase 9 (NEK9), Nitric oxide synthase, NK cell receptor, NK3 receptor, NKG2 A B activating NK receptor, NLRP3 (NACHT LRR PYD domain protein 3) modulators, Noradrenaline transporter, Notch (such as Notch-2 receptor, Notch-3 receptor, Notch-4 receptor), Nuclear erythroid 2-related factor 2, Nuclear Factor (NF) kappa B, Nucleolin, Nucleophosmin, nucleophosmin-anaplastic lymphoma kinase (NPM-ALK), 2 oxoglutarate dehydrogenase, 2,5-oligoadenylate synthetase, O-methylguanine DNA methyltransferase, Opioid receptor (such as delta), Ornithine decarboxylase, Orotate phosphoribosyltransferase, orphan nuclear hormone receptor NR4A1, Osteocalcin, Osteoclast differentiation factor, Osteopontin, OX-40 (tumor necrosis factor receptor superfamily member 4 TNFRSF4, or CD134) receptor, P3 protein, p38 kinase, p38 MAP kinase, p53 tumor suppressor protein, Parathyroid hormone ligand, peroxisome proliferator-activated receptors (PPAR, such as alpha, delta, gamma), P-Glycoprotein (such as 1), phosphatase and tensin homolog (PTEN), phosphatidylinositol 3-kinase (PI3K), phosphoinositide-3 kinase (PI3K such as alpha, delta, gamma), phosphorylase kinase (PK), PKN3 gene, placenta growth factor, platelet-derived growth factor (PDGF, such as alpha, beta), Platelet-derived growth factor (PDGF, such as alpha, beta), Pleiotropic drug resistance transporter, Plexin B1, PLK1 gene, polo-like kinase (PLK), Polo-like kinase 1, Poly (ADP-ribose) polymerase (PARP, such as PARP1, PARP2 and PARP3, PARP7, and mono-PARPs), Preferentially expressed antigen in melanoma (PRAME) gene, Prenyl-binding protein (PrPB), Probable transcription factor PML, Progesterone receptor, Programmed cell death 1 (PD-1), Programmed cell death ligand 1 inhibitor (PD-L1), Prosaposin (PSAP) gene, Prostanoid receptor (EP4), Prostaglandin E2 synthase, prostate specific antigen, Prostatic acid phosphatase, proteasome, Protein E7, Protein farnesyltransferase, protein kinase (PK, such as A, B, C), protein tyrosine kinase, Protein tyrosine phosphatase beta, Proto-oncogene serine/threonine-protein kinase (PIM, such as PIM-1, PIM-2, PIM-3), P-Selectin, Purine nucleoside phosphorylase, purinergic receptor P2X ligand gated ion channel 7 (P2X7), Pyruvate dehydrogenase (PDH), Pyruvate dehydrogenase kinase, Pyruvate kinase (PYK), 5-Alpha-reductase, Raf protein kinase (such as 1, B), RAF1 gene, Ras gene, Ras GTPase, RET gene, Ret tyrosine kinase receptor, retinoblastoma associated protein, retinoic acid receptor (such as gamma), Retinoid X receptor, Rheb (Ras homolog enriched in brain) GTPase, Rho (Ras homolog) associated protein kinase 2, ribonuclease, Ribonucleotide reductase (such as M2 subunit), Ribosomal protein S6 kinase, RNA polymerase (such as I, II), Ron (Recepteur d'Origine Nantais) tyrosine kinase, ROS1 (ROS proto-oncogene 1, receptor tyrosine kinase) gene, Ros1 tyrosine kinase, Runt-related transcription factor 3, Gamma-secretase, S100 calcium binding protein A9, Sarco endoplasmic calcium ATPase, Second mitochondria-derived activator of caspases (SMAC) protein, Secreted frizzled related protein-2, Secreted phospholipase A2, Semaphorin-4D, Serine protease, serine/threonine kinase (STK), serine/threonine-protein kinase (TBK, such as TBK1), signal transduction and transcription (STAT, such as STAT-1, STAT-3, STAT-5), Signaling lymphocytic activation molecule (SLAM) family member 7, six-transmembrane epithelial antigen of the prostate (STEAP) gene, SL cytokine ligand, smoothened (SMO) receptor, Sodium iodide cotransporter, Sodium phosphate cotransporter 2B, Somatostatin receptor (such as 1, 2, 3, 4, 5), Sonic hedgehog protein, Son of sevenless (SOS), Specific protein 1 (Sp1) transcription factor, Sphingomyelin synthase, Sphingosine kinase (such as 1, 2), Sphingosine-1-phosphate receptor-1, spleen tyrosine kinase (SYK), SRC gene, Src tyrosine kinase, Stabilin-1 (STAB1), STAT3 gene, Steroid sulfatase, Stimulator of interferon genes (STING) receptor, stimulator of interferon genes protein, Stromal cell-derived factor 1 ligand, SUMO (small ubiquitin-like modifier), Superoxide dismutase, Suppressor of cytokine signaling modulators (SOCS), Survivin protein, Synapsin 3, Syndecan-1, Synuclein alpha, T cell surface glycoprotein CD28, tank-binding kinase (TBK), TATA box-binding protein-associated factor RNA polymerase I subunit B (TAF1B) gene, T-cell CD3 glycoprotein zeta chain, T-cell differentiation antigen CD6, T-cell immunoglobulin and mucin-domain containing-3 (TIM-3), T-cell surface glycoprotein CD8, Tec protein tyrosine kinase, Tek tyrosine kinase receptor, telomerase, Telomerase reverse transcriptase (TERT) gene, Tenascin, Three prime repair exonuclease 1 (TREX1), Three prime repair exonuclease 2 (TREX2), Thrombopoietin receptor, Thymidine kinase, Thymidine phosphorylase, Thymidylate synthase, Thymosin (such as alpha 1), Thyroid hormone receptor, Thyroid stimulating hormone receptor, Tissue factor, TNF related apoptosis inducing ligand, TNFR1 associated death domain protein, TNF-related apoptosis-inducing ligand (TRAIL) receptor, TNFSF11 gene, TNFSF9 gene, Toll-like receptor (TLR such as 1-13), topoisomerase (such as I, II, III), Transcription factor, Transferase, transferrin (TF), transforming growth factor alpha (TGFα), transforming growth factor beta (TGFB) and isoforms thereof, TGF beta 2 ligand, Transforming growth factor TGF-β receptor kinase, Transglutaminase, Translocation associated protein, Transmembrane glycoprotein NMB, Trop-2 calcium signal transducer, trophoblast glycoprotein (TPBG) gene, Trophoblast glycoprotein, Tropomyosin receptor kinase (Trk) receptor (such as TrkA, TrkB, TrkC), tryptophan 2,3-dioxygenase (TDO), Tryptophan 5-hydroxylase, Tubulin, Tumor necrosis factor (TNF, such as alpha, beta), Tumor necrosis factor 13C receptor, tumor progression locus 2 (TPL2), Tumor protein 53 (TP53) gene, Tumor suppressor candidate 2 (TUSC2) gene, Tumor specific neoantigens, Tyrosinase, Tyrosine hydroxylase, tyrosine kinase (TK), Tyrosine kinase receptor, Tyrosine kinase with immunoglobulin-like and EGF-like domains (TIE) receptor, Tyrosine protein kinase ABL1 inhibitor, Ubiquitin, Ubiquitin carboxyl hydrolase isozyme L5, Ubiquitin thioesterase-14, Ubiquitin-conjugating enzyme E21 (UBE2I, UBC9), Ubiquitin-specific-processing protease 7 (USP7), Urease, Urokinase plasminogen activator, Uteroglobin, Vanilloid VR1, Vascular cell adhesion protein 1, vascular endothelial growth factor receptor (VEGFR), V-domain Ig suppressor of T-cell activation (VISTA), VEGF-1 receptor, VEGF-2 receptor, VEGF-3 receptor, VEGF-A, VEGF-B, Vimentin, Vitamin D3 receptor, Proto-oncogene tyrosine-protein kinase, Mer (Mer tyrosine kinase receptor modulators), YAP (Yes-associated protein modulators)es, Wee-1 protein kinase, Werner Syndrome RecQ Like Helicase (WRN), Wilms' tumor antigen 1, Wilms' tumor protein, WW domain containing transcription regulator protein 1 (TAZ), X-linked inhibitor of apoptosis protein, Zinc finger protein transcription factor or any combination thereof.

Illustrative Mechanisms of Action

In some embodiments, the one or more additional therapeutic agents may be categorized by their mechanism of action into, for example, the following groups:

anti-metabolites/anti-cancer agents, such as pyrimidine analogs floxuridine, capecitabine, cytarabine, CPX-351 (liposomal cytarabine, daunorubicin), and TAS-118;

Alpha 1 adrenoceptor/Alpha 2 adrenoceptor antagonists, such as phenoxybenzamine hydrochloride (injectable, pheochromocytoma);

Androgen receptor antagonists, such as nilutamide;

anti-cadherin antibodies, such as HKT-288;

anti-leucine-rich repeat containing 15 (LRRC15) antibodies, such as ABBV-085. ARGX-110;

angiotensin receptor blockers, nitric oxide donors;

antisense oligonucleotides, such as AEG35156, IONIS-KRAS-2.5Rx, EZN-3042, RX-0201, IONIS-AR-2.5Rx, BP-100 (prexigebersen), IONIS-STAT3-2.5Rx;

anti-angiopoietin (ANG)-2 antibodies, such as MEDI3617, and LY3127804;

anti-ANG-1/ANG-2 antibodies, such as AMG-780;

anti-CSF1R antibodies, such as emactuzumab, LY3022855, AMG-820, FPA-008 (cabiralizumab);

anti-endoglin antibodies, such as TRC105 (carotuximab);

anti-ERBB antibodies, such as CDX-3379, HLX-02, seribantumab;

anti-HER2 antibodies, such as HERCEPTIN® (trastuzumab), trastuzumab biosimimar, margetuximab, MEDI4276, BAT-8001, Pertuzumab (Perjeta), RG6264, ZW25 (a bispecific HER2-directed antibody targeting the extracellular domains 2 and 4; Cancer Discov. 2019 January; 9(1):8; PMID: 30504239);

anti-HLA-DR antibodies, such as IMMU-114;

anti-IL-3 antibodies, such as JNJ-56022473;

anti-TNF receptor superfamily member 18 (TNFRSF18, GITR; NCBI Gene ID: 8784) antibodies, such as MK-4166, MEDI1873, FPA-154, INCAGN-1876, TRX-518, BMS-986156, MK-1248, GWN-323; and those described, e.g. in Intl. Patent Publ. Nos. WO 2017/096179, WO 2017/096276, WO 2017/096189; and WO 2018/089628;

anti-EphA3 antibodies, such as KB-004;
anti-CD37 antibodies, such as otlertuzumab (TRU-016);
anti-FGFR-3 antibodies, such as LY3076226, B-701;
anti-FGFR-2 antibodies, such as GAL-F2;
anti-C5 antibodies, such as ALXN-1210;
anti-EpCAM antibodies, such as VB4-845;
anti-CEA antibodies, such as RG-7813;
CD66C) antibodies, such as BAY-1834942, NEO-201 (CEACAM 5/6);
anti-GD2 antibodies, such as APN-301;
anti-interleukin-17 (IL-17) antibodies, such as CJM-112;
anti-interleukin-1 beta antibodies, such as canakinumab (ACZ885), VPM087;
anti-carbonic anhydrase 9 (CA9, CAIX) antibodies, such as TX-250;
anti-CD38 antibodies, such as isatuximab, MOR-202, TAK-079;
anti-CD38-attenukine, such as TAK573;
anti-Mucin 1 (MUC1) antibodies, such as gatipotuzumab, Mab-AR-20.5;
anti-CD33 antibodies, such as IMGN-779;
anti-KMA antibodies, such as MDX-1097;
anti-CD55 antibodies, such as PAT-SC1;
anti-c-Met antibodies, such as ABBV-399;
anti-PSMA antibodies, such as ATL-101;
anti-CD100 antibodies, such as VX-15;
anti-EPHA3 antibodies, such as fibatuzumab;
anti-APRIL antibodies, such as BION-1301;
anti-fibroblast activation protein (FAP)/IL-2R antibodies, such as RG7461;
anti-fibroblast activation protein (FAP)/TRAIL-R2 antibodies, such as RG7386;
anti-fucosyl-GM1 antibodies, such as BMS-986012;
anti-IL-8 (Interleukin-8) antibodies, such as HuMax-Inflam;
anti-myostatin inhibitors, such as landogrozumab;
anti-delta-like protein ligand 3 (DDL3) antibodies, such as rovalpituzumab tesirine;
anti-DLL4 (delta like ligand 4) antibodies, such as demcizumab;
anti-clusterin antibodies, such as AB-16B5;
anti-Ephrin-A4 (EFNA4) antibodies, such as PF-06647263;
anti-RANKL antibodies, such as denosumab;
anti-mesothelin antibodies, such as BMS-986148, Anti-MSLN-MMAE;
anti-sodium phosphate cotransporter 2B (NaP2B) antibodies, such as lifastuzumab
anti-TGFb antibodies, such as SAR439459;
anti-transforming growth factor-beta (TGF-beta) antibodies, such as ABBV-151, LY3022859, NIS793, XOMA 089;
purine analogs, folate antagonists (such as pralatrexate), cladribine, pentostatin, fludarabine and related inhibitors;
antiproliferative/antimitotic agents including natural products, such as vinca alkaloids (vinblastine, vincristine) and microtubule disruptors such as taxane (paclitaxel, docetaxel), vinblastin, nocodazole, epothilones, vinorelbine (NAVELBINE®), and epipodophyllotoxins (etoposide, teniposide);
DNA damaging agents, such as actinomycin, amsacrine, anthracyclines, bleomycin, busulfan, carboplatin, chlorambucil, cisplatin, cyclophosphamide (CYTOXAN®), dactinomycin, daunorubicin, doxorubicin, DEBDOX, epirubicin, iphosphamide, melphalan, merchlorethamine, mitomycin C, mitoxantrone, nitrosourea, procarbazine, taxol, Taxotere, teniposide, etoposide, and triethylenethiophosphoramide;
DNA-hypomethylating agents, such as guadecitabine (SGI-110), ASTX727;
antibiotics such as dactinomycin, daunorubicin, doxorubicin, idarubicin, anthracyclines, mitoxantrone, bleomycins, plicamycin (mithramycin);
enzymes such as L-asparaginase which systemically metabolizes L-asparagine and deprives cells which do not have the capacity to synthesize their own asparagine;
DNAi oligonucleotides targeting Bcl-2, such as PNT2258; agents that activate or reactivate latent human immunodeficiency virus (HIV), such as panobinostat and romidepsin;
asparaginase stimulators, such as crisantaspase (Erwinase®) and GRASPA (ERY-001, ERY-ASP), calaspargase pegol, pegaspargase;
pan-Trk, ROS1 and ALK inhibitors, such as entrectinib, TPX-0005;
anaplastic lymphoma kinase (ALK) inhibitors, such as alectinib, ceritinib, alecensa (RG7853), ALUNBRIG® (brigatinib);
antiproliferative/antimitotic alkylating agents, such as nitrogen mustard cyclophosphamide and analogs (e.g., melphalan, chlorambucil, hexamethylmelamine, thiotepa), alkyl nitrosoureas (e.g., carmustine) and analogs, streptozocin, and triazenes (e.g., dacarbazine);
antiproliferative/antimitotic antimetabolites, such as folic acid analogs (methotrexate);
platinum coordination complexes (e.g., cisplatin, oxiloplatinim, and carboplatin), procarbazine, hydroxyurea, mitotane, and aminoglutethimide;
hormones, hormone analogs (e.g., estrogen, tamoxifen, goserelin, bicalutamide, and nilutamide), and aromatase inhibitors (e.g., letrozole and anastrozole);
antiplatelet agents; anticoagulants such as heparin, synthetic heparin salts, and other inhibitors of thrombin;
fibrinolytic agents such as tissue plasminogen activator, streptokinase, urokinase, aspirin, dipyridamole, ticlopidine, and clopidogrel;
antimigratory agents; antisecretory agents (e.g., breveldin);
immunosuppressives, such as tacrolimus, sirolimus, azathioprine, and mycophenolate;
growth factor inhibitors, and vascular endothelial growth factor inhibitors;
fibroblast growth factor inhibitors, such as FPA14;
AMP activated protein kinase stimulators, such as metformin hydrochloride;
ADP ribosyl cyclase-1 inhibitors, such as daratumumab (DARZALEX®);
Caspase recruitment domain protein-15 stimulators, such as mifamurtide (liposomal);
CCR5 chemokine antagonists, such as MK-7690 (vicriviroc);
CDC7 protein kinase inhibitors, such as TAK-931;
Cholesterol side-chain cleavage enzyme inhibitors, such as ODM-209;
Dihydropyrimidine dehydrogenase/Orotate phosphoribosyltransferase inhibitors, such as Cefesone (tegafur+gimeracil+oteracil potassium);
DNA polymerase/Ribonucleotide reductase inhibitors, such as clofarabine;
DNA interference oligonucleotides, such as PNT2258, AZD-9150;

Estrogen receptor modulators, such as bazedoxifene;
Estrogen receptor agonists/Progesterone receptor antagonists, such as TRI-CYCLEN LO (norethindrone+ethinyl estradiol);
HLA class I antigen A-2 alpha modulators, such as FH-MCVA2TCR;
HLA class I antigen A-2 alpha/MART-1 melanoma antigen modulators, such as MART-1 F5 TCR engineered PBMC;
Human Granulocyte Colony Stimulating Factors, such as PF-06881894;
GNRH receptor agonists, such as leuprorelin acetate, leuprorelin acetate sustained release depot (ATRIGEL), triptorelin pamoate, goserelin acetate;
GNRH receptor antagonists, such as elagolix, relugolix, degarelix;
Endoplasmin modulators, such as anlotinib;
H+K+ATPase inhibitors, such as omeprazole, esomeprazole;
ICAM-1/CD55 modulators, such as cavatak (V-937);
IL-15/IL-12 modulators, such as SAR441000;
Interleukin 23A inhibitors, such as guselkumab;
Lysine specific histone demethylase 1 inhibitors, such as CC-90011;
IL-12 Mrna, such as MEDI1191;
RIG-I modulators, such as RGT-100;
NOD2 modulators, such as SB-9200, and IR-103.
Progesterone receptor agonists, such as levonorgestrel;
Protein cereblon modulators, such as CC-92480, CC-90009;
Protein cereblon modulators/DNA binding protein Ikaros inhibitors/Zinc finger binding protein Aiolos inhibitors, such as iberdomide;
Retinoid X receptor modulators, such as alitretinoin, bexarotene (oral formulation);
RIP-1 kinase inhibitors, such as GSK-3145095;
selective oestrogen receptor degraders, such as AZD9833;
SUMO inhibitors, such as TAK-981;
Thrombopoietin receptor agonists, such as eltrombopag;
Thyroid hormone receptor agonists, such as levothyroxine sodium;
TNF agonists, such as tasonermin;
Tyrosine phosphatase substrate 1 inhibitors, such as CC-95251;
HER2 inhibitors, such as neratinib, tucatinib (ONT-380);
EGFR/ErbB2/Ephb4 inhibitors, such as tesevatinib;
EGFR/IER2 inhibitors, such as TAK-788;
EGFR family tyrosine kinase receptor inhibitors, such as DZD-9008
EGFR/ErbB-2 inhibitors, such as varlitinib;
Mutant selective EGFR inhibitors, such as PF-06747775, EGF816 (nazartinib), ASP8273, ACEA-0010, BI-1482694;
epha2 inhibitors, such as MM-310;
polycomb protein (EED) inhibitors, such as MAK683;
DHFR inhibitor/Folate transporter 1 modulator/Folate receptor antagonist, such as pralatrexate;
DHFR/GAR transformylase/Thymidylate synthase/Transferase inhibitors, such as pemetrexed disodium;
p38 MAP kinase inhibitors, such as ralimetinib;
PRMT inhibitors, such as MS203, PF-06939999, GSK3368715, GSK3326595;
Sphingosine kinase 2 (SK2) inhibitors, such as opaganib;
Nuclear erythroid 2-related factor 2 stimulators, such as omaveloxolone (RTA-408);
Tropomyosin receptor kinase (TRK) inhibitors, such as LOXO-195, ONO-7579;
Mucin 1 inhibitors, such as GO-203-2C;
MARCKS protein inhibitors, such as BIO-11006;
Folate antagonists, such as arfolitixorin;
Galectin-3 inhibitors, such as GR-MD-02;
Phosphorylated P68 inhibitors, such as RX-5902;
CD95/TNF modulators, such as ofranergene obadenovec;
pan-PIM kinase inhibitors, such as INCB-053914;
IL-12 gene stimulators, such as EGEN-001, tavokinogene telseplasmid;
Heat shock protein HSP90 inhibitors, such as TAS-116, PEN-866;
VEGF/HGF antagonists, such as MP-0250;
VEGF ligand inhibitors, such as bevacizumab biosimilar;
VEGF receptor antagonists/VEGF ligand inhibitors, such as ramucirumab;
VEGF-1/VEGF-2/VEGF-3 receptor antagonists; such as fruquintinib;
VEGF-1/VEGF-2 receptor modulators, such as HLA-A2402/HLA-A0201 restricted epitope peptide vaccine;
Placenta growth factor ligand inhibitor/VEGF-A ligand inhibitor, such as aflibercept;
SYK tyrosine kinase/JAK tyrosine kinase inhibitors, such as ASN-002;
Trk tyrosine kinase receptor inhibitors, such as larotrectinib sulfate;
JAK3/JAK1/TBK1 kinase inhibitors, such as CS-12912;
IL-24 antagonist, such as AD-IL24;
NLRP3 (NACHT LRR PYD domain protein 3) modulators, such as BMS-986299;
RIG-I agonists, such as RGT-100;
Aerolysin stimulators, such as topsalysin;
P-Glycoprotein 1 inhibitors, such as HM-30181A;
CSF-1 antagonists, such as ARRY-382, BLZ-945;
CCR8 inhibitors, such as I-309, SB-649701, HG-1013, RAP-310;
anti-Mesothelin antibodies, such as SEL-403;
Thymidine kinase stimulators, such as aglatimagene besadenovec;
Polo-like kinase 1 inhibitors, such as PCM-075, onvansertib;
NAE inhibitors, such as pevonedistat (MLN-4924), TAS-4464;
Pleiotropic pathway modulators, such as avadomide (CC-122);
Amyloid protein binding protein-1 inhibitorS/Ubiquitin ligase modulators, such as pevonedistat;
FoxM1 inhibitors, such as thiostrepton;
UBA1 inhibitors, such as TAK-243;
Src tyrosine kinase inhibitors, such as VAL-201;
VDAC/HK inhibitors, such as VDA-1102;
Elf4a inhibitors, such as rohinitib, eFT226;
TP53 gene stimulators, such as ad-p53;
Retinoic acid receptor agonists, such as tretinoin;
Retinoic acid receptor alpha (RARα) inhibitors, such as SY-1425;
SIRT3 inhibitors, such as YC8-02;
Stromal cell-derived factor 1 ligand inhibitors, such as olaptesed pegol (NOX-A12);
IL-4 receptor modulators, such as MDNA-55;
Arginase-I stimulators, such as pegzilarginase;
Topoisomerase I inhibitors, such as irinotecan hydrochloride, Onivyde;
Topoisomerase I inhibitor/hypoxia inducible factor-1 alpha inhibitors, such as PEG-SN38 (firtecan pegol);
Hypoxia inducible factor-1 alpha inhibitors, such as PT-2977, PT-2385;

CD122 (IL-2 receptor) agonists, such as proleukin (aldesleukin, IL-2); pegylated IL-2 (eg NKTR-214); modified variants of IL-2 (eg THOR-707);
TLR7/TLR8 agonist, such as NKTR-262;
TLR7 agonists, such as DS-0509, GS-9620, LHC-165, TMX-101 (imiquimod);
p53 tumor suppressor protein stimulators such as kevetrin;
Mdm4/Mdm2 p53-binding protein inhibitors, such as ALRN-6924;
kinesin spindle protein (KSP) inhibitors, such as filanesib (ARRY-520);
CD80-fc fusion protein inhibitors, such as FPT-155;
Menin and mixed lineage leukemia (MLL) inhibitors such as KO-539;
Liver x receptor agonists, such as RGX-104;
IL-10 agonists, such as Pegilodecakin (AM-0010);
VEGFR/PDGFR inhibitors, such as vorolanib;
IRAK4 inhibitors, such as CA-4948;
anti-TLR-2 antibodies, such as OPN-305;
Calmodulin modulators, such as CBP-501;
Glucocorticoid receptor antagonists, such as relacorilant (CORT-125134);
Second mitochondria-derived activator of caspases (SMAC) protein inhibitors, such as BI-891065;
Lactoferrin modulators, such as LTX-315;
KIT proto-oncogene, receptor tyrosine kinase (KIT) inhibitors, such as PLX-9486;
platelet derived growth factor receptor alpha (PDGFRA)/ KIT proto-oncogene, receptor tyrosine kinase (KIT) mutant-specific antagonists/inhibitors such as BLU-285, DCC-2618;
Exportin 1 inhibitors, such as eltanexor;
CHST15 gene inhibitors, such as STNM-01;
Somatostatin receptor antagonist, such as OPS-201;
CEBPA gene stimulators, such as MTL-501;
DKK3 gene modulators, such as MTG-201;
Chemokine (CXCR1/CXCR2) inhibitors, such as SX-682;
p70s6k inhibitors, such as MSC2363318A;
methionine aminopeptidase 2 (MetAP2) inhibitors, such as M8891, APL-1202;
arginine N-methyltransferase 5 inhibitors, such as GSK-3326595;
CD71 modulators, such as CX-2029 (ABBV-2029);
ATM (ataxia telangiectasia) inhibitors, such as AZD0156, AZD1390;
CHK1 inhibitors, such as GDC-0575, LY2606368 (prexasertib), SRA737, RG7741 (CHK1/2);
CXCR4 antagonists, such as BL-8040, LY2510924, burixafor (TG-0054), X4P-002, X4P-001-IO, Plerixafor;
EXH2 inhibitors, such as GSK2816126;
KDM1 inhibitors, such as ORY-1001, IMG-7289, INCB-59872, GSK-2879552;
CXCR2 antagonists, such as AZD-5069;
GM-CSF antibodies, such as lenzilumab;
DNA dependent protein kinase inhibitors, such as MSC2490484A (nedisertib), VX-984, AsiDNA (DT-01); protein kinase C (PKC) inhibitors, such as LXS-196, sotrastaurin;
Selective estrogen receptor downregulators (SERD), such as fulvestrant (Faslodex®), RG6046, RG6047, RG6171, elacestrant (RAD-1901), SAR439859 and AZD9496;
Selective estrogen receptor covalent antagonists (SERCAs), such as H3B-6545;
selective androgen receptor modulator (SARM), such as GTX-024, darolutamide;
transforming growth factor-beta (TGF-beta) kinase antagonists, such as galunisertib, LY3200882; TGF-beta inhibitors described in WO 2019/103203;
TGF beta receptor 1 inhibitors, such as PF-06952229;
bispecific antibodies, such as ABT-165 (DLL4/VEGF), MM-141 (IGF-1/ErbB3), MM-111 (Erb2/Erb3), JNJ-64052781 (CD19/CD3), PRS-343 (CD-137/HiER2), AFM26 (BCMA/CD16A), JNJ-61186372 (EGFR/cMET), AMG-211 (CEA/CD3), RG7802 (CEA/CD3), ERY-974 (CD3/GPC3) vancizumab (angiopoietins/VEGF), PF-06671008 (Cadherins/CD3), AFM-13 (CD16/CD30), APV0436 (CD123/CD3), flotetuzumab (CD123/CD3), REGN-1979 (CD20/CD3), MCLA-117 (CD3/CLEC12A), MCLA-128 (HER2/HER3), JNJ-0819, JNJ-7564 (CD3/heme), AMG-757 (DLL3-CD3), MGD-013 (PD-1/LAG-3), FS-118 (LAG-3/PD-L1) MGD-019 (PD-1/CTLA-4), KN-046 (PD-1/CTLA-4), MEDI-5752 (CTLA-4/PD-1), RO-7121661 (PD-1/TIM-3), XmAb-20717 (PD-1/CTLA-4), AK-104 (CTLA-4/PD-1), AMG-330 (CD33/CD3), AMG-420 (BCMA/CD3), BI-836880 (VEFG/ANG2), JNJ-63709178 (CD123/CD3), MGD-007 (CD3/gpA33), MGD-009 (CD3/B7H3), AGEN1223, IMCgp100 (CD3/gp100), AGEN-1423, ATOR-1015 (CTLA-4/OX40), LY-3415244 (TIM-3/PDL1), INHIBRX-105 (4-1BB/PDL1), faricimab (VEGF-A/ANG-2), FAP-4-IBBL (4-1BB/FAP), XmAb-13676 (CD3/CD20), TAK-252 (PD-1/OX40L), TG-1801 (CD19/CD47), XmAb-18087 (SSTR2/CD3), catumaxomab (CD3/EpCAM), SAR-156597 (IL4/IL13), EMB-01 (EGFR/cMET), REGN-4018 (MUC16/CD3), REGN-1979 (CD20/CD3), RG-7828 (CD20/CD3), CC-93269 (CD3/BCMA), REGN-5458 (CD3/BCMA), navicixizumab (DLL4/VEGF), GRB-1302 (CD3/Erbb2), vanucizumab (VEGF-A/ANG-2), GRB-1342 (CD38/CD3), GEM-333 (CD3/CD33), IMM-0306 (CD47/CD20), RG6076, MEDI5752 (PD-1/CTLA-4), LY3164530 (MET/EGFR);
Alpha-ketoglutarate dehydrogenase (KGDH) inhibitors, such as CPI-613;
XPO1 inhibitors, such as selinexor (KPT-330);
Isocitrate dehydrogenase 2 (IDH2) inhibitors, such as enasidenib (AG-221);
IDH1 inhibitors such as AG-120, and AG-881 (IDH1 and IDH2), IDH-305, BAY-1436032;
IDH1 gene inhibitors, such as ivosidenib;
interleukin-3 receptor (IL-3R) modulators, such as SL-401;
Arginine deiminase stimulators, such as pegargiminase (ADI-PEG-20);
claudin-18 inhibitors, such as claudiximab;
β-catenin inhibitors, such as CWP-291;
chemokine receptor 2 (CCR) inhibitors, such as PF-04136309, CCX-872, BMS-813160 (CCR2/CCR5)
thymidylate synthase inhibitors, such as ONX-0801;
ALK/ROS1 inhibitors, such as lorlatinib;
tankyrase inhibitors, such as G007-LK;
Mdm2 p53-binding protein inhibitors, such as CMG-097, HDM-201; c-PIM inhibitors, such as PIM447;
sphingosine kinase-2 (SK2) inhibitors, such as Yeliva® (ABC294640);
DNA polymerase inhibitors, such as sapacitabine;
Cell cycle/Microtubule inhibitors, such as eribulin mesylate;

c-MET inhibitors, such as AMG-337, savolitinib, tivantinib (ARQ-197), capmatinib, and tepotinib, ABT-700, AG213, AMG-208, JNJ-38877618 (OMO-1), merestinib, HQP-8361;

c-Met/VEGFR inhibitors, such as BMS-817378, TAS-115;

c-Met/RON inhibitors, such as BMS-777607;

BCR/ABL inhibitors, such as rebastinib, asciminib, ponatinib (ICLUSIG®);

MNK1/MNK2 inhibitors, such as eFT-508;

Cytochrome P450 11B2/Cytochrome P450 17/AKT protein kinase inhibitors, such as LAE-201;

Cytochrome P450 3A4 stimulators, such as mitotane;

lysine-specific demethylase-1 (LSD1) inhibitors, such as CC-90011;

CSF1R/KIT and FLT3 inhibitors, such as pexidartinib (PLX3397);

Flt3 tyrosine kinase/Kit tyrosine kinase inhibitor and PDGF receptor antagonists, such as quizartinib dihydrochloride;

kinase inhibitors, such as vandetanib;

E selectin antagonists, such as GMI-1271;

differentiation inducers, such as tretinoin;

epidermal growth factor receptor (EGFR) inhibitors, such as osimertinib (AZD-9291), cetuximab;

topoisomerase inhibitors, such as Adriamycin, doxorubicin, daunorubicin, dactinomycin, DaunoXome, Caelyx, eniposide, epirubicin, etoposide, idarubicin, irinotecan, mitoxantrone, pixantrone, sobuzoxane, topotecan, irinotecan, MM-398 (liposomal irinotecan), vosaroxin and GPX-150, aldoxorubicin, AR-67, mavelertinib, AST-2818, avitinib (ACEA-0010), irofulven (MGI-114);

corticosteroids, such as cortisone, dexamethasone, hydrocortisone, methylprednisolone, prednisone, prednisolone;

growth factor signal transduction kinase inhibitors;

nucleoside analogs, such as DFP-10917;

Axl inhibitors, such as BGB-324 (bemcentinib), SLC-0211;

Axl/Flt3 inhibitors, such as gilteritinib;

Inhibitors of bromodomain and extraterminal motif (BET) proteins, including ABBV-744, BRD2 (NCBI Gene ID: 6046), BRD3 (NCBI Gene ID: 8019), BRD4 (NCBI Gene ID: 23476), and bromodomain testis-specific protein (BRDT; NCBI Gene ID: 676), such as INCB-054329, INCB057643, TEN-010, AZD-5153, ABT-767, BMS-986158, CC-90010, GSK525762 (molibresib), NHWD-870, ODM-207, GSK-2820151, GSK-1210151A, ZBC246, ZBC260, ZEN3694, FT-1101, RG-6146, CC-90010, CC-95775, mivebresib, BI-894999, PLX-2853, PLX-51107, CPI-0610, GS-5829;

PARP inhibitors, such as olaparib (MK7339), rucaparib, veliparib, talazoparib, ABT-767, BGB-290, fluzolepali (SHR-3162), niraparib (JNJ-64091742), bendamustine hydrochloride, PARP/Tankyrase inhibitors such as 2X-121 (e-7499);

IP-4297, SC-10914, IDX-1197, HWH-340, CK-102, simmiparib;

Proteasome inhibitors, such as ixazomib (NINLARO®), carfilzomib (Kyprolis®), marizomib, bortezomib;

Glutaminase inhibitors, such as CB-839 (telaglenastat), bis-2-(5-phenylacetamido-1,3,4-thiadiazol-2-yl)ethyl sulfide (BPTES);

mitochondrial complex I inhibitors, such as metformin, phenformin;

Vaccines, such as peptide vaccine TG-01 (RAS), GALE-301, GALE-302, nelipepimut-s, SurVaxM, DSP-7888, TPIV-200, PVX-410, VXL-100, DPX-E7, ISA-101, 6MHP, OSE-2101, galinpepimut-S, SVN53-67/M57-KLH, IMU-131, peptide subunit vaccine (acute lymphoblastic leukemia, University Children's Hospital Tuebingen); bacterial vector vaccines such as CRS-207/GVAX, axalimogene filolisbac (ADXS11-001); adenovirus vector vaccines such as nadofaragene firadenovec; autologous Gp96 vaccine; dendritic cells vaccines, such as CVactm, tapuldencel-T, eltrapuldencel-T, SL-701, BSKO1TM, rocapuldencel-T (AGS-003), DCVAC, CVactm, stapuldencel-T, eltrapuldencel-T, SL-701, BSKO1TM, ADXS31-142, autologous dendritic cell vaccine (metastatic malignant melanoma, intradermal/intravenous, Universitatsklinikum Erlangen); oncolytic vaccines such as, talimogene laherparepvec, pexastimogene devacirepvec, GL-ONC1, MG1-MA3, parvovirus H-1, ProstAtak, enadenotucirev, MG1MA3, ASN-002 (TG-1042); therapeutic vaccines, such as CVAC-301, CMP-001, CreaVax-BC, PF-06753512, VBI-1901, TG-4010, ProscaVax™; tumor cell vaccines, such as Vigil® (IND-14205), Oncoquest-L vaccine; live attenuated, recombinant, serotype 1 poliovirus vaccine, such as PVS-RIPO; Adagloxad simolenin; MEDI-0457; DPV-001 a tumor-derived, autophagosome enriched cancer vaccine; RNA vaccines such as, CV-9209, LV-305; DNA vaccines, such as MEDI-0457, MVI-816, INO-5401; modified vaccinia virus Ankara vaccine expressing p53, such as MVA-p53; DPX-Survivac; BriaVax™; GI-6301; GI-6207; GI-4000; IO-103; Neoantigen peptide vaccines, such as AGEN-2017, GEN-010, NeoVax, RG-6180, GEN-009, PGV-001 (TLR-3 agonist), GRANITE-001, NEO-PV-01; Peptide vaccines that target heat shock proteins, such as PhosphoSynVax™; Vitespen (HSPPC-96-C), NANT Colorectal Cancer Vaccine containing aldoxorubicin, autologous tumor cell vaccine+systemic CpG-B+IFN-alpha (cancer), IO-120+IO-103 (PD-L1/PD-L2 vaccines), HB-201, HB-202, HB-301, TheraT®*-based vaccines;

TLR-3 agonist/interferon inducers, such as Poly-ICLC (NSC-301463);

STAT-3 inhibitors, such as napabucasin (BBI-608);

ATPase p97 inhibitors, such as CB-5083;

smoothened (SMO) receptor inhibitors, such as Odomzo® (sonidegib, formerly LDE-225), LEQ506, vismodegib (GDC-0449), BMS-833923, glasdegib (PF-04449913), LY2940680, and itraconazole;

interferon alpha ligand modulators, such as interferon alpha-2b, interferon alpha-2a biosimilar (Biogenomics), ropeginterferon alfa-2b (AOP-2014, P-1101, PEG IFN alpha-2b), Multiferon (Alfanative, Viragen), interferon alpha 1b, Roferon-A (Canferon, Ro-25-3036), interferon alfa-2a follow-on biologic (Biosidus)(Inmutag, Inter 2A), interferon alfa-2b follow-on biologic (Biosidus—Bioferon, Citopheron, Ganapar, Beijing Kawin Technology—Kaferon), Alfaferone, pegylated interferon alpha-1b, peginterferon alfa-2b follow-on biologic (Amega), recombinant human interferon alpha-1b, recombinant human interferon alpha-2a, recombinant human interferon alpha-2b, veltuzumab-IFN alpha 2b conjugate, Dynavax (SD-101), and interferon alfa-n1 (Humoferon, SM-10500, Sumiferon);

interferon gamma ligand modulators, such as interferon gamma (OH-6000, Ogamma 100);

IL-6 receptor modulators, such as tocilizumab, AS-101 (CB-06-02, IVX-Q-101);
Heat shock protein inhibitors/IL-6 receptor antagonists, such as siltuximab;
Telomerase modulators, such as, tertomotide (GV-1001, HR-2802, Riavax) and imetelstat (GRN-163, JNJ-63935937);
DNA methyltransferases inhibitors, such as temozolomide (CCRG-81045), decitabine, guadecitabine (S-110, SGI-110), KRX-0402, RX-3117, RRx-001, and azacytidine (CC-486);
DNA gyrase inhibitors, such as pixantrone and sobuzoxane;
DNA gyrase inhibitors/Topoisimerase II inhibitors, such as amrubicin;
Bcl-2 family protein inhibitors, such as ABT-263, venetoclax (ABT-199), ABT-737, RG7601, and AT-101;
Bcl-2/Bcl-XL inhibitors, such as novitoclax;
Notch inhibitors, such as LY3039478 (crenigacestat), tarextumab (anti-Notch2/3), BMS-906024;
hyaluronidase stimulators, such as PEGPH-20;
Erbb2 tyrosine kinase receptor inhibitors/Hyaluronidase stimulators, such as Herceptin Hylecta;
Wnt pathway inhibitors, such as SM-04755, PRI-724, WNT-974;
gamma-secretase inhibitors, such as PF-03084014, MK-0752, RO-4929097;
Grb-2 (growth factor receptor bound protein-2) inhibitors, such as BP1001;
TRAIL pathway-inducing compounds, such as ONC201, ABBV-621;
TRAIL modulators, such as SCB-313;
Focal adhesion kinase inhibitors, such as VS-4718, defactinib, GSK2256098;
hedgehog inhibitors, such as saridegib, sonidegib (LDE225), glasdegib;
Aurora kinase inhibitors, such as alisertib (MLN-8237), and AZD-2811, AMG-900, barasertib, ENMD-2076;
HSPB1 modulators (heat shock protein 27, HSP27), such as brivudine, apatorsen;
ATR inhibitors, such as BAY-937, AZD6738, AZD6783, VX-803, VX-970 (berzosertib) and VX-970;
Hsp90 inhibitors, such as AUY922, onalespib (AT13387), SNX-2112, SNX5422;
Murine double minute (mdm2) oncogene inhibitors, such as DS-3032b, RG7775, AMG-232, HDM201, and idasanutlin (RG7388);
CD137 agonists, such as urelumab, utomilumab (PF-05082566), AGEN2373, ADG-106, BT-7480;
STING agonists, such as ADU-S100 (MIW-815), SB-11285, MK-1454, SR-8291, AdVCA0848, GSK-532, SYN-STING, MSA-1, SR-8291, GSK3745417;
FGFR inhibitors, such as FGF-401, INCB-054828, BAY-1163877, AZD4547, JNJ-42756493, LY2874455, Debio-1347;
fatty acid synthase (FASN) inhibitors, such as TVB-2640;
Antigen CD19 inhibitors, such as MOR208, MEDI-551, AFM-11, inebilizumab;
CD44 binders, such as A6;
protein phosphatase 2A (PP2A) inhibitors, such as LB-100;
CYP17 inhibitors, such as seviteronel (VT-464), ASN-001, ODM-204, CFG920, abiraterone acetate;
RXR agonists, such as IRX4204;
hedgehog/smoothened (hh/Smo) antagonists, such as taladegib, patidegib, vismodegib;
complement C3 modulators, such as Imprime PGG;

IL-15 agonists, such as ALT-803, NKTR-255, interleukin-15/Fc fusion protein, AM-0015, NIZ-985, and hetIL-15;
EZH2 (enhancer of zeste homolog 2) inhibitors, such as tazemetostat, CPI-1205, GSK-2816126, PF-06821497;
Oncolytic viruses, such as pelareorep, CG-0070, MV-NIS therapy, HSV-1716, DS-1647, VCN-01, ONCOS-102, TBI-1401, tasadenoturev (DNX-2401), vocimagene amiretrorepvec, RP-1, CVA21, Celyvir, LOAd-703, OBP-301, IMLYGIC®;
DOT1L (histone methyltransferase) inhibitors, such as pinometostat (EPZ-5676);
toxins such as Cholera toxin, ricin, *Pseudomonas exotoxin, Bordetella pertussis* adenylate cyclase toxin, diphtheria toxin, and caspase activators;
DNA plasmids, such as BC-819
PLK inhibitors of PLK 1, 2, and 3, such as volasertib (PLK1);
WEE1 inhibitors, such as AZD-1775 (adavosertib); Rho kinase (ROCK) inhibitors, such as AT13148, KD025;
Inhibition of Apoptosis Protein (IAP) inhibitors, such as ASTX660, debio-1143, birinapant, APG-1387, LCL-161;
RNA polymerase inhibitors, such has lurbinectedin (PM-1183), CX-5461;
Tubulin inhibitors, such as PM-184, BAL-101553 (lisavanbulin), and OXI-4503, fluorapacin (AC-0001), plinabulin, vinflunine;
Toll-like receptor 4 (TLR-4) agonists, such as G100, GSK1795091, and PEPA-10;
Elongation factor 1 alpha 2 inhibitors, such as plitidepsin;
Elongation factor 2 inhibitors/Interleukin-2 ligands/NAD ADP ribosyltransferase stimulators, such as denileukin diftitox;
CD95 inhibitors, such as APG-101, APO-010, asunercept;
WT1 inhibitors, such as DSP-7888;
splicing factor 3B subunit1 (SF3B1) inhibitors, such as H3B-8800
retinoid Z receptor gamma (RORγ) agonists, such as LYC-55716; and
Microbiome modulators, such as SER-401, EDP-1503, MRx-0518.

In some embodiments, a compound as described herein, is co-administered with one or more additional therapeutic agents comprising an inhibitor or antagonist of: myeloid cell leukemia sequence 1 (MCL1) apoptosis regulator (NCBI Gene ID: 4170); mitogen-activated protein kinase 1 (MAP4K1) (also called Hematopoietic Progenitor Kinase 1 (HPK1), NCBI Gene ID: 11184); diacylglycerol kinase alpha (DGKA, DAGK, DAGK1 or DGK-alpha; NCBI Gene ID: 1606); 5'-nucleotidase ecto (NT5E or CD73; NCBI Gene ID: 4907); ectonucleoside triphosphate diphosphohydrolase 1 (ENTPD1 or CD39; NCBI Gene ID: 593); transforming growth factor beta 1 (TGFB1 or TGFβ; NCBI Gene ID: 7040); heme oxygenase 1 (HMOX1, HO-1 or HO1; NCBI Gene ID: 3162); heme oxygenase 2 (HMOX2, HO-2 or HO2; NCBI Gene ID: 3163); vascular endothelial growth factor A (VEGFA or VEGF; NCBI Gene ID: 7422); erb-b2 receptor tyrosine kinase 2 (ERBB2, HER2, HER2/neu or CD340; NCBI Gene ID: 2064), epidermal growth factor receptor (EGFR, ERBB, ERBB1 or HER1; NCBI Gene ID: 1956); ALK receptor tyrosine kinase (ALK, CD246; NCBI Gene ID: 238); poly(ADP-ribose) polymerase 1 (PARP1; NCBI Gene ID: 142); poly(ADP-ribose) polymerase 2 (PARP2; NCBI Gene ID: 10038); TCDD inducible poly (ADP-ribose) polymerase (TIPARP, PARP7; NCBI Gene ID: 25976); cyclin dependent kinase 4 (CDK4; NCBI Gene ID: 1019); cyclin dependent kinase 6 (CDK6; NCBI Gene ID: 1021); TNF receptor superfamily member 14 (TNFRSF14, HVEM, CD270; NCBI Gene ID: 8764); T cell immunoreceptor with Ig and ITIM domains (TIGIT; NCBI Gene ID: 201633); X-linked inhibitor of apoptosis (XIAP, BIRC4, IAP-3; NCBI Gene ID: 331); baculoviral IAP repeat containing 2 (BIRC2, cIAP1; NCBI Gene ID: 329); baculoviral IAP repeat containing 3 (BIRC3, cIAP2; NCBI Gene ID: 330); baculoviral IAP repeat containing 5 (BIRC5, surviving; NCBI Gene ID: 332); C-C motif chemokine receptor 2 (CCR2, CD192; NCBI Gene ID: 729230); C-C motif chemokine receptor 5 (CCR5, CD195; NCBI Gene ID: 1234); C-C motif chemokine receptor 8 (CCR8, CDw198; NCBI Gene ID: 1237); C-X-C motif chemokine receptor 2 (CXCR2, CD182; NCBI Gene ID: 3579); C-X-C motif chemokine receptor 3 (CXCR3, CD182, CD183; NCBI Gene ID: 2833); C-X-C motif chemokine receptor 4 (CXCR4, CD184; NCBI Gene ID: 7852); arginase (ARG1 (NCBI Gene ID: 383), ARG2 (NCBI Gene ID: 384)), carbonic anhydrase (CA1 (NCBI Gene ID: 759), CA2 (NCBI Gene ID: 760), CA3 (NCBI Gene ID: 761), CA4 (NCBI Gene ID: 762), CA5A (NCBI Gene ID: 763), CA5B (NCBI Gene ID: 11238), CA6 (NCBI Gene ID: 765), CA7 (NCBI Gene ID: 766), CA8 (NCBI Gene ID: 767), CA9 (NCBI Gene ID: 768), CA10 (NCBI Gene ID: 56934), CA11 (NCBI Gene ID: 770), CA12 (NCBI Gene ID: 771), CA13 (NCBI Gene ID: 377677), CA14 (NCBI Gene ID: 23632)), prostaglandin-endoperoxide synthase 1 (PTGS1, COX-1; NCBI Gene ID: 5742), prostaglandin-endoperoxide synthase 2 (PTGS2, COX-2; NCBI Gene ID: 5743), secreted phospholipase A2, prostaglandin E synthase (PTGES, PGES; Gene ID: 9536), arachidonate 5-lipoxygenase (ALOX5, 5-LOX; NCBI Gene ID: 240) and/or soluble epoxide hydrolase 2 (EPHX2, SEH; NCBI Gene ID: 2053); a secreted phospholipase A2 (e.g., PLA2G1B (NCBI Gene ID: 5319); PLA2G7 (NCBI Gene ID: 7941), PLA2G3 (NCBI Gene ID: 50487), PLA2G2A (NCBI Gene ID: 5320); PLA2G4A (NCBI Gene ID: 5321); PLA2G12A (NCBI Gene ID: 81579); PLA2G12B (NCBI Gene ID: 84647); PLA2G10 (NCBI Gene ID: 8399); PLA2G5 (NCBI Gene ID: 5322); PLA2G2D (NCBI Gene ID: 26279); PLA2G15 (NCBI Gene ID: 23659)); indoleamine 2,3-dioxygenase 1 (IDO1; NCBI Gene ID: 3620); indoleamine 2,3-dioxygenase 2 (IDO2; NCBI Gene ID: 169355); hypoxia inducible factor 1 subunit alpha (HIF1A; NCBI Gene ID: 3091); angiopoietin 1 (ANGPT1; NCBI Gene ID: 284); Endothelial TEK tyrosine kinase (TIE-2, TEK, CD202B; NCBI Gene ID: 7010); Janus kinase 1 (JAK1; NCBI Gene ID: 3716); catenin beta 1 (CTNNB1; NCBI Gene ID: 1499); histone deacetylase 9 (HDAC9; NCBI Gene ID: 9734) and/or 5'-3' exoribonuclease 1 (XRN1; NCBI Gene ID: 54464).

TCR Signaling Modulators

In some embodiments, a compound as described herein, is combined with one or more agonist or antagonist of T-Cell Receptor (TCR) signaling modulators. Activation of T cells through the TCR and is essential for thymocyte development and effector T cell function. TCR activation promotes signaling cascades that ultimately determine cell fate through regulating cytokine production, cell survival, proliferation, and differentiation. Examples of TCR signaling modulators include without limitation CD2 (cluster of differentiation 2, LFA-2, T11, LFA-3 receptor), CD3 (cluster of differentiation 3), CD4 (cluster of differentiation 4), CD8 (cluster of differentiation 8), CD28 (cluster of differentiation 28), CD45 (PTPRC, B220, GP180), LAT (Linker for activation of T cells, LAT1), Lck, LFA-1 (ITGB2, CD18, LAD, LCAMB), Src, Zap-70, SLP-76, DGKalpha, CBL-b, CISH, HPK1.

Examples of agonist of cluster of differentiation 3 (CD3) that can be co-administered include without limitation MGD015.

In some embodiments, a compound as described herein, is combined with one or more blockers or inhibitors of inhibitory immune checkpoint proteins or receptors and/or with one or more stimulators, activators or agonists of one or more stimulatory immune checkpoint proteins or receptors. Blockade or inhibition of inhibitory immune checkpoints can positively regulate T-cell or NK cell activation and prevent immune escape of cancer cells within the tumor microenvironment. Activation or stimulation of stimulatory immune check points can augment the effect of immune checkpoint inhibitors in cancer therapeutics. In some embodiments, the immune checkpoint proteins or receptors regulate T cell responses (e.g., reviewed in Xu, et al., *J Exp Clin Cancer Res.* (2018) 37:110). In some embodiments, the immune checkpoint proteins or receptors regulate NK cell responses (e.g., reviewed in Davis, et al., *Semin Immunol.* (2017) 31:64-75 and Chiossone, et al., *Nat Rev Immunol.* (2018) 18(11):671-688).

Examples of immune checkpoint proteins or receptors include without limitation CD27, CD70; CD40, CD40LG; CD47, CD48 (SLAMF2), transmembrane and immunoglobulin domain containing 2 (TMIGD2, CD28H), CD84 (LY9B, SLAMF5), CD96, CD160, MS4A1 (CD20), CD244 (SLAMF4); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); natural killer cell cytotoxicity receptor 3 ligand 1 (NCR3LG1, B7H6); HERV-H LTR-associating 2 (HHLA2, B7H7); inducible T cell co-stimulator (ICOS, CD278); inducible T cell costimulator ligand (ICOSLG, B7H2); TNF receptor superfamily member 4 (TNFRSF4, OX40); TNF superfamily member 4 (TNFSF4, OX40L); TNFRSF8 (CD30), TNFSF8 (CD30L); TNFRSF10A (CD261, DR4, TRAILR1), TNFRSF9 (CD137), TNFSF9 (CD137L); TNFRSF10B (CD262, DR5, TRAILR2), TNFRSF10 (TRAIL); TNFRSF14 (HVEM, CD270), TNFSF14 (HVEML); CD272 (B and T lymphocyte associated (BTLA)); TNFRSF17 (BCMA, CD269), TNFSF13B (BAFF); TNFRSF18 (GITR), TNFSF18 (GITRL); MHC class I polypeptide-related sequence A (MICA); MHC class I polypeptide-related sequence B (MICB); CD274 (PDL1, PD-L1); programmed cell death 1 (PDCD1, PD-1, PD-1); cytotoxic T-lymphocyte associated protein 4 (CTLA4, CD152); CD80 (B7-1), CD28; nectin cell adhesion molecule 2 (NECTIN2, CD112); CD226 (DNAM-1); Poliovirus receptor (PVR) cell adhesion molecule (PVR, CD155); PVR related immunoglobulin domain containing (PVRIG, CD112R); T cell immunoreceptor with Ig and ITIM domains (TIGIT); T cell immunoglobulin and mucin domain containing 4 (TIMD4; TIM4); hepatitis A virus cellular receptor 2 (HAVCR2, TIMD3, TIM-3); galectin 9 (LGALS9); lymphocyte activating 3 (LAG-3, CD223); signaling lymphocytic activation molecule family member 1 (SLAMF1, SLAM, CD150); lymphocyte antigen 9 (LY9, CD229, SLAMF3); SLAM family member 6 (SLAMF6, CD352); SLAM family member 7 (SLAMF7, CD319); UL16 binding protein 1 (ULBP1); UL16 binding protein 2 (ULBP2); UL16 binding protein 3 (ULBP3); retinoic acid early transcript 1E (RAET1E; ULBP4); retinoic acid early transcript 1G (RAET1G; ULBP5); retinoic acid early transcript 1L (RAET1L; ULBP6); lymphocyte activating 3 (CD223); killer cell immunoglobulin like receptor(KIR); killer cell lectin like receptor C1 (KLRC1, NKG2A, CD159A); killer cell lectin like receptor K1 (KLRK1, NKG2D, CD314); killer cell lectin like receptor C2 (KLRC2, CD159c, NKG2C); killer cell lectin like receptor C3 (KLRC3, NKG2E); killer cell lectin like receptor C4 (KLRC4, NKG2F); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor D1 (KLRD1).

In some embodiments, a compound as described herein, is combined with one or more blockers or inhibitors of one or more T-cell inhibitory immune checkpoint proteins or receptors. Illustrative T-cell inhibitory immune checkpoint proteins or receptors include without limitation CD274 (PDL1, PD-L1); programmed cell death 1 ligand 2 (PDCDILG2, PD-L2, CD273); programmed cell death 1 (PDCD1, PD1, PD-1); cytotoxic T-lymphocyte associated protein 4 (CTLA4, CD152); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); TNFRSF14 (HVEM, CD270), TNFSF14 (HVEML); CD272 (B and T lymphocyte associated (BTLA)); PVR related immunoglobulin domain containing (PVRIG, CD112R); T cell immunoreceptor with Ig and ITIM domains (TIGIT); lymphocyte activating 3 (LAG-3, CD223); hepatitis A virus cellular receptor 2 (HAVCR2, TIMD3, TIM-3); galectin 9 (LGALS9); killer cell immunoglobulin like receptor(KIR); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); and killer cell immunoglobulin like receptor, three Ig domains and long cytoplasmic tail 1 (KIR3DL1). In some embodiments, a compound as described herein, is combined with one or more agonist or activators of one or more T-cell stimulatory immune checkpoint proteins or receptors. Illustrative T-cell stimulatory immune checkpoint proteins or receptors include without limitation CD27, CD70; CD40, CD40LG; inducible T cell costimulator (ICOS, CD278); inducible T cell costimulator ligand (ICOSLG, B7H2); TNF receptor superfamily member 4 (TNFRSF4, OX40); TNF superfamily member 4 (TNFSF4, OX40L); TNFRSF9 (CD137), TNFSF9 (CD137L); TNFRSF18 (GITR), TNFSF18 (GITRL); CD80 (B7-1), CD28; nectin cell adhesion molecule 2 (NECTIN2, CD112); CD226 (DNAM-1); CD244 (2B4, SLAMF4), Poliovirus receptor (PVR) cell adhesion molecule (PVR, CD155). See, e.g., Xu, et al., *J Exp Clin Cancer Res.* (2018) 37:110.

In some embodiments, a compound as described herein, is combined with one or more blockers or inhibitors of one or more NK-cell inhibitory immune checkpoint proteins or receptors. Illustrative NK-cell inhibitory immune checkpoint proteins or receptors include without limitation killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor C1 (KLRC1, NKG2A, CD159A); and killer cell lectin like receptor D1 (KLRD1, CD94). In some embodiments, a compound as described herein, is combined with one or more agonist or activators of one or more NK-cell stimulatory immune checkpoint proteins or receptors. Illustrative NK-cell stimulatory immune checkpoint proteins or receptors include without limitation CD16, CD226 (DNAM-1); CD244 (2B4, SLAMF4); killer cell lectin like receptor K1 (KLRK1, NKG2D, CD314); SLAM family member 7 (SLAMF7). See, e.g., Davis, et al., *Semin Immunol.* (2017) 31:64-75; Fang, et al., *Semin Immunol.* (2017) 31:37-54; and Chiossone, et al., *Nat Rev Immunol.* (2018) 18(11):671-688.

In some embodiments, a compound as described herein, is combined with an inhibitor of CD47 (IAP, MER6, OA3; NCBI Gene ID: 961; UniProt Q08722). Examples of CD47 inhibitors include without limitation to anti-CD47 mAbs (Vx-1004), anti-human CD47 mAbs (CNTO-7108), CC-90002, CC-90002-ST-001, humanized anti-CD47 antibody (Hu5F9-G4), NI-1701, NI-1801, RCT-1938, ALX-148, TTI-621, RRx-001, DSP-107, VT-1021, TTI-621, TTI-622, and IM-02 SGN-CD47M. Examples of anti-CD47 antibodies include IBI-188, TJC-4, SHR-1603, HLX-24, LQ-001, IMC-002, ZL-1201, IMM-01, B6H12, GenSci-059, TAY-018, PT-240, 1F8-GMCSF, SY-102, KD-015.

In some embodiments, the inhibitor of CD47 is a bi-specific antibody targeting CD47. Examples of bi-specific antibodies targeting CD47 include IBI-322 (CD47/PD-L1), IMM-0306 (CD47/CD20), TJ-L1C4 (CD47/PD-L1), HX-009 (CD47/PD-1), PMC-122 (CD47/PD-L1), PT-217, (CD47/DLL3), IMM-26011 (CD47/FLT3), IMM-0207 (CD47/VEGF), IMM-2902 (CD47/HER2), BH29xx (CD47/PD-L1), IMM-03 (CD47/CD20), IMM-2502 (CD47/PD-L1), HMBD-004B (CD47/BCMA), and HMBD-004A (CD47/CD33).

In some embodiments, the anti-CD47 targeting agent is one described in patent publication numbers WO199727873, WO199940940, WO2002092784, WO2005044857, WO2009046541, WO2010070047, WO2011143624, WO2012170250, WO2013109752, WO2013119714, WO2014087248, WO2015191861, WO2016022971, WO2016023040, WO2016024021, WO2016081423, WO2016109415, WO2016141328, WO2016188449, WO2017027422, WO2017049251, WO2017053423, WO2017121771, WO2017194634, WO2017196793, WO2017215585, WO2018075857, WO2018075960, WO2018089508, WO2018095428, WO2018137705, WO2018233575, WO2019027903, WO2019034895, WO2019042119, WO2019042285, WO2019042470, WO2019086573, WO2019108733, WO2019138367, WO2019144895, WO2019157843, WO2019179366, WO2019184912, WO2019185717, WO2019201236, WO2019238012, WO2019241732, WO2020019135, WO2020036977, WO2020043188, or WO2020009725.

In some embodiments, the one or more immune checkpoint inhibitors comprises a proteinaceous (e.g., antibody or fragment thereof, or antibody mimetic) inhibitor of PD-L1 (CD274), PD-1 (PDCD1) or CTLA4. In some embodiments, the one or more immune checkpoint inhibitors comprises a small organic molecule inhibitor of PD-L1 (CD274), PD-1 (PDCD1) or CTLA4.

Examples of inhibitors of CTLA4 that can be co-administered include without limitation ipilimumab, tremelimumab, BMS-986218, AGEN1181, AGEN1884, BMS-986249, MK-1308, REGN-4659, ADU-1604, CS-1002, BCD-145, APL-509, JS-007, BA-3071, ONC-392, AGEN-2041, JHL-1155, KN-044, CG-0161, ATOR-1144, PBI-5D3H5, BPI-002, HBM-4003, as well as multi-specific inhibitors FPT-155 (CTLA4/PD-L1/CD28), PF-06936308 (PD-1/CTLA4), MGD-019 (PD-1/CTLA4), KN-046 (PD-1/CTLA4), MEDI-5752 (CTLA4/PD-1), XmAb-20717 (PD-1/CTLA4), and AK-104 (CTLA4/PD-1).

Examples of inhibitors/antibodies of PD-L1 (CD274) or PD-1 (PDCD1) that can be co-administered include without limitation pembrolizumab, nivolumab, cemiplimab, pidilizumab, AMG-404, AMP-224, MEDI0680 (AMP-514), spartalizumab, atezolizumab, avelumab, durvalumab, BMS-936559, CK-301, PF-06801591, BGB-A317 (tislelizumab), GEN-1046 (PD-L1/4-1BB), GLS-010 (WBP-3055), AK-103 (HX-008), AK-105, CS-1003, HLX-10, MGA-012, BI-754091, AGEN-2034, JS-001 (toripalimab), JNJ-63723283, genolimzumab (CBT-501), LZM-009, BCD-100, LY-3300054, SHR-1201, SHR-1210 (camrelizumab), Sym-021, ABBV-181, PD1-PIK, BAT-1306, (MSB0010718C), CX-072, CBT-502, TSR-042 (dostarlimab), MSB-2311, JTX-4014, BGB-A333, SHR-1316, CS-1001 (WBP-3155, KN-035, IBI-308 (sintilimab), HLX-20, KL-A167, STI-A1014, STI-A1015 (IMC-001), BCD-135, FAZ-053, TQB-2450, MDX1105-01, GS-4224, GS-4416, INCB086550, MAX10181, as well as multi-specific inhibitors FPT-155 (CTLA4/PD-L1/CD28), PF-06936308 (PD-1/CTLA4), MGD-013 (PD-1/LAG-3), RO-7247669 (PD-1/LAG-3), FS-118 (LAG-3/PD-L1) MGD-019 (PD-1/CTLA4), KN-046 (PD-1/CTLA4), MEDI-5752 (CTLA4/PD-1), RO-7121661 (PD-1/TIM-3), XmAb-20717 (PD-1/CTLA4), AK-104 (CTLA4/PD-1), M7824 (PD-L1/TGFβ-EC domain), CA-170 (PD-L1/VISTA), CDX-527 (CD27/PD-L1), LY-3415244 (TIM-3/PDL1), RG7769 (PD-1/TIM-3) and INBRX-105 (4-1BB/PDL1), GNS-1480 (PD-L1/EGFR), RG-7446 (Tecentriq, atezolizumab), ABBV-181, nivolumab (OPDIVO®, BMS-936558, MDX-1106), pembrolizumab (KEYTRUDA®, MK-3477, SCH-900475, lambrolizumab, CAS Reg. No. 1374853-91-4), pidilizumab, PF-06801591, BGB-A317 (tislelizumab), GLS-010 (WBP-3055), AK-103 (HX-008), CS-1003, HLX-10, MGA-012, BI-754091, REGN-2810 (cemiplimab), AGEN-2034, JS-001 (toripalimab), JNJ-63723283, genolimzumab (CBT-501), LZM-009, BCD-100, LY-3300054, SHR-1201, SHR-1210 (camrelizumab), Sym-021, ABBV-181, AK-105, PD1-PIK, BAT-1306, BMS-936559, atezolizumab (MPDL3280A), durvalumab (MEDI-4736), avelumab, CK-301, (MSB0010718C), MEDI-0680, CX-072, CBT-502, PDR-001 (spartalizumab), PDR001+Tafinlar®+Mekinist®, MSB-2311, JTX-4014, BGB-A333, SHR-1316, CS-1001 (WBP-3155, KN-035, IBI-308 (sintilimab), HLX-20, KL-A167, STI-A1014, STI-A1015 (IMC-001), BCD-135, FAZ-053, TQB-2450, and MDX1105-01; and those described, e.g. in Intl. Patent Publ. Nos. WO2018195321, WO2020014643, WO2019160882, and WO2018195321.

Examples of inhibitors of PVRIG that can be co-administered include without limitation: COM-701.

Examples of inhibitors of TIGIT that can be co-administered include without limitation: BMS-986207, RG-6058, AGEN-1307, COM-902.

Examples of inhibitors of TIM-3 that can be co-administered include without limitation: TSR-022, LY-3321367, MBG-453, INCAGN-2390, RO-7121661 (PD-1/TIM-3), LY-3415244 (TIM-3/PDL1), RG7769 (PD-1/TIM-3).

Examples of inhibitors of LAG-3 that can be co-administered include without limitation: relatlimab (ONO-4482), LAG-525, MK-4280, REGN-3767, INCAGN2385, TSR-033, MGD-013 (PD-1/LAG-3), FS-118 (LAG-3/PD-L1).

Examples of anti-killer cell immunoglobulin like receptor, three Ig domains and long cytoplasmic tail 1 (KIR3DL1; KIR; NCBI Gene ID: 3811) monoclonal antibodies, such as lirilumab (IPH-2102), IPH-4102.

Examples of anti-NKG2a antibodies that can be co-administered include without limitation: monalizumab.

Examples of anti-VISTA antibodies that can be co-administered include without limitation: HM1BD-002, CA-170 (PD-L1/VISTA).

Examples of anti-CD70 antibodies that can be co-administered include without limitation: AMG-172.

Examples of anti-CD20 antibodies that can be co-administered include without limitation: obinutuzumab, IGN-002, PF-05280586.

Examples of anti-ICOS antibodies that can be co-administered include without limitation: JTX-2011, GSK3359609.

Examples of ICOS agonists that can be co-administered include without limitation: ICOS-L.COMP (Gariepy, J. et al. 106th Annu Meet Am Assoc Immunologists (AAI) (May 9-13, San Diego) 2019, Abst 71.5).

TNF Receptor Superfamily (TNFRSF) Member Agonists or Activators

In some embodiments, a compound as described herein, is combined with an agonist of one or more TNF receptor superfamily (TNFRSF) members, e.g., an agonist of one or more of TNFRSF1A (NCBI Gene ID: 7132), TNFRSF1B (NCBI Gene ID: 7133), TNFRSF4 (OX40, CD134; NCBI Gene ID: 7293), TNFRSF5 (CD40; NCBI Gene ID: 958), TNFRSF6 (FAS, NCBI Gene ID: 355), TNFRSF7 (CD27, NCBI Gene ID: 939), TNFRSF8 (CD30, NCBI Gene ID: 943), TNFRSF9 (4-1BB, CD137, NCBI Gene ID: 3604), TNFRSF10A (CD261, DR4, TRAILR1, NCBI Gene ID: 8797), TNFRSF10B (CD262, DR5, TRAILR2, NCBI Gene ID: 8795), TNFRSF10C (CD263, TRAILR3, NCBI Gene ID: 8794), TNFRSF10D (CD264, TRAILR4, NCBI Gene ID: 8793), TNFRSF11A (CD265, RANK, NCBI Gene ID: 8792), TNFRSF11B (NCBI Gene ID: 4982), TNFRSF12A (CD266, NCBI Gene ID: 51330), TNFRSF13B (CD267, NCBI Gene ID: 23495), TNFRSF13C (CD268, NCBI Gene ID: 115650), TNFRSF16 (NGFR, CD271, NCBI Gene ID: 4804), TNFRSF17 (BCMA, CD269, NCBI Gene ID: 608), TNFRSF18 (GITR, CD357, NCBI Gene ID: 8784), TNFRSF19 (NCBI Gene ID: 55504), TNFRSF21 (CD358, DR6, NCBI Gene ID: 27242), and TNFRSF25 (DR3, NCBI Gene ID: 8718).

Example anti-TNFRSF4 (OX40) antibodies that can be co-administered include without limitation, MEDI6469, MEDI6383, MEDI0562 (tavolixizumab), MOXR0916, PF-04518600, RG-7888, GSK-3174998, INCAGN1949, BMS-986178, GBR-8383, ABBV-368, and those described in WO2016179517, WO2017096179, WO2017096182, WO2017096281, and WO2018089628.

Examples anti-TNF receptor superfamily member 10b (TNFRSF10B, DR5, TRATLR2) antibodies that can be co-administered include without limitation, such as DS-8273, CTB-006, INBRX-109, GEN-1029.

Example anti-TNFRSF5 (CD40) antibodies that can be co-administered include without limitation RG7876, SEA-CD40, APX-005M and ABBV-428, ABBV-927, JNJ-64457107.

In some embodiments, the anti-TNFRSF7 (CD27) antibody varlilumab (CDX-1 127) is co-administered.

Example anti-TNFRSF9 (4-1BB, CD137) antibodies that can be co-administered include without limitation urelumab, utomilumab (PF-05082566), AGEN2373 and ADG-106.

In some embodiments, the anti-TNFRSF17 (BCMA) antibody GSK-2857916 is co-administered.

Example anti-TNFRSF18 (GITR) antibodies that can be co-administered include without limitation, MEDI1873, FPA-154, INCAGN-1876, TRX-518, BMS-986156, MK-1248, GWN-323, and those described in WO2017096179, WO2017096276, WO2017096189, and WO2018089628. In some embodiments, an antibody, or fragment thereof, co-targeting TNFRSF4 (OX40) and TNFRSF18 (GITR) is co-administered. Such antibodies are described, e.g., in WO2017096179 and WO2018089628.

Example anti-TRAILR1, anti-TRAILR2, anti-TRAILR3, anti-TRAILR4 antibodies that can be co-administered include without limitation ABBV-621.

Bi-specific antibodies targeting TNFRSF family members that can be co-administered include without limitation PRS-343 (CD-137/HER2), AFM26 (BCMA/CD16A), AFM-13 (CD16/CD30), REGN-1979 (CD20/CD3), AMG-420 (BCMA/CD3), INHIBRX-105 (4-1BB/PDL1), FAP-4-IBBL (4-1BB/FAP), XmAb-13676 (CD3/CD20), RG-7828 (CD20/CD3), CC-93269 (CD3/BCMA), REGN-5458 (CD3/BCMA), and IMM-0306 (CD47/CD20), AMG-424 (CD38.CD3).

Adenosine Generation and Signaling

In some embodiments, a compound as described herein, is combined with an agonist or antagonist of A1R, A2AR, A2BR, A3R, CD73, CD39, CD26.

Examples of Adenosine A3 receptor (A3R) agonists, such as namodenoson (CF102).

Examples of A2aR/A2bR antagonists, such as AB928.

Examples of anti-CD73 antibodies, such as MEDI-9447 (oleclumab), CPX-006, IPH-53, BMS-986179, NZV-930, CPI-006.

Examples of CD73 inhibitors, such as AB-680, PSB-12379, PSB-12441, PSB-12425, CB-708; and those described in Int Patent Publication No. WO19173692.

Examples of CD39/CD73 inhibitors, such as PBF-1662.

Examples of anti-CD39 antibodies, such as TTX-030.

Examples of Adenosine A2A receptor antagonists, such as CPI-444, AZD-4635, preladenant, PBF-509.

Examples of Adenosine deaminase inhibitors, such as pentostatin, cladribine.

c-Kit Targeting Agents

In various embodiments, a compound as described herein, is combined with an inhibitor of c-kit (PBT, SCFR, CD117, MASTC; NCBI Gene ID:3815; Uniprot—P10721).

Examples of c-kit inhibitors include imatinib mesylate, JSP-191, BLU-263, CD117-ADC, AZD3229 (c-kit/PDGFR inhibitor), telatinib (c-kit/PDGF/VEGF2 inhibitor), quizartinib dihydrochloride (FLT3/c-kit), pexidartinib hydrochloride (CSF1R/FLT3/c-kit), avapritinib (PDGFR/c-Kit inhibitor), vorolanib (multikinase VEGF/PDGFR/c-kit inhibitor), and ripretinib (c-kit/PDGFRa inhibitor).

Examples of c-kit multi-kinase inhibitors include dasatinib, imatinib, nilotinib, sorafenib, lenvatinib mesylate, cabozantinib malate, AL-8326, ZLJ-33, KBP-7018, sunitinib malate, pazopanib derivatives, AGX-73, rebastinib, NMS-088, lucitanib hydrochloride, midostaurin, cediranib, dovitinib, sitravatinib, tivozanib, masitinib, regorafenib, HQP-1351, cabozantinib, ponatinib, and famitinib L-malate. Examples of anti-c-kit antibodies include CDX-0158, CDX-0159 and FSI-174.

In some embodiments, the anti-c-kit targeting agent is one described in patent publication numbers WO199203459, WO199221766, WO2004080462, WO2005020921, WO2006009755, WO2007078034, WO2007092403, WO2007127317, WO2008005877, WO2012154480, WO2014100620, WO2014039714, WO2015134536, WO2017167182, WO2018112136, WO2018112140, WO2019155067, WO2020076105, and patent application no. PCT/US2019/063091.

SIRPα Targeting Agents

In various embodiments, a compound as described herein, is combined with an inhibitor of SIRPα (NCBI Gene ID: 140885; UniProt P78324).

Examples of SIRPα inhibitors, such as AL-008, RRx-001, and CTX-5861.

Examples of anti-SIRPα-antibodies, such as FSI-189, ES-004, BI765063, ADU1805, and CC-95251.

In some embodiments, the SIRPα-targeting agent is one described in WO200140307, WO2002092784, WO2007133811, WO2009046541, WO2010083253, WO2011076781, WO2013056352, WO2015138600, WO2016179399, WO2016205042, WO2017178653, WO2018026600, WO2018057669, WO2018107058, WO2018190719, WO2018210793, WO2019023347, WO2019042470, WO2019175218, WO2019183266, WO2020013170, or WO2020068752.

Bi-Specific T-Cell Engagers

In some embodiments, a compound as described herein, is combined with a bi-specific T-cell engager (e.g., not having an Fc) or an anti-CD3 bi-specific antibody (e.g., having an Fc). Illustrative anti-CD3 bi-specific antibodies or BiTEs that can be co-administered include AMG-160 (PSMA/CD3), AMG-212 (PSMA/CD3), AMG-330 (CD33/CD3), AMG-420 (BCMA/CD3), AMG-427 (FLT3/CD3), AMG-562 (CD19/CD3), AMG-596 (EGFRvIII/CD3), AMG-673 (CD33/CD3), AMG-701 (BCMA/CD3), AMG-757 (DLL3/CD3), JNJ-64052781 (CD19/CD3), AMG-211 (CEA/CD3), BLINCYTO® (CD19/CD3), RG7802 (CEA/CD3), ERY-974 (CD3/GPC3), huGD2-BsAb (CD3/GD2), PF-06671008 (Cadherins/CD3), APV0436 (CD123/CD3), ERY974, flotetuzumab (CD123/CD3), GEM333 (CD3/CD33), GEMoab (CD3/PSCA), REGN-1979 (CD20/CD3), REGN-5678 (PSMA/CD28), MCLA-117 (CD3/CLEC12A), JNJ-0819, JNJ-7564 (CD3/heme), JNJ-63709178 (CD123/CD3), MGD-007 (CD3/gpA33), MGD-009 (CD3/B7H3), IMCgp100 (CD3/gp100), XmAb-14045 (CD123/CD3), XmAb-13676 (CD3/CD20), XmAb-18087 (SSTR2/CD3), catumaxomab (CD3/EpCAM), REGN-4018 (MUC16/CD3), RG6026, RG6076, RG6194, RG-7828 (CD20/CD3), CC-93269 (CD3/BCMA), REGN-5458 (CD3/BCMA), GRB-1302 (CD3/Erbb2), GRB-1342 (CD38/CD3), GEM-333 (CD3/CD33), PF-06863135 (BCMA/CD3), SAR440234 (CD3/CDw123). As appropriate, the anti-CD3 binding bi-specific molecules may or may not have an Fc. Illustrative bi-specific T-cell engagers that can be co-administered target CD3 and a tumor-associated antigen as described herein, including, e.g., CD19 (e.g., blinatumomab); CD33 (e.g., AMG330); CEA (e.g., MEDI-565); receptor tyrosine kinase-like orphan receptor 1 (ROR1) (Gohil, et al., Oncoimmunology. (2017) May 17; 6(7):e1326437); PD-L1 (Horn, et al., Oncotarget. 2017 Aug. 3; 8(35):57964-57980); and EGFRvIII (Yang, et al., Cancer Lett. 2017 Sep. 10; 403:224-230).

Bi- and Tri-Specific Natural Killer (NK)-Cell Engagers

In some embodiments, a compound as described herein, is combined with a bi-specific NK-cell engager (BiKE) or a tri-specific NK-cell engager (TriKE) (e.g., not having an Fc) or bi-specific antibody (e.g., having an Fc) against an NK cell activating receptor, e.g., CD16A, C-type lectin receptors (CD94/NKG2C, NKG2D, NKG2E/H and NKG2F), natural cytotoxicity receptors (NKp30, NKp44 and NKp46), killer cell C-type lectin-like receptor (NKp65, NKp80), Fc receptor FcTR (which mediates antibody-dependent cell cytotoxicity), SLAM family receptors (e.g., 2B4, SLAM6 and SLAM7), killer cell immunoglobulin-like receptors (KIR) (KIR-2DS and KIR-3DS), DNAM-1 and CD137 (41BB).

Illustrative anti-CD16 bi-specific antibodies, BiKEs or TriKEs that can be co-administered include AFM26 (BCMA/CD16A) and AFM-13 (CD16/CD30). As appropriate, the anti-CD16 binding bi-specific molecules may or may not have an Fc. Illustrative bi-specific NK-cell engagers that can be co-administered target CD16 and one or more tumor-associated antigens as described herein, including, e.g., CD19, CD20, CD22, CD30, CD33, CD123, EGFR, EpCAM, ganglioside GD2, HER2/neu, HLA Class II and FOLR1. BiKEs and TriKEs are described, e.g., in Felices, et al., *Methods Mol Biol.* (2016) 1441:333-346; Fang, et al., *Semin Immunol.* (2017) 31:37-54.

MCL1 Apoptosis Regulator, BCL2 Family Member (MCL1) Inhibitors

In some embodiments, a compound as described herein, is combined with an inhibitor of MCL1 apoptosis regulator, BCL2 family member (MCL1, TM; EAT; MCL1L; MCL1S; Mcl-1; BCL2L3; MCL1-ES; bcl2-L-3; mcl1/EAT; NCBI Gene ID: 4170). Examples of MCL1 inhibitors include AMG-176, AMG-397, S-64315, and AZD-5991, 483-LM, A-1210477, UMI-77, JKY-5-037, and those described in WO2018183418, WO2016033486, and WO2017147410.

Hematopoietic Progenitor Kinase 1 (HPK1) Inhibitors

In some embodiments, a compound as described herein, is combined with an inhibitor of mitogen-activated protein kinase kinase kinase kinase 1 (MAP4K1, HPK1; NCBI Gene ID: 11184). Examples of Hematopoietic Progenitor Kinase 1 (HPK1) inhibitors include without limitation, those described in WO-2018183956, WO-2018183964, WO-2018167147, WO-2018183964, WO-2016205942, WO-2018049214, WO-2018049200, WO-2018049191, WO-2018102366, WO-2018049152, WO2020092528, WO2020092621, and WO-2016090300.

Apoptosis Signal-Regulating Kinase (ASK) Inhibitors

In some embodiments, a compound as described herein, is combined with an inhibitor of an ASK inhibitor, e.g., mitogen-activated protein kinase kinase kinase 5 (MAP3K5; ASK1, MAPKKK5, MEKK5; NCBI Gene ID: 4217). Examples of ASK1 inhibitors include without limitation, those described in WO 2011/008709 (Gilead Sciences) and WO 2013/112741 (Gilead Sciences).

Bruton Tyrosine Kinase (BTK) Inhibitors

In some embodiments, a compound as described herein, is combined with an inhibitor of Bruton tyrosine kinase (BTK, AGMX1, AT, ATK, BPK, IGHD3, IMD1, PSCTK1, XLA; NCBI Gene ID: 695). Examples of BTK inhibitors include without limitation, (S)-6-amino-9-(1-(but-2-ynoyl)pyrrolidin-3-yl)-7-(4-phenoxyphenyl)-7H-purin-8(9H)-one, acalabrutinib (ACP-196), BGB-3111, CB988, HM71224, ibrutinib (Imbruvica), M-2951 (evobrutinib), M7583, tirabrutinib (ONO-4059), PRN-1008, spebrutinib (CC-292), TAK-020, vecabrutinib, ARQ-531, SHR-1459, DTRMWXHS-12, TAS-5315, Calquence+AZD6738, Calquence+danvatirsen.

Cyclin-Dependent Kinase (CDK) Inhibitors

In some embodiments, a compound as described herein, is combined with an inhibitor of cyclin dependent kinase 1 (CDK1, CDC2; CDC28A; P34CDC2; NCBI Gene ID: 983); cyclin dependent kinase 2 (CDK2, CDKN2; p33(CDK2); NCBI Gene ID: 1017); cyclin dependent kinase 3 (CDK3; NCBI Gene ID: 1018); cyclin dependent kinase 4 (CDK4, CMM3; PSK-J3; NCBI Gene ID: 1019); cyclin dependent kinase 6 (CDK6, MCPH12; PLSTTRE; NCBI Gene ID: 1021); cyclin dependent kinase 7 (CDK7, CAK; CAK1; HCAK; MO15; STK1; CDKN7; p39MO15; NCBI Gene ID: 1022); cyclin dependent kinase 9 (CDK9, TAK; C-2k; CTK1; CDC2L4; PITALRE; NCBI Gene ID: 1025). Inhibitors of CDK 1, 2, 3, 4, 6, 7 and/or 9, include without limitation abemaciclib, alvocidib (HMR-1275, flavopiridol), AT-7519, dinaciclib, ibrance, FLX-925, LEE001, palbociclib, ribociclib, rigosertib, selinexor, UCN-01, SY1365, CT-7001, SY-1365, G1T38, milciclib, trilaciclib, PF-06873600, AZD4573, and TG-02.

Discoidin Domain Receptor (DDR) Inhibitors

In some embodiments, a compound as described herein, is combined with an inhibitor of discoidin domain receptor tyrosine kinase 1 (DDR1, CAK, CD167, DDR, EDDR1, HGK2, MCK10, NEP, NTRK4, PTK3, PTK3A, RTK6, TRKE; NCBI Gene ID: 780); and/or discoidin domain receptor tyrosine kinase 2 (DDR2, MIG20a, NTRKR3, TKT, TYRO10, WRCN; NCBI Gene ID: 4921). Examples of DDR inhibitors include without limitation, dasatinib and those disclosed in WO2014/047624 (Gilead Sciences), US 2009-0142345 (Takeda Pharmaceutical), US 2011-0287011 (Oncomed Pharmaceuticals), WO 2013/027802 (Chugai Pharmaceutical), and WO2013/034933 (Imperial Innovations).

Histone Deacetylase (HDAC) Inhibitors

In some embodiments, a compound as described herein, is combined with an inhibitor of a histone deacetylase, e.g., histone deacetylase 9 (HDAC9, HD7, HD7b, HD9, HDAC, HDAC7, HDAC7B, HDAC9B, HDAC9FL, HDRP, MITR; Gene ID: 9734). Examples of HDAC inhibitors include without limitation, abexinostat, ACY-241, AR-42, BEBT-908, belinostat, CKD-581, CS-055 (HBI-8000), CUDC-907 (fimepinostat), entinostat, givinostat, mocetinostat, panobinostat, pracinostat, quisinostat (JNJ-26481585), resminostat, ricolinostat, SHP-141, valproic acid (VAL-001), vorinostat, tinostamustine, remetinostat, entinostat, romidepsin, tucidinostat.

Indoleamine-Pyrrole-2,3-Dioxygenase (IDO1) Inhibitors

In some embodiments, a compound as described herein, is combined with an inhibitor of indoleamine 2,3-dioxygenase 1 (IDO1; NCBI Gene ID: 3620). Examples of IDO1 inhibitors include without limitation, BLV-0801, epacadostat, F-001287, GBV-1012, GBV-1028, GDC-0919, indoximod, NKTR-218, NLG-919-based vaccine, PF-06840003, pyranonaphthoquinone derivatives (SN-35837), resminostat, SBLK-200802, BMS-986205, and shIDO-ST, EOS-200271, KHK-2455, LY-3381916.

Janus Kinase (JAK) Inhibitors

In some embodiments, a compound as described herein, is combined with an inhibitor of Janus kinase 1 (JAK1, JAK1A, JAK1B, JTK3; NCBI Gene ID: 3716); Janus kinase 2 (JAK2, JTK10, THCYT3; NCBI Gene ID: 3717); and/or Janus kinase 3 (JAK3, JAK-3, JAK3_HUMAN, JAKL, L-JAK, LJAK; NCBI Gene ID: 3718). Examples of JAK inhibitors include without limitation, AT9283, AZD1480, baricitinib, BMS-911543, fedratinib, filgotinib (GLPG0634), gandotinib (LY2784544), INCB039110 (itacitinib), lestaurtinib, momelotinib (CYT0387), NS-018, pacritinib (SB1518), peficitinib (ASP015K), ruxolitinib, tofacitinib (formerly tasocitinib), INCB052793, and XL019.

Matrix Metalloprotease (MMP) Inhibitors

In some embodiments, a compound as described herein, is combined with an inhibitor of a matrix metallopeptidase (MMP), e.g., an inhibitor of MMP1 (NCBI Gene ID: 4312), MMP2 (NCBI Gene ID: 4313), MMP3 (NCBI Gene ID: 4314), MMP7 (NCBI Gene ID: 4316), MMP8 (NCBI Gene ID: 4317), MMP9 (NCBI Gene ID: 4318); MMP10 (NCBI Gene ID: 4319); MMP11 (NCBI Gene ID: 4320); MMP12 (NCBI Gene ID: 4321), MMP13 (NCBI Gene ID: 4322), MMP14 (NCBI Gene ID: 4323), MMP15 (NCBI Gene ID: 4324), MMP16 (NCBI Gene ID: 4325), MMP17 (NCBI Gene ID: 4326), MMP19 (NCBI Gene ID: 4327), MMP20 (NCBI Gene ID: 9313), MMP21 (NCBI Gene ID: 118856), MMP24 (NCBI Gene ID: 10893), MMP25 (NCBI Gene ID: 64386), MMP26 (NCBI Gene ID: 56547), MMP27 (NCBI Gene ID: 64066) and/or MMP28 (NCBI Gene ID: 79148). Examples of MMP9 inhibitors include without limitation, marimastat (BB-2516), cipemastat (Ro 32-3555), GS-5745 (andecaliximab) and those described in WO 2012/027721 (Gilead Biologics).

RAS and RAS Pathway Inhibitors

In some embodiments, a compound as described herein, is combined with an inhibitor of KRAS proto-oncogene, GTPase (KRAS; a.k.a., NS; NS3; CFC2; RALD; K-Ras; KRAS1; KRAS2; RASK2; KI-RAS; C-K-RAS; K-RAS2A; K-RAS2B; K-RAS4A; K-RAS4B; c-Ki-ras2; NCBI Gene ID: 3845); NRAS proto-oncogene, GTPase (NRAS; a.k.a., NS6; CMNS; NCMS; ALPS4; N-ras; NRAS1; NCBI Gene ID: 4893); HRas proto-oncogene, GTPase (HRAS; a.k.a., CTLO; KRAS; HAMSV; HRAS1; KRAS2; RASH1; RASK2; Ki-Ras; p21ras; C-H-RAS; c-K-ras; H-RASIDX; c-Ki-ras; C-BAS/HAS; C-HA-RAS1; NCBI Gene ID: 3265). The Ras inhibitors can inhibit Ras at either the polynucleotide (e.g., transcriptional inhibitor) or polypeptide (e.g., GTPase enzyme inhibitor) level. In some embodiments, the inhibitors target one or more proteins in the Ras pathway, e.g., inhibit one or more of EGFR, Ras, Raf (A-Raf, B-Raf, C-Raf), MEK (MEK1, MEK2), ERK, PI3K, AKT and mTOR.

In some embodiments, a compound as described herein, is combined with an inhibitor of KRAS. Examples of KRAS inhibitors include AMG-510, COTI-219, MRTX-1257, ARS-3248, ARS-853, WDB-178, BI-3406, BI-1701963, ARS-1620 (G12C), SML-8-73-1 (G12C), Compound 3144 (G12D), Kobe0065/2602 (Ras GTP), RT11, MRTX-849 (G12C) and K-Ras(G12D)-selective inhibitory peptides, including KRpep-2 (Ac-RRCPLYISYDPVCRR-NH$_2$) (SEQ ID NO:108) and KRpep-2d (Ac-RRRRCPLYI-SYDPVCRRRR-NH$_2$) (SEQ ID NO:109).

In some embodiments, a compound as described herein, is combined with an inhibitor of KRAS mRNA. Illustrative KRAS mRNA inhibitors include anti-KRAS U1 adaptor, AZD-4785, siG12D-LODER™, and siG12D exosomes.

In some embodiments, a compound as described herein, is combined with an inhibitor of MEK. Illustrative MEK inhibitors that can be co-administered include binimetinib, cobimetinib, PD-0325901, pimasertib, RG-7304, selumetinib, trametinib, selumetinib.

In some embodiments, a compound as described herein, is combined with an inhibitor of AKT. Illustrative AKT inhibitors that can be co-administered include RG7440, MK-2206, ipatasertib, afuresertib, AZD5363, and ARQ-092, capivasertib, triciribine, ABTL-0812 (PI3K/Akt/mTOR).

In some embodiments, a compound as described herein, is combined with an inhibitor of Raf Illustrative Raf inhibitors that can be co-administered BGB-283 (Raf/EGFR), HM-95573, LXH-254, LY-3009120, RG7304, TAK-580, dabrafenib, vemurafenib, encorafenib (LGX818), PLX8394. RAF-265 (Raf/VEGFR), ASN-003 (Raf/PI3K).

In some embodiments, a compound as described herein, is combined with an inhibitor of ERK. Illustrative ERK inhibitors that can be co-administered include LTT-462, LY-3214996, MK-8353, ravoxertinib, GDC-0994, and ulixertinib.

In some embodiments, a compound as described herein, is combined with an inhibitor of PI3K. Illustrative PI3K inhibitors that can be co-administered include idelalisib (Zydelig®), alpelisib, buparlisib, pictilisib. Illustrative PI3K/mTOR inhibitors that can be co-administered include dactolisib, omipalisib, voxtalisib, gedatolisib, GSK2141795, RG6114.

In some embodiments, a compound as described herein, is combined with an inhibitor of mTOR. Illustrative mTOR inhibitors that can be co-administered include as sapanisertib, vistusertib (AZD2014), ME-344, sirolimus (oral nano-amorphous formulation, cancer), TYMIE-88 (mTOR/cytochrome P450 3A4).

In some embodiments, Ras-driven cancers (e.g., NSCLC) having CDKN2A mutations can be inhibited by co-administration of the MEK inhibitor selumetinib and the CDK4/6 inhibitor palbociclib. See, e.g., Zhou, et al., *Cancer Lett.* 2017 Nov. 1; 408:130-137. Also, K-RAS and mutant N-RAS can be reduced by the irreversible ERBB1/2/4 inhibitor neratinib. See, e.g., Booth, et al., *Cancer Biol Ther.* 2018 Feb. 1; 19(2):132-137.

In some embodiments, a compound as described herein, is combined with an inhibitor of RAS. Examples of RAS inhibitors include NEO-100, rigosertib.

In some embodiments, a compound as described herein, is combined with an antagonist of EGFR, such as AMG-595, necitumumab, ABBV-221, depatuxizumab mafodotin (ABT-414), tomuzotuximab, ABT-806, vectibix, modotuximab, RM-1929.

In some embodiments, a compound as described herein, is combined with an inhibitor of protein tyrosine phosphatase non-receptor type 11 (PTPN11; BPTP3, CFC, JMML, METCDS, NS1, PTP-1D, PTP2C, SH-PTP2, SH-PTP3, SHP2; NCBI Gene ID: 5781). Examples of SHP2 inhibitors include TNO155 (SHP-099), RMC-4550, JAB-3068, RMC-4630, SAR442720 and those described in WO2018172984 and WO2017211303.

In some embodiments, a compound as described herein, is combined with an inhibitor of mitogen-activated protein kinase 7 (MAP2K7, JNKK2, MAPKK7, MEK, MEK 7, MKK7, PRKMK7, SAPKK-4, SAPKK4; NCBI Gene ID: 5609). Examples of MEK inhibitors include antroquinonol, binimetinib, CK-127, cobimetinib (GDC-0973, XL-518), MT-144, selumetinib (AZD6244), sorafenib, trametinib (GSK1120212), uprosertib+trametinib, PD-0325901, pimasertib, LTT462, AS703988, CC-90003, refametinib, TAK-733, CI-1040, RG7421.

Phosphatidylinositol 3-Kinase (PI3K) Inhibitors

In some embodiments, a compound as described herein, is combined with an inhibitor of a phosphatidylinositol-4,5-bisphosphate 3-kinase catalytic subunit, e.g., phosphatidylinositol-4,5-bisphosphate 3-kinase catalytic subunit alpha (PIK3CA, CLAPO, CLOVE, CWS5, MCAP, MCM, MCMTC, PI3K, PI3K-alpha, p110-alpha; NCBI Gene ID: 5290); phosphatidylinositol-4,5-bisphosphate 3-kinase catalytic subunit beta (PIK3CB, P110BETA, PI3K, PI3KBETA, PIK3C1; NCBI Gene ID: 5291); phosphatidylinositol-4,5-bisphosphate 3-kinase catalytic subunit gamma (PIK3CG, PI3CG, PI3K, PI3Kgamma, PIK3, p110gamma, p120-PI3K; Gene ID: 5494); and/or phosphatidylinositol-4,5-bisphosphate 3-kinase catalytic subunit delta (PIK3CD, APDS, IMD14, P110DELTA, PI3K, p110D, NCBI Gene ID: 5293). In some embodiments, the PI3K inhibitor is a pan-PI3K inhibitor. Examples of PI3K inhibitors include without limitation, ACP-319, AEZA-129, AMG-319, AS252424, AZD8186, BAY 10824391, BEZ235, buparlisib (BKM120), BYL719 (alpelisib), CH5132799, copanlisib (BAY 80-6946), duvelisib, GDC-0032, GDC-0077, GDC-0941, GDC-0980, GSK2636771, GSK2269557, idelalisib (Zydelig®), INCB50465, IPI-145, IPI-443, IPI-549, KAR4141, LY294002, LY3023414, MLN1117, OXY111A, PA799, PX-866, RG7604, rigosertib, RP5090, RP6530, SRX3177, taselisib, TG100115, TGR-1202 (umbralisib), TGX221, WX-037, X-339, X-414, XL147 (SAR245408), XL499, XL756, wortmannin, ZSTK474, and the compounds described in WO 2005/113556 (ICOS), WO 2013/052699 (Gilead Calistoga), WO 2013/116562 (Gilead Calistoga), WO 2014/100765 (Gilead Calistoga), WO 2014/100767 (Gilead Calistoga), and WO 2014/201409 (Gilead Sciences).

Mitogen-Activated Protein Kinase (MEK) Inhibitors

In some embodiments, a compound as described herein, is combined with an inhibitor of mitogen-activated protein kinase kinase 7 (MAP2K7, JNKK2, MAPKK7, MEK, MEK 7, MKK7, PRKMK7, SAPKK-4, SAPKK4; NCBI Gene ID: 5609). Examples of MEK inhibitors include antroquinonol, binimetinib, cobimetinib (GDC-0973, XL-518), MT-144, selumetinib (AZD6244), sorafenib, trametinib (GSK1120212), uprosertib+trametinib, PD-0325901, pimasertib, LTT462, AS703988, CC-90003, refametinib.

Spleen Tyrosine Kinase (SYK) Inhibitors

In some embodiments, a compound as described herein, is combined with an inhibitor of spleen associated tyrosine kinase (SYK, p72-Syk, Gene ID: 6850). Examples of SYK inhibitors include without limitation, 6-(1H-indazol-6-yl)-N-(4-morpholinophenyl)imidazo[1,2-a]pyrazin-8-amine, BAY-61-3606, cerdulatinib (PRT-062607), entospletinib, fostamatinib (R788), HMPL-523, NVP-QAB 205 AA, R112, R343, tamatinib (R406), and those described in U.S. Pat. No. 8,450,321 (Gilead Connecticut) and those described in U.S. 2015/0175616.

Toll-Like Receptor (TLR) Agonists

In some embodiments, a compound as described herein, is combined with an agonist of a toll-like receptor (TLR), e.g., an agonist of TLR1 (NCBI Gene ID: 7096), TLR2 (NCBI Gene ID: 7097), TLR3 (NCBI Gene ID: 7098), TLR4 (NCBI Gene ID: 7099), TLR5 (NCBI Gene ID: 7100), TLR6 (NCBI Gene ID: 10333), TLR7 (NCBI Gene ID: 51284), TLR8 (NCBI Gene ID: 51311), TLR9 (NCBI Gene ID: 54106), and/or TLR10 (NCBI Gene ID: 81793). Example TLR7 agonists that can be co-administered include without limitation DS-0509, GS-9620, LHC-165, TMX-101 (imiquimod), GSK-2245035, resiquimod, DSR-6434, DSP-3025, IMO-4200, MCT-465, MEDI-9197, 3M-051, SB-9922, 3M-052, Limtop, TMX-30X, TMX-202, RG-7863, RG-7795, and the compounds disclosed in US20100143301 (Gilead Sciences), US20110098248 (Gilead Sciences), and US20090047249 (Gilead Sciences), US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), and US20130251673 (Novira Therapeutics). An TLR7/TLR8 agonist that can be co-administered is NKTR-262. Example TLR8 agonists that can be co-administered include without limitation E-6887, IMO-4200, IMO-8400, IMO-9200, MCT-465, MEDI-9197, motolimod, resiquimod, GS-9688, VTX-1463, VTX-763, 3M-051, 3M-052, and the compounds disclosed in US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), and US20130251673 (Novira Therapeutics). Example TLR9 agonists that can be co-administered include without limitation AST-008, CMP-001, IMO-2055, IMO-2125, litenimod, MGN-1601, BB-001, BB-006, IMO-3100, IMO-8400, IR-103, IMO-9200, agatolimod, DIMS-9054, DV-1079, DV-1179, AZD-1419, leftolimod (MGN-1703), CYT-003, CYT-003-QbG10 and PUL-042. Examples of TLR3 agonist include rintatolimod, poly-ICLC, RIBOXXON®, Apoxxim, RIBOXXIM®, IPH-33, MCT-465, MCT-475, and ND-1.1.

Examples of TLR8 inhibitors include, but are not limited to, E-6887, IMO-8400, IMO-9200 and VTX-763.

Examples of TLR8 agonists include, but are not limited to, MCT-465, motolimod, GS-9688, and VTX-1463.

Examples of TLR9 inhibitors include but are not limited to, AST-008, IMO-2055, IMO-2125, lefitolimod, litenimod, MGN-1601, and PUL-042.

Examples of TLR7/TLR8 agonist, such as NKTR-262, IMO-4200, MEDI-9197 (telratolimod), resiquimod.

Examples of TLR agonists include without limitation: lefitolimod, tilsotolimod, rintatolimod, DSP-0509, AL-034, G-100, cobitolimod, AST-008, motolimod, GSK-1795091, GSK-2245035, VTX-1463, GS-9688, LHC-165, BDB-001, RG-7854, telratolimod.

In some embodiments, the therapeutic agent is a stimulator of interferon genes (STING) In some embodiments, the STING receptor agonist or activator is selected from the group consisting of ADU-S100 (MIW-815), SB-11285, MK-1454, SR-8291, AdVCA0848, GSK-532, SYN-STING, MSA-1, SR-8291, 5,6-dimethylxanthenone-4-acetic acid (DMXAA), cyclic-GAMP (cGAMP) and cyclic-di-AMP.

Indoleamine-Pyrrole-2,3-Dioxygenase (IDO1) Inhibitors

In some embodiments, a compound as described herein, is combined with an inhibitor of indoleamine 2,3-dioxygenase 1 (IDO1; NCBI Gene ID: 3620). Examples of IDO1 inhibitors include without limitation, BLV-0801, epacadostat, F-001287, GBV-1012, GBV-1028, GDC-0919, indoximod, NKTR-218, NLG-919-based vaccine, PF-06840003, pyranonaphthoquinone derivatives (SN-35837), resminostat, SBLK-200802, BMS-986205, and shIDO-ST, EOS-200271, KHK-2455, LY-3381916.

In some embodiments, the therapeutic agent is a small organic compound. In some embodiments, the therapeutic agent is an agonist or activator of a toll-like receptor (TLR) or a stimulator of interferon genes (STING) In some embodiments, the STING receptor agonist or activator is selected from the group consisting of ADU-S100 (MIW-815), SB-11285, MK-1454, SR-8291, AdVCA0848, GSK-532, SYN-STING, MSA-1, SR-8291, 5,6-dimethylxanthenone-4-acetic acid (DMXAA), cyclic-GAMP (cGAMP) and cyclic-di-AMP.

Tyrosine-Kinase Inhibitors (TKIs)

In some embodiments, a compound as described herein, is combined with a tyrosine kinase inhibitor (TKI). TKIs may target epidermal growth factor receptors (EGFRs) and receptors for fibroblast growth factor (FGF), platelet-derived growth factor (PDGF), and vascular endothelial growth factor (VEGF). Examples of TKIs include without limitation, axitinib, afatinib, ARQ-087 (derazantinib), asp5878, AZD3759, AZD4547, bosutinib, brigatinib, cabozantinib, cediranib, crenolanib, dacomitinib, dasatinib, dovitinib, E-6201, erdafitinib, erlotinib, gefitinib, gilteritinib (ASP-2215), FP-1039, HM61713, icotinib, imatinib, KX2-391 (Src), lapatinib, lestaurtinib, lenvatinib, midostaurin, nintedanib, ODM-203, olmutinib, osimertinib (AZD-9291), pazopanib, ponatinib, poziotinib, quizartinib, radotinib, rociletinib, sulfatinib (HMPL-012), sunitinib, famitinib L-malate, (MAC-4), tivoanib, TH-4000, tivoanib, and MEDI-575 (anti-PDGFR antibody), TAK-659, Cabozantinib.

Chemotherapeutic Agents (Standard of Care)

In some embodiments, a compound as described herein, is combined with a chemotherapeutic agent or anti-neoplastic agent.

As used herein, the term "chemotherapeutic agent" or "chemotherapeutic" (or "chemotherapy" in the case of treatment with a chemotherapeutic agent) is meant to encompass any non-proteinaceous (e.g., non-peptidic) chemical compound useful in the treatment of cancer. Examples of chemotherapeutic agents include but not limited to: alkylating agents such as thiotepa and cyclophosphamide (CYTOXAN®); alkyl sulfonates such as busulfan, improsulfan, and piposulfan; aziridines such as benzodepa, carboquone, meturedepa, and uredepa; ethylenimines and methylamelamines including altretamine, triethylenemelamine, triethylenephosphoramide, triethylenethiophosphoramide, and trimemylolomelamine; acetogenins, e.g., bullatacin and bullatacinone; a camptothecin, including synthetic analog topotecan; bryostatin, callystatin; CC-1065, including its adozelesin, carzelesin, and bizelesin synthetic analogs; cryptophycins, particularly cryptophycin 1 and cryptophycin 8; dolastatin; duocarmycin, including the synthetic analogs KW-2189 and CBI-TMI; eleutherobin; 5-azacytidine; pancratistatin; a sarcodictyin; spongistatin; nitrogen mustards such as chlorambucil, chlornaphazine, cyclophosphamide, glufosfamide, evofosfamide, bendamustine, estramustine, ifosfamide, mechlorethamine, mechlorethamine oxide hydrochloride, melphalan, novembichin, phenesterine, prednimustine, trofosfamide, and uracil mustard; nitrosoureas such as carmustine, chlorozotocin, foremustine, lomustine, nimustine, and ranimustine; antibiotics such as the enediyne antibiotics (e.g., calicheamicin, especially calicheamicin gammaII and calicheamicin phiI1), dynemicin including dynemicin A, bisphosphonates such as clodronate, an esperamicin, neocarzinostatin chromophore and related chromoprotein enediyne antibiotic chromomophores, aclacinomycins, actinomycin, authramycin, azaserine, bleomycins, cactinomycin, carabicin, carrninomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin, and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, and zorubicin; anti-metabolites such as methotrexate and 5-fluorouracil (5-FU); folic acid analogs such as demopterin, methotrexate, pteropterin, and trimetrexate; purine analogs such as cladribine, pentostatin, fludarabine, 6-mercaptopurine, thiamiprine, and thioguanine; pyrimidine analogs such as ancitabine, azacitidine, 6-azauridine, carmofur, cytarabine, dideoxyuridine, doxifluridine, enocitabine, and floxuridine; androgens such as calusterone, dromostanolone propionate, epitiostanol, mepitiostane, and testolactone; anti-adrenals such as aminoglutethimide, mitotane, and trilostane; folic acid replinishers such as frolinic acid; radiotherapeutic agents such as Radium-223; trichothecenes, especially T-2 toxin, verracurin A, roridin A, and anguidine; taxoids such as paclitaxel (TAXOL®), abraxane, docetaxel (TAXOTERE®), cabazitaxel, BIND-014, tesetaxel; platinum analogs such as cisplatin and carboplatin, NC-6004 nanoplatin; aceglatone; aldophosphamide glycoside; aminolevulinic acid; eniluracil; amsacrine; hestrabucil; bisantrene; edatraxate; defofamine; demecolcine; diaziquone; elformthine; elliptinium acetate; an epothilone; etoglucid; gallium nitrate; hydroxyurea; lentinan; leucovorin; lonidamine; maytansinoids such as maytansine and ansamitocins; mitoguazone; mitoxantrone; mopidamol; nitracrine; pentostatin; phenamet; pirarubicin; losoxantrone; fluoropyrimidine; folinic acid; podophyllinic acid; 2-ethylhydrazide; procarbazine; polysaccharide-K (PSK); razoxane; rhizoxin; sizofiran; spirogermanium; tenuazonic acid; trabectedin, triaziquone; 2,2',2"-trichlorotriemylamine; urethane; vindesine; dacarbazine; mannomustine; mitobronitol; mitolactol; pipobroman; gacytosine; arabinoside ("Ara-C"); cyclophosphamide; thiopeta; chlorambucil; gemcitabine (GEMZAR®); 6-thioguanine; mercaptopurine; methotrexate; vinblastine; platinum; etoposide (VP-16); ifosfamide; mitroxantrone; vancristine; vinorelbine (NAVELBINE®); novantrone; teniposide; edatrexate; daunomycin; aminopterin; xeoloda; ibandronate; CPT-11; topoisomerase inhibitor RFS 2000; difluoromethylornithine (DFMO); retinoids such as retinoic acid; capecitabine; NUC-1031; FOLFOX (folinic acid, 5-fluorouracil, oxaliplatin); FOLFIRI (folinic acid, 5-fluorouracil, irinotecan); FOLFOXIRI (folinic acid, 5-fluorouracil, oxaliplatin, irinotecan), FOLFIRINOX (folinic acid, 5-fluorouracil, irinotecan, oxaliplatin), and pharmaceutically acceptable salts, acids, or derivatives of any of the above. Such agents can be conjugated onto an antibody or any targeting agent described herein to create an antibody-drug conjugate (ADC) or targeted drug conjugate.

Anti-Hormonal Agents

Also included in the definition of "chemotherapeutic agent" are anti-hormonal agents such as anti-estrogens and selective estrogen receptor modulators (SERMs), inhibitors of the enzyme aromatase, anti-androgens, and pharmaceutically acceptable salts, acids or derivatives of any of the above that act to regulate or inhibit hormone action on tumors.

Examples of anti-estrogens and SERMs include, for example, tamoxifen (including NOLVADEX™), raloxifene, droloxifene, 4-hydroxytamoxifen, trioxifene, keoxifene, LY117018, onapristone, and toremifene (FARESTON®).

Inhibitors of the enzyme aromatase regulate estrogen production in the adrenal glands. Examples include 4(5)-imidazoles, aminoglutethimide, megestrol acetate (MEGACE®), exemestane, formestane, fadrozole, vorozole (RIVISOR®), letrozole (FEMARA®), and anastrozole (ARIMIDEX®).

Examples of anti-androgens include apalutamide, abiraterone, enzalutamide, flutamide, galeterone, nilutamide, bicalutamide, leuprolide, goserelin, ODM-201, APC-100, ODM-204.

An example progesterone receptor antagonist includes onapristone.

Anti-Angiogenic Agents

In some embodiments, a compound as described herein, is combined with an anti-angiogenic agent. Anti-angiogenic agents that can be co-administered include, but are not limited to, retinoid acid and derivatives thereof, 2-methoxyestradiol, ANGIOSTATIN®, ENDOSTATIN®, regorafenib, necuparanib, suramin, squalamine, tissue inhibitor of metalloproteinase-1, tissue inhibitor of metalloproteinase-2, plasminogen activator inhibitor-1, plasminogen activator inbibitor-2, cartilage-derived inhibitor, paclitaxel (nab-paclitaxel), platelet factor 4, protamine sulphate (clupeine), sulphated chitin derivatives (prepared from queen crab shells), sulphated polysaccharide peptidoglycan complex (sp-pg), staurosporine, modulators of matrix metabolism including proline analogs such as 1-azetidine-2-carboxylic acid (LACA), cishydroxyproline, d,I-3,4-dehydroproline, thiaproline, α,α'-dipyridyl, beta-aminopropionitrile fumarate, 4-propyl-5-(4-pyridinyl)-2(3h)-oxazolone, methotrexate, mitoxantrone, heparin, interferons, 2 macroglobulin-serum, chicken inhibitor of metalloproteinase-3 (ChTIP-3), chymostatin, beta-cyclodextrin tetradecasulfate, eponemycin, fumagillin, gold sodium thiomalate, d-penicillamine, beta-1-anticollagenase-serum, alpha-2-antiplasmin, bisantrene, lobenzarit disodium, n-2-carboxyphenyl-4-chloroanthronilic acid disodium or "CCA", thalidomide, angiostatic steroid, carboxy aminoimidazole, metalloproteinase inhibitors such as BB-94, inhibitors of S100A9 such as tasquinimod. Other antiangiogenesis agents include antibodies, e.g., monoclonal antibodies against these angiogenic growth factors: beta-FGF, alpha-FGF, FGF-5, VEGF isoforms, VEGF-C, HGF/SF, and Ang-1/Ang-2.

Anti-Fibrotic Agents

In some embodiments, a compound as described herein, is combined with an anti-fibrotic agent. Anti-fibrotic agents that can be co-administered include, but are not limited to, the compounds such as beta-aminoproprionitrile (BAPN), as well as the compounds disclosed in U.S. Pat. No. 4,965,288 relating to inhibitors of lysyl oxidase and their use in the treatment of diseases and conditions associated with the abnormal deposition of collagen and U.S. Pat. No. 4,997,854 relating to compounds which inhibit LOX for the treatment of various pathological fibrotic states, which are herein incorporated by reference. Further exemplary inhibitors are described in U.S. Pat. No. 4,943,593 relating to compounds such as 2-isobutyl-3-fluoro-, chloro-, or bromo-allylamine, U.S. Pat. Nos. 5,021,456, 5,059,714, 5,120,764, 5,182,297, 5,252,608 relating to 2-(1-naphthyloxymemyl)-3-fluoroallylamine, and US 2004-0248871, which are herein incorporated by reference.

Exemplary anti-fibrotic agents also include the primary amines reacting with the carbonyl group of the active site of the lysyl oxidases, and more particularly those which produce, after binding with the carbonyl, a product stabilized by resonance, such as the following primary amines: emylenemamine, hydrazine, phenylhydrazine, and their derivatives; semicarbazide and urea derivatives; aminonitriles such as BAPN or 2-nitroethylamine; unsaturated or saturated haloamines such as 2-bromo-ethylamine, 2-chloroethylamine, 2-trifluoroethylamine, 3-bromopropylamine, and p-halobenzylamines; and selenohomocysteine lactone.

Other anti-fibrotic agents are copper chelating agents penetrating or not penetrating the cells. Exemplary compounds include indirect inhibitors which block the aldehyde derivatives originating from the oxidative deamination of the lysyl and hydroxylysyl residues by the lysyl oxidases. Examples include the thiolamines, particularly D-penicillamine, and its analogs such as 2-amino-5-mercapto-5-methylhexanoic acid, D-2-amino-3-methyl-3-((2-acetamidoethyl)dithio)butanoic acid, p-2-amino-3-methyl-3-((2-aminoethyl)dithio)butanoic acid, sodium-4-((p-1-dimethyl-2-amino-2-carboxyethyl)dithio)butane sulphurate, 2-acetamidoethyl-2-acetamidoethanethiol sulphanate, and sodium-4-mercaptobutanesulphinate trihydrate.

Anti-Inflammatory Agents

In some embodiments, a compound as described herein, is combined with an anti-inflammatory agent. Example anti-inflammatory agents include without limitation inhibitors of one or more of arginase (ARG1 (NCBI Gene ID: 383), ARG2 (NCBI Gene ID: 384)), carbonic anhydrase (CA1 (NCBI Gene ID: 759), CA2 (NCBI Gene ID: 760), CA3 (NCBI Gene ID: 761), CA4 (NCBI Gene ID: 762), CA5A (NCBI Gene ID: 763), CA5B (NCBI Gene ID: 11238), CA6 (NCBI Gene ID: 765), CA7 (NCBI Gene ID: 766), CA8 (NCBI Gene ID: 767), CA9 (NCBI Gene ID: 768), CA10 (NCBI Gene ID: 56934), CA11 (NCBI Gene ID: 770), CA12 (NCBI Gene ID: 771), CA13 (NCBI Gene ID: 377677), CA14 (NCBI Gene ID: 23632)), prostaglandin-endoperoxide synthase 1 (PTGS1, COX-1; NCBI Gene ID: 5742), prostaglandin-endoperoxide synthase 2 (PTGS2, COX-2; NCBI Gene ID: 5743), secreted phospholipase A2, prostaglandin E synthase (PTGES, PGES; Gene ID: 9536), arachidonate 5-lipoxygenase (ALOX5, 5-LOX; NCBI Gene ID: 240), soluble epoxide hydrolase 2 (EPHX2, SEH; NCBI Gene ID: 2053) and/or mitogen-activated protein kinase kinase kinase 8 (MAP3K8, TPL2; NCBI Gene ID: 1326). In some embodiments, the inhibitor is a dual inhibitor, e.g., a dual inhibitor of COX-2/COX-1, COX-2/SEH, COX-2/CA, COX-2/5-LOX.

Examples of inhibitors of prostaglandin-endoperoxide synthase 1 (PTGS1, COX-1; NCBI Gene ID: 5742) that can be co-administered include without limitation mofezolac, GLY-230, and TRK-700.

Examples of inhibitors of prostaglandin-endoperoxide synthase 2 (PTGS2, COX-2; NCBI Gene ID: 5743) that can be co-administered include without limitation diclofenac, meloxicam, parecoxib, etoricoxib, AP-101, celecoxib, AXS-06, diclofenac potassium, DRGT-46, AAT-076, meisuoshuli, lumiracoxib, meloxicam, valdecoxib, zaltoprofen, nimesulide, Anitrazafen, Apricoxib, Cimicoxib, Deracoxib, Flumizole, Firocoxib, Mavacoxib, NS-398, Pamicogrel, Parecoxib, Robenacoxib, Rofecoxib, Rutecarpine, Tilmacoxib, and Zaltoprofen. Examples of dual COX1/COX2 inhibitors that can be co-administered include without limitation, HP-5000, lornoxicam, ketorolac tromethamine, bromfenac sodium, ATB-346, HP-5000. Examples of dual COX-2/carbonic anhydrase (CA) inhibitors that can be co-administered include without limitation polmacoxib and imrecoxib.

Examples of inhibitors of secreted phospholipase A2, prostaglandin E synthase (PTGES, PGES; Gene ID: 9536) that can be co-administered include without limitation LY3023703, GRC 27864, and compounds described in WO2015158204, WO2013024898, WO2006063466, WO2007059610, WO2007124589, WO2010100249, WO2010034796, WO2010034797, WO2012022793, WO2012076673, WO2012076672, WO2010034798, WO2010034799, WO2012022792, WO2009103778, WO2011048004, WO2012087771, WO2012161965, WO2013118071, WO2013072825, WO2014167444, WO2009138376, WO2011023812, WO2012110860, WO2013153535, WO2009130242, WO2009146696, WO2013186692, WO2015059618, WO2016069376, WO2016069374, WO2009117985, WO2009064250, WO2009064251, WO2009082347, WO2009117987, and WO2008071173. Metformin has further been found to repress the COX2/PGE2/STAT3 axis, and can be co-administered. See, e.g., Tong, et al., *Cancer Lett.* (2017) 389:23-32; and Liu, et al., *Oncotarget.* (2016) 7(19):28235-46.

Examples of inhibitors of carbonic anhydrase (e.g., one or more of CA1 (NCBI Gene ID: 759), CA2 (NCBI Gene ID: 760), CA3 (NCBI Gene ID: 761), CA4 (NCBI Gene ID: 762), CA5A (NCBI Gene ID: 763), CA5B (NCBI Gene ID:

11238), CA6 (NCBI Gene ID: 765), CA7 (NCBI Gene ID: 766), CA8 (NCBI Gene ID: 767), CA9 (NCBI Gene ID: 768), CA10 (NCBI Gene ID: 56934), CA11 (NCBI Gene ID: 770), CA12 (NCBI Gene ID: 771), CA13 (NCBI Gene ID: 377677), CA14 (NCBI Gene ID: 23632)) that can be co-administered include without limitation acetazolamide, methazolamide, dorzolamide, zonisamide, brinzolamide and dichlorphenamide. A dual COX-2/CA1/CA2 inhibitor that can be co-administered includes CG100649.

Examples of inhibitors of arachidonate 5-lipoxygenase (ALOX5, 5-LOX; NCBI Gene ID: 240) that can be co-administered include without limitation meclofenamate sodium, zileuton.

Examples of inhibitors of soluble epoxide hydrolase 2 (EPHX2, SEH; NCBI Gene ID: 2053) that can be co-administered include without limitation compounds described in WO2015148954. Dual inhibitors of COX-2/SEH that can be co-administered include compounds described in WO2012082647. Dual inhibitors of SEH and fatty acid amide hydrolase (FAAH; NCBI Gene ID: 2166) that can be co-administered include compounds described in WO2017160861.

Examples of inhibitors of mitogen-activated protein kinase kinase kinase 8 (MAP3K8, tumor progression loci-2, TPL2; NCBI Gene ID: 1326) that can be co-administered include without limitation GS-4875, GS-5290, BHM-078 and those described, e.g., in WO2006124944, WO2006124692, WO2014064215, WO2018005435, Teli, et al., *J Enzyme Inhib Med Chem*. (2012) 27(4):558-70; Gangwall, et al., *Curr Top Med Chem*. (2013) 13(9):1015-35; Wu, et al., *Bioorg Med Chem Lett*. (2009) 19(13):3485-8; Kaila, et al., *Bioorg Med Chem*. (2007) 15(19):6425-42; and Hu, et al., *Bioorg Med Chem Lett*. (2011) 21(16):4758-61.

Tumor Oxygenation Agents

In some embodiments, a compound as described herein, is combined with an agent that promotes or increases tumor oxygenation or reoxygenation, or prevents or reduces tumor hypoxia. Illustrative agents that can be co-administered include, e.g., Hypoxia inducible factor-1 alpha (HIF-1α) inhibitors, such as PT-2977, PT-2385; VEGF inhibitors, such as bevasizumab, IMC-3C5, GNR-011, tanibirumab, LYN-00101, ABT-165; and/or an oxygen carrier protein (e.g., a heme nitric oxide and/or oxygen binding protein (HNOX)), such as OMX-302 and HNOX proteins described in WO 2007/137767, WO 2007/139791, WO 2014/107171, and WO 2016/149562.

Immunotherapeutic Agents

In some embodiments, a compound as described herein, is combined with an immunotherapeutic agent. Example immunotherapeutic agents that can be co-administered include without limitation abagovomab, ABP-980, adecatumumab, afutuzumab, alemtuzumab, altumomab, amatuximab, anatumomab, arcitumomab, bavituximab, bectumomab, bevacizumab, bivatuzumab, blinatumomab, brentuximab, cantuzumab, catumaxomab, CC49, cetuximab, citatuzumab, cixutumumab, clivatuzumab, conatumumab, dacetuzumab, dalotuzumab, daratumumab, detumomab, dinutuximab, drozitumab, duligotumab, dusigitumab, ecromeximab, elotuzumab, emibetuzumab, ensituximab, ertumaxomab, etaracizumab, farletuzumab, ficlatuzumab, figitumumab, flanvotumab, futuximab, ganitumab, gemtuzumab, girentuximab, glembatumumab, ibritumomab, igovomab, imgatuzumab, indatuximab, inotuzumab, intetumumab, ipilimumab (YERVOY®, MDX-010, BMS-734016, and MDX-101), iratumumab, labetuzumab, lexatumumab, lintuzumab, lorvotuzumab, lucatumumab, mapatumumab, matuzumab, milatuzumab, minretumomab, mitumomab, mogamulizumab, moxetumomab, naptumomab, narnatumab, necitumumab, nimotuzumab, nofetumomab, OBI-833, obinutuzumab, ocaratuzumab, ofatumumab, olaratumab, onartuzumab, oportuzumab, oregovomab, panitumumab, parsatuzumab, pasudotox, patritumab, pemtumomab, pertuzumab, pintumomab, pritumumab, racotumomab, radretumab, ramucirumab (Cyramza®), rilotumumab, rituximab, robatumumab, samalizumab, satumomab, sibrotuzumab, siltuximab, solitomab, simtuzumab, tacatuzumab, taplitumomab, tenatumomab, teprotumumab, tigatuzumab, tositumomab, trastuzumab, tucotuzumab, ubilituximab, veltuzumab, vorsetuzumab, votumumab, zalutumumab, and 3F8. Rituximab can be used for treating indolent B-cell cancers, including marginal-zone lymphoma, WM, CLL and small lymphocytic lymphoma. A combination of Rituximab and chemotherapy agents is especially effective.

The exemplified therapeutic antibodies may be further labeled or combined with a radioisotope particle such as indium-111, yttrium-90 (90Y-clivatuzumab), or iodine-131.

In some embodiments, the immunotherapeutic agent is an antibody-drug conjugate (ADC). Illustrative ADCs that can be co-administered include without limitation drug-conjugated antibodies, fragments thereof, or antibody mimetics targeting the proteins or antigens listed above and herein. Example ADCs that can be co-administered include without limitation gemtuzumab, brentuximab, trastuzumab, inotuzumab, glembatumumab, anetumab, mirvetuximab, depatuxizumab, rovalpituzumab, vadastuximab, labetuzumab, sacituzumab, lifastuzumab, indusatumab, polatzumab, pinatuzumab, coltuximab, indatuximab, milatuzumab, rovalpituzumab, ABBV-399, AGS-16C3F, ASG-22ME, AGS67E, AMG172, AMG575, BAY1129980, BAY1187982, BAY94-9343, GSK2857916, Humax-TF-ADC, IMGN289, IMGN529, IMGN853, LOP628, PCA062, MDX-1203 (BMS936561), MEDI-547, PF-06263507, PF-06647020, PF-06647263, PF-06664178, RG7450, RG7458, RG7598, SAR566658, SGN-CD19A, SGN-CD33A, SGN-CD70A, SGN-LIV1A and SYD985. ADCs that can be co-administered are described, e.g., in Lambert, et al., *Adv Ther* (2017) 34:1015-1035 and in de Goeij, *Current Opinion in Immunology* (2016) 40:14-23.

Illustrative therapeutic agents (e.g., anticancer or antineoplastic agents) that can be conjugated to the drug-conjugated antibodies, fragments thereof, or antibody mimetics include without limitation monomethyl auristatin E (MMAE), monomethyl auristatin F (MMAF), a calicheamicin, ansamitocin, maytansine or an analog thereof (e.g., mertansine/emtansine (DM1), ravtansine/soravtansine (DM4)), an anthracyline (e.g., doxorubicin, daunorubicin, epirubicin, idarubicin), pyrrolobenzodiazepine (PBD) DNA cross-linking agent SC-DR002 (D6.5), duocarmycin, a microtubule inhibitors (MTI) (e.g., a taxane, a vinca alkaloid, an epothilone), a pyrrolobenzodiazepine (PBD) or dimer thereof, a duocarmycin (A, B1, B2, C1, C2, D, SA, CC-1065), and other anticancer or anti-neoplastic agents described herein.

Cancer Gene Therapy and Cell Therapy

In some embodiments, a compound as described herein, is combined with a cancer gene therapy and cell therapy. Cancer gene therapies and cell therapies include the insertion of a normal gene into cancer cells to replace a mutated or altered gene; genetic modification to silence a mutated gene; genetic approaches to directly kill the cancer cells; including the infusion of immune cells designed to replace most of the patient's own immune system to enhance the immune response to cancer cells, or activate the patient's own immune system (T cells or Natural Killer cells) to kill cancer cells, or find and kill the cancer cells; genetic approaches to modify cellular activity to further alter endogenous immune responsiveness against cancer.

Cellular Therapies

In some embodiments, a compound as described herein, is combined with one or more cellular therapies. Illustrative cellular therapies include without limitation co-administration of one or more of a population of immune cells. In some embodiments, the immune cells are natural killer (NK) cells, NK-T cells, T cells, gamma delta T cells, B-cells, cytokine-induced killer (CIK) cells, macrophage (MAC) cells, tumor infiltrating lymphocytes (TILs) a granulocyte, an innate lymphoid cell, a megakaryocyte, a monocyte, a macrophage, a platelet, a thymocyte, a myeloid cell, and/or dendritic cells (DCs). In some embodiments, the cellular therapy entails a T cell therapy, e.g., co-administering a population of alpha/beta TCR T cells, gamma/delta TCR T cells, regulatory T (Treg) cells and/or TRuC™ T cells. In some embodiments, the cellular therapy entails a NK cell therapy, e.g., co-administering NK-92 cells. As appropriate, a cellular therapy can entail the co-administration of cells that are autologous, syngeneic or allogeneic to the subject.

In some embodiments, the cellular therapy entails co-administering immune cells engineered to express chimeric antigen receptors (CARs) or T cell receptors (TCRs) TCRs. In particular embodiments, a population of immune cells is engineered to express a CAR, wherein the CAR comprises a tumor antigen-binding domain. In other embodiments, a population of immune cells is engineered to express T cell receptors (TCRs) engineered to target tumor derived peptides presented on the surface of tumor cells. In one embodiment, the immune cell engineered to express chimeric antigen receptors (CARs) or T cell receptors (TCRs) TCRs is a T cell. In another embodiment, the immune cell engineered to express chimeric antigen receptors (CARs) or T cell receptors (TCRs) TCRs is an NK cell.

With respect to the structure of a CAR, in some embodiments, the CAR comprises an antigen binding domain, a transmembrane domain, and an intracellular signaling domain. In some embodiments, the intracellular domain comprises a primary signaling domain, a costimulatory domain, or both of a primary signaling domain and a costimulatory domain. In some embodiments, the primary signaling domain comprises a functional signaling domain of one or more proteins selected from the group consisting of CD3 zeta, CD3 gamma, CD3 delta, CD3 epsilon, common FcR gamma (FCERIG), FcR beta (Fc Epsilon Rlb), CD79a, CD79b, Fcgamma RIIa, DAP10, and DAP12 4-1BB/CD137, activating NK cell receptors, an Immunoglobulin protein, B7-H3, BAFFR, BLAME (SLAMF8), BTLA, CD100 (SEMA4D), CD103, CD160 (BY55), CD18, CD19, CD19a, CD2, CD247, CD27, CD276 (B7-H3), CD28, CD29, CD3 delta, CD3 epsilon, CD3 gamma, CD30, CD4, CD40, CD49a, CD49D, CD49f, CD69, CD7, CD84, CD8alpha, CD8beta, CD96 (Tactile), CD11a, CD11b, CD11c, CD11d, CDS, CEACAMI, CRT AM, cytokine receptor, DAP-10, DNAM1 (CD226), Fc gamma receptor, GADS, GITR, HVEM (LIGHTR), IA4, ICAM-1, ICAM-1, Ig alpha (CD79a), IL-2R beta, IL-2R gamma, IL-7R alpha, inducible T cell costimulator (ICOS), integrins, ITGA4, ITGA4, ITGA6, ITGAD, ITGAE, ITGAL, ITGAM, ITGAX, ITGB2, ITGB7, ITGB1, KIRDS2, LAT, LFA-1, LFA-1, ligand that binds with CD83, LIGHT, LIGHT, LTBR, Ly9 (CD229), Ly108), lymphocyte function-associated antigen-1 (LFA-1; CD1-1a/CD18), MHC class 1 molecule, NKG2C, NKG2D, NKp30, NKp44, NKp46, NKp80 (KLRF1), OX-40, PAG/Cbp, programmed death-1 (PD-1), PSGL1, SELPLG (CD162), Signaling Lymphocytic Activation Molecules (SLAM proteins), SLAM (SLAMF1; CD150; IPO-3), SLAMF4 (CD244; 2B4), SLAMF6 (NTB-A, SLAMF7, SLP-76, TNF receptor proteins, TNFR2, TNFSF14, a Toll ligand receptor, TRANCE/RANKL, VLA1, or VLA-6, or a fragment, truncation, or a combination thereof.

In some embodiments, the costimulatory domain comprises a functional domain of one or more proteins selected from the group consisting of CD27, CD28, 4-1BB(CD137), OX40, CD30, CD40, PD-1, ICOS, CD2, CD7, LIGHT, NKG2C, lymphocyte function-associated antigen-1 (LFA-1), MYD88, B7-H3, a ligand that specifically binds with CD83, CDS, ICAM-1, GITR, BAFFR, HVEM (LIGHTR), SLAMF7, NKp80 (KLRF1), CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, ITGAE, CD103, ITGAL, CD1A (NCBI Gene ID: 909), CD1B (NCBI Gene ID: 910), CD1C (NCBI Gene ID: 911), CD1D (NCBI Gene ID: 912), CD1E (NCBI Gene ID: 913), ITGAM, ITGAX, ITGB1, CD29, ITGB2 (CD18, LFA-1), ITGB7, TNFR2, TRANCE/RANKL, DNAM1 (CD226), SLAMF4 (CD244, 2B4), CD84, CD96 (Tactile), CEACAMI, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, and NKG2D.

In some embodiments, the transmembrane domain comprises a transmembrane domain derived from a protein selected from the group consisting of the alpha, beta or zeta chain of the T-cell receptor, CD28, CD3 epsilon, CD3 delta, CD3 gamma, CD45, CD4, CD5, CD7, CD8 alpha, CD8 beta, CD9, CD11a, CD11b, CD11c, CD11d, CD16, CD18, CD22, CD33, CD37, CD64, CD80, CD86, CD134, CD137, CD154, KIRDS2, OX40, CD2, CD27, ICOS (CD278), 4-1BB(CD137), GITR, CD40, BAFFR, HVEM (LIGHTR), SLAMF7, NKp80 (KLRF1), CD19, CD19a, IL2R beta, IL2R gamma, IL7R alpha, ITGA1, VLA1, CD49a, ITGA4, IA4, CD49D, ITGA6, VLA-6, CD49f, ITGAD, CD1A, CD1B, CD1C, CD1D, CD1E, ITGAE, CD103, ITGAL, ITGAM, ITGAX, ITGB1, ITGB2, ITGB7, CD29, ITGB2 (LFA-1, CD18), ITGB7, TNFR2, DNAM1 (CD226), SLAMF4 (CD244, 2B4), CD84, CD96 (TACTILE), CEACAMI, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, PAG/Cbp, NKp44, NKp30, NKp46, NKG2D, and NKG2C activating NK cell receptors, an Immunoglobulin protein, BTLA, CD247, CD276 (B7-H3), CD30, CD84, CDS, cytokine receptor, Fc gamma receptor, GADS, ICAM-1, Ig alpha (CD79a), integrins, LAT, a ligand that binds with CD83, LIGHT, MHC class 1 molecule, PAG/Cbp, TNFSF14, a Toll ligand receptor, TRANCE/RANKL, or a fragment, truncation, or a combination thereof.

In some embodiments, the CAR comprises a hinge domain. A hinge domain may be derived from a protein selected from the group consisting of the CD2, CD3 delta, CD3 epsilon, CD3 gamma, CD4, CD7, CD8.alpha., CD8.beta., CD11a (ITGAL), CD11b (ITGAM), CD11c (ITGAX), CD11 d (ITGAD), CD18 (ITGB2), CD19 (B4), CD27 (TNFRSF7), CD28, CD28T, CD29 (ITGB1), CD30 (TNFRSF8), CD40 (TNFRSF5), CD48 (SLAMF2), CD49a (ITGA1), CD49d (ITGA4), CD49f (ITGA6), CD66a (CEACAM1), CD66b (CEACAM8), CD66c (CEACAM6), CD66d (CEACAM3), CD66e (CEACAM5), CD69 (CLEC2), CD79A (B-cell antigen receptor complex-associated alpha chain), CD79B (B-cell antigen receptor complex-associated beta chain), CD84 (SLAMF5), CD96 (Tactile), CD100 (SEMA4D), CD103 (ITGAE), CD134 (OX40), CD137 (4-1BB), CD150 (SLAMF1), CD158A (KIR2DL1), CD158B1 (KIR2DL2), CD158B2 (KIR2DL3), CD158C (KIR3DP1), CD158D (KIRDL4), CD158F1 (KIR2DL5A), CD158F2 (KIR2DL5B), CD158K (KIR3DL2), CD160 (BY55), CD162 (SELPLG), CD226 (DNAM1), CD229 (SLAMF3), CD244 (SLAMF4), CD247 (CD3-zeta), CD258 (LIGHT), CD268 (BAFFR), CD270 (TNFSF14), CD272 (BTLA), CD276 (B7-H3), CD279 (PD-1), CD314 (NKG2D), CD319 (SLAMF7), CD335 (NK-p46), CD336 (NK-p44), CD337 (NK-p30), CD352 (SLAMF6), CD353 (SLAMF8), CD355 (CRTAM), CD357 (TNFRSF18), inducible T cell co-stimulator (ICOS), LFA-1 (CD11 a/CD18), NKG2C, DAP-10, ICAM-1, NKp80 (KLRF1), IL-2R beta, IL-2R gamma, IL-7R alpha, LFA-1, SLAMF9, LAT, GADS (GrpL), SLP-76 (LCP2), PAG1/CBP, a CD83 ligand, Fc gamma receptor, MHC class 1 molecule, MHC class 2 molecule, a TNF receptor protein, an immunoglobulin protein, a cytokine receptor, an integrin, activating NK cell receptors, or Toll ligand receptor, IgG1, IgG2, IgG3, IgG4, IgA, IgD, IgE, IgM or fragment or combination thereof.

In some embodiments, the one or more additional therapeutic agents comprises an immunotherapy, an immunostimulatory therapy, a cytokine therapy, a chemokine therapy, a cellular therapy, a gene therapy, and combinations thereof. In some embodiments, the immunotherapy comprises co-administering one or more antibodies or antigen-binding antibody fragments thereof, or antibody-drug conjugates thereof, CD3-targeting multi-specific molecules, CD16-targeting multi-specific molecules, or non-immunoglobulin antigen-binding domains or antibody mimetic proteins directed against one or more targets or tumor associated antigens (TAAs).

In some embodiments, the TCR or CAR antigen binding domain or the immunotherapeutic agent described herein (e.g., monospecific or multi-specific antibody or antigen-binding fragment thereof or antibody mimetic) binds a tumor-associated antigen (TAA). In some embodiments, the tumor-associated antigen is selected from the group consisting of: CD19; CD123; CD22; CD30; CD171; CS-1 (also referred to as CD2 subset 1, CRACC, SLAMF7, CD319, and 19A24); C-type lectin-like molecule-1 (CLL-1 or CLECL1); CD33; epidermal growth factor receptor variant III (EGFRvIII); ganglioside G2 (GD2); ganglioside GD3 (αNeuSAc(2-8)αNeuSAc(2-3)βDGaip(1-4)bDGlcp(1-1) Cer); ganglioside GM3 (αNeuSAc(2-3)βDGalp(1-4)βDGlcp(1-1)Cer); GM-CSF receptor; TNF receptor superfamily member 17 (TNFRSF17, BCMA); B-lymphocyte cell adhesion molecule; Tn antigen ((Tn Ag) or (GalNAcu-Ser/Thr)); prostate-specific membrane antigen (PSMA); Receptor tyrosine kinase-like orphan receptor 1 (ROR1); Tumor-associated glycoprotein 72 (TAG72); CD38; CD44v6; Carcinoembryonic antigen (CEA); Epithelial cell adhesion molecule (EPCAM); B7H3 (CD276); KIT (CD117); Interleukin-13 receptor subunit alpha-2 (IL-13Ra2 or CD213A2); Mesothelin; Interleukin 11 receptor alpha (IL-11Ra); prostate stem cell antigen (PSCA); Protease Serine 21 (Testisin or PRSS21); vascular endothelial growth factor receptor 2 (VEGFR2); HLA class I antigen A-2 alpha; HLA antigen; Lewis(Y)antigen; CD24; Platelet-derived growth factor receptor beta (PDGFR-beta); Stage-specific embryonic antigen-4 (SSEA-4); CD20; delta like 3 (DLL3); Folate receptor alpha; Folate receptor beta, GDNF alpha 4 receptor, Receptor tyrosine-protein kinase, ERBB2 (Her2/neu); Mucin 1, cell surface associated (MUC1); APRIL receptor; ADP ribosyl cyclase-1; Ephb4 tyrosine kinase receptor, DCAMKL1 serine threonine kinase, Aspartate beta-hydroxylase, epidermal growth factor receptor (EGFR); neural cell adhesion molecule (NCAM); Prostase; prostatic acid phosphatase (PAP); elongation factor 2 mutated (ELF2M); Ephrin B2; fibroblast activation protein alpha (FAP); insulin-like growth factor 1 receptor (IGF-I receptor), carbonic anhydrase IX (CAIX); Proteasome (Prosome, Macropain) Subunit, Beta Type, 9 (LMP2); glycoprotein 100 (gp100); oncogene fusion protein consisting of breakpoint cluster region (BCR) and Abelson murine leukemia viral oncogene homolog 1 (Abl) (bcr-abl); tyrosinase; ephrin type-A receptor 2 (EphA2); ephrin type-A receptor 3 (EphA3), Fucosyl GM1; sialyl Lewis adhesion molecule (sLe); transglutaminase 5 (TGS5); high molecular weight-melanomaassociatedantigen (HMWMAA); o-acetyl-GD2 ganglioside (OAcGD2); Folate receptor beta; tumor endothelial marker 1 (TEM1/CD248); tumor endothelial marker 7-related (TEM7R); six transmembrane epithelial antigen of the prostate I (STEAP1); claudin 6 (CLDN6); thyroid stimulating hormone receptor (TSHR); G protein-coupled receptor class C group 5, member D (GPRCSD); IL-15 receptor (IL-15); chromosome X open reading frame 61 (CXORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (OR5 IE2); TCR Gamma Alternate Reading Frame Protein (TARP); Wilms tumor protein (WT1); Cancer/testis antigen 1 (NY-ESO-1); Cancer/testis antigen 2 (LAGE-la); Melanoma associated antigen 1 (MAGE-A1); Melanoma associated antigen 3 (MAGE-A3); Melanoma associated antigen 4 (MAGE-A4); T cell receptor beta 2 chain C; ETS translocation-variant gene 6, located on chromosome 12p (ETV6-AML); sperm protein 17 (SPA17); X Antigen Family, Member 1A (XAGE1); angiopoietin-binding cell surface receptor 2 (Tie 2); melanoma cancer testis antigen-1 (MADCT-1); melanoma cancer testis antigen-2 (MAD-CT-2); Fos-related antigen 1; tumor protein p53, (p53); p53 mutant; prostein; survivin; telomerase; prostate carcinoma tumor antigen-1 (PCTA-1 or Galectin 8), melanoma antigen recognized by T cells 1 (MelanA or MART1); Rat sarcoma (Ras) mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); Androgen receptor; Cyclin-A1; Cyclin B1; v-myc avian myelocytomatosis viral oncogene neuroblastoma derived homolog (MYCN); Ras Homolog Family Member C (RhoC); Tyrosinase-related protein 2 (TRP-2); Cytochrome P450 1B1(CYP IBI); CCCTC-Binding Factor (Zinc Finger Protein)-Like (BORIS or Brother of the Regulator of Imprinted Sites), Squamous Cell Carcinoma Antigen Recognized By T Cells 3 (SART3); Paired box protein Pax-5 (PAX5); proacrosin binding protein sp32 (OY-TES I); lymphocyte-specific protein tyrosine kinase (LCK); A kinase anchor protein 4 (AKAP-4); Peptidoglycan recognition protein, synovial sarcoma, X breakpoint 2

(SSX2); Receptor for Advanced Glycation Endproducts (RAGE-I); renal ubiquitous 1 (RUI); renal ubiquitous 2 (RU2); legumain; human papilloma virus E6 (HPV E6); human papilloma virus E7 (HPV E7); intestinal carboxyl esterase; heat shock protein 70-2 mutated (mut hsp70-2); CD79a; CD79b; CD72; Leukocyte-associated immunoglobulin-like receptor 1 (LAIR1); Fc fragment of IgA receptor (FCAR or CD89); Leukocyte immunoglobulin-like receptor subfamily A member 2 (LILRA2); CD300 molecule-like family member f (CD300LF); C-type lectin domain family 12 member A (CLEC12A); bone marrow stromal cell antigen 2 (BST2); EGF-like module containing mucin-like hormone receptor-like 2 (EMR2); lymphocyte antigen 75 (LY75); Glypican-2 (GPC2); Glypican-3 (GPC3); Fc receptor-like 5 (FCRL5); and immunoglobulin lambda-like polypeptide 1 (IGLL1). In some embodiments, the target is an epitope of the tumor associated antigen presented in an MHC.

In some embodiments, the tumor antigen is selected from CD150, 5T4, ActRIIA, B7, TNF receptor superfamily member 17 (TNFRSF17, BCMA), CA-125, CCNA1, CD123, CD126, CD138, CD14, CD148, CD15, CD19, CD20, CD200, CD21, CD22, CD23, CD24, CD25, CD26, CD261, CD262, CD30, CD33, CD362, CD37, CD38, CD4, CD40, CD40L, CD44, CD46, CD5, CD52, CD53, CD54, CD56, CD66a-d, CD74, CD8, CD80, CD92, CE7, CS-1, CSPG4, ED-B fibronectin, EGFR, EGFRvIII, EGP-2, EGP-4, EPHa2, ErbB2, ErbB3, ErbB4, FBP, HER1-HER2 in combination, HER2-HER3 in combination, HERV-K, HIV-1 envelope glycoprotein gp120, HIV-1 envelope glycoprotein gp41, HLA-DR, HLA class I antigen alpha G, HM1.24, K-Ras GTPase, HMW-MAA, Her2, Her2/neu, IGF-1R, IL-11 Ralpha, IL-13R-alpha2, IL-2, IL-22R-alpha, IL-6, IL-6R, Ia, Ii, L1-CAM, L1-cell adhesion molecule, Lewis Y, L1-CAM, MAGE A3, MAGE-A1, MART-1, MUC1, NKG2C ligands, NKG2D Ligands, NYESO-1, OEPHa2, PIGF, PSCA, PSMA, ROR1, T101, TAC, TAG72, TIM-3, TRAIL-R1, TRAIL-R1 (DR4), TRAIL-R2 (DR5), VEGF, VEGFR2, WT-I, a G-protein coupled receptor, alphafetoprotein (AFP), an angiogenesis factor, an exogenous cognate binding molecule (ExoCBM), oncogene product, anti-folate receptor, c-Met, carcinoembryonic antigen (CEA), cyclin (D 1), ephrinB2, epithelial tumor antigen, estrogen receptor, fetal acetylcholine e receptor, folate binding protein, gp100, hepatitis B surface antigen, Epstein-Barr nuclear antigen 1, Latent membrane protein 1, Secreted protein BARF1, P2X7 purinoceptor, Syndecan-1, kappa chain, kappa light chain, kdr, lambda chain, livin, melanoma-associated antigen, mesothelin, mouse double minute 2 homolog (MDM2), mucin 16 (MUC16), mutated p53, mutated ras, necrosis antigens, oncofetal antigen, ROR2, progesterone receptor, prostate specific antigen, tEGFR, tenascin, P2-Microgiobuiin, Fc Receptor-like 5 (FcRL5).

Examples of cell therapies include without limitation: AMG-119, Algenpantucel-L, ALOFISEL®, Sipuleucel-T, (BPX-501) rivogenlecleucel U.S. Pat. No. 9,089,520, WO2016100236, AU-105, ACTR-087, activated allogeneic natural killer cells CNDO-109-AANK, MG-4101, AU-101, BPX-601, FATE-NK100, LFU-835 hematopoietic stem cells, Imilecleucel-T, baltaleucel-T, PNK-007, UCARTCS1, ET-1504, ET-1501, ET-1502, ET-190, CD19-ARTEMIS, ProHema, FT-1050-treated bone marrow stem cell therapy, CD4CARNK-92 cells, SNK-01, NEXI-001, CryoStim, AlloStim, lentiviral transduced huCART-meso cells, CART-22 cells, EGFRt/19-28z/4-1BBL CAR T cells, autologous 4H11-28z/fIL-12/EFGRt T cell, CCR5-SBC-728-HSPC, CAR4-1BBZ, CH-296, dnTGFbRII-NY-ESOc259T, Ad-RTS-IL-12, IMA-101, IMA-201, CARMA-0508, TT-18, CMD-501, CMD-503, CMD-504, CMD-502, CMD-601, CMD-602, CSG-005, LAAP T-cell therapy, PD-1 knockout T cell therapy (esophageal cancer/NSCLC), anti-MUC1 CAR T-cell therapy (esophageal cancer/NSCLC), anti-MUC1 CAR T-cell therapy+PD-1 knockout T cell therapy (esophageal cancer/NSCLC), anti-KRAS G12D mTCR PBL, anti-CD123 CAR T-cell therapy, anti-mutated neoantigen TCR T-cell therapy, tumor lysate/MUC1/survivin Pep-Tivator-loaded dendritic cell vaccine, autologous dendritic cell vaccine (metastatic malignant melanoma, intradermal/intravenous), anti-LeY-scFv-CD28-zeta CAR T-cells, PRGN-3005, iC9-GD2-CAR-IL-15 T-cells, HSC-100, ATL-DC-101, MIDRIX4-LUNG, MIDRIXNEO, FCR-001, PLX stem cell therapy, MDR-101, GeniusVac-Mel4, ilixadencel, allogeneic mesenchymal stem cell therapy, romyelocel L, CYNK-001, ProTrans, ECT-100, MSCTRAIL, dilanubicel, FT-516, ASTVAC-2, E-CEL UVEC, CK-0801, allogenic alpha/beta CD3+ T cell and CD19+ B cell depleted stem cells (hematologic diseases, TBX-1400, HLCN-061, umbilical cord derived Hu-PHEC cells (hematological malignancies/aplastic anemia), AP-011, apceth-201, apceth-301, SENTI-101, stem cell therapy (pancreatic cancer), ICO-VIR15-cBiTE, CD33HSC/CD33 CAR-T, PLX-Immune, SUBCUVAX, CRISPR allogeneic gamma-delta T-cell based gene therapy (cancer), ex vivo CRISPR allogeneic healthy donor NK-cell based gene therapy (cancer), ex-vivo allogeneic induced pluripotent stem cell-derived NK-cell based gene therapy (solid tumor), and anti-CD20 CAR T-cell therapy (non-Hodgkin's lymphoma).

Additional Agents for Targeting Tumors Include without Limitation:

Alpha-fetoprotein, such as ET-1402, and AFP-TCR;

Anthrax toxin receptor 1, such as anti-TEM8 CAR T-cell therapy;

TNF receptor superfamily member 17 (TNFRSF17, BCMA), such as bb-2121 (ide-cel), bb-21217, JCARH125, UCART-BCMA, ET-140, KITE-585, MCM-998, LCAR-B38M, CART-BCMA, SEA-BCMA, BB212, ET-140, P-BCMA-101, AUTO-2 (APRIL-CAR), JNJ-68284528;

Anti-CLL-1 antibodies, such as KITE-796. See, for example, PCT/US2017/025573;

Anti-PD-L1-CAR tank cell therapy, such as KD-045;

Anti-PD-L1 t-haNK, such as PD-L1 t-haNK;

anti-CD45 antibodies, such as 131I-BC8 (lomab-B);

anti-HER3 antibodies, such as LJM716, GSK2849330;

anti-CD52 antibodies, such as alemtuzumab;

APRIL receptor modulator, such as anti-BCMA CAR T-cell therapy, Descartes-011;

ADP ribosyl cyclase-1/APRIL receptor modulator, such as dual anti-BCMA/anti-CD38 CAR T-cell therapy; CART-ddBCMA;

B7 homolog 6, such as CAR-NKp30 and CAR-B7H6;

B-lymphocyte antigen CD19, such as TBI-1501, CTL-119 huCART-19 T cells, liso-cel, JCAR-015 U.S. Pat. No. 7,446,190, JCAR-014, JCAR-017, (WO2016196388, WO2016033570, WO2015157386), axicabtagene ciloleucel (KTE-C19, Yescarta®), KTE-X19, U.S. Pat. Nos. 7,741,465, 6,319,494, UCART-19, EBV-CTL, T tisagenlecleucel-T (CTL019), WO2012079000, WO2017049166, CD19CAR-CD28-CD3zeta-EGFRt-expressing T cells, CD19/4-1BBL armored CAR T cell therapy, C-CAR-011, CIK-CAR.CD19, CD19CAR-28-zeta T cells, PCAR-019, MatchCART, DSCAR-01, IM19 CAR-T, TC-110; anti-CD19 CAR T-cell therapy (B-cell acute lymphoblastic leukemia, Universiti Kebangsaan Malaysia); anti-CD19 CAR T-cell therapy (acute lymphoblastic leukemia/Non-Hodgkin's lymphoma, University Hospital Heidelberg), anti-CD19 CAR T-cell therapy (silenced IL-6 expression, cancer, Shanghai Unicar-Therapy Biomedicine Technology), MB-CART2019.1 (CD19/CD20), GC-197 (CD19/CD7), CLIC-1901, ET-019003, anti-CD19-STAR-T cells, AVA-001, BCMA-CD19 cCAR (CD19/APRIL), ICG-134, ICG-132 (CD19/CD20), CTA-101, WZTL-002, dual anti-CD19/anti-CD20 CAR T-cells (chronic lymphocytic leukemia/B-cell lymphomas), HY-001, ET-019002, YTB-323, GC-012 (CD19/APRIL), GC-022 (CD19/CD22), CD19CAR-CD28-CD3zeta-EGFRt-expressing Tn/mem; UCAR-011, ICTCAR-014, GC-007F, PTG-01, CC-97540;

Allogeneic anti-CD19 CART cells, such as GC-007G;
Allogenic T cells expressing CD20 CAR, such as LB-1905;
APRIL receptor modulator; SLAM family member 7 modulator, BCMA-CS1 cCAR;
Autologous dendritic cell tumor antigen (ADCTA), such as ADCTA-SSI-G;
B-lymphocyte antigen CD20, such as ACTR707 ATTCK-20, PBCAR-20A;
B-lymphocyte antigen CD19/B-lymphocyte antigen 22, such as TC-310;
B-lymphocyte antigen 22 cell adhesion, such as UCART-22, JCAR-018 WO2016090190;
NY-ESO-1 modulators, such as GSK-3377794, TBI-1301, GSK3537142;
Carbonic anhydrase, such as DC-Ad-GMCAIX;
Caspase 9 suicide gene, such as CaspaCIDe DLI, BPX-501;
CCR5, such as SB-728;
CCR5 gene inhibitor/TAT gene/TRIM5 gene stimulator, such as lentivirus vector CCR5 shRNA/TRIM5alpha/TAR decoy-transduced autologous CD34-positive hematopoietic progenitor cells;
CDw123, such as MB-102, IM-23, JEZ-567, UCART-123;
CD4, such as ICG-122;
CD5 modulators, such as CD5.28z CART cells;
Anti-CD22, such as anti-CD22 CART;
Anti-CD30, such as TT-11;
CD33, such as CIK-CAR.CD33, CD33CART;
Dual anti-CD33/anti-CLL1, such as LB-1910;
CD38, such as T-007, UCART-38;
CD40 ligand, such as BPX-201, MEDI5083;
CD56, such as allogeneic CD56-positive CD3-negative natural killer cells (myeloid malignancies);
CD19/CD7 modulator, such as GC-197;
T-cell antigen CD7 modulator, such as anti-CD7 CAR T-cell therapy (CD7-positive hematological malignancies);
CD123 modulator, such as UniCAR02-T-CD123;
Anti-CD276, such as anti-CD276 CART;
CEACAM protein 5 modulators, such as MG7-CART;
Claudin 6, such as CSG-002;
Claudin 18.2, such as LB-1904;
Chlorotoxin, such as CLTX-CART;
EBV targeted, such as CMD-003;
MUC16EGFR, such as autologous 4H11-28z/fIL-12/EFGRt T cell;
Endonuclease, such as PGN-514, PGN-201;
Epstein-Barr virus specific T-lymphocytes, such as TT-10;
Epstein-Barr nuclear antigen 1/Latent membrane protein 1/Secreted protein BARF1 modulator, such as TT-10X;
Erbb2, such as CST-102, CIDeCAR;
Ganglioside (GD2), such as 4SCAR-GD2;
Gamma delta T cells, such as ICS-200;
folate hydrolase 1 (FOLH1, Glutamate carboxypeptidase II, PSMA; NCBI Gene ID: 2346), such as CIK-CAR.PSMA, CART-PSMA-TGFORDN, P-PSMA-101;
Glypican-3(GPC3), such as TT-16, GLYCAR;
Hemoglobin, such as PGN-236;
Hepatocyte growth factor receptor, such as anti-cMet RNA CAR T;
HLA class I antigen A-2 alpha modulator, such as FH-MCVA2TCR;
HLA class I antigen A-2 alpha/Melanoma associated antigen 4 modulator, such as ADP-A2M4CD8;
HLA antigen modulator, such as FIT-001, NeoTCR-P1;
Human papillomavirus E7 protein, such as KITE-439. See, for example, PCT/US2015/033129;
ICAM-1 modulator, such as AIC-100;
Immunoglobulin gamma Fc receptor III, such as ACTR087;
IL-12, such as DC-RTS-IL-12;
IL-12 agonist/mucin 16, such as JCAR-020;
IL-13 alpha 2, such as MB-101;
IL-15 receptor agonist, such as PRGN-3006, ALT-803; interleukin-15/Fc fusion protein (e.g., XmAb24306); recombinant interleukin-15 (e.g., AM0015, NIZ-985); pegylated IL-15 (e.g., NKTR-255);
IL-2, such as CST-101;
Interferon alpha ligand, such as autologous tumor cell vaccine+systemic CpG-B+IFN-alpha (cancer);
K-Ras GTPase, such as anti-KRAS G12V mTCR cell therapy;
Neural cell adhesion molecule L1 L1CAM (CD171), such as JCAR-023;
Latent membrane protein 1/Latent membrane protein 2, such as Ad5f35-LMPd1-2-transduced autologous dendritic cells;
MART-1 melanoma antigen modulator, such as MART-1 F5 TCR engineered PBMC;
Melanoma associated antigen 10, such as MAGE-A10C796T MAGE-A10 TCR;
Melanoma associated antigen 3/Melanoma associated antigen 6 (MAGE A3/A6) such as KITE-718 (see, for example, PCT/US2013/059608);
Mesothelin, such as CSG-MESO, TC-210;
Mucin 1 modulator, such as ICTCAR-052, Tn MUC-1 CAR-T, ICTCAR-053;
Anti-MICA/MICB, such as CYAD-02;
NKG2D, such as NKR-2;
Ntrkr1 tyrosine kinase receptor, such as JCAR-024;
PRAMET cell receptor, such as BPX-701;
Prostate stem cell antigen modulator, such as MB-105;
Roundabout homolog 1 modulator, such as ATCG-427;
Peptidoglycan recognition protein modulator, such as Tag-7 gene modified autologous tumor cell vaccine;
PSMA, such as PSMA-CAR T-cell therapy (lentiviral vector, castrate-resistant prostate cancer);
SLAM family member 7 modulator, such as IC9-Luc90-CD828Z;
TGF beta receptor modulator, such as DNR.NPC T-cells;
T-lymphocyte, such as TT-12;
T-lymphocyte stimulator, such as ATL-001;
TSH receptor modulator, such as ICTCAR-051;

Tumor infiltrating lymphocytes, such as LN-144, LN-145; and/or

Wilms tumor protein, such as JTCR-016, WT1-CTL.

Agonists of Fms Related Receptor Tyrosine Kinase 3 (FLT3)

In some embodiments, a compound as described herein, is combined with an agonist of fms related receptor tyrosine kinase 3 (FLT3); FLK2; STK1; CD135; FLK-2; NCBI Gene ID: 2322). Examples of FLT3 agonists include CDX-301 and GS-3583.

MCL1 Apoptosis Regulator, BCL2 Family Member (MCL1) Inhibitors

In some embodiments, a compound as described herein, is combined with an inhibitor of MCL1 apoptosis regulator, BCL2 family member (MCL1, TM; EAT; MCL1L; MCL1S; Mcl-1; BCL2L3; MCL1-ES; bcl2-L-3; mcl1/EAT; NCBI Gene ID: 4170). Examples of MCL1 inhibitors include AMG-176, AMG-397, S-64315, and AZD-5991, 483-LM, A-1210477, UMI-77, JKY-5-037, and those described in WO2018183418, WO2016033486, WO2019222112 and WO2017147410.

Cytokine Inducible SH2 Containing Protein (CISH) Inhibitors

In some embodiments, a compound as described herein, is combined with an inhibitor of cytokine inducible SH2 containing protein (CISH; CIS; G18; SOCS; CIS-1; BACTS2; NCBI Gene ID: 1154). Examples of CISH inhibitors include those described in WO2017100861, WO2018075664 and WO2019213610.

Gene Editors

In some embodiments, a compound as described herein, is combined with gene editor.

Illustrative gene editing system that can be co-administered include without limitation a CRISPR/Cas9 system, a zinc finger nuclease system, a TALEN system, a homing endonucleases system (e.g., an ARCUS), and a homing meganuclease system.

Others Drugs with Unspecified Targets

In some embodiments, a compound as described herein, is combined with human immunoglobulin (10% liquid formulation), Cuvitru (human immunoglobulin (20% solution), levofolinate disodium, IMSA-101, BMS-986288, IMUNO BGC Moreau RJ, R-OKY-034F, GP-2250, AR-23, calcium levofolinate, porfimer sodium, RG6160, ABBV-155, CC-99282, polifeprosan 20 with carmustine, Veregen, gadoxetate disodium, gadobutrol, gadoterate meglumine, gadoteridol, 99mTc-sestamibi, pomalidomide, pacibanil, or valrubicin.

2. Human Immunodeficiency Virus (HIV)

In some embodiments, the additional therapeutic agent may be an anti-HIV agent. In some instances, the additional therapeutic agent can be HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, HIV capsid inhibitors, HIV Tat or Rev inhibitors, immunomodulators, immunotherapeutic agents, antibody-drug conjugates, gene modifiers, gene editors (such as CRISPR/Cas9, zinc finger nucleases, homing nucleases, synthetic nucleases, TALENs), cell therapies (such as chimeric antigen receptor T-cell, CAR-T, and engineered T-cell receptors, TCR-T, autologous T-cell therapies, engineered B cells), latency reversing agents, immune-based therapies, phosphatidylinositol 3-kinase (PI3K) inhibitors, HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, HIV vif gene modulators, Vif dimerization antagonists, HIV-1 viral infectivity factor inhibitors, HIV-1 Nef modulators, Hck tyrosine kinase modulators, mixed lineage kinase-3 (MLK-3) inhibitors, HIV-1 splicing inhibitors, integrin antagonists, nucleoprotein inhibitors, splicing factor modulators, COMM domain containing protein 1 modulators, HIV ribonuclease H inhibitors, retrocyclin modulators, CDK-9 inhibitors, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, proprotein convertase PC9 stimulators, ATP dependent RNA helicase DDX3X inhibitors, reverse transcriptase priming complex inhibitors, G6PD and NADH-oxidase inhibitors, pharmacokinetic enhancers, HIV gene therapy, HIV vaccines, and combinations thereof.

In some embodiments, the additional therapeutic agent is selected from the group consisting of combination drugs for HIV, other drugs for treating HIV, HIV protease inhibitors, HIV reverse transcriptase inhibitors, HIV integrase inhibitors, HIV non-catalytic site (or allosteric) integrase inhibitors, HIV entry (fusion) inhibitors, HIV maturation inhibitors, latency reversing agents, capsid inhibitors, immune-based therapies, PI3K inhibitors, HIV antibodies, and bispecific antibodies, and "antibody-like" therapeutic proteins, and combinations thereof.

3. Hepatitis B Virus

In some embodiments, a compound of the present disclosure, or pharmaceutically acceptable salt thereof, is combined with one, two, three, four or more additional therapeutic agents selected from HBV combination drugs, HBV vaccines, HBV DNA polymerase inhibitors, immunomodulators, toll-like receptor (TLR) modulators, interferon alpha receptor ligands, hyaluronidase inhibitors, hepatitis b core antigen (HBcAg) inhibitors, hepatitis b surface antigen (HBsAg) inhibitors, cytotoxic T-lymphocyte-associated protein 4 (ipi4) inhibitors, cyclophilin inhibitors, HBV viral entry inhibitors, antisense oligonucleotide targeting viral mRNA, short interfering RNAs (siRNA) and ddRNAi, endonuclease modulators, ribonucleotide reductase inhibitors, HBV E antigen inhibitors, covalently closed circular DNA (cccDNA) inhibitors, farnesoid X receptor agonists, STING agonists, anti-HBV antibodies, CCR2 chemokine antagonists, thymosin agonists, cytokines, nucleoprotein modulators, retinoic acid-inducible gene 1 stimulators, NOD2 stimulators, phosphatidylinositol 3-kinase (PI3K) inhibitors, indoleamine-2, 3-dioxygenase (IDO) pathway inhibitors, PD-1 inhibitors, PD-L1 inhibitors, recombinant thymosin alpha-1, bruton's tyrosine kinase (BTK) inhibitors, KDM inhibitors, HBV replication inhibitors, arginase inhibitors, gene therapy and cell therapy, gene editors, CAR-T cell therapy, TCR-T cell therapy, and other HBV drugs.

In some embodiments, a compound of the present disclosure, or pharmaceutically acceptable salt thereof, may be used or combined with one or more of a chemotherapeutic agent, an immunomodulator, an immunotherapeutic agent, a therapeutic antibody, a therapeutic vaccine, a bispecific antibody and "antibody-like" therapeutic protein (such as DARPins®, anti-pMHC TCR-like antibodies, DARTs®, Duobodies®, Bites®, XmAbs®, TandAbs®, Fab derivatives), an antibody-drug conjugate (ADC), gene modifiers or gene editors (such as CRISPR Cas9, zinc finger nucleases, homing endonucleases, homing meganucleases (e.g., ARCUS), synthetic nucleases, TALENs), cell therapies such as CAR-T (chimeric antigen receptor T-cell), and TCR-T (an engineered T cell receptor) agent or any combination thereof.

In some embodiments, an agent as described herein, is combined with one, two, three, four or more additional therapeutic agents, e.g., as 3-dioxygenase (IDO) inhibitors, apolipoprotein A1 modulator, arginase inhibitors, B- and T-lymphocyte attenuator inhibitors, Bruton's tyrosine kinase (BTK) inhibitors, CCR2 chemokine antagonist, CD137 inhibitors, CD160 inhibitors, CD305 inhibitors, CD4 agonist and modulator, compounds targeting hepatitis B core antigen (HBcAg), core protein allosteric modulators, covalently closed circular DNA (cccDNA) inhibitors, cyclophilin inhibitors, cytotoxic T-lymphocyte-associated protein 4 (ipi4) inhibitors, DNA polymerase inhibitor, endonuclease modulators, epigenetic modifiers, Farnesoid X receptor agonists, HBV DNA polymerase inhibitors, HBV replication inhibitors, HBV RNAse inhibitors, HBV viral entry inhibitors, HBx inhibitors, Hepatitis B large envelope protein modulator, Hepatitis B large envelope protein stimulator, Hepatitis B structural protein modulator, hepatitis B surface antigen (HBsAg) inhibitors, hepatitis B surface antigen (HBsAg) secretion or assembly inhibitors, hepatitis B virus E antigen inhibitors, hepatitis B virus replication inhibitors, Hepatitis virus structural protein inhibitor, HIV-1 reverse transcriptase inhibitor, Hyaluronidase inhibitor, inhibitor of apoptosis proteins family proteins (IAPs) inhibitors, IL-2 agonist, IL-7 agonist, immunomodulators, indoleamine-2 inhibitors, inhibitors of ribonucleotide reductase, Interleukin-2 ligand, ipi4 inhibitors, lysine demethylase inhibitors, histone demethylase inhibitors, KDM1 inhibitors, KDM5 inhibitors, killer cell lectin-like receptor subfamily G member 1 inhibitors, lymphocyte-activation gene 3 inhibitors, lymphotoxin beta receptor activators, modulators of Axl, modulators of B7-H3, modulators of B7-H4, modulators of CD160, modulators of CD161, modulators of CD27, modulators of CD47, modulators of CD70, modulators of GITR, modulators of HEVEM, modulators of ICOS, modulators of Mer, modulators of NKG2A, modulators of NKG2D, modulators of OX40, modulators of SIRPalpha, modulators of TIGIT, modulators of Tim-4, modulators of Tyro, Na+-taurocholate cotransporting polypeptide (NTCP) inhibitors, natural killer cell receptor 2B4 inhibitors, NOD2 gene stimulator, Nucleoprotein inhibitor, nucleoprotein modulators, OX-40 receptor agonist, PD-1 inhibitors, PD-L1 inhibitors, peptidylprolyl isomerase inhibitor, phosphatidylinositol-3 kinase (PI3K) inhibitors, Retinoic acid-inducible gene 1 stimulator, Reverse transcriptase inhibitor, Ribonuclease inhibitor, RNA DNA polymerase inhibitor, SLC10A1 gene inhibitor, SMAC mimetics, Src tyrosine kinase inhibitor, stimulator of interferon gene (STING) agonists, stimulators of NOD1, T cell surface glycoprotein CD28 inhibitor, T-cell surface glycoprotein CD8 modulator, Thymosin agonist, Thymosin alpha 1 ligand, Tim-3 inhibitors, TLR-3 agonists, TLR-7 agonists, TLR-9 agonists, TLR9 agonists or gene stimulator, toll-like receptor (TLR) modulators, viral ribonucleotide reductase inhibitors, and combinations thereof.

B. Exemplified Combination Therapies
1. Cancer
Lymphoma or Leukemia Combination Therapy Some chemotherapy agents are suitable for treating lymphoma or leukemia. These agents include aldesleukin, alvocidib, amifostine trihydrate, aminocamptothecin, antineoplaston A10, antineoplaston AS2-1, anti-thymocyte globulin, arsenic trioxide, Bcl-2 family protein inhibitor ABT-263, beta alethine, BMS-345541bortezomib (VELCADE®, PS-341), bryostatin 1, bulsulfan, campath-1H, carboplatin, carfilzomib (Kyprolis®), carmustine, caspofungin acetate, CC-5103, chlorambucil, CHOP (cyclophosphamide, doxorubicin, vincristine, and prednisone), cisplatin, cladribine, clofarabine, curcumin, CVP (cyclophosphamide, vincristine, and prednisone), cyclophosphamide, cyclosporine, cytarabine, denileukin diftitox, dexamethasone, docetaxel, dolastatin 10, doxorubicin, doxorubicin hydrochloride, DT-PACE (dexamethasone, thalidomide, cisplatin, doxorubicin, cyclophosphamide, and etoposide), enzastaurin, epoetin alfa, etoposide, everolimus (RAD001), FCM (fludarabine, cyclophosphamide, and mitoxantrone), FCR (fludarabine, cyclophosphamide, and rituximab), fenretinide, filgrastim, flavopiridol, fludarabine, FR (fludarabine and rituximab), geldanamycin (17 AAG), hyperCVAD (hyperfractionated cyclophosphamide, vincristine, doxorubicin, dexamethasone, methotrexate, and cytarabine), ICE (iphosphamide, carboplatin, and etoposide), ifosfamide, irinotecan hydrochloride, interferon alpha-2b, ixabepilone, lenalidomide (REVLIMID®, CC-5013), pomalidomide (POMALYST®/IEMNOVID®)lymphokine-activated killer cells, MCP (mitoxantrone, chlorambucil, and prednisolone), melphalan, mesna, methotrexate, mitoxantrone hydrochloride, motexafin gadolinium, mycophenolate mofetil, nelarabine, obatoclax (GX15-070), oblimersen, octreotide acetate, omega-3 fatty acids, Omr-IgG-am (WNIG, Omrix), oxaliplatin, paclitaxel, palbociclib (PD0332991), pegfilgrastim, PEGylated liposomal doxorubicin hydrochloride, perifosin, prednisolone, prednisone, recombinant flt3 ligand, recombinant human thrombopoietin, recombinant interferon alfa, recombinant interleukin-11, recombinant interleukin-12, rituximab, R-CHOP (rituximab and CHOP), R-CVP (rituximab and CVP), R-FCM (rituximab and FCM), R-ICE (rituximab and ICE), and R MCP (rituximab and MCP), R-roscovitine (seliciclib, CYC202), sargramostim, sildenafil citrate, simvastatin, sirolimus, styryl sulphones, tacrolimus, tanespimycin, temsirolimus (CCl-779), thalidomide, therapeutic allogeneic lymphocytes, thiotepa, tipifarnib, vincristine, vincristine sulfate, vinorelbine ditartrate, SAHA (suberanilohydroxamic acid, or suberoyl, anilide, and hydroxamic acid), vemurafenib (Zelboraf®), venetoclax (ABT-199).

One modified approach is radioimmunotherapy, wherein a monoclonal antibody is combined with a radioisotope particle, such as indium-111, yttrium-90, and iodine-131. Examples of combination therapies include, but are not limited to, iodine-131 tositumomab (BEXXAR®), yttrium-90 ibritumomab tiuxetan (ZEVALIN®), and BEXXAR® with CHOP.

The abovementioned therapies can be supplemented or combined with stem cell transplantation or treatment. Therapeutic procedures include peripheral blood stem cell transplantation, autologous hematopoietic stem cell transplantation, autologous bone marrow transplantation, antibody therapy, biological therapy, enzyme inhibitor therapy, total body irradiation, infusion of stem cells, bone marrow ablation with stem cell support, in vitro-treated peripheral blood stem cell transplantation, umbilical cord blood transplantation, immunoenzyme technique, low-LET cobalt-60 gamma ray therapy, bleomycin, conventional surgery, radiation therapy, and nonmyeloablative allogeneic hematopoietic stem cell transplantation.

Non-Hodgkin's Lymphomas Combination Therapy

Treatment of non-Hodgkin's lymphomas (NHL), especially those of B cell origin, includes using monoclonal antibodies, standard chemotherapy approaches (e.g., CHOP (cyclophosphamide, doxorubicin, vincristine, and prednisone), CVP (cyclophosphamide, vincristine, and prednisone), FCM (fludarabine, cyclophosphamide, and mitoxantrone), MCP (Mitoxantrone, Chlorambucil, Prednisolone), all optionally including rituximab (R) and the like), radioimmunotherapy, and combinations thereof, especially integration of an antibody therapy with chemotherapy.

Examples of unconjugated monoclonal antibodies for the treatment of NHL/B-cell cancers include rituximab, alemtuzumab, human or humanized anti-CD20 antibodies, lumiliximab, anti-TNF-related apoptosis-inducing ligand (anti-TRAIL), bevacizumab, galiximab, epratuzumab, SGN-40, and anti-CD74.

Examples of experimental antibody agents used in treatment of NHL/B-cell cancers include ofatumumab, ha20, PRO131921, alemtuzumab, galiximab, SGN-40, CHIR-12.12, epratuzumab, lumiliximab, apolizumab, milatuzumab, and bevacizumab.

Examples of standard regimens of chemotherapy for NHL/B-cell cancers include CHOP, FCM, CVP, MCP, R-CHOP (rituximab, cyclophosphamide, doxorubicin, vincristine, and prednisone), R-FCM, R-CVP, and R MCP.

Examples of radioimmunotherapy for NHL/B-cell cancers include yttrium-90 ibritumomab tiuxetan (ZEVALIN®) and iodine-131 tositumomab (BEXXAR®).

Mantle Cell Lymphoma Combination Therapy

Therapeutic treatments for mantle cell lymphoma (MCL) include combination chemotherapies such as CHOP, hyperCVAD, and FCM. These regimens can also be supplemented with the monoclonal antibody rituximab to form combination therapies R-CHOP, hyperCVAD-R, and R-FCM. Any of the abovementioned therapies may be combined with stem cell transplantation or ICE in order to treat MCL.

An alternative approach to treating MCL is immunotherapy. One immunotherapy uses monoclonal antibodies like rituximab. Another uses cancer vaccines, such as GTOP-99, which are based on the genetic makeup of an individual patient's tumor.

A modified approach to treat MCL is radioimmunotherapy, wherein a monoclonal antibody is combined with a radioisotope particle, such as iodine-131 tositumomab (BEXXAR®) and yttrium-90 ibritumomab tiuxetan (ZEVALIN®). In another example, BEXXAR® is used in sequential treatment with CHOP.

Other approaches to treating MCL include autologous stem cell transplantation coupled with high-dose chemotherapy, administering proteasome inhibitors such as bortezomib (VELCADE® or PS-341), or administering antiangiogenesis agents such as thalidomide, especially in combination with rituximab.

Another treatment approach is administering drugs that lead to the degradation of Bcl-2 protein and increase cancer cell sensitivity to chemotherapy, such as oblimersen, in combination with other chemotherapeutic agents.

A further treatment approach includes administering mTOR inhibitors, which can lead to inhibition of cell growth and even cell death. Non-limiting examples are sirolimus, temsirolimus (TORISEL®, CCI-779), CC-115, CC-223, SF-1126, PQR-309 (bimiralisib), voxtalisib, GSK-2126458, and temsirolimus in combination with RITUXAN®, VELCADE®, or other chemotherapeutic agents.

Other recent therapies for MCL have been disclosed. Such examples include flavopiridol, palbociclib (PD0332991), R-roscovitine (selicicilib, CYC202), styryl sulphones, obatoclax (GX15-070), TRAIL, Anti-TRAIL death receptors DR4 and DR5 antibodies, temsirolimus (TORISEL®, CCl-779), everolimus (RAD001), BMS-345541, curcumin, SAHA, thalidomide, lenalidomide (REVLIMID®, CC-5013), and geldanamycin (17 AAG).

Waldenstrom's Macroglobulinemia Combination Therapy

Therapeutic agents used to treat Waldenstrom's Macroglobulinemia (WM) include aldesleukin, alemtuzumab, alvocidib, amifostine trihydrate, aminocamptothecin, antineoplaston A10, antineoplaston AS2-1, anti-thymocyte globulin, arsenic trioxide, autologous human tumor-derived HSPPC-96, Bcl-2 family protein inhibitor ABT-263, beta alethine, bortezomib (VELCADE®), bryostatin 1, busulfan, campath-1H, carboplatin, carmustine, caspofungin acetate, CC-5103, cisplatin, clofarabine, cyclophosphamide, cyclosporine, cytarabine, denileukin diftitox, dexamethasone, docetaxel, dolastatin 10, doxorubicin hydrochloride, DT-PACE, enzastaurin, epoetin alfa, epratuzumab (hLL2-anti-CD22 humanized antibody), etoposide, everolimus, fenretinide, filgrastim, fludarabine, ibrutinib, ifosfamide, indium-111 monoclonal antibody MN-14, iodine-131 tositumomab, irinotecan hydrochloride, ixabepilone, lymphokine-activated killer cells, melphalan, mesna, methotrexate, mitoxantrone hydrochloride, monoclonal antibody CD19 (such as tisagenlecleucel-T, CART-19, CTL-019), monoclonal antibody CD20, motexafin gadolinium, mycophenolate mofetil, nelarabine, oblimersen, octreotide acetate, omega-3 fatty acids, oxaliplatin, paclitaxel, pegfilgrastim, PEGylated liposomal doxorubicin hydrochloride, pentostatin, perifosine, prednisone, recombinant flt3 ligand, recombinant human thrombopoietin, recombinant interferon alfa, recombinant interleukin-11, recombinant interleukin-12, rituximab, sargramostim, sildenafil citrate (VIAGRA®), simvastatin, sirolimus, tacrolimus, tanespimycin, thalidomide, therapeutic allogeneic lymphocytes, thiotepa, tipifarnib, tositumomab, ulocuplumab, veltuzumab, vincristine sulfate, vinorelbine ditartrate, vorinostat, WT1 126-134 peptide vaccine, WT-1 analog peptide vaccine, yttrium-90 ibritumomab tiuxetan, yttrium-90 humanized epratuzumab, and any combination thereof.

Examples of therapeutic procedures used to treat WM include peripheral blood stem cell transplantation, autologous hematopoietic stem cell transplantation, autologous bone marrow transplantation, antibody therapy, biological therapy, enzyme inhibitor therapy, total body irradiation, infusion of stem cells, bone marrow ablation with stem cell support, in vitro-treated peripheral blood stem cell transplantation, umbilical cord blood transplantation, immunoenzyme techniques, low-LET cobalt-60 gamma ray therapy, bleomycin, conventional surgery, radiation therapy, and nonmyeloablative allogeneic hematopoietic stem cell transplantation.

Diffuse Large B-cell Lymphoma Combination Therapy

Therapeutic agents used to treat diffuse large B-cell lymphoma (DLBCL) include cyclophosphamide, doxorubicin, vincristine, prednisone, anti-CD20 monoclonal antibodies, etoposide, bleomycin, many of the agents listed for WM, and any combination thereof, such as ICE and R ICE.

Chronic Lymphocytic Leukemia Combination Therapy

Examples of therapeutic agents used to treat chronic lymphocytic leukemia (CLL) include chlorambucil, cyclophosphamide, fludarabine, pentostatin, cladribine, doxorubicin, vincristine, prednisone, prednisolone, alemtuzumab, many of the agents listed for WM, and combination chemotherapy and chemoimmunotherapy, including the following common combination regimens: CVP, R-CVP, ICE, R-ICE, FCR, and FR.

Myelofibrosis Combination Therapy

Myelofibrosis inhibiting agents include, but are not limited to, hedgehog inhibitors, histone deacetylase (HDAC)

inhibitors, and tyrosine kinase inhibitors. Non-limiting examples of hedgehog inhibitors are saridegib and vismodegib. Examples of HDAC inhibitors include, but are not limited to, pracinostat and panobinostat. Non-limiting examples of tyrosine kinase inhibitors are lestaurtinib, bosutinib, imatinib, radotinib, and cabozantinib.

Hyperproliferative Disorder Combination Therapy

Gemcitabine, nab-paclitaxel, and gemcitabine/nab-paclitaxel may be used with a JAK inhibitor and/or PI3Kδ inhibitor to treat hyperproliferative disorders.

Bladder Cancer Combination Therapy

Therapeutic agents used to treat bladder cancer include atezolizumab, carboplatin, cisplatin, docetaxel, doxorubicin, fluorouracil (5-FU), gemcitabine, idosfamide, Interferon alfa-2b, methotrexate, mitomycin, nab-paclitaxel, paclitaxel, pemetrexed, thiotepa, vinblastine, and any combination thereof.

Breast Cancer Combination Therapy

Therapeutic agents used to treat breast cancer include albumin-bound paclitaxel, anastrozole, capecitabine, carboplatin, cisplatin, cyclophosphamide, docetaxel, doxorubicin, epirubicin, everolimus, exemestane, fluorouracil, fulvestrant, gemcitabine, Ixabepilone, lapatinib, Letrozole, methotrexate, mitoxantrone, paclitaxel, pegylated liposomal doxorubicin, pertuzumab, tamoxifen, toremifene, trastuzumab, vinorelbine, and any combinations thereof.

Triple Negative Breast Cancer Combination Therapy

Therapeutic agents used to treat triple negative breast cancer include cyclophosphamide, docetaxel, doxorubicin, epirubicin, fluorouracil, paclitaxel, and combinations thereof.

Colorectal Cancer Combination Therapy

Therapeutic agents used to treat colorectal cancer include bevacizumab, capecitabine, cetuximab, fluorouracil, irinotecan, leucovorin, oxaliplatin, panitumumab, ziv-aflibercept, and any combinations thereof.

Castration-Resistant Prostate Cancer Combination Therapy

Therapeutic agents used to treat castration-resistant prostate cancer include abiraterone, cabazitaxel, docetaxel, enzalutamide, prednisone, sipuleucel-T, and any combinations thereof.

Esophageal and Esophagogastric Junction Cancer Combination Therapy

Therapeutic agents used to treat esophageal and esophagogastric junction cancer include capecitabine, carboplatin, cisplatin, docetaxel, epirubicin, fluoropyrimidine, fluorouracil, irinotecan, leucovorin, oxaliplatin, paclitaxel, ramucirumab, trastuzumab, and any combinations thereof.

Gastric Cancer Combination Therapy

Therapeutic agents used to treat gastric cancer include capecitabine, carboplatin, cisplatin, docetaxel, epirubicin, fluoropyrimidine, fluorouracil, Irinotecan, leucovorin, mitomycin, oxaliplatin, paclitaxel, ramucirumab, trastuzumab, and any combinations thereof.

Head and Neck Cancer Combination Therapy

Therapeutic agents used to treat head & neck cancer include afatinib, bleomycin, capecitabine, carboplatin, cetuximab, cisplatin, docetaxel, fluorouracil, gemcitabine, hydroxyurea, methotrexate, nivolumab, paclitaxel, pembrolizumab, vinorelbine, and any combinations thereof.

Hepatobiliary Cancer Combination Therapy

Therapeutic agents used to treat hepatobiliary cancer include capecitabine, cisplatin, fluoropyrimidine, 5-fluorourcil, gemecitabine, oxaliplatin, sorafenib, and any combinations thereof.

Hepatocellular Carcinoma Combination Therapy

Therapeutic agents used to treat hepatocellular carcinoma include capecitabine, doxorubicin, gemcitabine, sorafenib, and any combinations thereof.

Non-Small Cell Lung Cancer Combination Therapy

Therapeutic agents used to treat non-small cell lung cancer (NSCLC) include afatinib, albumin-bound paclitaxel, alectinib, bevacizumab, bevacizumab, cabozantinib, carboplatin, cisplatin, crizotinib, dabrafenib, docetaxel, erlotinib, etoposide, gemcitabine, nivolumab, paclitaxel, pembrolizumab, pemetrexed, ramucirumab, trametinib, trastuzumab, vandetanib, vemurafenib, vinblastine, vinorelbine, and any combinations thereof.

Small Cell Lung Cancer Combination Therapy

Therapeutic agents used to treat small cell lung cancer (SCLC) include bendamustine, carboplatin, cisplatin, cyclophosphamide, docetaxel, doxorubicin, etoposide, gemcitabine, ipilimumab, irinotecan, nivolumab, paclitaxel, temozolomide, topotecan, vincristine, vinorelbine, and any combinations thereof.

Melanoma Combination Therapy

Therapeutic agents used to treat melanoma cancer include albumin bound paclitaxel, carboplatin, cisplatin, cobiemtinib, dabrafenib, dacrabazine, IL-2, imatinib, interferon alfa-2b, ipilimumab, nitrosourea, nivolumab, paclitaxel, pembrolizumab, pilimumab, temozolomide, trametinib, vemurafenib, vinblastine, and any combinations thereof.

Ovarian Cancer Combination Therapy

Therapeutic agents used to treat ovarian cancer include 5-flourouracil, albumin bound paclitaxel, altretamine, anastrozole, bevacizumab, capecitabine, carboplatin, cisplatin, cyclophosphamide, docetaxel, doxorubicin, etoposide, exemestane, gemcitabine, ifosfamide, irinotecan, letrozole, leuprolide acetate, liposomal doxorubicin, megestrol acetate, melphalan, olaparib, oxaliplatin, paclitaxel, Pazopanib, pemetrexed, tamoxifen, topotecan, vinorelbine, and any combinations thereof.

Pancreatic Cancer Combination Therapy

Therapeutic agents used to treat pancreatic cancer include 5-fluorourcil, albumin-bound paclitaxel, capecitabine, cisplatin, docetaxel, erlotinib, fluoropyrimidine, gemcitabine, irinotecan, leucovorin, oxaliplatin, paclitaxel, and any combinations thereof.

Renal Cell Carcinoma Combination Therapy

Therapeutic agents used to treat renal cell carcinoma include axitinib, bevacizumab, cabozantinib, erlotinib, everolimus, levantinib, nivolumab, pazopanib, sorafenib, sunitinib, temsirolimus, and any combinations thereof.

Serum Half-Life-Extending Fc Mutations

In some embodiments, the Fc region or Fc domain of the directed antibody comprise amino acid modifications that promote an increased serum half-life of the anti-binding molecule. Mutations that increase the half-life of an antibody have been described. In one embodiment, the Fc region or Fc domain of one or both of the CD3-targeting heavy chain and the HIV antigen-targeting heavy chain comprise a methionine to tyrosine substitution at position 252 (EU numbering), a serine to threonine substitution at position 254 (EU numbering), and a threonine to glutamic acid substitution at position 256 (EU numbering). See, e.g., U.S. Pat. No. 7,658,921. This type of mutant, designated as a "YTE mutant" exhibits a four-fold increased half-life relative to wild-type versions of the same antibody (Dall'Acqua, et al., J Biol Chem, 281: 23514-24 (2006); Robbie, et al., Antimicrob Agents Chemotherap., 57(12):6147-6153 (2013)). In certain embodiments, the Fc region or Fc domain of one or both of the CD3-targeting heavy chain and the HIV antigen-targeting heavy chain comprise an IgG constant domain comprising one, two, three or more amino acid substitutions of amino acid residues at positions 251-257, 285-290, 308-314, 385-389, and 428-436 (EU numbering). Alternatively, M428L and N434S ("LS") substitutions can increase the pharmacokinetic half-life of the multi-specific antigen binding molecule. In other embodiments, the Fc region or Fc domain of one or both of the CD3-targeting heavy chain and the HIV antigen-targeting heavy chain comprise a M428L and N434S substitution (EU numbering). In other embodiments, the Fc region or Fc domain of one or both of the CD3-targeting heavy chain and the HIV antigen-targeting heavy chain comprise T250Q and M428L (EU numbering) mutations. In other embodiments, the Fc region or Fc domain of one or both of the CD3-targeting heavy chain and the HIV antigen-targeting heavy chain comprise H433K and N434F (EU numbering) mutations.

Effector Enhancing Fc Mutations

In some embodiments, the Fc region or Fe domain of the antibody comprise post-translational and/or amino acid modifications that increase effector activity, e.g., have improved FcγIIIa binding and increased antibody-dependent cellular cytotoxicity (ADCC). In some embodiments, the Fc region or Fe domain of the antibody comprises DE modifications (i.e., S239D and I332E by EU numbering) in the Fc region. In some embodiments, the Fc region or Fe domain of the antibody comprises DEL modifications (i.e., S239D, I332E and A330L by EU numbering) in the Fc region. In some embodiments, the Fc region or Fe domain of the antibody comprises DEA modifications (i.e., S239D, I332E and G236A by EU numbering) in the Fc region. In some embodiments, the Fc region or Fe domain of the antibody comprises DEAL modifications (i.e., S239D, I332E, G236A and A330L by EU numbering) in the Fc region. See, e.g., U.S. Pat. Nos. 7,317,091; 7,662,925; 8,039,592; 8,093,357; 8,093,359; 8,383,109; 8,388,955; 8,735,545; 8,858,937; 8,937,158; 9,040,041; 9,353,187; 10,184,000; and 10,584,176. Additional amino acid modifications that increase effector activity, e.g., have improved FcγIIIa binding and increased antibody-dependent cellular cytotoxicity (ADCC) include without limitation (EU numbering) F243L/R292P/Y300L/V305I/P396L; S298A/E333A/K334A; or L234Y/L235Q/G236W/S239M/H268D/D270E/S298A on a first Fe domain and D270E/K326D/A330M/K334E on a second Fe domain. Amino acid mutations that increase C1q binding and complement-dependent cytotoxicity (CDC) include without limitation (EU numbering) S267E/H268F/S324T or K326W/E333S. Fc region mutations that enhance effector activity are reviewed in, e.g., Wang, et al., *Protein Cell* (2018) 9(1): 63-73; and Saunders, *Front Immunol.* (2019) 10:1296.

In other embodiments, the antibody or antigen-binding fragment thereof has modified glycosylation, which, e.g., may be introduced post-translationally or through genetic engineering. In some embodiments, the antibody or antigen-binding fragment thereof is afucosylated, e.g., at a glycosylation site present in the antibody or antigen-binding fragment thereof. Most approved monoclonal antibodies are of the IgG1 isotype, where two N-linked biantennary complex-type oligosaccharides are bound to the Fc region. The Fc region exercises the effector function of ADCC through its interaction with leukocyte receptors of the FcγR family. Afucosylated monoclonal antibodies are monoclonal antibodies engineered so that the oligosaccharides in the Fc region of the antibody do not have any fucose sugar units.

2. Human Immunodeficiency Virus (HIV)

In some embodiments, the agents described herein are combined with an HIV combination drug. Examples of combination drugs that can be employed with an agent of this disclosure include ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); darunavir, tenofovir alafenamide hemifumarate, emtricitabine, and cobicistat; efavirenz, lamivudine, and tenofovir disoproxil fumarate; lamivudine and tenofovir disoproxil fumarate; tenofovir and lamivudine; tenofovir alafenamide and emtricitabine; tenofovir alafenamide hemifumarate and emtricitabine; tenofovir alafenamide hemifumarate, emtricitabine, and rilpivirine; tenofovir alafenamide hemifumarate, emtricitabine, cobicistat, and elvitegravir; COMBIVIR® (zidovudine and lamivudine; AZT+3TC); EPZICOM® (LIVEXA®; abacavir sulfate and lamivudine; ABC+3TC); KALETRA® (ALUVIA®; lopinavir and ritonavir); TRIUMEQ® (dolutegravir, abacavir, and lamivudine); BIKTARVY (bictegravir+emtricitabine+tenofovir alafenamide), DOVATO, TRIZIVIR® (abacavir sulfate, zidovudine, and lamivudine; ABC+AZT+3TC); atazanavir and cobicistat; atazanavir sulfate and cobicistat; atazanavir sulfate and ritonavir; darunavir and cobicistat; dolutegravir and rilpivirine; dolutegravir and rilpivirine hydrochloride; dolutegravir, abacavir sulfate, and lamivudine; lamivudine, nevirapine, and zidovudine; raltegravir and lamivudine; doravirine, lamivudine, and tenofovir disoproxil fumarate; doravirine, lamivudine, and tenofovir disoproxil; dolutegravir+lamivudine, lamivudine+abacavir+zidovudine, lamivudine+abacavir, lamivudine+tenofovir disoproxil fumarate, lamivudine+zidovudine+nevirapine, lopinavir+ritonavir, lopinavir+ritonavir+abacavir+lamivudine, lopinavir+ritonavir+zidovudine+lamivudine, tenofovir+lamivudine, and tenofovir disoproxil fumarate+emtricitabine+rilpivirine hydrochloride, lopinavir, ritonavir, zidovudine and lamivudine; cabotegravir+rilpivirine; elpida (elsulfavirine; VM-1500; VM-1500A).

Examples of other drugs for treating HIV that can be combined with an agent of this disclosure include acemannan, alisporivir, BanLec, deferiprone, Gamimune, metenkefalin, naltrexone, Prolastin, REP 9, RPI-MN, VSSP, Hlviral, SB-728-T, 1,5-dicaffeoylquinic acid, rHIV7-shl-TAR-CCR5RZ, AAV-eCD4-Ig gene therapy, MazF gene therapy, BlockAide, ABX-464, AG-1105, APH-0812, BIT-225, CYT-107, HGTV-43, HPH-116, HS-10234, IMO-3100, IND-02, MK-1376, MK-2048, MK-4250, MK-8507, MK-8591, NOV-205, PA-1050040 (PA-040), PGN-007, SCY-635, SB-9200, SCB-719, TR-452, TEV-90110, TEV-90112, TEV-90111, TEV-90113, RN-18, Immuglo, and VIR-576.

HIV Protease Inhibitors

In some embodiments, the agents described herein are combined with an HIV protease inhibitor. Examples of HIV protease inhibitors that can be combined with an agent of this disclosure include amprenavir, atazanavir, brecanavir, darunavir, fosamprenavir, fosamprenavir calcium, indinavir, indinavir sulfate, lopinavir, nelfinavir, nelfinavir mesylate, ritonavir, saquinavir, saquinavir mesylate, tipranavir, DG-17, TMB-657 (PPL-100), T-169, BL-008, MK-8122, TMB-607, and TMC-310911.

HIV Reverse Transcriptase Inhibitors

In some embodiments, the agents described herein are combined with a non-nucleoside or non-nucleotide inhibitor. Examples of HIV non-nucleoside or non-nucleotide inhibitors of reverse transcriptase that can be combined with an agent of this disclosure include dapivirine, delavirdine, delavirdine mesylate, doravirine, efavirenz, etravirine, lentinan, nevirapine, rilpivirine, ACC-007, AIC-292, KM-023, PC-1005, and elsulfavirine (VM-1500).

In some embodiments, the agents described herein are combined with an HIV nucleoside or nucleotide inhibitor. Examples of HIV nucleoside or nucleotide inhibitors of reverse transcriptase that can be combined with an agent of this disclosure include adefovir, adefovir dipivoxil, azvudine, emtricitabine, tenofovir, tenofovir alafenamide, tenofovir alafenamide fumarate, tenofovir alafenamide hemifumarate, tenofovir disoproxil, tenofovir disoproxil fumarate, tenofovir disoproxil hemifumarate, VIDEX® and VIDEX EC® (didanosine, ddI), abacavir, abacavir sulfate, alovudine, apricitabine, censavudine, didanosine, elvucitabine, festinavir, fosalvudine tidoxil, CMX-157, dapivirine, doravirine, etravirine, OCR-5753, tenofovir disoproxil orotate, fozivudine tidoxil, lamivudine, phosphazid, stavudine, zalcitabine, zidovudine, rovafovir etalafenamide (GS-9131), GS-9148, MK-8504, MK-8591, MK-8583, VM-2500 and KP-1461.

HIV Integrase Inhibitors

In some embodiments, the agents described herein are combined with an HIV integrase inhibitor. Examples of HIV integrase inhibitors that can be combined with an agent of this disclosure include elvitegravir, curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, raltegravir, dolutegravir, JTK-351, bictegravir, AVX-15567, cabotegravir (long-acting injectable), diketo quinolin-4-1 derivatives, integrase-LEDGF inhibitor, ledgins, M-522, M-532, NSC-310217, NSC-371056, NSC-48240, NSC-642710, NSC-699171, NSC-699172, NSC-699173, NSC-699174, stilbenedisulfonic acid, T-169, VM-3500 and cabotegravir.

In some embodiments, the agents described herein are combined with a HIV non-catalytic site, or allosteric, integrase inhibitor (NCINI). Examples of HIV non-catalytic site, or allosteric, integrase inhibitors (NCINI) that can be combined with an agent of this disclosure include CX-05045, CX-05168, and CX-14442.

HIV Entry Inhibitors

In some embodiments, the agents described herein are combined with an HIV entry inhibitor. Examples of HIV entry (fusion) inhibitors that can be combined with an agent of this disclosure include cenicriviroc, CCR5 inhibitors, gp41 inhibitors, CD4 attachment inhibitors, gp120 inhibitors, and CXCR4 inhibitors.

In some embodiments, the agents described herein are combined with a CCR5 inhibitor. Examples of CCR5 inhibitors that can be combined with an agent of this disclosure include aplaviroc, vicriviroc, maraviroc, cenicriviroc, leronlimab (PRO-140), adaptavir (RAP-101), nifeviroc (TD-0232), anti-GP120/CD4 or CCR5 bispecific antibodies, B-07, MB-66, polypeptide C25P, TD-0680, and vMIP (Haimipu).

In some embodiments, the agents described herein are combined with a gp41 inhibitor. Examples of gp41 inhibitors that can be combined with an agent of this disclosure include albuvirtide, enfuvirtide, BMS-986197, enfuvirtide biobetter, enfuvirtide biosimilar, HIV-1 fusion inhibitors (P26-Bapc), ITV-1, ITV-2, ITV-3, ITV-4, PIE-12 trimer and sifuvirtide.

In some embodiments, the agents are combined with a CD4 attachment inhibitor. Examples of CD4 attachment inhibitors that can be combined with an agent of this disclosure include ibalizumab and CADA analogs.

In some embodiments, the agents described herein are combined with a gp120 inhibitor. Examples of gp120 inhibitors that can be combined with an agent of this disclosure include Radha-108 (receptol) 3B3-PE38, BanLec, bentonite-based nanomedicine, fostemsavir tromethamine, IQP-0831, and BMS-663068.

In some embodiments, the agent described herein are combined with a CXCR4 inhibitor. Examples of CXCR4 inhibitors that can be combined with an agent of this disclosure include plerixafor, ALT-1188, N15 peptide, and vMIP (Haimipu).

In some embodiments, the agents described herein are combined with a HIV maturation inhibitor. Examples of HIV maturation inhibitors that can be combined with an agent of this disclosure include BMS-955176, GSK-3640254 and GSK-2838232.

Latency Reversing Agents

In some embodiments, the agents described herein are combined with a latency reversing agent (LRA). Examples of latency reversing agents that can be combined with an agent of this disclosure include toll-like receptor (TLR) agonists (including TLR7 agonists, e.g., GS-9620), histone deacetylase (HDAC) inhibitors, proteasome inhibitors such as velcade, protein kinase C (PKC) activators, Smyd2 inhibitors, BET-bromodomain 4 (BRD4) inhibitors, ionomycin, IAP antagonists (inhibitor of apoptosis proteins, such as APG-1387, LBW-242), SMAC mimetics (including TL32711, LCL161, GDC-0917, HGS1029, AT-406), PMA, SAHA (suberanilohydroxamic acid, or suberoyl, anilide, and hydroxamic acid), NIZ-985, IL-15 modulating antibodies (including IL-15, IL-15 fusion proteins and IL-15 receptor agonists), JQ1, disulfiram, amphotericin B, and ubiquitin inhibitors such as largazole analogs, APH-0812, and GSK-343. Examples of PKC activators include indolactam, prostratin, ingenol B, and DAG-lactones.

Histone Deacetylase (HDAC) Inhibitors

In some embodiments, the agents as described herein are combined with an inhibitor of a histone deacetylase, e.g., histone deacetylase 9 (HDAC9, HD7, HD7b, HD9, HDAC, HDAC7, HDAC7B, HDAC9B, HDAC9FL, HDRP, MITR; Gene ID: 9734). Examples of HDAC inhibitors include without limitation, abexinostat, ACY-241, AR-42, BEBT-908, belinostat, CKD-581, CS-055 (HIBI-8000), CUDC-907 (fimepinostat), entinostat, givinostat, mocetinostat, panobinostat, pracinostat, quisinostat (JNJ-26481585), resminostat, ricolinostat, romidepsin, SHP-141, valproic acid (VAL-001), vorinostat, tinostamustine, remetinostat, entinostat.

Capsid Inhibitor

In some embodiments, the agents described herein are combined with a capsid inhibitor. Examples of capsid inhibitors that can be combined with an agent of this disclosure include capsid polymerization inhibitors or capsid disrupting compounds, HIV nucleocapsid p7 (NCp7) inhibitors such as azodicarbonamide, HIV p24 capsid protein inhibitors, GS-6207, GS-CA1, AVI-621, AVI-101, AVI-201, AVI-301, and AVI-CAN1-15 series, and compounds described in this patent (GSK WO2019/087016)

Immune Checkpoint Modulators

In some embodiments, the agents as described herein, are combined with one or more blockers or inhibitors of inhibitory immune checkpoint proteins or receptors and/or with one or more stimulators, activators or agonists of one or more stimulatory immune checkpoint proteins or receptors. Blockade or inhibition of inhibitory immune checkpoints can positively regulate T-cell or NK cell activation and prevent immune escape of infected cells. Activation or stimulation of stimulatory immune check points can augment the effect of immune checkpoint inhibitors in infective therapeutics. In some embodiments, the immune checkpoint proteins or receptors regulate T cell responses (e.g., reviewed in Xu, et al., *J Exp Clin Cancer Res.* (2018) 37:110). In some embodiments, the immune checkpoint proteins or receptors regulate NK cell responses (e.g., reviewed in Davis, et al., *Semin Immunol.* (2017) 31:64-75 and Chiossone, et al., *Nat Rev Immunol.* (2018) 18(11):671-688).

Examples of immune checkpoint proteins or receptors include without limitation CD27, CD70; CD40, CD40LG; CD47, CD48 (SLAMF2), transmembrane and immunoglobulin domain containing 2 (TMIGD2, CD28H), CD84 (LY9B, SLAMF5), CD96, CD160, MS4A1 (CD20), CD244 (SLAMF4); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); natural killer cell cytotoxicity receptor 3 ligand 1 (NCR3LG1, B7H6); HERV-H LTR-associating 2 (HHLA2, B7H7); inducible T cell co-stimulator (ICOS, CD278); inducible T cell costimulator ligand (ICOSLG, B7H2); TNF receptor superfamily member 4 (TNFRSF4, OX40); TNF superfamily member 4 (TNFSF4, OX40L); TNFRSF8 (CD30), TNFSF8 (CD30L); TNFRSF10A (CD261, DR4, TRAILR1), TNFRSF9 (CD137), TNFSF9 (CD137L); TNFRSF10B (CD262, DR5, TRAILR2), TNFRSF10 (TRAIL); TNFRSF14 (HVEM, CD270), TNFSF14 (HVEML); CD272 (B and T lymphocyte associated (BTLA)); TNFRSF17 (BCMA, CD269), TNFSF13B (BAFF); TNFRSF18 (GITR), TNFSF18 (GITRL); MHC class I polypeptide-related sequence A (MICA); MHC class I polypeptide-related sequence B (MICB); CD274 (CD274, PDL1, PD-L1); programmed cell death 1 (PDCD1, PD1, PD-1); cytotoxic T-lymphocyte associated protein 4 (CTLA4, CD152); CD80 (B7-1), CD28; nectin cell adhesion molecule 2 (NECTIN2, CD112); CD226 (DNAM-1); Poliovirus receptor (PVR) cell adhesion molecule (PVR, CD155); PVR related immunoglobulin domain containing (PVRIG, CDI 12R); T cell immunoreceptor with Ig and ITIM domains (TIGIT); T cell immunoglobulin and mucin domain containing 4 (TIMD4; TIM4); hepatitis A virus cellular receptor 2 (HAVCR2, TIMD3, TIM3); galectin 9 (LGALS9); lymphocyte activating 3 (LAG3, CD223); signaling lymphocytic activation molecule family member 1 (SLAMF1, SLAM, CD150); lymphocyte antigen 9 (LY9, CD229, SLAMF3); SLAM family member 6 (SLAMF6, CD352); SLAM family member 7 (SLAMF7, CD319); UL16 binding protein 1 (ULBP1); UL16 binding protein 2 (ULBP2); UL16 binding protein 3 (ULBP3); retinoic acid early transcript 1E (RAET1E; ULBP4); retinoic acid early transcript 1G (RAET1G; ULBP5); retinoic acid early transcript 1L (RAETIL; ULBP6); lymphocyte activating 3 (CD223); killer cell immunoglobulin like receptor, three Ig domains and long cytoplasmic tail 1 (KIR, CD158E1); killer cell lectin like receptor C1 (KLRC1, NKG2A, CD159A); killer cell lectin like receptor K1 (KLRK1, NKG2D, CD314); killer cell lectin like receptor C2 (KLRC2, CD159c, NKG2C); killer cell lectin like receptor C3 (KLRC3, NKG2E); killer cell lectin like receptor C4 (KLRC4, NKG2F); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor D1 (KLRD1); and SLAM family member 7 (SLAMF7).

In some embodiments, the agents described herein, are combined with one or more blockers or inhibitors of one or more T-cell inhibitory immune checkpoint proteins or receptors. Illustrative T-cell inhibitory immune checkpoint proteins or receptors include without limitation CD274 (CD274, PDL1, PD-L1); programmed cell death 1 ligand 2 (PDCDILG2, PD-L2, CD273); programmed cell death 1 (PDCD1, PD1, PD-1); cytotoxic T-lymphocyte associated protein 4 (CTLA4, CD152); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); TNFRSF14 (HVEM, CD270), TNFSF14 (HVEML); CD272 (B and T lymphocyte associated (BTLA)); PVR related immunoglobulin domain containing (PVRIG, CDI 12R); T cell immunoreceptor with Ig and ITIM domains (TIGIT); lymphocyte activating 3 (LAG3, CD223); hepatitis A virus cellular receptor 2 (HAVCR2, TIMD3, TIM3); galectin 9 (LGALS9); killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); and killer cell immunoglobulin like receptor, three Ig domains and long cytoplasmic tail 1 (KIR3DL1). In some embodiments, the agents, as described herein, are combined with one or more agonist or activators of one or more T-cell stimulatory immune checkpoint proteins or receptors. Illustrative T-cell stimulatory immune checkpoint proteins or receptors include without limitation CD27, CD70; CD40, CD40LG; inducible T cell costimulator (ICOS, CD278); inducible T cell costimulator ligand (ICOSLG, B7H2); TNF receptor superfamily member 4 (TNFRSF4, OX40); TNF superfamily member 4 (TNFSF4, OX40L); TNFRSF9 (CD137), TNFSF9 (CD137L); TNFRSF18 (GITR), TNFSF18 (GITRL); CD80 (B7-1), CD28; nectin cell adhesion molecule 2 (NECTIN2, CD112); CD226 (DNAM-1); CD244 (2B4, SLAMF4), Poliovirus receptor (PVR) cell adhesion molecule (PVR, CD155). See, e.g., Xu, et al., *J Exp Clin Cancer Res.* (2018) 37:110.

In some embodiments, the agents as described herein, are combined with one or more blockers or inhibitors of one or more NK-cell inhibitory immune checkpoint proteins or receptors. Illustrative NK-cell inhibitory immune checkpoint proteins or receptors include without limitation killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor C1 (KLRC1, NKG2A, CD159A); and killer cell lectin like receptor D1 (KLRD1, CD94). In some embodiments, the agents as described herein, are combined with one or more agonist or activators of one or more NK-cell stimulatory immune checkpoint proteins or receptors. Illustrative NK-cell stimulatory immune checkpoint proteins or receptors include without limitation CD16, CD226 (DNAM-1); CD244 (2B4, SLAMF4); killer cell lectin like receptor K1 (KLRK1, NKG2D, CD314); SLAM family member 7 (SLAMF7). See, e.g., Davis, et al., *Semin Immunol*. (2017) 31:64-75; Fang, et al., *Semin Immunol*. (2017) 31:37-54; and Chiossone, et al., *Nat Rev Immunol*. (2018) 18(11):671-688.

In some embodiments, the one or more immune checkpoint inhibitors comprises a proteinaceous (e.g., antibody or fragment thereof, or antibody mimetic) inhibitor of PD-L1 (CD274), PD-1 (PDCD1) or CTLA4. In some embodiments, the one or more immune checkpoint inhibitors comprises a small organic molecule inhibitor of PD-L1 (CD274), PD-1 (PDCD1) or CTLA4. In some embodiments, the small molecule inhibitor of CD274 or PDCD1 is selected from the group consisting of GS-4224, GS-4416, INCB086550 and MAX10181. In some embodiments, the small molecule inhibitor of CTLA4 comprises BPI-002.

Examples of inhibitors of CTLA4 that can be co-administered include without limitation ipilimumab, tremelimumab, BMS-986218, AGEN1181, AGEN1884, BMS-986249, MK-1308, REGN-4659, ADU-1604, CS-1002, BCD-145, APL-509, JS-007, BA-3071, ONC-392, AGEN-2041, JHL-1155, KN-044, CG-0161, ATOR-1144, PBI-5D3H5, BPI-002, as well as multi-specific inhibitors FPT-155 (CTLA4/PD-L1/CD28), PF-06936308 (PD-1/CTLA4), MGD-019 (PD-1/CTLA4), KN-046 (PD-1/CTLA4), MEDI-5752 (CTLA4/PD-1), XmAb-20717 (PD-1/CTLA4), and AK-104 (CTLA4/PD-1).

Examples of inhibitors of PD-L1 (CD274) or PD-1 (PDCD1) that can be co-administered include without limitation pembrolizumab, nivolumab, cemiplimab, pidilizumab, AMP-224, MEDI0680 (AMP-514), spartalizumab, atezolizumab, avelumab, durvalumab, BMS-936559, CK-301, PF-06801591, BGB-A317 (tislelizumab), GLS-010 (WBP-3055), AK-103 (HX-008), AK-105, CS-1003, HLX-10, MGA-012, BI-754091, AGEN-2034, JS-001 (toripalimab), JNJ-63723283, genolimzumab (CBT-501), LZM-009, BCD-100, LY-3300054, SHR-1201, SHR-1210 (camrelizumab), Sym-021, ABBV-181, PD1-PIK, BAT-1306, (MSB0010718C), CX-072, CBT-502, TSR-042 (dostarlimab), MSB-2311, JTX-4014, BGB-A333, SHR-1316, CS-1001 (WBP-3155, KN-035, IBI-308 (sintilimab), HLX-20, KL-A167, STI-A1014, STI-A1015 (IMC-001), BCD-135, FAZ-053, TQB-2450, MDX1105-01, GS-4224, GS-4416, INCB086550, MAX10181, as well as multi-specific inhibitors FPT-155 (CTLA4/PD-L1/CD28), PF-06936308 (PD-1/CTLA4), MGD-013 (PD-1/LAG-3), FS-118 (LAG-3/PD-L1) MGD-019 (PD-1/CTLA4), KN-046 (PD-1/CTLA4), MEDI-5752 (CTLA4/PD-1), RO-7121661 (PD-1/TIM-3), XmAb-20717 (PD-1/CTLA4), AK-104 (CTLA4/PD-1), M7824 (PD-L1/TGFβ-EC domain), CA-170 (PD-L1/VISTA), CDX-527 (CD27/PD-L1), LY-3415244 (TIM3/PDL1), and INBRX-105 (4-1BB/PDL1).

In some embodiments, the agents as described herein are combined with anti-TIGIT antibodies, such as BMS-986207, RG-6058, AGEN-1307

TNF Receptor Superfamily (TNFRSF) Member Agonists or Activators

In some embodiments, the agents as described herein are combined with an agonist of one or more TNF receptor superfamily (TNFRSF) members, e.g., an agonist of one or more of TNFRSF1A (NCBI Gene ID: 7132), TNFRSF1B (NCBI Gene ID: 7133), TNFRSF4 (OX40, CD134; NCBI Gene ID: 7293), TNFRSF5 (CD40; NCBI Gene ID: 958), TNFRSF6 (FAS, NCBI Gene ID: 355), TNFRSF7 (CD27, NCBI Gene ID: 939), TNFRSF8 (CD30, NCBI Gene ID: 943), TNFRSF9 (4-1BB, CD137, NCBI Gene ID: 3604), TNFRSF10A (CD261, DR4, TRAILR1, NCBI Gene ID: 8797), TNFRSF10B (CD262, DR5, TRAILR2, NCBI Gene ID: 8795), TNFRSF10C (CD263, TRAILR3, NCBI Gene ID: 8794), TNFRSF10D (CD264, TRAILR4, NCBI Gene ID: 8793), TNFRSF11A (CD265, RANK, NCBI Gene ID: 8792), TNFRSF11B (NCBI Gene ID: 4982), TNFRSF12A (CD266, NCBI Gene ID: 51330), TNFRSF13B (CD267, NCBI Gene ID: 23495), TNFRSF13C (CD268, NCBI Gene ID: 115650), TNFRSF16 (NGFR, CD271, NCBI Gene ID: 4804), TNFRSF17 (BCMA, CD269, NCBI Gene ID: 608), TNFRSF18 (GITR, CD357, NCBI Gene ID: 8784), TNFRSF19 (NCBI Gene ID: 55504), TNFRSF21 (CD358, DR6, NCBI Gene ID: 27242), and TNFRSF25 (DR3, NCBI Gene ID: 8718).

Example anti-TNFRSF4 (OX40) antibodies that can be co-administered include without limitation, MEDI6469, MEDI6383, MEDI0562 (tavolixizumab), MOXR0916, PF-04518600, RG-7888, GSK-3174998, INCAGN1949, BMS-986178, GBR-8383, ABBV-368, and those described in WO2016179517, WO2017096179, WO2017096182, WO2017096281, and WO2018089628.

Example anti-TNFRSF5 (CD40) antibodies that can be co-administered include without limitation RG7876, SEA-CD40, APX-005M and ABBV-428.

In some embodiments, the anti-TNFRSF7 (CD27) antibody varlilumab (CDX-1127) is co-administered.

Example anti-TNFRSF9 (4-1BB, CD137) antibodies that can be co-administered include without limitation urelumab, utomilumab (PF-05082566), AGEN2373 and ADG-106.

Example anti-TNFRSF18 (GITR) antibodies that can be co-administered include without limitation, MEDI1873, FPA-154, INCAGN-1876, TRX-518, BMS-986156, MK-1248, GWN-323, and those described in WO2017096179, WO2017096276, WO2017096189, and WO2018089628. In some embodiments, an antibody, or fragment thereof, co-targeting TNFRSF4 (OX40) and TNFRSF18 (GITR) is co-administered. Such antibodies are described, e.g., in WO2017096179 and WO2018089628.

Bi- and Tri-Specific Natural Killer (NK)-Cell Engagers

In some embodiments, the agents as described herein, are combined with a bi-specific NK-cell engager (BiKE) or a tri-specific NK-cell engager (TriKE) (e.g., not having an Fc) or bi-specific antibody (e.g., having an Fc) against an NK cell activating receptor, e.g., CD16A, C-type lectin receptors (CD94/NKG2C, NKG2D, NKG2E/H and NKG2F), natural cytotoxicity receptors (NKp30, NKp44 and NKp46), killer cell C-type lectin-like receptor (NKp65, NKp80), Fc receptor FcTR (which mediates antibody-dependent cell cytotoxicity), SLAM family receptors (e.g., 2B4, SLAM6 and SLAM7), killer cell immunoglobulin-like receptors (KIR) (KIR-2DS and KIR-3DS), DNAM-1 and CD137 (41BB). As appropriate, the anti-CD16 binding bi-specific molecules may or may not have an Fc. Illustrative bi-specific NK-cell engagers that can be co-administered target CD16 and one or more HIV-associated antigens as described herein. BiKEs and TriKEs are described, e.g., in Felices, et al., *Methods Mol Biol*. (2016) 1441:333-346; Fang, et al., *Semin Immunol*. (2017) 31:37-54. Examples of a trispecific NK cell engager (TRiKE) include OXS-3550, and CD16-IL-15-B7H3 TriKe.

Indoleamine-Pyrrole-2,3-Dioxygenase (IDO1) Inhibitors

In some embodiments, the agents as described herein, are combined with an inhibitor of indoleamine 2,3-dioxygenase 1 (IDO1; NCBI Gene ID: 3620). Examples of IDO1 inhibitors include without limitation, BLV-0801, epacadostat, F-001287, GBV-1012, GBV-1028, GDC-0919, indoximod, NKTR-218, NLG-919-based vaccine, PF-06840003, pyranonaphthoquinone derivatives (SN-35837), resminostat, SBLK-200802, BMS-986205, and shIDO-ST, EOS-200271, KHK-2455, LY-3381916.

Toll-Like Receptor (TLR) Agonists

In some embodiments, the agents as described herein, are combined with an agonist of a toll-like receptor (TLR), e.g., an agonist of TLR1 (NCBI Gene ID: 7096), TLR2 (NCBI Gene ID: 7097), TLR3 (NCBI Gene ID: 7098), TLR4 (NCBI Gene ID: 7099), TLR5 (NCBI Gene ID: 7100), TLR6 (NCBI Gene ID: 10333), TLR7 (NCBI Gene ID: 51284), TLR8 (NCBI Gene ID: 51311), TLR9 (NCBI Gene ID: 54106), and/or TLR10 (NCBI Gene ID: 81793). Example TLR7 agonists that can be co-administered include without limitation AL-034, DSP-0509, GS-9620 (vesatolimod), LHC-165, TMX-101 (imiquimod), GSK-2245035, resiquimod, DSR-6434, DSP-3025, IMO-4200, MCT-465, MEDI-9197, 3M-051, SB-9922, 3M-052, Limtop, TMX-30X, TMX-202, RG-7863, RG-7854, RG-7795, and the compounds disclosed in US20100143301 (Gilead Sciences), US20110098248 (Gilead Sciences), and US20090047249 (Gilead Sciences), US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), and US20130251673 (Novira Therapeutics). An TLR7/TLR8 agonist that can be co-administered is NKTR-262, telratolimod and BDB-001. Example TLR8 agonists that can be co-administered include without limitation E-6887, IMO-4200, IMO-8400, IMO-9200, MCT-465, MEDI-9197, motolimod, resiquimod, GS-9688, VTX-1463, VTX-763, 3M-051, 3M-052, and the compounds disclosed in US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), and US20130251673 (Novira Therapeutics). Example TLR9 agonists that can be co-administered include without limitation AST-008, cobitolimod, CMP-001, IMO-2055, IMO-2125, litenimod, MGN-1601, BB-001, BB-006, IMO-3100, IMO-8400, IR-103, IMO-9200, agatolimod, DIMS-9054, DV-1079, DV-1179, AZD-1419, lefitolimod (MGN-1703), CYT-003, CYT-003-QbG10, tilsotolimod and PUL-042. Examples of TLR3 agonist include rintatolimod, poly-ICLC, RIBOXXON®, Apoxxim, RIBOXXIM®, IPH-33, MCT-465, MCT-475, and ND-1.1. Examples of TLR4 agonist include G-100, and GSK-1795091.

STING Agonists, RIG-I and NOD2 Modulators

In some embodiments, the agents described herein are combined with a stimulator of interferon genes (STING). In some embodiments, the STING receptor agonist or activator is selected from the group consisting of ADU-S100 (MIW-815), SB-11285, MK-1454, SR-8291, AdVCA0848, GSK-532, SYN-STING, MSA-1, SR-8291, 5,6-dimethylxanthenone-4-acetic acid (DMXAA), cyclic-GAMP (cGAMP) and cyclic-di-AMP. In some embodiments, the agents described herein are combined with a RIG-I modulator such as RGT-100, or NOD2 modulator, such as SB-9200, and IR-103.

LAG-3 and TIM-3 Inhibitors

In some embodiments, the agents as described herein are combined with an anti-TIM-3 antibody, such as TSR-022, LY-3321367, MBG-453, INCAGN-2390.

In some embodiments, the antibodies or antigen-binding fragments described herein are combined with an anti LAG-3 (Lymphocyte-activation) antibody, such as relatlimab (ONO-4482), LAG-525, MK-4280, REGN-3767, INCAGN2385.

Interleukin Agonists

In some embodiments, the agents described herein are combined with an interleukin agonist, such as IL-2, IL-7, IL-15, IL-10, IL-12 agonists; examples of IL-2 agonists such as proleukin (aldesleukin, IL-2); pegylated IL-2 (eg NKTR-214); modified variants of IL-2 (eg THOR-707), bempegaldesleukin, AIC-284, ALKS-4230, CUI-101, Neo-2/15; examples of IL-15 agonists, such as ALT-803, NKTR-255, and hetIL-15, interleukin-15/Fc fusion protein, AM-0015, NIZ-985, SO-C101, IL-15 Synthorin (pegylated Il-15), P-22339, and a IL-15-PD-1 fusion protein N-809; examples of IL-7 include CYT-107.

Examples of additional immune-based therapies that can be combined with an agent of this disclosure include interferon alfa; interferon alfa-2b; interferon alfa-n3; pegylated interferon alfa; interferon gamma; Flt3 agonists; gepon; normferon, peginterferon alfa-2a, peginterferon alfa-2b, RPI-MN.

Phosphatidylinositol 3-Kinase (PI3K) Inhibitors

In some embodiments, the agents described herein are combined with a PI3K inhibitor. Examples of PI3K inhibitors that can be combined with an agent of this disclosure include idelalisib, alpelisib, buparlisib, CAI orotate, copanlisib, duvelisib, gedatolisib, neratinib, panulisib, perifosine, pictilisib, pilaralisib, puquitinib mesylate, rigosertib, rigosertib sodium, sonolisib, taselisib, AMG-319, AZD-8186, BAY-1082439, CLR-1401, CLR-457, CUDC-907, DS-7423, EN-3342, GSK-2126458, GSK-2269577, GSK-2636771, INCB-040093, LY-3023414, MLN-1117, PQR-309, RG-7666, RP-6530, RV-1729, SAR-245409, SAR-260301, SF-1126, TGR-1202, UCB-5857, VS-5584, XL-765, and ZSTK-474.

Alpha-4/Beta-7 Antagonists

In some embodiments, the agents described herein are combined with an alpha-4/beta-7 antagonist. Examples of Integrin alpha-4/beta-7 antagonists that can be combined with an agent of this disclosure include PTG-100, TRK-170, abrilumab, etrolizumab, carotegrast methyl, and vedolizumab.

HIV Targeting Antibodies

Examples of HIV antibodies, bispecific antibodies, and "antibody-like" therapeutic proteins that can be combined with an agent of this disclosure include DARTs®, DUO-BODIES®, BITES®, XmAbs®, TandAbs®, Fab derivatives, bNAbs (broadly neutralizing HIV-1 antibodies), TMB-360, and those targeting HIV gp120 or gp41, antibody-Recruiting Molecules targeting HIV, anti-CD63 monoclonal antibodies, anti-GB virus C antibodies, anti-GP120/ CD4, CCR5 bispecific antibodies, anti-Nef single domain antibodies, anti-Rev antibody, camelid derived anti-CD18 antibodies, camelid-derived anti-ICAM-1 antibodies, DCVax-001, gp140 targeted antibodies, gp41-based HIV therapeutic antibodies, human recombinant mAbs (PGT-121), ibalizumab, Immuglo, MB-66.

Various bNAbs are known in the art and may be used in this invention. Examples include, but are not limited to, those described in U.S. Pat. Nos. 8,673,307, 9,493,549, 9,783,594, WO2014/063059, WO2012/158948, WO2015/117008, and PCT/US2015/41272, and WO2017/096221, including antibodies 12A12, 12A21, NIH45-46, bANC131, 8ANC134, 132530, INC9, 8ANC195. 8ANC196, 10-259, 10-303, 10-410, 10-847, 10-996, 10-1074, 10-1121, 10-1130, 10-1146, 10-1341, 10-1369, and 10-1074GM. Additional examples include those described in Klein et al., Nature, 492(7427): 118-22 (2012), Horwitz et al., Proc Natl Acad Sci USA, 110(41): 16538-43 (2013), Scheid, et al., Science, 333: 1633-1637 (2011), Scheid, et al., Nature, 458:636-640 (2009), Eroshkin et al, Nucleic Acids Res., 42 (Database issue):Dl 133-9 (2014), Mascola et al., Immunol Rev., 254(1):225-44 (2013), such as 2F5, 4E10, M66.6, CAP206-CH12, 10E81 (all of which bind the MPER of gp41); PG9, PG16, CHO1-04 (all of which bind V1V2-glycan), 2G12 (which binds to outer domain glycan); b12, HJ16, CH103-106, VRC01-03, VRC-PG04, 04b, VRC-CH30-34, 3BNC62, 3BNC89, 3BNC91, 3BNC95, 3BNC104, 3BNC176, and 8ANC131 (all of which bind to the CD4 binding site).

Additional broadly neutralizing antibodies which can be used as a second therapeutic agent in a combination therapy are described, e.g., in U.S. Pat. Nos. 8,673,307; 9,493,549; 9,783,594; and WO 2012/154312; WO2012/158948; WO 2013/086533; WO 2013/142324; WO2014/063059; WO 2014/089152, WO 2015/048462; WO 2015/103549; WO 2015/117008; WO2016/014484; WO 2016/154003; WO 2016/196975; WO 2016/149710; WO2017/096221; WO 2017/133639; WO 2017/133640, which are hereby incorporated herein by reference in their entireties for all purposes. Additional examples include those described in Sajadi, et al., Cell. (2018) 173(7):1783-1795; Sajadi, et al., J Infect Dis. (2016) 213(1):156-64; Klein et al., Nature, 492(7427): 118-22 (2012), Horwitz et al., Proc Natl Acad Sci USA, 110(41): 16538-43 (2013), Scheid, et al., Science, 333: 1633-1637 (2011), Scheid, et al., Nature, 458:636-640 (2009), Eroshkin et al, Nucleic Acids Res., 42 (Database issue):Dl 133-9 (2014), Mascola et al., Immunol Rev., 254(1):225-44 (2013), such as 2F5, 4E10, M66.6, CAP206-CH12, 10E8, 10E8v4, 10E8-5R-100cF, DH511.11P, 7b2, and LN01 (all of which bind the MPER of gp41).

Examples of additional antibodies include bavituximab, UB-421, BF520.1, CHO1, CH59, C2F5, C4E10, C2F5+ C2G12+C4E10, 3BNC117, 3BNC117-LS, 3BNC60, DH270.1, DH270.6, D1D2, 10-1074-LS, GS-9722, DH411-2, BG18, PGT145, PGT121, PGT-121.60, PGT-121.66, PGT122, PGT-123, PGT-124, PGT-125, PGT-126, PGT-151, PGT-130, PGT-133, PGT-134, PGT-135, PGT-128, PGT-136, PGT-137, PGT-138, PGT-139, MDX010 (ipilimumab), DH511, DH511-2, N6, N6LS, N49P6, N49P7, N49P7.1, N49P9, N49P11, N60P1.1, N60P25.1, N60P2.1, N60P31.1, N60P22, NIH 45-46, PGC14, PGG14, PGT-142, PGT-143, PGT-144, PGDM1400, PGDM12, PGDM21, PCDN-33A, 2Dm2m, 4Dm2m, 6Dm2m, PGDM1400, MDX010 (ipilimumab), VRC01, VRC-01-LS, A32, 7B2, 10E8, VRC-07-523, VRC07-523LS, VRC24, VRC41.01, 10E8VLS, 3810109, 10E8v4, IMC-HIV, iMabm36, eCD4-Ig, IOMA, CAP256-VRC26.25, DRVIA7, VRC-HIVMAB080-00-AB, VRC-HIVMAB060-00-AB, P2G12, VRC07, 354BG8, 354BG18, 354BG42, 354BG33, 354BG129, 354BG188, 354BG411, 354BG426, VRC29.03, CAP256, CAP256-VRC26.08, CAP256-VRC26.09, CAP256-VRC26.25, PCT64-24E and VRC38.01, PGT-151, CAP248-2B, 35022, ACS202, VRC34 and VRC34.01, 10E8, 10E8v4, 10E8-5R-100cF, 4E10, DH511.11P, 2F5, 7b2, and LN01.

Example of HIV bispecific and trispecific antibodies include MGD014, B12BiTe, TMB-bispecific, SAR-441236, VRC-01/PGDM-1400/10E8v4, 10E8.4/iMab, 10E8v4/ PGT121-VRC01.

Example of in vivo delivered bnabs such as AAV8-VRC07; mRNA encoding anti-HIV antibody VRC01; and engineered B-cells encoding 3BNC117 (Hartweger et al, J. Exp. Med. 2019, 1301).

Pharmacokinetic Enhancers

In some embodiments, the agents described herein are combined with a pharmacokinetic enhancer. Examples of pharmacokinetic enhancers that can be combined with an agent of this disclosure include cobicistat and ritonavir.

Additional Therapeutic Agents

Examples of additional therapeutic agents that can be combined with an agent of this disclosure include the compounds disclosed in WO 2004/096286 (Gilead Sciences), WO 2006/015261 (Gilead Sciences), WO 2006/110157 (Gilead Sciences), WO 2012/003497 (Gilead Sciences), WO 2012/003498 (Gilead Sciences), WO 2012/145728 (Gilead Sciences), WO 2013/006738 (Gilead Sciences), WO 2013/159064 (Gilead Sciences), WO 2014/100323 (Gilead Sciences), US 2013/0165489 (University of Pennsylvania), US 2014/0221378 (Japan Tobacco), US 2014/0221380 (Japan Tobacco), WO 2009/062285 (Boehringer Ingelheim), WO 2010/130034 (Boehringer Ingelheim), WO 2013/006792 (Pharma Resources), US 20140221356 (Gilead Sciences), US 20100143301 (Gilead Sciences) and WO 2013/091096 (Boehringer Ingelheim).

HIV Vaccines

In some embodiments, the agents described herein are combined with an HIV vaccine. Examples of HIV vaccines that can be combined with an agent of this disclosure include peptide vaccines, recombinant subunit protein vaccines, live vector vaccines, DNA vaccines, CD4-derived peptide vaccines, vaccine combinations, adenoviral vector vaccines (an adenoviral vector such as Ad5, Ad26 or Ad35), simian adenovirus (chimpanzee, gorilla, rhesus i.e. rhAd), adeno-associated virus vector vaccines, Chimpanzee adenoviral vaccines (e.g., ChAdOX1, ChAd68, ChAd3, ChAd63, ChAd83, ChAd155, ChAd157, Pan5, Pan6, Pan7, Pan9), Coxsackieviruses based vaccines, enteric virus based vaccines, Gorilla adenovirus vaccines, lentiviral vector based vaccine, arenavirus vaccines (such as LCMV, Pichinde), bi-segmented or tri-segmented arenavirus based vaccine, measles virus based vaccine, flavivirus vector based vaccines, tobacco mosaic virus vector based vaccine, Varicella-zoster virus based vaccine, Human parainfluenza virus 3 (PIV3) based vaccines, poxvirus based vaccine (modified vaccinia virus Ankara (MVA), orthopoxvirus-derived NYVAC, and avipoxvirus-derived ALVAC (canarypox virus) strains); fowlpox virus based vaccine, rhabdovirus-based vaccines, such as VSV and marabavirus; recombinant human CMV (rhCMV) based vaccine, alphavirus-based vaccines, such as semliki forest virus, venezuelan equine encephalitis virus and sindbis virus; (see Lauer, Clinical and Vaccine Immunology, 2017, DOI: 10.1128/CVI.00298-16);

LNP formulated mRNA based therapeutic vaccines; LNP-formulated self-replicating RNA/self-amplifying RNA vaccines.

Examples of vaccines include: rgp120 (AIDSVAX), ALVAC HIV (vCP1521)/AIDSVAX B/E (gp120) (RV144), monomeric gp120 HIV-1 subtype C vaccine, Remune, ITV-1, Contre Vir, Ad5-ENVA-48, DCVax-001 (CDX-2401), Vacc-4x, Vacc-C5, VAC-3S, multiclade DNA recombinant adenovirus-5 (rAd5), rAd5 gag-pol env A/B/C vaccine, Pennvax-G, Pennvax-GP, Pennvax-G/MVA-CMDR, HIV-TriMix-mRNA vaccine, HIV-LAMP-vax, Ad35, Ad35-GRIN, NAcGM3/VSSP ISA-51, poly-ICLC adjuvanted vaccines, TatImmune, GTU-multiHIV (FIT-06), gp140 [delta]V2.TV1+MF-59, rVSVIN HIV-1 gag vaccine, SeV-Gag vaccine, AT-20, DNK-4, ad35-Grin/ENV, TBC-M4, HIVAX, HIVAX-2, NYVAC-HIV-PT1, NYVAC-HIV-PT4, DNA-HIV-PT123, rAAV1-PG9DP, GOVX-B11, GOVX-B21, TVI-HIV-1, Ad-4 (Ad4-env Clade C+Ad4-mGag), Paxvax, EN41-UGR7C, EN41-FPA2, PreVaxTat, AE-H, MYM-V101, CombiHIVvac, ADVAX, MYM-V201, MVA-CMDR, DNA-Ad5 gag/pol/nef/nev (HVTN505), MVATG-17401, ETV-01, CDX-1401, rcAD26.MOSI.HIV-Env, Ad26.Mod.HIV vaccine, Ad26.Mod.HIV+MVA mosaic vaccine+gp140, AGS-004, AVX-101, AVX-201, PEP-6409, SAV-001, ThV-01, TL-01, TUTI-16, VGX-3300, IHV-001, and virus-like particle vaccines such as pseudovirion vaccine, CombiVICHvac, LFn-p24 B/C fusion vaccine, GTU-based DNA vaccine, HIV gag/pol/nef/env DNA vaccine, anti-TAT HIV vaccine, conjugate polypeptides vaccine, dendritic-cell vaccines (such as DermaVir), gag-based DNA vaccine, GI-2010, gp41 HIV-1 vaccine, HIV vaccine (PIKA adjuvant), i-key/MHC class II epitope hybrid peptide vaccines, ITV-2, ITV-3, ITV-4, LIPO-5, multiclade Env vaccine, MVA vaccine, Pennvax-GP, pp71-deficient HCMV vector HIV gag vaccine, rgp160 HIV vaccine, RNActive HIV vaccine, SCB-703, Tat Oyi vaccine, TBC-M4, UBI HIV gp120, Vacc-4x+romidepsin, variant gp120 polypeptide vaccine, rAd5 gag-pol env A/B/C vaccine, DNA.HTI and MVA.HTI, VRC-HIVDNA016-00-VP+VRC-HIVADV014-00-VP, INO-6145, JNJ-9220, gp145 C.6980; eOD-GT8 60mer based vaccine, PD-201401, env (A, B, C, A/E)/gag (C) DNA Vaccine, gp120 (A,B,C,A/E) protein vaccine, PDPHV-201401, Ad4-EnvCN54, EnvSeq-1 Envs HIV-1 vaccine (GLA-SE adjuvanted), HIV p24gag prime-boost plasmid DNA vaccine, arenavirus vector-based vaccines (Vaxwave, TheraT), MVA-BN HIV-1 vaccine regimen, UBI HIV gp120, mRNA based prophylactic vaccines, and TBL-1203HI.

Birth Control (Contraceptive) Combination Therapy

In some embodiments, the agents described herein are combined with a birth control or contraceptive regimen. Therapeutic agents used for birth control (contraceptive) that can be combined with an agent of this disclosure include cyproterone acetate, desogestrel, dienogest, drospirenone, estradiol valerate, ethinyl Estradiol, ethynodiol, etonogestrel, levomefolate, levonorgestrel, lynestrenol, medroxyprogesterone acetate, mestranol, mifepristone, misoprostol, nomegestrol acetate, norelgestromin, norethindrone, noretynodrel, norgestimate, ormeloxifene, segestersone acetate, ulipristal acetate, and any combinations thereof.

In some embodiments, an agent disclosed herein, or a pharmaceutically acceptable salt thereof, is combined with one, two, three, four or more additional therapeutic agents selected from ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); BIKTARVY (bictegravir+emtricitabine+tenofovir alafenamide), adefovir; adefovir dipivoxil; cobicistat; emtricitabine; tenofovir; tenofovir disoproxil; tenofovir disoproxil fumarate; tenofovir alafenamide; tenofovir alafenamide hemifumarate; TRI-UMEQ® (dolutegravir, abacavir, and lamivudine); dolutegravir, abacavir sulfate, and lamivudine; raltegravir; raltegravir and lamivudine; maraviroc; enfuvirtide; ALUVIA® (KALETRA®; lopinavir and ritonavir); COMBIVIR® (zidovudine and lamivudine; AZT+3TC); EPZICOM® (LIVEXA®; abacavir sulfate and lamivudine; ABC+3TC); TRIZIVIR® (abacavir sulfate, zidovudine, and lamivudine; ABC+AZT+3TC); rilpivirine; rilpivirine hydrochloride; atazanavir sulfate and cobicistat; atazanavir and cobicistat; darunavir and cobicistat; atazanavir; atazanavir sulfate; dolutegravir; elvitegravir; ritonavir; atazanavir sulfate and ritonavir; darunavir; lamivudine; prolastin; fosamprenavir; fosamprenavir calcium efavirenz; etravirine; nelfinavir; nelfinavir mesylate; interferon; didanosine; stavudine; indinavir; indinavir sulfate; tenofovir and lamivudine; zidovudine; nevirapine; saquinavir; saquinavir mesylate; aldesleukin; zalcitabine; tipranavir; amprenavir; delavirdine; delavirdine mesylate; Radha-108 (receptol); lamivudine and tenofovir disoproxil fumarate; efavirenz, lamivudine, and tenofovir disoproxil fumarate; phosphazid; lamivudine, nevirapine, and zidovudine; abacavir; and abacavir sulfate.

In some embodiments, an agent disclosed herein, or a pharmaceutical composition thereof, is combined with an HIV nucleoside or nucleotide inhibitor of reverse transcriptase and an HIV non-nucleoside inhibitor of reverse transcriptase. In another specific embodiment, an agent disclosed herein, or a pharmaceutical composition thereof, is combined with an HIV nucleoside or nucleotide inhibitor of reverse transcriptase, and an HIV protease inhibiting compound. In an additional embodiment, an agent disclosed herein, or a pharmaceutical composition thereof, is combined with an HIV nucleoside or nucleotide inhibitor of reverse transcriptase, an HIV non-nucleoside inhibitor of reverse transcriptase, and a pharmacokinetic enhancer. In some embodiments, an agent disclosed herein, or a pharmaceutical composition thereof, is combined with at least one HIV nucleoside inhibitor of reverse transcriptase, an integrase inhibitor, and a pharmacokinetic enhancer. In some embodiments, an agent disclosed herein, or a pharmaceutical composition thereof, is combined with two HIV nucleoside or nucleotide inhibitors of reverse transcriptase.

In some embodiments, an agent disclosed herein, or a pharmaceutical composition thereof, is combined with abacavir sulfate, tenofovir, tenofovir disoproxil, tenofovir disoproxil fumarate, tenofovir disoproxil hemifumarate, tenofovir alafenamide, or tenofovir alafenamide hemifumarate.

In some embodiments, an agent disclosed herein, or a pharmaceutical composition thereof, is combined with tenofovir, tenofovir disoproxil, tenofovir disoproxil fumarate, tenofovir alafenamide, or tenofovir alafenamide hemifumarate.

In some embodiments, an agent disclosed herein, or a pharmaceutical composition thereof, is combined with a first additional therapeutic agent selected from the group consisting of abacavir sulfate, tenofovir, tenofovir disoproxil, tenofovir disoproxil fumarate, tenofovir alafenamide, and tenofovir alafenamide hemifumarate, and a second additional therapeutic agent selected from the group consisting of emtricitabine and lamivudine.

In some embodiments, an agent disclosed herein, or a pharmaceutical composition thereof, is combined with a first additional therapeutic agent selected from the group consisting of tenofovir, tenofovir disoproxil, tenofovir disoproxil fumarate, tenofovir alafenamide, and tenofovir alafenamide hemifumarate, and a second additional therapeutic agent, wherein the second additional therapeutic agent is emtricitabine.

In some embodiments, an agent disclosed herein, or a pharmaceutical composition thereof, is combined with a first additional therapeutic agent (a contraceptive) selected from the group consisting of cyproterone acetate, desogestrel, dienogest, drospirenone, estradiol valerate, ethinyl Estradiol, ethynodiol, etonogestrel, levomefolate, levonorgestrel, lynestrenol, medroxyprogesterone acetate, mestranol, mifepristone, misoprostol, nomegestrol acetate, norelgestromin, norethindrone, noretynodrel, norgestimate, ormeloxifene, segesterone acetate, ulipristal acetate, and any combinations thereof.

Gene Therapy and Cell Therapy

In some embodiments, the agents described herein are combined with a gene or cell therapy regimen. Gene therapy and cell therapy include without limitation the genetic modification to silence a gene; genetic approaches to directly kill the infected cells; the infusion of immune cells designed to replace most of the patient's own immune system to enhance the immune response to infected cells, or activate the patient's own immune system to kill infected cells, or find and kill the infected cells; genetic approaches to modify cellular activity to further alter endogenous immune responsiveness against the infection. Examples of dendritic cell therapy include AGS-004. CCR5 gene editing agents include SB-728T. CCR5 gene inhibitors include Cal-1. In some embodiments, C34-CCR5/C34-CXCR4 expressing CD4-positive T-cells are co-administered with one or more multi-specific antigen binding molecules. In some embodiments, the agents described herein are co-administered with AGT-103-transduced autologous T-cell therapy or AAV-eCD4-Ig gene therapy.

Gene Editors

In some embodiments, the agents described herein are combined with a gene editor, e.g., an HIV targeted gene editor. In some embodiments, the genome editing system can be selected from the group consisting of: a CRISPR/Cas9 complex, a zinc finger nuclease complex, a TALEN complex, a homing endonucleases complex, and a meganuclease complex. An illustrative HIV targeting CRISPR/Cas9 system includes without limitation EBT-101.

CAR-T-Cell Therapy

In some embodiments, the agents described herein can be co-administered with a population of immune effector cells engineered to express a chimeric antigen receptor (CAR), wherein the CAR comprises an HIV antigen binding domain. The HIV antigen include an HIV envelope protein or a portion thereof, gp120 or a portion thereof, a CD4 binding site on gp120, the CD4-induced binding site on gp120, N glycan on gp120, the V2 of gp120, the membrane proximal region on gp41. The immune effector cell is a T-cell or an NK cell. In some embodiments, the T-cell is a CD4+ T-cell, a CD8+ T-cell, or a combination thereof. Cells can be autologous or allogeneic. Examples of HIV CAR-T include VC-CAR-T, CMV-N6-CART, anti-CD4 CART-cell therapy, CD4 CAR+C34-CXCR4+CCR5 ZFN T-cells, autologous hematopoietic stem cells genetically engineered to express a CD4 CAR and the C46 peptide.

TCR-T-Cell Therapy

In some embodiments, the agents described herein are combined with a population of TCR-T-cells. TCR-T-cells are engineered to target HIV derived peptides present on the surface of virus-infected cells, for example ImmTAV B-Cell Therapy In some embodiments, the antibodies or antigen-binding fragments described herein are combined with a population of B cells genetically modified to express broadly neutralizing antibodies, such as 3BNC117 (Hartweger et al, J. Exp. Med. 2019, 1301, Moffett et al., Sci. Immunol. 4, eaax0644 (2019) 17 May 2019).

3. Hepatitis B Virus

Examples of other drugs for the treatment of HBV include alpha-hydroxytropolones, amdoxovir, antroquinonol, beta-hydroxycytosine nucleosides, ARB-199, CCC-0975, ccc-R08, elvucitabine, ezetimibe, cyclosporin A, gentiopicrin (gentiopicroside), HH-003, hepalatide, JNJ-56136379, nitazoxanide, birinapant, NJK14047, NOV-205 (molixan, BAM-205), oligotide, mivotilate, feron, GST-HG-131, levamisole, Ka Shu Ning, alloferon, WS-007, Y-101 (Ti Fen Tai), rSIFN-co, PEG-IIFNm, KW-3, BP-Inter-014, oleanolic acid, HepB-nRNA, cTP-5 (rTP-5), HSK-II-2, HEISCO-106-1, HEISCO-106, Hepbarna, IBPB-0061A, Hepuyinfen, DasKloster 0014-01, ISA-204, Jiangantai (Ganxikang), MIV-210, OB-AI-004, PF-06, picroside, DasKloster-0039, hepulantai, IMB-2613, TCM-800B, reduced glutathione, RO-6864018, RG-7834, QL-007sofosbuvir, ledipasvir, UB-551, and ZH-2N, and the compounds disclosed in US20150210682, (Roche), US 2016/0122344 (Roche), WO2015173164, WO2016023877, US2015252057A (Roche), WO16128335A1 (Roche), WO16120186A1 (Roche), US2016237090A (Roche), WO16107833A1 (Roche), WO16107832A1 (Roche), US2016176899A (Roche), WO16102438A1 (Roche), WO16012470A1 (Roche), US2016220586A (Roche), and US2015031687A (Roche).

HBV Vaccines

HBV vaccines include both prophylactic and therapeutic vaccines. Examples of HBV prophylactic vaccines include Vaxelis, Hexaxim, Heplisav, Mosquirix, DTwP-HBV vaccine, Bio-Hep-B, D/T/P/HBV/M (LBVP-0101; LBVW-0101), DTwP-Hepb-Hib-IPV vaccine, Heberpenta L, DTwP-HepB-Hib, V-419, CVI-HBV-001, Tetrabhay, hepatitis B prophylactic vaccine (Advax Super D), Hepatrol-07, GSK-223192A, ENGERIX B®, recombinant hepatitis B vaccine (intramuscular, Kangtai Biological Products), recombinant hepatitis B vaccine (Hansenual polymorpha yeast, intramuscular, Hualan Biological Engineering), recombinant hepatitis B surface antigen vaccine, Bimmugen, CARG-101, Euforavac, Eutravac, anrix-DTaP-IPV-Hep B, HBAI-20, Infanrix-DTaP-IPV-Hep B-Hib, Pentabio Vaksin DTP-HB-Hib, Comvac 4, Twinrix, Euvax-B, Tritanrix HB, Infanrix Hep B, Comvax, DTP-Hib-HBV vaccine, DTP-HBV vaccine, Yi Tai, Heberbiovac HB, Trivac HB, GerVax, DTwP-Hep B-Hib vaccine, Bilive, Hepavax-Gene, SUPERVAX, Comvac5, Shanvac-B, Hebsulin, Recombivax HB, Revac B mcf, Revac B+, Fendrix, DTwP-HepB-Hib, DNA-001, Shan5, Shan6, rhHBsAG vaccine, HBI pentavalent vaccine, LBVD, Infanrix HeXa, YS-HBV-001 and DTaP-rHB-Hib vaccine.

Examples of HBV therapeutic vaccines include HBsAG-HBIG complex, ARB-1598, Bio-Hep-B, NASVAC, abi-HB (intravenous), ABX-203, Tetrabhay, GX-110E, GS-4774, peptide vaccine (epsilonPA-44), Hepatrol-07, NASVAC (NASTERAP), IMP-321, BEVAC, Revac B mcf, Revac B+, MGN-1333, KW-2, CVI-HBV-002, AltraHepB, VGX-6200, FP-02, FP-02.2 (HepTcell), NU-500, HBVax, im/TriGrid/antigen vaccine, Mega-CD40L-adjuvanted vaccine, HepB-v, RG7944 (INO-1800), recombinant VLP-based therapeutic vaccine (HBV infection, VLP Biotech), AdTG-17909, AdTG-17910 AdTG-18202, ChronVac-B, TG-1050, VVX-001, GSK-3528869A (ChAd155-hli-HBV+MVA-HBV+Hbc-HBs/ASO1B-4), VBI-2601, VTP-300 (ChAdOx1-SIi-HBV-CPmut-TPA-Ssh prime and MVA-SIi-HBV-CPmut-TPA-Ssh boost), MVA-BN, and Lm HBV. HBV Arenavirus vaccines are described, e.g., in WO2017076988 and WO2017198726.

HBV DNA Polymerase Inhibitors

Examples of HBV DNA polymerase inhibitors include adefovir (HEPSERA®), emtricitabine (EMTRIVA®), tenofovir disoproxil fumarate (VIREAD®), tenofovir alafenamide, tenofovir, tenofovir disoproxil, tenofovir alafenamide fumarate, tenofovir alafenamide hemifumarate, tenofovir dipivoxil, tenofovir dipivoxil fumarate, tenofovir octadecyloxyethyl ester, CMX-157, tenofovir exalidex, besifovir, entecavir (BARACLUDE®), entecavir maleate, telbivudine (TYZEKA®), filocilovir, pradefovir, clevudine, ribavirin, lamivudine (EPIVIR-HBV®), phosphazide, famciclovir, fusolin, metacavir, SNC-019754, FMCA, AGX-1009, AR-II-04-26, HIP-1302, tenofovir disoproxil aspartate, tenofovir disoproxil orotate, and HS-10234.

Immunomodulators

Examples of immunomodulators include rintatolimod, imidol hydrochloride, ingaron, dermaVir, plaquenil (hydroxychloroquine), proleukin, hydroxyurea, mycophenolate mofetil (MPA) and its ester derivative mycophenolate mofetil (MMF), JNJ-440, WF-10, AB-452, ribavirin, IL-12, INO-9112, polymer polyethyleneimine (PEI), Gepon, VGV-1, MOR-22, CRV-431, JNJ-0535, TG-1050, ABI-H2158, BMS-936559, GS-9688, RO-7011785, RG-7854, RO-6871765, AIC-649, and IR-103.

Toll-Like Receptor (TLR) Agonists

In some embodiments, the agents as described herein, are combined with an agonist of a toll-like receptor (TLR), e.g., an agonist of TLR1 (NCBI Gene ID: 7096), TLR2 (NCBI Gene ID: 7097), TLR3 (NCBI Gene ID: 7098), TLR4 (NCBI Gene ID: 7099), TLR5 (NCBI Gene ID: 7100), TLR6 (NCBI Gene ID: 10333), TLR7 (NCBI Gene ID: 51284), TLR8 (NCBI Gene ID: 51311), TLR9 (NCBI Gene ID: 54106), and/or TLR10 (NCBI Gene ID: 81793), TLR11, TLR12 and TLR13.

Examples of TLR3 modulators include rintatolimod, poly-ICLC, RIBOXXON®, Apoxxim, RIBOXXIM®, IPH-33, MCT-465, MCT-475 and ND-1.1. Examples of TLR4 agonist include G-100, and GSK-1795091.

Example TLR7 agonists that can be co-administered include without limitation AL-034, DSP-0509, GS-9620 (vesatolimod), LHC-165, TMX-101 (imiquimod), GSK-2245035, resiquimod, DSR-6434, DSP-3025, IMO-4200, MCT-465, MEDI-9197, 3M-051, SB-9922, 3M-052, Limtop, TMX-30X, TMX-202, RG-7863, RG-7854, RG-7795, and the compounds disclosed in US20100143301 (Gilead Sciences), US20110098248 (Gilead Sciences), and US20090047249 (Gilead Sciences), US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), and US20130251673 (Novira Therapeutics).

An TLR7/TLR8 agonist that can be co-administered is NKTR-262, telratolimod and BDB-001.

Example TLR8 agonists that can be co-administered include without limitation E-6887, IMO-4200, IMO-8400, IMO-9200, MCT-465, MEDI-9197, motolimod, resiquimod, selgantolimod (GS-9688), VTX-1463, VTX-763, 3M-051, 3M-052, ZG-170607, and the compounds disclosed in US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), and US20130251673 (Novira Therapeutics), U.S. Pat. No. 9,670,205 (Gilead Sciences, Inc.), US20160289229 (Gilead Sciences, Inc.), WO20-17/048727 (Gilead Sciences, Inc.), US20180065938 (Gilead Sciences, Inc.), and US20180086755 (Gilead Sciences, Inc.).

Example TLR9 agonists that can be co-administered include without limitation AST-008, cobitolimod, CMP-001, IMO-2055, IMO-2125, litenimod, MGN-1601, BB-001, BB-006, IMO-3100, IMO-8400, IR-103, IMO-9200, agatolimod, DIMS-9054, DV-1079, DV-1179, AZD-1419, lefitolimod (MGN-1703), CYT-003, CYT-003-QbG10, tilsotolimod and PUL-042.

Examples of TLR7, TLR8 and TLR9 modulators include the compounds disclosed in WO2017047769 (Teika Seiyaku), WO2015014815 (Janssen), WO2018045150 (Gilead Sciences Inc), WO2018045144 (Gilead Sciences Inc), WO2015162075 (Roche), WO2017034986 (University of Kansas), WO2018095426 (Jiangsu Hengrui Medicine Co Ltd), WO2016091698 (Roche), WO2016075661 (GlaxoSmithKline Biologicals), WO2016180743 (Roche), WO2018089695 (Dynavax Technologies), WO2016055553 (Roche), WO2015168279 (Novartis), WO2016107536 (Medshine Discovery), WO2018086593 (Livo (Shanghai) Pharmaceutical), WO2017106607 (Merck), WO2017061532 (Sumitomo Dainippon Pharma), WO2016023511 (Chia Tai Tianqing Pharmaceutical), WO2017076346 (Chia Tai Tianqing Pharmaceutical), WO2017046112 (Roche), WO2018078149 (Roche), WO2017040233 (3M Co), WO2016141092 (Gilead Sciences), WO2018049089 (BristolMyers Squibb), WO2015057655 (Eisai Co Ltd), WO2017001307 (Roche), WO2018005586 (BristolMyers Squibb), WO201704023 (3M Co), WO2017163264 (Council of Scientific and Industrial Research (India)), WO2018046460 (GlaxoSmithKline Biologicals), WO2018047081 (Novartis), WO2016142250 (Roche), WO2015168269 (Novartis), WO201804163 (Roche), WO2018038877 (3M Co), WO2015057659 (Eisai Co Ltd), WO2017202704 (Roche), WO2018026620 (BristolMyers Squibb), WO2016029077 (Janus Biotherapeutics), WO201803143 (Merck), WO2016096778 (Roche), WO2017190669 (Shanghai De Novo Pharmatech), U.S. Ser. No. 09/884,866 (University of Minnesota), WO2017219931 (Sichuan KelunBiotech Biopharmaceutical), WO2018002319 (Janssen Sciences), WO2017216054 (Roche), WO2017202703 (Roche), WO2017184735 (IFM Therapeutics), WO2017184746 (IFM Therapeutics), WO2015088045 (Takeda Pharmaceutical), WO2017038909 (Takeda Pharmaceutical), WO2015095780 (University of Kansas), WO2015023958 (University of Kansas).

In some embodiments, an agent as described herein is co-administered with a TLR7, TLR8 or TLR9 agonist.

Interferon Alpha Receptor Ligands

Examples of interferon alpha receptor ligands include interferon alpha-2b (INTRON A®), pegylated interferon alpha-2a (PEGASYS®), PEGylated interferon alpha-1b, interferon alpha 1b (HAPGEN®), Veldona, Infradure, Roferon-A, YPEG-interferon alfa-2a (YPEG-rhIFNalpha-2a), P-1101, Algeron, Alfarona, Ingaron (interferon gamma), rSIFN-co (recombinant super compound interferon), Ypeginterferon alfa-2b (YPEG-rhIFNalpha-2b), MOR-22, peginterferon alfa-2b (PEG-INTRON®), Bioferon, Novaferon, Inmutag (Inferon), MULTIFERON®, interferon alfa-n1 (HUMOFERON®), interferon beta-1a (AVONEX®), Shaferon, interferon alfa-2b (Axxo), Alfaferone, interferon alfa-2b (BioGeneric Pharma), interferon-alpha 2 (CJ), Laferonum, VIPEG, BLAUFERON-A, BLAUFERON-B, Intermax Alpha, Realdiron, Lanstion, Pegaferon, PDferon-B PDferon-B, interferon alfa-2b (IFN, Laboratorios Bioprofarma), alfainterferona 2b, Kalferon, Pegnano, Feronsure, PegiHep, interferon alfa 2b (Zydus-Cadila), interferon alfa 2a, Optipeg A, Realfa 2B, Reliferon, interferon alfa-2b (Amega), interferon alfa-2b (Virchow), ropeginterferon alfa-2b, rHSA-IFN alpha-2a (recombinant human serum albumin intereferon alpha 2a fusion protein), PEG-IFN-alpha, rHSA-IFN alpha 2b, recombinant human interferon alpha-(1b, 2a, 2b), peginterferon alfa-2b (Amega), peginterferon alfa-2a, Reaferon-EC, Proquiferon, Uniferon, Urifron, interferon alfa-2b (Changchun Institute of Biological Products), Anterferon, Shanferon, Layfferon, Shang Sheng Lei Tai, INTEFEN, SINOGEN, Fukangtai, Pegstat, rHSA-IFN alpha-2b, SFR-9216, and Interapo (Interapa).

Hyaluronidase Inhibitors

Examples of hyaluronidase inhibitors include astodrimer.

Hepatitis B Surface Antigen (HBsAg) Inhibitors

Examples of HBsAg inhibitors include AK-074, HBF-0259, PBHBV-001, PBHBV-2-15, PBHBV-2-1, REP-9AC, REP-9C, REP-9, REP-2139, REP-2139-Ca, REP-2055, REP-2163, REP-2165, REP-2053, REP-2031, REP-006, and REP-9AC'.

Examples of HBsAg secretion inhibitors include BM601, GST-HG-131, AB-452

Cytotoxic T-Lymphocyte-Associated Protein 4 (Ipi4) Inhibitors

Examples of Cytotoxic T-lymphocyte-associated protein 4 (ipi4) inhibitors include AGEN-2041, AGEN-1884, ipilumimab, belatacept, PSI-001, PRS-010, Probody mAbs, tremelimumab, and JUL-1155.

Cyclophilin Inhibitors

Examples of cyclophilin inhibitors include CPI-431-32, EDP-494, OCB-030, SCY-635, NVP-015, NVP-018, NVP-019, STG-175, and the compounds disclosed in U.S. Pat. No. 8,513,184 (Gilead Sciences), US20140030221 (Gilead Sciences), US20130344030 (Gilead Sciences), and US20130344029 (Gilead Sciences).

HBV Viral Entry Inhibitors

Examples of HBV viral entry inhibitors include Myrcludex B.

Antisense Oligonucleotide Targeting Viral mRNA

Examples of antisense oligonucleotide targeting viral mRNA include ISIS-HBVRx, IONIS-HBVRx, IONIS-HBV-LRx, IONIS-GSK6-LRx, GSK-3389404, and RG-6004.

Short Interfering RNAs (siRNA) and ddRNAi

Examples of siRNA include TKM-HBV (TKM-HepB), ALN-HBV, SR-008, HepB-nRNA, ARC-520, ARC-521, ARB-1740, ARB-1467, AB-729, DCR-HBVS, RG-6084 (PD-L1), RG-6217, ALN-HBV-02, JNJ-3989 (ARO-HBV), STSG-0002, ALG-010133, ALG-ASO, LUNAR-HBV and DCR-HBVS (DCR-S219).

Examples of DNA-directed RNA interference (ddRNAi) include BB-HB-331.

Endonuclease Modulators

Examples of endonuclease modulators include PGN-514.

Ribonucleotide Reductase Inhibitors

Examples of inhibitors of ribonucleotide reductase include Trimidox.

Nonnucleoside Reverse Transcriptase Inhibitors

Examples of Nonnucleoside Reverse Transcriptase Inhibitors (NNRTIs) include the compounds disclosed in WO2018118826 (Merck), WO2018080903 (Merck), WO2018119013 (Merck), WO2017100108 (Idenix), WO2017027434 (Merck), WO2017007701 (Merck), WO2008005555 (Gilead).

HBV Replication Inhibitors

Examples of hepatitis B virus replication inhibitors include GP-31502, isothiafludine, IQP-HBV, RM-5038, and Xingantie.

Covalently Closed Circular DNA (cccDNA) Inhibitors

Examples of cccDNA inhibitors include BSBI-25, ccc-R08, and CHR-101.

Farnesoid X Receptor Agonist

Examples of farnesoid x receptor agonists include, e.g., EYP-001, GS-9674, EDP-305, MET-409, Tropifexor, AKN-083, RDX-023, BWD-100, LMB-763, INV-3, NTX-023-1, EP-024297 and GS-8670.

Additional HBV Antibodies

Examples of HBV antibodies targeting the surface antigens of the hepatitis B virus include lenvervimab (GC-1102), XTL-17, XTL-19, KN-003, IV Hepabulin SN, VIR-3434, and fully human monoclonal antibody therapy (hepatitis B virus infection, Humabs BioMed).

Examples of HBV antibodies, including monoclonal antibodies and polyclonal antibodies, include Zutectra, Shang Sheng Gan Di, Uman Big (Hepatitis B Hyperimmune), Omri-Hep-B, Nabi-HB, Hepatect CP, HepaGam B, igantibe, Niuliva, CT-P24, hepatitis B immunoglobulin (intravenous, pH4, HBV infection, Shanghai RAAS Blood Products), and Fovepta (BT-088).

Examples of fully human monoclonal antibodies include HBC-34.

Antibodies against HBV viral peptide/major histocompatibility complex (MHC) class I (pMHC) complexes are described, e.g., in Sastry, et al., J Virol. 2011 March; 85(5):1935-42 and in WO2011062562.

CCR2 Chemokine Antagonists

Examples of CCR2 chemokine antagonists include propagermanium.

Thymosin Agonists

Examples of thymosin agonists include Thymalfasin, and recombinant thymosin alpha 1 (GeneScience).

Cytokines

Examples of cytokines include recombinant IL-7, CYT-107, interleukin-2 (IL-2, Immunex), recombinant human interleukin-2 (Shenzhen Neptunus), IL-15, IL-21, IL-24, and celmoleukin.

Interleukin Agonists

In some embodiments, the agents described herein are combined with an interleukin agonist, such as IL-2, IL-7, IL-15, IL-10, IL-12 agonists; examples of IL-2 agonists such as proleukin (aldesleukin, IL-2); pegylated IL-2 (eg NKTR-214); modified variants of IL-2 (eg THOR-707); bempegaldesleukin, AIC-284, ALKS-4230, CUI-101, Neo-2/15; examples of IL-15 agonists, such as ALT-803, NKTR-255, and hetIL-15, interleukin-15/Fc fusion protein, AM-0015, NIZ-985, SO-C101, IL-15 Synthorin (pegylated Il-15), P-22339, and a IL-15-PD-1 fusion protein N-809; examples of IL-7 include CYT-107.

Nucleoprotein Modulators

Nucleoprotein modulators may be either HBV core or capsid protein inhibitors. Examples of nucleoprotein modulators include GS-4882, AB-423, AT-130, ALG-001075, ALG-001024, ALG-000184, EDP-514, GLS4, NVR-1221, NVR-3778, AL-3778, BAY 41-4109, morphothiadine mesilate, ARB-168786, ARB-880, ARB-1820, GST-HG-141, JNJ-379, JNJ-632, RG-7907, GST-HG-141, HEC-72702, KL-060332, AB-506, ABI-H0731, ABI-H3733, JNJ-440, ABI-H2158, CB-HBV-001 and DVR-23.

Examples of capsid inhibitors include the compounds disclosed in US20140275167 (Novira Therapeutics), US20130251673 (Novira Therapeutics), US20140343032 (Roche), WO2014037480 (Roche), US20130267517 (Roche), WO2014131847 (Janssen), WO2014033176 (Janssen), WO2014033170 (Janssen), WO2014033167 (Janssen), WO2015/059212 (Janssen), WO2015118057 (Janssen), WO2015011281 (Janssen), WO2014184365 (Janssen), WO2014184350 (Janssen), WO2014161888 (Janssen), WO2013096744 (Novira), US20150225355 (Novira), US20140178337 (Novira), US20150315159 (Novira), US20150197533 (Novira), US20150274652 (Novira), US20150259324, (Novira), US20150132258 (Novira), U.S. Pat. No. 9,181,288 (Novira), WO2014184350 (Janssen), WO2013144129 (Roche), WO2017198744 (Roche), US 20170334882 (Novira), US 20170334898 (Roche), WO2017202798 (Roche), WO2017214395 (Enanta), WO2018001944 (Roche), WO2018001952 (Roche), WO2018005881 (Novira), WO2018005883 (Novira), WO2018011100 (Roche), WO2018011160 (Roche), WO2018011162 (Roche), WO2018011163 (Roche), WO2018036941 (Roche), WO2018043747 (Kyoto Univ), US20180065929 (Janssen), WO2016168619 (Indiana University), WO2016195982 (The Penn State Foundation), WO2017001655 (Janssen), WO2017048950 (Assembly Biosciences), WO2017048954 (Assembly Biosciences), WO2017048962 (Assembly Biosciences), US20170121328 (Novira), US20170121329 (Novira).

Examples of transcript inhibitors include the compounds disclosed in WO2017013046 (Roche), WO2017016960 (Roche), WO2017017042 (Roche), WO2017017043 (Roche), WO2017061466 (Toyoma chemicals), WO2016177655 (Roche), WO2016161268 (Enanta). WO2017001853 (Redex Pharma), WO2017211791 (Roche), WO2017216685 (Novartis), WO2017216686 (Novartis), WO2018019297 (Ginkgo Pharma), WO2018022282 (Newave Pharma), US20180030053 (Novartis), WO2018045911 (Zhejiang Pharma).

STING Agonists, RIG-I and NOD2 Modulators

In some embodiments, the agents described herein are combined with a stimulator of interferon genes (STING). In some embodiments, the STING receptor agonist or activator is selected from the group consisting of ADU-S100 (MIW-815), SB-11285, MK-1454, SR-8291, AdVCA0848, STINGVAX, GSK-532, SYN-STING, MSA-1, SR-8291, 5,6-dimethylxanthenone-4-acetic acid (DMXAA), cyclic-GAMP (cGAMP) and cyclic-di-AMP. In some embodiments, the agents described herein are combined with a RIG-I modulator such as RGT-100, or NOD2 modulator, such as SB-9200, and IR-103.

Examples of STING agonists include the compounds disclosed in WO 2018065360 ("Biolog Life Science Institute Forschungslabor und Biochemica-Vertrieb GmbH, Germany), WO 2018009466 (Aduro Biotech), WO 2017186711 (InvivoGen), WO 2017161349 (Immune Sensor), WO 2017106740 (Aduro Biotech), US 20170158724 (Glaxo Smithkiline), WO 2017075477 (Aduro Biotech), US 20170044206 (Merck), WO 2014179760 (University of California), WO2018098203 (Janssn), WO2018118665 (Merck), WO2018118664 (Merck), WO2018100558 (Takeda), WO2018067423 (Merck), WO2018060323 (Boehringer).

Retinoic Acid-Inducible Gene 1 Stimulators

Examples of stimulators of retinoic acid-inducible gene 1 include inarigivir soproxil (SB-9200), SB-40, SB-44, ORI-7246, ORI-9350, ORI-7537, ORI-9020, ORI-9198, ORI-7170, and RGT-100.

NOD2 Stimulators

Examples of stimulators of NOD2 include inarigivir soproxil (SB-9200).

Phosphatidylinositol 3-Kinase (PI3K) Inhibitors

Examples of PI3K inhibitors include idelalisib, ACP-319, AZD-8186, AZD-8835, buparlisib, CDZ-173, CLR-457, pictilisib, neratinib, rigosertib, rigosertib sodium, EN-3342, TGR-1202, alpelisib, duvelisib, IPI-549, UCB-5857, taselisib, XL-765, gedatolisib, ME-401, VS-5584, copanlisib, CAI orotate, perifosine, RG-7666, GSK-2636771, DS-7423, panulisib, GSK-2269557, GSK-2126458, CUDC-907, PQR-309, INCB-40093, pilaralisib, BAY-1082439, puquitinib mesylate, SAR-245409, AMG-319, RP-6530, ZSTK-474, MLN-1117, SF-1126, RV-1729, sonolisib, LY-3023414, SAR-260301, TAK-117, HMPL-689, tenalisib, voxtalisib, and CLR-1401.

Immune Checkpoint Modulators

In some embodiments, the agents as described herein, are combined with one or more blockers or inhibitors of inhibitory immune checkpoint proteins or receptors and/or with one or more stimulators, activators or agonists of one or more stimulatory immune checkpoint proteins or receptors. Blockade or inhibition of inhibitory immune checkpoints can positively regulate T-cell or NK cell activation and prevent immune escape of infected cells. Activation or stimulation of stimulatory immune check points can augment the effect of immune checkpoint inhibitors in infective therapeutics. In some embodiments, the immune checkpoint proteins or receptors regulate T cell responses (e.g., reviewed in Xu, et al., *J Exp Clin Cancer Res*. (2018) 37:110). In some embodiments, the immune checkpoint proteins or receptors regulate NK cell responses (e.g., reviewed in Davis, et al., *Semin Immunol*. (2017) 31:64-75 and Chiossone, et al., *Nat Rev Immunol*. (2018) 18(11):671-688).

Examples of immune checkpoint proteins or receptors include without limitation CD27, CD70; CD40, CD40LG; CD47, CD48 (SLAMF2), transmembrane and immunoglobulin domain containing 2 (TMIGD2, CD28H), CD84 (LY9B, SLAMF5), CD96, CD160, MS4A1 (CD20), CD244 (SLAMF4); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); natural killer cell cytotoxicity receptor 3 ligand 1 (NCR3LG1, B7H6); HERV-H LTR-associating 2 (HHLA2, B7H7); inducible T cell costimulator (ICOS, CD278); inducible T cell costimulator ligand (ICOSLG, B7H2); TNF receptor superfamily member 4 (TNFRSF4, OX40); TNF superfamily member 4 (TNFSF4, OX40L); TNFRSF8 (CD30), TNFSF8 (CD30L); TNFRSF10A (CD261, DR4, TRAILR1), TNFRSF9 (CD137), TNFSF9 (CD137L); TNFRSF10B (CD262, DR5, TRAILR2), TNFRSF10 (TRAIL); TNFRSF14 (HVEM, CD270), TNFSF14 (HVEML); CD272 (B and T lymphocyte associated (BTLA)); TNFRSF17 (BCMA, CD269), TNFSF13B (BAFF); TNFRSF18 (GITR), TNFSF18 (GITRL); MHC class I polypeptide-related sequence A (MICA); MHC class I polypeptide-related sequence B (MICB); CD274 (CD274, PDL1, PD-L1); programmed cell death 1 (PDCD1, PD1, PD-1); cytotoxic T-lymphocyte associated protein 4 (CTLA4, CD152); CD80 (B7-1), CD28; nectin cell adhesion molecule 2 (NECTIN2, CD112); CD226 (DNAM-1); Poliovirus receptor (PVR) cell adhesion molecule (PVR, CD155); PVR related immunoglobulin domain containing (PVRIG, CDI 12R); T cell immunoreceptor with Ig and ITIM domains (TIGIT); T cell immunoglobulin and mucin domain containing 4 (TIMD4; TIM4); hepatitis A virus cellular receptor 2 (HAVCR2, TIMD3, TIM3); galectin 9 (LGALS9); lymphocyte activating 3 (LAG3, CD223); signaling lymphocytic activation molecule family member 1 (SLAMF1, SLAM, CD150); lymphocyte antigen 9 (LY9, CD229, SLAMF3); SLAM family member 6 (SLAMF6, CD352); SLAM family member 7 (SLAMF7, CD319); UL16 binding protein 1 (ULBP1); UL16 binding protein 2 (ULBP2); UL16 binding protein 3 (ULBP3); retinoic acid early transcript 1E (RAET1E; ULBP4); retinoic acid early transcript 1G (RAET1G; ULBP5); retinoic acid early transcript 1L (RAETIL; ULBP6); lymphocyte activating 3 (CD223); killer cell immunoglobulin like receptor, three Ig domains and long cytoplasmic tail 1 (KIR, CD158E1); killer cell lectin like receptor C1 (KLRC1, NKG2A, CD159A); killer cell lectin like receptor K1 (KLRK1, NKG2D, CD314); killer cell lectin like receptor C2 (KLRC2, CD159c, NKG2C); killer cell lectin like receptor C3 (KLRC3, NKG2E); killer cell lectin like receptor C4 (KLRC4, NKG2F); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor D1 (KLRD1); and SLAM family member 7 (SLAMF7).

In some embodiments, the agents described herein, are combined with one or more blockers or inhibitors of one or more T-cell inhibitory immune checkpoint proteins or receptors. Illustrative T-cell inhibitory immune checkpoint proteins or receptors include without limitation CD274 (CD274, PDL1, PD-L1); programmed cell death 1 ligand 2 (PDCDILG2, PD-L2, CD273); programmed cell death 1 (PDCD1, PD1, PD-1); cytotoxic T-lymphocyte associated protein 4 (CTLA4, CD152); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); TNFRSF14 (HVEM, CD270), TNFSF14 (HVEML); CD272 (B and T lymphocyte associated (BTLA)); PVR related immunoglobulin domain containing (PVRIG, CD112R); T cell immunoreceptor with Ig and ITIM domains (TIGIT); lymphocyte activating 3 (LAG3, CD223); hepatitis A virus cellular receptor 2 (HAVCR2, TIMD3, TIM3); galectin 9 (LGALS9); killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); and killer cell immunoglobulin like receptor, three Ig domains and long cytoplasmic tail 1 (KIR3DL1). In some embodiments, the agents, as described herein, are combined with one or more agonist or activators of one or more T-cell stimulatory immune checkpoint proteins or receptors. Illustrative T-cell stimulatory immune checkpoint proteins or receptors include without limitation CD27, CD70; CD40, CD40LG; inducible T cell costimulator (ICOS, CD278); inducible T cell costimulator ligand (ICOSLG, B7H2); TNF receptor superfamily member 4 (TNFRSF4, OX40); TNF superfamily member 4 (TNFSF4, OX40L); TNFRSF9 (CD137), TNFSF9 (CD137L); TNFRSF18 (GITR), TNFSF18 (GITRL); CD80 (B7-1), CD28; nectin cell adhesion molecule 2 (NECTIN2, CD112); CD226 (DNAM-1); CD244 (2B4, SLAMF4), Poliovirus receptor (PVR) cell adhesion molecule (PVR, CD155). See, e.g., Xu, et al., *J Exp Clin Cancer Res*. (2018) 37:110.

In some embodiments, the agents as described herein, are combined with one or more blockers or inhibitors of one or more NK-cell inhibitory immune checkpoint proteins or receptors. Illustrative NK-cell inhibitory immune checkpoint proteins or receptors include without limitation killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor C1 (KLRC1, NKG2A, CD159A); and killer cell lectin like receptor D1 (KLRD1, CD94). In some embodiments, the agents as described herein, are combined with one or more agonist or activators of one or more NK-cell stimulatory immune checkpoint proteins or receptors. Illustrative NK-cell stimulatory immune checkpoint proteins or receptors include without limitation CD16, CD226 (DNAM-1); CD244 (2B4, SLAMF4); killer cell lectin like receptor K1 (KLRK1, NKG2D, CD314); SLAM family member 7 (SLAMF7). See, e.g., Davis, et al., *Semin Immunol*. (2017) 31:64-75; Fang, et al., *Semin Immunol*. (2017) 31:37-54; and Chiossone, et al., *Nat Rev Immunol*. (2018) 18(11):671-688.

In some embodiments, the one or more immune checkpoint inhibitors comprises a proteinaceous (e.g., antibody or fragment thereof, or antibody mimetic) inhibitor of PD-L1 (CD274), PD-1 (PDCD1) or CTLA4. In some embodiments, the one or more immune checkpoint inhibitors comprises a small organic molecule inhibitor of PD-L1 (CD274), PD-1 (PDCD1) or CTLA4. In some embodiments, the small molecule inhibitor of CD274 or PDCD1 is selected from the group consisting of GS-4224, GS-4416, INCB086550 and MAX10181. In some embodiments, the small molecule inhibitor of CTLA4 comprises BPI-002.

Examples of inhibitors of CTLA4 that can be co-administered include without limitation ipilimumab, tremelimumab, BMS-986218, AGEN1181, AGEN1884, BMS-986249, MK-1308, REGN-4659, ADU-1604, CS-1002, BCD-145, APL-509, JS-007, BA-3071, ONC-392, AGEN-2041, JHL-1155, KN-044, CG-0161, ATOR-1144, PBI-5D3H5, BPI-002, as well as multi-specific inhibitors FPT-155 (CTLA4/PD-L1/CD28), PF-06936308 (PD-1/CTLA4), MGD-019 (PD-1/CTLA4), KN-046 (PD-1/CTLA4), MEDI-5752 (CTLA4/PD-1), XmAb-20717 (PD-1/CTLA4), and AK-104 (CTLA4/PD-1).

Examples of inhibitors of PD-L1 (CD274) or PD-1 (PDCD1) that can be co-administered include without limitation pembrolizumab, nivolumab, cemiplimab, pidilizumab, AMP-224, MEDI0680 (AMP-514), spartalizumab, atezolizumab, avelumab, durvalumab, ALN-PDL, BMS-936559, CK-301, PF-06801591, BGB-108, BGB-A317 (tislelizumab), GLS-010 (WBP-3055), AK-103 (HX-008), GB-226, AK-105, CS-1003, HLX-10, MGA-012, BI-754091, PDR-001, AGEN-2034, JS-001 (toripalimab), JNJ-63723283, genolimzumab (CBT-501), LZM-009, BCD-100, LY-3300054, SHR-1201, SHR-1210 (camrelizumab), Sym-021, ABBV-181, PD1-PIK, BAT-1306, RO-6084 (PD-L1 antisense oligonucleotide), STI-1110, GX-P2, RG-7446, mDX-400, (MSB0010718C), CX-072, CBT-502, TSR-042 (dostarlimab), MSB-2311, JTX-4014, BGB-A333, SHR-1316, CS-1001 (WBP-3155), MEDI-0680, envafolimab (KN-035), KD-033, KY-1003, IBI-308 (sintilimab), HLX-20, KL-A167, STI-A1014, STI-A1015 (IMC-001), BCD-135, FAZ-053, TQB-2450, MDX1105-01, MSB-0010718C, GS-4224, GS-4416, INCB086550, MAX10181, as well as multi-specific inhibitors FPT-155 (CTLA4/PD-L1/CD28), PF-06936308 (PD-1/CTLA4), MGD-013 (PD-1/LAG-3), FS-118 (LAG-3/PD-L1) MGD-019 (PD-1/CTLA4), KN-046 (PD-1/CTLA4), MEDI-5752 (CTLA4/PD-1), RO-7121661 (PD-1/TIM-3), XmAb-20717 (PD-1/CTLA4), AK-104 (CTLA4/PD-1), M7824 (PD-L1/TGFβ-EC domain), CA-170 (PD-L1/VISTA), CDX-527 (CD27/PD-L1), LY-3415244 (TIM3/PDL1), GNS-1480 (Epidermal growth factor receptor antagonist; Programmed cell death ligand 1 inhibitor), M-7824 (PD-L1/TGF-β bifunctional fusion protein), and INBRX-105 (4-1BB/PDL1).

Examples of PD-1 inhibitors include the compounds disclosed in WO2017112730 (Incyte Corp), WO2017087777 (Incyte Corp), WO2017017624, WO2014151634 (BristolMyers Squibb Co), WO201317322 (BristolMyers Squibb Co), WO2018119286 (Incyte Corp), WO2018119266 (Incyte Corp), WO2018119263 (Incyte Corp), WO2018119236 (Incyte Corp), WO2018119221 (Incyte Corp), WO2018118848 (BristolMyers Squibb Co), WO2016126646 0 (BristolMyers Squibb Co), WO2017087678 (BristolMyers Squibb Co), WO2016149351 (BristolMyers Squibb Co), WO2015033299 (Aurigene Discovery Technologies Ltd), WO2015179615 (Eisai Co Ltd; Eisai Research Institute), WO2017066227 (BristolMyers Squibb Co), WO2016142886 (Aurigene Discovery Technologies Ltd), WO2016142852 (Aurigene Discovery Technologies Ltd), WO2016142835 (Aurigene Discovery Technologies Ltd; Individual), WO2016142833 (Aurigene Discovery Technologies Ltd), WO2018085750 (BristolMyers Squibb Co), WO2015033303 (Aurigene Discovery Technologies Ltd), WO2017205464 (Incyte Corp), WO2016019232 (3M Co; Individual; Texas A&M University System), WO2015160641 (BristolMyers Squibb Co), WO2017079669 (Incyte Corp), WO2015033301 (Aurigene Discovery Technologies Ltd), WO2015034820 (BristolMyers Squibb Co), WO2018073754 (Aurigene Discovery Technologies Ltd), WO2016077518 (BristolMyers Squibb Co), WO2016057624 (BristolMyers Squibb Co), WO2018044783 (Incyte Corp), WO2016100608 (BristolMyers Squibb Co), WO2016100285 (BristolMyers Squibb Co), WO2016039749 (BristolMyers Squibb Co), WO2015019284 (Cambridge Enterprise Ltd), WO2016142894 (Aurigene Discovery Technologies Ltd), WO2015134605 (BristolMyers Squibb Co), WO2018051255 (Aurigene Discovery Technologies Ltd), WO2018051254 (Aurigene Discovery Technologies Ltd), WO2017222976 (Incyte Corp), WO2017070089 (Incyte Corp), WO2018044963 (BristolMyers Squibb Co), WO2013144704 (Aurigene Discovery Technologies Ltd), WO2018013789 (Incyte Corp), WO2017176608 (BristolMyers Squibb Co), WO2018009505 (BristolMyers Squibb Co), WO2011161699 (Aurigene Discovery Technologies Ltd), WO2015119944 (Incyte Corp; Merck Sharp & Dohme Corp), WO2017192961 (Incyte Corp), WO2017106634 (Incyte Corp), WO2013132317 (Aurigene Discovery Technologies Ltd), WO2012168944 (Aurigene Discovery Technologies Ltd), WO2015036927 (Aurigene Discovery Technologies Ltd), WO2015044900 (Aurigene Discovery Technologies Ltd), WO2018026971 (Arising International).

In some embodiments, the agents as described herein are combined with anti-TIGIT antibodies, such as BMS-986207, RG-6058, AGEN-1307.

TNF Receptor Superfamily (TNFRSF) Member Agonists or Activators

In some embodiments, the agents as described herein are combined with an agonist of one or more TNF receptor superfamily (TNFRSF) members, e.g., an agonist of one or more of TNFRSF1A (NCBI Gene ID: 7132), TNFRSF1B (NCBI Gene ID: 7133), TNFRSF4 (OX40, CD134; NCBI Gene ID: 7293), TNFRSF5 (CD40; NCBI Gene ID: 958), TNFRSF6 (FAS, NCBI Gene ID: 355), TNFRSF7 (CD27, NCBI Gene ID: 939), TNFRSF8 (CD30, NCBI Gene ID: 943), TNFRSF9 (4-1BB, CD137, NCBI Gene ID: 3604), TNFRSF10A (CD261, DR4, TRAILR1, NCBI Gene ID: 8797), TNFRSF10B (CD262, DR5, TRAILR2, NCBI Gene ID: 8795), TNFRSF10C (CD263, TRAILR3, NCBI Gene ID: 8794), TNFRSF10D (CD264, TRAILR4, NCBI Gene ID: 8793), TNFRSF11A (CD265, RANK, NCBI Gene ID: 8792), TNFRSF11B (NCBI Gene ID: 4982), TNFRSF12A (CD266, NCBI Gene ID: 51330), TNFRSF13B (CD267, NCBI Gene ID: 23495), TNFRSF13C (CD268, NCBI Gene ID: 115650), TNFRSF16 (NGFR, CD271, NCBI Gene ID: 4804), TNFRSF17 (BCMA, CD269, NCBI Gene ID: 608), TNFRSF18 (GITR, CD357, NCBI Gene ID: 8784), TNFRSF19 (NCBI Gene ID: 55504), TNFRSF21 (CD358, DR6, NCBI Gene ID: 27242), and TNFRSF25 (DR3, NCBI Gene ID: 8718).

Example anti-TNFRSF4 (OX40) antibodies that can be co-administered include without limitation, MEDI6469, MEDI6383, MEDI0562 (tavolixizumab), MOXR0916, PF-04518600, RG-7888, GSK-3174998, INCAGN1949, BMS-986178, GBR-8383, ABBV-368, IBI-101 and those described in WO2016179517, WO2017096179, WO2017096182, WO2017096281, and WO2018089628.

Example anti-TNFRSF5 (CD40) antibodies that can be co-administered include without limitation RG7876, SEA-CD40, APX-005M and ABBV-428.

In some embodiments, the anti-TNFRSF7 (CD27) antibody varlilumab (CDX-1127) is co-administered.

Example anti-TNFRSF9 (4-1BB, CD137) antibodies that can be co-administered include without limitation urelumab, utomilumab (PF-05082566), AGEN2373 and ADG-106.

Example anti-TNFRSF18 (GITR) antibodies that can be co-administered include without limitation, MEDI1873, FPA-154, INCAGN-1876, TRX-518, BMS-986156, MK-1248, GWN-323, and those described in WO2017096179, WO2017096276, WO2017096189, and WO2018089628. In some embodiments, an antibody, or fragment thereof, co-targeting TNFRSF4 (OX40) and TNFRSF18 (GITR) is co-administered. Such antibodies are described, e.g., in WO2017096179 and WO2018089628.

Indoleamine-Pyrrole-2,3-Dioxygenase (IDO1) Inhibitors

In some embodiments, the agents as described herein, are combined with an inhibitor of indoleamine 2,3-dioxygenase 1 (IDO1; NCBI Gene ID: 3620). Examples of IDO1 inhibitors include without limitation, BLV-0801, epacadostat, resminostat, F-001287, GBV-1012, GBV-1028, GDC-0919, indoximod, NKTR-218, NLG-919-based vaccine, PF-06840003, pyranonaphthoquinone derivatives (SN-35837), SBLK-200802, BMS-986205, and shIDO-ST, EOS-200271, KHK-2455, LY-3381916, and the compounds disclosed in US20100015178 (Incyte), US2016137652 (*Flexus* Biosciences, Inc.), WO2014073738 (*Flexus* Biosciences, Inc.), and WO2015188085 (*Flexus* Biosciences, Inc.).

LAG-3 and TIM-3 Inhibitors

In some embodiments, the agents as described herein are combined with an anti-TIM-3 antibody, such as TSR-022, LY-3321367, MBG-453, INCAGN-2390.

In some embodiments, the antibodies or antigen-binding fragments described herein are combined with an anti LAG-3 (Lymphocyte-activation) antibody, such as relatlimab (ONO-4482), LAG-525, MK-4280, REGN-3767, INCAGN2385.

Examples of additional immune-based therapies that can be combined with an agent of this disclosure include interferon alfa; interferon alfa-2b; interferon alfa-n3; pegylated interferon alfa; interferon gamma; Flt3 agonists; gepon; normferon, peginterferon alfa-2a, peginterferon alfa-2b, RPI-MN.

Inhibitor of Apoptosis Proteins Family Proteins (IAPs)

Examples of IAP inhibitors include APG-1387.

Recombinant Thymosin Alpha-1

Examples of recombinant thymosin alpha-1 include NL-004 and PEGylated thymosin alpha-1.

Bruton's Tyrosine Kinase (BTK) Inhibitors

Examples of BTK inhibitors include ABBV-105, acalabrutinib (ACP-196), ARQ-531, BMS-986142, dasatinib, ibrutinib, GDC-0853, PRN-1008, SNS-062, ONO-4059, BGB-3111, ML-319, MSC-2364447, RDX-022, X-022, AC-058, RG-7845, spebrutinib, TAS-5315, TP-0158, TP-4207, HM-71224, KBP-7536, M-2951, TAK-020, AC-0025, and the compounds disclosed in US20140330015 (Ono Pharmaceutical), US20130079327 (Ono Pharmaceutical), and US20130217880 (Ono Pharmaceutical).

KDM Inhibitors

Examples of KDM5 inhibitors include the compounds disclosed in WO2016057924 (Genentech/Constellation Pharmaceuticals), US20140275092 (Genentech/Constellation Pharmaceuticals), US20140371195 (Epitherapeutics), US20140371214 (Epitherapeutics), US20160102096 (Epitherapeutics), US20140194469 (Quanticel), US20140171432, US20140213591 (Quanticel), US20160039808 (Quanticel), US20140275084 (Quanticel), and WO2014164708 (Quanticel).

Examples of KDM1 inhibitors include the compounds disclosed in U.S. Pat. No. 9,186,337B2 (Oryzon Genomics), GSK-2879552, RG-6016, and ORY-2001.

Arginase Inhibitors

Examples of Arginase inhibitors include CB-1158, C-201, and resminostat.

Bi- and Tri-Specific Natural Killer (NK)-Cell Engagers

In some embodiments, the agents as described herein, are combined with a bi-specific NK-cell engager (BiKE) or a tri-specific NK-cell engager (TriKE) (e.g., not having an Fc) or bi-specific antibody (e.g., having an Fc) against an NK cell activating receptor, e.g., CD16A, C-type lectin receptors (CD94/NKG2C, NKG2D, NKG2E/H and NKG2F), natural cytotoxicity receptors (NKp30, NKp44 and NKp46), killer cell C-type lectin-like receptor (NKp65, NKp80), Fc receptor FcTR (which mediates antibody-dependent cell cytotoxicity), SLAM family receptors (e.g., 2B4, SLAM6 and SLAM7), killer cell immunoglobulin-like receptors (KIR) (KIR-2DS and KIR-3DS), DNAM-1 and CD137 (41BB). As appropriate, the anti-CD16 binding bi-specific molecules may or may not have an Fc. Illustrative bi-specific NK-cell engagers that can be co-administered target CD16 and one or more HBV-associated antigens as described herein. BiKEs and TriKEs are described, e.g., in Felices, et al., *Methods Mol Biol.* (2016) 1441:333-346; Fang, et al., *Semin Immunol.* (2017) 31:37-54.

Long Acting Treatments

Long acting entecavir (subcutaneous depot), long acting tenofovir (TFD and TAF) implants (devices) or subcutaneous depot. An example of long acting entecavir is described in Exploration of long-acting implant formulations of hepatitis B drug entecavir., Eur J Pharm Sci. 2019 Aug. 1; 136:104958;

Gene Therapy and Cell Therapy

In some embodiments, the agents described herein are combined with a gene or cell therapy regimen. Gene therapy and cell therapy include without limitation the genetic modification to silence a gene; genetic approaches to directly kill the infected cells; the infusion of immune cells designed to replace most of the patient's own immune system to enhance the immune response to infected cells, or activate the patient's own immune system to kill infected cells, or find and kill the infected cells; genetic approaches to modify cellular activity to further alter endogenous immune responsiveness against the infection.

Gene Editors

The genome editing system is selected from the group consisting of: a CRISPR/Cas9 system, a zinc finger nuclease system, a TALEN system, a homing endonucleases system, and a meganuclease system (e.g., an ARCUS system); e.g., cccDNA elimination via targeted cleavage, and altering one or more of the hepatitis B virus (HBV) viral genes. Altering (e.g., knocking out and/or knocking down) the PreC, C, X, PreSI, PreS2, S, P or SP gene refers to (1) reducing or eliminating PreC, C, X, PreSI, PreS2, S, P or SP gene expression, (2) interfering with Precore, Core, X protein, Long surface protein, middle surface protein, S protein (also known as HBs antigen and HBsAg), polymerase protein, and/or Hepatitis B spliced protein function (HBe, HBc, HBx, PreS1, PreS2, S, Pol, and/or HBSP or (3) reducing or eliminating the intracellular, serum and/or intraparenchymal levels of HBe, HBc, HBx, LHBs, MHBs, SHBs, Pol, and/or HBSP proteins. Knockdown of one or more of the PreC, C, X, PreSI, PreS2, S, P and/or SP gene(s) is performed by targeting the gene(s) within HBV cccDNA and/or integrated HBV DNA.

Example of gene therapy, such as liver targeted anti-HBV gene therapy (using ARCUS technology), or using CRISPR/Cas9 gene editing technology, or EBT-106 (LNP-delivered CRISPR/CasX nuclease.

CAR-T Cell Therapy

CAR-T cell therapy includes a population of immune effector cells engineered to express a chimeric antigen receptor (CAR), wherein the CAR includes an HBV antigen-binding domain. In some embodiments, the antigen-binding domain is a domain disclosed herein. In some embodiments, the antigen-binding domain is other than a domain disclosed herein. In some embodiments, the antigen is HBsAg (i.e.

HbsAg-CART). The immune effector cell is a T-cell or an NK cell. In some embodiments, the T-cell is a CD4+ T-cell, a CD8+ T-cell, a NK cell or a combination thereof. Cells can be autologous or allogeneic. An example of a CART directed to HBV is described in Cytotherapy. 2018 May; 20(5):697-705. doi: 10.1016/j.jcyt.2018.02.

TCR-T Cell Therapy

TCR-T cell therapy includes T cells expressing HBV-specific T cell receptors. TCR-T cells are engineered to target HBV derived peptides presented on the surface of virus-infected cells. An example of a TCR directed to HBV is described in Wisskirchen, K. et al. T cell receptor grafting allows virological control of hepatitis B virus infection. J Clin Invest. 2019; 129(7):2932-2945.

TCR-T cell therapy includes T-Cells expressing HBV surface antigen (HBsAg)-specific TCR.

TCR-T cell therapy includes TCR-T therapy directed to treatment of HBV, such as LTCR-H2-1.

In another specific embodiment, an agent disclosed herein, or a pharmaceutically acceptable salt thereof, is combined with an HBV DNA polymerase inhibitor, one or two additional therapeutic agents selected from the group consisting of immunomodulators, TLR modulators, HBsAg inhibitors, HBsAg secretion or assembly inhibitors, HBV therapeutic vaccines, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, or TCR-like antibodies), cyclophilin inhibitors, stimulators of retinoic acid-inducible gene 1, stimulators of RIG-I like receptors, PD-1 inhibitors, PD-L1 inhibitors, Arginase inhibitors, PI3K inhibitors, IDO inhibitors, and stimulators of NOD2, and one or two additional therapeutic agents selected from the group consisting of HBV viral entry inhibitors, NTCP inhibitors, HBx inhibitors, cccDNA inhibitors, HBV antibodies targeting the surface antigens of the hepatitis B virus, siRNA, miRNA gene therapy agents, sshRNAs, KDM5 inhibitors, and nucleoprotein modulators (HBV core or capsid protein modulators).

In another specific embodiment, an agent disclosed herein, or a pharmaceutically acceptable salt thereof, is combined with at least a second additional therapeutic agent selected from the group consisting of: HBV DNA polymerase inhibitors, immunomodulator, TLR modulators, HBsAg inhibitors, HBV therapeutic vaccines, HBV antibodies including HBV antibodies targeting the surface antigens of the hepatitis B virus and bispecific antibodies and "antibody-like" therapeutic proteins (such as DARPins®, anti-pMHC TCR-like antibodies, DARTs®, DUOBODIES®, BITES®, XmAbs®, TandAbs®, Fab derivatives, or TCR-like antibodies), cyclophilin inhibitors, stimulators of retinoic acid-inducible gene 1, stimulators of RIG-I like receptors, PD-1 inhibitors, PD-L1 inhibitors, Arginase inhibitors, PI3K inhibitors, IDO inhibitors, and stimulators of NOD2.

In another specific embodiment, an agent disclosed herein, or a pharmaceutically acceptable salt thereof, is combined with at least a second additional therapeutic agent selected from the group consisting of: HBV DNA polymerase inhibitors, HBV viral entry inhibitors, NTCP inhibitors, HBx inhibitors, cccDNA inhibitors, HBV antibodies targeting the surface antigens of the hepatitis B virus, siRNA, miRNA gene therapy agents, sshRNAs, KDM5 inhibitors, and nucleoprotein modulators (HBV core or capsid protein inhibitors).

In a particular embodiment, an agent disclosed herein, or a pharmaceutically acceptable salt thereof, is combined with compounds such as those disclosed in U.S. Publication No. 2010/0143301 (Gilead Sciences), U.S. Publication No. 2011/0098248 (Gilead Sciences), U.S. Publication No. 2009/0047249 (Gilead Sciences), U.S. Pat. No. 8,722,054 (Gilead Sciences), U.S. Publication No. 2014/0045849 (Janssen), U.S. Publication No. 2014/0073642 (Janssen), WO2014/056953 (Janssen), WO2014/076221 (Janssen), WO2014/128189 (Janssen), U.S. Publication No. 2014/0350031 (Janssen), WO2014/023813 (Janssen), U.S. Publication No. 2008/0234251 (Array Biopharma), U.S. Publication No. 2008/0306050 (Array Biopharma), U.S. Publication No. 2010/0029585 (Ventirx Pharma), U.S. Publication No. 2011/0092485 (Ventirx Pharma), US2011/0118235 (Ventirx Pharma), U.S. Publication No. 2012/0082658 (Ventirx Pharma), U.S. Publication No. 2012/0219615 (Ventirx Pharma), U.S. Publication No. 2014/0066432 (Ventirx Pharma), U.S. Publication No. 2014/0088085 (Ventirx Pharma), U.S. Publication No. 2014/0275167 (Novira Therapeutics), U.S. Publication No. 2013/0251673 (Novira Therapeutics), U.S. Pat. No. 8,513,184 (Gilead Sciences), U.S. Publication No. 2014/0030221 (Gilead Sciences), U.S. Publication No. 2013/0344030 (Gilead Sciences), U.S. Publication No. 2013/0344029 (Gilead Sciences), US20140275167 (Novira Therapeutics), US20130251673 (Novira Therapeutics), U.S. Publication No. 2014/0343032 (Roche), WO2014037480 (Roche), U.S. Publication No. 2013/0267517 (Roche), WO2014131847 (Janssen), WO2014033176 (Janssen), WO2014033170 (Janssen), WO2014033167 (Janssen), WO2015/059212 (Janssen), WO2015118057 (Janssen), WO2015011281 (Janssen), WO2014184365 (Janssen), WO2014184350 (Janssen), WO2014161888 (Janssen), WO2013096744 (Novira), US20150225355 (Novira), US20140178337 (Novira), US20150315159 (Novira), US20150197533 (Novira), US20150274652 (Novira), US20150259324, (Novira), US20150132258 (Novira), U.S. Pat. No. 9,181,288 (Novira), WO2014184350 (Janssen), WO2013144129 (Roche), US20100015178 (Incyte), US2016137652 (*Flexus* Biosciences, Inc.), WO2014073738 (*Flexus* Biosciences, Inc.), WO2015188085 (*Flexus* Biosciences, Inc.), U.S. Publication No. 2014/0330015 (Ono Pharmaceutical), U.S. Publication No. 2013/0079327 (Ono Pharmaceutical), U.S. Publication No. 2013/0217880 (Ono pharmaceutical), WO2016057924 (Genentech/Constellation Pharmaceuticals), US20140275092 (Genentech/Constellation Pharmaceuticals), US20140371195 (Epitherapeutics) and US20140371214 (Epitherapeutics), US20160102096 (Epitherapeutics), US20140194469 (Quanticel), US20140171432, US20140213591 (Quanticel), US20160039808 (Quanticel), US20140275084 (Quanticel), WO2014164708 (Quanticel), U.S. Pat. No. 9,186,337B2 (Oryzon Genomics), and other drugs for treating HBV, and combinations thereof.

In some embodiments, an agent disclosed herein, or a pharmaceutically acceptable salt thereof, is combined with 5-30 mg tenofovir alafenamide fumarate, tenofovir alafenamide hemifumarate, or tenofovir alafenamide. In some embodiments, an agent disclosed herein, or a pharmaceutically acceptable salt thereof, is combined with 5-10; 5-15; 5-20; 5-25; 25-30; 20-30; 15-30; or 10-30 mg tenofovir alafenamide fumarate, tenofovir alafenamide hemifumarate, or tenofovir alafenamide. In some embodiments, an agent disclosed herein, or a pharmaceutically acceptable salt thereof, is combined with 10 mg tenofovir alafenamide fumarate, tenofovir alafenamide hemifumarate, or tenofovir alafenamide. In some embodiments, an agent disclosed herein, or a pharmaceutically acceptable salt thereof, is combined with 25 mg tenofovir alafenamide fumarate, tenofovir alafenamide hemifumarate, or tenofovir alafenamide. An agent as disclosed herein may be combined with the agents provided herein in any dosage amount of the compound (e.g., from 50 mg to 500 mg of compound) the same as if each combination of dosages were specifically and individually listed.

In some embodiments, an agent disclosed herein, or a pharmaceutically acceptable salt thereof, is combined with 100-400 mg tenofovir disoproxil fumarate, tenofovir disoproxil hemifumarate, or tenofovir disoproxil. In some embodiments, an agent disclosed herein, or a pharmaceutically acceptable salt thereof, is combined with 100-150; 100-200, 100-250; 100-300; 100-350; 150-200; 150-250; 150-300; 150-350; 150-400; 200-250; 200-300; 200-350; 200-400; 250-350; 250-400; 350-400 or 300-400 mg tenofovir disoproxil fumarate, tenofovir disoproxil hemifumarate, or tenofovir disoproxil. In some embodiments, an agent disclosed herein, or a pharmaceutically acceptable salt thereof, is combined with 300 mg tenofovir disoproxil fumarate, tenofovir disoproxil hemifumarate, or tenofovir disoproxil. In some embodiments, an agent disclosed herein, or a pharmaceutically acceptable salt thereof, is combined with 250 mg tenofovir disoproxil fumarate, tenofovir disoproxil hemifumarate, or tenofovir disoproxil. In some embodiments, an agent herein, or a pharmaceutically acceptable salt thereof, is combined with 150 mg tenofovir disoproxil fumarate, tenofovir disoproxil hemifumarate, or tenofovir disoproxil. An agent as disclosed herein may be combined with the agents provided herein in any dosage amount of the compound (e.g., from 50 mg to 500 mg of compound) the same as if each combination of dosages were specifically and individually listed.

VI. Methods of Treatment

In some embodiments, the present disclosure provides method of inhibiting DGKα in a subject in need thereof, the method comprising administering to the subject a therapeutically effective amount of a compound of the present disclosure, or a pharmaceutically acceptable salt thereof, or a pharmaceutical composition of the present disclosure. In some embodiments, the present disclosure provides method of inhibiting DGKα in a subject in need thereof, the method comprising administering to the subject a therapeutically effective amount of a compound of the present disclosure, e.g., a compound of Formula (I), a compound shown in Table 1, or a pharmaceutically acceptable salt thereof, or a pharmaceutical composition of the present disclosure.

In some embodiments, the present disclosure provides a method of inhibiting DGKα in a subject in need thereof that comprises administering to the subject a therapeutically effective amount of a compound of Formula (I) or a compound having the structure of a compound in Table 1.

In some embodiments, a method of inhibiting DGKα in a subject in need thereof comprises administering to the subject a therapeutically effective amount of the compound having the structure of a compound in Table 1 or a pharmaceutically acceptable salt thereof, or a pharmaceutical composition thereof.

In some embodiments, the present disclosure provides a method of treating cancer in a subject in need thereof, the method comprising administering to the subject a therapeutically effective amount of a compound of the present disclosure, or a pharmaceutically acceptable salt thereof, or a pharmaceutical composition thereof.

In some embodiments, the cancer is pancreatic cancer, bladder cancer, colorectal cancer, breast cancer, prostate cancer, renal cancer, hepatocellular cancer, lung cancer, ovarian cancer, cervical cancer, gastric cancer, esophageal cancer, head and neck cancer, melanoma, neuroendocrine cancer, CNS cancer, brain cancer, bone cancer, soft tissue sarcoma, non-small cell lung cancer, small-cell lung cancer or colon cancer. In some embodiments, the cancer is acute lymphocytic leukemia (ALL), acute myeloid leukemia (AML), chronic lymphocytic leukemia (CLL), small lymphocytic lymphoma (SLL), myelodysplastic syndrome (MDS), myeloproliferative disease (MPD), chronic myeloid leukemia (CML), multiple myeloma (MM), non-Hodgkin's lymphoma (NHL), mantle cell lymphoma (MCL), follicular lymphoma, Waldestrom's macroglobulinemia (WM), T-cell lymphoma, B-cell lymphoma or diffuse large B-cell lymphoma (DLBCL). In some embodiments, the cancer is brain (gliomas), glioblastomas, astrocytomas, glioblastoma multiforme, Bannayan-Zonana syndrome, Cowden disease, Lhermitte-Duclos disease, breast, colon, head and neck, kidney, lung, liver, melanoma, ovarian, pancreatic, adenocarcinoma, ductal adenocarcinoma, adenosquamous carcinoma, acinar cell carcinoma, glucagonoma, insulinoma, prostate, sarcoma or thyroid.

In some embodiments, the cancer is a solid tumor, a hematological cancer, or a metastatic lesion. In some embodiments, the solid tumor is a sarcoma, a fibroblastic sarcoma, a carcinoma, or an adenocarcinoma. In some embodiments, the hematological cancer is a leukemia, a lymphoma, or a myeloma.

In some embodiments, the cancer is a lung cancer, a melanoma, a renal cancer, a liver cancer, a myeloma, a prostate cancer, a breast cancer, an ovarian cancer, a colorectal cancer, a pancreatic cancer, a head and neck cancer, an anal cancer, a gastro-esophageal cancer, a mesothelioma, a nasopharyngeal cancer, a thyroid cancer, a cervical cancer, an epithelial cancer, a peritoneal cancer, a lymphoproliferative disease, an acute lymphoblastic leukemia (ALL), an acute myelogenous leukemia (AML), a chronic lymphocytic leukemia (CLL), a chronic myelogenous leukemia (CML), a chronic myelomonocytic leukemia (CMML), a hairy cell leukemia, a B cell lymphoma, a diffuse large B-cell lymphoma (DLBCL), an activated B-cell like (ABC) diffuse large B cell lymphoma, a germinal center B cell (GCB) diffuse large B cell lymphoma, a mantle cell lymphoma, a Hodgkin lymphoma, a non-Hodgkin lymphoma, a relapsed non-Hodgkin lymphoma, a refractory non-Hodgkin lymphoma, a recurrent follicular non-Hodgkin lymphoma, a Burkitt lymphoma, a small lymphocytic lymphoma, a follicular lymphoma, a lymphoplasmacytic lymphoma, or an extranodal marginal zone lymphoma.

In some embodiments, the cancer is an epithelial tumor (e.g., a carcinoma, a squamous cell carcinoma, a basal cell carcinoma, a squamous intraepithelial neoplasia), a glandular tumor (e.g., an adenocarcinoma, an adenoma, an adenomyoma), a mesenchymal or soft tissue tumor (e.g., a sarcoma, a rhabdomyosarcoma, a leiomyosarcoma, a liposarcoma, a fibrosarcoma, a dermatofibrosarcoma, a neurofibrosarcoma, a fibrous histiocytoma, an angiosarcoma, an angiomyxoma, a leiomyoma, a chondroma, a chondrosarcoma, an alveolar soft-part sarcoma, an epithelioid hemangioendothelioma, a Spitz tumor, a synovial sarcoma), or a lymphoma.

In some embodiments, the cancer is a solid tumor in or arising from a tissue or organ selected from the group consisting of: bone (e.g., adamantinoma, aneurysmal bone cysts, angiosarcoma, chondroblastoma, chondroma, chondromyxoid fibroma, chondrosarcoma, chordoma, dedifferentiated chondrosarcoma, enchondroma, epithelioid hemangioendothelioma, fibrous dysplasia of the bone, giant cell tumour of bone, haemangiomas and related lesions, osteoblastoma, osteochondroma, osteosarcoma, osteoid osteoma, osteoma, periosteal chondroma, Desmoid tumor, Ewing sarcoma); lips and oral cavity (e.g., odontogenic ameloblastoma, oral leukoplakia, oral squamous cell carcinoma, primary oral mucosal melanoma); salivary glands (e.g., pleomorphic salivary gland adenoma, salivary gland adenoid cystic carcinoma, salivary gland mucoepidermoid carcinoma, salivary gland Warthin's tumors); esophagus (e.g., Barrett's esophagus, dysplasia and adenocarcinoma); gastrointestinal tract, including stomach (e.g., gastric adenocarcinoma, primary gastric lymphoma, gastrointestinal stromal tumors (GISTs), metastatic deposits, gastric carcinoids, gastric sarcomas, neuroendocrine carcinoma, gastric primary squamous cell carcinoma, gastric adenoacanthomas), intestines and smooth muscle (e.g., intravenous leiomyomatosis), colon (e.g., colorectal adenocarcinoma), rectum, anus; pancreas (e.g., serous neoplasms, including microcystic or macrocystic serous cystadenoma, solid serous cystadenoma, Von Hippel-Landau (VHL)-associated serous cystic neoplasm, serous cystadenocarcinoma, mucinous cystic neoplasms (MCN), intraductal papillary mucinous neoplasms (IPMN), intraductal oncocytic papillary neoplasms (IOPN), intraductal tubular neoplasms, cystic acinar neoplasms, including acinar cell cystadenoma, acinar cell cystadenocarcinoma, pancreatic adenocarcinoma, invasive pancreatic ductal adenocarcinomas, including tubular adenocarcinoma, adenosquamous carcinoma, colloid carcinoma, medullary carcinoma, hepatoid carcinoma, signet ring cell carcinoma, undifferentiated carcinoma, undifferentiated carcinoma with osteoclast-like giant cells, acinar cell carcinoma, neuroendocrine neoplasms, neuroendocrine microadenoma, neuroendocrine tumors (NET), neuroendocrine carcinoma (NEC), including small cell or large cell NEC, insulinoma, gastrinoma, glucagonoma, serotonin-producing NET, somatostatinoma, VIPoma, solid-pseudopapillary neoplasms (SPN), pancreatoblastoma); gall bladder (e.g. carcinoma of the gallbladder and extrahepatic bile ducts, intrahepatic cholangiocarcinoma); neuro-endocrine (e.g., adrenal cortical carcinoma, carcinoid tumors, phaeochromocytoma, pituitary adenomas); thyroid (e.g., anaplastic (undifferentiated) carcinoma, medullary carcinoma, oncocytic tumors, papillary carcinoma, adenocarcinoma); liver (e.g., adenoma, combined hepatocellular and cholangiocarcinoma, fibrolamellar carcinoma, hepatoblastoma, hepatocellular carcinoma, mesenchymal, nested stromal epithelial tumor, undifferentiated carcinoma, hepatocellular carcinoma, intrahepatic cholangiocarcinoma, bile duct cystadenocarcinoma, epithelioid hemangioendothelioma, angiosarcoma, embryonal sarcoma, rhabdomyosarcoma, solitary fibrous tumor, teratoma, York sac tumor, carcinosarcoma, rhabdoid tumor); kidney (e.g., ALK-rearranged renal cell carcinoma, chromophobe renal cell carcinoma, clear cell renal cell carcinoma, clear cell sarcoma, metanephric adenoma, metanephric adenofibroma, mucinous tubular and spindle cell carcinoma, nephroma, nephroblastoma (Wilms tumor), papillary adenoma, papillary renal cell carcinoma, renal oncocytoma, renal cell carcinoma, succinate dehydrogenase-deficient renal cell carcinoma, collecting duct carcinoma); breast (e.g., invasive ductal carcinoma, including without limitation, acinic cell carcinoma, adenoid cystic carcinoma, apocrine carcinoma, cribriform carcinoma, glycogen-rich/clear cell, inflammatory carcinoma, lipid-rich carcinoma, medullary carcinoma, metaplastic carcinoma, micropapillary carcinoma, mucinous carcinoma, neuroendocrine carcinoma, oncocytic carcinoma, papillary carcinoma, sebaceous carcinoma, secretory breast carcinoma, tubular carcinoma, lobular carcinoma, including without limitation, pleomorphic carcinoma, signet ring cell carcinoma, peritoneum (e.g., mesothelioma, primary peritoneal cancer)); female sex organ tissues, including ovary (e.g., choriocarcinoma, epithelial tumors, germ cell tumors, sex cord-stromal tumors), Fallopian tubes (e.g., serous adenocarcinoma, mucinous adenocarcinoma, endometrioid adenocarcinoma, clear cell adenocarcinoma, transitional cell carcinoma, squamous cell carcinoma, undifferentiated carcinoma, mullerian tumors, adenosarcoma, leiomyosarcoma, teratoma, germ cell tumors, choriocarcinoma, trophoblastic tumors), uterus (e.g., carcinoma of the cervix, endometrial polyps, endometrial hyperplasia, intraepithelial carcinoma (EIC), endometrial carcinoma (e.g., endometrioid carcinoma, serous carcinoma, clear cell carcinoma, mucinous carcinoma, squamous cell carcinoma, transitional carcinoma, small cell carcinoma, undifferentiated carcinoma, mesenchymal neoplasia), leiomyoma (e.g., endometrial stromal nodule, leiomyosarcoma, endometrial stromal sarcoma (ESS), mesenchymal tumors), mixed epithelial and mesenchymal tumors (e.g., adenofibroma, carcinofibroma, adenosarcoma, carcinosarcoma (malignant mixed mesodermal sarcoma—MMMT)), endometrial stromal tumors, endometrial malignant mullerian mixed tumours, gestational trophoblastic tumors (partial hydatiform mole, complete hydatiform mole, invasive hydatiform mole, placental site tumour)), vulva, vagina; male sex organ tissues, including prostate, testis (e.g., germ cell tumors, spermatocytic seminoma), penis; bladder (e.g., squamous cell carcinoma, urothelial carcinoma, bladder urothelial carcinoma); brain, (e.g., gliomas (e.g., astrocytomas, including non-infiltrating, low-grade, anaplastic, glioblastomas; oligodendrogliomas, ependymomas), meningiomas, gangliogliomas, schwannomas (neurilemmomas), craniopharyngiomas, chordomas, Non-Hodgkin lymphomas, pituitary tumors; eye (e.g., retinoma, retinoblastoma, ocular melanoma, posterior uveal melanoma, iris hamartoma); head and neck (e.g., nasopharyngeal carcinoma, Endolymphatic Sac Tumor (ELST), epidermoid carcinoma, laryngeal cancers including squamous cell carcinoma (SCC) (e.g., glottic carcinoma, supraglottic carcinoma, subglottic carcinoma, transglottic carcinoma), carcinoma in situ, verrucous, spindle cell and basaloid SCC, undifferentiated carcinoma, laryngeal adenocarcinoma, adenoid cystic carcinoma, neuroendocrine carcinomas, laryngeal sarcoma), head and neck paragangliomas (e.g., carotid body, jugulotympanic, vagal); thymus (e.g., thymoma); heart (e.g., cardiac myxoma); lung (e.g., small cell carcinoma (SCLC), non-small cell lung carcinoma (NSCLC), including squamous cell carcinoma (SCC), adenocarcinoma and large cell carcinoma, carcinoids (typical or atypical), carcinosarcomas, pulmonary blastomas, giant cell carcinomas, spindle cell carcinomas, pleuropulmonary blastoma); lymph (e.g., lymphomas, including Hodgkin's lymphoma, non-Hodgkin's lymphoma, Epstein-Barr virus (EBV)-associated lymphoproliferative diseases, including B cell lymphomas and T cell lymphomas (e.g., Burkitt lymphoma, large B cell lymphoma, diffuse large B-cell lymphoma (DLBCL), mantle cell lymphoma, indolent B-cell lymphoma, low grade B cell lymphoma, fibrin-associated diffuse large cell lymphoma; primary effusion lymphoma; plasmablastic lymphoma; extranodal NK/T cell lymphoma, nasal type; peripheral T cell lymphoma, cutaneous T cell lymphoma, angioimmunoblastic T cell lymphoma; follicular T cell lymphoma; systemic T cell lymphoma), lymphangioleiomyomatosis); central nervous system (CNS) (e.g., gliomas including astrocytic tumors (e.g., pilocytic astrocytoma, pilomyxoid astrocytoma, subependymal giant cell astrocytoma, pleomorphic xanthoastrocytoma, diffuse astrocytoma, fibrillary astrocytoma, gemistocytic astrocytoma, protoplasmic astrocytoma, anaplastic astrocytoma, glioblastoma (e.g., giant cell glioblastoma, gliosarcoma, glioblastoma multiforme) and gliomatosis cerebri), oligodendroglial tumors (e.g., oligodendroglioma, anaplastic oligodendroglioma), oligoastrocytic tumors (e.g., oligoastrocytoma, anaplastic oligoastrocytoma), ependymal tumors (e.g., subependymom, myxopapillary ependymoma, ependymomas (e.g., cellular, papillary, clear cell, tanycytic), anaplastic ependymoma), optic nerve glioma, and non-gliomas (e.g., choroid plexus tumors, neuronal and mixed neuronal-glial tumors, pineal region tumors, embryonal tumors, medulloblastoma, meningeal tumors, primary CNS lymphomas, germ cell tumors, pituitary adenomas, cranial and paraspinal nerve tumors, stellar region tumors), neurofibroma, meningioma, peripheral nerve sheath tumors, peripheral neuroblastic tumours (including without limitation neuroblastoma, ganglioneuroblastoma, ganglioneuroma), trisomy 19 ependymoma); neuroendocrine tissues (e.g., paraganglionic system including adrenal medulla (pheochromocytomas) and extra-adrenal paraganglia ((extra-adrenal) paragangliomas); skin (e.g., clear cell hidradenoma, cutaneous benign fibrous histiocytomas, cylindroma, hidradenoma, melanoma (including cutaneous melanoma, mucosal melanoma), pilomatricoma, Spitz tumors); and soft tissues (e.g., aggressive angiomyxoma, alveolar rhabdomyosarcoma, alveolar soft part sarcoma, angiofibroma, angiomatoid fibrous histiocytoma, synovial sarcoma, biphasic synovial sarcoma, clear cell sarcoma, dermatofibrosarcoma protuberans, desmoid-type fibromatosis, small round cell tumor, desmoplastic small round cell tumor, elastofibroma, embryonal rhabdomyosarcoma, Ewing's tumors/primitive neurectodermal tumors (PNET), extraskeletal myxoid chondrosarcoma, extraskeletal osteosarcoma, paraspinal sarcoma, inflammatory myofibroblastic tumor, bpoblastoma, lipoma, chondroid lipoma, bposarcoma/malignant lipomatous tumors, bposarcoma, myxoid bposarcoma, fibromyxoid sarcoma, lymphangioleiomyoma, malignant myoepithelioma, malignant melanoma of soft parts, myoepithelial carcinoma, myoepithelioma, myxoinflammatory fibroblastic sarcoma, undifferentiated sarcoma, pericytoma, rhabdomyosarcoma, non rhabdomyosarcoma soft tissue sarcoma (NRSTS), soft tissue leiomyosarcoma, undifferentiated sarcoma, well-differentiated bposarcoma.

In some embodiments, the cancer is a melanoma, a gastric cancer, a triple-negative breast cancer (TNBC), a non-small cell lung cancer (NSCLC), a rectal adenocarcinoma, a colorectal cancer, a renal cell carcinoma, an ovarian cancer, a prostate cancer, an oral squamous cell carcinoma (SCC), a head and neck squamous cell carcinoma (HNSCC), a urothelial bladder cancer, a glioblastoma (GBM), a meningioma, adrenal cancer, or an endometrial cancer.

In some embodiments, the method further comprises administering one or more additional therapeutic agents to the subject. The additional therapeutic agent can include any therapeutic agent described above for combination therapy. In some embodiments, the additional therapeutic agent is independently an anti-neoplastic agent, nivolumab, pembrolizumab, atezolizumab, ipilimumab, chemotherapy, radiation therapy, or resection therapy. In some embodiments, the additional therapeutic agent is independently rituxan, doxorubicin, gemcitabine, nivolumab, pembrolizumab, artezolizumab, nivolumab, pembrolizumab, atezolizumab, or ipilimumab.

In some embodiments, the method comprises one or more additional therapeutic agents, wherein the additional therapeutic agent is a PD-1/PD-L1 inhibitor.

In some embodiments, the anti-neoplastic agent is an anti-microtubule agent, a platinum coordination complex, an alkylating agent, an antibiotic agent, a topoisomerase II inhibitor, an antimetabolite, a topoisomerase I inhibitor, a hormone or hormonal analogue, a signal transduction pathway inhibitor, a non-receptor tyrosine kinase angiogenesi, an inhibitor, an immunotherapeutic agent, a proapoptotic agent, a cell cycle signaling inhibitor, a proteasome inhibitor, a inhibitor of cancer metabolism, an anti-PD-L1 agent, a PD-1 antagonist, an immunomodulator, a STING modulating compound, a CD39 inhibitor, an A2a and A2a adenosine antagonist, a TLR4 antagonist, an antibody to ICOS, or OX40.

In some embodiments, the compound or pharmaceutical composition is co-administered with one or more additional therapeutic agents comprising an activator or agonist of a fms related tyrosine kinase 3 (FLT3; CD 135) receptor, a toll-like receptor (TLR) or a stimulator of interferon genes (STING) receptor.

In some embodiments, the TLR agonist or activator is a TLR2 agonist, a TLR3 agonist, a TLR7 agonist, a TLR8 agonist and a TLR9 agonist.

In some embodiments, the STING receptor agonist or activator is ADU-S100 (MIW-815), SB-11285, MK-1454, SR-8291, AdVCA0848, GSK-532, SYN-STING, MSA-1, SR-8291, 5,6-dimethylxanthenone-4-acetic acid (DMXAA), cyclic-GAMP (cGAMP) and cyclic-di-AMP.

In some embodiments, the compound or pharmaceutical composition is co-administered with one or more additional therapeutic agents comprising an inhibitor or antagonist of: protein tyrosine phosphatase, non-receptor type 11 (PTPN11 or SHP2), myeloid cell leukemia sequence 1 (MCL1) apoptosis regulator; mitogen-activated protein kinase kinase kinase kinase 1 (MAP4K1) (also called Hematopoietic Progenitor Kinase 1 (HPK1)); diacylglycerol kinase alpha (DGKA, DAGK, DAGK1 or DGK-alpha); 5'-nucleotidase ecto (NT5E or CD73); transforming growth factor beta 1 (TGFB1 or TGF); heme oxygenase 1 (HMOX1, HO-1 or HOl); vascular endothelial growth factor A (VEGFA or VEGF); erb-b2 receptor tyrosine kinase 2 (ERBB2 HER2, HER2/neu or CD340); epidermal growth factor receptor (EGFR, ERBB, ERBB1 or HER1); ALK receptor tyrosine kinase (ALK, CD246); poly(ADP-ribose) polymerase 1 (PARP1 or PARP); cyclin dependent kinase 4 (CDK4); cyclin dependent kinase 6 (CDK6); C-C motif chemokine receptor 8 (CCR8, CDwl98); CD274 molecule (CD274, PDL1 or PD-L1); programmed cell death 1 (PDCD1, PD1 or PD-1); and/or cytotoxic T-lymphocyte associated protein 4 (CTLA4, CTLA-4, CD 152).

In some embodiments, the inhibitor comprises an antigen binding molecule, an antibody or an antigen-binding fragment thereof.

In some embodiments, the inhibitor of MCL1 is AMG-176, AMG-397, S-64315, AZD-5991, 483-LM, A1210477, UMI-77, or JKY-5-037.

In some embodiments, the inhibitor of PTPN11 or SHP2 is TN0155 (SHP-099), RMC-4550, JAB-3068 and RMC-4630.

In some embodiments, the additional therapeutic agent is a chemotherapeutic, an anti-neoplastic, a radiotherapeutic, or a checkpoint targeting agent. In some embodiments, the one or more anti-neoplastic or chemotherapeutic agents are a nucleoside analog (e.g., 5-fluorouracil, gemcitabine, cytarabine), a taxane (e.g., paclitaxel, nab-paclitaxel, docetaxel, cabazitaxel), a platinum coordination complex (cisplatin, carboplatin, oxaliplatin, nedaplatin, triplatin tetranitrate, phenanthriplatin, picoplatin, satraplatin, dicycloplatin, eptaplatin, lobaplatin, miriplatin), a dihydrofolate reductase (DHFR) inhibitor (e.g., methotrexate, trimetrexate, pemetrexed), a topoisomerase inhibitor (e.g., doxorubicin, daunorubicin, dactinomycin, eniposide, epirubicin, etoposide, idarubicin, irinotecan, mitoxantrone, pixantrone, sobuzoxane, topotecan, irinotecan, MM-398 (liposomal irinotecan), vosaroxin and GPX-150, al doxorubicin, AR-67, mavelertinib, AST-2818, avitinib (ACEA-0010), irofulven (MGI-114)), an alkylating agent (e.g., a nitrogen mustard (e.g., cyclophosphamide, chlormethine, uramustine or uracil mustard, melphalan, chlorambucil, ifosfamide, bendamustine, temozolomide, carmustine), a nitrosourea (e.g., carmustine, lomustine, streptozocin), an alkyl sulfonate (e.g., busulfan)), or mixtures thereof.

In some embodiments, the checkpoint targeting agent is an antagonist anti-PD-1 antibody, an antagonist anti-PD-L1 antibody, an antagonist anti-PD-L2 antibody, an antagonist anti-CTLA-4 antibody, an antagonist anti-TIM-3 antibody, an antagonist anti-LAG-3 antibody, an antagonist anti-CEACAMI antibody, an agonist anti-GITR antibody, an antagonist anti-TIGIT antibody, an antagonist anti-VISTA antibody, an agonist anti-CD 137 antibody, or an agonist anti-OX40 antibody.

In some embodiments, the additional therapeutic agent comprises one or more cellular therapies. In some embodiments, the cellular therapy comprises one or more of a population of natural killer (NK) cells, NK-T cells, T cells, cytokine-induced killer (CIK) cells, macrophage (MAC) cells, tumor infiltrating lymphocytes (TTLs) and/or dendritic cells (DCs). In some embodiments, the cellular therapy entails a T cell therapy, e.g., co-administering a population of alpha/beta TCR T cells, gamma/delta TCR T cells, regulatory T (Treg) cells and/or TRuC™ T cells. In some embodiments, the cellular therapy entails a NK cell therapy, e.g., co-administering NK-92 cells. A cellular therapy can entail the co-administration of cells that are autologous, syngeneic or allogeneic to the subject. In some embodiments, the one or more of a population of immune cells comprise one or more chimeric antigen receptors (CARs).

In some embodiments, the additional therapeutic agent comprises an antibody or an antigen-binding fragment thereof, or antibody-drug conjugate thereof, CD3-targeting multi-specific molecule, CD16-targeting multi-specific molecule, non-immunoglobulin antigen binding molecule or antibody mimetic protein.

In some embodiments, the one or more additional therapeutic agents comprises an immunotherapy, an immunostimulatory therapy, a cytokine therapy, a chemokine therapy, a cellular therapy, a gene therapy, and combinations thereof. In some embodiments, the immunotherapy comprises co-administering one or more antibodies or antigen-binding antibody fragments thereof, or antibody-drug conjugates thereof, CD3-targeting multi-specific molecules, CD16-targeting multi-specific molecules, or non-immunoglobulin antigen-binding domains or antibody mimetic proteins directed against one or more targets or tumor associated antigens (TAAs).

In some embodiments, the present disclosure provides method of treating an HIV or hepatitis B virus infection in a subject in need thereof, the method comprising administering to the subject a therapeutically effective amount of a compound of the present disclosure, or a pharmaceutically acceptable salt thereof, or a pharmaceutical composition thereof. In some embodiments, the compound or pharmaceutical composition is co-administered with one or more additional therapeutic agents. In some embodiments, the one or more additional therapeutic agents comprises a vaccine.

In some embodiments, a method for manufacturing a medicament for treating cancer in a subject in need thereof is characterized in that a compound of the present disclosure, or a pharmaceutically acceptable salt thereof, is used.

In some embodiments, a method for manufacturing a medicament for inhibiting cancer metastasis in a subject in need thereof is characterized in that a compound of the present disclosure, or a pharmaceutically acceptable salt thereof, is used.

In some embodiments, a method for manufacturing a medicament for treating an HIV or hepatitis B virus infection in a subject in need thereof is characterized in that a compound of the present disclosure, or a pharmaceutically acceptable salt thereof, is used.

In some embodiments, a use of the compound of the present disclosure, or a pharmaceutically acceptable salt thereof, is for the manufacture of a medicament for the treatment of cancer in a subject.

In some embodiments, a use of the compound of the present disclosure, or a pharmaceutically acceptable salt thereof, is for the manufacture of a medicament for inhibiting cancer metastasis in a subject.

In some embodiments, a use of the compound of the present disclosure, or a pharmaceutically acceptable salt thereof, is for the manufacture of a medicament for the treatment of an HIV or hepatitis B infection in a subject.

In some embodiments, a compound of the present disclosure is for use in therapy. In some embodiments, the compound is for use in the treatment of a cancer in a subject in need thereof. In some embodiments, the compound is for use in inhibiting cancer metastasis in a subject in need thereof. In some embodiments, the compound is for use in the treatment of an HIV or hepatitis B virus infection in a subject in need thereof.

VII. Methods of Synthesis

Abbreviations. Certain abbreviations and acronyms are used in describing the experimental details. Although most of these would be understood by one skilled in the art, Table 4 contains a list of many of these abbreviations and acronyms.

TABLE 4

List of abbreviations and acronyms.

| Abbreviation | Meaning |
| --- | --- |
| Ac | acetyl |
| AcOEt | ethyl acetate (also EtOAc) |
| ACN | acetonitrile |
| Bn | benzyl |
| Boc | tert-butoxycarbonyl |
| BOP | benzotriazol-1-yloxytris(dimethylamino)phosphonium hexafluorophosphate |
| BroP | bromotris(dimethylamino)phosphonium hexafluorophosphate |
| Bu | butyl |
| nBuLi | n-butyllithium |
| $CDCl_3$ | Chloroform-d |
| dba | dibenzylideneacetone |
| DBU | 1,8-Diazabicyclo[5.4.0]undec-7-ene |
| DCM | dichloromethane |

TABLE 4-continued

List of abbreviations and acronyms.

| Abbreviation | Meaning |
| --- | --- |
| DMSO | dimethylsulfoxide |
| DMF | dimethylformamide |
| dppf | 1,1'-Bis(diphenylphosphino)ferrocene |
| EA | Ethyl acetate |
| Et | ethyl |
| iBu | isobutyl |
| IPA | isopropanol |
| iPr | isopropyl |
| LC | liquid chromatography |
| LDA | lithium diisopropylamide |
| Me | methyl |
| m/z | mass to charge ratio |
| MS or ms | mass spectrum |
| Abbreviation | Meaning |
| NMP | N-methyl-2-pyrrolidone |
| Ph | phenyl |
| $Ph_3P$ | triphenylphosphine |
| prep. HPLC | preparative high performance liquid chromatography (also prep-HPLC) |
| RT | room temperature |
| SEM | 2-(Trimethylsilyl)ethoxymethyl |
| SEM-Cl | 2-(Trimethylsilyl)ethoxymethyl Chloride |
| Si-column | Silica column |
| tBu | tert-butyl |
| TFA | trifluoroacetic acid |
| THF | tetrahydrofuran |
| TLC | thin layer chromatography |
| δ | parts per million referenced to residual non-deuterated solvent peak |

General Synthetic Schemes

Compounds of Formula (I) of the present disclosure and compounds as shown in Table 1 can be prepared, for example, according to the following schemes. During any of the processes for preparation of the subject compounds, it may be necessary and/or desirable to protect sensitive or reactive groups on any of the molecules concerned. This may be achieved by means of conventional protecting groups as described in standard works, such as T. W. Greene and P. G. M. Wuts, "Protective Groups in Organic Synthesis," 4th ed., Wiley, New York 2006. For example, in some embodiments, a protecting includes a benzyloxycarbonyl group or a tert-butyloxycarbonyl group as an amino-protecting group, and/or a tert-butylmethylsilyl group etc. as a hydroxy-protecting group. The protecting groups may be removed at a convenient subsequent stage using methods known from the art.

Exemplary chemical entities useful in methods of the embodiments will now be described by reference to illustrative synthetic schemes for their general preparation herein and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Furthermore, one of skill in the art will recognize that the transformations shown in the schemes below may be performed in any order that is compatible with the functionality of the particular pendant groups. Each of the reactions depicted in the general schemes, unless otherwise specified, can be run at a temperature from about 0° C. to the reflux temperature of the organic solvent used. Each of variable sites disclosed in the following schemes is applicable to every functional group in the compounds of Formula (I) and compounds as shown in Table 1 provided by the present disclosure.

The embodiments are also directed to processes and intermediates useful for preparing the subject compounds or pharmaceutically acceptable salts thereof.

General Synthetic Scheme 1

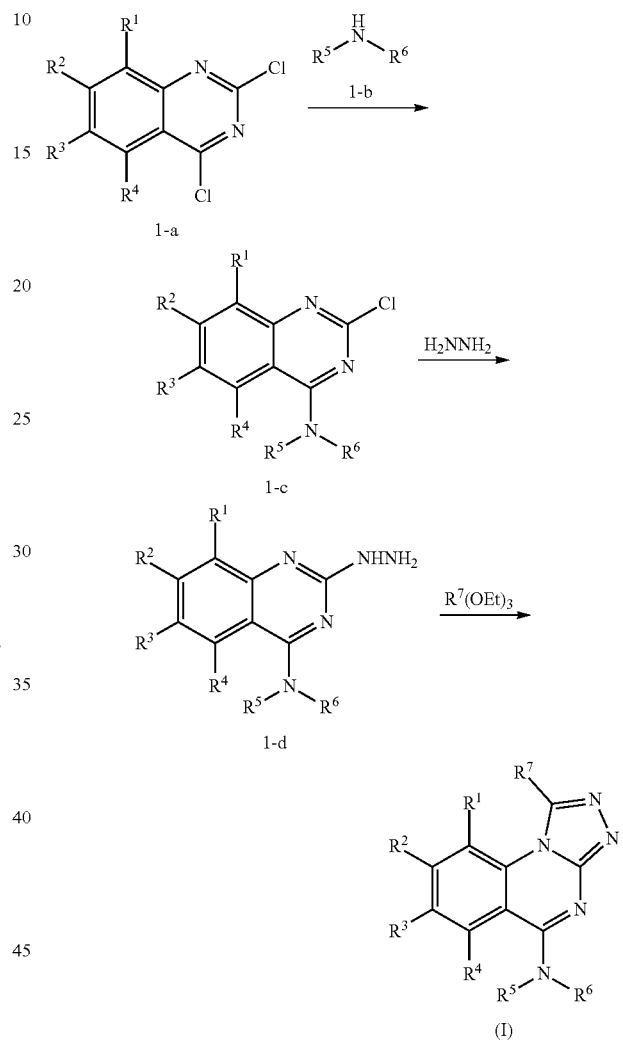

Compounds of Formula (I) and compounds as shown in Table 1 can be prepared according to General Synthetic Scheme 1, wherein $R^1$, $R^2$, $R^3$, $R^4$, $R^5$, $R^6$, and $R^7$ are as described above.

In accordance with General Synthetic Scheme 1, a compound of Formula (1-a) can react with a compound of Formula (1-b) in the presence of a base to generate a compound of Formula (1-c). It is contemplated that any suitable non-reactive solvent can be used for this reaction, such as DMF. This reaction can be carried out at a time and temperature suitable to generate a desired quantity of a compound of Formula (1-c), for example at a temperature ranging from room temperature to 100° C. and at a time ranging for several minutes to several hours, for instance at room temperature for an hour.

A compound of Formula (1-a), can be purchased or readily synthesized through methods known to those skilled in the art, such as methods described at J. Med. Chem. 2014, 57, 5141-5156 or similar methods. Compounds of Formula (1-b) are commercially available, or can be readily prepared by persons skilled in the art according to known methods.

A compound of Formula (1-c) can be combined with hydrazine in a suitable solvent, such as an alcohol, to generate a compound of Formula (1-d). Suitable solvents can include non-reactive solvents, and the reaction can be carried out at a time and temperature suitable to generate a desired quantity of a compound of Formula (1-d), such as a temperature ranging from room temperature to 100° C. and a time ranging from several minutes to several hours. For example, the reaction can be conducted in ethanol solvent at a temperature below 50° C. for an hour.

A compound of Formula (1-d) can be converted to a compound of Formula (I), or a compound shown in Table 1 by reacting 1 to 5 mole equivalents of triethyl orthoformate with a compound of Formula (1-d) at a time and temperature suitable to generate a desired quantity of a compound of Formula (I), a compound shown in Table 1. For example, a compound of Formula (1-d) can undergo reaction with triethyl orthoformate at a temperature ranging from room temperature to 120° C., for instance at a temperature of 100° C., for several minutes to several days, such as from one minute to an hour.

General Synthetic Scheme 2

A compound of Formula can also be prepared according to the following General Synthetic Scheme 2:

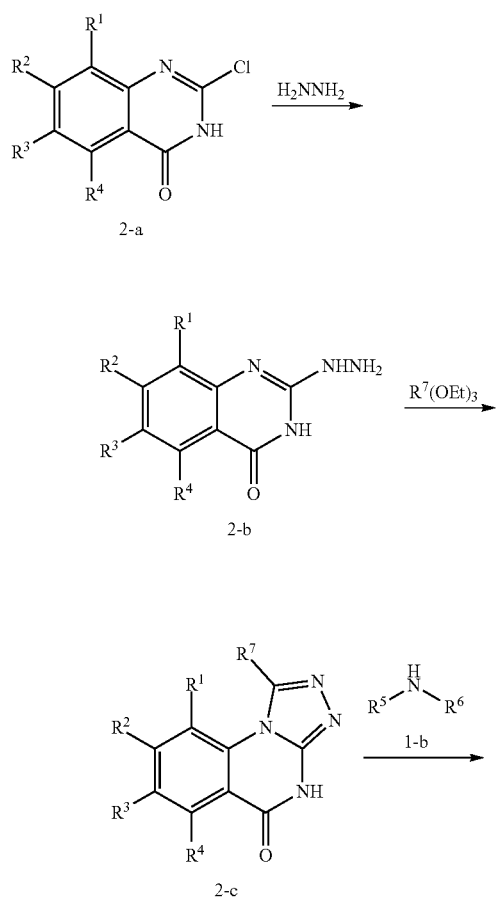

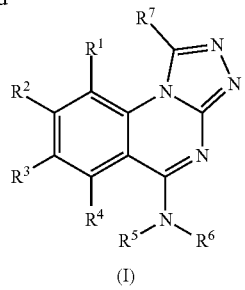

wherein $R^1$, $R^2$, $R^3$, $R^4$, $R^5$, $R^6$, and $R^7$ are as described herein.

In accordance with General Synthetic Scheme 2, a compound of Formula (2-a) can be combined with hydrazine in a suitable non-reactive solvent, such as an alcohol. The reaction can be carried out at a temperature ranging from room temperature to 100° C., at a time sufficient to produce a desired quantity of a compound of Formula (2-b), for example ranging from several minutes to several hours. For example, a compound of Formula (2-b) can be suitably generated at a temperature between room temperature and 50° C. for an hour. A compound of Formula (2-a) can be obtained commercially or can be readily prepared by a person of ordinary skill in the art through known methods, such as through a reaction of a compound of Formula (1-a) with a base in a suitable solvent.

A compound of Formula (2-b) can be combined with 1 to 5 mole equivalents of suitable orthoester under suitable reaction conditions to produce a compound according to Formula (2-c). For example, a reaction to generate a compound of Formula (2-c) can be carried out at a temperature ranging from room temperature to 120° C. at a time ranging from several minutes to several days. For example, a desired quantity of the compound of Formula (2-c) can be generated at a reaction temperature of 100° C. for 1 minute to an hour.

A compound of Formula (I), a compound shown in Table 1 can be obtained, in accordance with General Synthetic Scheme 2, by reacting a compound of Formula (2-c) with 1 to 5 mole equivalents of a compound of Formula (1-b) using 1 to 5 mole equivalents of a dehydrating condensing agent in a solvent in the presence of a base. Any suitable solvent may be used, including solvents that are not reactive in the reaction. Non-limiting examples of suitable solvents for this reaction include acetonitrile, NMP, DMF, and the like. Suitable dehydrating condensing agents are known to those skilled in the art, including for instance, but not by way of limitation, a phosphonium-based dehydrating condensing agent such as BOP reagent. Exemplary bases suitable for this reaction include, for example, an inorganic base such as cesium carbonate, or an organic amine such as triethylamine.

The reaction can be carried out, for instance, using an acetonitrile solvent, using 1 to 5 mole equivalents of BroP (bromotris(dimethylamino)phosphonium hexafluorophosphate) reagent as the dehydrating condensing agent and 1 to 5 mole equivalents of DBU as the base at a temperature between room temperature and 120° C. for several minutes to several days, such as at 50° C. for 1 minute to an hour.

Further a compound of the present disclosure having a desired functional group at a desired position can be prepared by a suitable combination of the methods above, or a procedure usually carried out in an organic synthesis (for example, alkylation reaction of an amino group, oxidation reaction of an alkylthio group into a sulfoxide group or a sulfone group, converting reaction of an alkoxy group into a hydroxy group, or opposite converting reaction thereof).

VII. Examples

Many general references providing commonly known chemical synthetic schemes and conditions useful for synthesizing the disclosed compounds are available (see, e.g., Smith, March's Advanced Organic Chemistry: Reactions, Mechanisms, and Structure, 7$^{th}$ edition, Wiley-Interscience, 2013.)

Compounds as described herein can be purified by any of the means known in the art, including chromatographic means, such as high performance liquid chromatography (HPLC), preparative thin layer chromatography, flash column chromatography and ion exchange chromatography. Any suitable stationary phase can be used, including normal and reversed phases as well as ionic resins. For example, disclosed compounds can be purified via silica gel chromatography. See, e.g., Introduction to Modern Liquid Chromatography, 2nd ed., ed. L. R. Snyder and J. J. Kirkland, John Wiley and Sons, 1979; and Thin Layer Chromatography, E. Stahl (ed.), Springer-Verlag, New York, 1969.

Compounds were characterized using standard instrumentation methods. Identification of the compound was carried out by hydrogen nuclear magnetic resonance spectrum ($^1$H-NMR) and mass spectrum (MS). $^1$H-NMR was measured at 400 MHz, unless otherwise specified. In some cases, exchangeable hydrogen could not be clearly observed depending on the compound and measurement conditions. The designation br. or broad, used herein, refers to a broad signal. HPLC preparative chromatography was carried out by a commercially available ODS column in a gradient mode using water/methanol (containing formic acid) as eluents, unless otherwise specified.

The Examples provided herein describe the synthesis of compounds disclosed herein as well as intermediates used to prepare the compounds. It is to be understood that individual steps described herein may be combined. It is also to be understood that separate batches of a compound may be combined and then carried forth in the next synthetic step.

In the following description of the Examples, specific embodiments are described. These embodiments are described in sufficient detail to enable those skilled in the art to practice certain embodiments of the present disclosure. Other embodiments may be utilized and logical and other changes may be made without departing from the scope of the disclosure. The following description is, therefore, not intended to limit the scope of the present disclosure.

Representative syntheses of compounds of the present disclosure are described in schemes below, and the particular examples that follow.

A. Intermediates

Intermediate 1: 6-bromo-2,3,4,5-tetrahydro-1H-pyrido[3,4-b]azepine

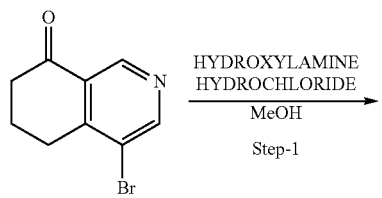

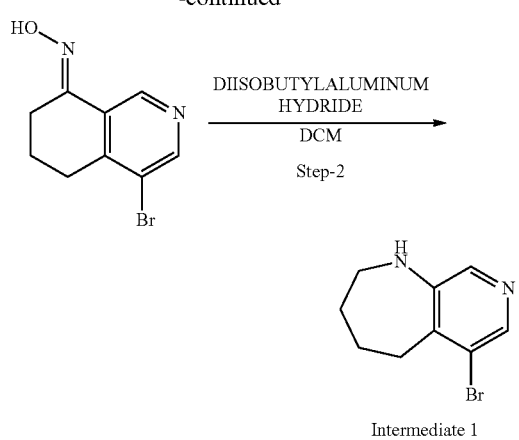

Intermediate 1

Step-1: To a solution of 4-Bromo-1-indanone (10 g, 50.0 mmol) in MeOH (140.0 ml) hydroxylamine hydrochloride (14 g, 200.0 mmol) was added. The resulting mixture was heated to reflux for 1 h and then cooled to room temperature. The mixture was concentrated under vacuum. DCM (150 ml) and 50% NaHCO$_3$ (150 ml) were added. The mixture was vigorously stirred for another 30 min. Filtered off the solid. Washed with water and Hex. Dried over a stream of air overnight. Used as is for the next step.

Step-2: The obtained white solid 4-bromo-6,7-dihydro-5H-isoquinolin-8-one oxime (2.50 g, 10.4 mmol) in DCM (75.0 ml) at 0° C. was treated with AlH(Bu-i)$_2$ (93.0 ml, 93.0 mmol, 1.0M in toluene) dropwise and stirred for 30 min. The reaction mixture was warmed to room temperature, stirred for another 16 h and quenched with cold water 100 mL and. Saturated Potassium Sodium Tartrate 100 mL was added. Stirred for 24 hr. Extracted with DCM. The organic concentrated under vacuum. Purified on ISCO DCM:EtOAc (0%-100%). Pure 5-bromo-tetrahydroquinoline (3) was obtained as a yellow solid (200.0 mg, yield 8%). ES/MS m/z: 211.0 $^1$H NMR (400 MHz, Chloroform-d) δ 8.23 (s, 1H), 7.94 (s, 1H), 3.89 (d, J=12.1 Hz, 1H), 3.11 (dt, J=8.3, 3.3 Hz, 2H), 3.06-2.93 (m, 2H), 1.91-1.76 (m, 2H), 1.76-1.63 (m, 2H).

Intermediate 2: 6-chloro-7-fluoro-5-(5-iodo-3,4-dihydroquinolin-1(2H)-yl)-1-methyl-[1,2,4]triazolo[4,3-a]quinazoline

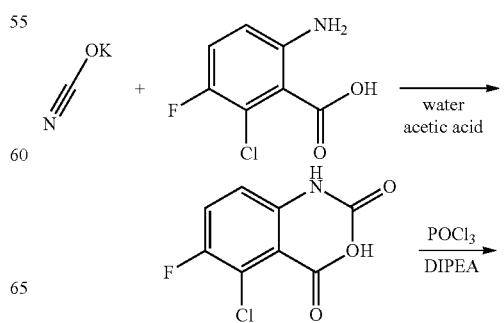

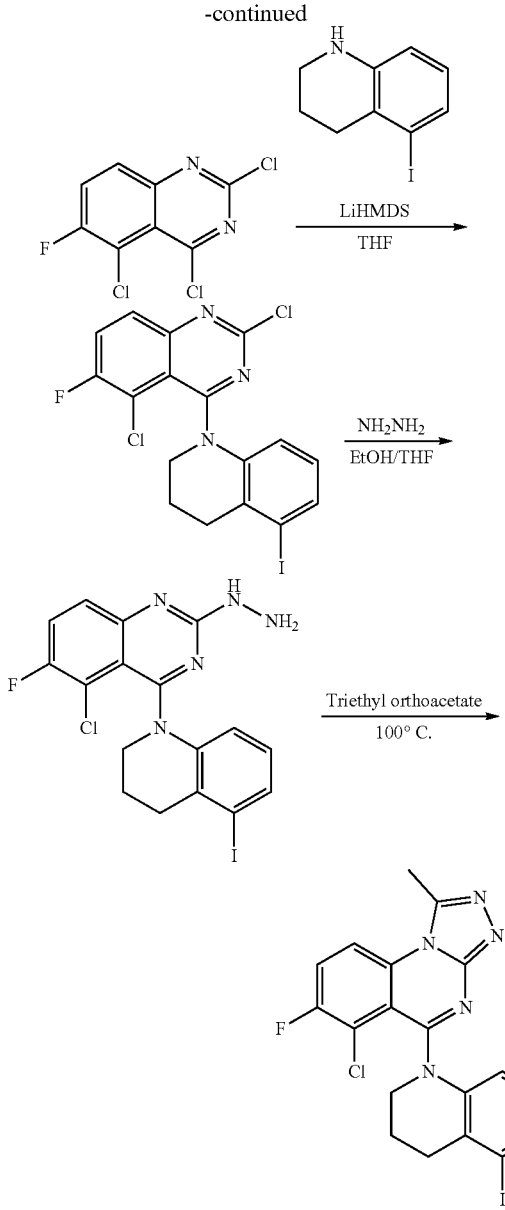

and THF (3.59 mL). The mixture was cooled to 0° C. and LiHMDS was added in one portion (1.21 mL, 1.21 mmol). After stirring for 1 hour the reaction was diluted with EtOAc (20 mL) and saturated NH₄Cl solution was added (2 mL). The organic layer was separated and dried over Na₂SO₄, filtered, and concentrated. Organic residue then triturated with heptanes and filtered to yield 2,5-dichloro-6-fluoro-4-(5-iodo-3,4-dihydro-2H-quinolin-1-yl)quinazoline (364 mg).

Step 4: A vial with stir bar was charged with 2,5-dichloro-6-fluoro-4-(5-iodo-3,4-dihydro-2H-quinolin-1-yl)quinazoline (409 mg, 0.863 mmol), THF (2.92 mL), and EtOH (2.92 mL). Mixture cooled to 0° C. and hydrazine (0.325 mL, 10.4 mmol) added. Mixture allowed to warm to room temperature and stir for 30 minutes. Reaction mixture diluted with water, extracted with DCM, and organic layer washed with brine. Organic layer separated, dried over Na₂SO₄, filtered, and evaporated under vacuum to yield [5-chloro-6-fluoro-4-(5-iodo-3,4-dihydro-2H-quinolin-1-yl)quinazolin-2-yl]hydrazine (300 mg).

Step 5: A vial with stir bar was charged with [5-chloro-6-fluoro-4-(5-iodo-3,4-dihydro-2H-quinolin-1-yl)quinazolin-2-yl]hydrazine (300 mg, 0.64 mmol) and triethylorthoacetate (2.93 mL, 16.0 mmol). Mixture heated to 110° C. and allowed to stir overnight. Mixture cooled and concentrated under vacuum. Resulting organic residue triturated with heptanes, solids filtered and washed with heptanes, dried under vacuum to yield 6-chloro-7-fluoro-5-(5-iodo-3,4-dihydro-2H-quinolin-1-yl)-1-methyl-[1,2,4]triazolo[4,3-a]quinazoline.

Intermediate 3: 9-chloro-7-fluoro-5-(5-iodo-3,4-dihydro-2H-quinolin-1-yl)-[1,2,4]triazolo[4,3-a]quinazoline

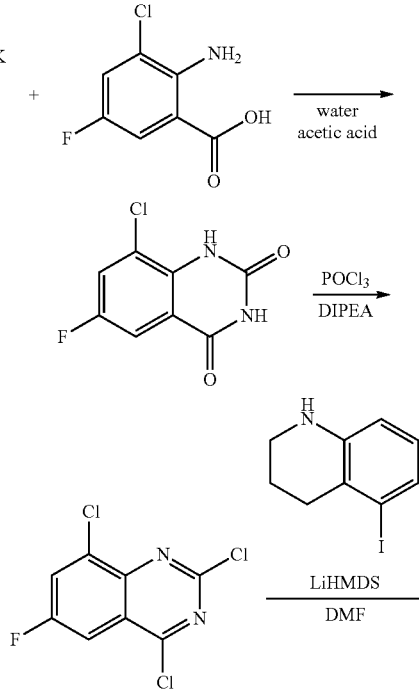

Step 1: A vial with stir bar was charged with cyanatopotassium (856 mg, 10.6 mmol), 6-amino-2-chloro-3-fluorobenzoic acid (1000 mg, 5.28 mmol), water (10.0 mL), and acetic acid (10 mL). Mixture allowed to stir at room temperature for 24 hours. Resulting precipitate was collected via vacuum filtration and washed with water to yield 5-chloro-6-fluoro-1H-quinazoline-2,4-dione (233 mg).

Step 2: A vial with stir bar was charged with 5-chloro-6-fluoro-1H-quinazoline-2,4-dione (233 mg, 1.09 mmol), POCl₃ (0.76 mL. 8.13 mmol), and DIPEA (0.38 mL, 2.17 mmol). Mixture heated to reflux for 1 hour. Mixture then poured over warm water and stirred vigorously. DCM added to dissolve solid and the aqueous layer was then extracted with DCM, washed with brine, dried over Na₂SO₄ and concentrated to yield 2,4,5-trichloro-6-fluoro-quinazoline (123 mg).

Step 3: A vial with stir bar was charged with 2,4,5-trichloro-6-fluoro-quinazoline (203 mg, 0.807 mmol), 5-iodo-1,2,3,4-tetrahydroquinoline (209 mg, 0.807 mmol),

297

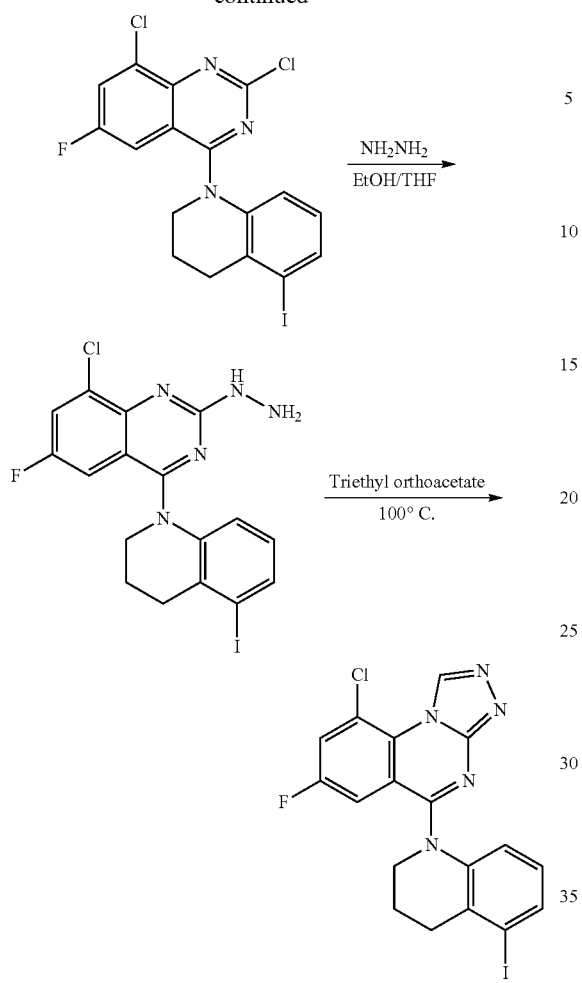

The title compound was synthesized in a manner similar to Intermediate 2 using 2-amino-3-chloro-5-fluoro-benzoic acid instead of 6-amino-2-chloro-3-fluoro-benzoic acid, and triethyl orthoformate instead of triethyl orthoacetate.

Intermediate 4: 1-(9-chloro-6-fluoro-[1,2,4]triazolo [4,3-a]quinazolin-5-yl)-6-iodo-3,5-dihydro-2H-4,1-benzoxazepine

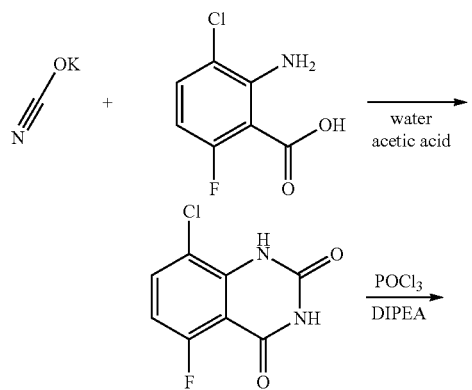

298

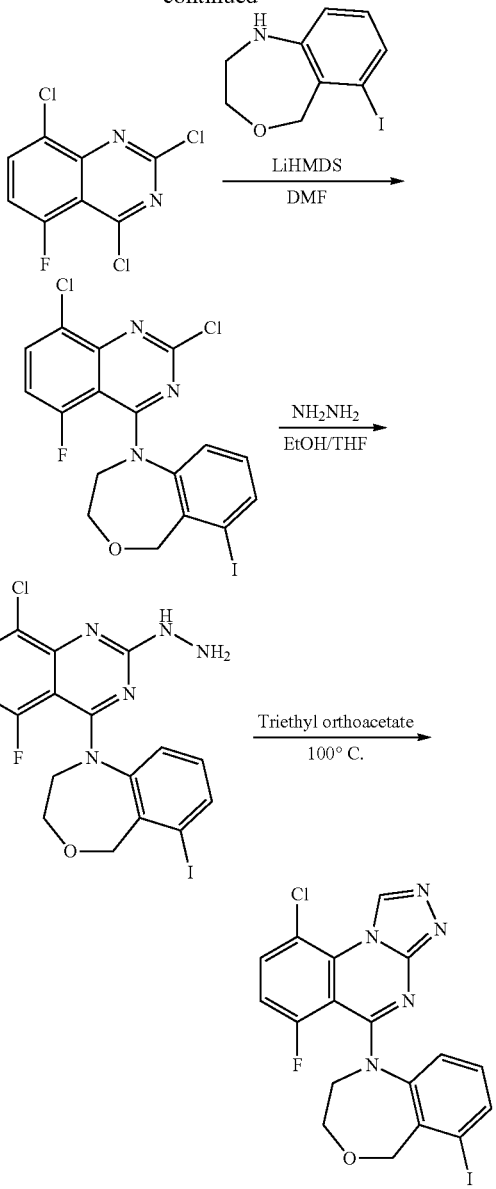

The title compound was synthesized in a manner similar to Intermediate 3, using 2-amino-3-chloro-6-fluoro-benzoic acid instead of 2-amino-3-chloro-5-fluoro-benzoic acid, and 6-iodo-1,2,3,5-tetrahydro-4,1-benzoxazepine instead of 5-iodo-1,2,3,4-tetrahydroquinoline.

Intermediate 5: N-(2-bromo-3-fluoro-4-pyridyl)-N-(2,2-difluoroethyl)-6-fluoro-1-methyl-[1,2,4]triazolo [4,3-a]quinazolin-5-amine

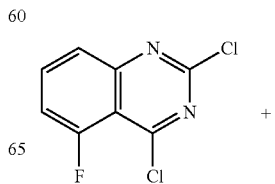

+

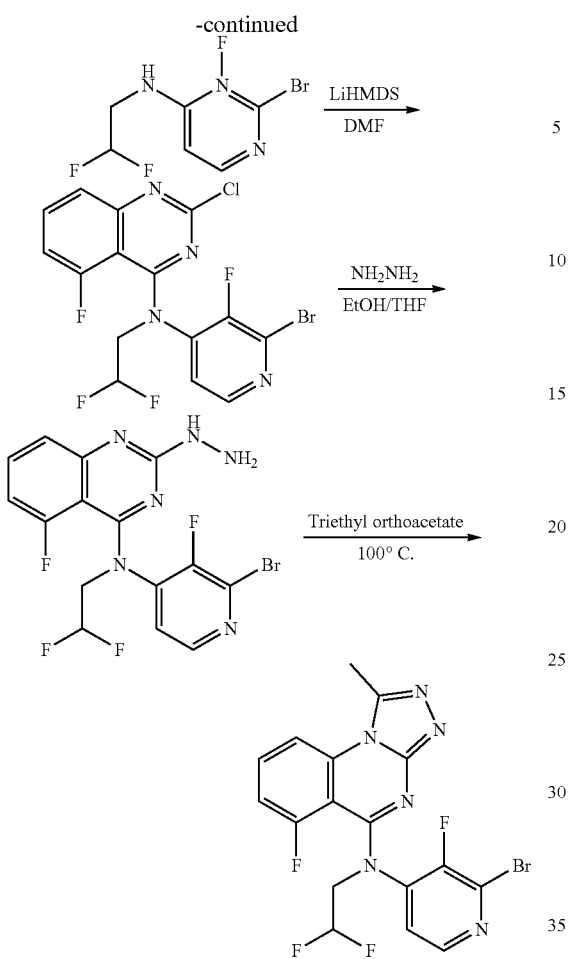

Step 1: A vial with stir bar was charged with 2,4-dichloro-5-fluoro-quinazoline (500 mg, 2.3 mmol), 2-bromo-N-(2,2-difluoroethyl)-3-fluoro-pyridin-4-amine (588 mg, 2.3 mmol), and THF (10.2 mL). The mixture was cooled to 0° C. and LiHMDS was added in one portion (2.76 mL, 2.76 mmol). After stirring for 1 hour the reaction was diluted with EtOAc (20 mL) and saturated NH₄Cl solution was added (2 mL). The organic layer was separated and dried over Na₂SO₄, filtered, and concentrated. Organic residue then triturated with heptanes and filtered to yield N-(2-bromo-3-fluoro-4-pyridyl)-2-chloro-N-(2,2-difluoroethyl)-5-fluoro-quinazolin-4-amine (799 mg).

Step 2: A vial with stir bar was charged with N-(2-bromo-3-fluoro-4-pyridyl)-2-chloro-N-(2,2-difluoroethyl)-5-fluoro-quinazolin-4-amine (397 mg, 0.911 mmol), THF (4.88 mL), and EtOH (4.88 mL). Mixture cooled to 0° C. and hydrazine (0.343 mL, 10.9 mmol) added. Mixture allowed to warm to room temperature and stir for 30 minutes. Reaction mixture diluted with water, extracted with DCM, and organic layer washed with brine. Organic layer separated, dried over Na₂SO₄, filtered, and evaporated under vacuum to yield N-(2-bromo-3-fluoro-4-pyridyl)-N-(2,2-difluoroethyl)-5-fluoro-2-hydrazino-quinazolin-4-amine (364 mg).

Step 3: A vial with stir bar was charged with N-(2-bromo-3-fluoro-4-pyridyl)-N-(2,2-difluoroethyl)-5-fluoro-2-hydrazino-quinazolin-4-amine (364 mg, 0.84 mmol) and triethylorthoacetate (6.19 mL, 22.5 mmol). Mixture heated to 110° C. and allowed to stir overnight. Mixture cooled and concentrated under vacuum. Resulting organic residue triturated with heptanes, solids filtered and washed with heptanes, dried under vacuum to yield N-(2-bromo-3-fluoro-4-pyridyl)-N-(2,2-difluoroethyl)-6-fluoro-1-methyl-[1,2,4]triazolo[4,3-a]quinazolin-5-amine (275 mg).

Intermediate 6: 9-chloro-N-(2,2-difluoroethyl)-7-fluoro-N-(3-fluoro-5-iodo-phenyl)-[1,2,4]triazolo[4,3-a]quinazolin-5-amine

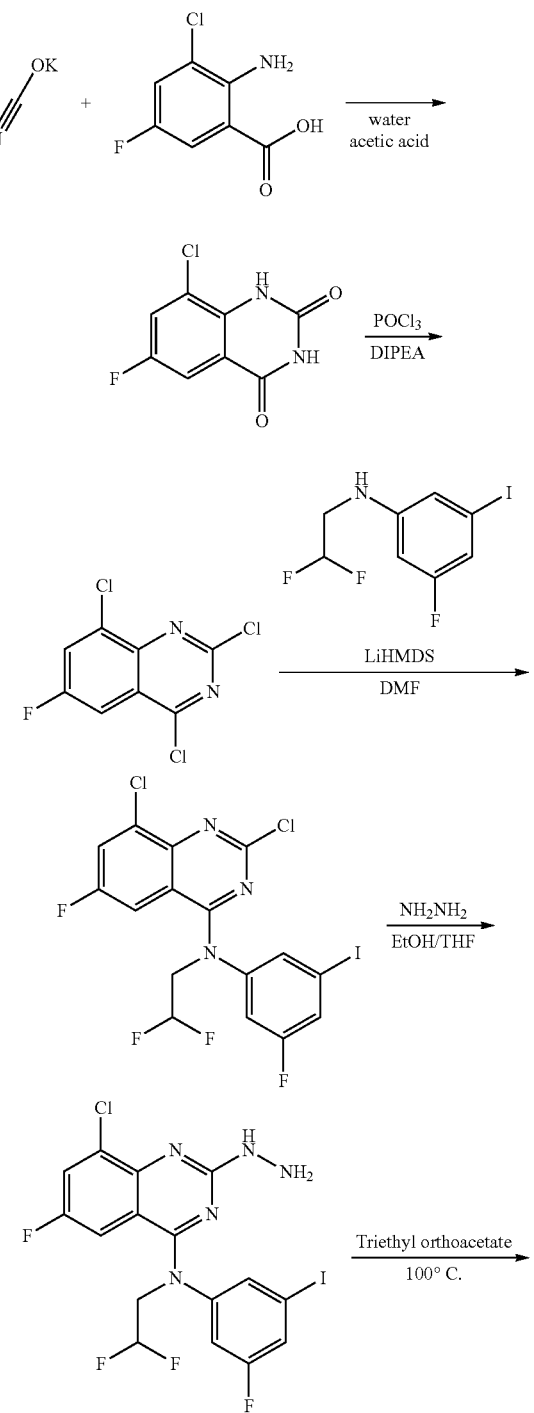

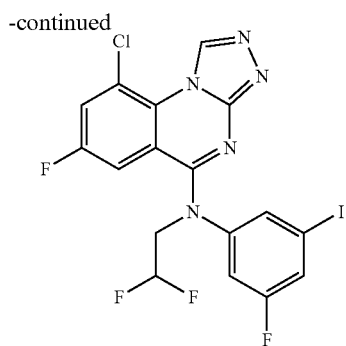

The title compound was synthesized in a manner similar to Intermediate 3, using N-(2,2-difluoroethyl)-3-fluoro-5-iodo-aniline instead of 5-iodo-1,2,3,4-tetrahydroquinoline.

Intermediate 7: N-(3-bromo-2-fluoro-phenyl)-N-(2,2-difluoroethyl)-6-fluoro-1-methyl-[1,2,4]triazolo[4,3-a]quinazolin-5-amine

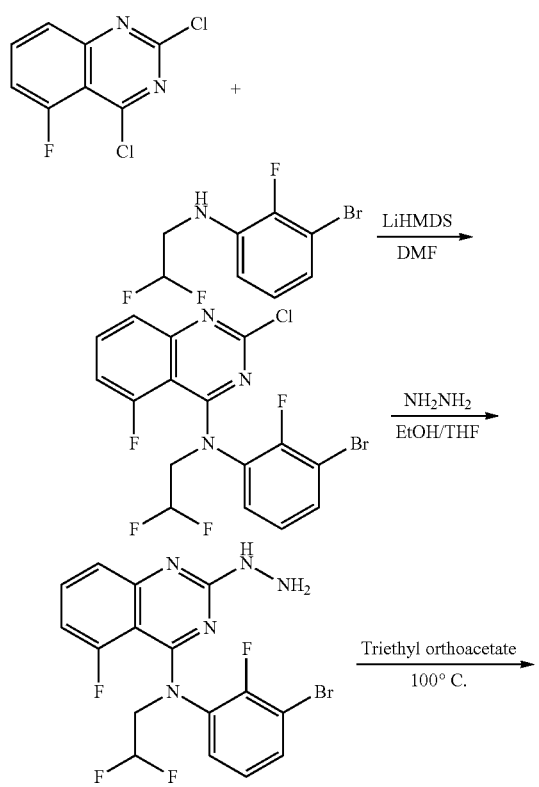

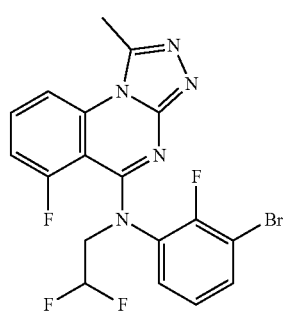

The title compound was synthesized in a manner similar to Intermediate 5, using 3-bromo-N-(2,2-difluoroethyl)-2-fluoro-aniline instead of 2-bromo-N-(2,2-difluoroethyl)-3-fluoro-pyridin-4-amine.

Intermediate 8: N-(3-bromo-2-fluoro-phenyl)-N-(2,2-difluoroethyl)-7-fluoro-[1,2,4]triazolo[4,3-a]quinazolin-5-amine

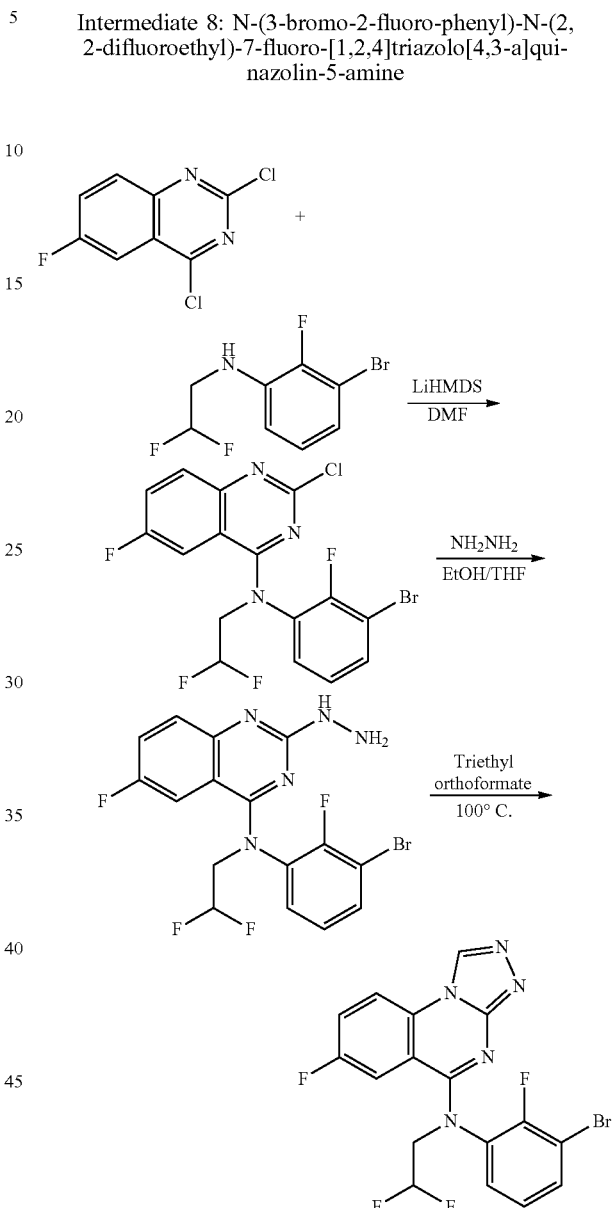

The title compound was synthesized in a manner similar to Intermediate 7, using 2,4-dichloro-6-fluoro-quinazoline instead of 2,4-dichloro-5-fluoro-quinazoline.

Intermediate 9: 6-iodo-1,2,3,5-tetrahydro-4,1-benzoxazepine

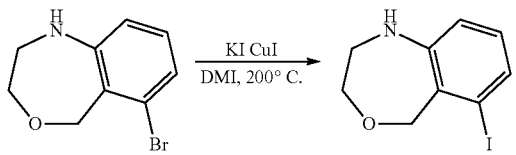

Step 1: A pressure vessel with stir bar was charged with 6-bromo-1,2,3,5-tetrahydro-4,1-benzoxazepine (1000 mg, 4.38 mmol), KI (29.1 g, 175 mmol), CuI (10 g, 52.6 mmol), and DMI (44.0 mL). Mixture heated to 200° C. and allowed to stir for 4 hours. Upon complete conversion, reaction mixture diluted with brine (20 mL) and EtOAc (20 mL), filtered through celite, concentrated, and purified via flash column chromatography (hexanes to 25% EtOAc). Fractions collected and concentrated under vacuum to yield 6-iodo-1,2,3,5-tetrahydro-4,1-benzoxazepine (791 mg).

Intermediate 10: 2-bromo-N-(2,2-difluoroethyl)-3-fluoro-pyridin-4-amine

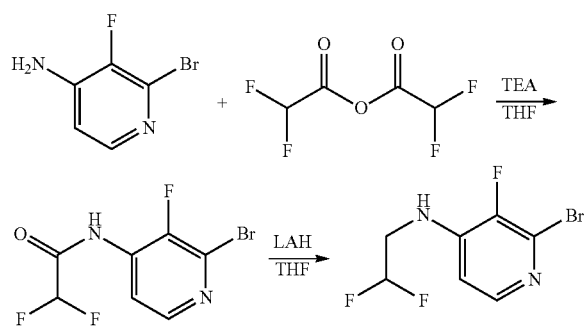

Step 1: A vial with stir bar was charged with 2-bromo-3-fluoro-pyridin-4-amine (2500 mg, 13.1 mmol), TEA (2.08 mL, 14.4 mmol), and THF (74.6 mL). The mixture was allowed to stir and (2,2-difluoroacetyl) 2,2-difluoroacetate (1.58 mL, 14.4 mmol) was added dropwise. The mixture stirred for 3 hours, poured into ice water, basified with saturated aqueous NaHCO$_3$, and extracted with EtOAc. The organic layer was dried over Na$_2$SO$_4$ and concentrated under vacuum to afford N-(2-bromo-3-fluoro-4-pyridyl)-2,2-difluoro-acetamide (3212 mg).

Step 2: A vial with stir bar was charged with N-(2-bromo-3-fluoro-4-pyridyl)-2,2-difluoro-acetamide (3212 mg, 11.9 mmol) and THF (26.4 mL). The mixture was cooled to 0° C. and placed under a nitrogen atmosphere. LAH (6.57 mL, 13.1 mmol) was added dropwise to the solution, and the mixture allowed to warm to room temperature and stir for 6 hours. The mixture was diluted with ether (10 mL) and cool to 0° C. To the solution water (0.5 mL) was added dropwise, followed by 2M NaOH solution (1.0 mL), and water (1.5 mL). The reaction was warmed to room temperature and magnesium sulfate (1000 mg) was added to the solution and allowed to stir for 15 minutes. Solution was filtered, concentrated, and purified via flash column chromatography (hexanes to 70% EtOAc) to yield 2-bromo-N-(2,2-difluoro-ethyl)-3-fluoro-pyridin-4-amine.

Intermediate 11:
N-(2,2-difluoroethyl)-3-fluoro-5-iodo-aniline

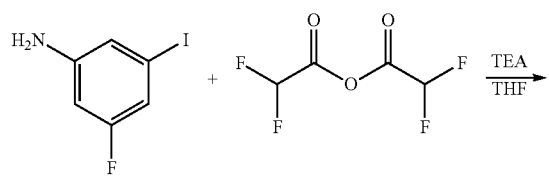

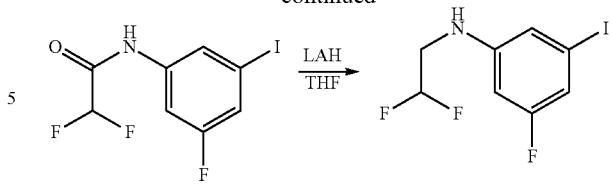

The title compound was synthesized in a manner similar to Intermediate 10, using 3-fluoro-5-iodo-aniline instead of 2-bromo-3-fluoro-pyridin-4-amine.

Intermediate 12:
3-bromo-N-(2,2-difluoroethyl)-2-fluoro-aniline

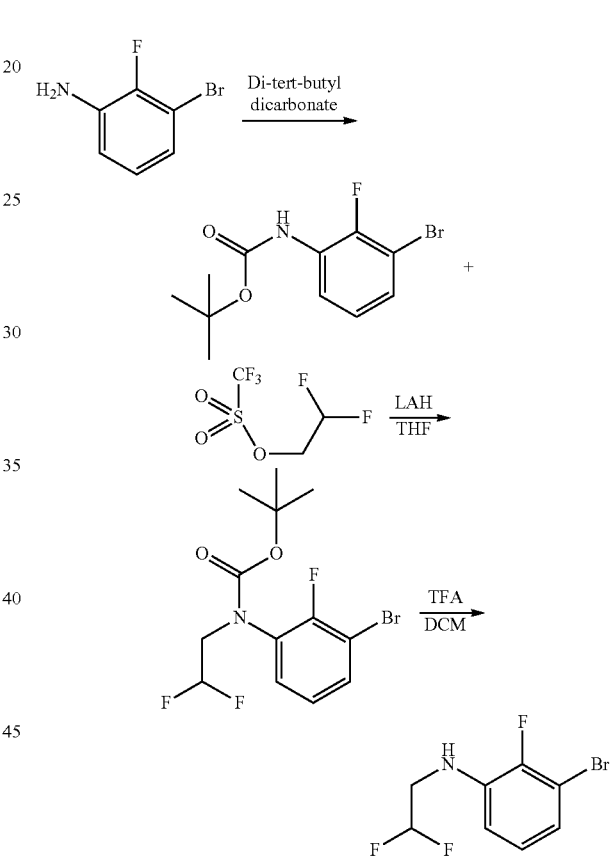

Step 1: A vial with stir bar was charged with 3-bromo-2-fluoro-aniline (3000 mg, 15.8 mmol) and di-tert-butyl dicarbonate (6890 mg, 31.6 mmol). The mixture was heated to 80° C. and stirred for 7 hours, cooled to room temperature, concentrated under vacuum, and purified via flash column chromatography (hexanes to 15% EtOAc). Fractions combined and concentrated to yield tert-butyl N-(3-bromo-2-fluoro-phenyl)carbamate (3.65 g).

Step 2: A vial with stir bar was charged with tert-butyl N-(3-bromo-2-fluoro-phenyl)carbamate (750 mg, 2.59 mmol) and DMF (8.93 mL). Mixture cooled to 0° C., NaH added (149 mg, 2.88 mmol), and stirred for 5 minutes. To the solution 2,2-difluoroethyl trifluoromethanesulfonate (664 mg, 3.10 mmol) was added, mixture warmed to room temperature, and stirred for 1 hour. Reaction quenched with saturated ammonium chloride solution (2 mL), poured into water (20 mL), extracted with EtOAc, washed with water, washed with brine, organics dried over Na₂SO₄, filtered, and concentrated to yield tert-butyl N-(3-bromo-2-fluoro-phenyl)-N-(2,2-difluoroethyl)carbamate (916 mg).

Step 3: A vial with stir bar was charged with tert-butyl N-(3-bromo-2-fluoro-phenyl)-N-(2,2-difluoroethyl)carbamate (916 mg, 2.59 mmol), DCM (11.6 mL), and TFA (4.62 mL. 60.4 mmol). Mixture stirred at room temperature for one hour. Reaction concentrated under vacuum, purified via flash column chromatography (hexanes to 40% EtOAc), and fractions concentrated to yield 3-bromo-N-(2,2-difluoroethyl)-2-fluoro-aniline.

Intermediate 13: methyl 4-(1-(6-fluoro-1-methyl-[1,2,4]triazolo[4,3-a]quinazolin-5-yl)-1,2,3,4-tetrahydroquinolin-5-yl)-2,2-dimethylbut-3-ynoate

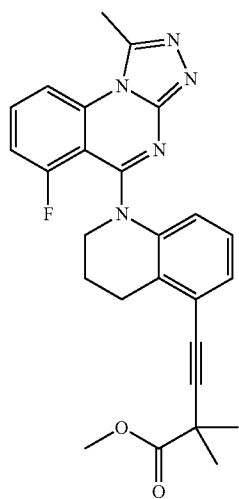 [SMILES: COC(=O)C(C)(C)C#Cc1cccc2c1CCCN2c1nc2nnc(C)n2c2cccc(F)c12]

The title compound was synthesized as described in Example 74, using 5-bromo-1,2,3,4-tetrahydroquinoline instead of 2-bromo-N-(2,2-difluoroethyl)pyridin-4-amine and methyl 2,2-dimethylbut-3-ynoate instead of 5-ethynyl-2-methoxypyridine.

Intermediate 14: 4-(1-(6,7-difluoro-1-methyl-[1,2,4]triazolo[4,3-a]quinazolin-5-yl)-1,2,3,5-tetrahydrobenzo[e][1,4]oxazepin-6-yl)-2,2-dimethylbut-3-ynoic acid

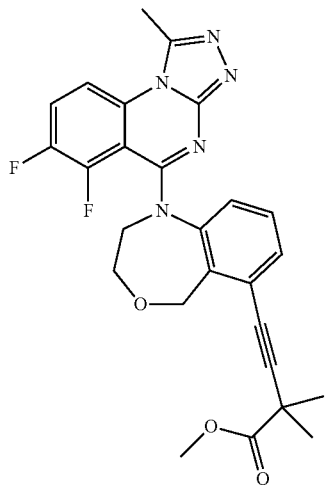 [SMILES: COC(=O)C(C)(C)C#Cc1cccc2c1COCCN2c1nc2nnc(C)n2c2ccc(F)c(F)c12]

The title compound was synthesized as described in Example 74, using 6-bromo-1,2,3,5-tetrahydrobenzo[e][1,4]oxazepine instead of 2-bromo-N-(2,2-difluoroethyl)pyridin-4-amine and methyl 2,2-dimethylbut-3-ynoate instead of 5-ethynyl-2-methoxypyridine.

Intermediate 15: 2-bromo-N-(2,2-difluoroethyl)pyridin-4-amine

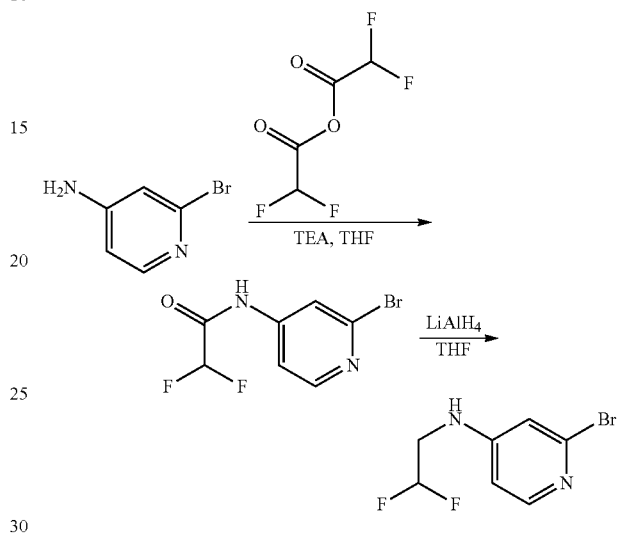

To a solution of 2-bromopyridin-4-amine (9.1 g, 52.6 mmol) in dry THF (20 mL) under argon was added TEA (8.36 mL, 57.9 mmol) and dropwise 2,2-difluoroacetic anhydride (10.1 g, 57.9 mmol). The solution was stirred at room temperature for 3 h. The reaction was poured into ice water, basified by saturated aqueous NaHCO₃, and then extracted with ethyl acetate. The combined organic phases were dried over MgSO₄, concentrated and dried under vacuum to afford N-(2-bromopyridin-4-yl)-2,2-difluoroacetamide.

A solution of LiAlH₄ in THF (1M, 52.6 mmol) was added portion-wise to a solution of 2,2-difluoroacetic anhydride (12 g, 47.8 mmol) in THF (40 ml) at 0° C. under nitrogen-atmosphere. After 10 min at 0° C. the reaction mixture was allowed to reach room temperature and stirring was continued for 6 h. The mixture was quenched with water at 0° C. and extracted with ethyl acetate. The aqueous phase was washed with saturated sodium chloride solution, dried with MgSO₄ and concentrated under reduced pressure. The crude product was purified by column-chromatography on silica (Hexanes: Ethyl acetate 3:1) to give 2-bromo-N-(2,2-difluoroethyl)pyridin-4-amine.

Intermediate 16: 5-bromo-2-methyl-1,2,3,4-tetrahydroquinoline

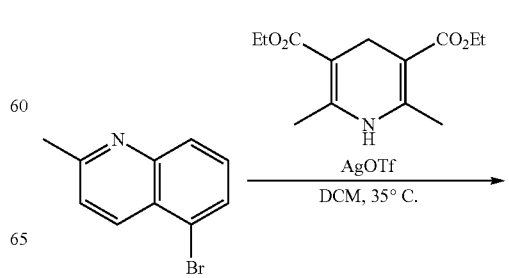

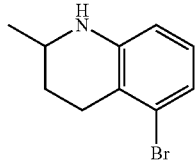

A suspension of 5-bromo-2-methylquinoline (1.00 g, 4.5 mmol), diethyl 2,6-dimethyl-1,4-dihydropyridine-3,5-dicarboxylate (2.85 g, 11.3 mmol), and AgOTf (57.8 mg, 225 umol) in DCM (15 mL) was stirred at 35° C. for 4 h. The reaction mixture was then cooled to RT, filtered through celite to remove solids, and concentrated under vacuum. The resulting residue was purified by silica gel chromatography (0→20% EtOAc in hexanes) to afford 5-bromo-2-methyl-1,2,3,4-tetrahydroquinoline. LCMS(m/z) 226.3, 228.2 [M+H]⁺.

Intermediate 17: 6-bromo-1,2,3,5-tetrahydropyrido[4,3-e][1,4]oxazepine

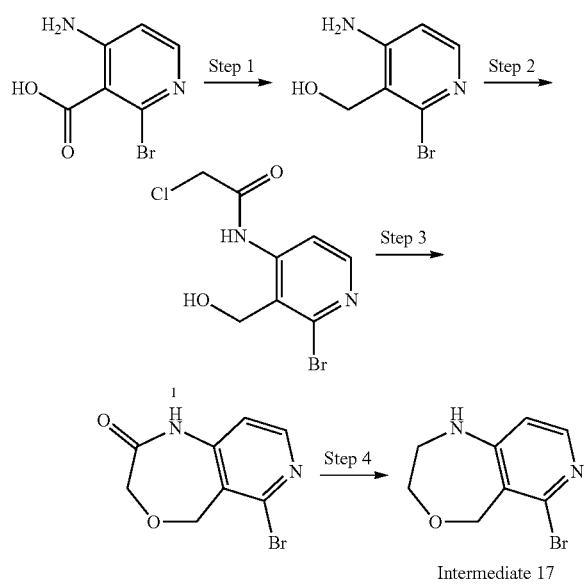

Intermediate 17

Step 1. Synthesis of (4-amino-2-bromopyridin-3-yl)methanol. 1.0 N THF solution of Lithium aluminum hydride (20.7 mL, 20.7 mmol) was added to a suspension of aluminum chloride (1.54 g, 11.5 mmol) in THF (100 mL) at 0° C. The reaction mixture was stirred at 0° C. for 20 min. 4-amino-2-bromonicotinic acid (2.50 g, 11.5 mmol) was added and the reaction mixture was stirred at 0° C. for 3.5 h. An aqueous solution of potassium sodium (+)-tartrate tetrahydrate (29 mL, 2.0M) was added to the reaction mixture at 0° C. and it was stirred overnight. The precipitate was removed by filtration. The filtrate was concentrated, and the residue was diluted with water (30 ml). It was then extracted with 20% ethanol in dichloromethane (100 mL×2). The organic layers were washed with brine, dried over Na₂SO4 and concentrated. The crude was used directly in next step. LCMS-ESI+ (m/z): [M+H]⁺=203.0.

Step 2. Synthesis of N-(2-bromo-3-(hydroxymethyl)pyridin-4-yl)-2-chloroacetamide. To the above residue (2.50 g, 11.1 mmol) obtained from step 1 in DMF (20 mL) and THF (100 mL) was added triethylamine (3.09 mL, 22.2 mmol), 2-chloroacetic acid (1.20 g, 12.7 mmol) and HATU (5.27 g, 13.9 mmol) at 0° C. in sequence. It was stirred at rt for 3 h. The reaction mixture with EtOAc (100 ml), washed with water (50 mL), brine, dried and concentrated. The resulting residue was purified by ISCO using 10-80% EtOAc in hexanes to afford the desired product. LCMS-ESI+ (m/z): [M+H]⁺=279.06.

Step 3. Synthesis of 6-bromo-1,5-dihydropyrido[4,3-e][1,4]oxazepin-2(3H)-one. To the acetamide (2.35 g, 8.41 mmol) obtained above in THF (50 mL) at 0° C. was added 60% sodium hydride (0.644 g, 16.8 mmol). After 1 h, the reaction mixture was stirred at room temperature for another 2 h. The reaction was quenched with saturated aqueous NH₄Cl solution (30 mL), diluted with EtOAc (100 mL), washed with water, brine, dried and concentrated. 15 mL of DCM was added to the residue and the resulting precipitate was collected by filtration. The filtrate was concentrated and purified by ISCO using 35-100% EtOAc in hexanes.

The precipitate and the batch from the column purification were combined to afford the desired product. LCMS-ESI+ (m/z): [M+H]⁺=243.06.

Step 4. Synthesis of 6-bromo-1,2,3,5-tetrahydropyrido[4,3-e][1,4]oxazepane. THF solution of lithium aluminum hydride (9.4 mL, 1.0 N) was added to a suspension of aluminum chloride (0.70 g, 5.2 mmol) in THF (52 mL) at 0° C. The reaction mixture was stirred at 0° C. for 20 min. 6-bromo-1,5-dihydropyrido[4,3-e][1,4]oxazepin-2(3H)-one (1.27 g, 5.22 mmol) was added and the reaction mixture was stirred at 0° C. for 3.5 h. An aqueous solution of potassium sodium (+)-tartrate tetrahydrate (13 mL, 2.0 M) was added to the reaction mixture at 0° C. and it was stirred overnight. The precipitate was removed by filtration. The filtrate was concentrated, and the residue was diluted with water (30 ml). It was then extracted with EtOAc (100 mL), the organic layer was washed with brine, dried over Na₂SO₄ and concentrated to dryness. It was used directly in next step. LCMS-ESI+ (m/z): [M+H]⁺=229.03. ¹H NMR (400 MHz, Acetonitrile-d₃) δ 7.80 (d, J=5.5 Hz, 1H), 6.67 (d, J=5.4 Hz, 1H), 5.45 (s, 1H), 4.84 (s, 2H), 3.87-3.77 (m, 2H), 3.35 (dt, J=5.2, 4.0 Hz, 2H).

Intermediate 18: 6-bromo-1-(6-fluoro-1-methyl-[1,2,4]triazolo[4,3-a]quinazolin-5-yl)-1,2,3,5-tetrahydropyrido[4,3-e][1,4]oxazepine

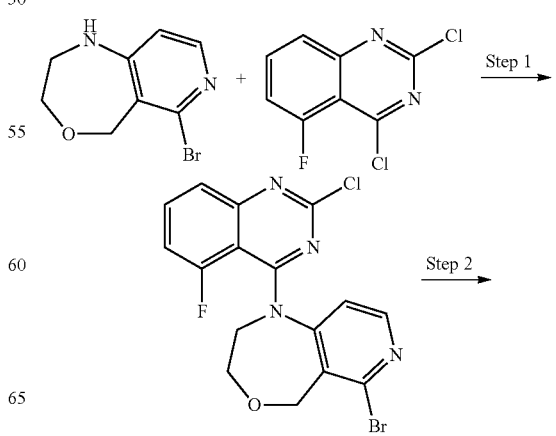

-continued

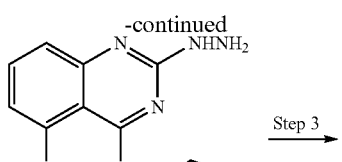

Step 3 →

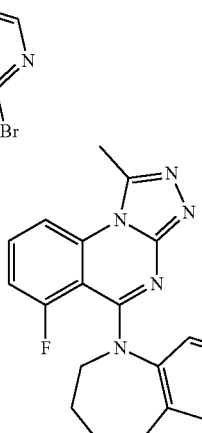

Intermediate 18

6-bromo-1,2,3,5-tetrahydropyrido[4,3-e][1,4]oxazepane (0.38 g, 1.66 mmol) and 2,4-dichloro-5-fluoroquinazoline (0.43 g, 1.99 mmol) were dissolved in THF (6 mL). The reaction mixture was cooled to 0° C., and 1.5 M THF solution of LiHMDS (1.66 mL, 2.49 mmol) was added dropwise It was stirred at this temperature for 2 h. AcOH (47 uL, 0.83 mmol) was added to quench the reaction. After stirring for 2 min, hydrazine monohydrate (1.21 mL, 24.9 mmol) was added followed by addition of ethanol (4 mL). Reaction mixture was allowed to warm up to rt and stirred for 2 h. EtOAc (60 mL) and water (30 mL) were added to the mixture. The two layers were separated, and the organic layer was washed with brine, dried over MgSO$_4$ and concentrated to dryness.

To the crude residue obtained above was added 1,1,1-triethoxyethane (7 mL) and reaction mixture was heated to 100° C. for 8 h. Upon cooling to room temperature, hexanes (35 mL) was added to the reaction mixture. The resulting solid was collected by filtration. The solid was further purified by column chromatography using 0-15% MeOH in DCM to afford the title compound as a yellow solid. LCMS-ESI+ (m/z): [M+H]$^+$=429.30.

Intermediate 19: 6-bromo-1-(7-fluoro-1-methyl-[1,2,4]triazolo[4,3-a]quinazolin-5-yl)-1,2,3,5-tetrahydropyrido[4,3-e][1,4]oxazepine

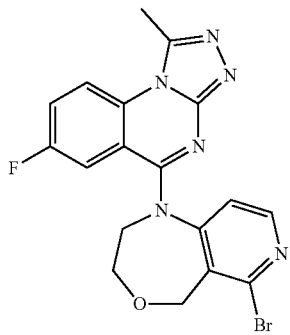 [SMILES: Cc1nnc2nc(N3CCOCc4c3ccnc4Br)c3cc(F)ccc3n12]

The title compound was synthesized as described in Intermediate 18 using 2,4-dichloro-6-fluoroquinazoline instead of 2,4-dichloro-5-fluoroquinazoline. LCMS-ESI+ (m/z): [M+H]$^+$=429.32

Intermediate 20: N-(2-methylbut-3-yn-2-yl)-1-(trifluoromethyl)cyclopropane-1-carboxamide

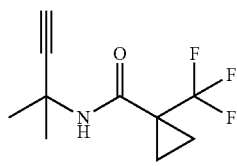

2-methylbut-3-yn-2-amine (211 mg, 2.54 mmol) and 1-(trifluoromethyl)cyclopropane-1-carboxylic acid (330 mg, 2.11 mmol) were treated with HATU (1.21 g, 3.17 mmol) in the presence of TEA (0.88 mL, 6.34 mmol) in DCM (10 mL). Reaction mixture was stirred at rt for 16 h. Reaction mixture was quenched with water (30 mL), extracted with EtOAc (60 mL). The organic layer was washed with brine (30 mL), dried over Na$_2$SO$_4$ and concentrated. The crude residue was purified by column chromatography using 0% to 50% EtOAc in hexanes afford the desired product. $^1$H NMR (400 MHz, Acetonitrile-d3) δ 6.50-6.36 (br, 1H), 2.56 (s, 1H), 1.59 (s, 6H), 1.31-1.25 (m, 2H), 1.23 (dd, J=3.7, 2.0 Hz, 2H).

Intermediate 21: 3,3,3-trifluoro-2,2-dimethyl-N-(2-methylbut-3-yn-2-yl)propanamid

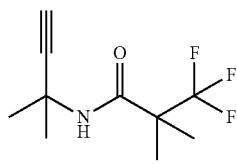

The title compound was synthesized as described in Intermediate 20 using 3,3,3-trifluoro-2,2-dimethyl-propanoic acid instead of 1-(trifluoromethyl)cyclopropane-1-carboxylic acid. $^1$H NMR (400 MHz, Acetonitrile-d$_3$) δ 6.31 (s, 1H), 2.54 (s, 1H), 1.59 (s, 6H), 1.39 (s, 6H).

Intermediate 22: N-(1-ethynylcyclopropyl)-1-(trifluoromethyl)cyclopropane-1-carboxamide

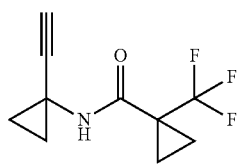

The title compound was synthesized as described in Intermediate 20 using 1-ethynylcyclopropanamine hydrochloride salt instead of 2-methylbut-3-yn-2-amine. $^1$H NMR (400 MHz, Acetonitrile-d$_3$) δ 7.08 (s, 1H), 2.37 (s, 1H), 1.26 (dt, J=9.4, 2.2 Hz, 4H), 1.22-1.15 (m, 2H), 1.12-1.03 (m, 2H).

Intermediate 23: 6-bromo-1-(6-fluoro-1-methyl-[1,2,4]triazolo[4,3-a]quinazolin-5-yl)-3,5-dihydro-2H-4,1-benzoxazepine

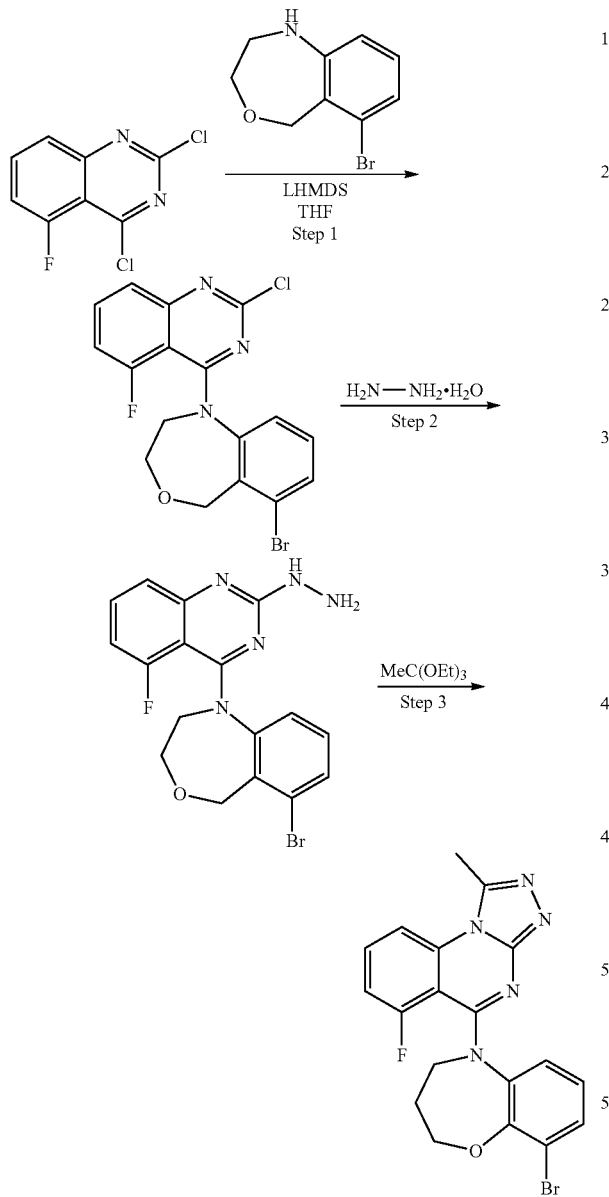

Step 1: Preparation of 6-bromo-1-(2-chloro-5-fluoro-quinazolin-4-yl)-3,5-dihydro-2H-4,1-benzoxazepine:
6-Bromo-1,2,3,5-tetrahydro-4,1-benzoxazepine (300 mg, 1.32 mmol) was treated with LHMDS (1.0 M THF solution Aldrich, 1.45 mL, 1.45 mmol, 1.1 equiv) in THF (10 mL) at rt for 20 min. To the reaction mixture was added 2,4-dichloro-5-fluoro-quinazoline (285 mg, 1.32 mmol, 1 equiv.) to stir at the same temperature for 1 h. The mixture was subjected to the next step without a work-up procedure.

Step 2: Preparation of [4-(6-bromo-3,5-dihydro-2H-4,1-benzoxazepin-1-yl)-5-fluoro-quinazolin-2-yl]hydrazine:
The reaction mixture containing 6-bromo-1-(2-chloro-5-fluoro-quinazolin-4-yl)-3,5-dihydro-2H-4,1-benzoxazepine (from the step 1) in ethanol (2 mL) and THF (4 mL) was treated with hydrazine hydrate (1912 mg, 38.2 mmol, 27 eq) at 60° C. for 1 h. To the mixture was added water (30 mL) and the whole was extracted with EtOAc (30 mL, ×3). Organic layer was washed with brine (30 mL) and dried over Na$_2$SO$_4$. Organic solvent was removed under a reduced pressure to give crude product. The crude product was purified by preparative reverse phase high performance liquid chromatography to give [4-(6-bromo-3,5-dihydro-2H-4,1-benzoxazepin-1-yl)-5-fluoro-quinazolin-2-yl]hydrazine: LCMS-ESI+ (m/z): [M+H]+ calcd for C$_{17}$H$_{15}$BrFN$_5$O: 404.04 (M−1+1), 406.04 (M+1+1), found: 404.29 (M−1+1), 406.20 (M+1+1).

Step 3: Preparation of 6-bromo-1-(6-fluoro-1-methyl-[1,2,4]triazolo[4,3-a]quinazolin-5-yl)-3,5-dihydro-2H-4,1-benzoxazepine: A solution of [4-(6-bromo-3,5-dihydro-2H-4,1-benzoxazepin-1-yl)-5-fluoro-quinazolin-2-yl]hydrazine (275 mg, 0.68 mol, from step 2) in triethyl orthoacetate (552 mg, 3.40 mmol, 5 eq) was heated at 120° C. for 16 h. To the reaction mixture was added hexane (5 mL) to form precipitate. The precipitate was collected by a filtration through a glass filter to give the title compound: $^1$H NMR (400 MHz, Methanol-d$_4$) δ 8.18-8.09 (m, 1H), 7.94-7.81 (m, 1H), 7.43 (d, J=8.0 Hz, 1H), 7.09 (dd, J=12.3, 8.4 Hz, 1H), 6.91 (t, J=8.1 Hz, 1H), 6.65 (d, J=7.9 Hz, 1H), 5.20 (br s, 4H), 4.06 (br s, 2H), 3.05 (s, 3H); LCMS-ESI+ (m/z): [M+H]+ calcd for C$_{19}$H$_{15}$BrFN$_5$O: 428.04 (M-1+1), 430.04 (M+1+1), found: 428.25 (M-1+1), 430.20 (M+1+1).

Intermediate 24: 4-(5-bromo-3,4-dihydro-2H-quinolin-1-yl)-2-chloro-quinazoline

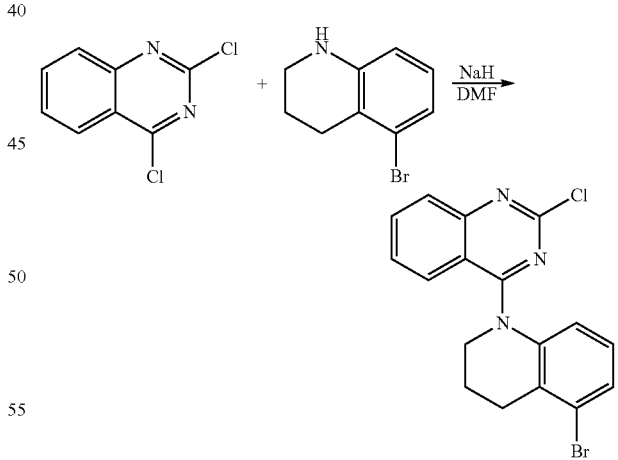

To a suspension of NaH (145 mg, 3.77 mmol) in DMF (6 mL) at 0° C. was added a solution of 5-bromo-1,2,3,4-tetrahydroquinoline (500 mg, 2.36 mmol) in DMF (6 mL). The resulting mixture was stirred at 0° C. for 30 min followed by the addition of 2,4-dichloroquinazoline (845 mg, 4.24 mmol) as a solution in DMF (12 mL). The resulting mixture was then warmed to room temperature for 1 h, followed by heating to 60° C. for 30 min. The reaction mixture was then cooled to 0° C., slowly quenched with water, then poured into water, extracted with EtOAc, washed with water (2×), then brine, dried with anhydrous magnesium sulfate, filtered, and concentrated under reduced pressure. Purification via column chromatography (gradient elution with 0 to 100% EtOAc in hexanes) afforded the title compound (305 mg, 0.801 mmol, 34%).

Intermediate 25: 5-(5-bromo-3,4-dihydro-2H-quinolin-1-yl)-[1,2,4]triazolo[4,3-a]quinazoline

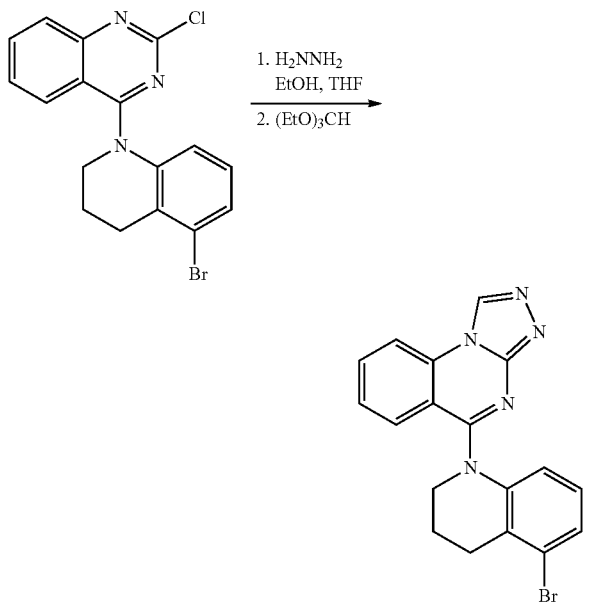

To a solution of 4-(5-bromo-3,4-dihydro-2H-quinolin-1-yl)-2-chloro-quinazoline (300 mg, 0.801 mmol) in THF (3.5 mL) and EtOH (7 mL) was added hydrazine hydrate (3.89 mL, 8.01 mmol). The resulting solution was heated to 50° C. for 3 h, then concentrated under reduced pressure. Half of the resulting hydrazine adduct was removed, and to the remaining solid was added triethyl orthoformate (7 mL, 42 mmol). The resulting mixture was then heated to 100° C. for 16 h, then cooled to room temperature, and diluted with heptane. The resulting precipitate was then collected by filtration to afford the title compound as an amorphous yellow solid (128 mg, 84%).

Intermediate 26: 3-bromo-4-(3-bromopropoxy)-5-nitro-pyridine

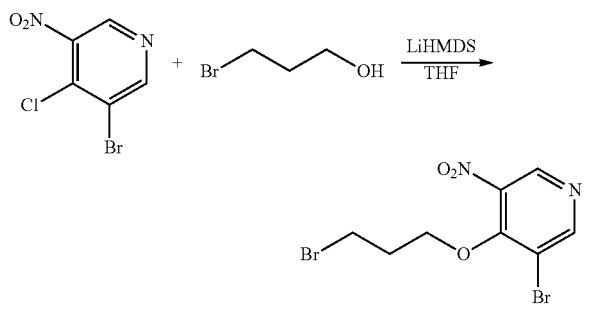

To a solution of 3-bromo-4-chloro-5-nitro-pyridine (5.3 g, 22.3 mmol) and 3-Bromo-1-propanol (3.10 g, 22.3 mmol) in THF (100 mL) at −20° C. was added LiHMDS (1M in THF, 25 mL, 25 mmol). The resulting solution was stirred at this temperature for 1 h, then at room temperature for 1.5 h. The reaction mixture was then quenched with sat. aq. NH$_4$Cl, poured into water, extracted with EtOAc, washed with brine, dried over anhydrous magnesium sulfate, filtered, and concentrated under reduced pressure. Purification via column chromatography (gradient elution from 0 to 50% EtOAc/EtOH [3:1] in heptane) afforded the title compound (4.14 g, 55%).

Intermediate 27: 5-bromo-4-(3-bromopropoxy)pyridin-3-amine

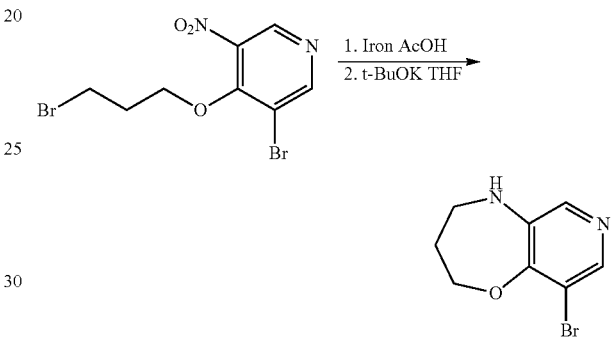

Iron powder (6.8 g, 0.122 mol) was added to a solution of 3-bromo-4-(3-bromopropoxy)-5-nitro-pyridine (4.14 g, 12.2 mmol) in AcOH (100 mL). The resulting solution was stirred at room temperature for 1 h, then filtered and the precipitate was washed with MeOH. The filtrate was concentrated, then diluted with sat. aq. NaHCO$_3$, extracted with EtOAc, washed with brine, dried over anhydrous magnesium sulfate, and concentrated under reduced pressure. The resulting oil was dissolved in THF (150 mL) and cooled to −78° C. To the resulting solution was added t-BuOK (1 M in THF, 15.3 mL, 15.3 mmol), and the reaction mixture was warmed to 0° C. for 40 min, then quenched with sat. aq. NH$_4$Cl, poured into water, extracted with EtOAc, washed with brine, dried over anhydrous magnesium sulfate, filtered, and concentrated under reduced pressure. Purification via column chromatography (gradient elution from 0 to 60% EtOAc/EtOH [3:1] in heptane) afforded the title compound (1.07 g, 38%).

Intermediate 28: 9-bromo-5-(2-chloro-6-fluoro-quinazolin-4-yl)-3,4-dihydro-2H-pyrido[4,3-b][1,4]oxazepine

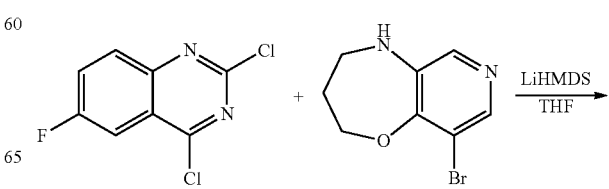

315

-continued

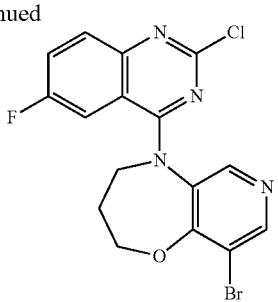

To a solution of 9-bromo-2,3,4,5-tetrahydropyrido[4,3-b][1,4]oxazepine (77 mg, 0.336 mmol) and 2,4-dichloro-6-fluoro-quinazoline (146 mg, 0.672 mmol) in THF (3 mL) at 0° C. was added LiHMDS (1M in THF, 0.5 mL, 0.5 mmol). The resulting solution was stirred at this temperature for 10 min then quenched with sat. aq. NH$_4$Cl, poured into water, extracted with EtOAc, washed with brine, dried over anhydrous magnesium sulfate, filtered, and concentrated under reduced pressure. Purification via column chromatography (gradient elution from 0 to 60% EtOAc in hexanes) afforded the title compound (118 mg, 86%).

Intermediate 29: 9-bromo-5-(7-fluoro-1-methyl-[1,2,4]triazolo[4,3-a]quinazolin-5-yl)-3,4-dihydro-2H-pyrido[4,3-b][1,4]oxazepine

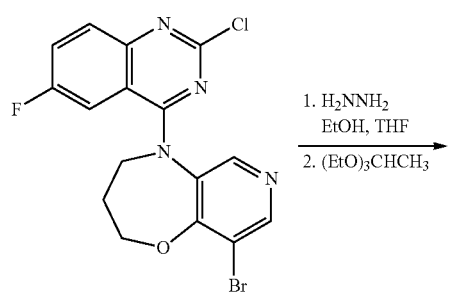

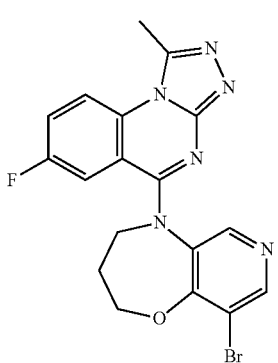

To a solution of 9-bromo-5-(2-chloro-6-fluoro-quinazolin-4-yl)-3,4-dihydro-2H-pyrido[4,3-b][1,4]oxazepine (189 mg, 0.461 mmol) in THF (2 mL) and EtOH (4 mL) was added hydrazine (0.145 mL, 4.61 mmol). The resulting solution was heated to 45° C. for 3 h, then concentrated under reduced pressure. To the resulting solid was added triethyl orthoacetate (4 mL, 21.8 mmol). The resulting mixture was then heated to 90° C. for 2 h, then cooled to room temperature, and diluted with heptane. The resulting precipitate was then collected by filtration to afford the title compound as an amorphous yellow solid (164 mg, 83%).

316

Intermediate 30: 9-bromo-5-(2-chloro-5,6-difluoro-quinazolin-4-yl)-3,4-dihydro-2H-pyrido[4,3-b][1,4]oxazepine

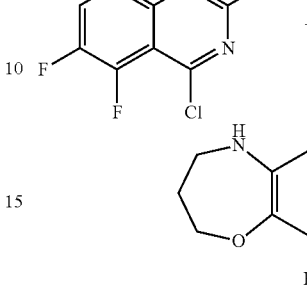

+

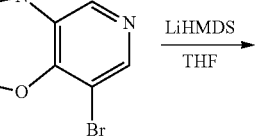

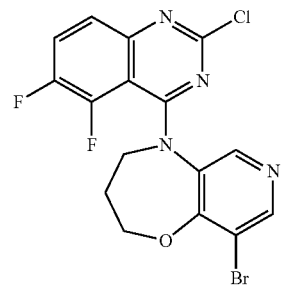

The title compound was synthesized as described in Intermediate 28, using 2,4-dichloro-5,6-difluoro-quinazoline instead of 2,4-dichloro-6-fluoro-quinazoline. This afforded the title compound as an amorphous yellow solid.

Intermediate 31: 9-bromo-5-(6,7-difluoro-1-methyl-[1,2,4]triazolo[4,3-a]quinazolin-5-yl)-3,4-dihydro-2H-pyrido[4,3-b][1,4]oxazepane

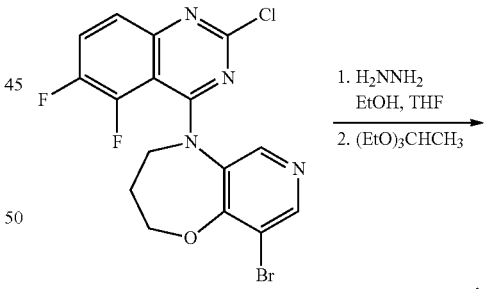

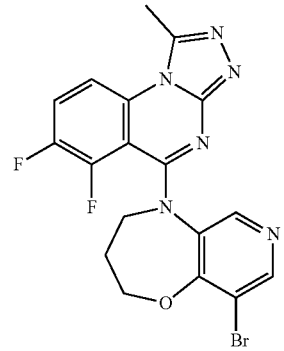

The title compound was synthesized as described in Intermediate 29, using 9-bromo-5-(2-chloro-5,6-difluoro-quinazolin-4-yl)-2,3,4,5-tetrahydropyrido[4,3-b][1,4]oxazepine instead of 9-bromo-5-(2-chloro-6-fluoro-quinazolin-4-yl)-3,4-dihydro-2H-pyrido[4,3-b][1,4]oxazepine. This afforded the title compound as an amorphous yellow solid.

Intermediate 32: 6-bromo-4-methyl-1,2,3,5-tetrahydro-1,4-benzodiazepine

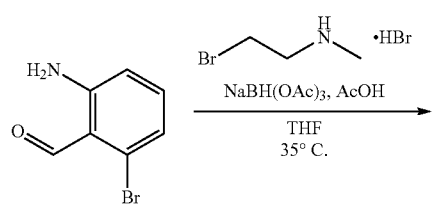

To a solution of 2-amino-6-bromo-benzaldehyde (700 mg, 3.5 mmol) and 2-bromo-N-methyl-ethanamine hydrobromide (1.53 g, 7 mmol) in THF (17 mL) was added AcOH (0.25 mL, 4.37 mmol). The resulting solution was stirred at room temperature for 45 min followed by the addition of NaBH(OAc)$_3$ (1.48 g, 7.00 mmol). The reaction mixture was then stirred at 35° C. for 1 h, then poured into water and washed with EtOAc to remove organic impurities. The aqueous fraction was then made basic (ca. pH 11) with 1 N NaOH and extracted with EtOAc (2×), washed with brine, dried over anhydrous magnesium sulfate, filtered, and concentrated under reduced pressure to afford title compound (619 mg, 73%).

Intermediate 33: 6-bromo-1-(2-chloro-6-fluoro-quinazolin-4-yl)-4-methyl-3,5-dihydro-2H-1,4-benzodiazepine

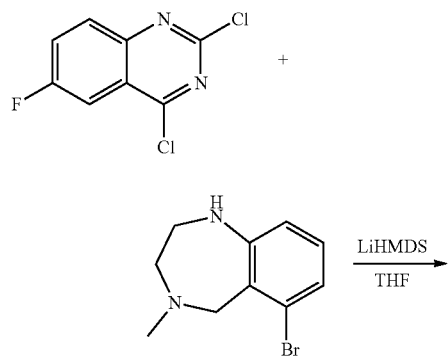

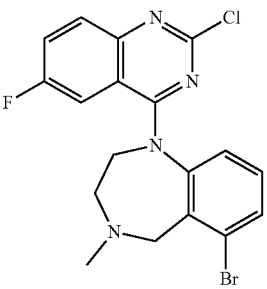

The title compound was synthesized as described in Intermediate 28, using 6-bromo-4-methyl-1,2,3,5-tetrahydro-1,4-benzodiazepine instead of 9-bromo-2,3,4,5-tetrahydropyrido[4,3-b][1,4]oxazepane. This afforded the title compound as an amorphous yellow solid.

Intermediate 34: 5-(6-bromo-4-methyl-3,5-dihydro-2H-1,4-benzodiazepin-1-yl)-7-fluoro-1-methyl-[1,2,4]triazolo[4,3-a]quinazoline

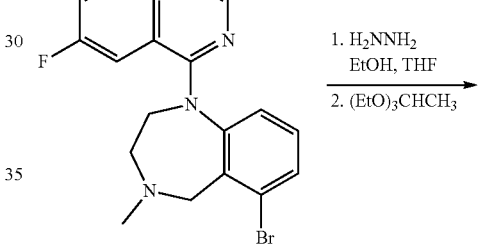

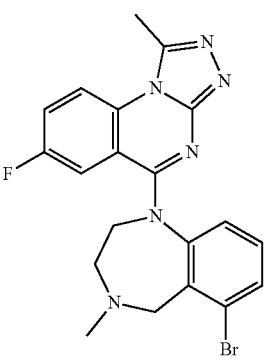

The title compound was synthesized as described in Intermediate 29, using 6-bromo-1-(2-chloro-6-fluoro-quinazolin-4-yl)-4-methyl-3,5-dihydro-2H-1,4-benzodiazepine instead of 9-bromo-5-(2-chloro-6-fluoro-quinazolin-4-yl)-3,4-dihydro-2H-pyrido[4,3-b][1,4]oxazepine. This afforded the title compound as an amorphous yellow solid.

Intermediate 35: 6-bromo-1-(2-chloro-5,6-difluoro-quinazolin-4-yl)-4-methyl-3,5-dihydro-2H-1,4-benzodiazepine

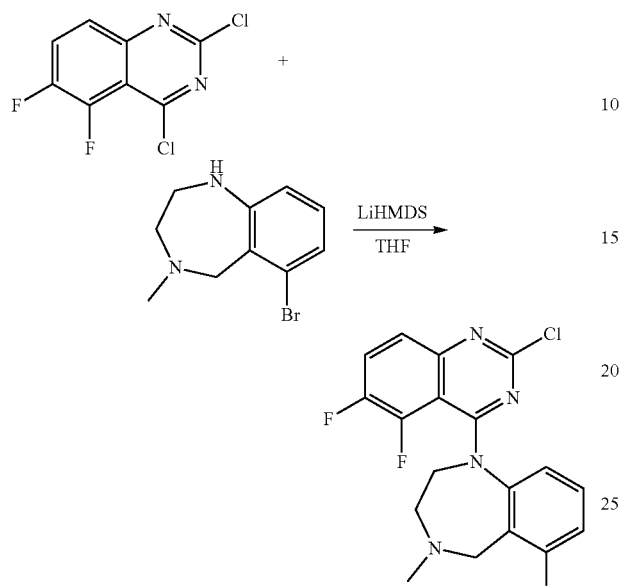

The title compound was synthesized as described in Intermediate 33, using 2,4-dichloro-5,6-difluoro-quinazoline instead of 2,4-dichloro-6-fluoroquinazoline. This afforded the title compound as an amorphous yellow solid.

Intermediate 36: 5-(6-bromo-4-methyl-3,5-dihydro-2H-1,4-benzodiazepin-1-yl)-6,7-difluoro-1-methyl-[1,2,4]triazolo[4,3-a]quinazoline

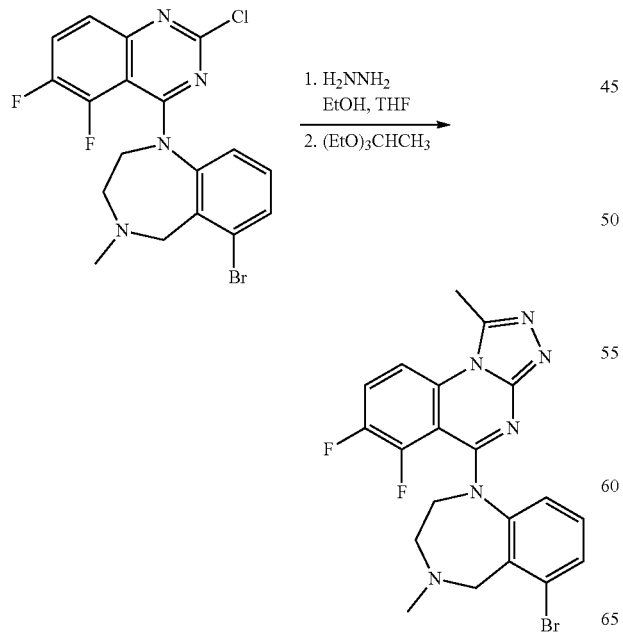

The title compound was synthesized as described in Intermediate 29, using 6-bromo-1-(2-chloro-5,6-difluoro-quinazolin-4-yl)-4-methyl-3,5-dihydro-2H-1,4-benzodiazepine instead of 9-bromo-5-(2-chloro-6-fluoro-quinazolin-4-yl)-3,4-dihydro-2H-pyrido[4,3-b][1,4]oxazepine. This afforded the title compound as an amorphous yellow solid.

Intermediate 37: 6-bromo-1-(2-chloro-5-fluoro-quinazolin-4-yl)-4-methyl-3,5-dihydro-2H-1,4-benzodiazepine

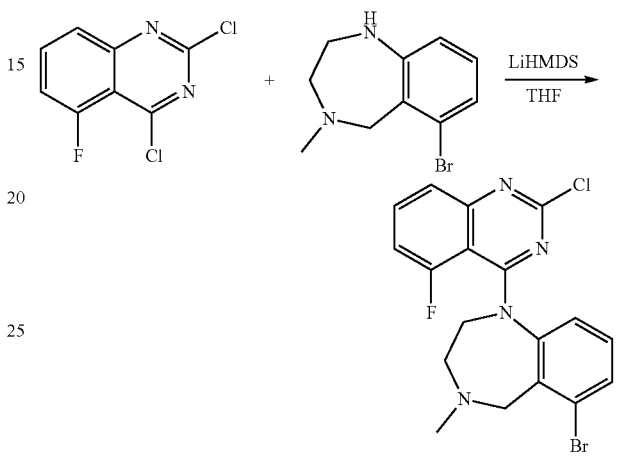

The title compound was synthesized as described in Intermediate 33, using 2,4-dichloro-5-fluoroquinazoline instead of 2,4-dichloro-6-fluoroquinazoline. This afforded the title compound as an amorphous yellow solid.

Intermediate 38: 5-(6-bromo-4-methyl-2,3,4,5-tetrahydro-1H-benzo[e][1,4]diazepin-1-yl)-6-fluoro-1-methyl-[1,2,4]triazolo[4,3-a]quinazoline

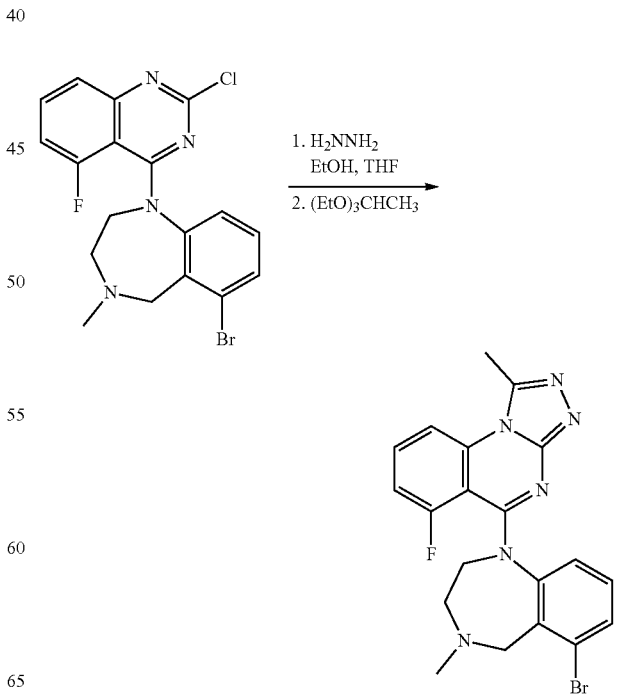

The title compound was synthesized as described in Intermediate 29, 6-bromo-1-(2-chloro-5-fluoro-quinazolin-4-yl)-4-methyl-3,5-dihydro-2H-1,4-benzodiazepine instead of 9-bromo-5-(2-chloro-6-fluoro-quinazolin-4-yl)-3,4-dihydro-2H-pyrido[4,3-b][1,4]oxazepine.

Intermediate 39: Synthesis of 1-(6-fluoro-1-methyl-[1,2,4]triazolo[4,3-a]quinazolin-5-yl)-6-iodo-1,2,3,5-tetrahydrobenzo[e][1,4]oxazepine

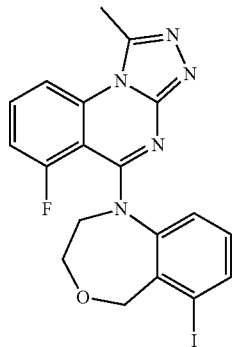 [SMILES: Cc1nnc2nc(N3CCOCc4c(I)cccc43)c3c(F)cccc3n12]

The title compound was synthesized in a manner similar to Intermediate 1.3 using 2,4-dichloro-5-fluoro-quinazoline and 6-iodo-1,2,3,5-tetrahydro-4,1-benzoxazepine as the starting materials. MS (m/z) 456.5 [M+H]⁺.

Intermediate 40: Synthesis of 3-(1-ethynylcyclopropyl)-5-pentyl-isoxazole

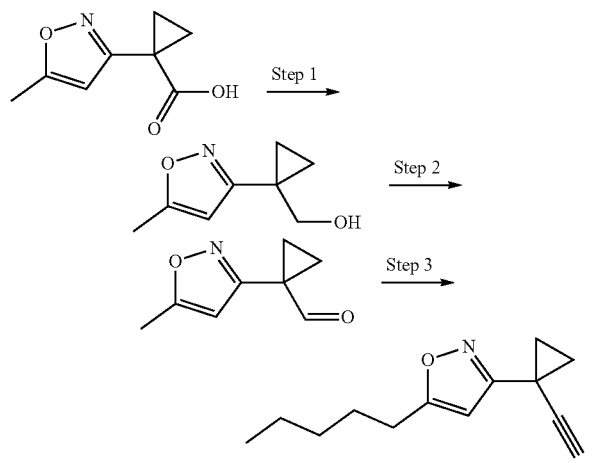

Step 1: Ethyl Chloroformate (345 mg, 3.18 mmol) was added to a stirred solution of 1-(5-methylisoxazol-3-yl)cyclopropanecarboxylic acid (531 mg, 3.18 mmol) and TEA (321 mg, 3.18 mmol) in THF (32.0 mL) at 0° C. and the mixture was stirred for 30 minutes. The solid was then filtered off and the filtrate was slowly added to a stirred suspension of NaBH$_4$ (361 mg, 9.53 mmol) in 20% aqueous THF (10.0 mL) and the temperature was maintained at 10° C. The mixture was stirred for 30 minutes, and then acidified with 1N HCl to pH~ 4. The reaction mixture was extracted with EA, washed with 2M NaOH solution, washed with brine, dried over Na$_2$SO$_4$ and concentrated under reduced pressure. The crude product was purified using column chromatography eluting with EA in hexanes 0-100% to afford the product as a colorless oil.

Step 2: To a solution of oxalyl chloride (377 mg, 2.97 mmol) in DCM (12.0 mL) was added a solution of DMSO (464 mg, 5.94 mmol) in DCM (3.0 mL) at −78° C. in a drop-wise manner. The mixture was stirred for 15 minutes, followed by the addition of [1-(5-methylisoxazol-3-yl)cyclopropyl]methanol (379 mg, 2.47 mmol) in DCM (6.10 mL). The reaction was stirred at −78° C. for 30 minutes, followed by the addition of TEA (1.2 g, 12.4 mmol). The reaction was stirred at −78° C. before the removal of the cold bath. The mixture was stirred for 12 h at room temperature and quenched with a saturated NH$_4$Cl solution and extracted with DCM. The combined organic layers were washed with sat aq NaHCO$_3$, washed with brine and dried with Na$_2$SO$_4$, filtered and concentrated in vacuo and used without further purification.

Step 3: To a mixture of PPh$_3$ (694 mg, 2.65 mmol) and CBr$_4$ (442 mg, 1.33 mmol) in DCM (3.30 mL) at 0° C. was added a solution of 1-(5-methylisoxazol-3-yl)cyclopropanecarbaldehyde (100 mg, 0.662 mmol) in DCM (3.30 mL) and the mixture was warmed to rt and stirred for 4 h. The reaction was then quenched with water and the solid was filtered off. The aqueous layer was extracted with DCM, and the combined organic layers were dried over Na$_2$SO$_4$, filtered and concentrated in vacuo. The crude product was purified using silica gel column chromatography eluting with EA in hexanes 0-100% to afford the product as a colorless oil. To a solution of 3-[1-(2,2-dibromovinyl)cyclopropyl]-5-methyl-isoxazole (118 mg, 0.384 mmol) in THF (3.40 mL) at −78° C. was slowly added a 2.5 M solution of n-BuLi in hexanes (0.62 mL, 1.54 mmol, 4 equiv.) and the reaction was stirred for 20 minutes. The reaction was then quenched with saturated NaHCO$_3$ and extracted with EA. Combined organics were dried over Na$_2$SO$_4$, filtered, and concentrated to afford the crude product which was used without further purification.

B. Synthesis of Compounds in Table 1

Example 1: 5-(6-(cyclopropylethynyl)-2,3,4,5-tetrahydro-1H-pyrido[3,4-b]azepin-1-yl)-6,7-difluoro-1-methyl-[1,2,4]triazolo[4,3-a]quinazoline

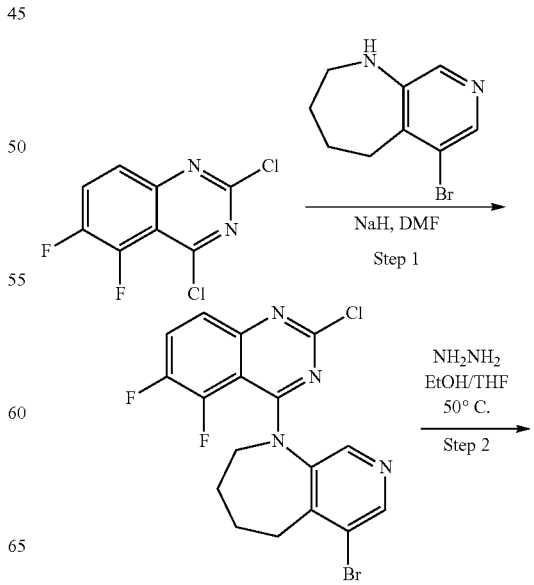

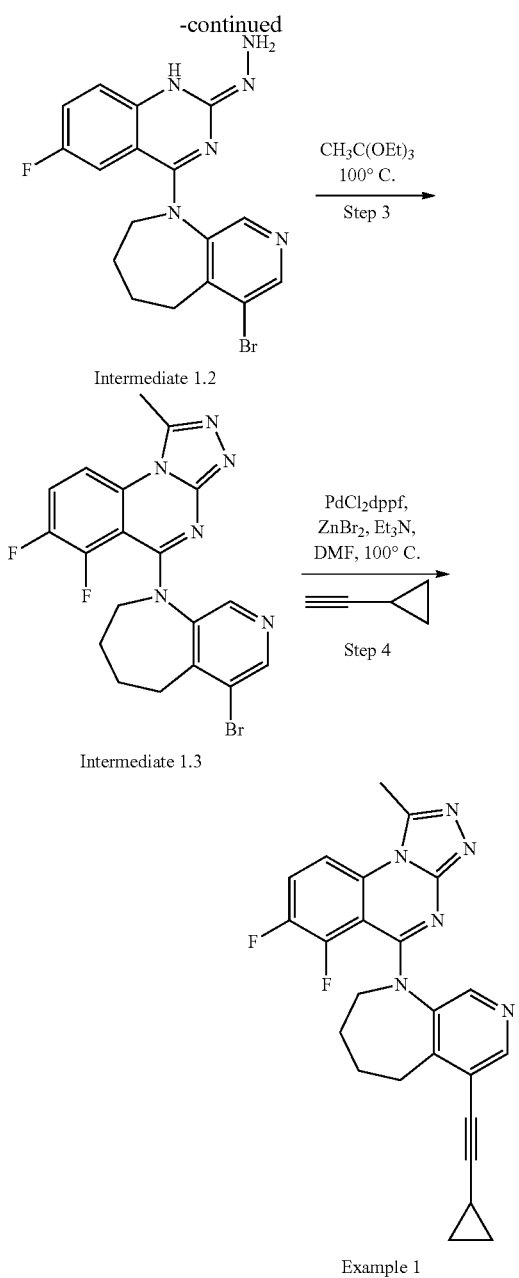

Synthesis of 6-bromo-1-(6-fluoro-2-hydrazineylidene-1,2-dihydroquinazolin-4-yl)-2,3,4,5-tetrahydro-1H-pyrido[3,4-b]azepine (Intermediate 1.2): To a solution of 6-bromo-1-(2-chloro-5,6-difluoroquinazolin-4-yl)-2,3,4,5-tetrahydro-1H-pyrido[3,4-b]azepine (Intermediate 1.1, 0.47 mmol) in THF (5 mL) and ethanol (5 mL) was added anhydrous hydrazine (4.71 mmol) and the mixture was stirred at room temperature for 5 hrs. Upon completion, the reaction was diluted with dichloromethane and washed with water followed by brine. The resulting organics were dried over $Na_2SO_4$, filtered, and concentrated under reduced pressure to afford Intermediate 1.2.

Synthesis of 5-(6-bromo-2,3,4,5-tetrahydro-1H-pyrido[3,4-b]azepin-1-yl)-6,7-difluoro-1-methyl-[1,2,4]triazolo[4,3-a]quinazoline (Intermediate 1.3): A solution of 6-bromo-1-(6-fluoro-2-hydrazineylidene-1,2-dihydroquinazolin-4-yl)-2,3,4,5-tetrahydro-1H-pyrido[3,4-b]azepine (Intermediate 1.2, 1.03 mmol) and triethyl orthoacetate (0.9 g, 5.62 mmol) was heated to 100° C. for 16 hrs. The reaction was then allowed to cool to room temperature, whereupon the mixture was concentrated under reduced pressure to afford the crude residue. This residue was triturated with heptane and the solids were collected by filtration, washed with heptanes and dried in vacuo to afford Intermediate 1.3.

Synthesis of 5-(6-(cyclopropylethynyl)-2,3,4,5-tetrahydro-1H-pyrido[3,4-b]azepin-1-yl)-6,7-difluoro-1-methyl-[1,2,4]triazolo[4,3-a]quinazoline (Example 1): A solution of 5-(6-bromo-2,3,4,5-tetrahydro-1H-pyrido[3,4-b]azepin-1-yl)-6,7-difluoro-1-methyl-[1,2,4]triazolo[4,3-a]quinazoline (Intermediate 1.3, 0.0641 mmol), zinc bromide (72.2 mg, 0.32 mmol), (1,1'-)bis(diphenylphosphino)ferrocene) palladium (II) dichloride (5.3 mg, 0.00641 mmol), and triethylamine (130 mg, 1.28 mmol) in DMF (2 mL) was purged with nitrogen gas for 2 minutes. ethynylcyclopropane (0.396 mmol) was then added and the mixture was heated at 100° C. for 2 hrs. The mixture was then allowed to cool to room temperature, and ethyl acetate and sat. $NH_4Cl$ (aq) were added. The aqueous layer was extracted with ethyl acetate. The combined organic layers were dried over $Na_2SO_4$ and concentrated in vacuo. The resulting crude residue was purified by reverse phase HPLC (0.1% trifluoroacetic acid in acetonitrile/water) to give the title compound as the mono-TFA salt.

Example 2: 4-(1-(6,7-difluoro-1-methyl-[1,2,4]triazolo[4,3-a]quinazolin-5-yl)-2,3,4,5-tetrahydro-1H-pyrido[3,4-b]azepin-6-yl)-2,2-dimethylbut-3-ynenitrile

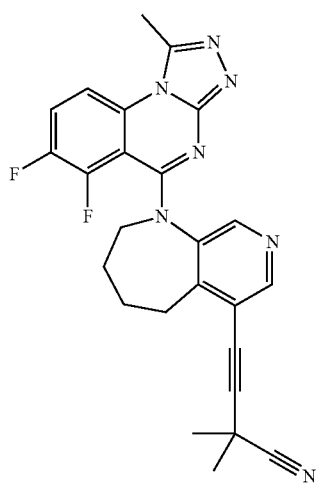 [SMILES: Cc1nnc2nc(N3CCCCc4c(C#CC(C)(C)C#N)cncc43)c3c(F)c(F)ccc3n12]

Synthesis of 6-bromo-1-(2-chloro-5,6-difluoroquinazolin-4-yl)-2,3,4,5-tetrahydro-1H-pyrido[3,4-b]azepine (Intermediate 1.1): To a solution of 6-bromo-2,3,4,5-tetrahydro-1H-pyrido[3,4-b]azepine (Intermediate 1, 0.92 mmol) in DMA (2.0 mL) at 0° C. was added NaH (60% dispersion in mineral oil) (1.84 mmol) in one portion. The mixture was stirred at 0° C. for 30 min, followed by addition of the 2,4-dichloro-5,6-difluoroquinazoline (0.92 mmol) in one portion. The resultant mixture was warmed to room temperature over 16 h. Upon completion, the mixture was poured into water (20 mL) and extracted with ethyl acetate (2×20 ml each). The organics were separated and dried over sodium sulfate, filtered, and concentrated under vacuum. The crude residue was purified by column chromatography on silica gel using ethyl acetate in hexanes 0-40% as the eluent. Appropriate fractions were combined and concentrated in vacuo to afford Intermediate 1.1.

The title compound was synthesized in a manner similar to Example 1. Using 6-bromo-2,3,4,5-tetrahydro-1H-pyrido[3,4-b]azepine instead of 5-bromo-1,2,3,4-tetrahydroquinoline. Using 2,2-dimethylbut-3-ynenitrile instead of ethynylcyclopropane.

Example 3: 7-fluoro-1-methyl-5-(6-((1-(trifluoromethyl)cyclopropyl)ethynyl)-2,3,4,5-tetrahydro-1H-pyrido[3,4-b]azepin-1-yl)-[1,2,4]triazolo[4,3-a]quinazoline

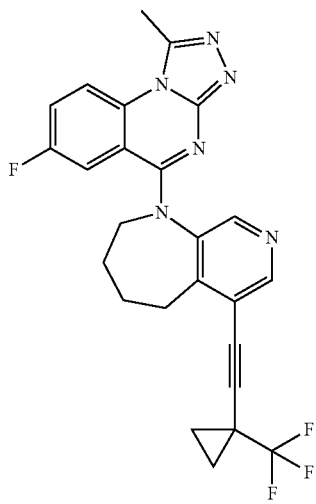 [SMILES: Cc1nnc2nc(N3CCCCc4c(C#CC5(C(F)(F)F)CC5)cncc43)c3cc(F)ccc3n12]

The title compound was synthesized in a manner similar to Example 1.

Example 4: 4-(1-(7-fluoro-1-methyl-[1,2,4]triazolo[4,3-a]quinazolin-5-yl)-2,3,4,5-tetrahydro-1H-pyrido[3,4-b]azepin-6-yl)-2,2-dimethylbut-3-ynenitrile

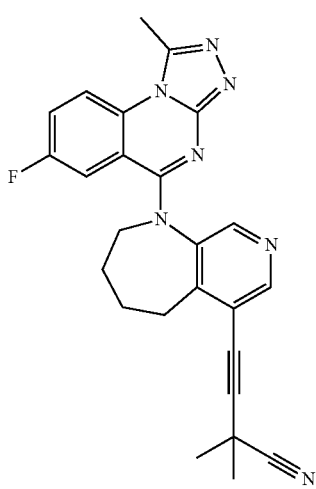 [SMILES: Cc1nnc2nc(N3CCCCc4c(C#CC(C)(C)C#N)cncc43)c3cc(F)ccc3n12]

The title compound was synthesized in a manner similar to Example 1, using 2,2-dimethylbut-3-ynenitrile instead of ethynylcyclopropane.

Example 5: 7-fluoro-1-methyl-5-(6-((1-methylcyclopropyl)ethynyl)-2,3,4,5-tetrahydro-1H-pyrido[3,4-b]azepin-1-yl)-[1,2,4]triazolo[4,3-a]quinazoline

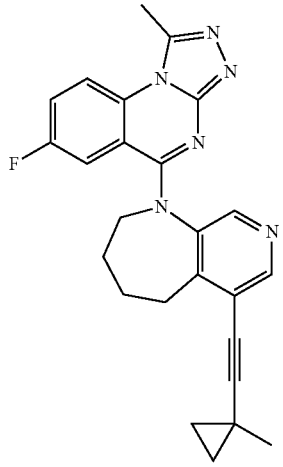 [SMILES: Cc1nnc2nc(N3CCCCc4c(C#CC5(C)CC5)cncc43)c3cc(F)ccc3n12]

The title compound was synthesized in a manner similar to Example 1, using 2 1-ethynyl-1-methylcyclopropane instead of ethynylcyclopropane.

Example 6: 6-fluoro-1-methyl-5-(6-((1-methylcyclopropyl)ethynyl)-2,3,4,5-tetrahydro-1H-pyrido[3,4-b]azepin-1-yl)-[1,2,4]triazolo[4,3-a]quinazoline

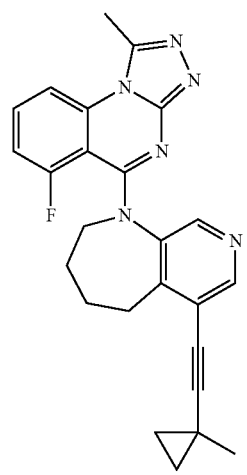 [SMILES: Cc1nnc2nc(N3CCCCc4c(C#CC5(C)CC5)cncc43)c3c(F)cccc3n12]

The title compound was synthesized in a manner similar to Example 1, using 2,4-dichloro-5-fluoroquinazoline instead of 2,4-dichloro-5,6-difluoroquinazoline. Using 1-ethynyl-1-methylcyclopropane instead of ethynylcyclopropane.

Example 7: 6,7-difluoro-1-methyl-5-(6-((1-methyl-cyclopropyl)ethynyl)-2,3,4,5-tetrahydro-1H-pyrido[3,4-b]azepin-1-yl)-[1,2,4]triazolo[4,3-a]quinazoline

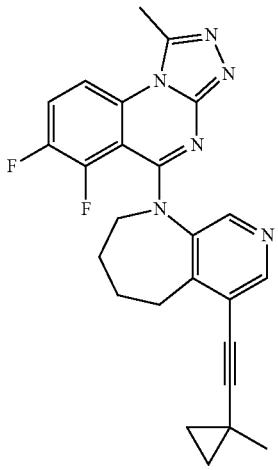 [SMILES: Cc1nnc2nc(N3CCCCc4c(C#CC5(C)CC5)cncc43)c3c(F)c(F)ccc3n12]

The title compound was synthesized in a manner similar to Example 1, using 1-ethynyl-1-methylcyclopropane instead of ethynylcyclopropane.

Example 8: 5-(6-((1-(difluoromethyl)cyclopropyl)ethynyl)-2,3,4,5-tetrahydro-1H-pyrido[3,4-b]azepin-1-yl)-6,7-difluoro-1-methyl-[1,2,4]triazolo[4,3-a]quinazoline

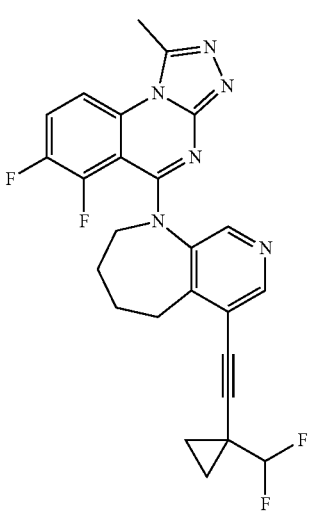 [SMILES: Cc1nnc2nc(N3CCCCc4c(C#CC5(C(F)F)CC5)cncc43)c3c(F)c(F)ccc3n12]

The title compound was synthesized in a manner similar to Example 1, using 1 1-(difluoromethyl)-1-ethynylcyclopropane instead of ethynylcyclopropane.

Example 9: 6,7-difluoro-1-methyl-5-(6-((1-(trifluoromethyl)cyclopropyl)ethynyl)-2,3,4,5-tetrahydro-1H-pyrido[3,4-b]azepin-1-yl)-[1,2,4]triazolo[4,3-a]quinazoline

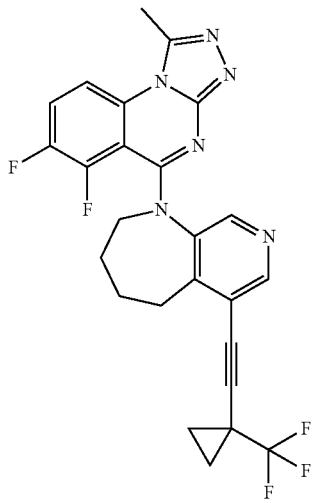 [SMILES: Cc1nnc2nc(N3CCCCc4c(C#CC5(C(F)(F)F)CC5)cncc43)c3c(F)c(F)ccc3n12]

The title compound was synthesized in a manner similar to Example 1.

Example 10: 4-(1-(6,7-difluoro-1-methyl-[1,2,4]triazolo[4,3-a]quinazolin-5-yl)-1,2,3,4-tetrahydro-1,7-naphthyridin-5-yl)-2,2-dimethylbut-3-ynenitrile

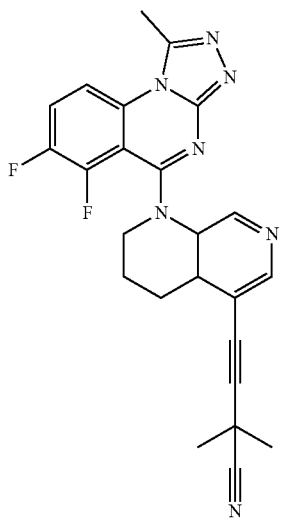 [SMILES: Cc1nnc2nc(N3CCCC4C(C#CC(C)(C)C#N)=CN=CC43)c3c(F)c(F)ccc3n12]

The title compound was synthesized in a manner similar to Example 1, using 5-bromo-1,2,3,4-tetrahydro-1,7-naphthyridine instead of 6-bromo-2,3,4,5-tetrahydro-1H-pyrido[3,4-b]azepine. Using 2,2-dimethylbut-3-ynenitrile instead of ethynylcyclopropane.

Example 11: 5-(5-((1-(difluoromethyl)cyclopropyl)ethynyl)-3,4-dihydro-1,7-naphthyridin-1(2H)-yl)-6,7-difluoro-1-methyl-[1,2,4]triazolo[4,3-a]quinazoline

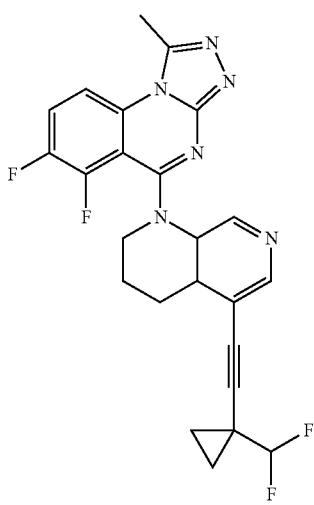 [SMILES: Cc1nnc2nc(N3CCCC4C(C#CC5(C(F)F)CC5)=CN=CC43)c3c(F)c(F)ccc3n12]

The title compound was synthesized in a manner similar to Example 1, using 5-bromo-1,2,3,4-tetrahydro-1,7-naphthyridine instead of 6-bromo-2,3,4,5-tetrahydro-1H-pyrido[3,4-b]azepine. Using 1-(difluoromethyl)-1-ethynylcyclopropane instead of ethynylcyclopropane.

Example 12: 5-(5-((1-(1,1-difluoroethyl)cyclopropyl)ethynyl)-3,4-dihydro-1,7-naphthyridin-1(2H)-yl)-6,7-difluoro-1-methyl-[1,2,4]triazolo[4,3-a]quinazoline

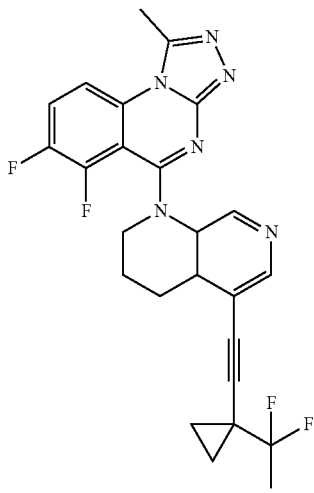 [SMILES: Cc1nnc2nc(N3CCCC4C(C#CC5(C(C)(F)F)CC5)=CN=CC43)c3c(F)c(F)ccc3n12]

The title compound was synthesized in a manner similar to Example 1, using 5-bromo-1,2,3,4-tetrahydro-1,7-naphthyridine instead of 6-bromo-2,3,4,5-tetrahydro-1H-pyrido[3,4-b]azepine. Using 1-(1,1-difluoroethyl)-1-ethynylcyclopropane instead of ethynylcyclopropane.

Example 13: 5-(5-(cyclobutylethynyl)-3,4-dihydro-1,7-naphthyridin-1(2H)-yl)-6,7-difluoro-[1,2,4]triazolo[4,3-a]quinazoline

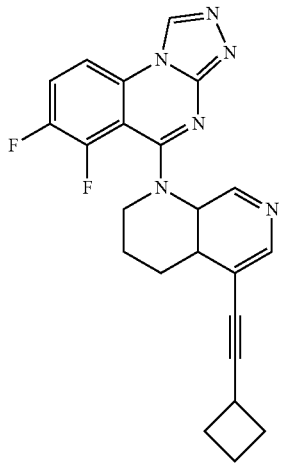 [SMILES: Fc1ccc2c(c(N3CCCC4C(C#CC5CCC5)=CN=CC43)nc3nncn32)c1F]

The title compound was synthesized in a manner similar to Example 1, using triethoxymethane instead of 1,1,1-triethoxyethane. Using 5-bromo-1,2,3,4-tetrahydro-1,7-naphthyridine instead of 6-bromo-2,3,4,5-tetrahydro-1H-pyrido[3,4-b]azepine. Using ethynylcyclobutane instead of ethynylcyclopropane.

Example 14: 5-(5-((3,3-difluorocyclobutyl)ethynyl)-3,4-dihydro-1,7-naphthyridin-1(2H)-yl)-6,7-difluoro-[1,2,4]triazolo[4,3-a]quinazoline

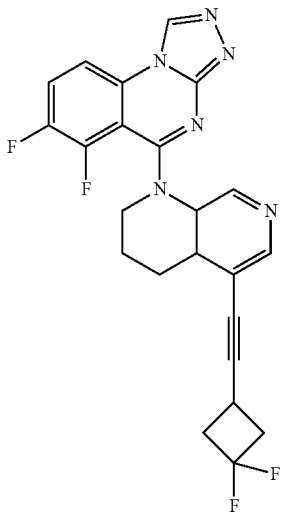 [SMILES: Fc1ccc2c(c(N3CCCC4C(C#CC5CC(F)(F)C5)=CN=CC43)nc3nncn32)c1F]

The title compound was synthesized in a manner similar to Example 1, using triethoxymethane instead of 1,1,1-triethoxyethane. Using 5-bromo-1,2,3,4-tetrahydro-1,7-naphthyridine instead of 6-bromo-2,3,4,5-tetrahydro-1H-pyrido[3,4-b]azepine. Using 3-ethynyl-1,1-difluorocyclobutane instead of ethynylcyclopropane.

Example 15: 5-(5-((1-(difluoromethyl)cyclopropyl)ethynyl)-3,4-dihydro-1,7-naphthyridin-1(2H)-yl)-6,7-difluoro-[1,2,4]triazolo[4,3-a]quinazoline

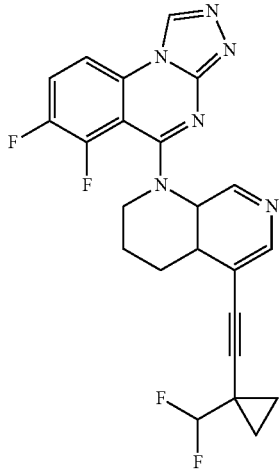 [SMILES: Fc1ccc2c(c(N3CCCC4C(C#CC5(C(F)F)CC5)=CN=CC43)nc3nncn32)c1F]

The title compound was synthesized in a manner similar to Example 1, using triethoxymethane instead of 1,1,1-triethoxyethane. Using 5-bromo-1,2,3,4-tetrahydro-1,7-naphthyridine instead of 6-bromo-2,3,4,5-tetrahydro-1H-pyrido[3,4-b]azepine. Using 1-(difluoromethyl)-1-ethynylcyclopropane instead of ethynylcyclopropane.

Example 16: 5-(5-((1-(1,1-difluoroethyl)cyclopropyl)ethynyl)-3,4-dihydro-1,7-naphthyridin-1(2H)-yl)-6,7-difluoro-[1,2,4]triazolo[4,3-a]quinazoline

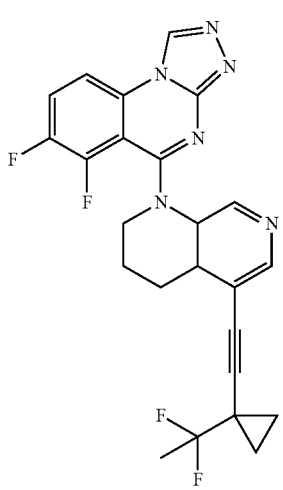 [SMILES: CC(F)(F)C1(C#CC2=CN=CC3C2CCCN3c2nc3nncn3c3ccc(F)c(F)c23)CC1]

The title compound was synthesized in a manner similar to Example 1, using triethoxymethane instead of 1,1,1-triethoxyethane. Using 5-bromo-1,2,3,4-tetrahydro-1,7-naphthyridine instead of 6-bromo-2,3,4,5-tetrahydro-1H-pyrido[3,4-b]azepine. Using 1-(1,1-difluoroethyl)-1-ethynylcyclopropane instead of ethynylcyclopropane.

Example 17: 5-(5-((3,3-difluorocyclobutyl)ethynyl)-3,4-dihydro-1,7-naphthyridin-1(2H)-yl)-6-fluoro-[1,2,4]triazolo[4,3-a]quinazoline

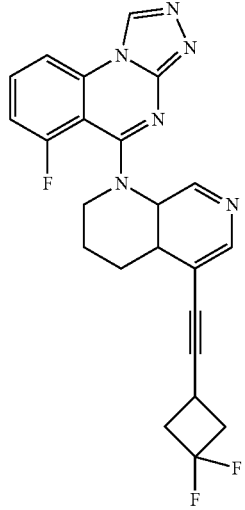 [SMILES: Fc1cccc2c1c(N1CCCC3C(C#CC4CC(F)(F)C4)=CN=CC31)nc1nncn12]

The title compound was synthesized in a manner similar to Example 1, using triethoxymethane instead of 1,1,1-triethoxyethane. Using 2,4-dichloro-5-fluoroquinazoline instead of 2,4-dichloro-5,6-difluoroquinazoline. Using 5-bromo-1,2,3,4-tetrahydro-1,7-naphthyridine instead of 6-bromo-2,3,4,5-tetrahydro-1H-pyrido[3,4-b]azepine. Using 3-ethynyl-1,1-difluorocyclobutane instead of ethynylcyclopropane.

Example 18: 5-(5-(cyclobutylethynyl)-3,4-dihydro-1,7-naphthyridin-1(2H)-yl)-6-fluoro-[1,2,4]triazolo[4,3-a]quinazoline

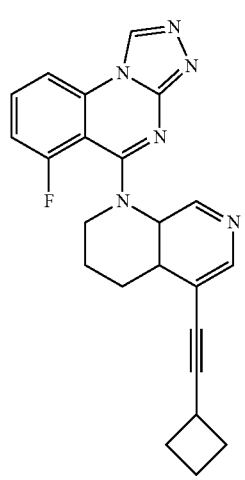

The title compound was synthesized in a manner similar to Example 1, using triethoxymethane instead of 1,1,1-triethoxyethane. Using 2,4-dichloro-5-fluoroquinazoline instead of 2,4-dichloro-5,6-difluoroquinazoline. Using 5-bromo-1,2,3,4-tetrahydro-1,7-naphthyridine instead of 6-bromo-2,3,4,5-tetrahydro-1H-pyrido[3,4-b]azepine. Using ethynylcyclobutane instead of ethynylcyclopropane.

Example 19: 5-(5-((1-(difluoromethyl)cyclopropyl)ethynyl)-3,4-dihydro-1,7-naphthyridin-1(2H)-yl)-6-fluoro-[1,2,4]triazolo[4,3-a]quinazoline

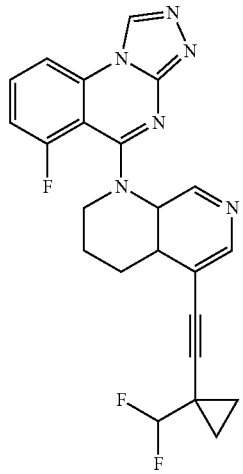 [SMILES: Fc1cccc2c1c(N1CCCC3C(C#CC4(C(F)F)CC4)=CN=CC31)nc1nncn12]

The title compound was synthesized in a manner similar to Example 1, using triethoxymethane instead of 1,1,1-triethoxyethane. Using 2,4-dichloro-5-fluoroquinazoline instead of 2,4-dichloro-5,6-difluoroquinazoline. Using 5-bromo-1,2,3,4-tetrahydro-1,7-naphthyridine instead of 6-bromo-2,3,4,5-tetrahydro-1H-pyrido[3,4-b]azepine. Using 1-(difluoromethyl)-1-ethynylcyclopropane instead of ethynylcyclopropane.

Example 20: N-(2,2-difluoroethyl)-6-fluoro-N-(3-fluoro-5-((tetrahydro-2H-pyran-4-yl)ethynyl)phenyl)-1-methyl-[1,2,4]triazolo[4,3-a]quinazolin-5-amine

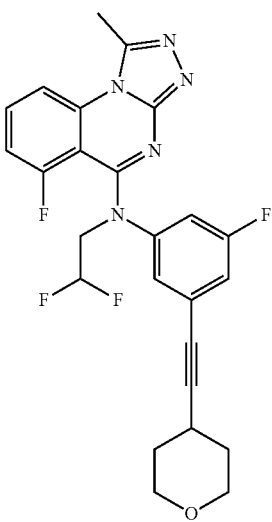 [SMILES: Cc1nnc2nc(N(CC(F)F)c3cc(F)cc(C#CC4CCOCC4)c3)c3c(F)cccc3n12]

The title compound was synthesized in a manner similar to Example 1, using 2,4-dichloro-5-fluoroquinazoline instead of 2,4-dichloro-5,6-difluoroquinazoline. Using 3-bromo-N-(2,2-difluoroethyl)-5-fluoroaniline instead of 6-bromo-2,3,4,5-tetrahydro-1H-pyrido[3,4-b]azepine. Using 4-ethynyltetrahydro-2H-pyran instead of ethynylcyclopropane.

Example 21: 1-((3-((2,2-difluoroethyl)(6-fluoro-1-methyl-[1,2,4]triazolo[4,3-a]quinazolin-5-yl)amino)-5-fluorophenyl)ethynyl)cyclobutan-1-ol

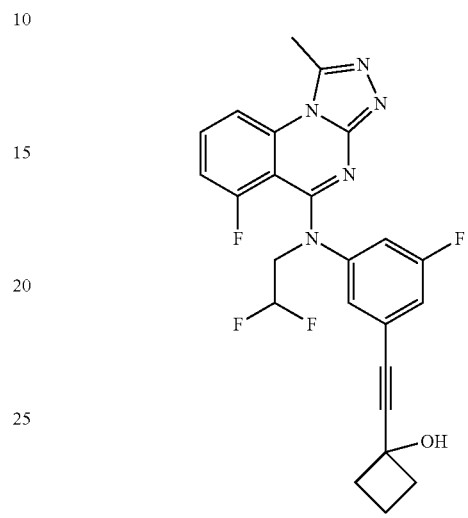

The title compound was synthesized in a manner similar to Example 1, using 2,4-dichloro-5-fluoroquinazoline instead of 2,4-dichloro-5,6-difluoroquinazoline. Using 3-bromo-N-(2,2-difluoroethyl)-5-fluoroaniline instead of 6-bromo-2,3,4,5-tetrahydro-1H-pyrido[3,4-b]azepine. Using 1-ethynylcyclobutan-1-ol instead of ethynylcyclopropane.

Example 22: N-(2,2-difluoroethyl)-6-fluoro-N-(3-fluoro-5-((3-methyloxetan-3-yl)ethynyl)phenyl)-1-methyl-[1,2,4]triazolo[4,3-a]quinazolin-5-amine

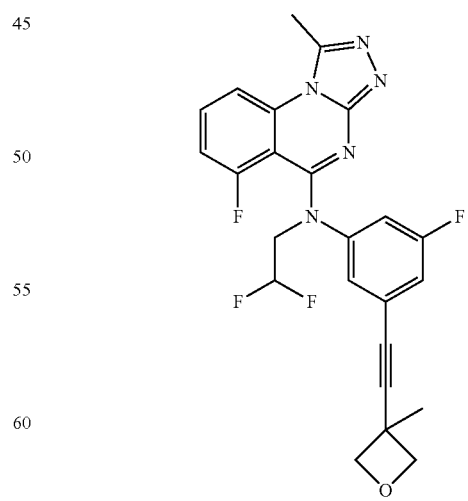

The title compound was synthesized in a manner similar to Example 1, using 2,4-dichloro-5-fluoroquinazoline instead of 2,4-dichloro-5,6-difluoroquinazoline. Using 3-bromo-N-(2,2-difluoroethyl)-5-fluoroaniline instead of 6-bromo-2,3,4,5-tetrahydro-1H-pyrido[3,4-b]azepine. Using 3-ethynyl-3-methyloxetane instead of ethynylcyclopropane.

Example 23: N-(2,2-difluoroethyl)-6-fluoro-N-(3-fluoro-5-(oxetan-3-ylethynyl)phenyl)-1-methyl-[1,2,4]triazolo[4,3-a]quinazolin-5-amine

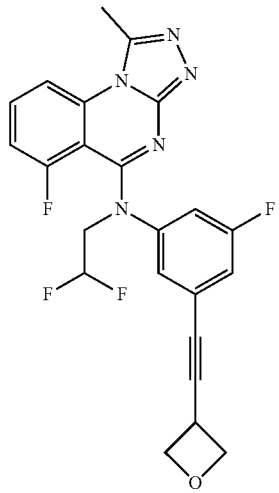

The title compound was synthesized in a manner similar to Example 1, using 2,4-dichloro-5-fluoroquinazoline instead of 2,4-dichloro-5,6-difluoroquinazoline. Using 3-bromo-N-(2,2-difluoroethyl)-5-fluoroaniline instead of 6-bromo-2,3,4,5-tetrahydro-1H-pyrido[3,4-b]azepine. Using 3 3-ethynyloxetane instead of ethynylcyclopropane.

Example 24: N-(2,2-difluoroethyl)-7-fluoro-N-(3-fluoro-5-((3-methyloxetan-3-yl)ethynyl)phenyl)-1-methyl-[1,2,4]triazolo[4,3-a]quinazolin-5-amine

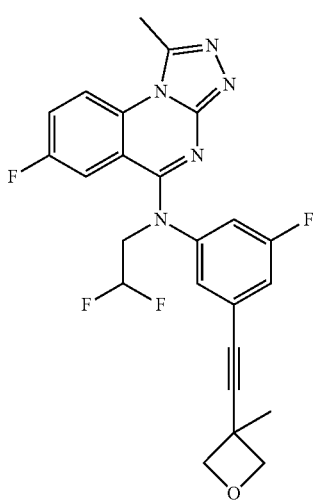 [SMILES: Cc1nnc2nc(N(CC(F)F)c3cc(F)cc(C#CC4(C)COC4)c3)c3cc(F)ccc3n12]

The title compound was synthesized in a manner similar to Example 1, using 3-bromo-N-(2,2-difluoroethyl)-5-fluoroaniline instead of 6-bromo-2,3,4,5-tetrahydro-1H-pyrido[3,4-b]azepine. Using 3-ethynyl-3-methyloxetane instead of ethynylcyclopropane.

Example 25: N-(2,2-difluoroethyl)-N-(3-((1-(difluoromethyl)cyclopropyl)ethynyl)-5-fluorophenyl)-6-fluoro-1-methyl-[1,2,4]triazolo[4,3-a]quinazolin-5-amine

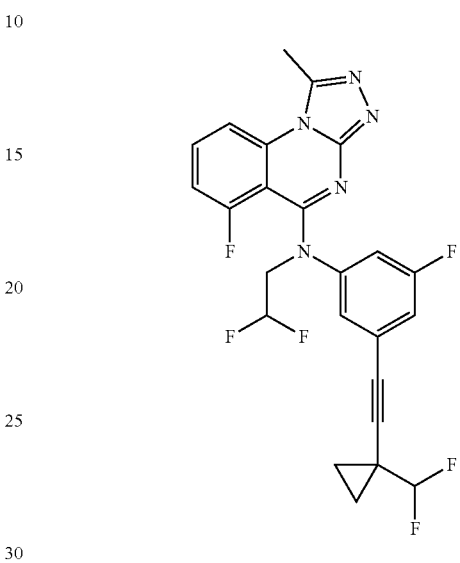

The title compound was synthesized in a manner similar to Example 1, using 2,4-dichloro-5-fluoroquinazoline instead of 2,4-dichloro-5,6-difluoroquinazoline. Using 3-bromo-N-(2,2-difluoroethyl)-5-fluoroaniline instead of 6-bromo-2,3,4,5-tetrahydro-1H-pyrido[3,4-b]azepine. Using 1-(difluoromethyl)-1-ethynylcyclopropane instead of ethynylcyclopropane.

Example 26: 6-fluoro-1-methyl-5-(5-((tetrahydro-2H-pyran-4-yl)ethynyl)-3,4-dihydroquinolin-1(2H)-yl)-[1,2,4]triazolo[4,3-a]quinazoline

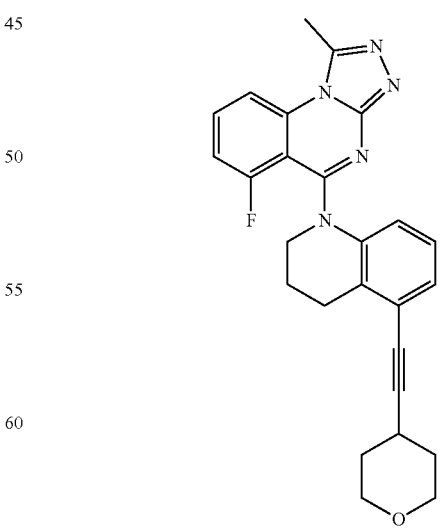

The title compound was synthesized in a manner similar to Example 1, using 2,4-dichloro-5-fluoroquinazoline instead of 2,4-dichloro-5,6-difluoroquinazoline. Using 4-ethynyltetrahydro-2H-pyran instead of ethynylcyclopropane.

Example 27: 6-fluoro-1-methyl-5-(5-((3-methyloxetan-3-yl)ethynyl)-3,4-dihydroquinolin-1(2H)-yl)-[1,2,4]triazolo[4,3-a]quinazoline

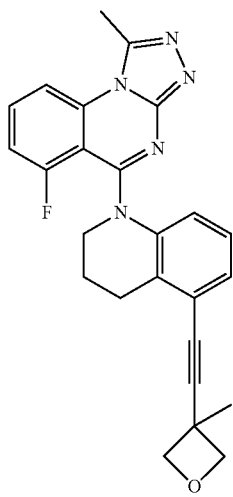 [SMILES: Cc1nnc2nc(N3CCCc4c(C#CC5(C)COC5)cccc43)c3c(F)cccc3n12]

The title compound was synthesized in a manner similar to Example 1, using 2,4-dichloro-5-fluoroquinazoline instead of 2,4-dichloro-5,6-difluoroquinazoline. Using 4-ethynyltetrahydro-2H-pyran instead of ethynylcyclopropane.

Example 28: 1-((1-(7-fluoro-1-methyl-[1,2,4]triazolo[4,3-a]quinazolin-5-yl)-1,2,3,4-tetrahydroquinolin-5-yl)ethynyl)cyclobutan-1-ol

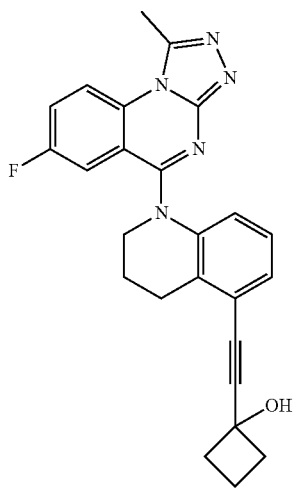 [SMILES: Cc1nnc2nc(N3CCCc4c(C#CC5(O)CCC5)cccc43)c3cc(F)ccc3n12]

The title compound was synthesized in a manner similar to Example 1, using 1-ethynylcyclobutan-1-ol instead of ethynylcyclopropane.

Example 29: 7-fluoro-1-methyl-5-(5-((3-methyloxetan-3-yl)ethynyl)-3,4-dihydroquinolin-1(2H)-yl)-[1,2,4]triazolo[4,3-a]quinazoline

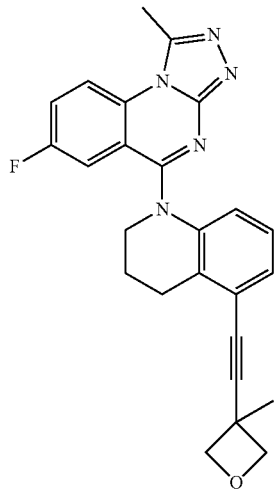 [SMILES: Cc1nnc2nc(N3CCCc4c(C#CC5(C)COC5)cccc43)c3cc(F)ccc3n12]

The title compound was synthesized in a manner similar to Example 1, using 3-ethynyl-3-methyloxetane instead of ethynylcyclopropane.

Example 30: 5-(5-(cyclobutylethynyl)-3,4-dihydroquinolin-1(2H)-yl)-7-fluoro-1-methyl-[1,2,4]triazolo[4,3-a]quinazoline

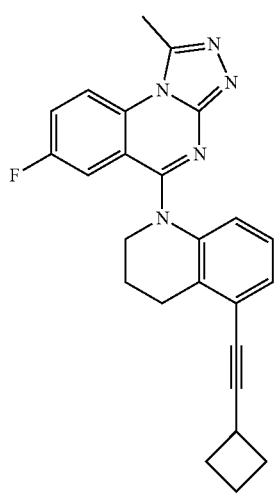 [SMILES: Cc1nnc2nc(N3CCCc4c(C#CC5CCC5)cccc43)c3cc(F)ccc3n12]

The title compound was synthesized in a manner similar to Example 1, using ethynylcyclobutane instead of ethynylcyclopropane.

Example 31: 5-(5-((1-(1,1-difluoroethyl)cyclopropyl)ethynyl)-3,4-dihydroquinolin-1(2H)-yl)-7-fluoro-1-methyl-[1,2,4]triazolo[4,3-a]quinazoline

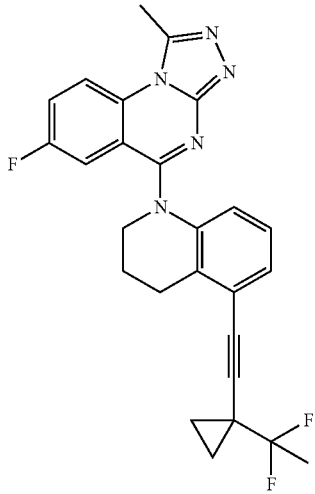

The title compound was synthesized in a manner similar to Example 1, using 1-(1,1-difluoroethyl)-1-ethynylcyclopropane instead of ethynylcyclopropane.

Example 32: 5-(5-((3,3-difluorocyclobutyl)ethynyl)-3,4-dihydroquinolin-1(2H)-yl)-7-fluoro-1-methyl-[1,2,4]triazolo[4,3-a]quinazoline

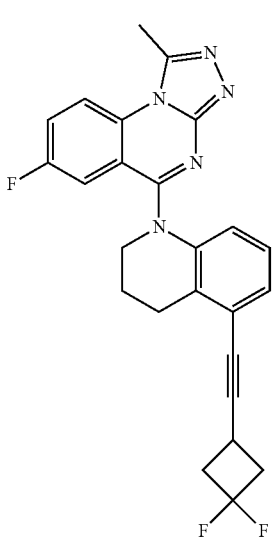 [SMILES: Cc1nnc2nc(N3CCCc4c(C#CC5CC(F)(F)C5)cccc43)c3cc(F)ccc3n12]

The title compound was synthesized in a manner similar to Example 1, using 3-ethynyl-1,1-difluorocyclobutane instead of ethynylcyclopropane.

Example 33: 6-chloro-7-fluoro-1-methyl-5-[5-[2-(1-methylcyclopropyl)ethynyl]-3,4-dihydro-2H-quinolin-1-yl]-[1,2,4]triazolo[4,3-a]quinazoline

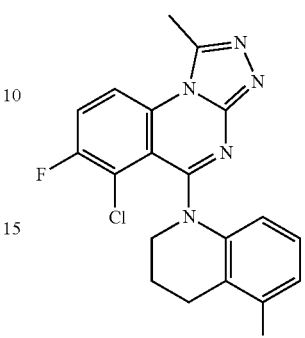

+

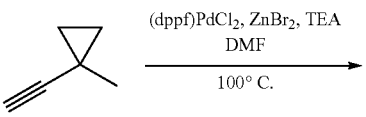

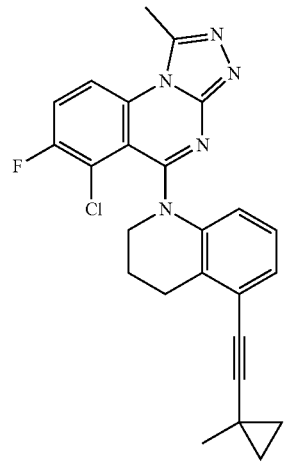

Step 1: A vial with stir bar was charged with 6-chloro-7-fluoro-5-(5-iodo-3,4-dihydro-2H-quinolin-1-yl)-1-methyl-[1,2,4]triazolo[4,3-a]quinazoline (25 mg, 0.0051 mmol), $ZnBr_2$ (57 mg, 0.25 mmol), DMF (0.57 mL), and TEA (0.035 mL, 0.25 mmol). Mixture sparged with nitrogen for 5 minutes and then 1-ethynyl-1-methyl-cyclopropane (4.6 mg, 0.0057 mmol) was added. The reaction was warmed to 100° C. and stirred for 10 minutes.

Step 2: Reaction diluted with EtOAC and filtered through a plug of celite. The filtrate was evaporated and purified via prep-HPLC to yield the pure trifluoroacetic acid salt.

Example 34: 6-chloro-5-[5-(4,4-difluoro-3,3-dimethyl-but-1-ynyl)-3,4-dihydro-2H-quinolin-1-yl]-7-fluoro-1-methyl-[1,2,4]triazolo[4,3-a]quinazoline

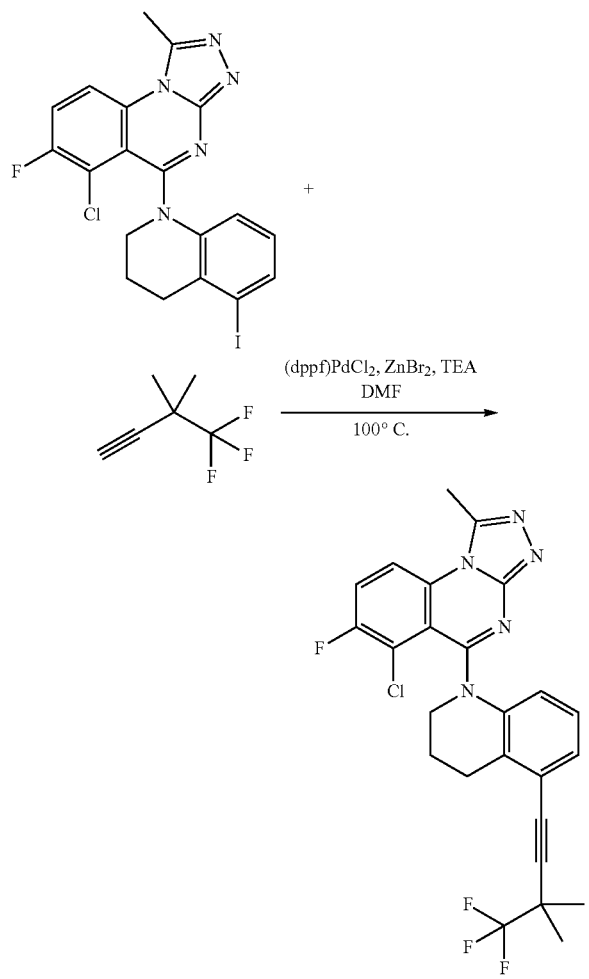

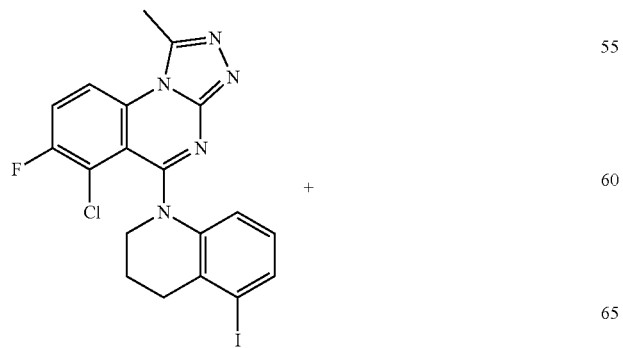

The title compound was synthesized in a manner similar to Example 33, using 4,4-difluoro-3,3-dimethyl-but-1-yne instead of 1-ethynyl-1-methyl-cyclopropane. ES/MS m/z: 484.1.

Example 35: 6-chloro-5-[5-[2-[1-(difluoromethyl)cyclopropyl]ethynyl]-3,4-dihydro-2H-quinolin-1-yl]-7-fluoro-1-methyl-[1,2,4]triazolo[4,3-a]quinazoline

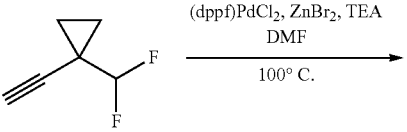

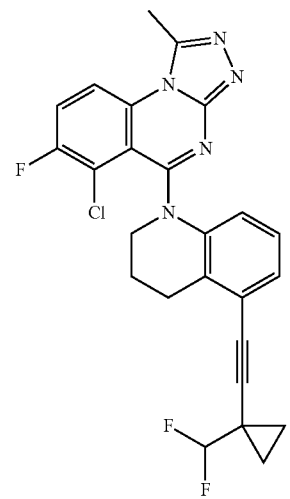

The title compound was synthesized in a manner similar to Example 33, using 1-(difluoromethyl)-1-ethynyl-cyclopropane instead of 1-ethynyl-1-methyl-cyclopropane.

Example 36: 4-[1-(6-chloro-7-fluoro-1-methyl-[1,2,4]triazolo[4,3-a]quinazolin-5-yl)-3,4-dihydro-2H-quinolin-5-yl]-2,2-dimethyl-but-3-ynenitrile

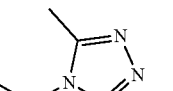

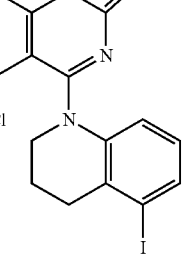

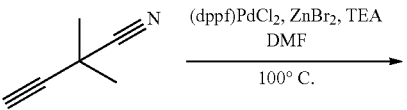

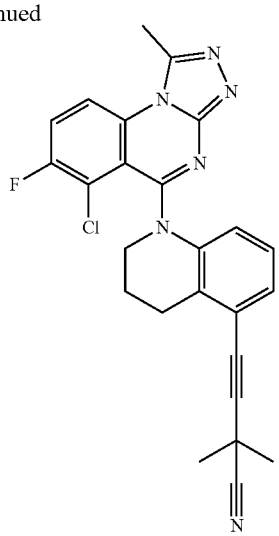

The title compound was synthesized in a manner similar to Example 33, using 2,2-dimethylbut-3-ynenitrile instead of 1-ethynyl-1-methyl-cyclopropane.

Example 37: 6-chloro-7-fluoro-1-methyl-5-[5-[2-[1-(trifluoromethyl)cyclopropyl]ethynyl]-3,4-dihydro-2H-quinolin-1-yl]-[1,2,4]triazolo[4,3-a]quinazoline The title compound was synthesized in a manner similar to Example 33, using 2,2-dimethylbut-3-ynenitrile instead of 1-ethynyl-1-(trifluoromethyl)cyclopropane.

Example 38: 9-chloro-7-fluoro-5-[5-[2-[1-(trifluoromethyl)cyclopropyl]ethynyl]-3,4-dihydro-2H-quinolin-1-yl]-[1,2,4]triazolo[4,3-a]quinazoline

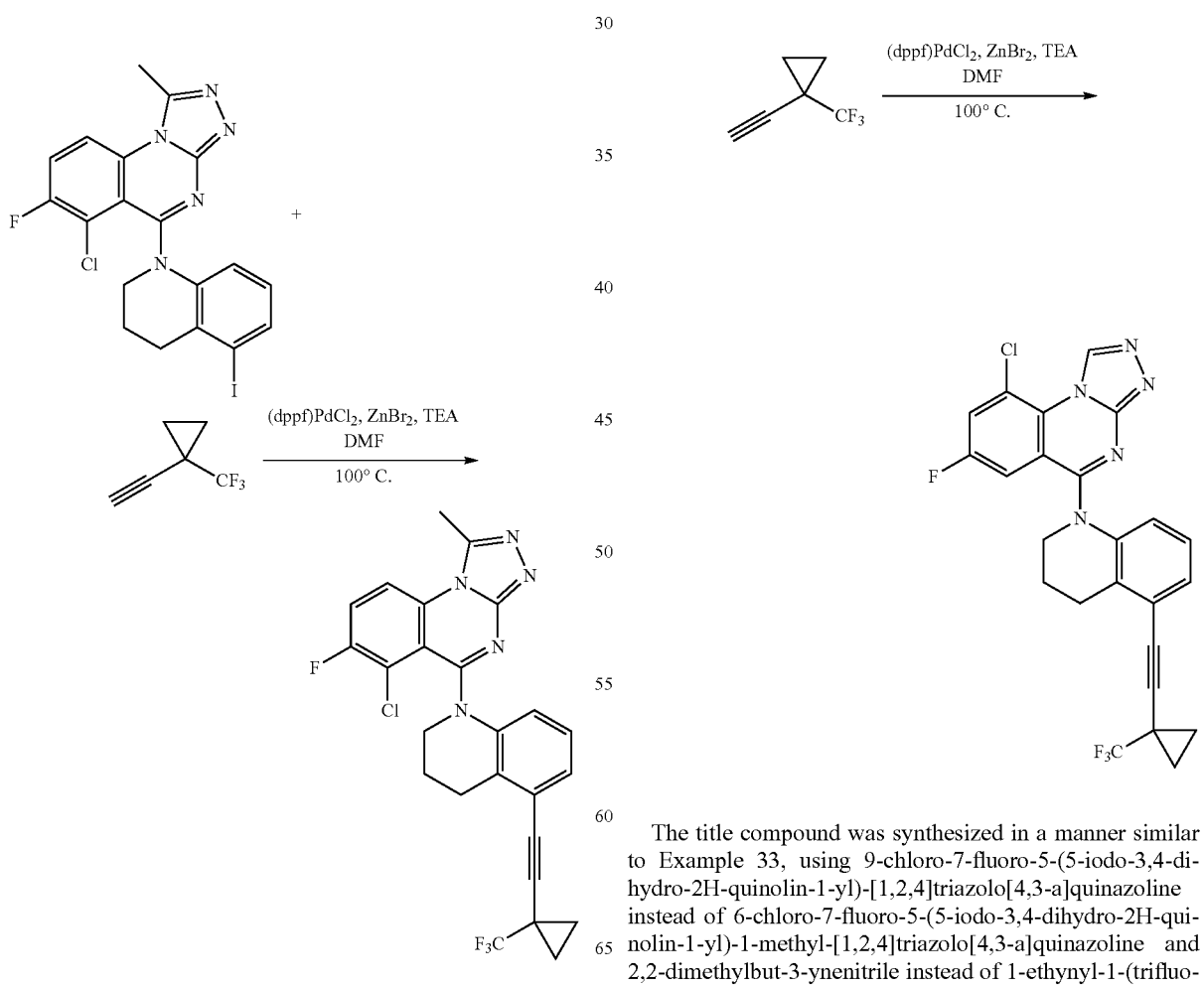

The title compound was synthesized in a manner similar to Example 33, using 9-chloro-7-fluoro-5-(5-iodo-3,4-dihydro-2H-quinolin-1-yl)-[1,2,4]triazolo[4,3-a]quinazoline instead of 6-chloro-7-fluoro-5-(5-iodo-3,4-dihydro-2H-quinolin-1-yl)-1-methyl-[1,2,4]triazolo[4,3-a]quinazoline and 2,2-dimethylbut-3-ynenitrile instead of 1-ethynyl-1-(trifluoromethyl)cyclopropane.

Example 39: 1-(9-chloro-6-fluoro-[1,2,4]triazolo[4,3-a]quinazolin-5-yl)-6-[2-[1-(difluoromethyl)cyclopropyl]ethynyl]-3,5-dihydro-2H-4,1-benzoxazepine

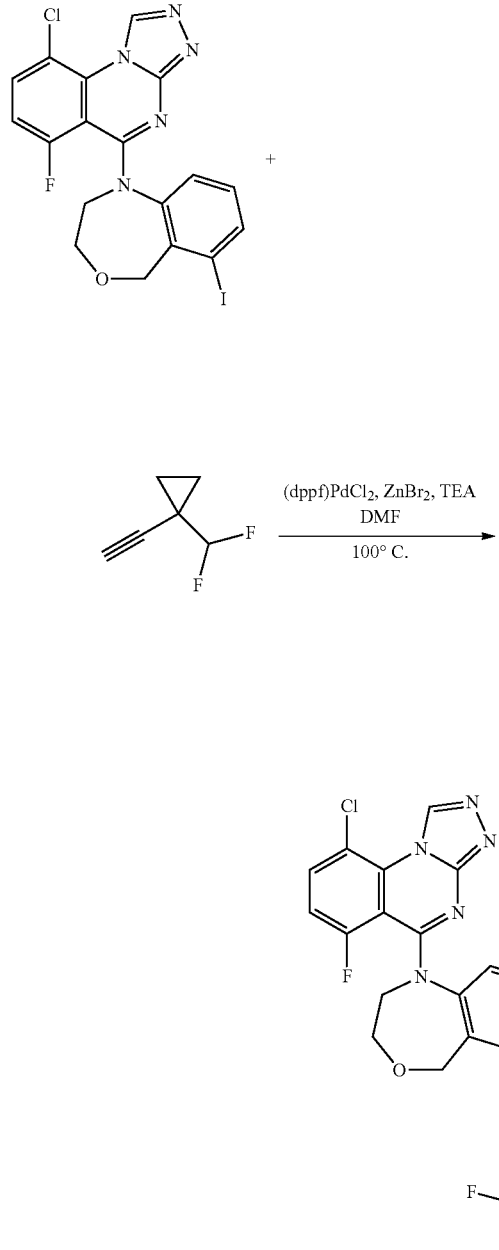

Step 1: A vial with stir bar was charged with 1-(9-chloro-6-fluoro-[1,2,4]triazolo[4,3-a]quinazolin-5-yl)-6-iodo-3,5-dihydro-2H-4,1-benzoxazepine (30 mg, 0.0061 mmol), ZnBr₂ (68 mg, 0.30 mmol), DMF (0.68 mL), and TEA (0.042 mL, 0.30 mmol). Mixture sparged with nitrogen for 5 minutes and then 1-(difluoromethyl)-1-ethynyl-cyclopropane (6.7 mg, 0.0067 mmol) was added. The reaction was warmed to 100° C. and stirred for 10 minutes.

Step 2: Reaction diluted with EtOAC and filtered through a plug of celite. The filtrate was evaporated and purified via prep-HPLC to yield the pure trifluoroacetic acid salt.

Example 40: 4-[1-(9-chloro-6-fluoro-[1,2,4]triazolo[4,3-a]quinazolin-5-yl)-3,5-dihydro-2H-4,1-benzoxazepin-6-yl]-2-methyl-but-3-yn-2-ol

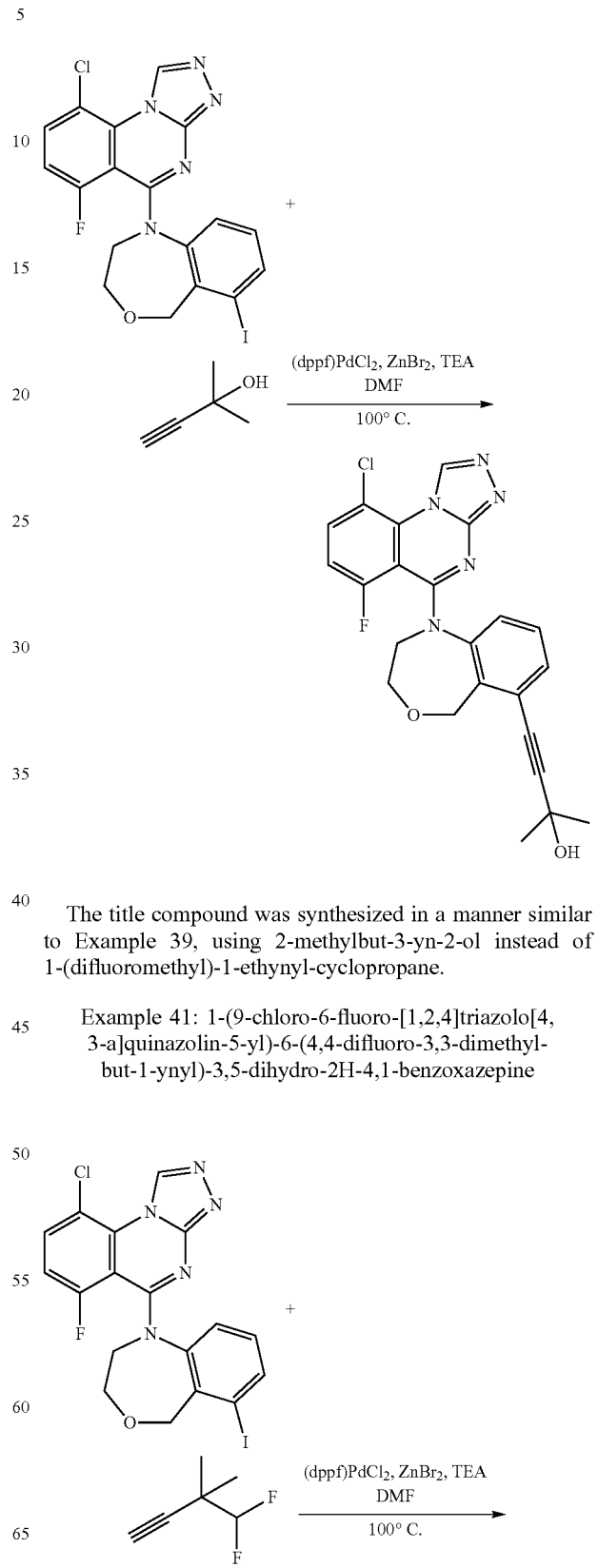

The title compound was synthesized in a manner similar to Example 39, using 2-methylbut-3-yn-2-ol instead of 1-(difluoromethyl)-1-ethynyl-cyclopropane.

Example 41: 1-(9-chloro-6-fluoro-[1,2,4]triazolo[4,3-a]quinazolin-5-yl)-6-(4,4-difluoro-3,3-dimethyl-but-1-ynyl)-3,5-dihydro-2H-4,1-benzoxazepine -continued

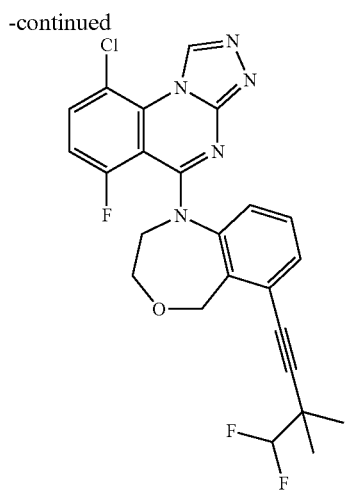

The title compound was synthesized in a manner similar to Example 39, using 4,4-difluoro-3,3-dimethyl-but-1-yne instead of 1-(difluoromethyl)-1-ethynyl-cyclopropane.

Example 42: N-[2-(4,4-difluoro-3,3-dimethyl-but-1-ynyl)-3-fluoro-4-pyridyl]-N-(2,2-difluoroethyl)-6-fluoro-1-methyl-[1,2,4]triazolo[4,3-a]quinazolin-5-amine

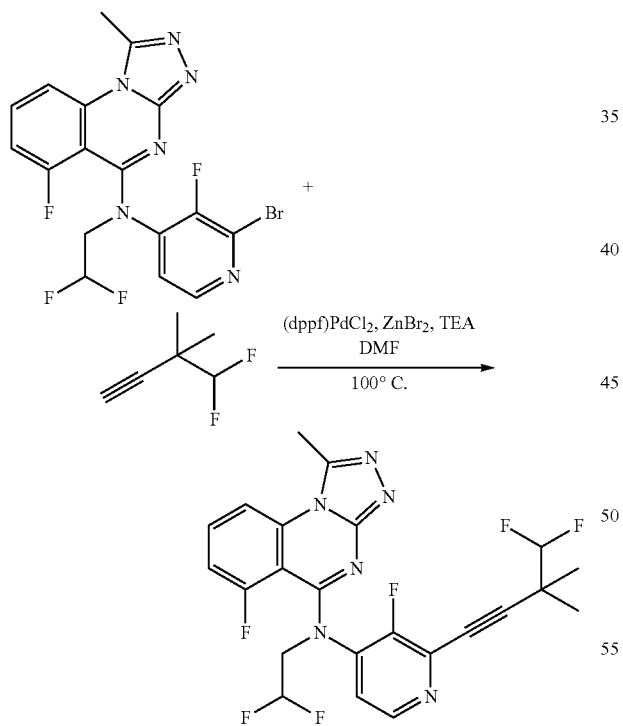

Step 1: A vial with stir bar was charged with N-(2-bromo-3-fluoro-4-pyridyl)-N-(2,2-difluoroethyl)-6-fluoro-1-methyl-[1,2,4]triazolo[4,3-a]quinazolin-5-amine (25 mg, 0.0055 mmol), ZnBr$_2$ (62 mg, 0.28 mmol), DMF (0.62 mL), and TEA (0.038 mL, 0.28 mmol). Mixture sparged with nitrogen for 5 minutes and then 4,4-difluoro-3,3-dimethyl-but-1-yne (7.8 mg, 0.0066 mmol) was added. The reaction was warmed to 100° C. and stirred for 10 minutes.

Step 2: Reaction diluted with EtOAC and filtered through a plug of celite. The filtrate was evaporated and purified via prep-HPLC to yield the pure trifluoroacetic acid salt.

Example 43: N-(2,2-difluoroethyl)-6-fluoro-N-[3-fluoro-2-(4,4,4-trifluoro-3,3-dimethyl-but-1-ynyl)-4-pyridyl]-1-methyl-[1,2,4]triazolo[4,3-a]quinazolin-5-amine

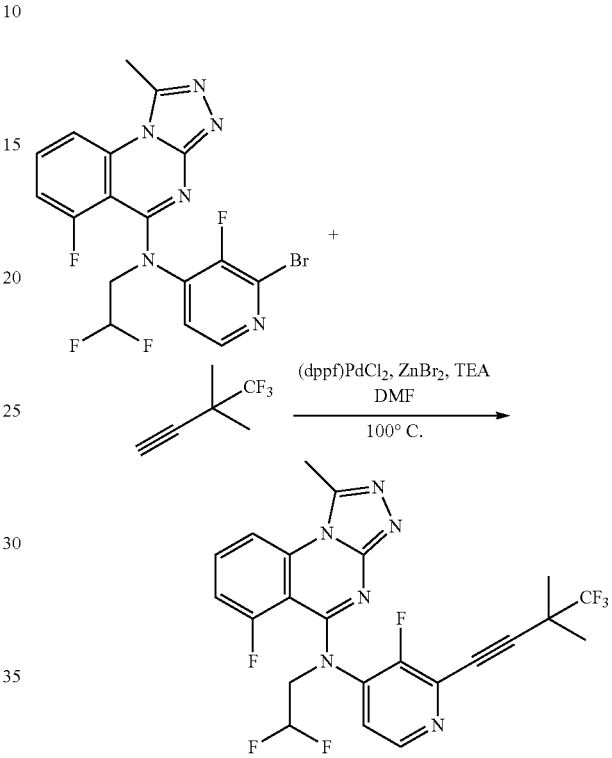

The title compound was synthesized in a manner similar to Example 42, using 4,4,4-trifluoro-3,3-dimethyl-but-1-yne instead of 4,4-difluoro-3,3-dimethyl-but-1-yne.

Example 44: N-(2,2-difluoroethyl)-N-[2-[2-[1-(difluoromethyl)cyclopropyl]ethynyl]-3-fluoro-4-pyridyl]-6-fluoro-1-methyl-[1,2,4]triazolo[4,3-a]quinazolin-5-amine

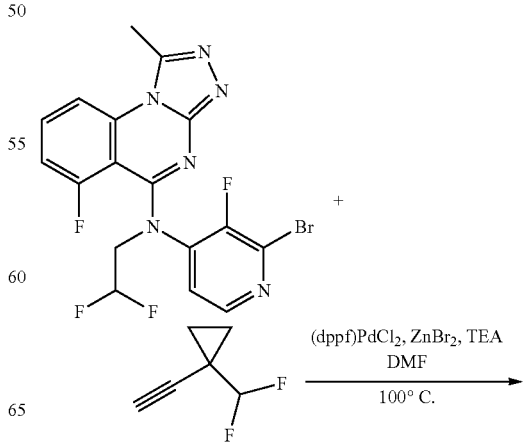

-continued

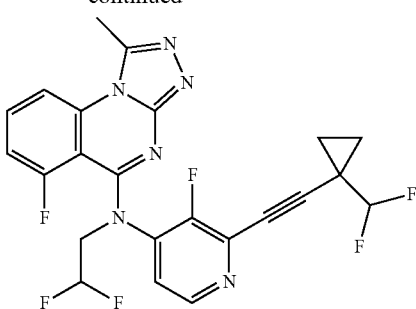

The title compound was synthesized in a manner similar to Example 42, using 1-(difluoromethyl)-1-ethynyl-cyclopropane instead of 4,4-difluoro-3,3-dimethyl-but-1-yne.

Example 45: 4-[4-[2,2-difluoroethyl-(6-fluoro-1-methyl-[1,2,4]triazolo[4,3-a]quinazolin-5-yl)amino]-3-fluoro-2-pyridyl]-2-methyl-but-3-yn-2-ol

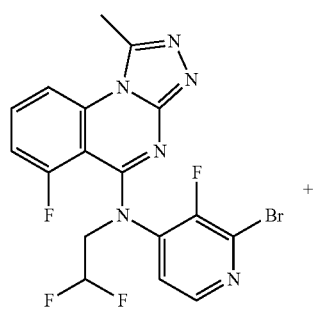

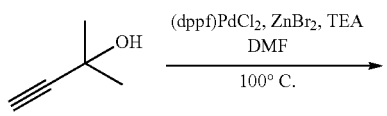

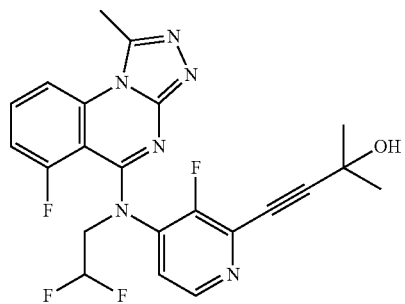

The title compound was synthesized in a manner similar to Example 42, using 2-methylbut-3-yn-2-ol instead of 4,4-difluoro-3,3-dimethyl-but-1-yne.

Example 46: 9-chloro-N-[3-(4,4-difluoro-3,3-dimethyl-but-1-ynyl)-5-fluoro-phenyl]-N-(2,2-difluoroethyl)-7-fluoro-[1,2,4]triazolo[4,3-a]quinazolin-5-amine

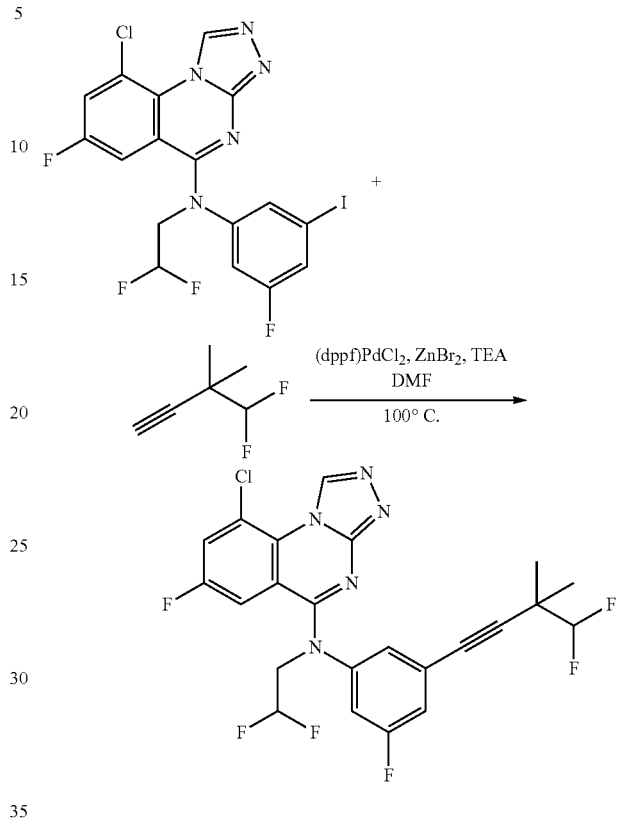

Step 1: A vial with stir bar was charged with 9-chloro-N-(2,2-difluoroethyl)-7-fluoro-N-(3-fluoro-5-iodo-phenyl)-[1,2,4]triazolo[4,3-a]quinazolin-5-amine (25 mg, 0.0048 mmol), ZnBr₂ (54 mg, 0.24 mmol), DMF (0.54 mL), and TEA (0.033 mL, 0.24 mmol). Mixture sparged with nitrogen for 5 minutes and then 4,4-difluoro-3,3-dimethyl-but-1-yne (6.8 mg, 0.0058 mmol) was added. The reaction was warmed to 100° C. and stirred for 10 minutes.

Step 2: Reaction diluted with EtOAC and filtered through a plug of celite. The filtrate was evaporated and purified via prep-HPLC to yield the pure trifluoroacetic acid salt.

Example 47: 9-chloro-N-(2,2-difluoroethyl)-N-[3-[2-[1-(difluoromethyl)cyclopropyl]ethynyl]-5-fluoro-phenyl]-7-fluoro-[1,2,4]triazolo[4,3-a]quinazolin-5-amine

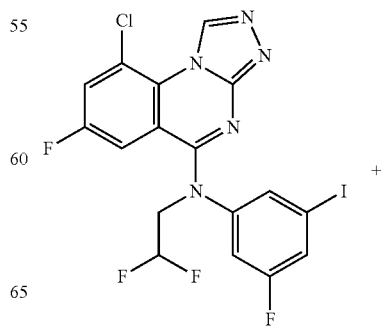

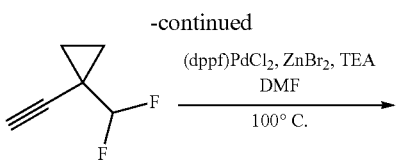

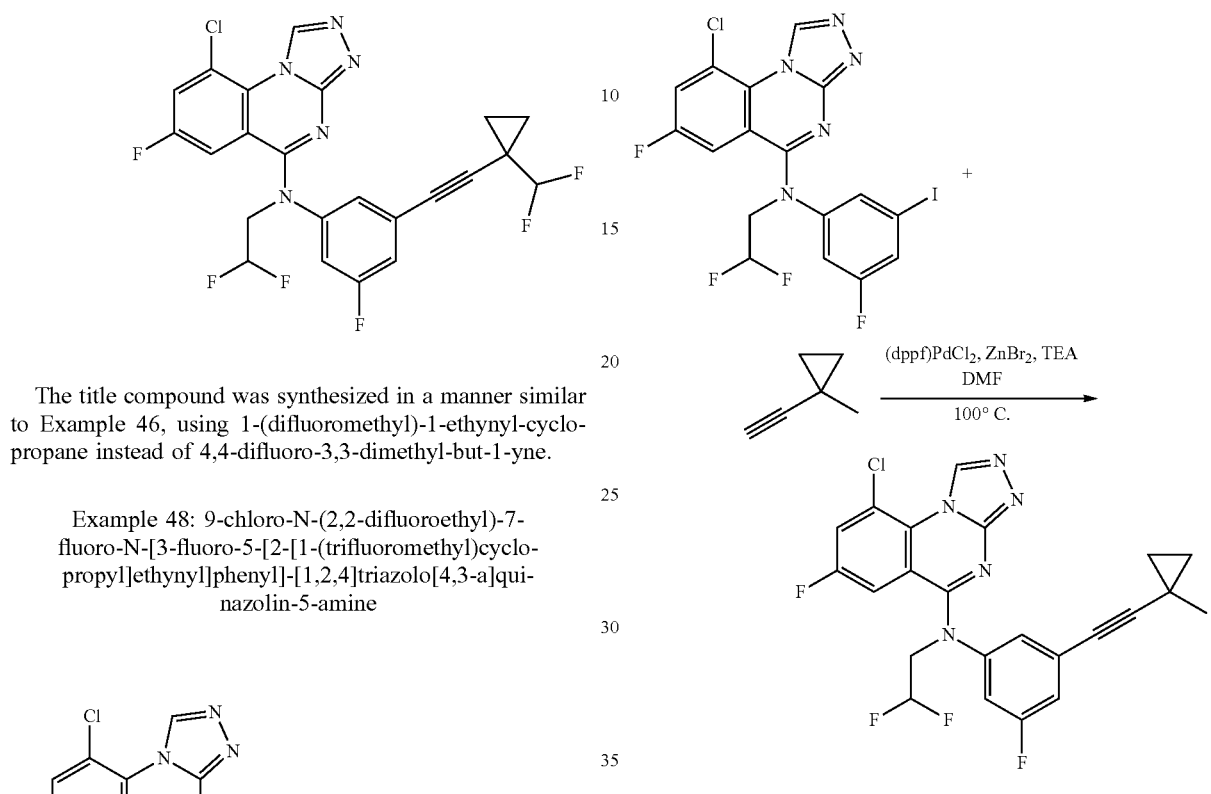

The title compound was synthesized in a manner similar to Example 46, using 1-(difluoromethyl)-1-ethynyl-cyclopropane instead of 4,4-difluoro-3,3-dimethyl-but-1-yne.

Example 48: 9-chloro-N-(2,2-difluoroethyl)-7-fluoro-N-[3-fluoro-5-[2-[1-(trifluoromethyl)cyclopropyl]ethynyl]phenyl]-[1,2,4]triazolo[4,3-a]quinazolin-5-amine

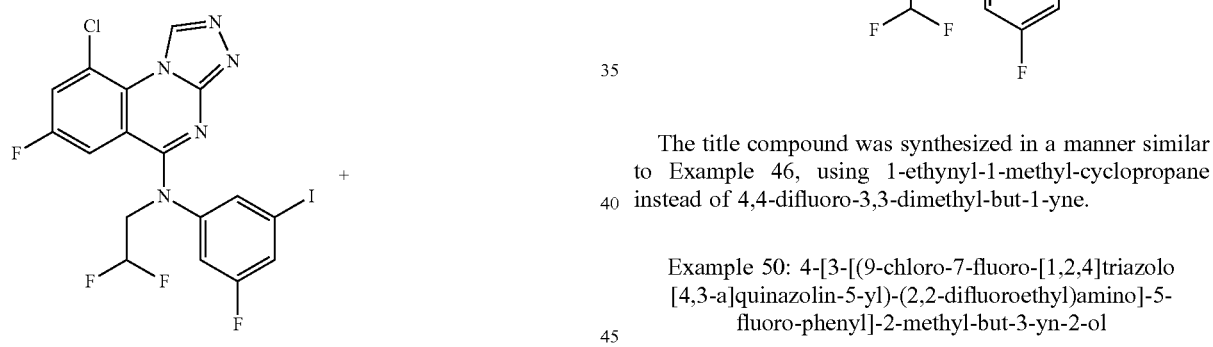

The title compound was synthesized in a manner similar to Example 46, using 1-ethynyl-1-(trifluoromethyl)cyclopropane instead of 4,4-difluoro-3,3-dimethyl-but-1-yne.

Example 49: 9-chloro-N-(2,2-difluoroethyl)-7-fluoro-N-[3-fluoro-5-[2-(1-methylcyclopropyl)ethynyl]phenyl]-[1,2,4]triazolo[4,3-a]quinazolin-5-amine The title compound was synthesized in a manner similar to Example 46, using 1-ethynyl-1-methyl-cyclopropane instead of 4,4-difluoro-3,3-dimethyl-but-1-yne.

Example 50: 4-[3-[(9-chloro-7-fluoro-[1,2,4]triazolo[4,3-a]quinazolin-5-yl)-(2,2-difluoroethyl)amino]-5-fluoro-phenyl]-2-methyl-but-3-yn-2-ol

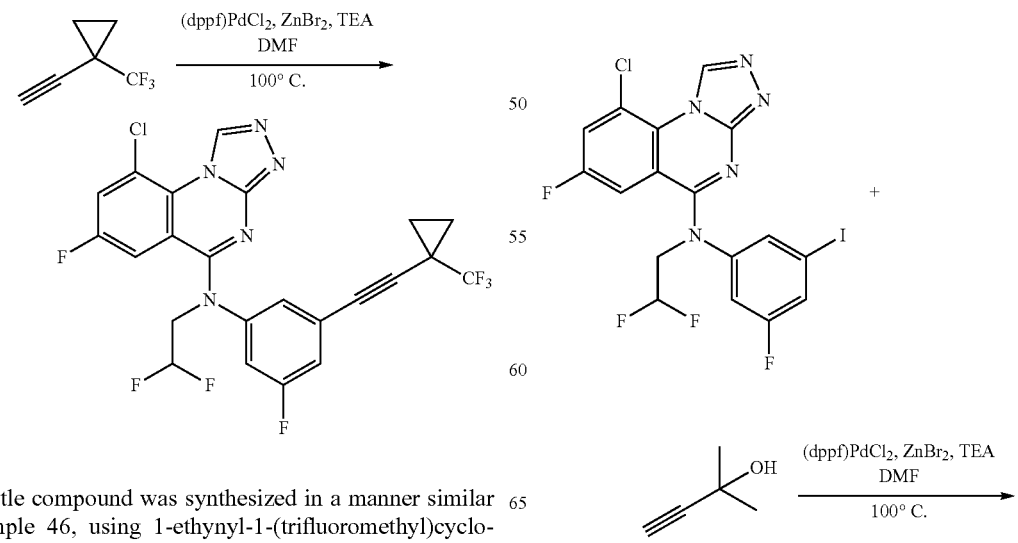

-continued

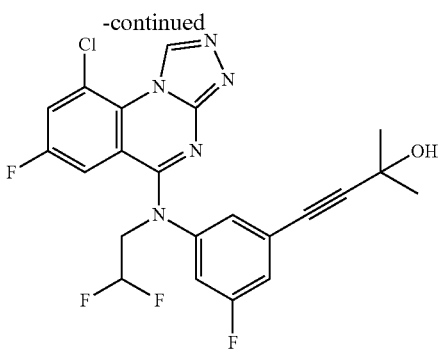

The title compound was synthesized in a manner similar to Example 46, using 2-methylbut-3-yn-2-ol instead of 4,4-difluoro-3,3-dimethyl-but-1-yne.

Example 51: N-(2,2-difluoroethyl)-N-[3-[2-[1-(difluoromethyl)cyclopropyl]ethynyl]-2-fluoro-phenyl]-6-fluoro-1-methyl-[1,2,4]triazolo[4,3-a]quinazolin-5-amine

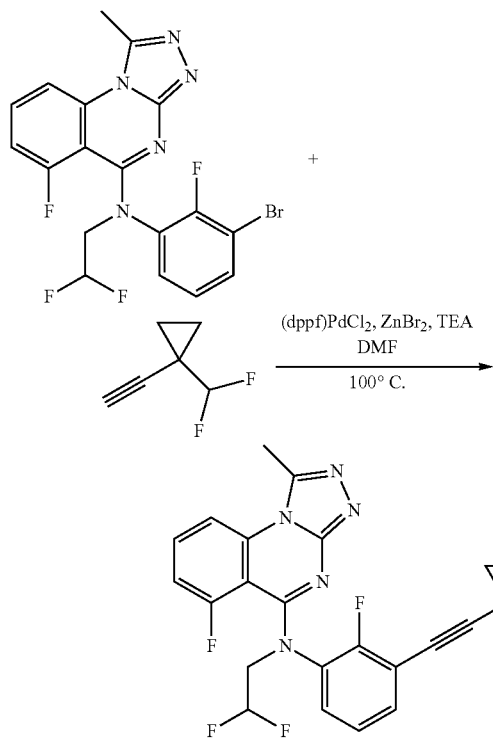

Step 1: A vial with stir bar was charged with N-(3-bromo-2-fluoro-phenyl)-N-(2,2-difluoroethyl)-6-fluoro-1-methyl-[1,2,4]triazolo[4,3-a]quinazolin-5-amine (22 mg, 0.0048 mmol), ZnBr₂ (55 mg, 0.24 mmol), DMF (0.54 mL), and TEA (0.034 mL, 0.24 mmol). Mixture sparged with nitrogen for 5 minutes and then 1-(difluoromethyl)-1-ethynyl-cyclopropane (6.8 mg, 0.0058 mmol) was added. The reaction was warmed to 100° C. and stirred for 10 minutes.

Step 2: Reaction diluted with EtOAC and filtered through a plug of celite. The filtrate was evaporated and purified via prep-HPLC to yield the pure trifluoroacetic acid salt.

Example 52: N-(2,2-difluoroethyl)-6-fluoro-N-[2-fluoro-3-[2-(1-methylcyclopropyl)ethynyl]phenyl]-1-methyl-[1,2,4]triazolo[4,3-a]quinazolin-5-amine

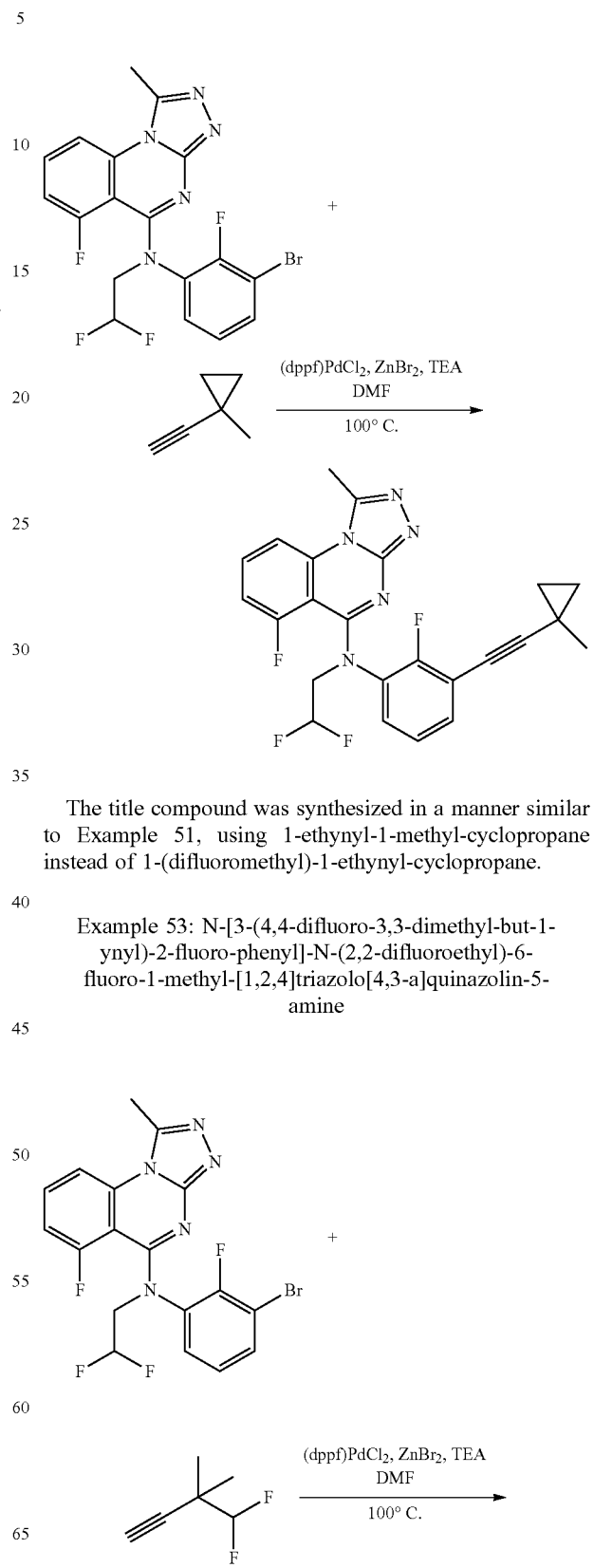

The title compound was synthesized in a manner similar to Example 51, using 1-ethynyl-1-methyl-cyclopropane instead of 1-(difluoromethyl)-1-ethynyl-cyclopropane.

Example 53: N-[3-(4,4-difluoro-3,3-dimethyl-but-1-ynyl)-2-fluoro-phenyl]-N-(2,2-difluoroethyl)-6-fluoro-1-methyl-[1,2,4]triazolo[4,3-a]quinazolin-5-amine

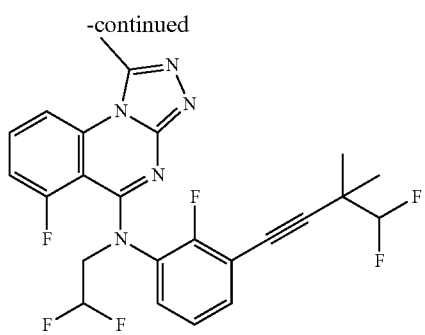

The title compound was synthesized in a manner similar to Example 51, using 4,4-difluoro-3,3-dimethyl-but-1-yne instead of 1-(difluoromethyl)-1-ethynyl-cyclopropane.

Example 54: N-(2,2-difluoroethyl)-6-fluoro-N-[2-fluoro-3-[2-[1-(trifluoromethyl)cyclopropyl]ethynyl]phenyl]-1-methyl-[1,2,4]triazolo[4,3-a]quinazolin-5-amine

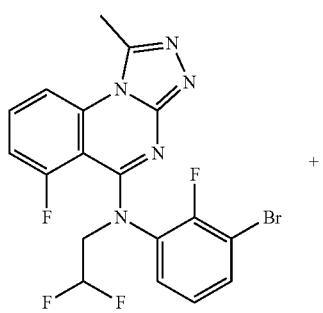

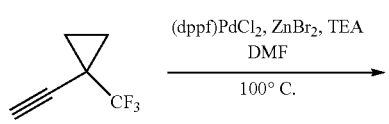

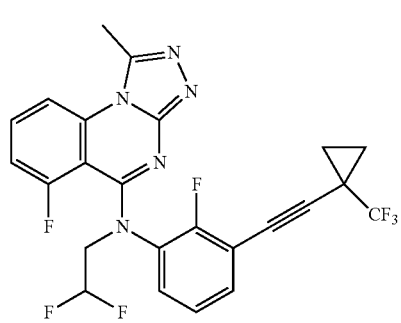

The title compound was synthesized in a manner similar to Example 51, using 1-ethynyl-1-(trifluoromethyl)cyclopropane instead of 1-(difluoromethyl)-1-ethynyl-cyclopropane.

Example 55: N-[3-(4,4-difluoro-3,3-dimethyl-but-1-ynyl)-2-fluoro-phenyl]-N-(2,2-difluoroethyl)-7-fluoro-1-methyl-[1,2,4]triazolo[4,3-a]quinazolin-5-amine

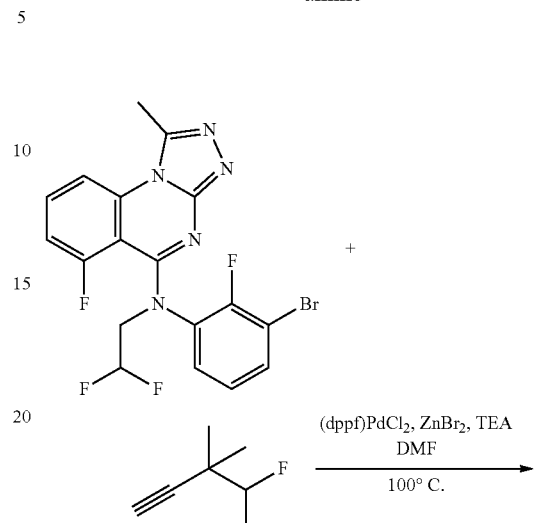

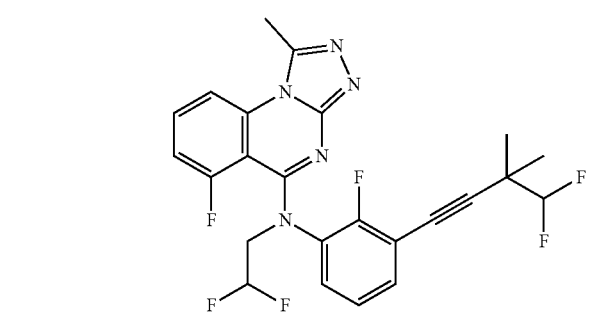

The title compound was synthesized in a manner similar to Example 51, using 4,4-difluoro-3,3-dimethyl-but-1-yne instead of 1-(difluoromethyl)-1-ethynyl-cyclopropane.

Example 56: N-(2,2-difluoroethyl)-7-fluoro-N-[2-fluoro-3-[2-(1-methylcyclopropyl)ethynyl]phenyl]-1-methyl-[1,2,4]triazolo[4,3-a]quinazolin-5-amine

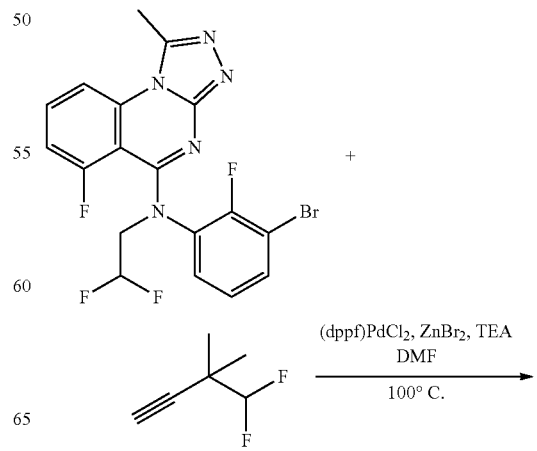

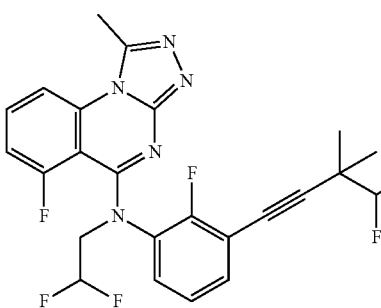

The title compound was synthesized in a manner similar to Example 51, using 1-ethynyl-1-methyl-cyclopropane instead of 1-(difluoromethyl)-1-ethynyl-cyclopropane.

Example 57: N-[3-(4,4-difluoro-3,3-dimethyl-but-1-ynyl)-2-fluoro-phenyl]-N-(2,2-difluoroethyl)-7-fluoro-[1,2,4]triazolo[4,3-a]quinazolin-5-amine

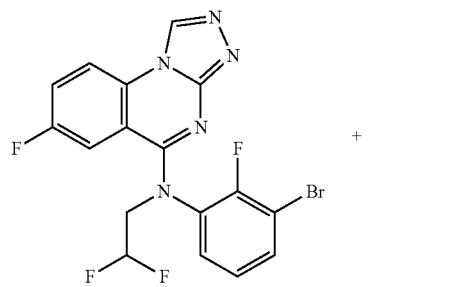

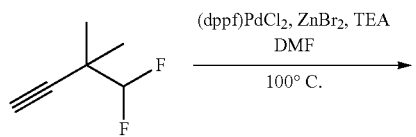

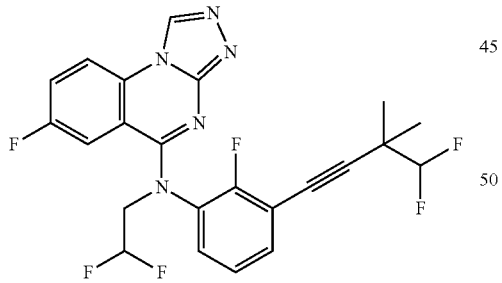

Step 1: A vial with stir bar was charged with N-(3-bromo-2-fluoro-phenyl)-N-(2,2-difluoroethyl)-7-fluoro-[1,2,4]triazolo[4,3-a]quinazolin-5-amine (22 mg, 0.0050 mmol), ZnBr₂ (56 mg, 0.25 mmol), DMF (0.56 mL), and TEA (0.035 mL, 0.25 mmol). Mixture sparged with nitrogen for 5 minutes and then 4,4-difluoro-3,3-dimethyl-but-1-yne (7.1 mg, 0.0060 mmol) was added. The reaction was warmed to 100° C. and stirred for 10 minutes.

Step 2: Reaction diluted with EtOAC and filtered through a plug of celite. The filtrate was evaporated and purified via prep-HPLC to yield the trifluoroacetic acid salt.

Example 58: 6-fluoro-1-methyl-5-(2-methyl-5-((1-(trifluoromethyl)cyclopropyl)ethynyl)-3,4-dihydroquinolin-1(2H)-yl)-[1,2,4]triazolo[4,3-a]quinazoline

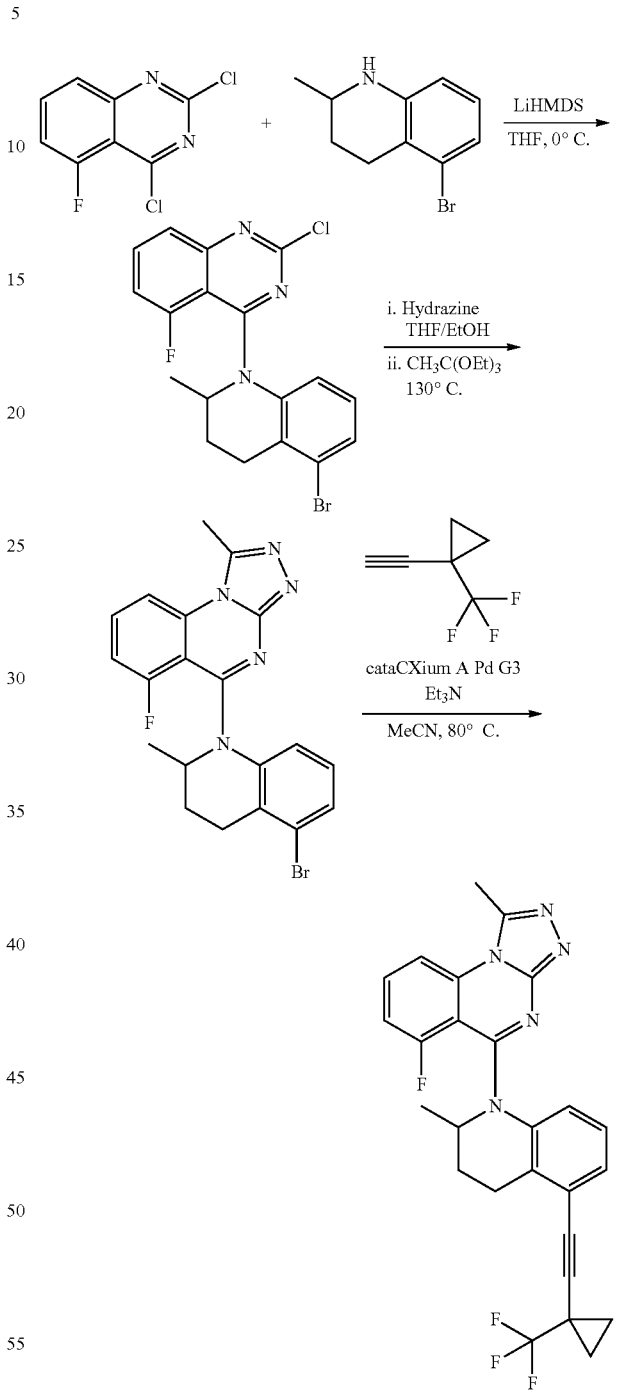

Step 1: A solution of 2,4-dichloro-5-fluoroquinazoline (435 mg, 2.00 mmol) and 5-bromo-2-methyl-1,2,3,4-tetrahydroquinoline (499 mg, 2.20 mmol) in THF (10.0 mL) under N₂ was cooled to 0° C. and treated with LiHMDS (1.0 M solution in THF, 2.20 mL, 2.20 mmol) dropwise and with stirring. After stirring for an additional 30 min at 0° C., the reaction mixture was diluted with sat. aqueous NH₄Cl followed by brine, then warmed to RT. The mixture was extracted 3× with EtOAc, and the combined organic layers were dried over Na2SO4, filtered, and concentrated under vacuum. The resulting residue was purified via silica gel chromatography (0→50% EtOAc in hexanes) to afford 4-(5-bromo-2-methyl-3,4-dihydroquinolin-1(2H)-yl)-2-chloro-5-fluoroquinazoline. LCMS(m/z) 406.3, 408.2 [M+H]+.

Step 2: A solution of 4-(5-bromo-2-methyl-3,4-dihydroquinolin-1(2H)-yl)-2-chloro-5-fluoroquinazoline (721 mg, 1.77 mmol) in 1:1 THF/EtOH (10 mL) was treated with anhydrous hydrazine (552 uL, 17.6 mmol) and stirred at RT overnight. The mixture was then diluted with EtOAc and washed with 4:1 water/brine. The organic layer was dried over MgSO₄, filtered, and concentrated under vacuum. The residue was co-evaporated once with PhMe, then suspended in triethyl orthoacetate (14.0 mL, 76.3 mmol). The mixture was stirred at 130° C. for 12 h, then cooled to RT. The precipitated product solids 5-(5-bromo-2-methyl-3,4-dihydroquinolin-1(2H)-yl)-6-fluoro-1-methyl-[1,2,4]triazolo[4,3-a]quinazoline were isolated via filtration, rinsing with hexanes, and dried under an air stream to afford 5-(5-bromo-2-methyl-3,4-dihydroquinolin-1(2H)-yl)-6-fluoro-1-methyl-[1,2,4]triazolo[4,3-a]quinazoline. LCMS(m/z) 426.4, 428.4 [M+H]+.

Step 3: A suspension of 5-(5-bromo-2-methyl-3,4-dihydroquinolin-1(2H)-yl)-6-fluoro-1-methyl-[1,2,4]triazolo[4,3-a]quinazoline (40 mg, 94 umol) and cataCXium A Pd G3 (6.8 mg, 9.4 umol) in MeCN (2.0 mL) was treated with Et₃N (262 uL, 1.88 mmol), then sparged with N₂ for 1 min. 1-Ethynyl-1-(trifluoromethyl)cyclopropane (101 mg, 751 umol) was then added, and the reaction mixture was stirred at 80° C. overnight. The mixture was cooled to RT and concentrated under vacuum, and the resulting residue was purified by silica gel chromatography (0→50% of pre-mixed 3:1 EtOAc/EtOH in DCM). Product-containing fractions were combined, concentrated, and further purified by reverse phase preparative HPLC to afford 6-fluoro-1-methyl-5-(2-methyl-5-((1-(trifluoromethyl)cyclopropyl)ethynyl)-3,4-dihydroquinolin-1(2H)-yl)-[1,2,4]triazolo[4,3-a]quinazoline.

Example 59: 4-(1-(6-fluoro-1-methyl-[1,2,4]triazolo[4,3-a]quinazolin-5-yl)-2-methyl-1,2,3,4-tetrahydroquinolin-5-yl)-2-methylbut-3-yn-2-ol

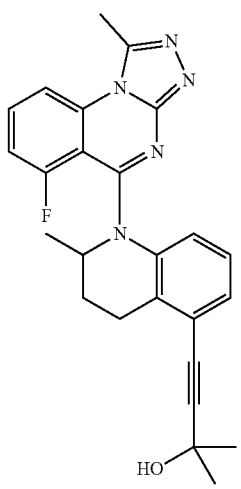 [SMILES: Cc1nnc2nc(N3c4cccc(C#CC(C)(C)O)c4CCC3C)c3c(F)cccc3n12]

The title compound was synthesized as described in Example 58, using 2-methylbut-3-yn-2-ol instead of 1-ethynyl-1-(trifluoromethyl)cyclopropane.

Example 60: 4-(4-((9-chloro-7-fluoro-[1,2,4]triazolo[4,3-a]quinazolin-5-yl)(2,2-difluoroethyl)amino)pyridin-2-yl)-2-methylbut-3-yn-2-ol

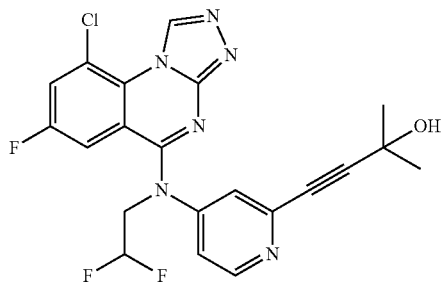

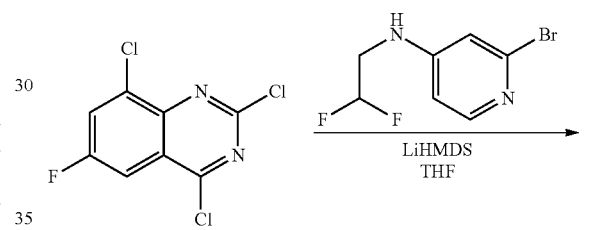

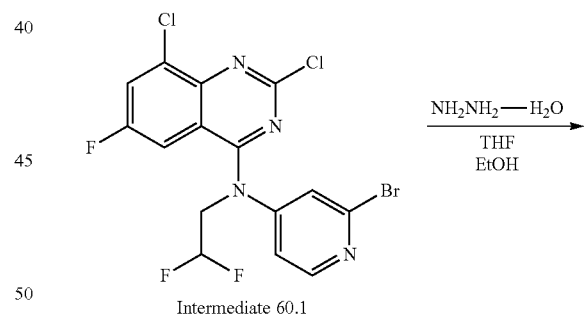

Intermediate 60.1

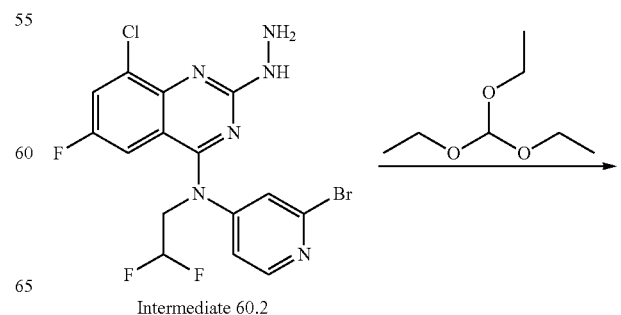

Intermediate 60.2

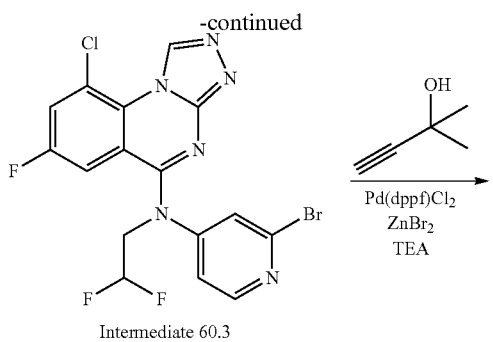

Intermediate 60.3

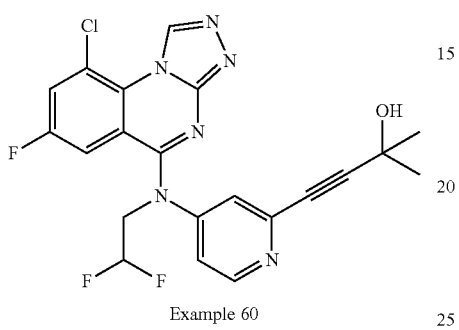

Example 60

Synthesis of N-(2-bromopyridin-4-yl)-2,8-dichloro-N-(2,2-difluoroethyl)-6-fluoroquinazolin-4-amine (Intermediate 60.1): A solution of 2,4,8-trichloro-6-fluoroquinazoline (2.3 mmol) in THF (5 ml) at −20° C. were added 2-bromo-N-(2,2-difluoroethyl)pyridin-4-amine (2.42 mmol) and LiHMDS in THE (1.0 M, 2.53 ml, 1.1 eq). The mixture was stirred for 2 hours at −20° C. Water and ethyl acetate were added to the mixture and the organic phase was dried over MgSO$_4$ and evaporated under reduced pressure. The crude product was used in the next step without further purification.

Synthesis of N-(2-bromopyridin-4-yl)-N-(2,2-difluoroethyl)-5-fluoro-2-hydrazineylquinazolin-4-amine (Intermediate 60.2): Hydrazine hydrate (0.23 mmol) was added slowly to a stirred solution of crude 2-chloro-6,7-difluoro-N-(3-fluorophenyl)-N-methylquinazolin-4-amine (Intermediate 60.1, 0.78 mmol) in ethanol (4 ml) at room temperature. The mixture was diluted with DCM, and then washed successively with water and brine, and dried over MgSO$_4$. The organic layer was concentrated in vacuo. The resulting residue was used in the next step without further purification.

Synthesis of N-(2-bromopyridin-4-yl)-9-chloro-N-(2,2-difluoroethyl)-7-fluoro-[1,2,4]triazolo[4,3-a]quinazolin-5-amine (Intermediate 60.3): Intermediate 60.2 (1.06 mmol) and triethoxymethane (5.32 mmol) was stirred at 100° C. for 4 h. The reaction mixture was concentrated in vacuo. The residue was purified reverse phase chromatography ACN/Water 15-95% with 0.1% TFA for 15 min to yield Intermediate 60.3.

Synthesis of 4-(4-((9-chloro-7-fluoro-[1,2,4]triazolo[4,3-a]quinazolin-5-yl)(2,2-difluoroethyl)amino)pyridin-2-yl)-2-methylbut-3-yn-2-ol (Example 60): N-(2-bromopyridin-4-yl)-9-chloro-N-(2,2-difluoroethyl)-7-fluoro-[1,2,4]triazolo[4,3-a]quinazolin-5-amine (0.044 mmol), 2-methylbut-3-yn-2-ol (30.048 mmol, 1.1 equiv.), TEA (0.86 mmol), zinc bromide (41.3 mg, 0.2 mmol, 5 equiv.) and [1,1'-bis(diphenylphosphino)ferrocene] dichloropalladium(II) (9.15 mg, 0.013 mmol, 0.3 equiv.) were heated in DMF (2 mL) at 100° C. for 10 min. After a filtration, the reaction mixture was purified by preparative reverse phase high performance liquid chromatography to give 4-(4-((9-chloro-7-fluoro-[1,2,4]triazolo[4,3-a]quinazolin-5-yl)(2,2-difluoroethyl)amino)pyridin-2-yl)-2-methylbut-3-yn-2-ol (Example 60).

Example 61: 9-chloro-N-(2,2-difluoroethyl)-7-fluoro-N-(2-((1-methylcyclopropyl)ethynyl)pyridin-4-yl)-[1,2,4]triazolo[4,3-a]quinazolin-5-amine

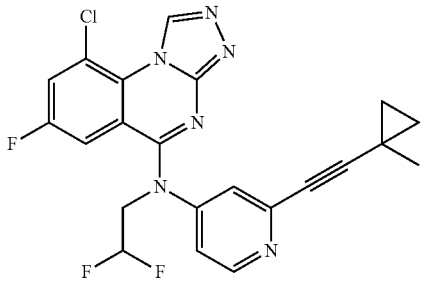 [SMILES: CC1(C#Cc2cc(N(CC(F)F)c3nc4nncn4c4c(Cl)cc(F)cc34)ccn2)CC1]

The title compound was synthesized in a manner similar to Example 60, using 1, 1-ethynyl-1-methylcyclopropane instead of 2-methylbut-3-yn-2-ol.

Example 62: N-(2,2-difluoroethyl)-6,7-difluoro-N-(3-fluoro-5-(3-methyl-3-(pyridin-4-yl)but-1-yn-1-yl)phenyl)-1-methyl-[1,2,4]triazolo[4,3-a]quinazolin-5-amine

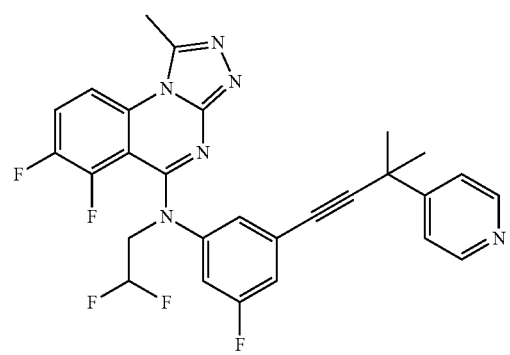 [SMILES: Cc1nnc2nc(N(CC(F)F)c3cc(F)cc(C#CC(C)(C)c4ccncc4)c3)c3c(F)c(F)ccc3n12]

The title compound was synthesized in a manner similar to Example 60, using 2,4-dichloro-5,6-difluoroquinazoline instead of 2,4,8-trichloro-6-fluoroquinazoline, using 3-bromo-N-(2,2-difluoroethyl)-5-fluoroaniline instead of 2-bromo-N-(2,2-difluoroethyl)pyridin-4-amine and 4-(2-methylbut-3-yn-2-yl)pyridine instead of 2-methylbut-3-yn-2-ol.

Example 63: 4-(1-(6,7-difluoro-1-methyl-[1,2,4]triazolo[4,3-a]quinazolin-5-yl)-1,2,3,5-tetrahydrobenzo[e][1,4]oxazepin-6-yl)-2,2-dimethyl-N-(1,1,1-trifluoro-2-methylpropan-2-yl)but-3-ynamide

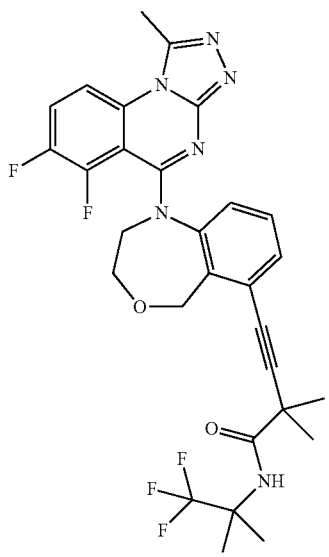 [SMILES: Cc1nnc2nc(N3CCOCc4c(C#CC(C)(C)C(=O)NC(C)(C)C(F)(F)F)cccc43)c3c(F)c(F)ccc3n12]

The title compound was synthesized in a manner similar to Example 65, using 2,4-dichloro-5,6-difluoroquinazoline, 6-bromo-1,2,3,5-tetrahydrobenzo[e][1,4]oxazepane and 1,1,1-trifluoro-2-methylpropan-2-amine instead of 2,4-dichloro-5-fluoroquinazoline, 5-bromo-1,2,3,4-tetrahydroquinoline and 1-(trifluoromethyl)cyclopropan-1-amine.

Example 64: 4-(1-(6,7-difluoro-1-methyl-[1,2,4]triazolo[4,3-a]quinazolin-5-yl)-1,2,3,5-tetrahydrobenzo[e][1,4]oxazepin-6-yl)-2,2-dimethyl-N-(1-(trifluoromethyl)cyclopropyl)but-3-ynamide

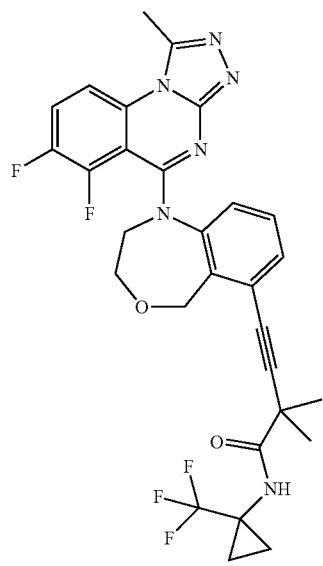 [SMILES: Cc1nnc2nc(N3CCOCc4c(C#CC(C)(C)C(=O)NC5(C(F)(F)F)CC5)cccc43)c3c(F)c(F)ccc3n12]

The title compound was synthesized in a manner similar to Example 63, using 1-(trifluoromethyl)cyclopropan-1-amine instead of 1,1,1-trifluoro-2-methylpropan-2-amine.

Example 65: 4-(1-(6-fluoro-1-methyl-[1,2,4]triazolo[4,3-a]quinazolin-5-yl)-1,2,3,4-tetrahydroquinolin-5-yl)-2,2-dimethyl-N-(1-(trifluoromethyl)cyclopropyl)but-3-ynamide

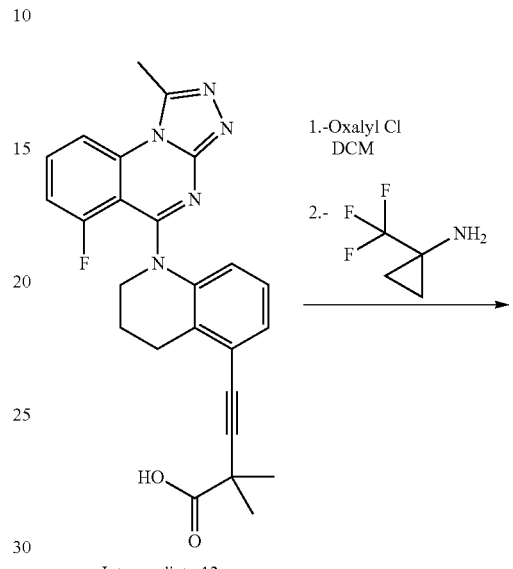

Intermediate 13

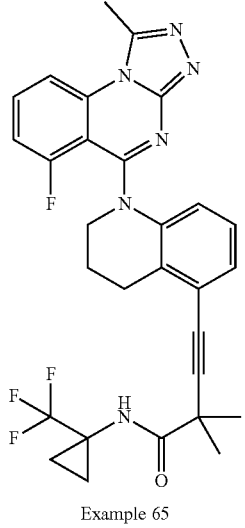

Example 65

To a suspension of 4-(1-(6-fluoro-1-methyl-[1,2,4]triazolo[4,3-a]quinazolin-5-yl)-1,2,3,4-tetrahydroquinolin-5-yl)-2,2-dimethylbut-3-ynoic acid (Intermediate 13) (46 mgs, 0.10 mmol) in DCM (2 mL) was added oxalyl chloride (1 mL) and 2 drops of DMF. The solution was stirred at room temperature for 20 min. Excess of oxalyl chloride was evaporated under reduced pressure. Solids were dissolved in THF (2 ml) and DIPEA (40 mgs, 0.31 mmol) and 1-(trifluoromethyl)cyclopropan-1-amine (50 mgs, 0.31 mmol) were added. Mixture was stirred at room temperature for 24 hrs. The reaction mixture was diluted with EtOAc, washed successively with water and brine, and dried over MgSO$_4$. The organic layer was concentrated in vacuo purified via reverse phase chromatography ACN/Water 15-95% with 0.1% TFA for 15 min to yield 4-(1-(6-fluoro-1-methyl-[1,2,4]triazolo[4,3-a]quinazolin-5-yl)-1,2,3,4-tetrahydroquinolin-5-yl)-2,2-dimethyl-N-(1-(trifluoromethyl)cyclopropyl)but-3-ynamide.

Example 66: 4-(1-(6-fluoro-1-methyl-[1,2,4]triazolo[4,3-a]quinazolin-5-yl)-1,2,3,4-tetrahydroquinolin-5-yl)-2,2-dimethyl-N-(1-(trifluoromethyl)cyclopropyl)but-3-ynamide

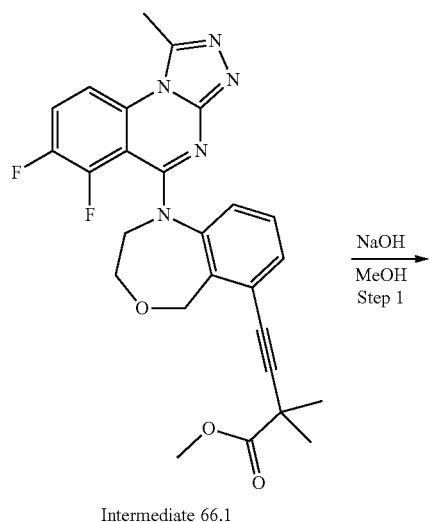

Intermediate 66.1

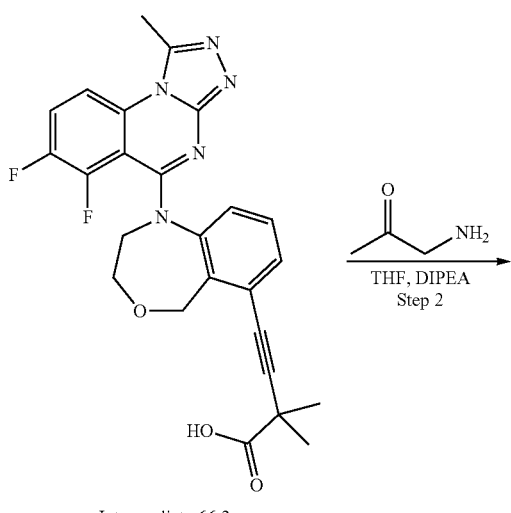

Intermediate 66.2

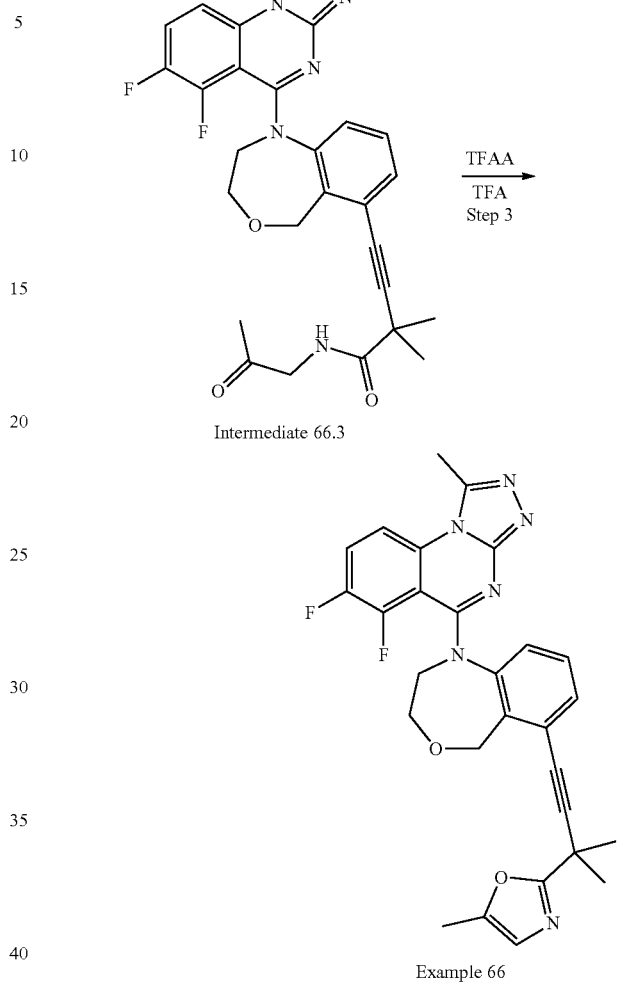

Step 1: Synthesis of 4-(1-(6,7-difluoro-1-methyl-[1,2,4]triazolo[4,3-a]quinazolin-5-yl)-1,2,3,5-tetrahydrobenzo[e][1,4]oxazepin-6-yl)-2,2-dimethylbut-3-ynoic acid (Intermediate 66.2)

The title compound was synthesized in a manner similar to Example 72.

Step 2: Synthesis of 4-(1-(6,7-difluoro-1-methyl-[1,2,4]triazolo[4,3-a]quinazolin-5-yl)-1,2,3,5-tetrahydrobenzo[e][1,4]oxazepin-6-yl)-2,2-dimethyl-N-(2-oxopropyl)but-3-ynamide (Intermediate 66.3)

The title compound was synthesized in a manner similar to Example 65, using 1-aminopropan-2-one instead of 1-(trifluoromethyl)cyclopropan-1-amine.

Step 3: Synthesis of 1-(6,7-difluoro-1-methyl-[1,2,4]triazolo[4,3-a]quinazolin-5-yl)-6-(3-methyl-3-(5-methyloxazol-2-yl)but-1-yn-1-yl)-1,2,3,5-tetrahydrobenzo[e][1,4]oxazepane (Example 66)

To a solution of 4-(1-(6,7-difluoro-1-methyl-[1,2,4]triazolo[4,3-a]quinazolin-5-yl)-1,2,3,5-tetrahydrobenzo[e][1, 4]oxazepin-6-yl)-2,2-dimethyl-N-(2-oxopropyl)but-3-ynamide (Intermediate 38-3) (48 mgs, 0.10 mmol) in TFA (1 mL) was added TFA-anhydride (25 mgs, 0.18 mmol) and then heated at 60C for 24 hrs. The reaction mixture was extracted in DCM, washed successively with water and brine, and dried over MgSO₄. The organic layer was concentrated in vacuo purified via reverse phase chromatography ACN/Water 15-95% with 0.1% TFA for 15 min to yield 1-(6,7-difluoro-1-methyl-[1,2,4]triazolo[4,3-a]quinazolin-5-yl)-6-(3-methyl-3-(5-methyloxazol-2-yl)but-1-yn-1-yl)-1,2,3,5-tetrahydrobenzo[e][1,4]oxazepine.

Example 67: N-(2,2-difluoroethyl)-6,7-difluoro-N-(3-fluoro-5-(3-methyl-3-(pyridin-3-yl)but-1-yn-1-yl)phenyl)-1-methyl-[1,2,4]triazolo[4,3-a]quinazolin-5-amine

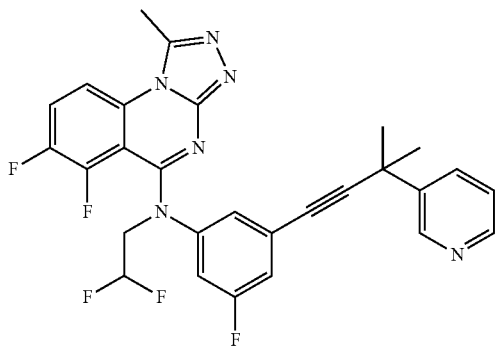 [SMILES: Cc1nnc2nc(N(CC(F)F)c3cc(F)cc(C#CC(C)(C)c4cccnc4)c3)c3c(F)c(F)ccc3n12]

The title compound was synthesized in a manner similar to Example 62, using 3-(2-methylbut-3-yn-2-yl)pyridine instead of 4-(2-methylbut-3-yn-2-yl)pyridine.

Example 68: N-(2,2-difluoroethyl)-6,7-difluoro-N-(3-fluoro-5-(3-methyl-3-(pyridin-2-yl)but-1-yn-1-yl)phenyl)-1-methyl-[1,2,4]triazolo[4,3-a]quinazolin-5-amine

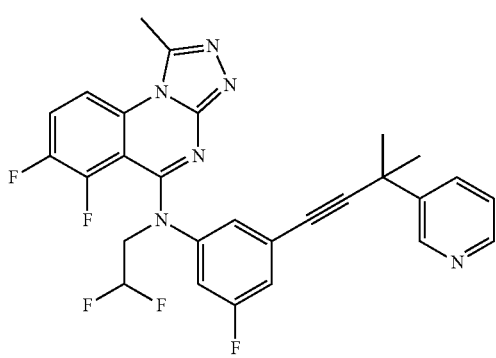 [SMILES: Cc1nnc2nc(N(CC(F)F)c3cc(F)cc(C#CC(C)(C)c4cccnc4)c3)c3c(F)c(F)ccc3n12]

The title compound was synthesized in a manner similar to Example 62, using 2-(2-methylbut-3-yn-2-yl)pyridine instead of 4-(2-methylbut-3-yn-2-yl)pyridine.

Example 69: 1-(4,4-difluoropiperidin-1-yl)-4-(1-(6-fluoro-1-methyl-[1,2,4]triazolo[4,3-a]quinazolin-5-yl)-1,2,3,4-tetrahydroquinolin-5-yl)-2,2-dimethylbut-3-yn-1-one

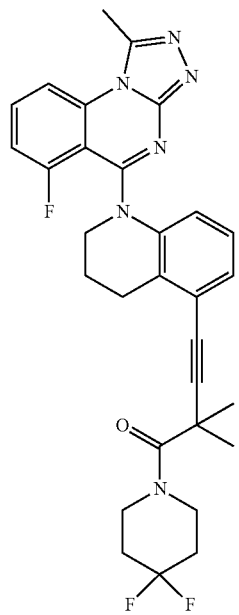 [SMILES: Cc1nnc2nc(N3CCCc4c(C#CC(C)(C)C(=O)N5CCC(F)(F)CC5)cccc43)c3c(F)cccc3n12]

The title compound was synthesized in a manner similar to Example 65, using 4,4-difluoropiperidine instead of 1-(trifluoromethyl)cyclopropan-1-amine.

Example 70: 1-(2,2-dimethylmorpholino)-4-(1-(6-fluoro-1-methyl-[1,2,4]triazolo[4,3-a]quinazolin-5-yl)-1,2,3,4-tetrahydroquinolin-5-yl)-2,2-dimethylbut-3-yn-1-one

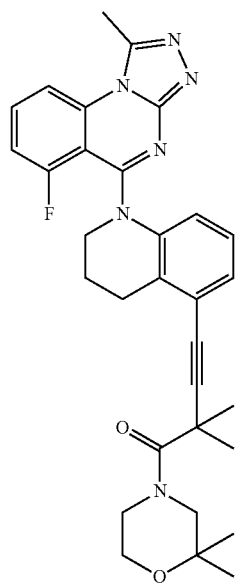 [SMILES: Cc1nnc2nc(N3CCCc4c(C#CC(C)(C)C(=O)N5CCOC(C)(C)C5)cccc43)c3c(F)cccc3n12]

The title compound was synthesized in a manner similar to Example 65, using 2,2-dimethylmorpholine instead of 1-(trifluoromethyl)cyclopropan-1-amine.

Example 71: 6-fluoro-1-methyl-5-(5-(3-methyl-3-(pyridin-2-yl)but-1-yn-1-yl)-3,4-dihydroquinolin-1(2H)-yl)-[1,2,4]triazolo[4,3-a]quinazoline

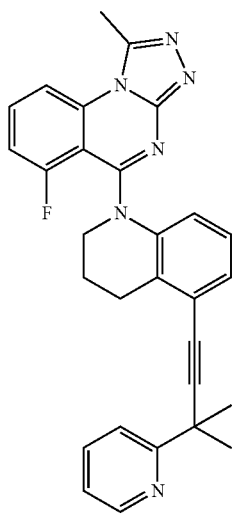 [SMILES: Cc1nnc2nc(N3CCCc4c(C#CC(C)(C)c5ccccn5)cccc43)c3c(F)cccc3n12]

The title compound was synthesized in a manner similar to Example 74, using 5-bromo-1,2,3,4-tetrahydroquinoline instead of 2-bromo-N-(2,2-difluoroethyl)pyridin-4-amine and 2-(2-methylbut-3-yn-2-yl)pyridine instead of 5-ethynyl-2-methoxypyridine.

Example 72: 2-(4-(1-(6-fluoro-1-methyl-[1,2,4]triazolo[4,3-a]quinazolin-5-yl)-1,2,3,4-tetrahydroquinolin-5-yl)-2-methylbut-3-yn-2-yl)-5-methyloxazole

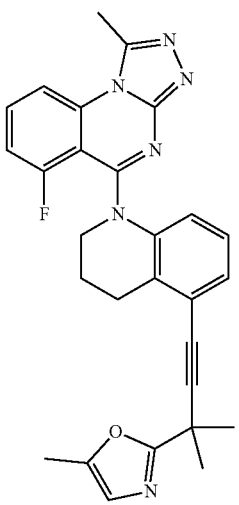 [SMILES: Cc1cnc(C(C)(C)C#Cc2cccc3c2CCCN3c2nc3nnc(C)n3c3cccc(F)c23)o1]

The title compound was synthesized in a manner similar to Example 65, using 2,4-dichloro-5-fluoroquinazoline, 5-bromo-1,2,3,4-tetrahydroquinoline instead of 2,4-dichloro-5-fluoroquinazoline and 6-bromo-1,2,3,5-tetrahydrobenzo[e][1,4]oxazepane.

Example 73: 4-(1-(6-fluoro-1-methyl-[1,2,4]triazolo[4,3-a]quinazolin-5-yl)-1,2,3,4-tetrahydroquinolin-5-yl)-2,2-dimethylbut-3-ynoic Acid

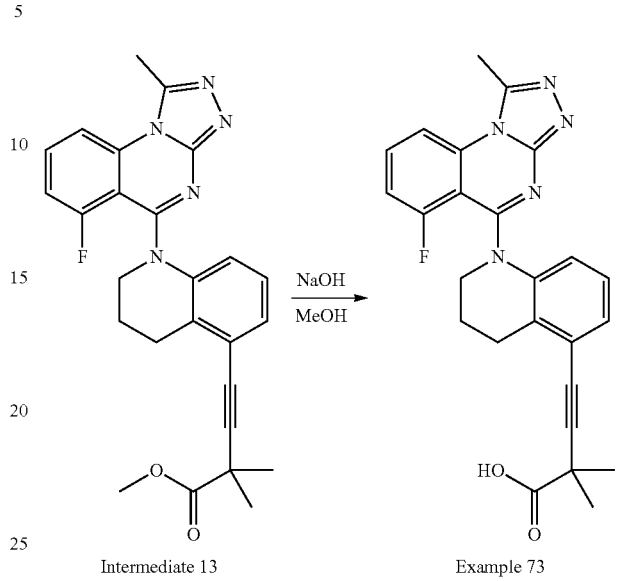

Intermediate 13    Example 73

To a solution of methyl 4-(1-(6-fluoro-1-methyl-[1,2,4]triazolo[4,3-a]quinazolin-5-yl)-1,2,3,4-tetrahydroquinolin-5-yl)-2,2-dimethylbut-3-ynoate (Intermediate 13) (600 mgs, 1.3 mmol) in MeOH (15 mL) was added 1N solution of NaOH (3.9 mL, 3.9 mmol). The solution was stirred at room temperature for 24 h. To this solution 1N HCl solution was added (4 ml) then organics were evaporated under reduced pressure. Solids filtered out and then purified via reverse phase chromatography ACN/Water 15-95% with 0.1% TFA for 15 min to yield 4-(1-(6-fluoro-1-methyl-[1,2,4]triazolo[4,3-a]quinazolin-5-yl)-1,2,3,4-tetrahydroquinolin-5-yl)-2,2-dimethylbut-3-ynoic acid.

Example 74: N-(2,2-difluoroethyl)-6-fluoro-N-(2-((6-methoxypyridin-3-yl)ethynyl)pyridin-4-yl)-1-methyl-[1,2,4]triazolo[4,3-a]quinazolin-5-amine

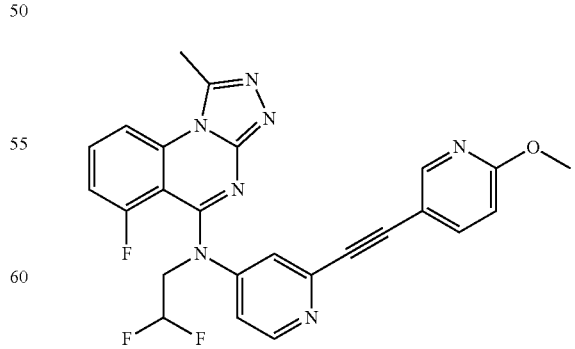

The title compound was synthesized in a manner similar to Example 60, using 5-ethynyl-2-methoxypyridine instead of 2-methylbut-3-yn-2-ol.

Example 75: 6-fluoro-5-(5-((6-methoxypyridin-3-yl)ethynyl)-3,4-dihydro-1,6-naphthyridin-1(2H)-yl)-1-methyl-[1,2,4]triazolo[4,3-a]quinazoline

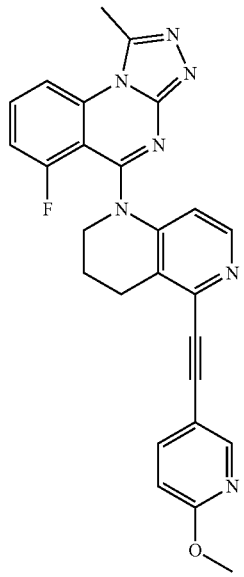 [SMILES: COc1ccc(C#Cc2nccc3c2CCCN3c2nc3nnc(C)n3c3cccc(F)c23)cn1]

The title compound was synthesized in a manner similar to Example 74, using 5-chloro-1,2,3,4-tetrahydro-1,6-naphthyridine instead of 2-bromo-N-(2,2-difluoroethyl)pyridin-4-amine.

Example 76: 6-fluoro-1-methyl-5-(5-(3-methyl-3-(2-methyl-1H-imidazol-1-yl)but-1-yn-1-yl)-3,4-dihydroquinolin-1(2H)-yl)-[1,2,4]triazolo[4,3-a]quinazoline

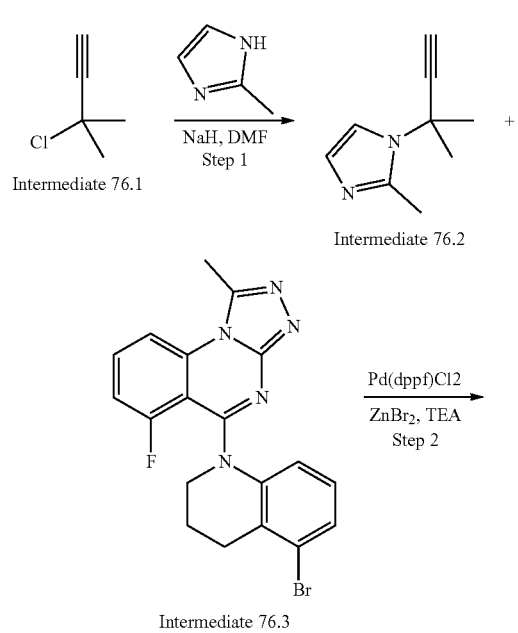

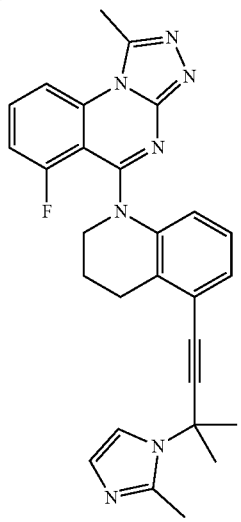

Example 76

Step 1: Preparation of Intermediate 2-methyl-1-(2-methylbut-3-yn-2-yl)-1H-imidazole (Intermediate 76.2)

3-chloro-3-methylbut-1-yne (250 mg, 2.44 mmol) and 2-methyl-1H-imidazole (200 mg, 2.44 mmol) were dissolved in DMF (5 mL) and the solution cooled to 0° C. NaH (117 mg, 2.9 mmol) was added slowly and the reaction was stirred for 1 hour at 0° C. The reaction was then diluted with EtOAc. Water was added, the phases were separated, and the organic layer was dried over $Mg_2SO_4$. The organics were then filtered, evaporated, and the crude chloride purified via reverse phase chromatography acetonitrile:water (0.1% TFA) 15-95% to provide the title compound.

Step 2: Preparation of 6-fluoro-1-methyl-5-(5-(3-methyl-3-(2-methyl-1H-imidazol-1-yl)but-1-yn-1-yl)-3,4-dihydroquinolin-1(2H)-yl)-[1,2,4]triazolo[4,3-a]quinazoline A vial with stir bar was charged with 5-(5-bromo-3,4-dihydroquinolin-1(2H)-yl)-6-fluoro-1-methyl-[1,2,4]triazolo[4,3-a]quinazoline (20 mgs, 0.04 mmol), (dppf)PdCl₂ (10.2 mg, 0.014 mmol), $ZnBr_2$ (46 mg, 0.24 mmol), DMF (2.0 mL), and TEA (0.13 mL, 0.9 mmol). The mixture was sparged with nitrogen for 5 minutes and then 2-methyl-1-(2-methylbut-3-yn-2-yl)-1H-imidazole (7.9 mgs, 0.053 mmol) was added. The reaction was warmed to 100° C. and stirred for ten minutes. The reaction was then diluted with EtOAc and filtered through a plug of Celite. The filtrate was evaporated and purified via reverse phase chromatography acetonitrile:water (0.1% TFA) 15-95% to provide the title compound.

Example 77: 2-(4-(1-(6-fluoro-1-methyl-[1,2,4]triazolo[4,3-a]quinazolin-5-yl)-1,2,3,4-tetrahydroquinolin-5-yl)-2-methylbut-3-yn-2-yl)-4,5-dimethyloxazole

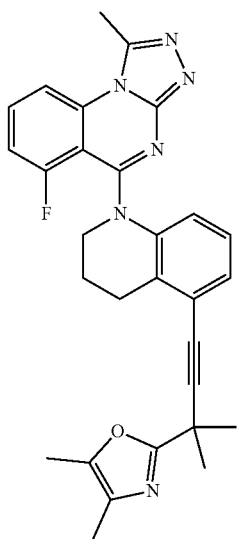 [SMILES: Cc1nc(C(C)(C)C#Cc2cccc3c2CCCN3c2nc3nnc(C)n3c3cccc(F)c23)oc1C]

The title compound was synthesized in a manner similar to Example 72, using 3-aminobutan-2-one instead of 1-aminopropan-2-one.

Example 78: 5-(5-(3-(1H-imidazol-1-yl)-3-methylbut-1-yn-1-yl)-3,4-dihydroquinolin-1(2H)-yl)-6-fluoro-1-methyl-[1,2,4]triazolo[4,3-a]quinazoline

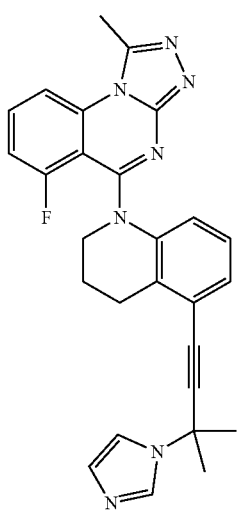 [SMILES: Cc1nnc2nc(N3CCCc4c(C#CC(C)(C)n5ccnc5)cccc43)c3c(F)cccc3n12]

The title compound was synthesized in a manner similar to Example 76, using 1-(2-methylbut-3-yn-2-yl)-1H-imidazole instead of 2-methyl-1-(2-methylbut-3-yn-2-yl)-1H-imidazole.

Example 79: 4-(1-(6-fluoro-1-methyl-[1,2,4]triazolo[4,3-a]quinazolin-5-yl)-1,2,3,4-tetrahydroquinolin-5-yl)-2,2-dimethyl-N-(1-(trifluoromethyl)cyclopropyl)but-3-ynamide

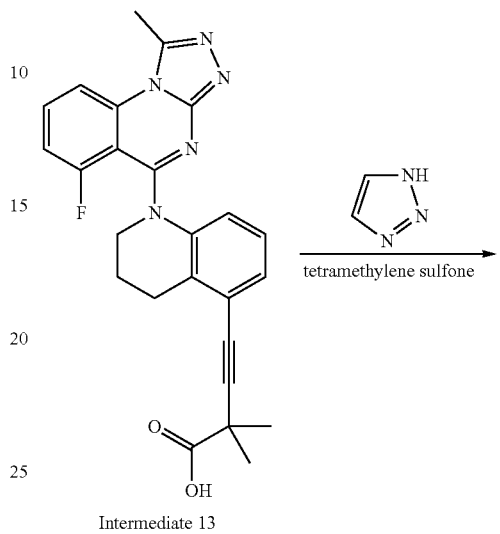

Intermediate 13

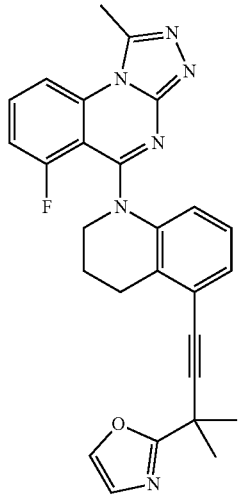

Example 79

To a suspension of 4-(1-(6-fluoro-1-methyl-[1,2,4]triazolo[4,3-a]quinazolin-5-yl)-1,2,3,4-tetrahydroquinolin-5-yl)-2,2-dimethylbut-3-ynoic acid (Intermediate 13) (46 mgs, 0.10 mmol) in DCM (2 mL) was added oxalyl chloride (1 mL) and 2 drops of DMF. The solution was stirred at room temperature for 20 min. Excess of oxalyl chloride was evaporated under reduced pressure.

To this oil was added 1,2,3-triazole (100 mg, 0.225 mmol), $K_2CO_3$ (62.2 mg, 0.45 mmol) and tetramethylene sulfone (5 mL) and the mixture was heated at 140° C. for 15 min and was allowed to cool to room temperature. The reaction mixture was added to water and extracted with ethylacetate. The organic layer was concentrated in vacuo, purified via reverse phase chromatography ACN/Water 15-95% with 0.1% TFA for 15 min to yield 2-(4-(1-(6-fluoro-1-methyl-[1,2,4]triazolo[4,3-a]quinazolin-5-yl)-1,2,3,4-tetrahydroquinolin-5-yl)-2-methylbut-3-yn-2-yl)oxazole.

Example 80: N-(2,2-difluoroethyl)-6,7-difluoro-N-(3-fluoro-2-(4,4,4-trifluoro-3,3-dimethylbut-1-yn-1-yl)pyridin-4-yl)-1-methyl-[1,2,4]triazolo[4,3-a]quinazolin-5-amine

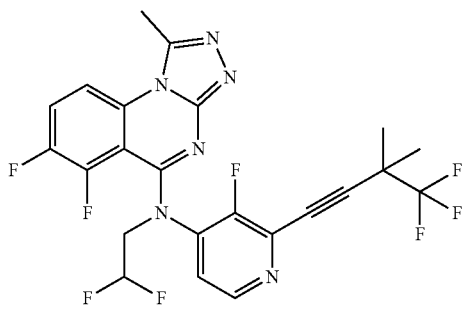 [SMILES: Cc1nnc2nc(N(CC(F)F)c3ccnc(C#CC(C)(C)C(F)(F)F)c3F)c3c(F)c(F)ccc3n12]

The title compound was synthesized in a manner similar to Example 62, using 2-bromo-N-(2,2-difluoroethyl)-3-fluoropyridin-4-amine instead of 2-bromo-N-(2,2-difluoroethyl)pyridin-4-amine and 4,4,4-trifluoro-3,3-dimethylbut-1-yne instead of 4-(2-methylbut-3-yn-2-yl)pyridine.

Example 81: N-(2-(cyclopropylethynyl)pyridin-4-yl)-N-(2,2-difluoroethyl)-6,7-difluoro-1-methyl-[1,2,4]triazolo[4,3-a]quinazolin-5-amine

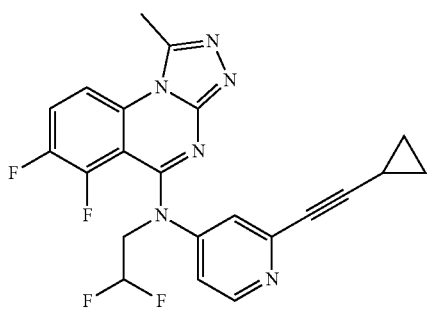 [SMILES: Cc1nnc2nc(N(CC(F)F)c3ccnc(C#CC4CC4)c3)c3c(F)c(F)ccc3n12]

The title compound was synthesized in a manner similar to Example 74, using 2,4-dichloro-5,6-difluoroquinazoline instead of 2,4-dichloro-5-fluoroquinazoline and ethynylcyclopropane instead of 5-ethynyl-2-methoxypyridine.

Example 82: N-(2-(cyclopropylethynyl)pyridin-4-yl)-N-(2,2-difluoroethyl)-6-fluoro-1-methyl-[1,2,4]triazolo[4,3-a]quinazolin-5-amine

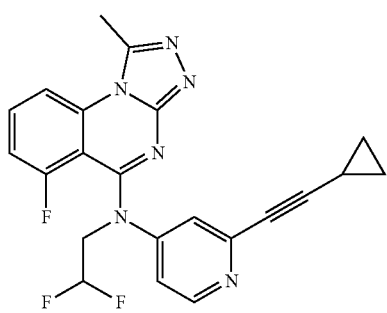 [SMILES: Cc1nnc2nc(N(CC(F)F)c3ccnc(C#CC4CC4)c3)c3c(F)cccc3n12]

The title compound was synthesized in a manner similar to Example 74, using ethynylcyclopropane instead of 5-ethynyl-2-methoxypyridine.

Example 83: 6,7-difluoro-1-methyl-5-(5-((1-methylcyclopropyl)ethynyl)-3,4-dihydro-1,7-naphthyridin-1(2H)-yl)-[1,2,4]triazolo[4,3-a]quinazoline

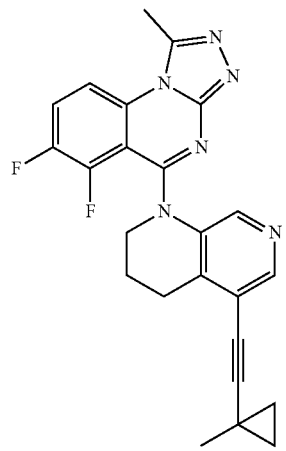 [SMILES: Cc1nnc2nc(N3CCCc4c(C#CC5(C)CC5)cncc43)c3c(F)c(F)ccc3n12]

The title compound was synthesized in a manner similar to Example 81, using 5-bromo-1,2,3,4-tetrahydro-1,7-naphthyridine instead of 2-bromo-N-(2,2-difluoroethyl)pyridin-4-amine and 1-ethynyl-1-methylcyclopropane instead of ethynylcyclopropane.

Example 84: N-(2,2-difluoroethyl)-6,7-difluoro-1-methyl-N-(2-(4,4,4-trifluoro-3,3-dimethylbut-1-yn-1-yl)pyridin-4-yl)-[1,2,4]triazolo[4,3-a]quinazolin-5-amine

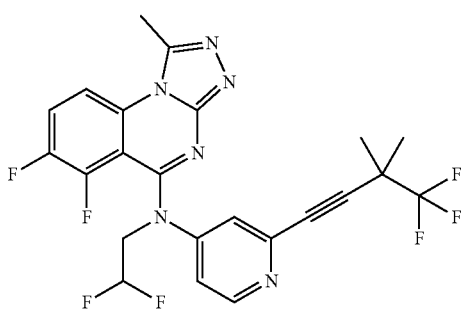 [SMILES: Cc1nnc2nc(N(CC(F)F)c3ccnc(C#CC(C)(C)C(F)(F)F)c3)c3c(F)c(F)ccc3n12]

The title compound was synthesized in a manner similar to Example 81, using 4,4,4-trifluoro-3,3-dimethylbut-1-yne instead of ethynyl-cyclopropane.

Example 85: 6,7-difluoro-1-methyl-5-(5-((1-methyl-cyclopropyl)ethynyl)-3,4-dihydro-1,6-naphthyridin-1(2H)-yl)-[1,2,4]triazolo[4,3-a]quinazoline

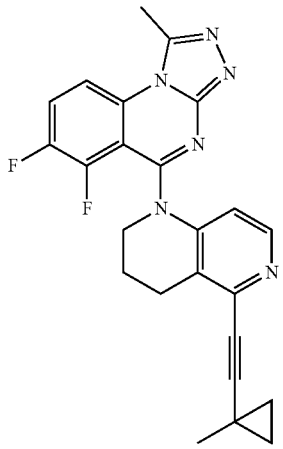 [SMILES: Cc1nnc2nc(N3CCCc4c3ccnc4C#CC3(C)CC3)c3c(F)c(F)ccc3n12]

The title compound was synthesized in a manner similar to Example 83, using 5-chloro-1,2,3,4-tetrahydro-1,6-naphthyridine instead of 5-bromo-1,2,3,4-tetrahydro-1,7-naphthyridine.

Example 86: 6,7-difluoro-1-methyl-5-(5-((1-(trifluoromethyl)cyclopropyl)ethynyl)-3,4-dihydro-1,6-naphthyridin-1(2H)-yl)-[1,2,4]triazolo[4,3-a]quinazoline

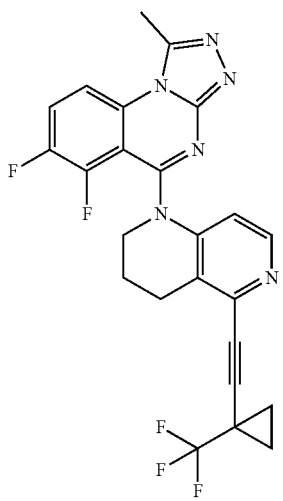 [SMILES: Cc1nnc2nc(N3CCCc4c3ccnc4C#CC3(C(F)(F)F)CC3)c3c(F)c(F)ccc3n12]

The title compound was synthesized in a manner similar to Example 85, using 1-ethynyl-1-(trifluoromethyl)cyclopropane instead of 1-ethynyl-1-methylcyclopropane.

Example 87: N-(2-(cyclopropylethynyl)pyridin-4-yl)-N-(2,2-difluoroethyl)-7-fluoro-1-methyl-[1,2,4]triazolo[4,3-a]quinazolin-5-amine

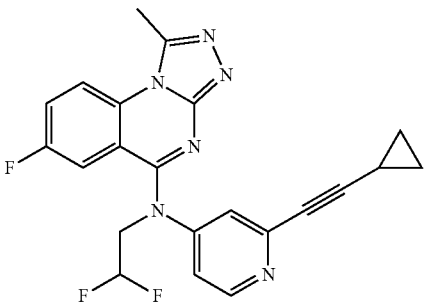 [SMILES: Cc1nnc2nc(N(CC(F)F)c3ccnc(C#CC4CC4)c3)c3cc(F)ccc3n12]

The title compound was synthesized in a manner similar to Example 81, using 2,4-dichloro-6-fluoroquinazoline instead of 2,4-dichloro-5,6-difluoroquinazoline.

Example 88: 6,7-difluoro-1-methyl-5-(5-((1-(trifluoromethyl)cyclopropyl)ethynyl)-3,4-dihydro-1,7-naphthyridin-1(2H)-yl)-[1,2,4]triazolo[4,3-a]quinazoline

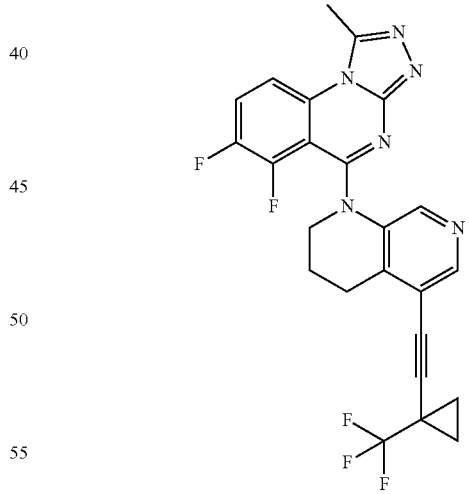

The title compound was synthesized in a manner similar to Example 83, using 1-ethynyl-1-(trifluoromethyl)cyclopropane instead of 1-ethynyl-1-methylcyclopropane.

Example 89: N-(2,2-difluoroethyl)-6,7-difluoro-N-(3-fluoro-2-(4,4,4-trifluoro-3,3-dimethylbut-1-yn-1-yl)pyridin-4-yl)-1-methyl-[1,2,4]triazolo[4,3-a]quinazolin-5-amine

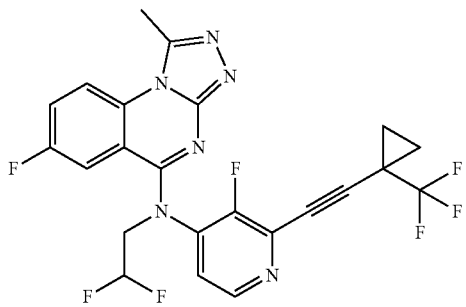 [SMILES: Cc1nnc2nc(N(CC(F)F)c3ccnc(C#CC4(C(F)(F)F)CC4)c3F)c3cc(F)ccc3n12]

The title compound was synthesized in a manner similar to Example 60, using 2,4-dichloro-6-fluoroquinazoline instead of 2,4,8-trichloro-6-fluoroquinazoline, 2-bromo-N-(2,2-difluoroethyl)-3-fluoropyridin-4-amine instead of 2-bromo-N-(2,2-difluoroethyl)pyridin-4-amine and 1-ethynyl-1-(trifluoromethyl)cyclopropane instead of 2-methyl-but-3-yn-2-ol.

Example 90: 6,7-difluoro-1-methyl-5-(5-(4,4,4-trifluoro-3,3-dimethylbut-1-yn-1-yl)-3,4-dihydro-1,7-naphthyridin-1(2H)-yl)-[1,2,4]triazolo[4,3-a]quinazoline

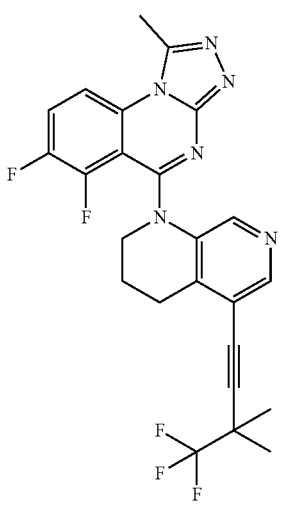 [SMILES: Cc1nnc2nc(N3CCCc4c(C#CC(C)(C)C(F)(F)F)cncc43)c3c(F)c(F)ccc3n12]

The title compound was synthesized in a manner similar to Example 83, using 4,4,4-trifluoro-3,3-dimethylbut-1-yne instead of 1-ethynyl-1-methylcyclopropane.

Example 91: N-(2,2-difluoroethyl)-6,7-difluoro-1-methyl-N-(2-((1-methylcyclopropyl)ethynyl)pyridin-4-yl)-[1,2,4]triazolo[4,3-a]quinazolin-5-amine

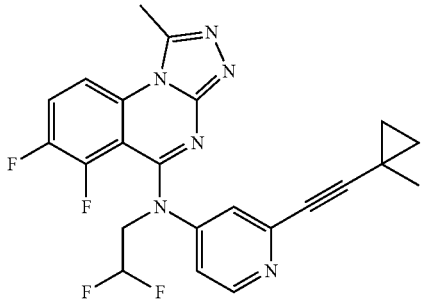 [SMILES: Cc1nnc2nc(N(CC(F)F)c3ccnc(C#CC4(C)CC4)c3)c3c(F)c(F)ccc3n12]

The title compound was synthesized in a manner similar to Example 81, using 1-ethynyl-1-methylcyclopropane instead of ethynylcyclopropane.

Example 92: N-(2,2-difluoroethyl)-6,7-difluoro-1-methyl-N-(2-((1-(trifluoromethyl)cyclopropyl)ethynyl)pyridin-4-yl)-[1,2,4]triazolo[4,3-a]quinazolin-5-amine

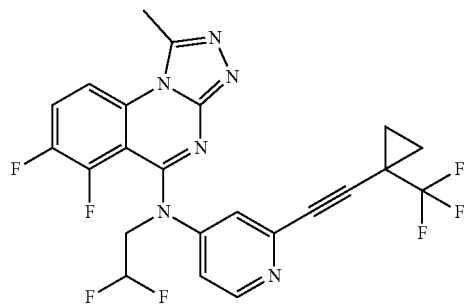 [SMILES: Cc1nnc2nc(N(CC(F)F)c3ccnc(C#CC4(C(F)(F)F)CC4)c3)c3c(F)c(F)ccc3n12]

The title compound was synthesized in a manner similar to Example 81, using 1-ethynyl-1-(trifluoromethyl)cyclopropane instead of ethynylcyclopropane.

Example 93: N-(2,2-difluoroethyl)-6,7-difluoro-N-(2-(4,4,4-trifluoro-3,3-dimethylbut-1-yn-1-yl)pyridin-4-yl)-[1,2,4]triazolo[4,3-a]quinazolin-5-amine

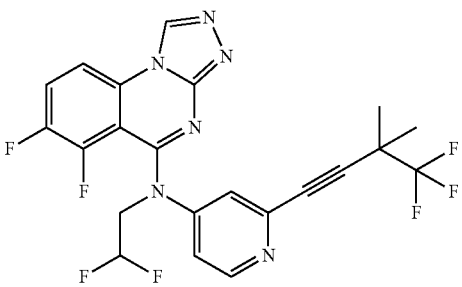 [SMILES: CC(C)(C#Cc1cc(N(CC(F)F)c2nc3nncn3c3ccc(F)c(F)c23)ccn1)C(F)(F)F]

The title compound was synthesized in a manner similar to Example 60, using 2,4-dichloro-5,6-difluoroquinazoline instead of 2,4,8-trichloro-6-fluoroquinazoline and 2-methylbut-3-yn-2-ol.

Example 94: N-(2,2-difluoroethyl)-6,7-difluoro-N-(2-((1-methylcyclopropyl)ethynyl)pyridin-4-yl)-[1,2,4]triazolo[4,3-a]quinazolin-5-amine

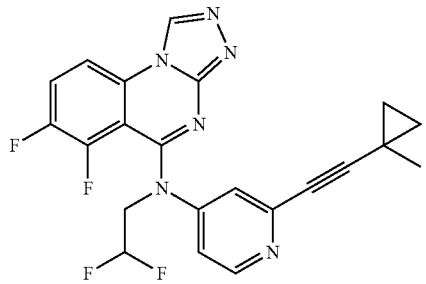

The title compound was synthesized in a manner similar to Example 93, using 1-ethynyl-1-methylcyclopropane instead of 4,4,4-trifluoro-3,3-dimethylbut-1-yne.

Example 95: N-(2,2-difluoroethyl)-6,7-difluoro-N-(2-((1-(trifluoromethyl)cyclopropyl)ethynyl)pyridin-4-yl)-[1,2,4]triazolo[4,3-a]quinazolin-5-amine

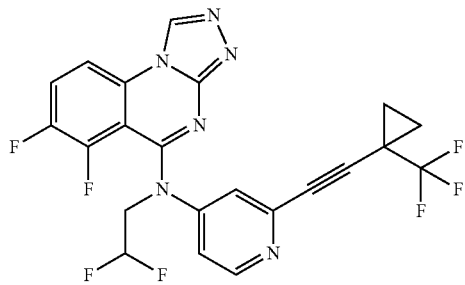 [SMILES: Fc1ccc2c(c(N(CC(F)F)c3ccnc(C#CC4(C(F)(F)F)CC4)c3)nc3nncn32)c1F]

The title compound was synthesized in a manner similar to Example 93, using 1-ethynyl-1-(trifluoromethyl)cyclopropane instead of 4,4,4-trifluoro-3,3-dimethylbut-1-yne.

Example 96: N-(2,2-difluoroethyl)-7-fluoro-1-methyl-N-(2-((1-methylcyclopropyl)ethynyl)pyridin-4-yl)-[1,2,4]triazolo[4,3-a]quinazolin-5-amine

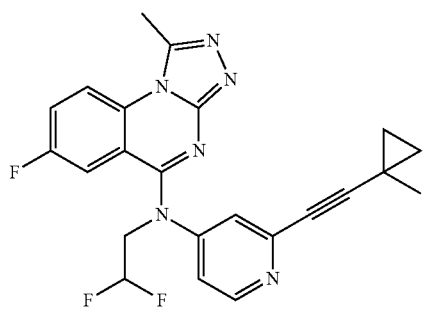 [SMILES: Cc1nnc2nc(N(CC(F)F)c3ccnc(C#CC4(C)CC4)c3)c3cc(F)ccc3n12]

The title compound was synthesized in a manner similar to Example 81, using 2,4-dichloro-6-fluoroquinazoline instead of 2,4-dichloro-5,6-difluoroquinazoline and 1-ethynyl-1-methylcyclopropane instead of ethynylcyclopropane.

Example 97: N-(2,2-difluoroethyl)-7-fluoro-N-(3-fluoro-2-(4,4,4-trifluoro-3,3-dimethylbut-1-yn-1-yl)pyridin-4-yl)-[1,2,4]triazolo[4,3-a]quinazolin-5-amine

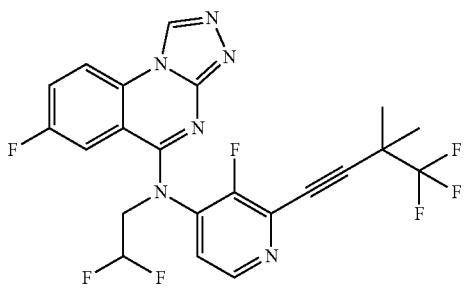 [SMILES: CC(C)(C#Cc1nccc(N(CC(F)F)c2nc3nncn3c3ccc(F)cc23)c1F)C(F)(F)F]

The title compound was synthesized in a manner similar to Example 60, using 2,4-dichloro-6-fluoroquinazoline instead of 2,4,8-trichloro-6-fluoroquinazoline, 2-bromo-N-(2,2-difluoroethyl)-3-fluoropyridin-4-amine instead of 2-bromo-N-(2,2-difluoroethyl)pyridin-4-amine and 4,4,4-trifluoro-3,3-dimethylbut-1-yne instead of 2-methylbut-3-yn-2-ol.

Example 98: 6-fluoro-N-(3-fluoro-5-((1-(trifluoromethyl)cyclopropyl)ethynyl)phenyl)-N-(2-methoxyethyl)-[1,2,4]triazolo[4,3-a]quinazolin-5-amine

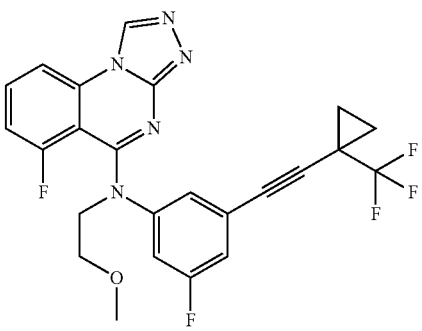 [SMILES: COCCN(c1cc(F)cc(C#CC2(C(F)(F)F)CC2)c1)c1nc2nncn2c2cccc(F)c12]

The title compound was synthesized in a manner similar to Example 60.

Example 99: 6,7-difluoro-5-(5-((1-methylcyclopropyl)ethynyl)-3,4-dihydro-1,7-naphthyridin-1(2H)-yl)-[1,2,4]triazolo[4,3-a]quinazoline

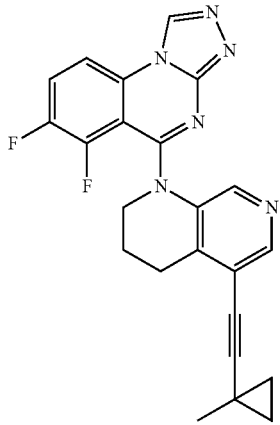 [SMILES: CC1(C#Cc2cncc3c2CCCN3c2nc3nncn3c3ccc(F)c(F)c23)CC1]

The title compound was synthesized in a manner similar to Example 93, using 5-bromo-1,2,3,4-tetrahydro-1,7-naphthyridine instead of 2-bromo-N-(2,2-difluoroethyl)pyridin-4-amine and 1-ethynyl-1-methylcyclopropane instead of 4,4,4-trifluoro-3,3-dimethylbut-1-yne.

Example 100: 6,7-difluoro-5-(5-(4,4,4-trifluoro-3,3-dimethylbut-1-yn-1-yl)-3,4-dihydro-1,7-naphthyridin-1(2H)-yl)-[1,2,4]triazolo[4,3-a]quinazoline

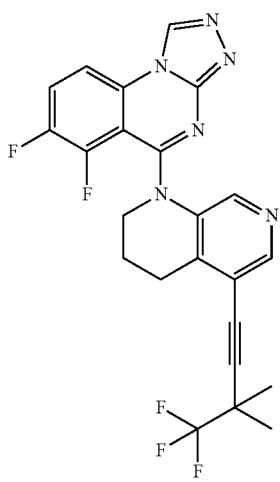 [SMILES: CC(C)(C#Cc1cncc2c1CCCN2c1nc2nncn2c2ccc(F)c(F)c12)C(F)(F)F]

The title compound was synthesized in a manner similar to Example 99, using 4,4,4-trifluoro-3,3-dimethylbut-1-yne instead of 1-ethynyl-1-methylcyclopropane.

Example 101: N-(2,2-difluoroethyl)-N-(2-(3,3-dimethylbut-1-yn-1-yl)pyridin-4-yl)-7-fluoro-[1,2,4]triazolo[4,3-a]quinazolin-5-amine

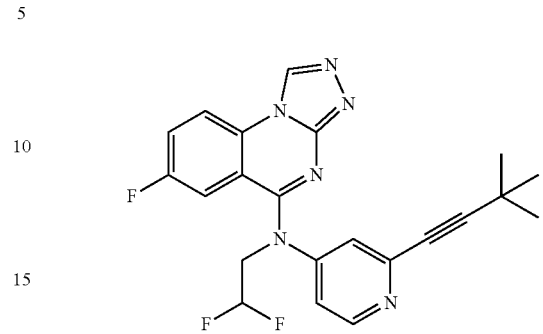

The title compound was synthesized in a manner similar to Example 93, using 2,4-dichloro-6-fluoroquinazoline instead of 2,4-dichloro-5,6-difluoroquinazoline and 3,3-dimethylbut-1-yne instead of 4,4,4-trifluoro-3,3-dimethylbut-1-yne.

Example 102: N-(2,2-difluoroethyl)-7-fluoro-N-(2-((1-methylcyclopropyl)ethynyl)pyridin-4-yl)-[1,2,4]triazolo[4,3-a]quinazolin-5-amine

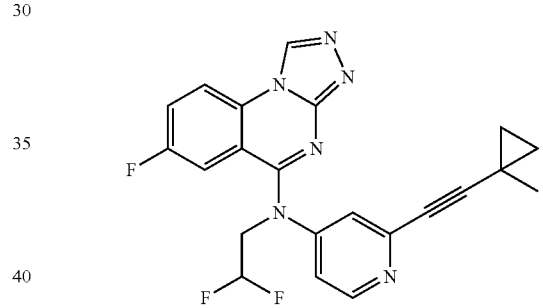

The title compound was synthesized in a manner similar to Example 101, using 1-ethynyl-1-methylcyclopropane instead of 3,3-dimethylbut-1-yne.

Example 103: N-(2,2-difluoroethyl)-7-fluoro-N-(2-((1-(trifluoromethyl)cyclopropyl)ethynyl)pyridin-4-yl)-[1,2,4]triazolo[4,3-a]quinazolin-5-amine

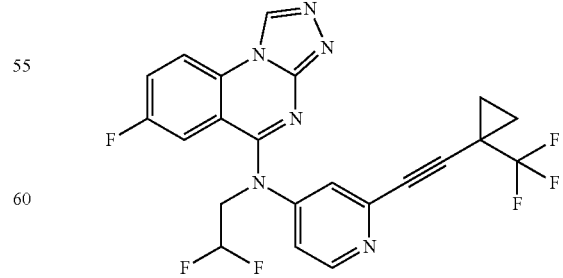

The title compound was synthesized in a manner similar to Example 101, using 1-ethynyl-1-(trifluoromethyl)cyclopropane instead of 1-ethynyl-1-methylcyclopropane.

Example 104: 4-(3-((8-chloro-6-fluoro-1-methyl-[1,2,4]triazolo[4,3-a]quinazolin-5-yl)(2,2-difluoroethyl)amino)-5-fluorophenyl)-2-methylbut-3-yn-2-ol

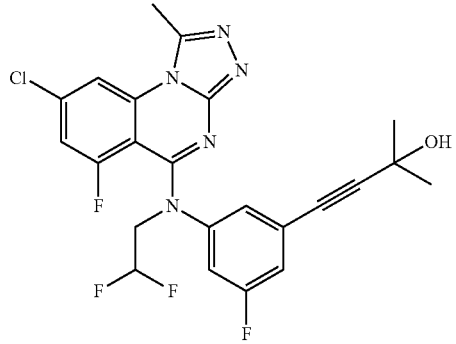 [SMILES: Cc1nnc2nc(N(CC(F)F)c3cc(F)cc(C#CC(C)(C)O)c3)c3c(F)cc(Cl)cc3n12]

The title compound was synthesized in a manner similar to Example 60, using 1,1,1-triethoxyethane instead of triethoxymethane.

Example 105 or 106 was synthesized in a manner similar to Example 104. Each of Examples 107-123 was synthesized in a manner similar to Example 1.

Example 124: Synthesis of 6-fluoro-5-(6-(4,4,4-trifluoro-3,3-dimethylbut-1-yn-1-yl)-2,3-dihydrobenzo[e][1,4]oxazepin-1(5H)-yl)-[1,2,4]triazolo[4,3-a]quinazolin-1-amine

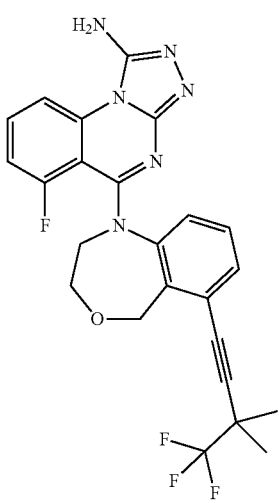 [SMILES: CC(C)(C#Cc1cccc2c1COCCN2c1nc2nnc(N)n2c2cccc(F)c12)C(F)(F)F]

The title compound was synthesized in a manner similar to Example 127.

Example 125: Synthesis of 4-(1-(6-chloro-1-methyl-[1,2,4]triazolo[4,3-a]quinazolin-5-yl)-1,2,3,4-tetrahydroquinolin-5-yl)-2,2-dimethylbut-3-ynenitrile

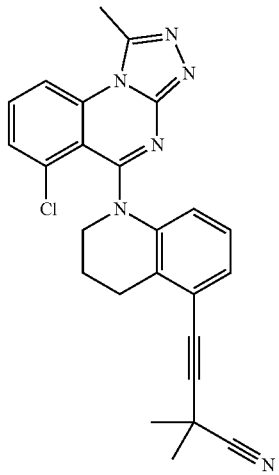 [SMILES: Cc1nnc2nc(N3CCCc4c(C#CC(C)(C)C#N)cccc43)c3c(Cl)cccc3n12]

The title compound was synthesized in a manner similar to Example 1.

Example 126: Synthesis of 6-chloro-5-(5-((1-(difluoromethyl)cyclopropyl)ethynyl)-3,4-dihydroquinolin-1(2H)-yl)-1-methyl-[1,2,4]triazolo[4,3-a]quinazoline

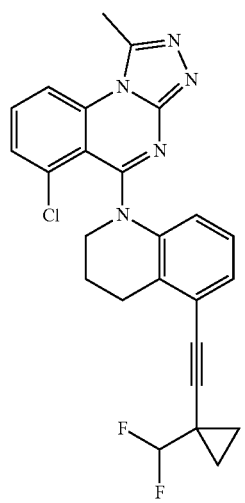 [SMILES: Cc1nnc2nc(N3CCCc4c(C#CC5(C(F)F)CC5)cccc43)c3c(Cl)cccc3n12]

The title compound was synthesized in a manner similar to Example 1.

387

Example 127: Synthesis of 2-(3'-((2,2-difluoroethyl) (6-fluoro-1-methyl-[1,2,4]triazolo[4,3-a]quinazolin-5-yl)amino)-5'-fluoro-[1,1'-biphenyl]-4-yl)propan-2-ol

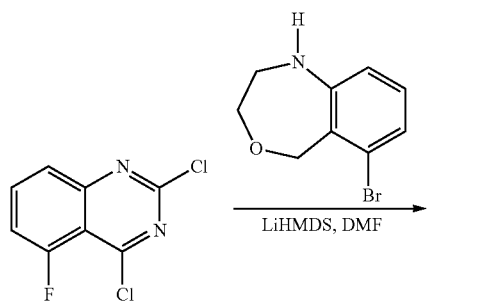

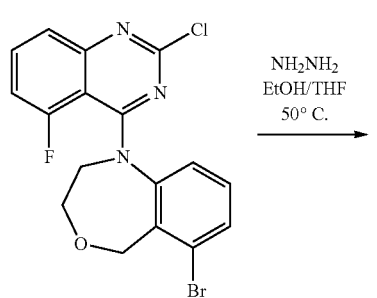

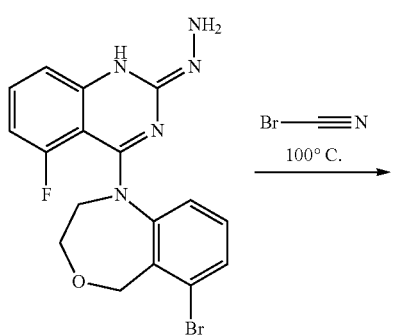

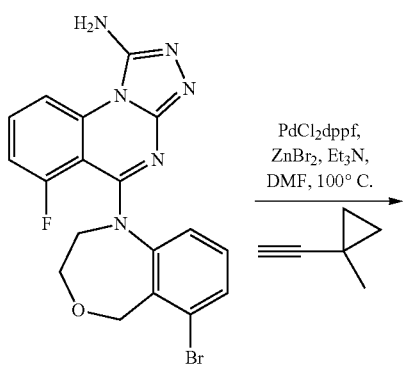

388

-continued

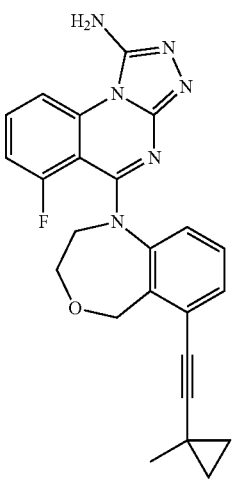

Example 127

Synthesis of 6-bromo-1-(2-chloro-5-fluoro-quinazolin-4-yl)-3,5-dihydro-2H-4,1-benzoxazepine To a solution of 6-bromo-1,2,3,5-tetrahydro-4,1-benzoxazepine (578 mg, 2.53 mmol) and 2,4-dichloro-5-fluoro-quinazoline (550 mg, 2.53 mmol) in DMF (5 mL) was added LiHMDS (1M in THF 5.07 mL, 5.07 mmol) dropwise at 0° C. The mixture was warmed to room temperature over 1 h. Upon completion, the mixture was poured into water (50 mL) and extracted with ethyl acetate (2×50 ml each). The organics were separated and dried over sodium sulfate, filtered and concentrated under vacuum. The crude was purified by column chromatography on silica gel using ethyl acetate in hexanes 0-40% as the eluent. Appropriate fractions were combined and concentrated in vacuo to afford the title compound as a yellow solid (820 mg, 79% yield). (MS (m/z) 409.6 [M+H]$^+$.

Synthesis of [4-(6-bromo-3,5-dihydro-2H-4,1-benzoxazepin-1-yl)-5-fluoro-quinazolin-2-yl]hydrazine To a solution of 6-bromo-1-(2-chloro-5-fluoro-quinazolin-4-yl)-3,5-dihydro-2H-4,1-benzoxazepine (400 mg, 0.978 mmol) in THF (10 mL) and ethanol (10 mL) was added anhydrous hydrazine (313 mg, 978 mmol) and the mixture was stirred at room temperature for 5 hrs. Upon completion, the reaction was diluted with dichloromethane and washed with water followed by brine. The resulting organics were dried over Na$_2$SO$_4$, filtered and concentrated under reduced pressure to afford the title compound as a solid (295 mg, 75% yield). MS (m/z) 405.2 [M+H]$^+$.

Synthesis of 5-(6-bromo-3,5-dihydro-2H-4,1-benzoxazepin-1-yl)-6-fluoro-[1,2,4]triazolo[4,3-a]quinazolin-1-amine A solution of cyanogen bromide (3.0M in dichloromethane) (655 mg, 6.18 mmol) was added to [4-(6-bromo-3,5-dihydro-2H-4,1-benzoxazepin-1-yl)-5-fluoro-quinazolin-2-yl]hydrazine (250 mg, 0.618 mmol) in ethanol (2 mL). The reaction was heated to 100° C. for 1 hrs. Upon completion, the reaction was cooled to room temperature, and concentrated under reduced pressure to afford the crude product. The crude product was triturated with heptane and the solids were collected by filtration, washed with heptanes and dried in vacuo to afford the title compound.

Synthesis of 2-(3'-((2,2-difluoroethyl)(6-fluoro-1-methyl-[1,2,4]triazolo[4,3-a]quinazolin-5-yl)amino)-5'-fluoro-[1,1'-biphenyl]-4-yl)propan-2-ol (Example 127)

A solution of 5-(6-bromo-3,5-dihydro-2H-4,1-benzoxazepin-1-yl)-6-fluoro-[1,2,4]triazolo[4,3-a]quinazolin-1-amine (30 mg, 0.07 mmol), zinc bromide (79 mg, 0.35 mmol), (1,1'-)bis(diphenylphosphino)ferrocene) palladium (II) dichloride (2.89 mg, 0.0035 mmol), and triethylamine (142 mg, 1.40 mmol) in DMF (2 mL) was purged with nitrogen gas for 2 minutes. 1-ethynyl-1-methyl-cyclopropane (45 mg, 0.560 mmol) was then added and the mixture was heated at 100° C. for 24 hrs. Upon completion, the mixture was cooled to room temperature, and ethyl acetate and sat. NH₄Cl (aq) were added to the mixture. The aqueous layer was extracted with EA and the combined organic layers were dried over Na₂SO₄ and concentrated in vacuo. The residue was purified by reverse phase HPLC (0.1% trifluoroacetic acid in acetonitrile/water) providing the title compound as the mono-TFA salt.

Example 128: Synthesis of 2-(3'-((2,2-difluoroethyl)(6-fluoro-1-methyl-[1,2,4]triazolo[4,3-a]quinazolin-5-yl)amino)-5'-fluoro-[1,1'-biphenyl]-4-yl)propan-2-ol

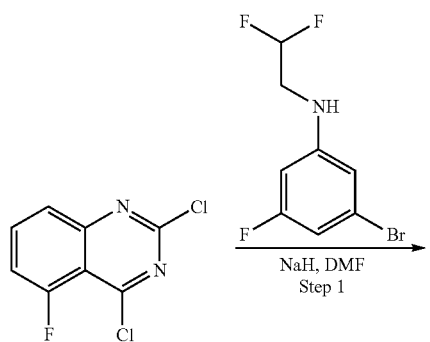

Intermediate 128.1

Intermediate 128.2

Intermediate 128.3

Example 128

(Step 1) Synthesis of N-(3-bromo-5-fluorophenyl)-2-chloro-N-(2,2-difluoroethyl)-5-fluoroquinazolin-4-amine (Intermediate 128.1). To a solution of 3-bromo-N-(2,2-difluoroethyl)-5-fluoroaniline (0.92 mmol) in in DMF (3.0 mL) at 0° C. was added NaH (60% dispersion in mineral oil) (1.01 mmol) in one portion. The mixture was stirred at 0° C. for 30 min, followed by the 2,4-dichloro-5-fluoroquinazoline (1.01 mmol) in one portion and the mixture was warmed to room temperature over 16 h. Upon completion, the mixture was cooled to 0° C. and quenched with a few drops of a solution of sat. NH₄Cl (aq) and stirred until solid crashed out. The solid was filtered off and washed with a mixture of hexanes:diethyl ether 4:1 and dried in vacuo and was used with no further purification.

(Step 2) Synthesis of N-(3-bromo-5-fluorophenyl)-N-(2,2-difluoroethyl)-5-fluoro-2-hydrazineylquinazolin-4-amine (Intermediate 128.2): To a solution of N-(3-bromo-5-fluorophenyl)-2-chloro-N-(2,2-difluoroethyl)-5-fluoroquinazolin-4-amine (Intermediate 128.1, 0.658 mmol) in THF (3.5 mL) and ethanol (3.5 mL) was added hydrazine monohydrate (7.9 mmol) and the mixture was stirred at room temperature for 12 h. Upon completion, the reaction was diluted with EA and washed with water, dried over Na$_2$SO$_4$ and concentrated under reduced pressure to afford Intermediate 128.1, 0.658 mmol.

(Step 3) Synthesis of N-(3-bromo-5-fluorophenyl)-N-(2,2-difluoroethyl)-6-fluoro-1-methyl-[1,2,4]triazolo[4,3-a]quinazolin-5-amine (Intermediate 128.3). A solution of N-(3-bromo-2-fluoro-phenyl)-N-(2,2-difluoroethyl)-6-fluoro-2-hydrazino-quinazolin-4-amine (0.818 mmol) and triethyl orthoacetate (27.5 mmol) was heated to 110° C. for 16 h. Upon completion, the reaction was cooled to room temperature, and concentrated under reduced pressure to afford the crude product. The crude product was triturated with heptane and the solids were collected by filtration, washed with hexanes:diethyl ether (4:1) and dried in vacuo to afford Intermediate 128.3.

(Step 4) Synthesis of Synthesis of 2-(3'-((2,2-difluoroethyl)(6-fluoro-1-methyl-[1,2,4]triazolo[4,3-a]quinazolin-5-yl)amino)-5'-fluoro-[1,1'-biphenyl]-4-yl)propan-2-ol (Example 128): N-(3-bromo-5-fluorophenyl)-N-(2,2-difluoroethyl)-6-fluoro-1-methyl-[1,2,4]triazolo[4,3-a]quinazolin-5-amine (Intermediate 128.3, 0.0591 mmol) was added 2-(4-(tributylstannyl)phenyl)propan-2-ol (0.0668 mmol) and tetrakis(triphenylphosphine)palladium(0) (6.83 mg, 0.00591 mmol). The reaction mixture was heated to 100° C. for 12 h. The reaction was cooled to room temperature and was diluted with ethyl acetate (5 mL) and water (5 mL) sequentially. The organic layer was separated and concentrated under reduced pressure. The residue was purified by reverse-phase preparative HPLC (0.1% trifluoroacetic acid in acetonitrile/water) to give the title compound.

Example 129: Synthesis of 6-fluoro-1-methyl-5-(5-((tetrahydro-2H-pyran-2-yl)ethynyl)-3,4-dihydroquinolin-1(2H)-yl)-[1,2,4]triazolo[4,3-a]quinazoline

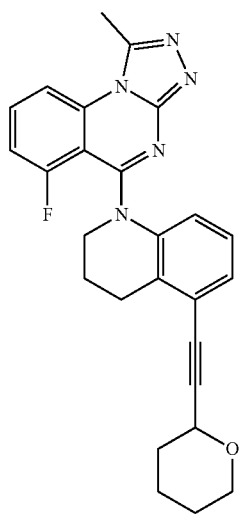

The title compound was synthesized in a manner similar to Example 1.

Example 130: Synthesis of 7-fluoro-1-methyl-5-(5-((tetrahydro-2H-pyran-2-yl)ethynyl)-3,4-dihydroquinolin-1(2H)-yl)-[1,2,4]triazolo[4,3-a]quinazoline

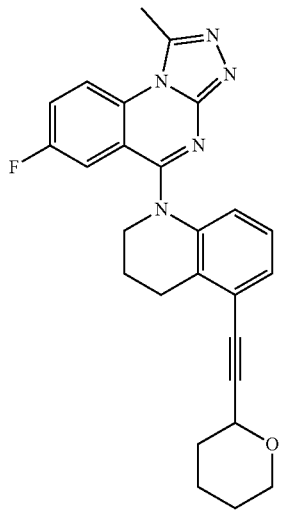 [SMILES: Cc1nnc2nc(N3CCCc4c(C#CC5CCCCO5)cccc43)c3cc(F)ccc3n12]

The title compound was synthesized in a manner similar to Example 1.

Example 131: Synthesis of 5-[5-(2-cyclopropylethynyl)-3,4-dihydro-2H-quinolin-1-yl]-6,7-difluoro-1-methyl-[1,2,4]triazolo[4,3-a]quinazoline

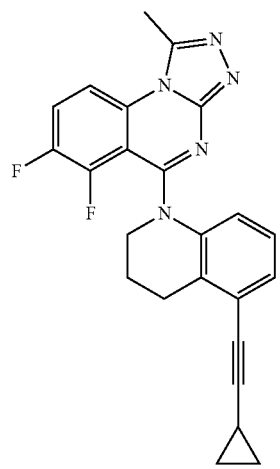 [SMILES: Cc1nnc2nc(N3CCCc4c(C#CC5CC5)cccc43)c3c(F)c(F)ccc3n12]

The title compound was synthesized in a manner similar to Example 60.

Example 132: 1-(7-fluoro-1-methyl-[1,2,4]triazolo[4,3-a]quinazolin-5-yl)-6-((1-methylcyclopropyl)ethynyl)-1,2,3,5-tetrahydropyrido[4,3-e][1,4]oxazepine

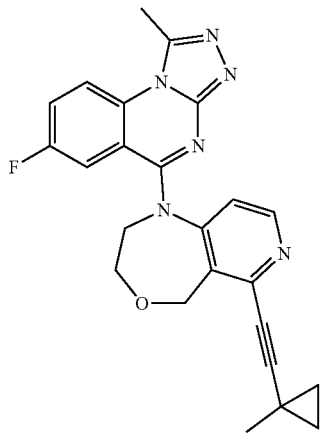 [SMILES: Cc1nnc2nc(N3CCOCc4c3ccnc4C#CC3(C)CC3)c3cc(F)ccc3n12]

The title compound was synthesized as described in Example 141 using 6-bromo-1-(7-fluoro-1-methyl-[1,2,4]triazolo[4,3-a]quinazolin-5-yl)-1,2,3,5-tetrahydropyrido[4,3-e][1,4]oxazepine instead of 6-bromo-1-(6-fluoro-1-methyl-[1,2,4]triazolo[4,3-a]quinazolin-5-yl)-1,2,3,5-tetrahydropyrido[4,3-e][1,4]oxazepine.

Example 133: 6-((1-(1,1-difluoroethyl)cyclopropyl)ethynyl)-1-(7-fluoro-1-methyl-[1,2,4]triazolo[4,3-a]quinazolin-5-yl)-1,2,3,5-tetrahydropyrido[4,3-e][1,4]oxazepine

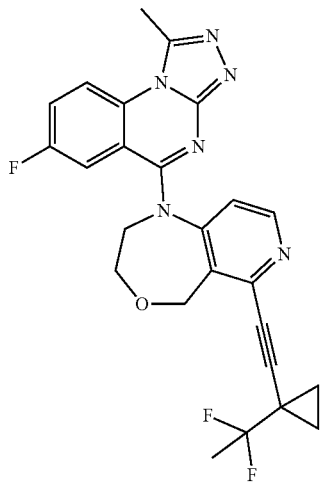 [SMILES: Cc1nnc2nc(N3CCOCc4c3ccnc4C#CC3(C(C)(F)F)CC3)c3cc(F)ccc3n12]

The title compound was synthesized as described in Example 141 using 6-bromo-1-(7-fluoro-1-methyl-[1,2,4]triazolo[4,3-a]quinazolin-5-yl)-1,2,3,5-tetrahydropyrido[4,3-e][1,4]oxazepine and 1-(1,1-difluoroethyl)-1-ethynyl-cyclopropane.

Example 134: 1-(7-fluoro-1-methyl-[1,2,4]triazolo[4,3-a]quinazolin-5-yl)-6-(4,4,4-trifluoro-3,3-dimethylbut-1-yn-1-yl)-1,2,3,5-tetrahydropyrido[4,3-e][1,4]oxazepane

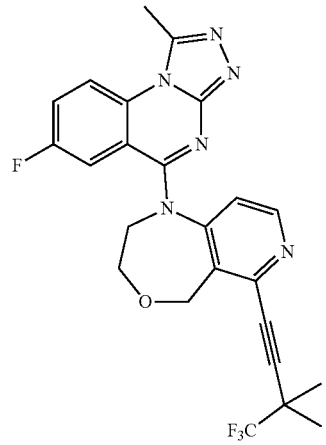 [SMILES: Cc1nnc2nc(N3CCOCc4c3ccnc4C#CC(C)(C)C(F)(F)F)c3cc(F)ccc3n12]

The title compound was synthesized as described in Example 141 using 6-bromo-1-(7-fluoro-1-methyl-[1,2,4]triazolo[4,3-a]quinazolin-5-yl)-1,2,3,5-tetrahydropyrido[4,3-e][1,4]oxazepine and 1-ethynyl-1-(trifluoromethyl)cyclopropane.

Example 135: 6-((1-(difluoromethyl)cyclopropyl)ethynyl)-1-(6-fluoro-1-methyl-[1,2,4]triazolo[4,3-a]quinazolin-5-yl)-1,2,3,5-tetrahydropyrido[4,3-e][1,4]oxazepine

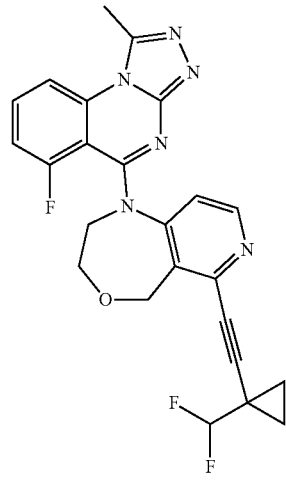 [SMILES: Cc1nnc2nc(N3CCOCc4c3ccnc4C#CC3(C(F)F)CC3)c3c(F)cccc3n12]

The title compound was synthesized as described in Example 141 using 1-(difluoromethyl)-1-ethynyl-cyclopropane instead of 1-ethynyl-1-methyl-cyclopropane.

Example 136: 6-(4,4-difluoro-3,3-dimethylbut-1-yn-1-yl)-1-(6-fluoro-1-methyl-[1,2,4]triazolo[4,3-a]quinazolin-5-yl)-1,2,3,5-tetrahydropyrido[4,3-e][1,4]oxazepine

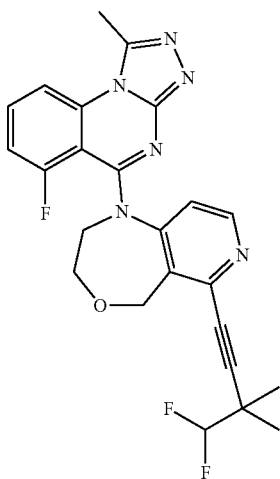 [SMILES: Cc1nnc2nc(N3CCOCc4c3ccnc4C#CC(C)(C)C(F)F)c3c(F)cccc3n12]

The title compound was synthesized as described in Example 141 using 4,4-difluoro-3,3-dimethyl-but-1-yne instead of 1-ethynyl-1-methyl-cyclopropane.

Example 137: N-(4-(1-(6-fluoro-1-methyl-[1,2,4]triazolo[4,3-a]quinazolin-5-yl)-1,2,3,5-tetrahydropyrido[4,3-e][1,4]oxazepin-6-yl)-2-methylbut-3-yn-2-yl)-1-(trifluoromethyl)cyclopropane-1-carboxamide

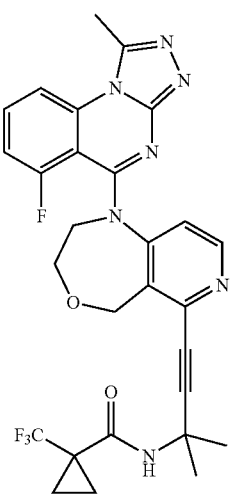

The title compound was synthesized as described in Example 141 using N-(1,1-dimethylprop-2-ynyl)-1-(trifluoromethyl)cyclopropanecarboxamide instead of 1-ethynyl-1-methyl-cyclopropane. The crude residue was purified by ISCO column using 5-20% MeOH in DCM instead of reverse phase HPLC.

Example 138: N-(4-(1-(6-fluoro-1-methyl-[1,2,4]triazolo[4,3-a]quinazolin-5-yl)-1,2,3,5-tetrahydrobenzo[e][1,4]oxazepin-6-yl)-2-methylbut-3-yn-2-yl)-1-methyl-3-(trifluoromethyl)-1H-pyrazole-4-carboxamide

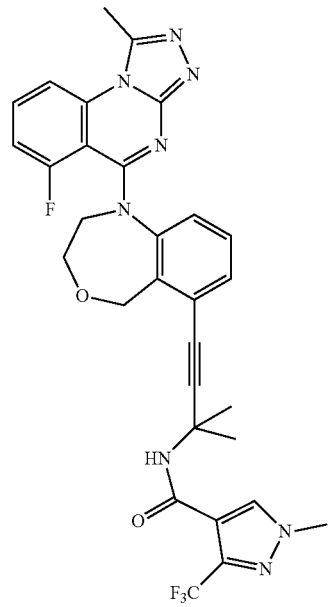 [SMILES: Cc1nnc2nc(N3CCOCc4c(C#CC(C)(C)NC(=O)c5cn(C)nc5C(F)(F)F)cccc43)c3c(F)cccc3n12]

The title compound was synthesized as described in Example 147 using 1-methyl-3-(trifluoromethyl)pyrazole-4-carboxylic acid instead of 1-(trifluoromethyl) cyclopropane carboxylic acid.

Example 139: 3-(difluoromethyl)-N-[3-[1-(6-fluoro-1-methyl-[1,2,4]triazolo[4,3-a]quinazolin-5-yl)-3,5-dihydro-2H-4,1-benzoxazepin-6-yl]-1,1-dimethyl-prop-2-ynyl]-1-methyl-pyrazole-4-carboxamide

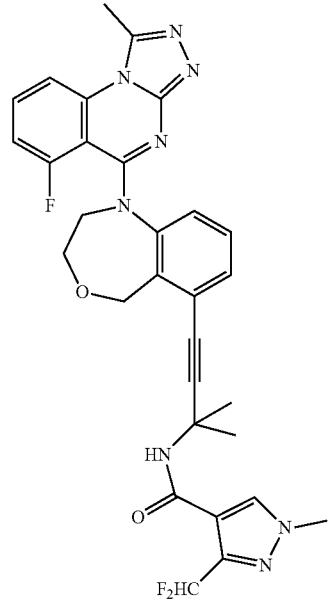 [SMILES: Cc1nnc2nc(N3CCOCc4c(C#CC(C)(C)NC(=O)c5cn(C)nc5C(F)F)cccc43)c3c(F)cccc3n12]

The title compound was synthesized in a manner similar to Example 147 using 3-(difluoromethyl)-1-methyl-pyrazole-4-carboxylic acid instead of 1-(trifluoromethyl) cyclopropane carboxylic acid.

Example 140: 1-(6-fluoro-1-methyl-[1,2,4]triazolo[4,3-a]quinazolin-5-yl)-6-(4,4,4-trifluoro-3,3-dimethylbut-1-yn-1-yl)-1,2,3,5-tetrahydropyrido[4,3-e][1,4]oxazepine

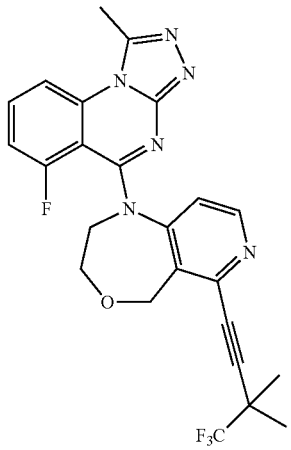 [SMILES: Cc1nnc2nc(N3CCOCc4c3ccnc4C#CC(C)(C)C(F)(F)F)c3c(F)cccc3n12]

The title compound was synthesized as described in Example 141 using 4,4,4-trifluoro-3,3-dimethyl-but-1-yne instead of 1-ethynyl-1-methyl-cyclopropane.

Example 141: 1-(6-fluoro-1-methyl-[1,2,4]triazolo[4,3-a]quinazolin-5-yl)-6-((1-methylcyclopropyl)ethynyl)-1,2,3,5-tetrahydropyrido[4,3-e][1,4]oxazepine

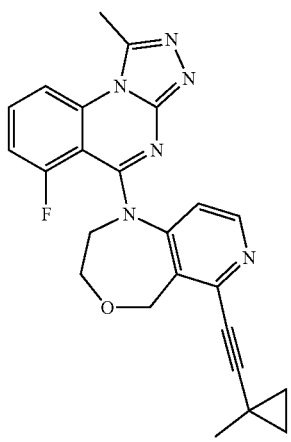 [SMILES: Cc1nnc2nc(N3CCOCc4c3ccnc4C#CC3(C)CC3)c3c(F)cccc3n12]

A mixture of 6-bromo-1-(6-fluoro-1-methyl-[1,2,4]triazolo[4,3-a]quinazolin-5-yl)-1,2,3,5-tetrahydropyrido[4,3-e][1,4]oxazepane (80 mg, 0.19 mmol), 1-ethynyl-1-methyl-cyclopropane (30 mg, 0.37 mmol), cesium carbonate (152 mg, 0.47 mmol) in acetonitrile (6 ml) was bubbled through with nitrogen for 30 seconds and then Xphos Pd G4 (8 mg, 9.3 umol) was added. It was bubbled through with nitrogen for another 30 seconds. The reaction tube was sealed and heated at 100° C. for 2 h. Acetonitrile (15 mL) wad added and the solid was filtered off. The filtrate was concentrated to dryness and the crude residue was purified by reverse phase HPLC to afford the desired product.

Example 142: 6-((1-(1,1-difluoroethyl)cyclopropyl)ethynyl)-1-(6-fluoro-1-methyl-[1,2,4]triazolo[4,3-a]quinazolin-5-yl)-1,2,3,5-tetrahydropyrido[4,3-e][1,4]oxazepine

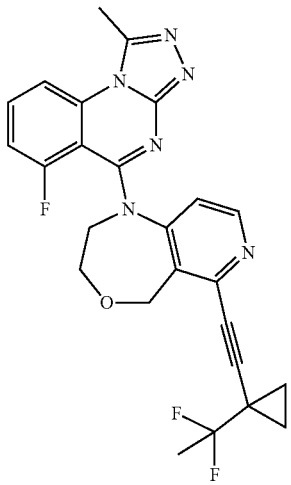 [SMILES: Cc1nnc2nc(N3CCOCc4c3ccnc4C#CC3(C(C)(F)F)CC3)c3c(F)cccc3n12]

The title compound was synthesized as described in Example 141 using 1-(1,1-difluoroethyl)-1-ethynyl-cyclopropane instead of 1-ethynyl-1-methyl-cyclopropane.

Example 143: 1-(6-fluoro-1-methyl-[1,2,4]triazolo[4,3-a]quinazolin-5-yl)-6-((1-(trifluoromethyl)cyclopropyl)ethynyl)-1,2,3,5-tetrahydropyrido[4,3-e][1,4]oxazepine

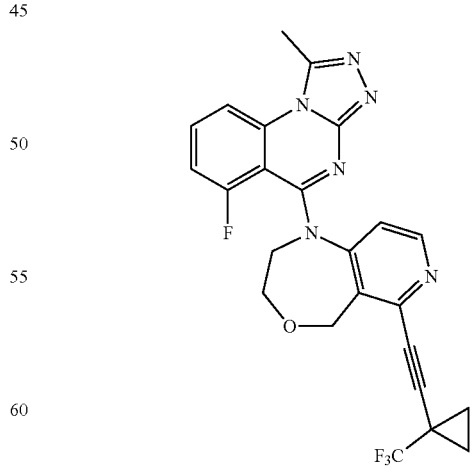

The title compound was synthesized as described in Example 141 using 1-ethynyl-1-(trifluoromethyl)cyclopropane instead of 1-ethynyl-1-methyl-cyclopropane.

Example 144: 3,3,3-trifluoro-N-(4-(1-(6-fluoro-1-methyl-[1,2,4]triazolo[4,3-a]quinazolin-5-yl)-1,2,3,5-tetrahydrobenzo[e][1,4]oxazepin-6-yl)-2-methyl-but-3-yn-2-yl)-2,2-dimethylpropanamide

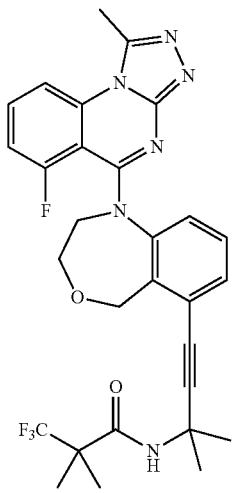 [SMILES: Cc1nnc2nc(N3CCOCc4c(C#CC(C)(C)NC(=O)C(C)(C)C(F)(F)F)cccc43)c3c(F)cccc3n12]

The title compound was synthesized as described in Example 148 using N-(1,1-dimethylprop-2-ynyl)-3,3,3-trifluoro-2,2-dimethyl-propanamide instead of tert-butyl N-(1,1-dimethylprop-2-ynyl)carbamate.

Example 145: N-(1-((1-(6-fluoro-1-methyl-[1,2,4]triazolo[4,3-a]quinazolin-5-yl)-1,2,3,5-tetrahydrobenzo[e][1,4]oxazepin-6-yl)ethynyl)cyclopropyl)-1-(trifluoromethyl) cyclopropane-1-carboxamide

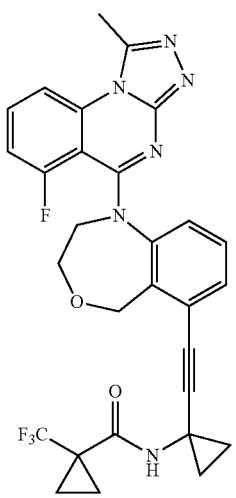 [SMILES: Cc1nnc2nc(N3CCOCc4c(C#CC5(NC(=O)C6(C(F)(F)F)CC6)CC5)cccc43)c3c(F)cccc3n12]

The title compound was synthesized as described in Example 148 using N-(1-ethynylcyclopropyl)-1-(trifluoromethyl)cyclopropanecarboxamide instead of tert-butyl N-(1,1-dimethylprop-2-ynyl)carbamate.

Example 146: 1,1,1-trifluoropropan-2-yl (4-(1-(6-fluoro-1-methyl-[1,2,4]triazolo[4,3-a]quinazolin-5-yl)-1,2,3,5-tetrahydrobenzo[e][1,4]oxazepin-6-yl)-2-methylbut-3-yn-2-yl)carbamate

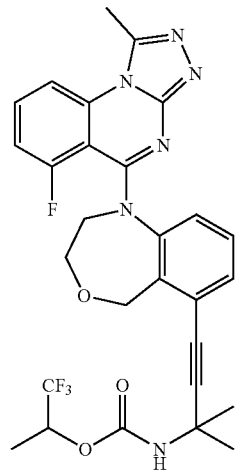 [SMILES: Cc1nnc2nc(N3CCOCc4c(C#CC(C)(C)NC(=O)OC(C)C(F)(F)F)cccc43)c3c(F)cccc3n12]

4-[1-(6-fluoro-1-methyl-[1,2,4]triazolo[4,3-a]quinazolin-5-yl)-3,5-dihydro-2H-4,1-benzoxazepin-6-yl]-2-methyl-but-3-yn-2-amine (22 mg, 0.051 mmol) was dissolved in DCM (4 mL). Triethylamine (0.014 mL, 0.10 mmol) and (2,2,2-trifluoro-1-methyl-ethyl) carbonochloridate (14 mg, 0.077 mmol) were added at 0° C. Reaction mixture was stirred at rt for 1 h. MeOH (0.1 mL) and Water (0.1 mL) were added to quench the reaction. It was diluted with EtOAc (30 ml), washed with water and brine. The organic layer was dried, and concentrated. The resulting residue was purified by RP-HPLC to afford the title product as a white solid.

Example 147: N-(4-(1-(6-fluoro-1-methyl-[1,2,4]triazolo[4,3-a]quinazolin-5-yl)-1,2,3,5-tetrahydrobenzo[e][1,4]oxazepin-6-yl)-2-methylbut-3-yn-2-yl)-1-(trifluoromethyl) cyclopropane-1-carboxamide

Example 148: tert-butyl (4-(1-(6-fluoro-1-methyl-[1,2,4]triazolo[4,3-a]quinazolin-5-yl)-1,2,3,5-tetrahydrobenzo[e][1,4]oxazepin-6-yl)-2-methylbut-3-yn-2-yl)carbamate

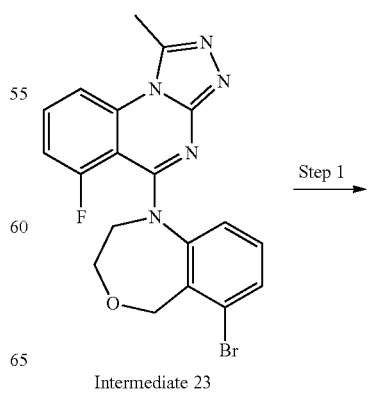

Intermediate 23

Step 1 →

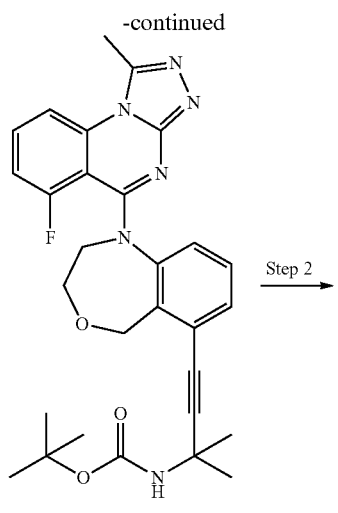

Example 148

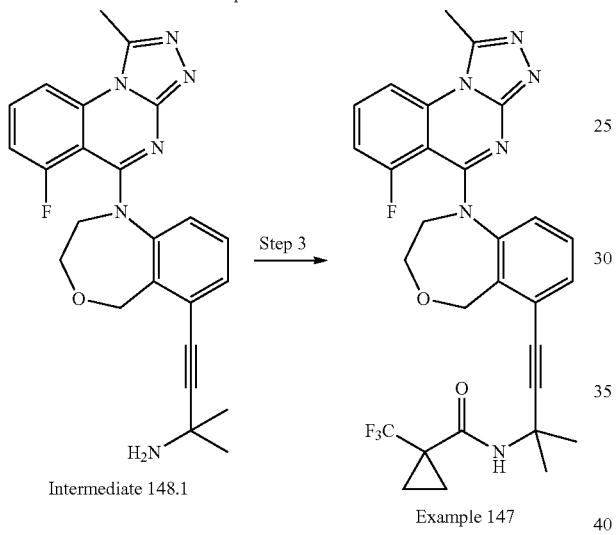

Step 1. Synthesis of Example 148: A mixture of Intermediate 23, 6-bromo-1-(6-fluoro-1-methyl-[1,2,4]triazolo[4,3-a]quinazolin-5-yl)-3,5-dihydro-2H-4,1-benzoxazepine (1.50 g, 3.33 mmol), tert-butyl N-(1,1-dimethylprop-2-ynyl)carbamate (1.22 g, 6.65 mmol), cesium carbonate (2.71 g, 8.32 mmol) in acetonitrile (60 ml) was bubbled through with nitrogen for 30 seconds and then Xphos Pd G4 (143 mg, 0.17 mmol) was added. It was bubbled through with nitrogen for another 30 seconds. The reaction was heated at 100° C. for 3 h. It was diluted with EtOAc (180 ml), washed with water (60 ml), brine (60 ml), dried and concentrated. The crude residue was purified by ISCO using 0-20% MeOH in DCM to afford Example 148.

Step 2: Synthesis of 4-[1-(6-fluoro-1-methyl-[1,2,4]triazolo[4,3-a]quinazolin-5-yl)-3,5-dihydro-2H-4,1-benzoxazepin-6-yl]-2-methyl-but-3-yn-2-amine (Intermediate 148.1)

tert-butyl (4-(1-(6-fluoro-1-methyl-[1,2,4]triazolo[4,3-a]quinazolin-5-yl)-1,2,3,5-tetrahydrobenzo[e][1,4]oxazepin-6-yl)-2-methylbut-3-yn-2-yl)carbamate (Example 148, 2.37 g, 4.46 mmol) in DCM (40 mL was cooled to 0° C. and treated with TFA (12 ml). Reaction mixture was stirred at rt for 3 h and then concentrated to dryness. The reaction mixture was dissolved in 200 mL of DCM/EtOH (9/1) and 60 mL of saturated Na$_2$CO$_3$ (60 mL) was added slowly. The two layers were separated, and the organic layer was washed with brine, dried and concentrated to dryness. The crude was purified by ISCO using 5-30% MeOH in DCM to afford the desired amine as a yellow solid. LCMS-ESI+ (m/z): [M+H]$^+$= 431.24.

Step 3. Synthesis of Example 147: A mixture of 4-[1-(6-fluoro-1-methyl-[1,2,4]triazolo[4,3-a]quinazolin-5-yl)-3,5-dihydro-2H-4,1-benzoxazepin-6-yl]-2-methyl-but-3-yn-2-amine (1.30 g, 3.02 mmol) in DMF (20 mL) and DCM (10 mL) was cooled to 0° C. Triethylamine (0.76 mL, 5.44 mmol), 1-(trifluoromethyl) cyclopropane carboxylic acid (698 mg, 4.53 mmol) and HATU (1.72 g, 4.53 mmol) were added in sequence. After stirring at 0° C. for 2 h, reaction mixture was stirred at rt for another 2 h. 200 mL of EtOAc and 60 mL of water were added. The two layers were separated, and the organic layer was washed with brine, dried, concentrated to dryness. The resulting residue was purified by column chromatography using 5-15% MeOH in DCM to afford the title compound.

Example 149: 1,1,1-trifluoropropan-2-yl (4-(1-(6-fluoro-1-methyl-[1,2,4]triazolo[4,3-a]quinazolin-5-yl)-1,2,3,4-tetrahydroquinolin-5-yl)-2-methylbut-3-yn-2-yl)carbamate

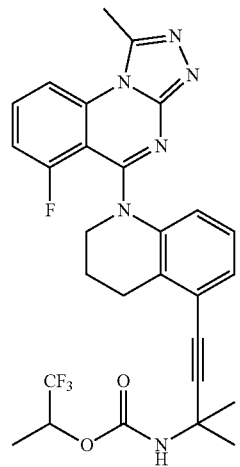 [SMILES: Cc1nnc2nc(N3CCCc4c(C#CC(C)(C)NC(=O)OC(C)C(F)(F)F)cccc43)c3c(F)cccc3n12]

The title compound was synthesized as described in Example 146 using 4-(1-(6-fluoro-1-methyl-[1,2,4]triazolo[4,3-a]quinazolin-5-yl)-1,2,3,4-tetrahydroquinolin-5-yl)-2-methylbut-3-yn-2-amine instead of 4-[1-(6-fluoro-1-methyl-[1,2,4]triazolo[4,3-a]quinazolin-5-yl)-3,5-dihydro-2H-4,1-benzoxazepin-6-yl]-2-methyl-but-3-yn-2-amine Example 150: Tert-Butyl (4-(1-(6-fluoro-1-methyl-[1,2,4]triazolo[4,3-a]quinazolin-5-yl)-1,2,3,4-tetrahydroquinolin-5-yl)-2-methylbut-3-yn-2-yl)carbamate Example 151: N-(4-(1-(6-fluoro-1-methyl-[1,2,4]triazolo[4,3-a]quinazolin-5-yl)-1,2,3,4-tetrahydroquinolin-5-yl)-2-methylbut-3-yn-2-yl)-1-(trifluoromethyl)cyclopropane-1-carboxamide

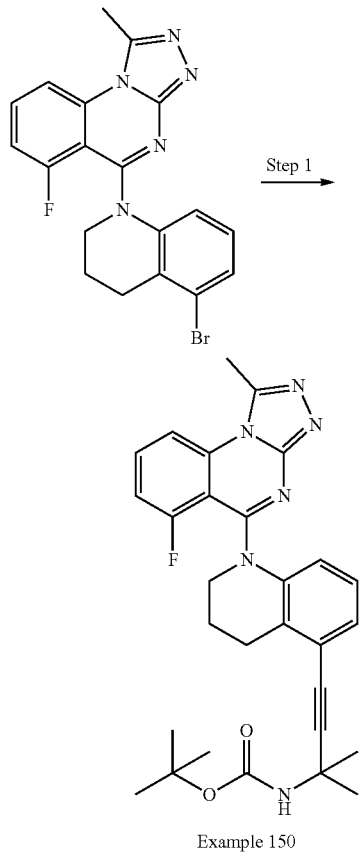
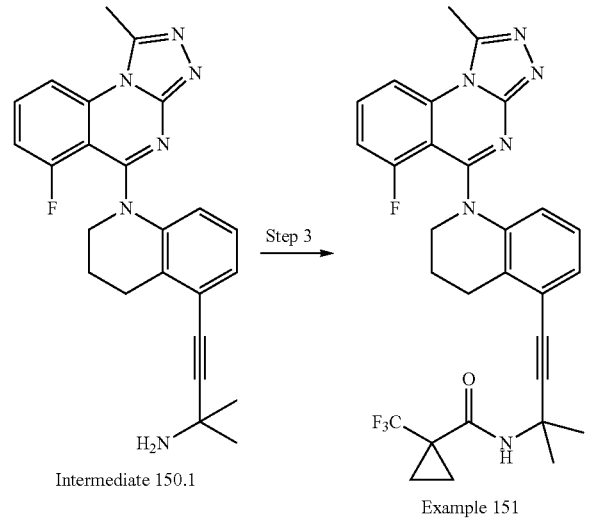

Step 1. Synthesis of Example 150: tert-butyl (4-(1-(6-fluoro-1-methyl-[1,2,4]triazolo[4,3-a]quinazolin-5-yl)-1,2,3,4-tetrahydroquinolin-5-yl)-2-methylbut-3-yn-2-yl)carbamate The title compound was synthesized as described in Example 148 using 5-(5-bromo-3,4-dihydroquinolin-1(2H)-yl)-6-fluoro-1-methyl-[1,2,4]triazolo[4,3-a]quinazoline instead of Intermediate 23.

Step 2: 4-(1-(6-fluoro-1-methyl-[1,2,4]triazolo[4,3-a]quinazolin-5-yl)-1,2,3,4-tetrahydroquinolin-5-yl)-2-methylbut-3-yn-2-amine (Intermediate 150.1) was synthesized according to procedure of step 2 for the synthesis of Example 147, LCMS-ESI+ (m/z): [M+H]$^+$=415.20.

Step 3: The title compound was synthesized as described in Example 147 using 4-(1-(6-fluoro-1-methyl-[1,2,4]triazolo[4,3-a]quinazolin-5-yl)-1,2,3,4-tetrahydroquinolin-5-yl)-2-methylbut-3-yn-2-amine instead of 4-[1-(6-fluoro-1-methyl-[1,2,4]triazolo[4,3-a]quinazolin-5-yl)-3,5-dihydro-2H-4,1-benzoxazepin-6-yl]-2-methyl-but-3-yn-2-amine.

Example 152: 4-(7-fluoro-1-(6-fluoro-1-methyl-[1,2,4]triazolo[4,3-a]quinazolin-5-yl)-1,2,3,4-tetrahydroquinolin-5-yl)-2-methylbut-3-yn-2-ol

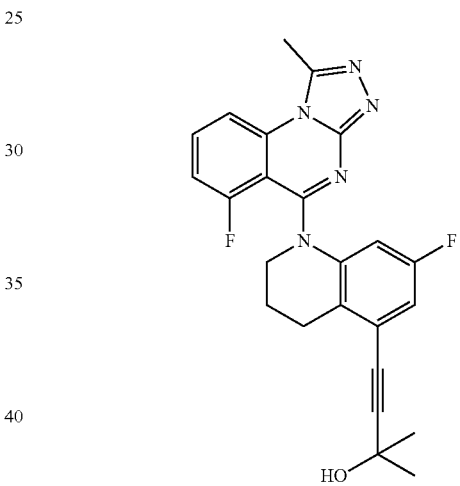

The title compound was prepared according to the general procedures described for Example 1.

Example 154: 1-[1-(6-fluoro-1-methyl-[1,2,4]triazolo[4,3-a]quinazolin-5-yl)-3,5-dihydro-2H-4,1-benzoxazepin-6-yl]-4-methyl-piperidine-4-carbonitrile

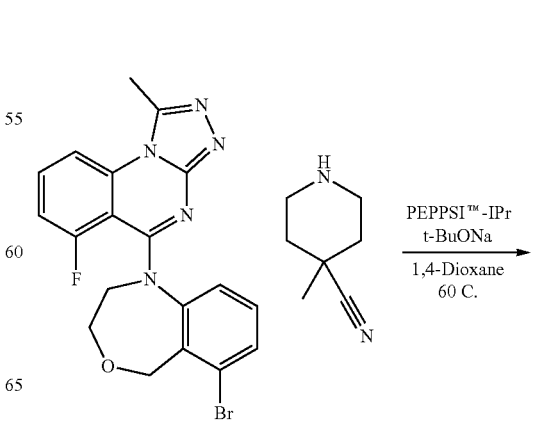

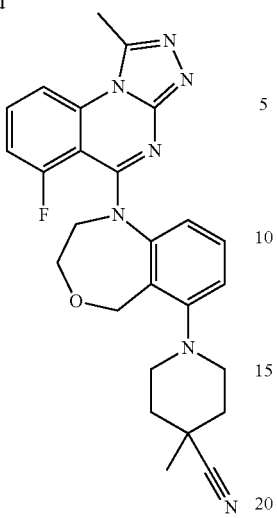

The title compound was synthesized as described in Example 155, using 6-bromo-1-(6-fluoro-1-methyl-[1,2,4]triazolo[4,3-a]quinazolin-5-yl)-3,5-dihydro-2H-4,1-benzoxazepine instead of 5-(5-bromo-3,4-dihydro-2H-quinolin-1-yl)-6-fluoro-1-methyl-[1,2,4]triazolo[4,3-a]quinazoline.

Example 155: 1-[1-(6-fluoro-1-methyl-[1,2,4]triazolo[4,3-a]quinazolin-5-yl)-3,4-dihydro-2H-quinolin-5-yl]-4-methyl-piperidine-4-carbonitrile

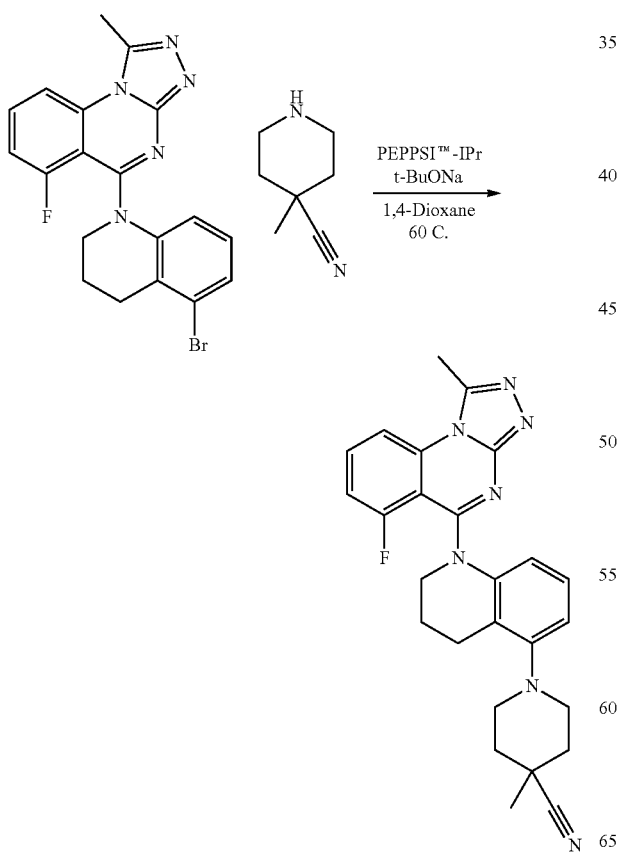

A solution of 5-(5-bromo-3,4-dihydro-2H-quinolin-1-yl)-6-fluoro-1-methyl-[1,2,4]triazolo[4,3-a]quinazoline (70 mg, 0.146 mmol), 4-methylpiperidine-4-carbonitrile (42 mg, 0.340 mmol), and PEPPSI™-IPr (5.79 mg, 8.49 μmol) in 1,4-dioxane (2 mL) was sparged with N₂ for 5 min, followed by the addition of t-BuONa (2M in THF, 0.297 mL, 0.594 mmol). The resulting solution was heated to 60° C. for 1 h, then quenched with AcOH (0.1 mL), diluted with MeCN, filtered through a plug of celite, and concentrated under reduced pressure. Purification via HPLC and subsequent lyophilization afforded the title compound.

Example 156: 6-fluoro-5-[5-(4-fluoro-4-methyl-1-piperidyl)-3,4-dihydro-2H-quinolin-1-yl]-1-methyl-[1,2,4]triazolo[4,3-a]quinazoline

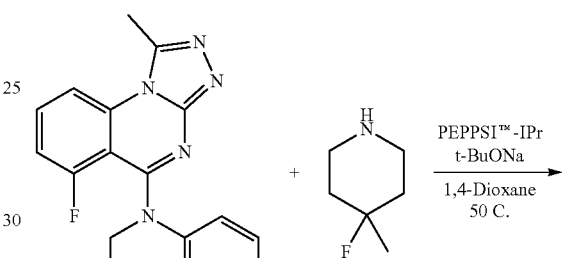

The title compound was synthesized as described in Example 157, using 4-fluoro-4-methyl-piperidine instead of 4,4-difluoropiperidine.

407

Example 157: 5-[5-(4,4-difluoro-1-piperidyl)-3,4-dihydro-2H-quinolin-1-yl]-6-fluoro-1-methyl-[1,2,4]triazolo[4,3-a]quinazoline

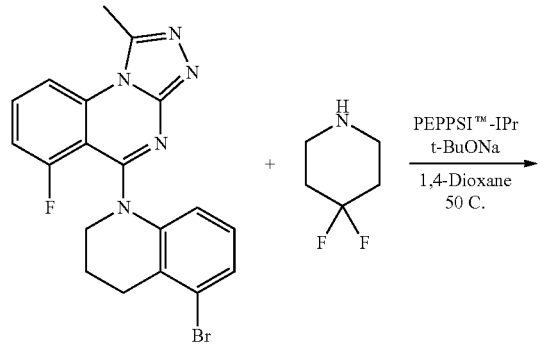

A solution of 5-(5-bromo-3,4-dihydro-2H-quinolin-1-yl)-6-fluoro-1-methyl-[1,2,4]triazolo[4,3-a]quinazoline (60 mg, 0.146 mmol), 4,4-difluoropiperidine (32.6 µL, 0.291 mmol), and PEPPSI™-IPr (4.96 mg, 7.28 µmol) in 1,4-dioxane (2 mL) was sparged with $N_2$ for 5 min, followed by the addition of t-BuONa (2M in THF, 0.109 mL, 0.218 mmol). The resulting solution was heated to 50° C. for 1 h, then cooled to room temperature and quenched with sat. aq. $NH_4Cl$. The resulting mixture was diluted with EtOAc and a minimal amount of MeOH (1 mL), filtered through celite, washed with a minimal amount of water (ca. 5 mL), then brine, dried over anhydrous magnesium sulfate, filtered, and concentrated under reduced pressure. Purification via HPLC and subsequent lyophilization afforded the title compound.

408

Example 158: 2,2-difluoro-1-[4-[1-(6-fluoro-1-methyl-[1,2,4]triazolo[4,3-a]quinazolin-5-yl)-3,4-dihydro-2H-quinolin-5-yl]piperazin-1-yl]ethanone

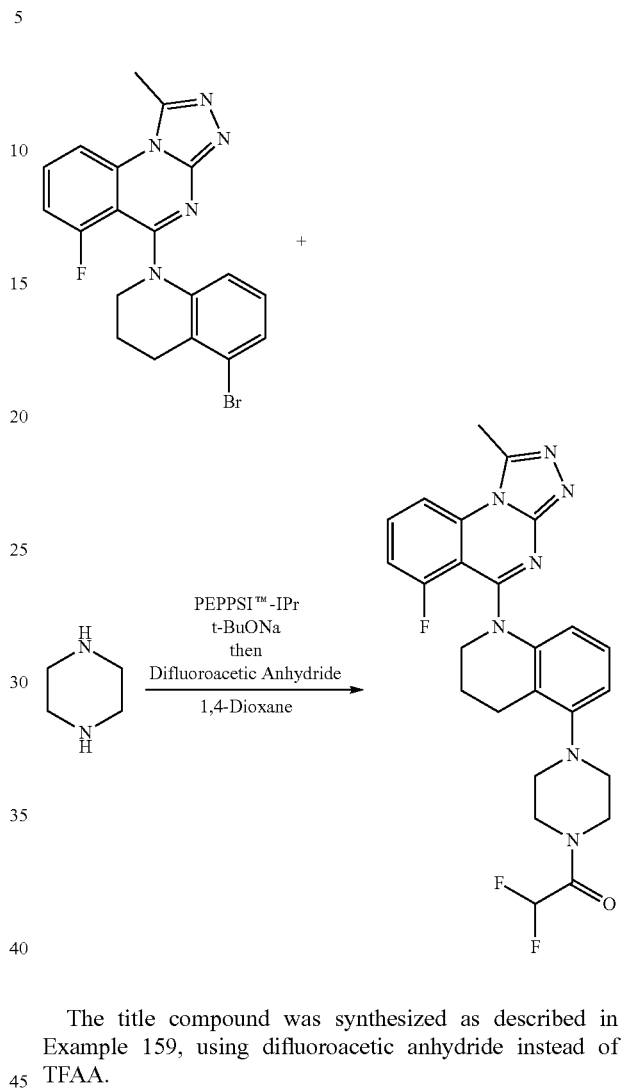

The title compound was synthesized as described in Example 159, using difluoroacetic anhydride instead of TFAA.

Example 159: 6-fluoro-1-methyl-5-(5-piperazin-1-yl-3,4-dihydro-2H-quinolin-1-yl)-[1,2,4]triazolo[4,3-a]quinazoline

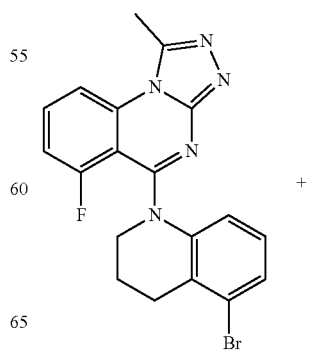

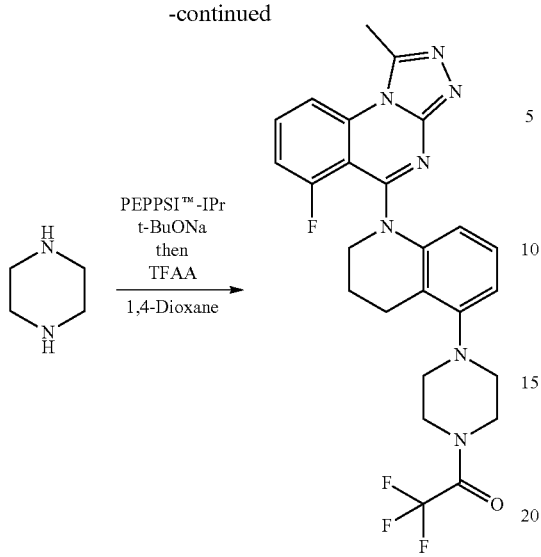

A solution of 5-(5-bromo-3,4-dihydro-2H-quinolin-1-yl)-6-fluoro-1-methyl-[1,2,4]triazolo[4,3-a]quinazoline (200 mg, 0.485 mmol), piperazine (46 mg, 0.534 mmol), and PEPPSI™-IPr (16.5 mg, 24.3 μmol) in 1,4-dioxane (7 mL) was sparged with N₂ for 5 min, followed by the addition of t-BuONa (2M in THF, 0.364 mL, 0.728 mmol). The resulting solution was heated to 50° C. for 1 h, then cooled to room temperature. TFAA (0.169 mL, 1.21 mmol) was added and the reaction mixture was stirred at room temperature for 20 min, then poured into water, extracted with EtOAc, washed with brine, dried over anhydrous magnesium sulfate, filtered, and concentrated under reduced pressure. Purification via column (gradient elution with EtOAc:MeOH (4:1)/DCM; elution at ca. 45%) afforded the title compound.

Example 160: 6-fluoro-1-methyl-5-[5-(4-methyl-sulfonylpiperazin-1-yl)-3,4-dihydro-2H-quinolin-1-yl]-[1,2,4]triazolo[4,3-a]quinazoline

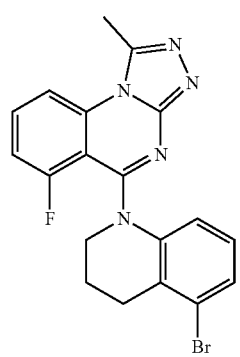

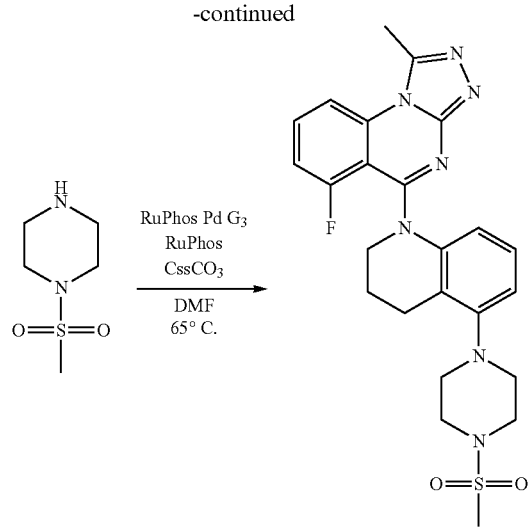

The title compound was synthesized as described in Example 161, using 1-methylsulfonylpiperazine instead of tert-butyl piperazine-1-carboxylate, and at 65° C. instead of at 130° C. This afforded the title compound as an amorphous yellow solid.

Example 161: tert-butyl 4-[1-(6-fluoro-1-methyl-[1,2,4]triazolo[4,3-a]quinazolin-5-yl)-3,4-dihydro-2H-quinolin-5-yl]piperazine-1-carboxylate To a solution of 5-(5-bromo-3,4-dihydro-2H-quinolin-1-yl)-6-fluoro-1-methyl-[1,2,4]triazolo[4,3-a]quinazoline (100 mg, 0.243 mmol) and tert-butyl piperazine-1-carboxylate (67.8 mg, 0.364 mmol) in DMF (2.5 mL) was added RuPhos Pd G3 (10.1 mg, 12.1 μmol), RuPhos (5.4 mg, 12.1 μmol), and Cs₂CO₃ (237 mg, 0.728 mmol). The resulting mixture was then heated to 130° C. for 6 h, then cooled to room temperature, poured into water, extracted with EtOAc, washed with water (2×), the brine, dried over anhydrous magnesium sulfate, filtered, and concentrated under reduced pressure. Purification via flash chromatography (gradient elution with EtOAc:MeOH (4:1) in DCM: 0-35%) afforded the title compound.

Example 162: 6-fluoro-1-methyl-5-[4-methyl-6-(4,4,4-trifluoro-3,3-dimethyl-but-1-ynyl)-3,5-dihydro-2H-1,4-benzodiazepin-1-yl]-[1,2,4]triazolo[4,3-a]quinazoline Example 163: 6-(6,6-difluoro-3-azabicyclo[3.1.1]heptan-3-yl)-1-(6-fluoro-1-methyl-[1,2,4]triazolo[4,3-a]quinazolin-5-yl)-3,5-dihydro-2H-4,1-benzoxazepine

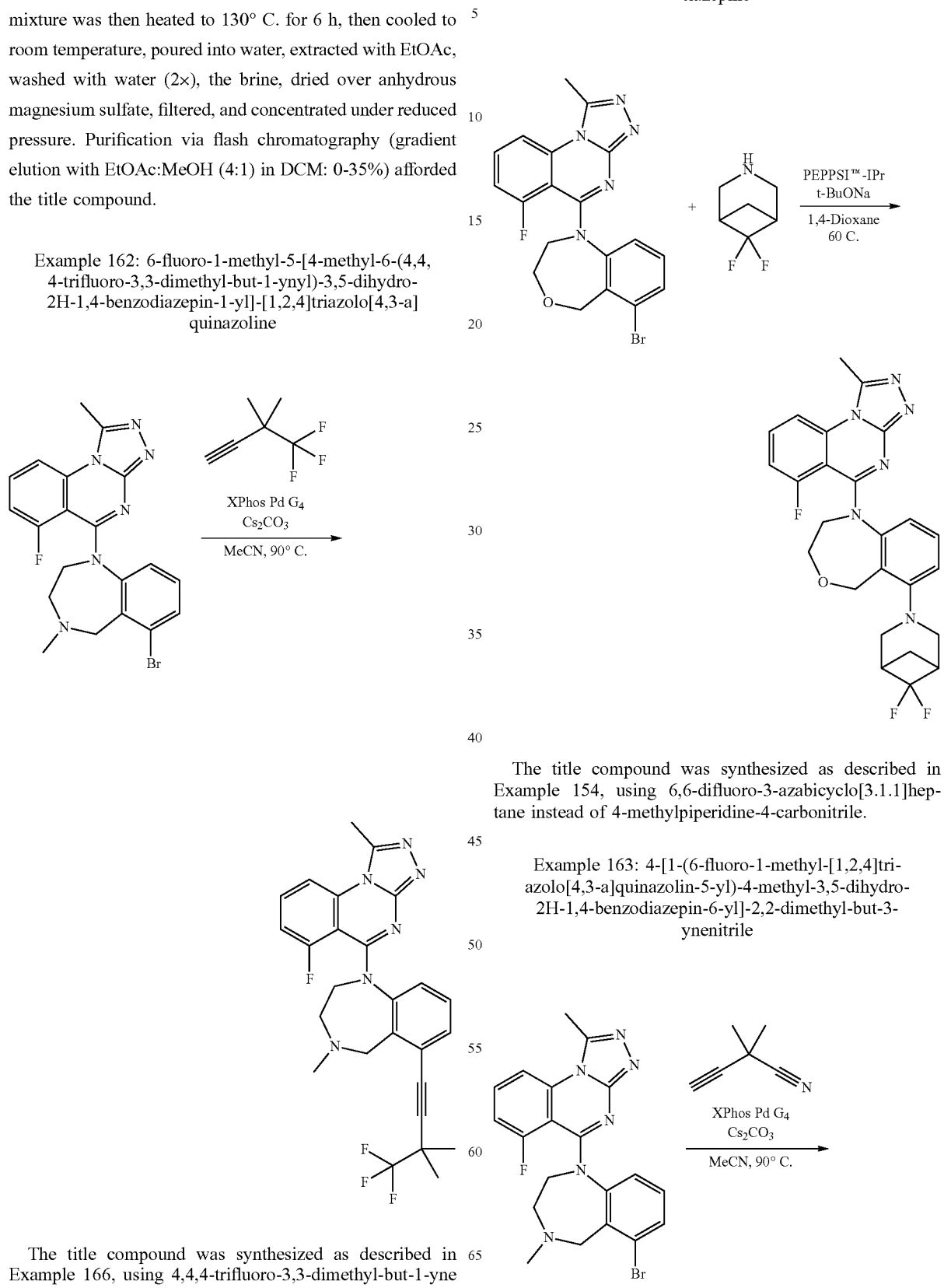

The title compound was synthesized as described in Example 154, using 6,6-difluoro-3-azabicyclo[3.1.1]heptane instead of 4-methylpiperidine-4-carbonitrile.

Example 163: 4-[1-(6-fluoro-1-methyl-[1,2,4]triazolo[4,3-a]quinazolin-5-yl)-4-methyl-3,5-dihydro-2H-1,4-benzodiazepin-6-yl]-2,2-dimethyl-but-3-ynenitrile The title compound was synthesized as described in Example 166, using 4,4,4-trifluoro-3,3-dimethyl-but-1-yne instead of 1-(1,1-difluoroethyl)-1-ethynyl-cyclopropane.

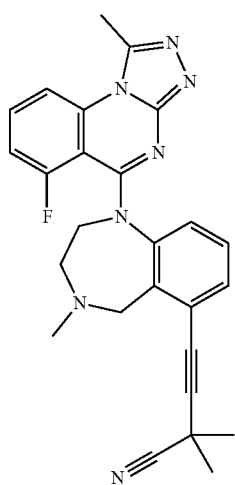

The title compound was synthesized as described in Example 166, using 2,2-dimethylbut-3-ynenitrile instead of 1-(1,1-difluoroethyl)-1-ethynyl-cyclopropane.

Example 164: 6-fluoro-1-methyl-5-[4-methyl-6-[2-[1-(trifluoromethyl)cyclopropyl]ethynyl]-3,5-dihydro-2H-1,4-benzodiazepin-1-yl]-[1,2,4]triazolo[4,3-a]quinazoline

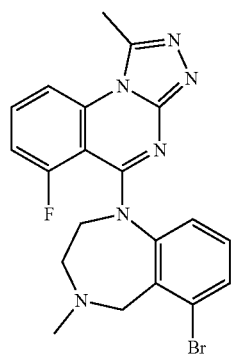 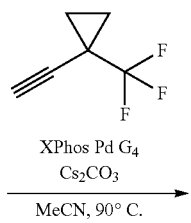

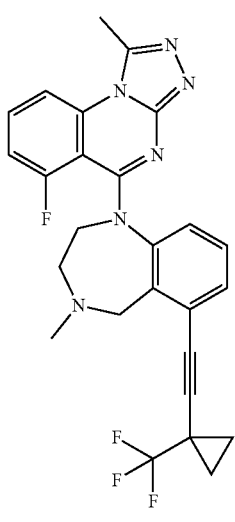

The title compound was synthesized as described in Example 166, using 1-ethynyl-1-(trifluoromethyl)cyclopropane instead of 1-(1,1-difluoroethyl)-1-ethynyl-cyclopropane.

Example 165: 6-fluoro-1-methyl-5-[4-methyl-6-[2-(1-methylcyclopropyl)ethynyl]-3,5-dihydro-2H-1,4-benzodiazepin-1-yl]-[1,2,4]triazolo[4,3-a]quinazoline

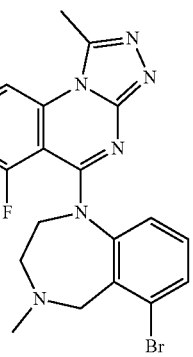 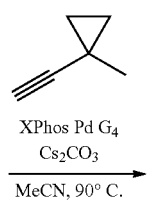

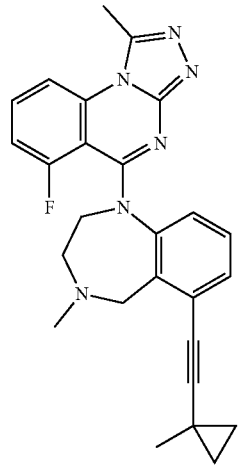

The title compound was synthesized as described in Example 166, using 1-ethynyl-1-methyl-cyclopropane instead of 1-(1,1-difluoroethyl)-1-ethynyl-cyclopropane. This afforded the title compound as an amorphous yellow solid.

Example 166: 5-[6-[2-[1-(1,1-difluoroethyl)cyclopropyl]ethynyl]-4-methyl-3,5-dihydro-2H-1,4-benzodiazepin-1-yl]-6-fluoro-1-methyl-[1,2,4]triazolo[4,3-a]quinazoline

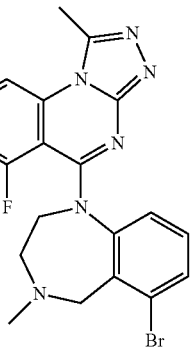 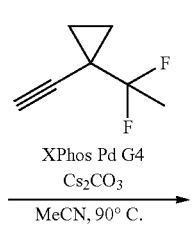

415
-continued

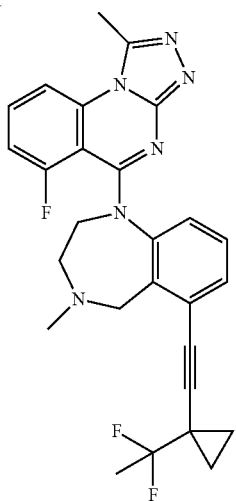

The title compound was synthesized as described in Example 169, using 5-(6-bromo-4-methyl-3,5-dihydro-2H-1,4-benzodiazepin-1-yl)-6-fluoro-1-methyl-[1,2,4]triazolo[4,3-a]quinazoline instead of 5-(6-bromo-4-methyl-3,5-di-hydro-2H-1,4-benzodiazepin-1-yl)-6,7-difluoro-1-methyl-[1,2,4]triazolo[4,3-a]quinazoline and 1-(1,1-difluoroethyl)-1-ethynyl-cyclopropane instead of 1-ethynyl-1-(trifluoromethyl)cyclopropane.

Example 167: 9-(2-cyclopropylethynyl)-5-(6,7-difluoro-1-methyl-[1,2,4]triazolo[4,3-a]quinazolin-5-yl)-3,4-dihydro-2H-pyrido[4,3-b][1,4]oxazepine

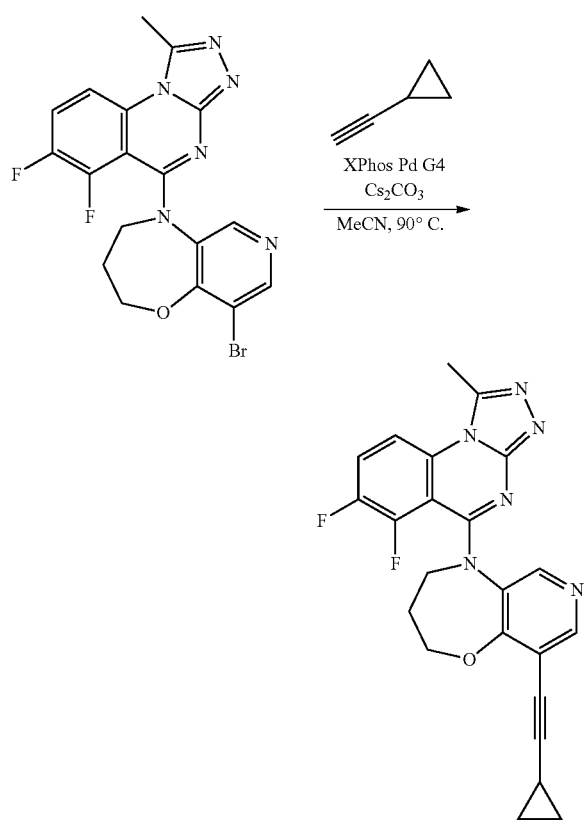

416

To a vial charged with 9-bromo-5-(6,7-difluoro-1-methyl-[1,2,4]triazolo[4,3-a]quinazolin-5-yl)-3,4-dihydro-2H-pyrido[4,3-b][1,4]oxazepine (35.0 mg, 74.3 µmol), XPhos Pd G4 (3.2 mg, 3.72 µmol), and $Cs_2CO_3$ (60.6 mg, 0.186 mmol) was added MeCN (1 mL). The resulting mixture was then sparged with $N_2$ for 5 min, followed by the addition of ethynylcyclopropane (14.7 mg, 223 µmol). The reaction mixture was then heated to 90° C. for 1 h, then cooled to room temperature, diluted with EtOAc, and filtered through a plug of Celite, and concentrated under reduced pressure. Purification via HPLC and subsequent lyophilization afforded the title compound.

Example 168: 6,7-difluoro-1-methyl-5-[4-methyl-6-(4,4,4-trifluoro-3,3-dimethyl-but-1-ynyl)-3,5-dihydro-2H-1,4-benzodiazepin-1-yl]-[1,2,4]triazolo[4,3-a]quinazoline

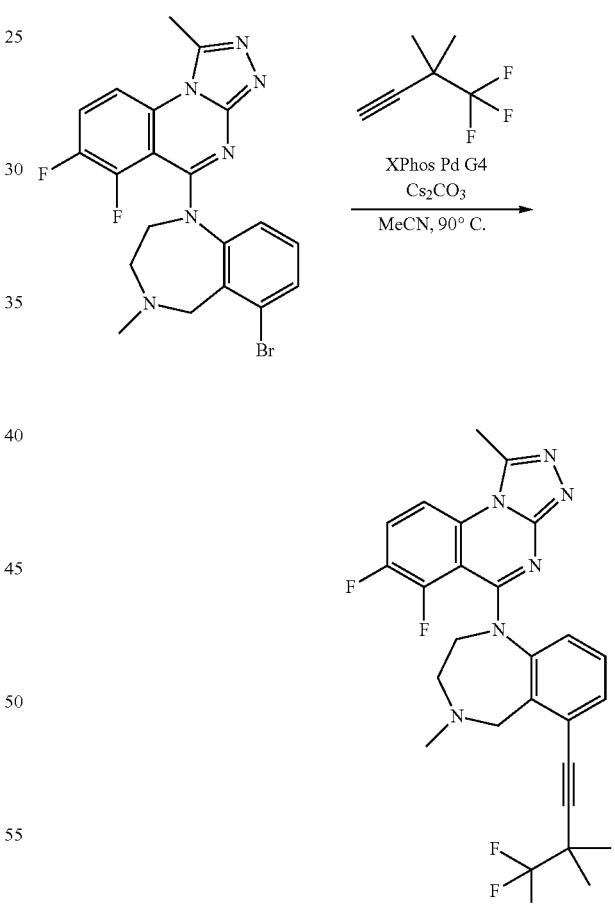

The title compound was synthesized as described in Example 167, using 5-(6-bromo-4-methyl-3,5-dihydro-2H-1,4-benzodiazepin-1-yl)-6,7-difluoro-1-methyl-[1,2,4]triazolo[4,3-a]quinazoline instead of 9-bromo-5-(6,7-difluoro-1-methyl-[1,2,4]triazolo[4,3-a]quinazolin-5-yl)-2,3,4,5-tetrahydropyrido[4,3-b][1,4]oxazepine and 4,4,4-trifluoro-3,3-dimethyl-but-1-yne instead of ethynylcyclopropane.

Example 169: 6,7-difluoro-1-methyl-5-[4-methyl-6-[2-[1-(trifluoromethyl)cyclopropyl]ethynyl]-3,5-dihydro-2H-1,4-benzodiazepin-1-yl]-[1,2,4]triazolo[4,3-a]quinazoline

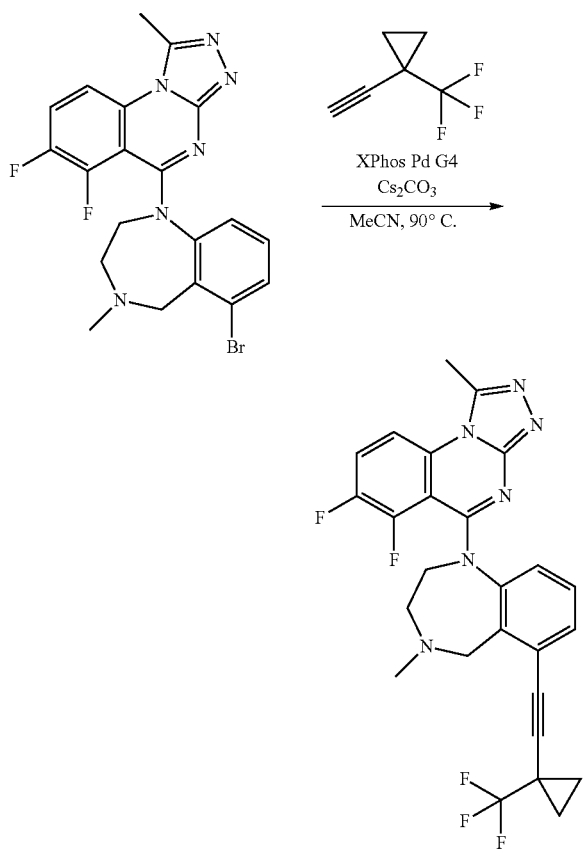

The title compound was synthesized as described in Example 167, using 5-(6-bromo-4-methyl-3,5-dihydro-2H-1,4-benzodiazepin-1-yl)-6,7-difluoro-1-methyl-[1,2,4]triazolo[4,3-a]quinazoline instead of 9-bromo-5-(6,7-difluoro-1-methyl-[1,2,4]triazolo[4,3-a]quinazolin-5-yl)-2,3,4,5-tetrahydropyrido[4,3-b][1,4]oxazepine and 1-ethynyl-1-(trifluoromethyl)cyclopropane instead of ethynylcyclopropane.

Example 170: 4-[1-(7-fluoro-1-methyl-[1,2,4]triazolo[4,3-a]quinazolin-5-yl)-4-methyl-3,5-dihydro-2H-1,4-benzodiazepin-6-yl]-2-methyl-but-3-yn-2-ol

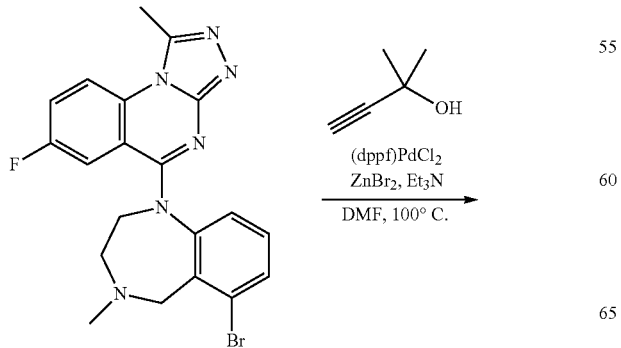

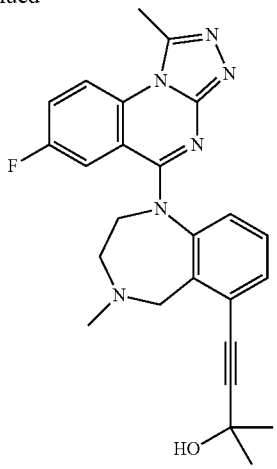

The title compound was synthesized as described in Example 172, using 2-methylbut-3-yn-2-ol instead of 1-ethynyl-1-(trifluoromethyl)cyclopropane.

Example 171: 7-fluoro-1-methyl-5-[4-methyl-6-(4,4,4-trifluoro-3,3-dimethyl-but-1-ynyl)-3,5-dihydro-2H-1,4-benzodiazepin-1-yl]-[1,2,4]triazolo[4,3-a]quinazoline

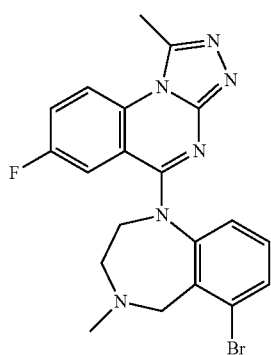

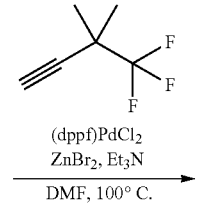

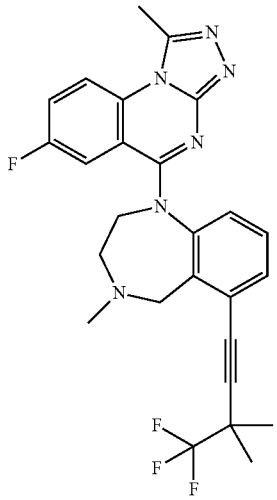

The title compound was synthesized as described in Example 172, using 4,4,4-trifluoro-3,3-dimethyl-but-1-yne instead of 1-ethynyl-1-(trifluoromethyl)cyclopropane.

Example 172: 7-fluoro-1-methyl-5-[4-methyl-6-[2-[1-(trifluoromethyl)cyclopropyl]ethynyl]-3,5-dihydro-2H-1,4-benzodiazepin-1-yl]-[1,2,4]triazolo[4,3-a]quinazoline

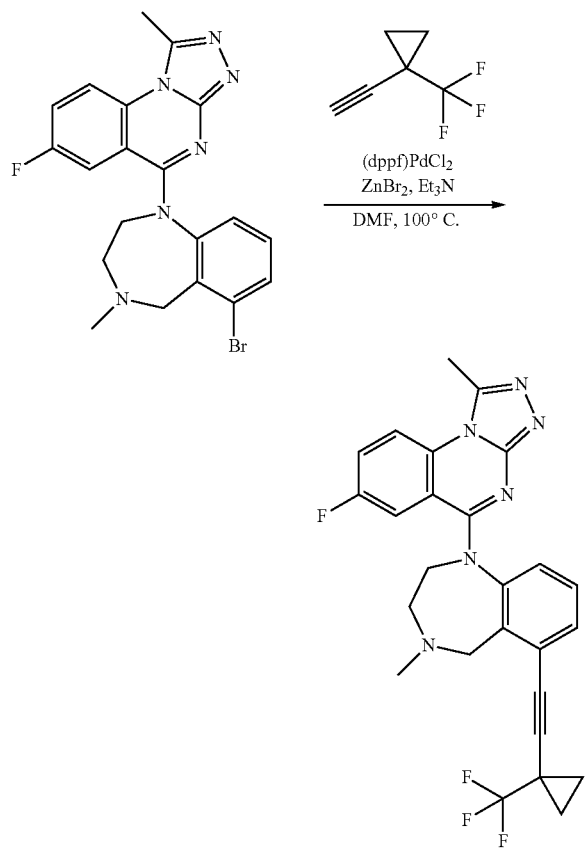

The title compound was synthesized as described in Example 175, using 5-(6-bromo-4-methyl-3,5-dihydro-2H-1,4-benzodiazepin-1-yl)-7-fluoro-1-methyl-[1,2,4]triazolo[4,3-a]quinazoline instead of 5-(5-bromo-3,4-dihydro-2H-quinolin-1-yl)-[1,2,4]triazolo[4,3-a]quinazoline.

Example 173: 5-(7-fluoro-1-methyl-[1,2,4]triazolo[4,3-a]quinazolin-5-yl)-9-[2-(1-methylcyclopropyl)ethynyl]-3,4-dihydro-2H-pyrido[4,3-b][1,4]oxazepine

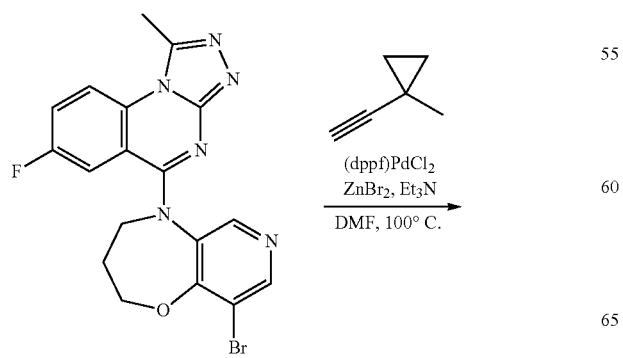

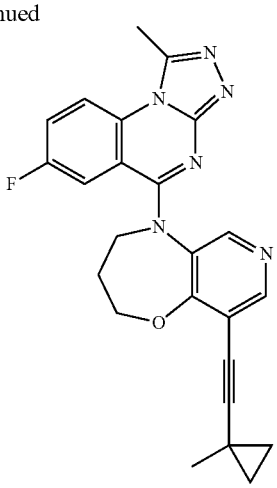

To a vial charged with 9-bromo-5-(7-fluoro-1-methyl-[1,2,4]triazolo[4,3-a]quinazolin-5-yl)-3,4-dihydro-2H-pyrido[4,3-b][1,4]oxazepine (25.0 mg, 58.2 μmol), (dppf)PdCl$_2$ (4.81 mg, 5.8 μmol), and ZnBr$_2$ (65.6 mg, 0.291 mmol) was added DMF (1 mL) and Et$_3$N (0.162 mL, 1.16 mmol). The resulting mixture was then sparged with N$_2$ for 5 min, followed by the addition of 1-ethynyl-1-methyl-cyclopropane (6 mg, 72.8 μmol). The reaction mixture was then heated to 100° C. for 1 h, then cooled to room temperature, diluted with EtOAc, and filtered through a plug of Celite. The filtrate was then diluted with water, extracted with EtOAc, washed with water (2×), then brine, dried with anhydrous magnesium sulfate, filtered, and concentrated under reduced pressure. Purification via HPLC and subsequent lyophilization afforded the title compound.

Example 174: 2-methyl-4-[1-([1,2,4]triazolo[4,3-a]quinazolin-5-yl)-3,4-dihydro-2H-quinolin-5-yl]but-3-yn-2-ol

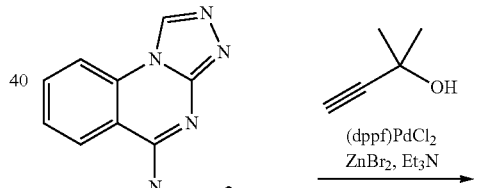

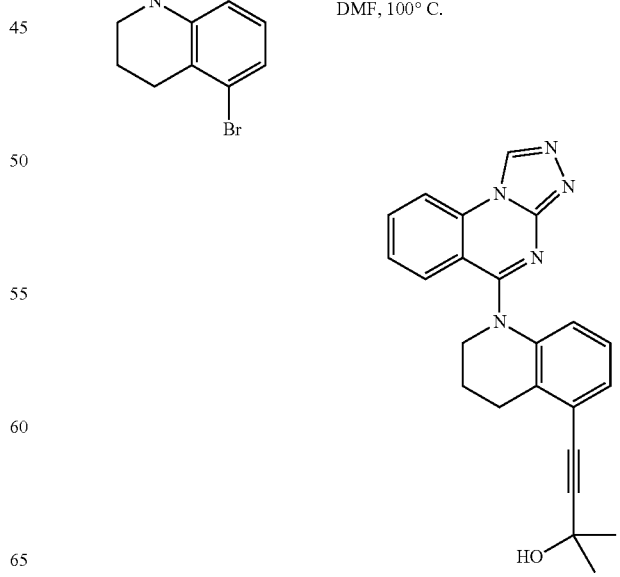

421

The title compound was synthesized as described in Example 175, using 2-methylbut-3-yn-2-ol instead of 1-ethynyl-1-(trifluoromethyl)cyclopropane.

Example 175: 5-[5-[2-[1-(trifluoromethyl)cyclopropyl]ethynyl]-3,4-dihydro-2H-quinolin-1-yl]-[1,2,4]triazolo[4,3-a]quinazoline

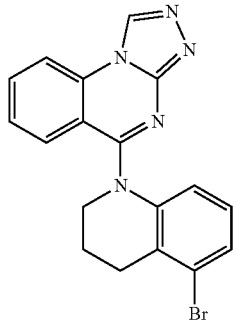 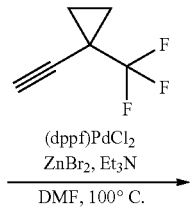

(dppf)PdCl$_2$
ZnBr$_2$, Et$_3$N
⟶
DMF, 100° C.

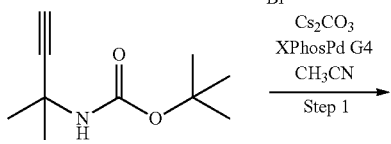

To a vial charged with 5-(5-bromo-3,4-dihydro-2H-quinolin-1-yl)-[1,2,4]triazolo[4,3-a]quinazoline (22.6 mg, 59.4 μmol), (dppf)PdCl$_2$ (4.91 mg, 5.9 μmol), and ZnBr$_2$ (70 mg, 0.297 mmol) was added DMF (1 mL) and Et$_3$N (0.162 mL, 1.16 mmol). The resulting mixture was then sparged with N$_2$ for 5 min, followed by the addition of 1-ethynyl-1-(trifluoromethyl)cyclopropane (10 mg, 74.6 μmol). The reaction mixture was then heated to 100° C. for 10 min, then cooled to room temperature, diluted with EtOAc, and filtered through a plug of Celite. The filtrate was then diluted with water, extracted with EtOAc, washed with water (2×), then brine, dried with anhydrous magnesium sulfate, filtered, and concentrated under reduced pressure. Purification via HPLC and subsequent lyophilization afforded the title compound.

422

Example 176: N-[3-[1-(6,7-Difluoro-1-methyl-[1,2,4]triazolo[4,3-a]quinazolin-5-yl)-3,5-dihydro-2H-4,1-benzoxazepin-6-yl]-1,1-dimethyl-prop-2-ynyl]-1-(trifluoromethyl)cyclopropanecarboxamide

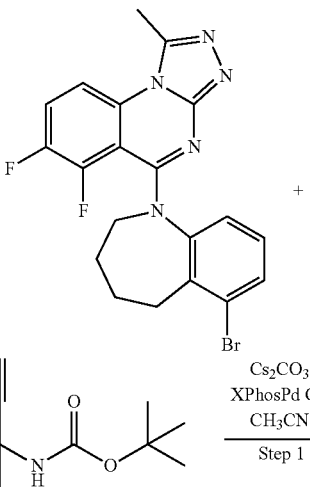

+

Cs$_2$CO$_3$
XPhosPd G4
CH$_3$CN
⟶
Step 1

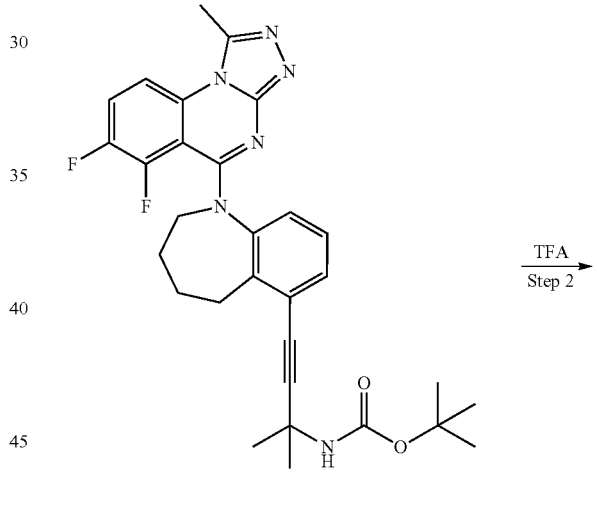

TFA
⟶
Step 2

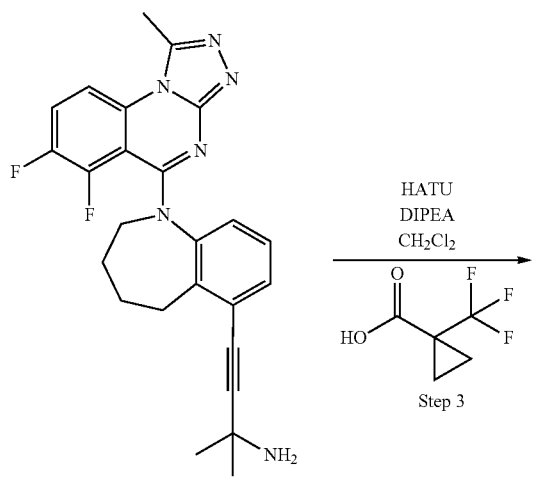

HATU
DIPEA
CH$_2$Cl$_2$
⟶
Step 3

-continued

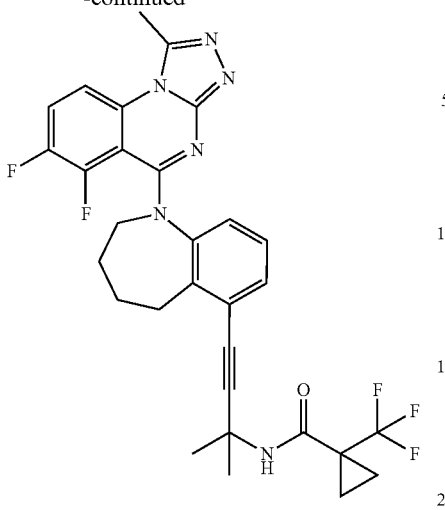

Step 1: tert-Butyl (4-(1-(6,7-difluoro-1-methyl-[1,2,4]triazolo[4,3-a]quinazolin-5-yl)-2,3,4,5-tetrahydro-1H-benzo[b]azepin-6-yl)-2-methylbut-3-yn-2-yl)carbamate was synthesized in the similar fashion as step 2 of Example 183 using 5-(6-bromo-2,3,4,5-tetrahydro-1H-benzo[b]azepin-1-yl)-6,7-difluoro-1-methyl-[1,2,4]triazolo[4,3-a]quinazoline and tert-butyl (1-ethynylcyclopropyl)carbamate. LCMS-ESI+ (m/z): [M+H]+ calcd for $C_{30}H_{32}F_2N_6O_2$: 547.26 (M+1), found: 547.25 (M+1).

Step 2: 4-(1-(6,7-difluoro-1-methyl-[1,2,4]triazolo[4,3-a]quinazolin-5-yl)-2,3,4,5-tetrahydro-1H-benzo[b]azepin-6-yl)-2-methylbut-3-yn-2-amine was synthesized in the similar fashion as step 2 of Example 177 using tert-butyl (4-(1-(6,7-difluoro-1-methyl-[1,2,4]triazolo[4,3-a]quinazolin-5-yl)-2,3,4,5-tetrahydro-1H-benzo[b]azepin-6-yl)-2-methylbut-3-yn-2-yl)carbamate: LCMS-ESI+ (m/z): [M+H]+ calcd for $C_{25}H_{24}F_2N_6$: 447.20 (M+1), found: 447.15 (M+1).

Step 3: Example 176 was synthesized in the similar fashion as step 1 of Example 183 using 1-(trifluoromethyl)cyclopropane-1-carboxylic acid.

Example 177: N-(1-((1-(6-Fluoro-1-methyl-[1,2,4]triazolo[4,3-a]quinazolin-5-yl)-2,3,4,5-tetrahydro-1H-benzo[b]azepin-6-yl)ethynyl)cyclopropyl)-1-(trifluoromethyl)cyclopropane-1-carboxamide

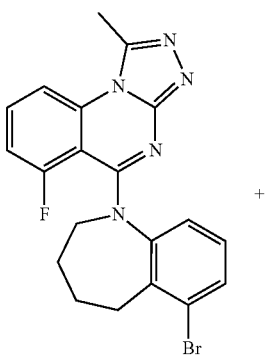

+

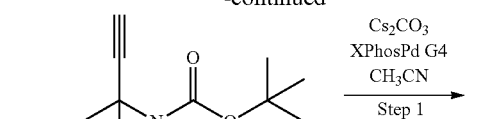

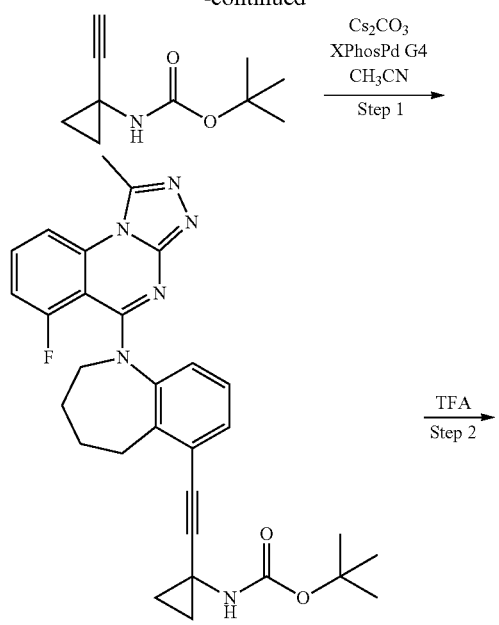

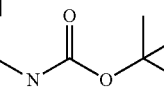

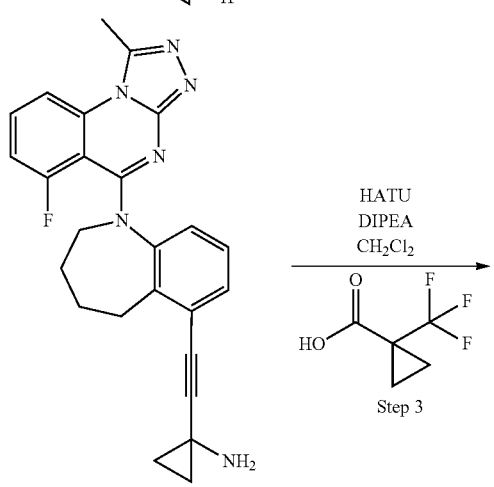

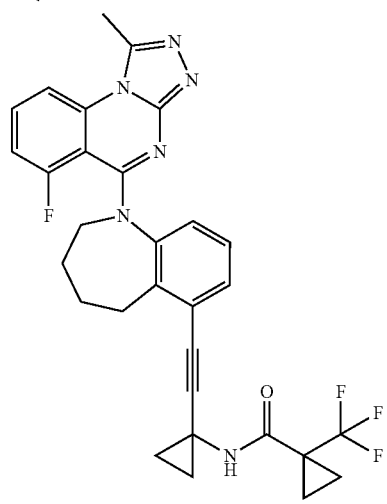

Step 1: tert-Butyl (1-((1-(6-fluoro-1-methyl-[1,2,4]triazolo[4,3-a]quinazolin-5-yl)-2,3,4,5-tetrahydro-1H-benzo[b]azepin-6-yl)ethynyl)cyclopropyl)carbamate was synthesized in the similar fashion as step 2 of Example 183 using tert-butyl (1-ethynylcyclopropyl)carbamate. LCMS-ESI+ (m/z): [M+H]+ calcd for $C_{30}H_{31}FN_6O_2$: 565.23 (M+1), found: 527.28 (M+1).

Step 2: Preparation of 1-((1-(6-fluoro-1-methyl-[1,2,4]triazolo[4,3-a]quinazolin-5-yl)-2,3,4,5-tetrahydro-1H-benzo[b]azepin-6-yl)ethynyl)cyclopropan-1-amine: tert-Butyl (1-((1-(6-fluoro-1-methyl-[1,2,4]triazolo[4,3-a]quinazolin-5-yl)-2,3,4,5-tetrahydro-1H-benzo[b]azepin-6-yl)ethynyl)cyclopropyl)carbamate (17.4 mg, 0.033 mmol) was treated with TFA (0.5 mL) in $CH_3CN$ (3 mL) at rt for 2 h. The reaction mixture was diluted in EtOAc (70 mL) and washed with sat. $NaHCO_3$ (30 mL×2) and brine (30 mL×2). The organic layer was dried over $Na_2SO_4$. The solvent was remove under a reduced pressure to give 1-((1-(6-fluoro-1-methyl-[1,2,4]triazolo[4,3-a]quinazolin-5-yl)-2,3,4,5-tetrahydro-1H-benzo[b]azepin-6-yl)ethynyl)cyclopropan-1-amine: LCMS-ESI+ (m/z): [M+H]+ calcd for $C_{25}H_{23}FN_6$: 427.20 (M+1), found: 427.33 (M+1).

Step 3: Example 177 was synthesized in the similar fashion as step 1 of Example 183 using 1-(trifluoromethyl) cyclopropane-1-carboxylic acid.

Example 178: 1-(Difluoromethyl)-N-[3-[1-(6-fluoro-1-methyl-[1,2,4]triazolo[4,3-a]quinazolin-5-yl)-3,5-dihydro-2H-4,1-benzoxazepin-6-yl]-1,1-dimethyl-prop-2-ynyl]cyclopropanesulfonamide

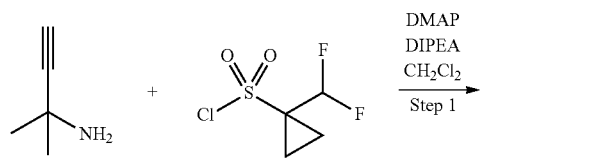

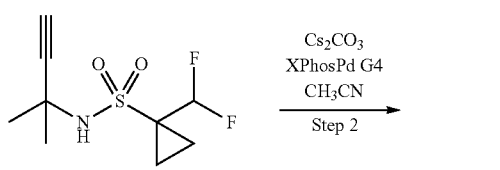

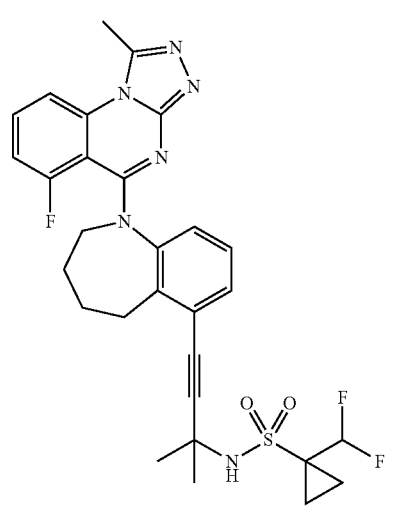

Step 1: Preparation of 1-(difluoromethyl)-N-(1,1-dimethylprop-2-ynyl)cyclopropanesulfonamide: was synthesized in the similar fashion as the step 1 of Example 183 2-Methylbut-3-yn-2-amine (100.0 mg, 1.20 mmol) was treated with 1-(difluoromethyl)cyclopropanesulfonyl chloride (229 mg, 1.20 mmol, 1 equiv.) in the presence of DMAP (147 mg, 1.20 mmol, 1.0 equiv.) and DIPEA (466 mg, 3.61 mmol, 3 equiv.) in $CH_2Cl_2$ (1 mL) at rt for 18 h. The reaction mixture was quenched with water (30 mL). The whole was extracted with EtOAc (30 mL×3). Organic layer was washed with brine (30 mL) and dried over Na2SO4. The organic solvent was removed under a reduced pressure. Obtained crude mixture was purified by a silica-gel column chromatography ($SiO_2$=12 g, 0% to 20% EtOAc/hexane) to give 1-(difluoromethyl)-N-(1,1-dimethylprop-2-ynyl)cyclopropanesulfonamide. $^1$H NMR (400 MHz, Methanol-$d_4$) δ 6.51 (t, J=56.7 Hz, 1H), 2.85 (s, 1H), 1.58 (s, 6H), 1.49 (ddd, J=4.0, 2.9, 2.0 Hz, 2H), 1.36-1.23 (m, 2H).

Step 2: Example 178 was synthesized in the similar fashion as the step 2 of Example 183 from 6-bromo-1-(6-fluoro-1-methyl-[1,2,4]triazolo[4,3-a]quinazolin-5-yl)-3,5-dihydro-2H-4,1-benzoxazepine and 1-(difluoromethyl)-N-(1,1-dimethylprop-2-ynyl)cyclopropanesulfonamide.

Example 179: 1-(6-Fluoro-1-methyl-[1,2,4]triazolo[4,3-a]quinazolin-5-yl)-6-[2-(2-methyloxazol-4-yl)ethynyl]-3,5-dihydro-2H-4,1-benzoxazepine

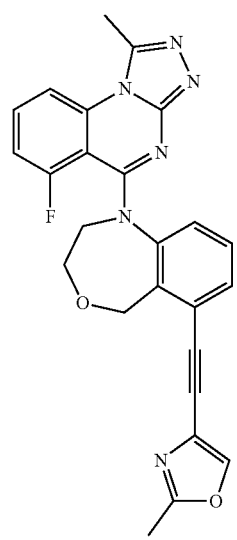 [SMILES: Cc1nc(C#Cc2cccc3c2COCCN3c2nc3nnc(C)n3c3cccc(F)c23)co1]

Example 179 1-(6-Fluoro-1-methyl-[1,2,4]triazolo[4,3-a]quinazolin-5-yl)-6-[2-(2-methyloxazol-4-yl)ethynyl]-3,5-dihydro-2H-4,1-benzoxazepine was synthesized in the similar fashion as the step 2 of Example 183 using 4-ethynyl-2-methyl-oxazole.

427

Example 180: 3,3-Difluoro-N-[3-[1-(6-fluoro-1-methyl-[1,2,4]triazolo[4,3-a]quinazolin-5-yl)-3,5-dihydro-2H-4,1-benzoxazepin-6-yl]-1,1-dimethyl-prop-2-ynyl]-2,2-dimethyl-butanamide

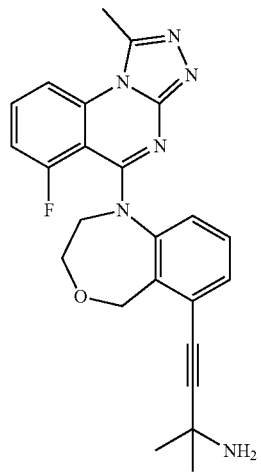

+

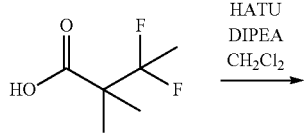

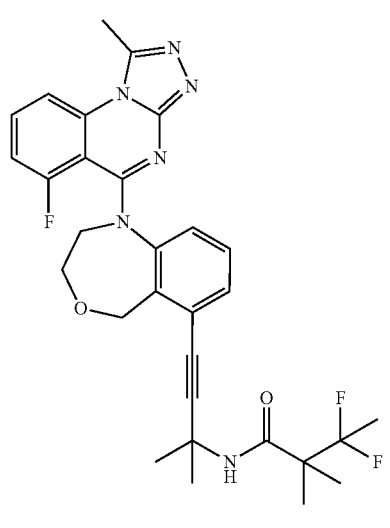

Example 180 was synthesized in the similar fashion as step 1 of Example 183 using 4-[1-(6-fluoro-1-methyl-[1,2,4]triazolo[4,3-a]quinazolin-5-yl)-3,5-dihydro-2H-4,1-benzoxazepin-6-yl]-2-methyl-but-3-yn-2-amine and 3,3-difluoro-2,2-dimethyl-butanoic acid.

428

Example 181: 1-(1,1-Difluoroethyl)-N-[3-[1-(6-fluoro-1-methyl-[1,2,4]triazolo[4,3-a]quinazolin-5-yl)-3,5-dihydro-2H-4,1-benzoxazepin-6-yl]-1,1-dimethyl-prop-2-ynyl]cyclopropanecarboxamide

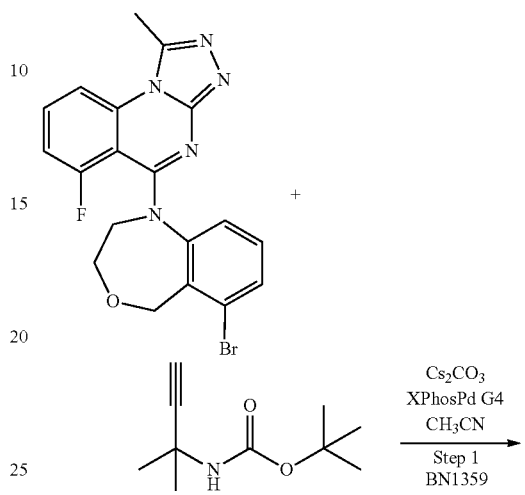

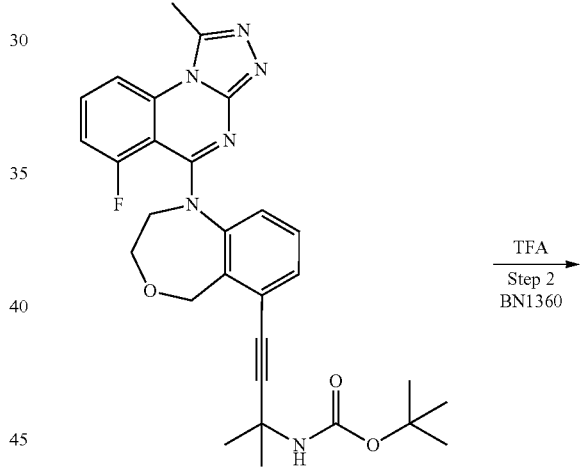

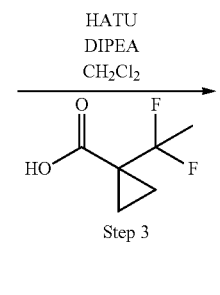

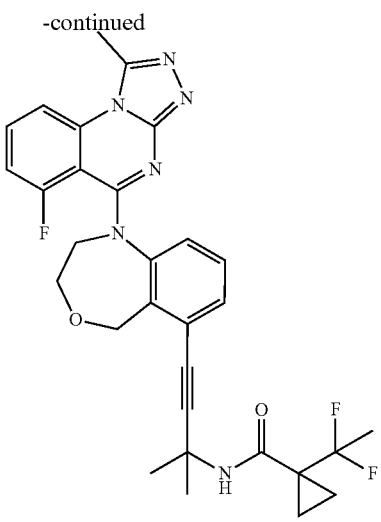

Step 1: tert-Butyl N-[3-[1-(6-fluoro-1-methyl-[1,2,4]triazolo[4,3-a]quinazolin-5-yl)-3,5-dihydro-2H-4,1-benzoxazepin-6-yl]-1,1-dimethyl-prop-2-ynyl]carbamate was synthesized in the similar fashion as step 2 of Example 183 using 6-bromo-1-(6-fluoro-1-methyl-[1,2,4]triazolo[4,3-a]quinazolin-5-yl)-1,2,3,5-tetrahydrobenzo[e][1,4]oxazepine and tert-butyl (2-methylbut-3-yn-2-yl)carbamate. LCMS-ESI+ (m/z): [M+H]+ calcd for $C_{29}H_{31}FN_6O_3$: 531.24 (M+1), found: 531.22 (M+1).

Step 2: 4-(1-(6-Fluoro-1-methyl-[1,2,4]triazolo[4,3-a]quinazolin-5-yl)-1,2,3,5-tetrahydrobenzo[e][1,4]oxazepin-6-yl)-2-methylbut-3-yn-2-amine was synthesized in the similar fashion as step 2 of Example 177 using tert-butyl N-[3-[1-(6-fluoro-1-methyl-[1,2,4]triazolo[4,3-a]quinazolin-5-yl)-3,5-dihydro-2H-4,1-benzoxazepin-6-yl]-1,1-dimethyl-prop-2-ynyl]carbamate: LCMS-ESI+ (m/z): [M+H]+ calcd for $C_{24}H_{23}FN_6O$: 431.19 (M+1), found: 431.20 (M+1).

Step 3: Example 181 was synthesized in the similar fashion as step 1 of Example 183 using 1-(1,1-difluoroethyl)cyclopropanecarboxylic acid.

Example 182: N-[3-[1-(6,7-Difluoro-1-methyl-[1,2,4]triazolo[4,3-a]quinazolin-5-yl)-3,5-dihydro-2H-4,1-benzoxazepin-6-yl]-1,1-dimethyl-prop-2-ynyl]-1-(trifluoromethyl)cyclopropanecarboxamide

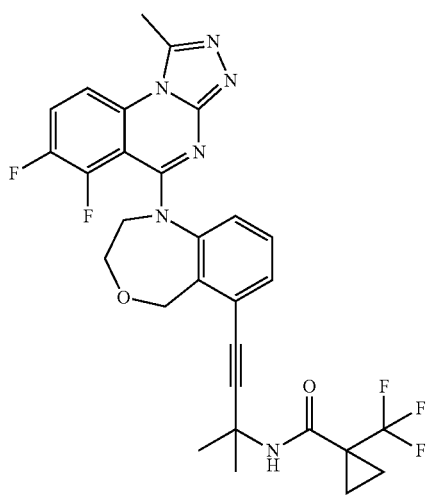 [SMILES: Cc1nnc2nc(N3CCOCc4c(C#CC(C)(C)NC(=O)C5(C(F)(F)F)CC5)cccc43)c3c(F)c(F)ccc3n12]

Example 182 N-[3-[1-(6,7-difluoro-1-methyl-[1,2,4]triazolo[4,3-a]quinazolin-5-yl)-3,5-dihydro-2H-4,1-benzoxazepin-6-yl]-1,1-dimethyl-prop-2-ynyl]-1-(trifluoromethyl)cyclopropanecarboxamide was synthesized in the similar fashion as the step 2 of Example 183 using 6-bromo-1-(6,7-difluoro-1-methyl-[1,2,4]triazolo[4,3-a]quinazolin-5-yl)-3,5-dihydro-2H-4,1-benzoxazepine and N-(1,1-dimethylprop-2-ynyl)-1-(trifluoromethyl)cyclopropanecarboxamide.

Example 183: N-(4-(1-(6-fluoro-1-methyl-[1,2,4]triazolo[4,3-a]quinazolin-5-yl)-2,3,4,5-tetrahydro-1H-benzo[b]azepin-6-yl)-2-methylbut-3-yn-2-yl)-1-(trifluoromethyl)cyclopropane-1-carboxamide

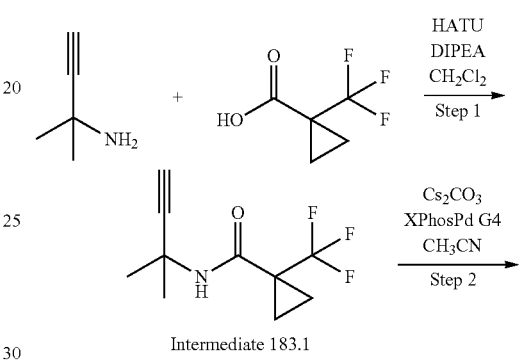

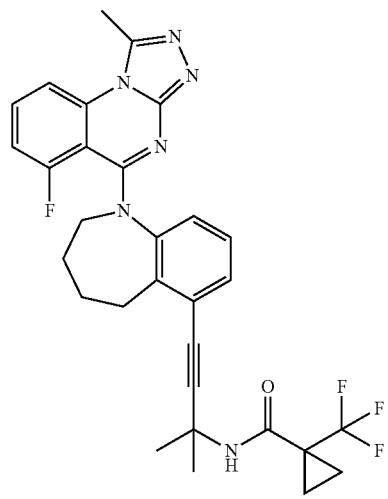

Example 183

Step 1: Preparation of N-(2-methylbut-3-yn-2-yl)-1-(trifluoromethyl)cyclopropane-1-carboxamide (Intermediate 183.1): 2-Methylbut-3-yn-2-amine (250.0 mg, 3.01 mmol) and 1-(trifluoromethyl)cyclopropane-1-carboxylic acid (463 mg, 3.01 mmol, 1 equiv.) were treated with HATU (1261 mg, 3.31 mmol, 1.1 equiv.) in the presence of DIPEA (777 mg, 6.01 mmol, 2 equiv.) in $CH_2Cl_2$ at rt for 15 h. The reaction mixture was quenched with water (30 mL). The whole was extracted with EtOAc (30 mL×3). Organic layer was washed with brine (30 mL) and dried over $Na_2SO_4$. The organic solvent was removed under a reduced pressure. Obtained crude mixture was purified by a silica-gel column chromatography ($SiO_2$=12 g, 0% to 50% EtOAc/hexane) to give N-(2-methylbut-3-yn-2-yl)-1-(trifluoromethyl)cyclopropane-1-carboxamide. $^1$H NMR (400 MHz, Methanol-$d_4$) δ 2.65 (s, 1H), 1.58 (s, 6H), 1.31-1.12 (m, 4H).

Step 2: 5-(6-Bromo-2,3,4,5-tetrahydro-1H-benzo[b]azepin-1-yl)-6,7-difluoro-[1,2,4]triazolo[4,3-a]quinazoline (11.0 mg, 0.0258 mmol) and N-(2-methylbut-3-yn-2-yl)-1-(trifluoromethyl)cyclopropane-1-carboxamide (11.3 mg, 0.0514 mmol, 2 equiv.) were treated with Xphos Pd G4 (2.2 mg, 0.00258 mmol, 0.1 equiv.) in the presence of cesium carbonate (21.0 mg, 0.0645 mmol, 2.5 equiv.) in CH₃CN (0.1 mL) at 110° C. for 60 min under a nitrogen atmosphere. The reaction mixture was filtered and injected into preparative HPLC to give Example 183.

Example 184: 6-(4,4-Difluoro-3,3-dimethyl-pent-1-ynyl)-1-(6,7-difluoro-1-methyl-[1,2,4]triazolo[4,3-a]quinazolin-5-yl)-3,5-dihydro-2H-4,1-benzoxazepine

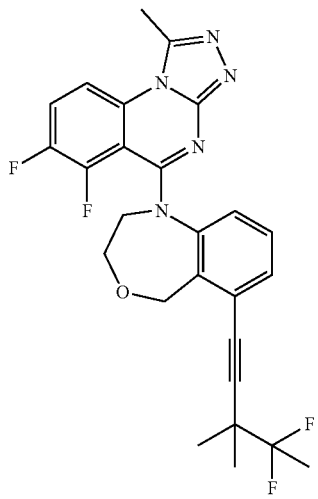 [SMILES: Cc1nnc2nc(N3CCOCc4c(C#CC(C)(C)C(C)(F)F)cccc43)c3c(F)c(F)ccc3n12]

Example 184 6-(4,4-Difluoro-3,3-dimethyl-pent-1-ynyl)-1-(6,7-difluoro-1-methyl-[1,2,4]triazolo[4,3-a]quinazolin-5-yl)-3,5-dihydro-2H-4,1-benzoxazepine was synthesized in the similar fashion as the step 2 Example 183 using 6-bromo-1-(6,7-difluoro-1-methyl-[1,2,4]triazolo[4,3-a]quinazolin-5-yl)-3,5-dihydro-2H-4,1-benzoxazepine and 4,4-difluoro-3,3,3-trimethyl-pent-1-yne.

Example 185: 6,7-Difluoro-1-methyl-5-[6-[2-(3-methyloxetan-3-yl)ethynyl]-2,3,4,5-tetrahydro-1-benzazepin-1-yl]-[1,2,4]triazolo[4,3-a]quinazoline

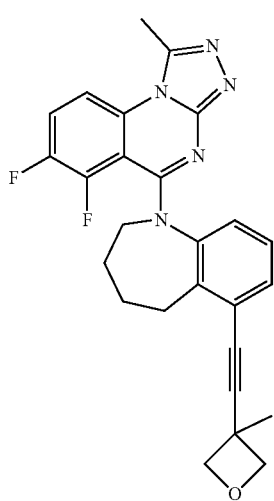 [SMILES: Cc1nnc2nc(N3CCCCc4c(C#CC5(C)COC5)cccc43)c3c(F)c(F)ccc3n12]

Example 185 6,7-Difluoro-1-methyl-5-[6-[2-(3-methyloxetan-3-yl)ethynyl]-2,3,4,5-tetrahydro-1-benzazepin-1-yl]-[1,2,4]triazolo[4,3-a]quinazoline was synthesized in the similar fashion as step 2 of Example 183 using 6-bromo-2,3,4,5-tetrahydro-1H-benzo[b]azepine and 3-ethynyl-3-methyloxetane.

Example 186: 4-[1-(6,7-Difluoro-1-methyl-[1,2,4]triazolo[4,3-a]quinazolin-5-yl)-2,3,4,5-tetrahydro-1-benzazepin-6-yl]-2,2-dimethyl-but-3-ynenitrile

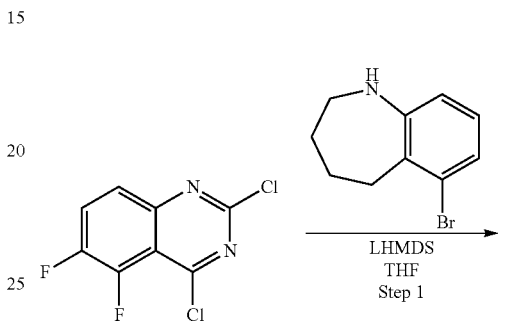

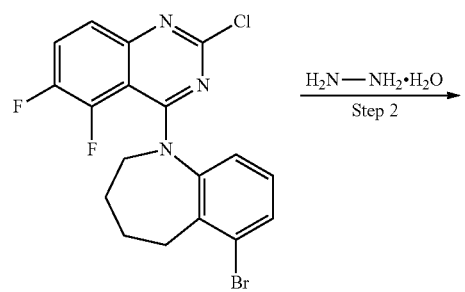

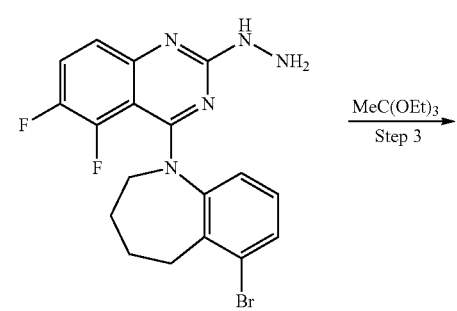

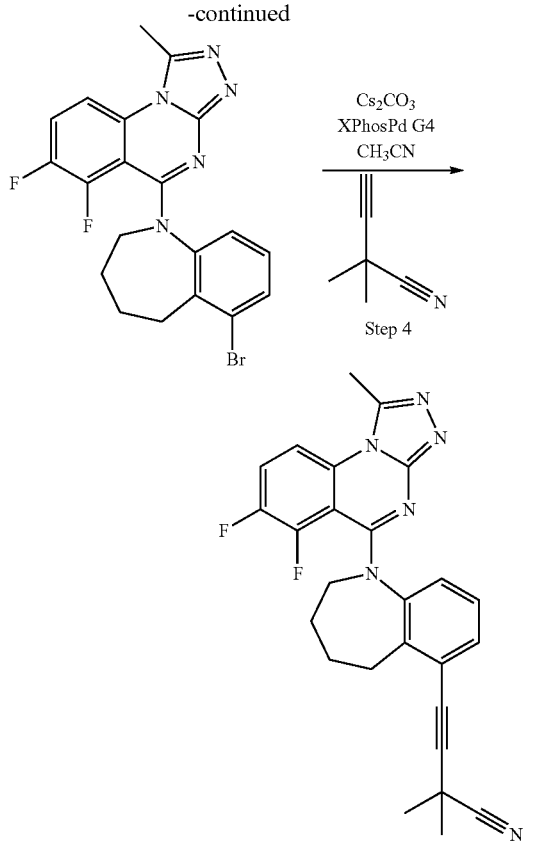

Example 187: 6-(4,4-Difluoro-3,3-dimethyl-pent-1-ynyl)-1-(6-fluoro-1-methyl-[1,2,4]triazolo[4,3-a]quinazolin-5-yl)-3,5-dihydro-2H-4,1-benzoxazepine

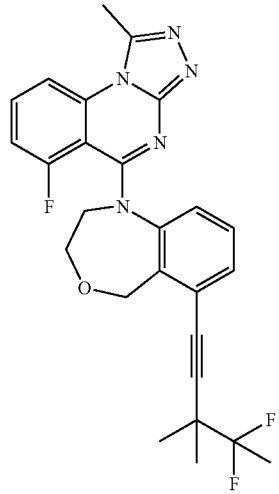 [SMILES: Cc1nnc2nc(N3CCOCc4c(C#CC(C)(C)C(C)(F)F)cccc43)c3c(F)cccc3n12]

Example 187 6-(4,4-Difluoro-3,3-dimethyl-pent-1-ynyl)-1-(6-fluoro-1-methyl-[1,2,4]triazolo[4,3-a]quinazolin-5-yl)-3,5-dihydro-2H-4,1-benzoxazepine was synthesized in the similar fashion as the Example 1 using 4,4-difluoro-3,3-dimethyl-pent-1-yne.

Example 188: 4-[1-(6-Fluoro-1-methyl-[1,2,4]triazolo[4,3-a]quinazolin-5-yl)-2,3,4,5-tetrahydro-1-benzazepin-6-yl]-2,2-dimethyl-but-3-ynenitrile

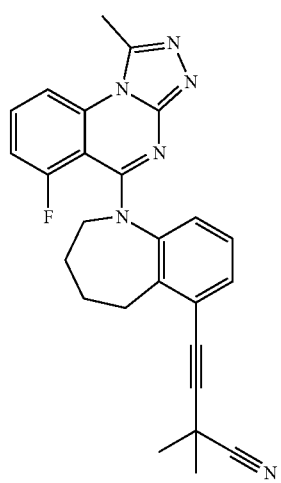 [SMILES: Cc1nnc2nc(N3CCCCc4c(C#CC(C)(C)C#N)cccc43)c3c(F)cccc3n12]

Example 188 was synthesized in the similar fashion as step 4 of Example 1 using 1-ethynyl-1-(trifluoromethyl)cyclopropane.

Step 1: 6-Bromo-1-(2-chloro-5,6-difluoroquinazolin-4-yl)-2,3,4,5-tetrahydro-1H-benzo[b]azepine was synthesized in the similar fashion as the Step 1 in Example 1 using 2,4-dichloro-5-fluoro-quinazoline and 6-bromo-2,3,4,5-tetrahydro-1H-benzo[b]azepine: LCMS-ESI+ (m/z): [M+H]+ calcd for $C_{28}H_{13}BrClF_2N_3$: 423.99 (M-1+1), 425.99 (M+1+1), found: 424.27 (M-1+1), 426.20 (M+1+1).

Step 2: 6-Bromo-1-(5,6-difluoro-2-hydrazineylquinazolin-4-yl)-2,3,4,5-tetrahydro-1H-benzo[b]azepine was synthesized in the similar fashion as the Step 2 in Example: LCMS-ESI+(m/z): [M+H]+ calcd for $C_{18}H_{16}BrF_2N_5$: 420.06 (M-1+1), 422.05 (M+1+1), found: 420.29 (M-1+1), 422.22 (M+1+1).

Step 3: 5-(6-Bromo-2,3,4,5-tetrahydro-1H-benzo[b]azepin-1-yl)-6,7-difluoro-1-methyl-[1,2,4]triazolo[4,3-a]quinazoline was synthesized in the similar fashion as the Step 3 in Example 1: LCMS-ESI+ (m/z): [M+H]+ calcd for $C_{20}H_{16}BrF_2N_5$: 444.06 (M-1+1), 446.05 (M+1+1), found: 444.31 (M-1+1), 446.23 (M+1+1).

Step 4: Example 186 4-(1-(6,7-difluoro-1-methyl-[1,2,4]triazolo[4,3-a]quinazolin-5-yl)-2,3,4,5-tetrahydro-1H-benzo[b]azepin-6-yl)-2,2-dimethylbut-3-ynenitrile was synthesized in the similar fashion as step 2 of Example 183 using 5-(5-bromo-3,4-dihydroquinolin-1(2H)-yl)-6-fluoro-1-methyl-[1,2,4]triazolo[4,3-a]quinazoline and 2,2-dimethylbut-3-ynenitrile.

Example 189: 4-[1-(6-Fluoro-1-methyl-[1,2,4]tri-
azolo[4,3-a]quinazolin-5-yl)-3,5-dihydro-2H-4,1-
benzoxazepin-6-yl]-2,2-dimethyl-but-3-ynenitrile

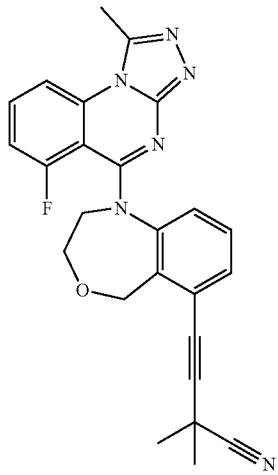 [SMILES: Cc1nnc2nc(N3CCOCc4c(C#CC(C)(C)C#N)cccc43)c3c(F)cccc3n12]

Example 189 4-[1-(6-Fluoro-1-methyl-[1,2,4]triazolo[4,3-a]quinazolin-5-yl)-3,5-dihydro-2H-4,1-benzoxazepin-6-yl]-2,2-dimethyl-but-3-ynenitrile was synthesized in the similar fashion as the Example 1 using 2,2-dimethylbut-3-ynenitrile.

Example 190: 6-(4,4-Difluoro-3,3-dimethyl-but-1-ynyl)-1-(6-fluoro-1-methyl-[1,2,4]triazolo[4,3-a]quinazolin-5-yl)-3,5-dihydro-2H-4,1-benzoxazepine

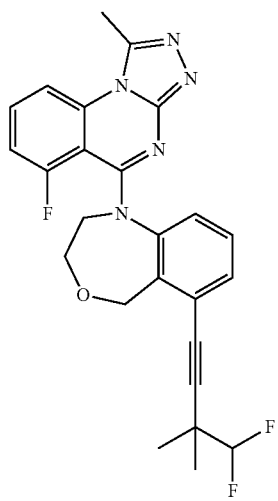 [SMILES: Cc1nnc2nc(N3CCOCc4c(C#CC(C)(C)C(F)F)cccc43)c3c(F)cccc3n12]

Example 190 6-(4,4-Difluoro-3,3-dimethyl-but-1-ynyl)-1-(6-fluoro-1-methyl-[1,2,4]triazolo[4,3-a]quinazolin-5-yl)-3,5-dihydro-2H-4,1-benzoxazepine was synthesized in the similar fashion as the Example 1 using 4,4-difluoro-3,3-dimethyl-but-1-yne.

Example 191: 6-[2-[1-(Difluoromethyl)cyclopropyl]
ethynyl]-1-(6-fluoro-1-methyl-[1,2,4]triazolo[4,3-a]
quinazolin-5-yl)-3,5-dihydro-2H-4,1-benzoxazepine

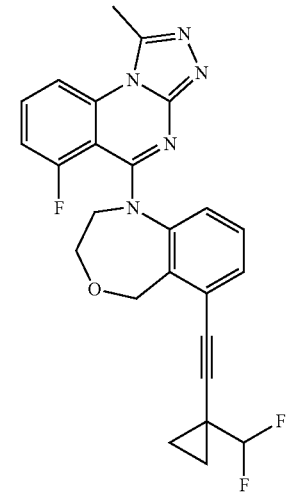 [SMILES: Cc1nnc2nc(N3CCOCc4c(C#CC5(C(F)F)CC5)cccc43)c3c(F)cccc3n12]

Example 191 6-[2-[1-(difluoromethyl)cyclopropyl]ethynyl]-1-(6-fluoro-1-methyl-[1,2,4]triazolo[4,3-a]quinazolin-5-yl)-3,5-dihydro-2H-4,1-benzoxazepine was synthesized in the similar fashion as the Example 1 using 1-(difluoromethyl)-1-ethynyl-cyclopropane.

Example 192: 1-((1-(6-fluoro-1-methyl-[1,2,4]tri-
azolo[4,3-a]quinazolin-5-yl)-1,2,3,4-tetrahydroqui-
nolin-5-yl)ethynyl)cyclopentan-1-ol

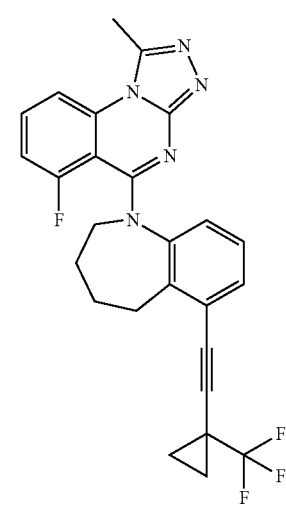 [SMILES: Cc1nnc2nc(N3CCCCc4c(C#CC5(C(F)(F)F)CC5)cccc43)c3c(F)cccc3n12]

Example 192 was synthesized in the similar fashion as step 4 of Example 1 using 1-ethynyl-1-(trifluoromethyl)cyclopropane.

Example 193: 1-((1-(6-fluoro-1-methyl-[1,2,4]triazolo[4,3-a]quinazolin-5-yl)-1,2,3,4-tetrahydroquinolin-5-yl)ethynyl)cyclopentan-1-ol

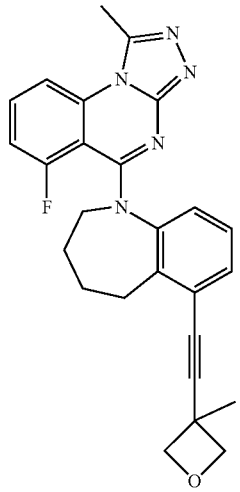 [SMILES: Cc1nnc2nc(N3CCCCc4c(C#CC5(C)COC5)cccc43)c3c(F)cccc3n12]

Example 193 was synthesized in the similar fashion as step 4 of Example 1 using 3-ethynyl-3-methyloxetane.

Example 194: 1-(6-Fluoro-1-methyl-[1,2,4]triazolo[4,3-a]quinazolin-5-yl)-6-[2-(3-methyloxetan-3-yl)ethynyl]-3,5-dihydro-2H-4,1-benzoxazepine

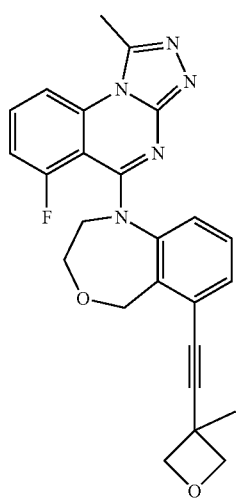 [SMILES: Cc1nnc2nc(N3CCOCc4c(C#CC5(C)COC5)cccc43)c3c(F)cccc3n12]

Example 194 1-(6-Fluoro-1-methyl-[1,2,4]triazolo[4,3-a]quinazolin-5-yl)-6-[2-(3-methyloxetan-3-yl)ethynyl]-3,5-dihydro-2H-4,1-benzoxazepine was synthesized in the similar fashion as the Example 1 using 6-bromo-1-(6-fluoro-1-methyl-[1,2,4]triazolo[4,3-a]quinazolin-5-yl)-3,5-dihydro-2H-4,1-benzoxazepine and 3-ethynyl-3-methyl-oxetane.

Example 195: 6-[2-(1-Ethylcyclopropyl)ethynyl]-1-(6-fluoro-1-methyl-[1,2,4]triazolo[4,3-a]quinazolin-5-yl)-3,5-dihydro-2H-4,1-benzoxazepine

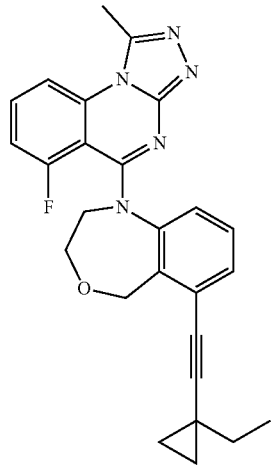 [SMILES: CCC1(C#Cc2cccc3c2COCCN3c2nc3nnc(C)n3c3cccc(F)c23)CC1]

Example 195 6-[2-(1-Ethylcyclopropyl)ethynyl]-1-(6-fluoro-1-methyl-[1,2,4]triazolo[4,3-a]quinazolin-5-yl)-3,5-dihydro-2H-4,1-benzoxazepine was synthesized in the similar fashion as the Example 1 using 6-bromo-1-(6-fluoro-1-methyl-[1,2,4]triazolo[4,3-a]quinazolin-5-yl)-3,5-dihydro-2H-4,1-benzoxazepine and 1-ethyl-1-ethynyl-cyclopropane: LCMS-ESI+ (m/z).

Example 196: 1-(6,7-Difluoro-1-methyl-[1,2,4]triazolo[4,3-a]quinazolin-5-yl)-6-((1-methylcyclopropyl)ethynyl)-1,2,3,5-tetrahydrobenzo[e][1,4]oxazepine

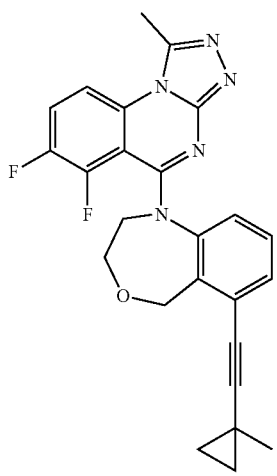 [SMILES: Cc1nnc2nc(N3CCOCc4c(C#CC5(C)CC5)cccc43)c3c(F)c(F)ccc3n12]

Example 196 1-(6,7-difluoro-1-methyl-[1,2,4]triazolo[4,3-a]quinazolin-5-yl)-6-((1-methylcyclopropyl)ethynyl)-1,2,3,5-tetrahydrobenzo[e][1,4]oxazepine was synthesized in the similar fashion as the Example 1 using 6-bromo-1-(6,7-difluoro-1-methyl-[1,2,4]triazolo[4,3-a]quinazolin-5-yl)-3,5-dihydro-2H-4,1-benzoxazepine and 1-ethynyl-1-methyl-cyclopropane.

Example 197: 3-((1-(6-fluoro-1-methyl-[1,2,4]tri-azolo[4,3-a]quinazolin-5-yl)-1,2,3,4-tetrahydroquinolin-5-yl)ethynyl)bicyclo[3.1.1]heptan-3-ol

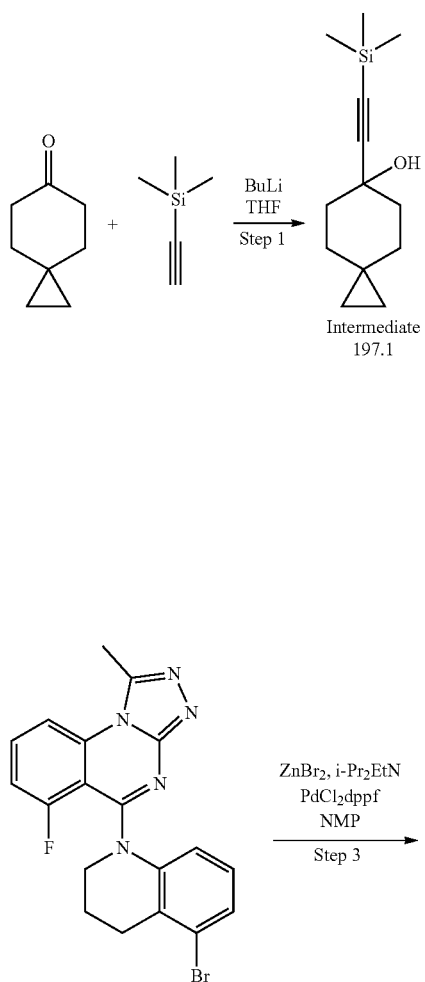

Step 1: 6-((Trimethylsilyl)ethynyl)spiro[2.5]octan-6-ol was synthesized in the similar fashion as the Step 1 in Example 199 using spiro[2.5]octan-6-one: $^1$H NMR (400 MHz, Methanol-$d_4$) δ 1.92-1.79 (m, 2H), 1.78-1.59 (m, 4H), 1.16 (d, J=11.8 Hz, 2H), 0.36-0.20 (m, 4H), 0.16 (s, 9H).

Step 2: 6-Ethynylspiro[2.5]octan-6-ol was synthesized in the similar fashion as the Step 2 in Example 199: $^1$H NMR (400 MHz, Methanol-$d_4$) δ 2.82 (s, 1H), 1.95-1.81 (m, 2H), 1.72 (t, J=9.7 Hz, 5H), 1.18 (s, 2H), 0.38-0.18 (m, 5H).

Step 3: Example 197 was synthesized in the similar fashion as Example 1 using 6-ethynylspiro[2.5]octan-6-ol.

Example 198: 3-((1-(6-fluoro-1-methyl-[1,2,4]tri-azolo[4,3-a]quinazolin-5-yl)-1,2,3,4-tetrahydroquinolin-5-yl)ethynyl)bicyclo[3.1.1]heptan-3-ol

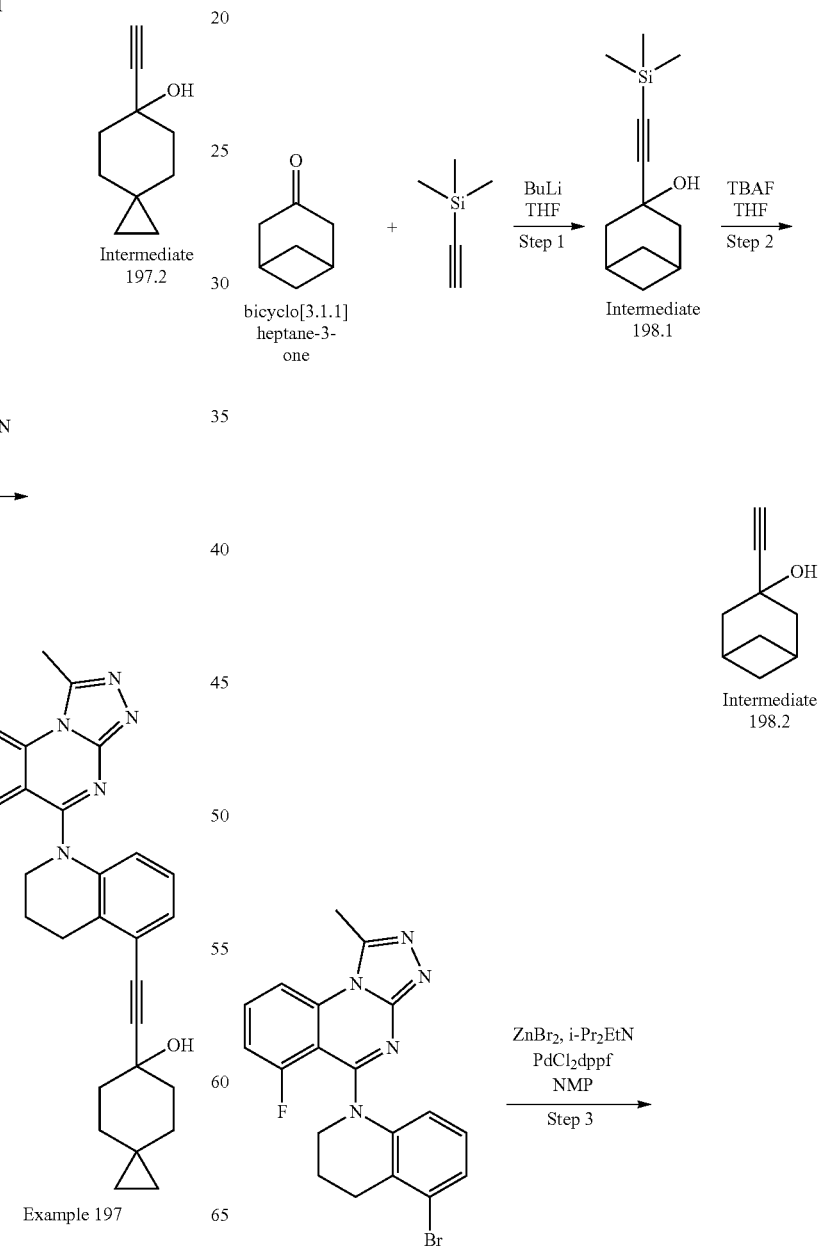

-continued

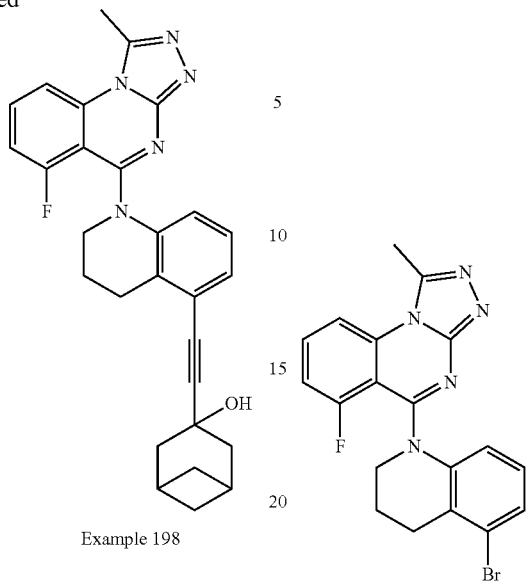

Example 198

Step 1: 3-((Trimethylsilyl)ethynyl)bicyclo[3.1.1]heptan-3-ol (Intermediate 198.1) was synthesized in the similar fashion as the Step 1 in Example 199 using bicyclo[3.1.1]heptan-3-one: $^1$H NMR (400 MHz, Methanol-$d_4$) δ 2.40 (dq, J=14.3, 1.4 Hz, 2H), 2.33 (td, J=5.9, 3.1 Hz, 2H), 2.16 (dd, J=13.7, 1.8 Hz, 2H), 2.13-2.04 (m, 1H), 1.98 (ddt, J=10.4, 5.8, 1.5 Hz, 1H), 1.73 (t, J=8.6 Hz, 1H), 1.56 (t, J=8.7 Hz, 1H), 0.14 (s, 9H).

Step 2: 3-Ethynylbicyclo[3.1.1]heptan-3-ol (Intermediate 198.2) was synthesized in the similar fashion as the Step 2 in Example 199: $^1$H NMR (400 MHz, Methanol-$d_4$) δ 2.81 (s, 1H), 2.42 (dq, J=14.4, 1.4 Hz, 2H), 2.37-2.26 (m, 2H), 2.25-2.15 (m, 2H), 2.11 (dtt, J=9.4, 6.1, 1.7 Hz, 1H), 1.98 (ddt, J=10.5, 6.0, 1.6 Hz, 1H), 1.76 (t, J=8.6 Hz, 1H), 1.52 (t, J=8.7 Hz, 1H).

Step 3: Example 198 was synthesized in the similar fashion as Example 1 using 3-Ethynylbicyclo[3.1.1]heptan-3-ol.

Example 199: (1R,5S)-3-((1-(6-fluoro-1-methyl-[1,2,4]triazolo[4,3-a]quinazolin-5-yl)-1,2,3,4-tetrahydroquinolin-5-yl)ethynyl)bicyclo[3.1.0]hexan-3-ol

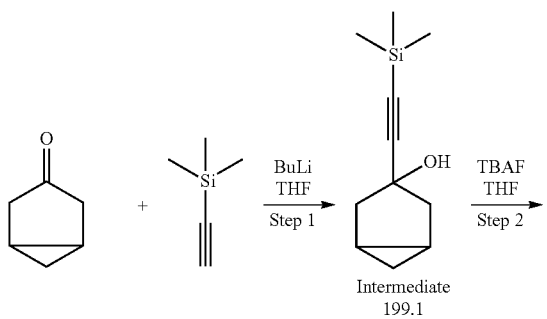

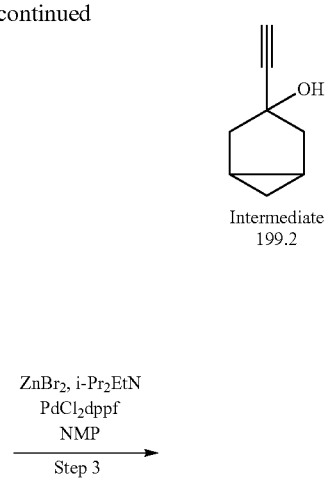

Step 1 Preparation of 3-((trimethylsilyl)ethynyl)bicyclo[3.1.0]hexan-3-ol (Intermediate 199.1): Ethynyltrimethylsilane (225.0 mg, 2.29 mmol, 1.1 equiv.) was treated with BuLi (2.3 mL, 2.29 mmol, 1.0 equiv) in THF (2 mL) at −78° C. The reaction mixture was allowed to warm up rt for 20 min and then again cooled down to −78° C. After waiting for 5 min, bicyclo[3.1.0]hexan-3-one (200.0 mg, 2.08 mmol) was added to the reaction mixture. The reaction mixture was allowed to warm up rt and stirred for 1 h to go to completion. The reaction mixture was diluted with EtOAc (70 mL) and whole was washed with water (30 mL) and sat. NaCl (30 mL). Organic layer was dried over Na$_2$SO$_4$ and the solvent was removed under a reduced pressure to give 3-((trimethylsilyl)ethynyl)bicyclo[3.1.0]hexan-3-ol: $^1$H NMR (400 MHz, Methanol-$d_4$) 2.28 (dd, J=14.1, 3.6 Hz, 2H), 2.01 (d, J=14.0 Hz, 2H), 1.33 (dtd, J=8.6, 3.8, 1.4 Hz, 2H), 0.73 (q, J=4.1 Hz, 1H), 0.40 (tdt, J=8.3, 4.5, 1.1 Hz, 1H), 0.12 (s, 9H).

Step 2 Preparation of 3-ethynylbicyclo[3.1.0]hexan-3-ol (Intermediate 199.2): 3-((Trimethylsilyl)ethynyl)bicyclo[3.1.0]hexan-3-ol was treated with TBAF-3H$_2$O (1313 mg, 4.16 mmol, 2 equiv) in THF (2 mL) at rt for 18 h. The reaction mixture was diluted with EtOAc (70 mL) and whole was washed with water (30 mL) and sat. NaCl (30 mL). Organic layer was dried over Na$_2$SO$_4$ and the solvent was removed under a reduced pressure to give a crude product. The crude product was purified by a silica-gel column chromatography (SiO2=12 g, 0% to 20% EtOAc/hexane) to give 3-ethynylbicyclo[3.1.0]hexan-3-ol: $^1$H NMR (400 MHz, Methanol-d$_4$) δ 2.76 (s, 1H), 2.36-2.21 (m, 3H), 2.03 (d, J=14.0 Hz, 2H), 1.34 (dtd, J=8.6, 3.8, 1.4 Hz, 2H), 0.74 (q, J=4.1 Hz, 1H), 0.41 (tdt, J=8.3, 4.5, 1.1 Hz, 1H).

Step 3: Example 199 was synthesized in the similar fashion as Example 1 using 3-ethynylbicyclo[3.1.0]hexan-3-ol.

Example 200: 6-[2-[1-(1,1-Difluoroethyl)cyclopropyl]ethynyl]-1-(6,7-difluoro-1-methyl-[1,2,4]triazolo[4,3-a]quinazolin-5-yl)-3,5-dihydro-2H-4,1-benzoxazepine

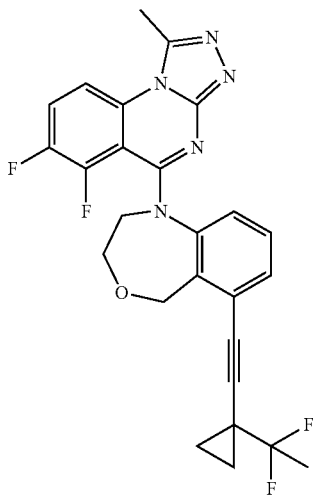 [SMILES: Cc1nnc2nc(N3CCOCc4c(C#CC5(C(C)(F)F)CC5)cccc43)c3c(F)c(F)ccc3n12]

Example 200 6-[2-[1-(1,1-difluoroethyl)cyclopropyl]ethynyl]-1-(6,7-difluoro-1-methyl-[1,2,4]triazolo[4,3-a]quinazolin-5-yl)-3,5-dihydro-2H-4,1-benzoxazepine was synthesized in the similar fashion as the Example 1 using 6-bromo-1-(6,7-difluoro-1-methyl-[1,2,4]triazolo[4,3-a]quinazolin-5-yl)-3,5-dihydro-2H-4,1-benzoxazepine and 1-(1,1-difluoroethyl)-1-ethynyl-cyclopropane.

Example 201: 6-[2-[1-(1,1-Difluoroethyl)cyclopropyl]ethynyl]-1-(6,7-difluoro-[1,2,4]triazolo[4,3-a]quinazolin-5-yl)-3,5-dihydro-2H-4,1-benzoxazepine

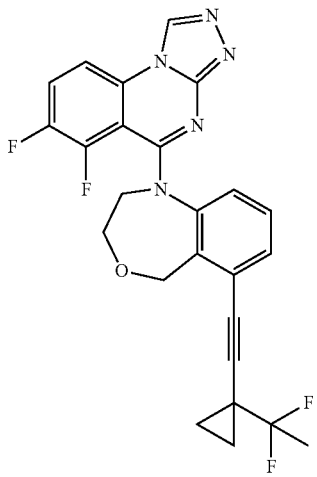 [SMILES: CC(F)(F)C1(C#Cc2cccc3c2COCCN3c2nc3nncn3c3ccc(F)c(F)c23)CC1]

Example 201 6-[2-[1-(1,1-Difluoroethyl)cyclopropyl]ethynyl]-1-(6,7-difluoro-[1,2,4]triazolo[4,3-a]quinazolin-5-yl)-3,5-dihydro-2H-4,1-benzoxazepine was synthesized in the similar fashion as the Example 1 using 6-bromo-1-(6,7-difluoro-[1,2,4]triazolo[4,3-a]quinazolin-5-yl)-3,5-dihydro-2H-4,1-benzoxazepine and 1-(1,1-difluoroethyl)-1-ethynyl-cyclopropane.

Example 202: 1-((1-(6-Fluoro-[1,2,4]triazolo[4,3-a]quinazolin-5-yl)-1,2,3,4-tetrahydroquinolin-5-yl)ethynyl)cyclohexan-1-ol

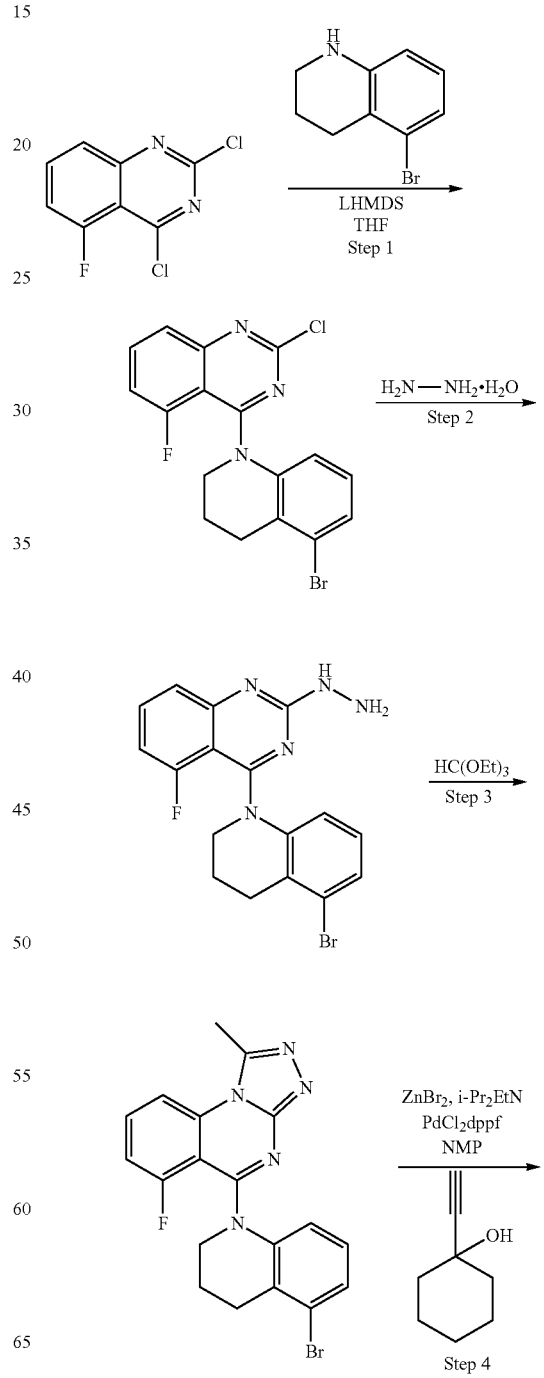

-continued

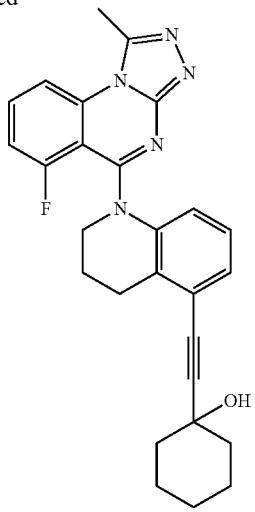

Step 1: 4-(5-Bromo-3,4-dihydroquinolin-1(2H)-yl)-2-chloro-5-fluoroquinazoline was synthesized in the similar fashion as the Step 1 in Example 1 using 5-bromo-1,2,3,4-tetrahydroquinoline: LCMS-ESI+ (m/z): [M+H]+ calcd for $C_{17}H_{12}BrClFN_3$: 391.99 (M-1+1), 393.99 (M+1+1), found: 392.23 (M-1+1), 394.15 (M+1+1).

Step 2: 4-(5-Bromo-3,4-dihydroquinolin-1(2H)-yl)-5-fluoro-2-hydrazineylquinazoline was synthesized in the similar fashion as the Step 2 in Example 1: LCMS-ESI+ (m/z): [M+H]+ calcd for $C_{17}H_{15}BrFN_5$: 388.05 (M-1+1), 390.05 (M+1+1), found: 388.28 (M-1+1), 390.20 (M+1+1).

Step 3: 5-(5-Bromo-3,4-dihydroquinolin-1(2H)-yl)-6-fluoro-[1,2,4]triazolo[4,3-a]quinazoline was synthesized in the similar fashion as the Step 3 in Example 1 using triethoxymethane: LCMS-ESI+ (m/z): [M+H]+ calcd for $C_{18}H_{13}BrFN_5$: 398.03 (M-1+1), 400.03 (M+1+1), found: 398.23 (M-1+1), 400.13 (M+1+1).

Step 4: Example 202 1-((1-(6-Fluoro-[1,2,4]triazolo[4,3-a]quinazolin-5-yl)-1,2,3,4-tetrahydroquinolin-5-yl)ethynyl)cyclohexan-1-ol was synthesized in the similar fashion as the Example 1 using 5-(5-bromo-3,4-dihydroquinolin-1(2H)-yl)-6-fluoro-[1,2,4]triazolo[4,3-a]quinazoline and 1-ethynylcyclohexan-1-ol.

Example 203: 1-(6,7-Difluoro-[1,2,4]triazolo[4,3-a]quinazolin-5-yl)-6-[2-[1-(trifluoromethyl)cyclopropyl]ethynyl]-3,5-dihydro-2H-4,1-benzoxazepine

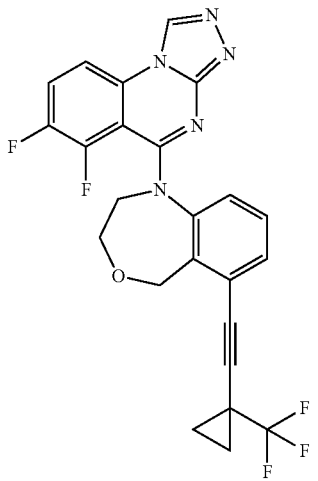

Example 203 1-(6,7-difluoro-[1,2,4]triazolo[4,3-a]quinazolin-5-yl)-6-(4,4,4-trifluoro-3,3-dimethyl-but-1-ynyl)-3,5-dihydro-2H-4,1-benzoxazepine was synthesized in the similar fashion as the Example 1 using 6-bromo-1-(6,7-difluoro-[1,2,4]triazolo[4,3-a]quinazolin-5-yl)-3,5-dihydro-2H-4,1-benzoxazepine and 1-ethynyl-1-(trifluoromethyl)cyclopropane.

Example 204: 1 1-(6,7-Difluoro-[1,2,4]triazolo[4,3-a]quinazolin-5-yl)-6-(4,4,4-trifluoro-3,3-dimethyl-but-1-ynyl)-3,5-dihydro-2H-4,1-benzoxazepine

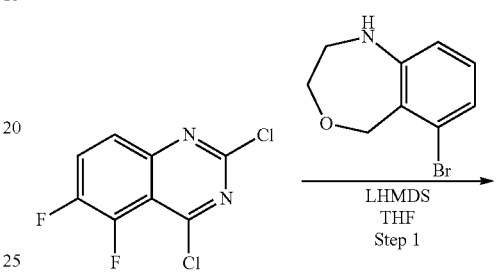

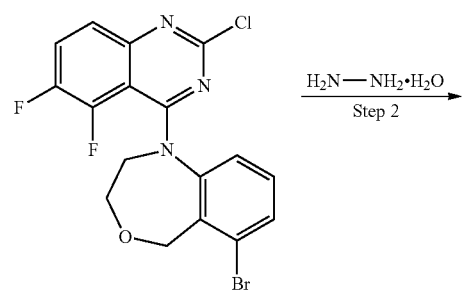

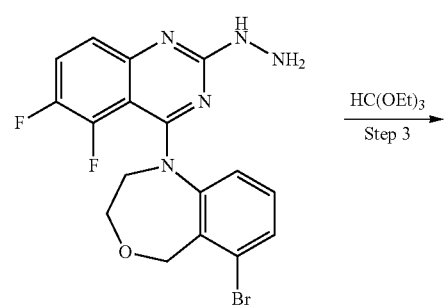

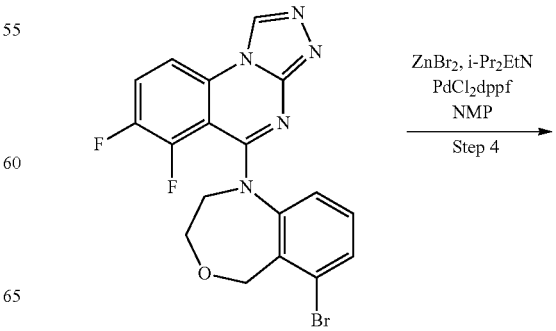

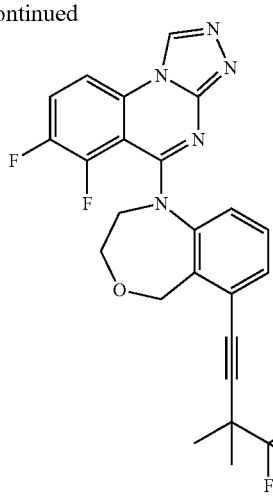

Step 1: 6-Bromo-1-(2-chloro-5,6-difluoro-quinazolin-4-yl)-3,5-dihydro-2H-4,1-benzoxazepine was synthesized in the similar fashion as the Step 1 in Example 1 using 2,4-dichloro-5,6-difluoro-quinazoline and 6-bromo-1,2,3,5-tetrahydro-4,1-benzoxazepine: LCMS-ESI+ (m/z): [M+H]+ calcd for $C_{17}H_{11}BrClF_2N_3O$: 425.97 (M-1+1), 427.97 (M+1+1), found: 426.21 (M-1+1), 428.15 (M+1+1).

Step 2: [4-(6-Bromo-3,5-dihydro-2H-4,1-benzoxazepin-1-yl)-5,6-difluoro-quinazolin-2-yl]hydrazine was synthesized in the similar fashion as the Step 2 in Example 1: LCMS-ESI+(m/z): [M+H]+ calcd for $C_{17}H_{14}BrClF_2N_5O$: 422.03 (M-1+1), 424.03 (M+1+1), found: 422.20 (M-1+1), 424.14 (M+1+1).

Step 3: 6-bromo-1-(6,7-difluoro-[1,2,4]triazolo[4,3-a]quinazolin-5-yl)-3,5-dihydro-2H-4,1-benzoxazepine was synthesized in the similar fashion as the Step 3 in Example 1 using triethoxymethane: LCMS-ESI+ (m/z): [M+H]+ calcd for $C_{18}H_{12}BrF_2N_5O$: 432.02 (M-1+1), 434.02 (M+1+1), found: 432.24 (M-1+1), 434.19 (M+1+1).

Step 4: Example 204 1-(6,7-difluoro-[1,2,4]triazolo[4,3-a]quinazolin-5-yl)-6-(4,4,4-trifluoro-3,3-dimethyl-but-1-ynyl)-3,5-dihydro-2H-4,1-benzoxazepine was synthesized in the similar fashion as the Example 1 using 6-bromo-1-(6,7-difluoro-[1,2,4]triazolo[4,3-a]quinazolin-5-yl)-3,5-dihydro-2H-4,1-benzoxazepine and 4,4,4-trifluoro-3,3-dimethyl-but-1-yne.

Example 205: 1-((1-(6-fluoro-1-methyl-[1,2,4]triazolo[4,3-a]quinazolin-5-yl)-1,2,3,4-tetrahydroquinolin-5-yl)ethynyl)cyclopentan-1-ol

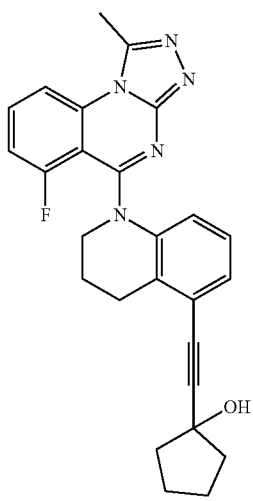 [SMILES: Cc1nnc2nc(N3CCCc4c(C#CC5(O)CCCC5)cccc43)c3c(F)cccc3n12]

Example 205 was synthesized in the similar fashion as Example 1 using 1-ethynylcyclopentan-1-ol.

Example 206: 1-((1-(6-fluoro-1-methyl-[1,2,4]triazolo[4,3-a]quinazolin-5-yl)-1,2,3,4-tetrahydroquinolin-5-yl)ethynyl)cyclohexan-1-ol

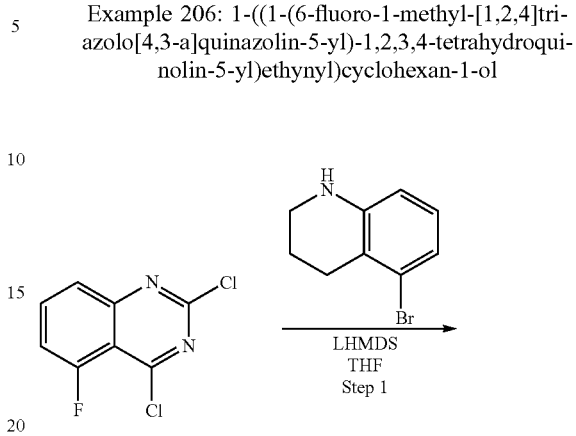

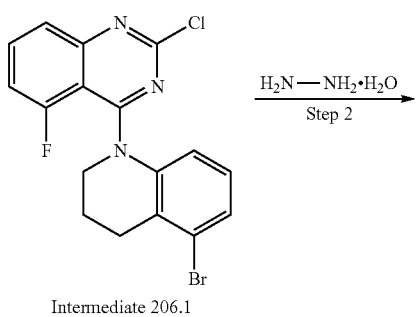

Intermediate 206.1

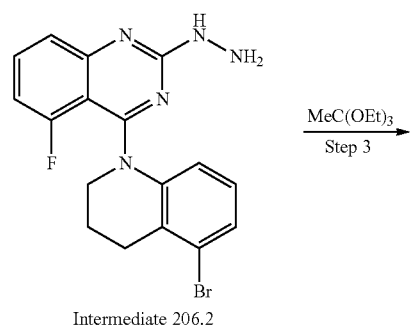

Intermediate 206.2

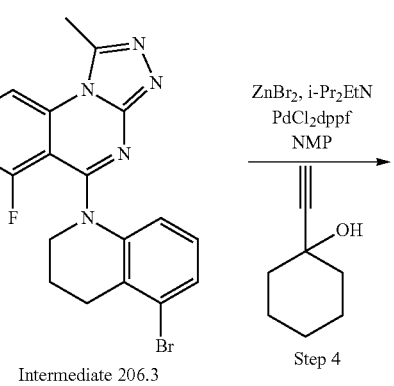

Intermediate 206.3

-continued

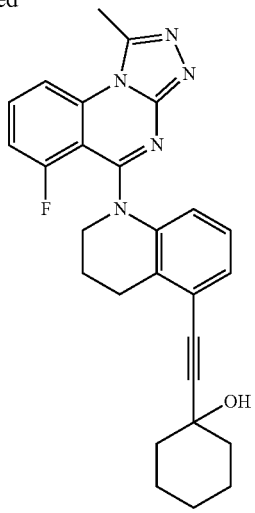

Example 206

Step 1: 4-(5-Bromo-3,4-dihydroquinolin-1(2H)-yl)-2-chloro-5-fluoroquinazoline (Intermediate 206.1) was synthesized in the similar fashion as the Step 1 in Example 1 using 5-bromo-1,2,3,4-tetrahydroquinoline: LCMS-ESI+ (m/z): [M+H]+ calcd for $C_{17}H_{12}BrClFN_3$: 391.99 (M-1+1), 393.99 (M+1+1), found: 392.23 (M-1+1), 394.15 (M+1+1).

Step 2: 4-(5-Bromo-3,4-dihydroquinolin-1(2H)-yl)-5-fluoro-2-hydrazineylquinazoline (Intermediate 206.2) was synthesized in the similar fashion as the Step 2 in Example 1: LCMS-ESI+ (m/z): [M+H]+ calcd for $C_{17}H_{15}BrFN_5$: 388.05 (M-1+1), 390.05 (M+1+1), found: 388.28 (M-1+1), 390.20 (M+1+1).

Step 3: 5-(5-Bromo-3,4-dihydroquinolin-1(2H)-yl)-6-fluoro-1-methyl-[1,2,4]triazolo[4,3-a]quinazoline (Intermediate 206.3) was synthesized in the similar fashion as the Step 3 in Example 1: LCMS-ESI+ (m/z): [M+H]+ calcd for $C_{19}H_{15}BrFN_5$: 412.05 (M-1+1), 414.05 (M+1+1), found: 412.28 (M-1+1), 414.22 (M+1+1).

Step 4: Example 206 1-((1-(6-Fluoro-1-methyl-[1,2,4] triazolo[4,3-a]quinazolin-5-yl)-1,2,3,4-tetrahydroquinolin-5-yl)ethynyl)cyclohexan-1-ol was synthesized in the similar fashion as the Step 4 in Example 1 using 5-(5-bromo-3,4-dihydroquinolin-1(2H)-yl)-6-fluoro-1-methyl-[1,2,4]triazolo[4,3-a]quinazoline and 1-ethynylcyclohexan-1-ol.

Example 207: 1-(6,7-Difluoro-1-methyl-[1,2,4]triazolo[4,3-a]quinazolin-5-yl)-6-(4,4,4-trifluoro-3,3-dimethyl-but-1-ynyl)-3,5-dihydro-2H-4,1-benzoxazepine

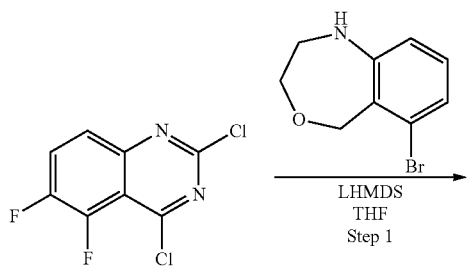

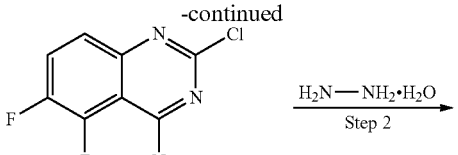

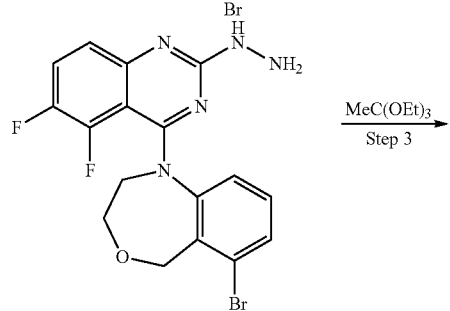

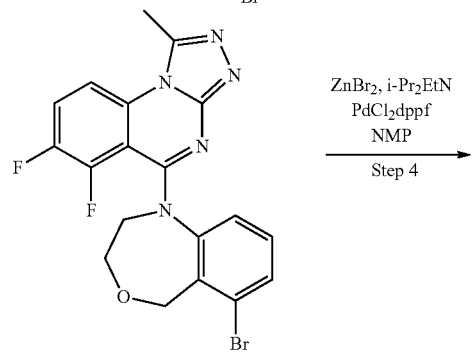

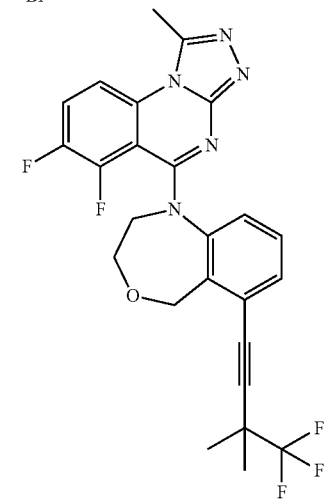

Step 1: 6-Bromo-1-(2-chloro-5,6-difluoro-quinazolin-4-yl)-3,5-dihydro-2H-4,1-benzoxazepine was synthesized in the similar fashion as the Step 1 in Example 1 using 2,4-dichloro-5,6-difluoro-quinazoline and 6-bromo-1,2,3,5-tetrahydro-4,1-benzoxazepine: LCMS-ESI+ (m/z): [M+H]+ calcd for $C_{17}H_{11}BrClF_2N_3O$: 425.97 (M-1+1), 427.97 (M+1+1), found: 426.21 (M-1+1), 428.15 (M+1+1).

Step 2: [4-(6-Bromo-3,5-dihydro-2H-4,1-benzoxazepin-1-yl)-5,6-difluoro-quinazolin-2-yl]hydrazine was synthesized in the similar fashion as the Step 2 in Example 1:

LCMS-ESI+(m/z): [M+H]+ calcd for $C_{17}H_{14}BrClF_2N_5O$: 422.03 (M-1+1), 424.03 (M+1+1), found: 422.20 (M-1+1), 424.14 (M+1+1).

Step 3: 6-Bromo-1-(6,7-difluoro-1-methyl-[1,2,4]triazolo[4,3-a]quinazolin-5-yl)-3,5-dihydro-2H-4,1-benzoxazepine was synthesized in the similar fashion as the Step 3 in Example 1: LCMS-ESI+ (m/z): [M+H]+ calcd for $C_{19}H_{15}BrFN_5O$: 446.03 (M-1+1), 448.03 (M+1+1), found: 446.30 (M-1+1), 448.20 (M+1+1).

Step 4: Example 207 1-(6,7-difluoro-1-methyl-[1,2,4]triazolo[4,3-a]quinazolin-5-yl)-6-(4,4,4-trifluoro-3,3-dimethyl-but-1-ynyl)-3,5-dihydro-2H-4,1-benzoxazepine was synthesized in the similar fashion as the Example 1 using 6-bromo-1-(6,7-difluoro-1-methyl-[1,2,4]triazolo[4,3-a]quinazolin-5-yl)-3,5-dihydro-2H-4,1-benzoxazepine and 4,4,4-trifluoro-3,3-dimethyl-but-1-yne.

Example 208: 5-(6-((1-(1,1-Difluoroethyl)cyclopropyl)ethynyl)-2,3,4,5-tetrahydro-1H-benzo[b]azepin-1-yl)-6,7-difluoro-[1,2,4]triazolo[4,3-a]quinazoline

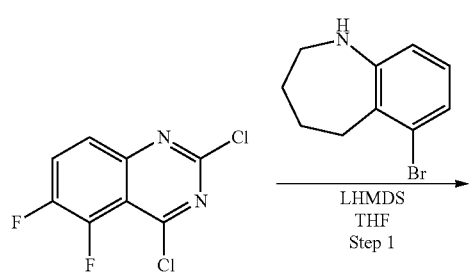

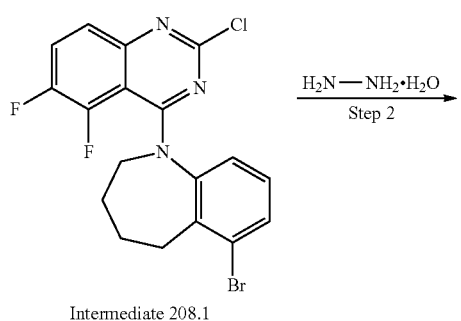

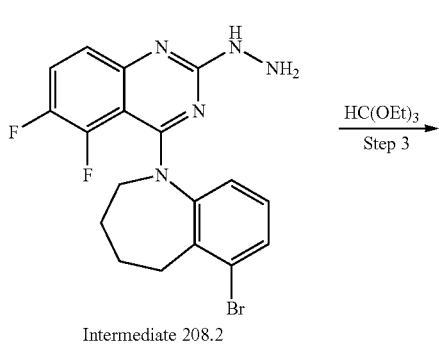

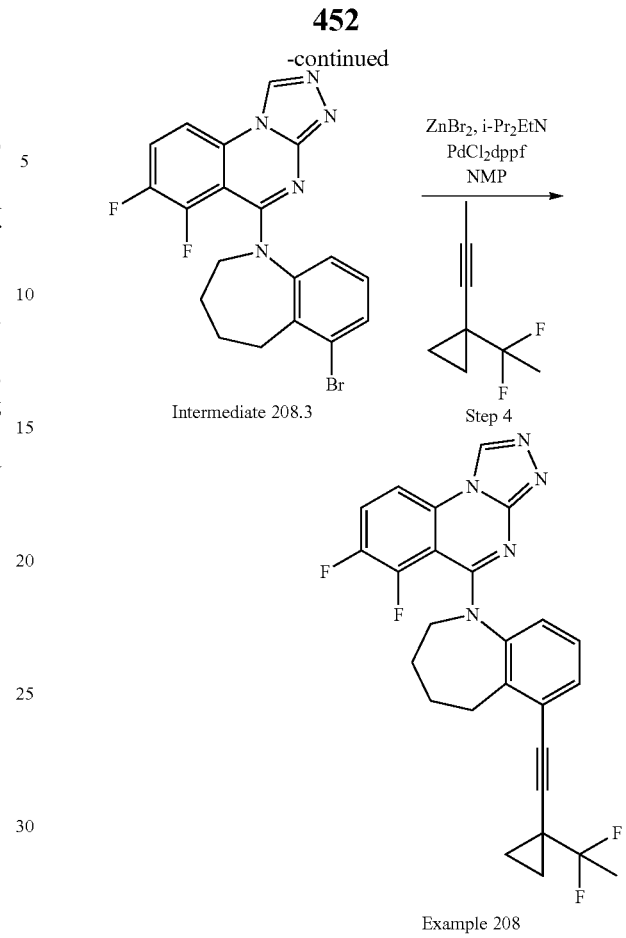

Step 1: 6-Bromo-1-(2-chloro-5,6-difluoroquinazolin-4-yl)-2,3,4,5-tetrahydro-1H-benzo[b]azepine was synthesized in the similar fashion as the Step 1 in Example 1 using 2,4-dichloro-5,6-difluoroquinazoline and 6-bromo-2,3,4,5-tetrahydro-1H-benzo[b]azepine: LCMS-ESI+ (m/z): [M+H]+ calcd for $C_{28}H_{13}BrClF_2N_3$: 423.99 (M-1+1), 425.99 (M+1+1), found: 424.27 (M-1+1), 426.20 (M+1+1).

Step 2: 6-Bromo-1-(5,6-difluoro-2-hydrazineylquinazolin-4-yl)-2,3,4,5-tetrahydro-1H-benzo[b]azepine was synthesized in the similar fashion as the Step 2 in Example 1: LCMS-ESI+ (m/z): [M+H]+ calcd for $C_{18}H_{16}BrF_2N_5$: 420.06 (M-1+1), 422.05 (M+1+1), found: 420.29 (M-1+1), 422.22 (M+1+1).

Step 3: 5-(6-Bromo-2,3,4,5-tetrahydro-1H-benzo[b]azepin-1-yl)-6,7-difluoro-[1,2,4]triazolo[4,3-a]quinazoline was synthesized in the similar fashion as the Step 3 in Example 1 using 6-bromo-1-(5,6-difluoro-2-hydrazineylquinazolin-4-yl)-2,3,4,5-tetrahydro-1H-benzo[b]azepine and triethoxymethane: LCMS-ESI+ (m/z): [M+H]+ calcd for $C_{19}H_{14}BrF_2N_5$: 430.04 (M-1+1), 432.04 (M+1+1), found: 430.30 (M-1+1), 432.24 (M+1+1).

Step 4: Example 208 5-(6-((1-(1,1-Difluoroethyl)cyclopropyl)ethynyl)-2,3,4,5-tetrahydro-1H-benzo[b]azepin-1-yl)-6,7-difluoro-[1,2,4]triazolo[4,3-a]quinazoline was synthesized in the similar fashion as the Example 1 using 5-(6-bromo-2,3,4,5-tetrahydro-1H-benzo[b]azepin-1-yl)-6,7-difluoro-[1,2,4]triazolo[4,3-a]quinazoline and 1-(1,1-difluoroethyl)-1-ethynylcyclopropane.

Example 209: 1-[2-[1-(6,7-Difluoro-[1,2,4]triazolo[4,3-a]quinazolin-5-yl)-3,4-dihydro-2H-quinolin-5-yl]ethynyl]cyclohexanol

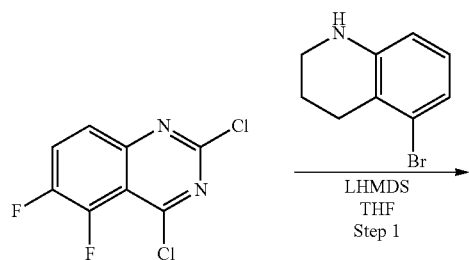

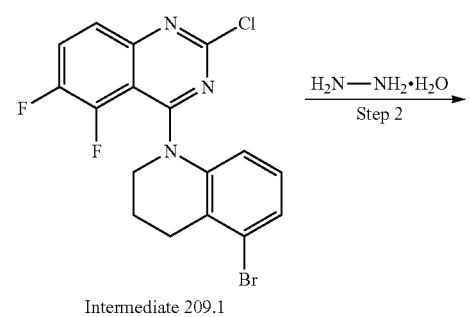

Intermediate 209.1

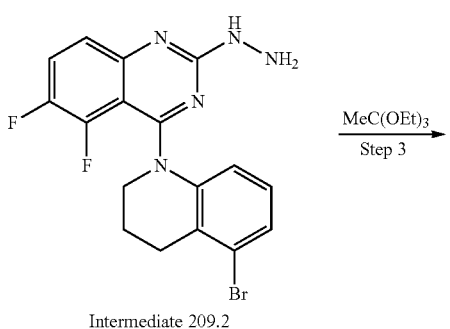

Intermediate 209.2

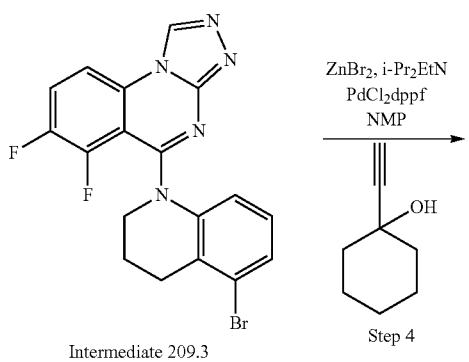

Intermediate 209.3

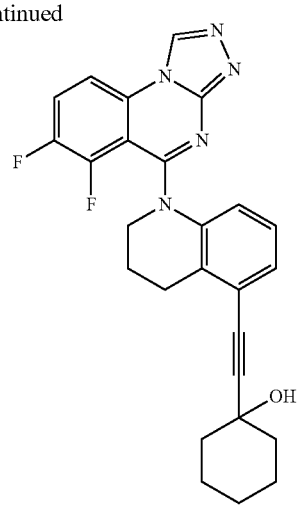

Example 209

Step 1: 4-(5-Bromo-3,4-dihydroquinolin-1(2H)-yl)-2-chloro-5,6-difluoroquinazoline was synthesized in the similar fashion as the Step 1 in Example 1 using 2,4-dichloro-5,6-difluoroquinazoline and 5-bromo-1,2,3,4-tetrahydroquinoline: LCMS-ESI+ (m/z): [M+H]+ calcd for $C_{17}H_{11}BrClF_2N_3$: 409.98 (M-1+1), 411.98 (M+1+1), found: 410.25 (M-1+1), 412.16 (M+1+1).

Step 2: 4-(5-Bromo-3,4-dihydroquinolin-1(2H)-yl)-5,6-difluoro-2-hydrazineylquinazoline was synthesized in the similar fashion as the Step 2 in Example 1: LCMS-ESI+ (m/z): [M+H]+ calcd for $C_{17}H_{14}BrF_2N_5$: 406.04 (M-1+1), 408.04 (M+1+1), found: 406.25 (M-1+1), 408.18 (M+1+1).

Step 3: 5-(5-Bromo-3,4-dihydroquinolin-1(2H)-yl)-6,7-difluoro-[1,2,4]triazolo[4,3-a]quinazoline was synthesized in the similar fashion as the Step 3 in Example 1 using 4-(5-bromo-3,4-dihydroquinolin-1(2H)-yl)-5,6-difluoro-2-hydrazineylquinazoline and triethoxymethane: LCMS-ESI+ (m/z): [M+H]+ calcd for $C_{18}H_{12}BrF_2N_5$: 416.02 (M-1+1), 418.02 (M+1+1), found: 416.25 (M-1+1), 418.20 (M+1+1).

Step 4: Example 209 1-((1-(6-Fluoro-[1,2,4]triazolo[4,3-a]quinazolin-5-yl)-1,2,3,4-tetrahydroquinolin-5-yl)ethynyl)cyclohexan-1-ol was synthesized in the similar fashion as the Example 1 using 5-(5-bromo-3,4-dihydroquinolin-1(2H)-yl)-6,7-difluoro-[1,2,4]triazolo[4,3-a]quinazoline and 1-ethynylcyclohexan-1-ol.

Example 210: 7-Fluoro-1-methyl-5-[6-[2-[1-(trifluoromethyl)cyclopropyl]ethynyl]-2,3,4,5-tetrahydro-1-benzazepin-1-yl]-[1,2,4]triazolo[4,3-a]quinazoline

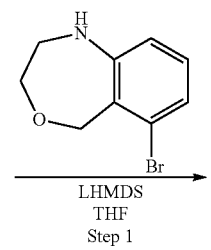

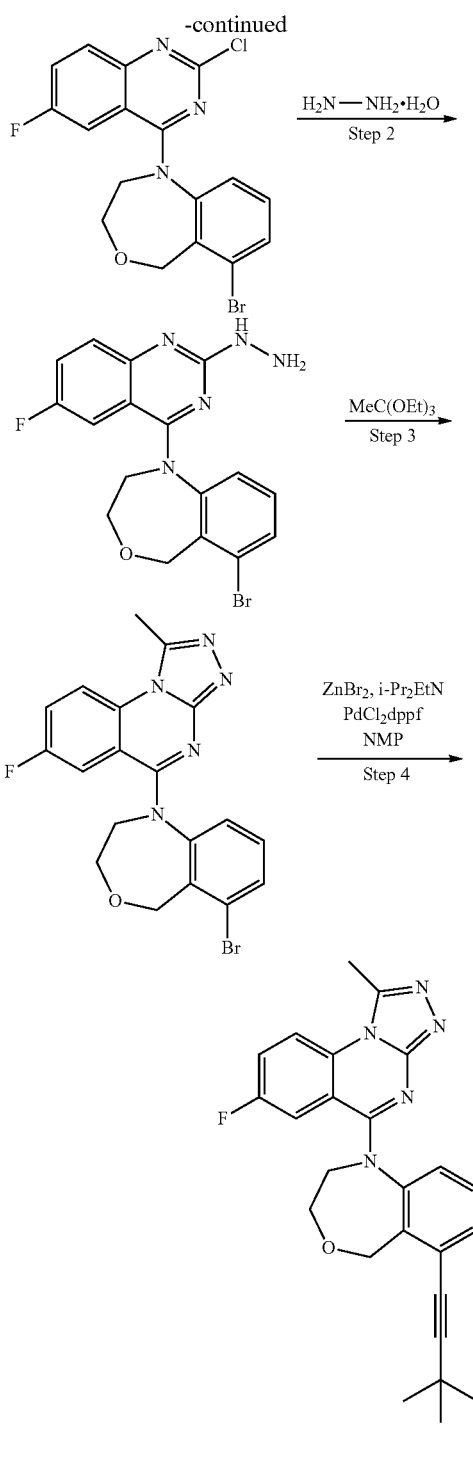

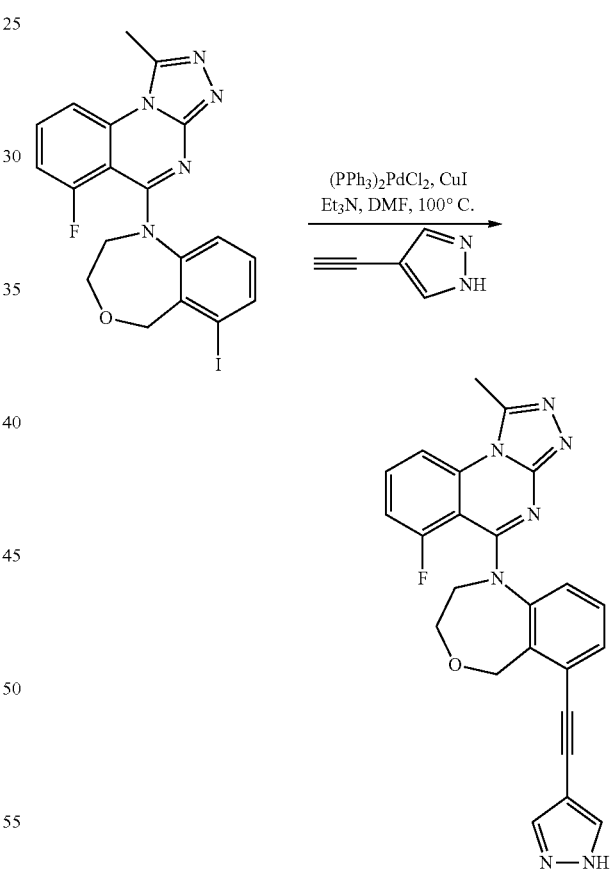

Step 1: 6-Bromo-1-(2-chloro-6-fluoro-quinazolin-4-yl)-3,5-dihydro-2H-4,1-benzoxazepine was synthesized in the similar fashion as the Step 1 in Example 1 using 2,4-dichloro-6-fluoro-quinazoline and 6-bromo-1,2,3,5-tetrahydro-4,1-benzoxazepine: LCMS-ESI+(m/z): [M+H]+ calcd for $C_{17}H_{12}BrClFN_3O$: 407.98 (M-1+1), 409.98 (M+1+1), found: 408.23 (M-1+1), 410.17 (M+1+1).

Step 2: [4-(6-Bromo-3,5-dihydro-2H-4,1-benzoxazepin-1-yl)-6-fluoro-quinazolin-2-yl]hydrazine was synthesized in the similar fashion as the Step 2 in Example 1: LCMS-ESI+ (m/z): [M+H]+ calcd for $C_{17}H_{15}BrClFN_5O$: 404.04 (M-1+1), 406.04 (M+1+1), found: 404.29 (M-1+1), 406.21 (M+1+1).

Step 3: 6-Bromo-1-(7-fluoro-1-methyl-[1,2,4]triazolo[4,3-a]quinazolin-5-yl)-3,5-dihydro-2H-4,1-benzoxazepine was synthesized in the similar fashion as the Step 3 in Example 1: LCMS-ESI+ (m/z): [M+H]+ calcd for $C_{19}H_{15}BrFN_5O$: 428.04 (M-1+1), 430.04 (M+1+1), found: 428.32 (M-1+1), 430.24 (M+1+1).

Step 4: Example 210 1-(7-fluoro-1-methyl-[1,2,4]triazolo[4,3-a]quinazolin-5-yl)-6-(4,4,4-trifluoro-3,3-dimethyl-but-1-ynyl)-3,5-dihydro-2H-4,1-benzoxazepine was synthesized in the similar fashion as the Example 1 using 6-bromo-1-(7-fluoro-1-methyl-[1,2,4]triazolo[4,3-a]quinazolin-5-yl)-3,5-dihydro-2H-4,1-benzoxazepine and 4,4,4-trifluoro-3,3-dimethyl-but-1-yne.

Example 211: Synthesis of 6-((1H-pyrazol-4-yl)ethynyl)-1-(6-fluoro-1-methyl-[1,2,4]triazolo[4,3-a]quinazolin-5-yl)-1,2,3,5-tetrahydrobenzo[e][1,4]oxazepine A solution of 1-(6-fluoro-1-methyl-[1,2,4]triazolo[4,3-a]quinazolin-5-yl)-6-iodo-1,2,3,5-tetrahydrobenzo[e][1,4]oxazepine (Intermediate 39, 20 mg, 0.042 mmol), copper (I) iodide (1.60 mg, 8.4 µmol), bis(triphenylphosphine) palladium (II) chloride (2.96 mg, 4.2 µmol), and triethylamine (12.8 mg, 0.126 mmol) in DMF (0.7 mL) was purged with nitrogen gas for 2 minutes. 4-Ethynyl-1H-pyrazole (11.6 mg, 0.126 mmol) was then added and the mixture was heated at 100° C. for 12 h. Upon completion, the mixture was cooled to room temperature, and ethyl acetate and water were added to the mixture. The aqueous layer was extracted with EA and the combined organic layers were dried over Na₂SO₄ and concentrated in vacuo. The residue was purified by normal phase flash chromatography eluting with EA in hexanes 0-100%, followed by MeOH in EA 0-30% to afford the product as a yellow solid. The solid was then further purified by reverse phase HPLC (0.1% trifluoroacetic acid in acetonitrile/water) providing the title compound as the mono-TFA salt.

Example 212: Synthesis of 5-(5-((1H-pyrazol-4-yl)ethynyl)-3,4-dihydroquinolin-1(2H)-yl)-6-fluoro-1-methyl-[1,2,4]triazolo[4,3-a]quinazoline

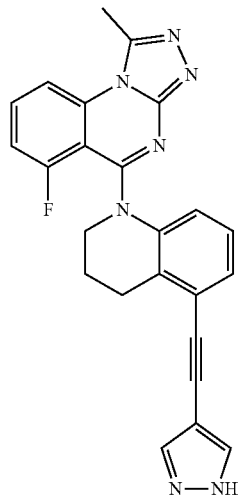 [SMILES: Cc1nnc2nc(N3CCCc4c(C#Cc5cn[nH]c5)cccc43)c3c(F)cccc3n12]

The title compound was synthesized as described in Example 211, except using 6-fluoro-5-(5-iodo-3,4-dihydro-2H-quinolin-1-yl)-1-methyl-[1,2,4]triazolo[4,3-a]quinazoline in place of 1-(6-fluoro-1-methyl-[1,2,4]triazolo[4,3-a]quinazolin-5-yl)-6-iodo-1,2,3,5-tetrahydrobenzo[e][1,4]oxazepine.

Example 213: Synthesis of 5-((1-(6-fluoro-1-methyl-[1,2,4]triazolo[4,3-a]quinazolin-5-yl)-1,2,3,4-tetrahydroquinolin-5-yl)ethynyl)picolinonitrile

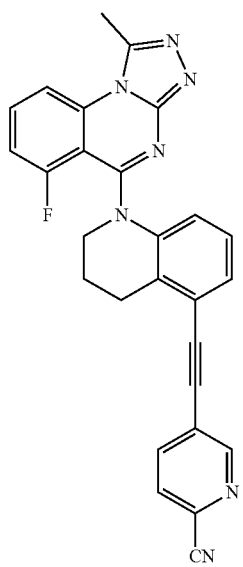 [SMILES: Cc1nnc2nc(N3CCCc4c(C#Cc5ccc(C#N)nc5)cccc43)c3c(F)cccc3n12]

The title compound was synthesized as described in Example 211, except using 6-fluoro-5-(5-iodo-3,4-dihydro-2H-quinolin-1-yl)-1-methyl-[1,2,4]triazolo[4,3-a]quinazoline in place of 1-(6-fluoro-1-methyl-[1,2,4]triazolo[4,3-a]quinazolin-5-yl)-6-iodo-1,2,3,5-tetrahydrobenzo[e][1,4]oxazepane and 5-ethynylpyridine-2-carbonitrile in place of 4-ethynyl-1H-pyrazole.

Example 214: Synthesis of 1-(6-fluoro-1-methyl-[1,2,4]triazolo[4,3-a]quinazolin-5-yl)-6-((1-methyl-1H-pyrazol-5-yl)ethynyl)-1,2,3,5-tetrahydrobenzo[e][1,4]oxazepine

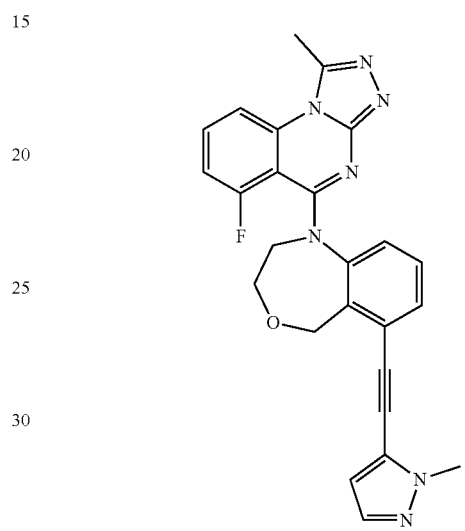

The title compound was synthesized as described in Example 211, except using 5-ethynyl-1-methyl-pyrazole in place of 4-ethynyl-1H-pyrazole.

Example 215: Synthesis of 5-(5-((1H-pyrazol-5-yl)ethynyl)-3,4-dihydroquinolin-1(2H)-yl)-6-fluoro-1-methyl-[1,2,4]triazolo[4,3-a]quinazoline

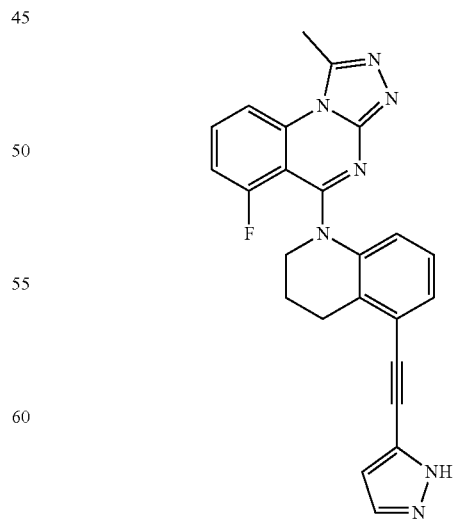

The title compound was synthesized as described in Example 211, except using 6-fluoro-5-(5-iodo-3,4-dihydro- 2H-quinolin-1-yl)-1-methyl-[1,2,4]triazolo[4,3-a]quinazoline in place of 1-(6-fluoro-1-methyl-[1,2,4]triazolo[4,3-a]quinazolin-5-yl)-6-iodo-1,2,3,5-tetrahydrobenzo[e][1,4]oxazepane.

Example 216: Synthesis of 1-(1,6-dimethyl-[1,2,4]triazolo[4,3-a]quinazolin-5-yl)-6-((1-methylcyclopropyl)ethynyl)-1,2,3,5-tetrahydrobenzo[e][1,4]oxazepine

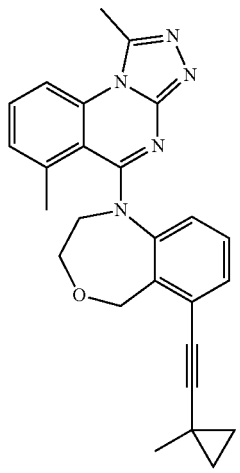 [SMILES: Cc1cccc2c1c(N1CCOCc3c(C#CC4(C)CC4)cccc31)nc1nnc(C)n12]

The title compound was synthesized in a manner similar to Example 1.

Example 217: Synthesis of 4-(1-(1,6-dimethyl-[1,2,4]triazolo[4,3-a]quinazolin-5-yl)-1,2,3,5-tetrahydrobenzo[e][1,4]oxazepin-6-yl)-2,2-dimethylbut-3-ynenitrile

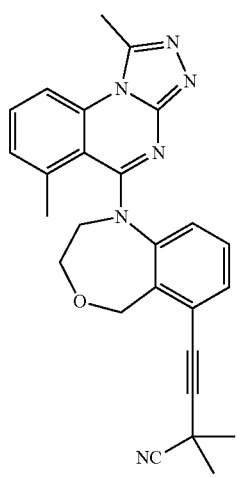 [SMILES: Cc1cccc2c1c(N1CCOCc3c(C#CC(C)(C)C#N)cccc31)nc1nnc(C)n12]

The title compound was synthesized in a manner similar to Example 1.

Example 218: Synthesis of 1-(6-fluoro-1-methyl-[1,2,4]triazolo[4,3-a]quinazolin-5-yl)-6-((1-methyl-1H-pyrazol-4-yl)ethynyl)-1,2,3,5-tetrahydrobenzo[e][1,4]oxazepine

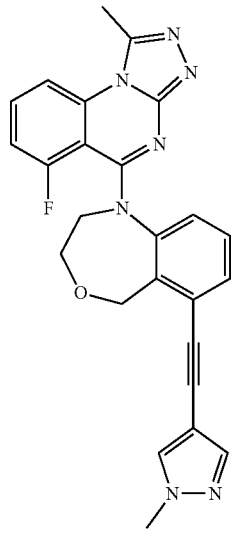 [SMILES: Cc1nnc2nc(N3CCOCc4c(C#Cc5cnn(C)c5)cccc43)c3c(F)cccc3n12]

The title compound was synthesized as described in Example 211, except using 4-ethynyl-1-methyl-pyrazole in place of 4-ethynyl-1H-pyrazole.

Example 219: Synthesis of 5-[5-[2-(5-methoxy-3-pyridyl)ethynyl]-3,4-dihydro-2H-quinolin-1-yl]-1-methyl-[1,2,4]triazolo[4,3-a]quinazoline

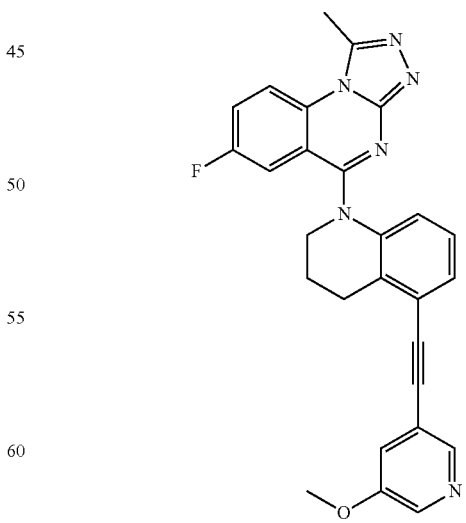

The title compound was synthesized in a similar manner to Example 1, using 7-fluoro-5-(5-iodo-3,4-dihydro-2H-quinolin-1-yl)-1-methyl-[1,2,4]triazolo[4,3-a]quinazoline Example 220: Synthesis of 6-fluoro-1-methyl-5-(5-((2-(trifluoromethyl)pyrimidin-5-yl)ethynyl)-3,4-dihydroquinolin-1(2H)-yl)-[1,2,4]triazolo[4,3-a]quinazoline

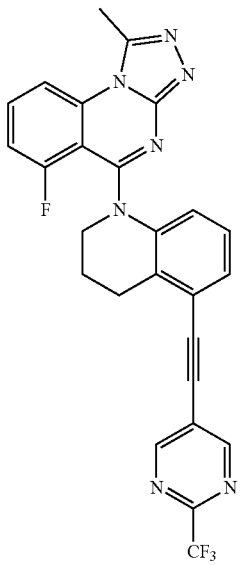 [SMILES: Cc1nnc2nc(N3CCCc4c(C#Cc5cnc(C(F)(F)F)nc5)cccc43)c3c(F)cccc3n12]

A solution of 6-fluoro-5-(5-iodo-3,4-dihydro-2H-quinolin-1-yl)-1-methyl-[1,2,4]triazolo[4,3-a]quinazoline (18 mg, 0.037 mmol), 5-ethynyl-2-(trifluoromethyl)pyrimidine (22 mg, 0.128 mmol), Cs$_2$CO$_3$ (30.3 mg, 0.093 mmol), and XPhos Pd G4 (1.60 mg, 1.86 μmol) in acetonitrile was purged with nitrogen gas for 2 minutes and the mixture was heated at 90° C. for 1 h. Upon completion, the mixture was diluted with EA and filtered through a pad of Celite® and concentrated in vacuo. The crude product was then further purified by reverse phase HPLC (0.1% trifluoroacetic acid in acetonitrile/water) providing the title compound as the mono-TFA salt.

Example 221: Synthesis of 3-(1-((1-(6-fluoro-1-methyl-[1,2,4]triazolo[4,3-a]quinazolin-5-yl)-1,2,3,4-tetrahydroquinolin-5-yl)ethynyl)cyclopropyl)-5-pentylisoxazole

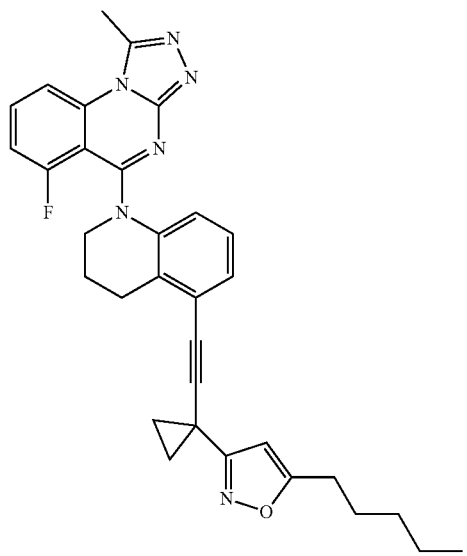 [SMILES: CCCCCc1cc(C2(C#Cc3cccc4c3CCCN4c3nc4nnc(C)n4c4cccc(F)c34)CC2)no1]

The title compound was synthesized as described in Example 211, except 3-(1-ethynylcyclopropyl)-5-pentylisoxazole (Intermediate 40) in place of 4-ethynyl-1H-pyrazole.

Example 222: Synthesis of 1-(6-fluoro-1-methyl-[1,2,4]triazolo[4,3-a]quinazolin-5-yl)-6-((6-methoxypyridin-3-yl)ethynyl)-1,2,3,5-tetrahydrobenzo[e][1,4]oxazepine

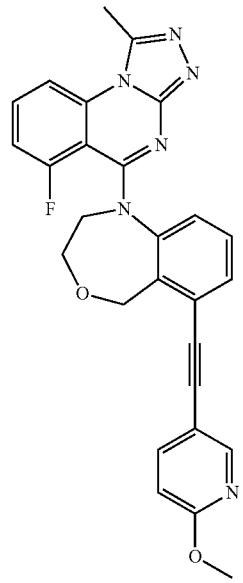 [SMILES: COc1ccc(C#Cc2cccc3c2COCCN3c2nc3nnc(C)n3c3cccc(F)c23)cn1]

The title compound was synthesized in a similar manner to Example 1, using 6-bromo-1-(6-fluoro-1-methyl-[1,2,4]triazolo[4,3-a]quinazolin-5-yl)-3,5-dihydro-2H-4,1-benzoxazepine.

Example 223: Synthesis of 7-fluoro-1-methyl-5-[5-[2-(2-methylpyrazol-3-yl)ethynyl]-3,4-dihydro-2H-quinolin-1-yl]-[1,2,4]triazolo[4,3-a]quinazoline

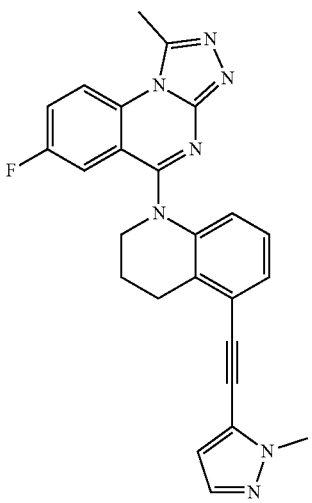 [SMILES: Cc1nnc2nc(N3CCCc4c(C#Cc5ccnn5C)cccc43)c3cc(F)ccc3n12]

The title compound was synthesized as described in Example 211, except using 7-fluoro-5-(5-iodo-3,4-dihydro-2H-quinolin-1-yl)-1-methyl-[1,2,4]triazolo[4,3-a]quinazoline in place of 1-(6-fluoro-1-methyl-[1,2,4]triazolo[4,3-a]quinazolin-5-yl)-6-iodo-1,2,3,5-tetrahydrobenzo[e][1,4]oxazepane.

Example 224: Synthesis of 7-fluoro-1-methyl-5-[5-[2-(1H-pyrazol-5-yl)ethynyl]-3,4-dihydro-2H-quinolin-1-yl]-[1,2,4]triazolo[4,3-a]quinazoline

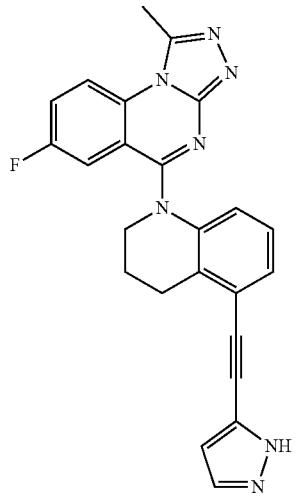 [SMILES: Cc1nnc2nc(N3CCCc4c(C#Cc5ccn[nH]5)cccc43)c3cc(F)ccc3n12]

The title compound was synthesized as described in Example 211, except using 7-fluoro-5-(5-iodo-3,4-dihydro-2H-quinolin-1-yl)-1-methyl-[1,2,4]triazolo[4,3-a]quinazoline in place of 1-(6-fluoro-1-methyl-[1,2,4]triazolo[4,3-a]quinazolin-5-yl)-6-iodo-1,2,3,5-tetrahydrobenzo[e][1,4]oxazepane.

Example 225: Synthesis of 7-fluoro-1-methyl-5-[5-[2-(1H-pyrazol-4-yl)ethynyl]-3,4-dihydro-2H-quinolin-1-yl]-[1,2,4]triazolo[4,3-a]quinazoline

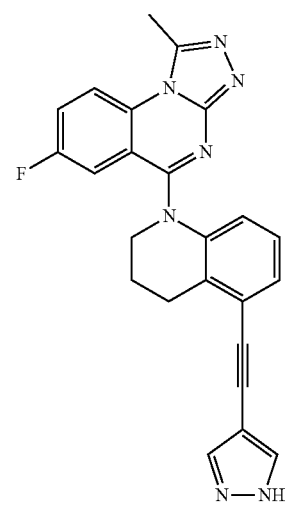 [SMILES: Cc1nnc2nc(N3CCCc4c(C#Cc5cn[nH]c5)cccc43)c3cc(F)ccc3n12]

The title compound was synthesized as described in Example 211), except using 5-(5-bromo-3,4-dihydro-2H-quinolin-1-yl)-7-fluoro-1-methyl-[1,2,4]triazolo[4,3-a]quinazoline in place of 1-(6-fluoro-1-methyl-[1,2,4]triazolo[4,3-a]quinazolin-5-yl)-6-iodo-1,2,3,5-tetrahydrobenzo[e][1,4]oxazepane.

Example 226: Synthesis of 6,7-difluoro-1-methyl-5-[5-[2-(1-methylpyrazol-4-yl)ethynyl]-3,4-dihydro-2H-quinolin-1-yl]-[1,2,4]triazolo[4,3-a]quinazoline

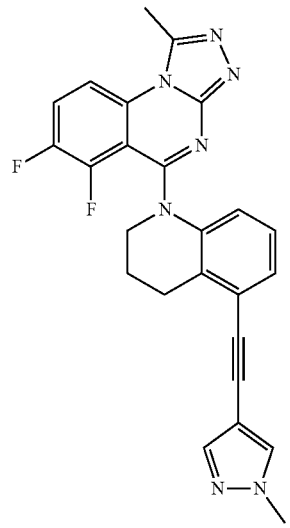 [SMILES: Cc1nnc2nc(N3CCCc4c(C#Cc5cnn(C)c5)cccc43)c3c(F)c(F)ccc3n12]

The title compound was synthesized in a similar manner to Example 1, using 5-(5-bromo-3,4-dihydro-2H-quinolin-1-yl)-6,7-difluoro-1-methyl-[1,2,4]triazolo[4,3-a]quinazoline.

Example 227: Synthesis of N-(2,2-difluoroethyl)-6,7-difluoro-N-[3-fluoro-5-[2-(1-methylpyrazol-4-yl)ethynyl]phenyl]-1-methyl-[1,2,4]triazolo[4,3-a]quinazolin-5-amine

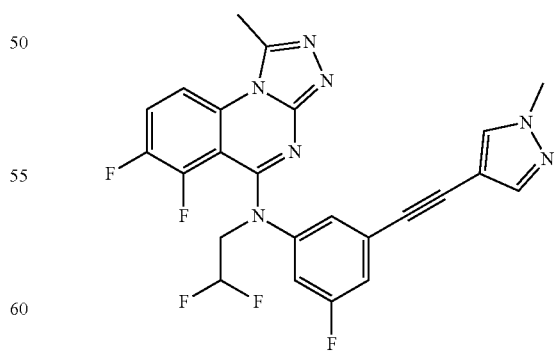

The title compound was synthesized in a similar manner to Example 1, using N-(3-bromo-5-fluoro-phenyl)-N-(2,2-difluoroethyl)-6,7-difluoro-1-methyl-[1,2,4]triazolo[4,3-a]quinazolin-5-amine.

Example 228: Synthesis of 7-fluoro-5-[5-[2-(6-methoxy-3-pyridyl)ethynyl]-3,4-dihydro-2H-quinolin-1-yl]-1-methyl-[1,2,4]triazolo[4,3-a]quinazoline

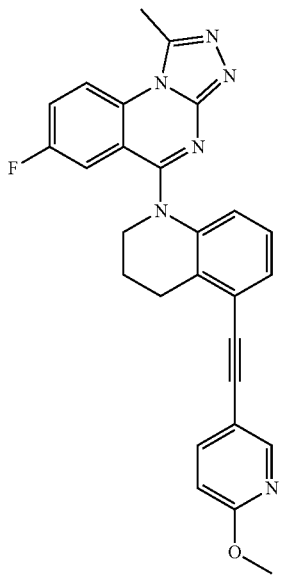 [SMILES: COc1ccc(C#Cc2cccc3c2CCCN3c2nc3nnc(C)n3c3ccc(F)cc23)cn1]

The title compound was synthesized as described in Example 211, except using 5-ethynyl-2-methoxy-pyridine in place of 4-ethynyl-1H-pyrazole and using 7-fluoro-5-(5-iodo-3,4-dihydro-2H-quinolin-1-yl)-1-methyl-[1,2,4]triazolo[4,3-a]quinazoline.

Example 229: Synthesis of 4-[2-[1-(7-fluoro-1-methyl-[1,2,4]triazolo[4,3-a]quinazolin-5-yl)-3,4-dihydro-2H-quinolin-5-yl]ethynyl]pyridine-2-carbonitrile

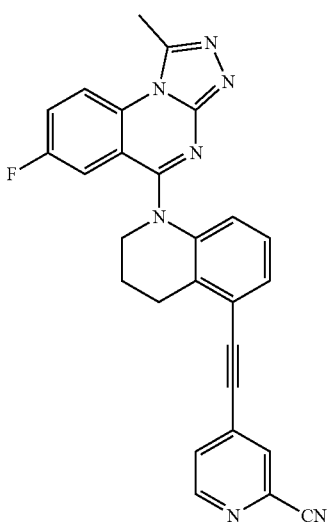 [SMILES: Cc1nnc2nc(N3CCCc4c(C#Cc5ccnc(C#N)c5)cccc43)c3cc(F)ccc3n12]

The title compound was synthesized as described in Example 211, except using 7-fluoro-5-(5-iodo-3,4-dihydro-2H-quinolin-1-yl)-1-methyl-[1,2,4]triazolo[4,3-a]quinazoline.

Example 230: Synthesis of 4-[2-[1-(7-fluoro-1-methyl-[1,2,4]triazolo[4,3-a]quinazolin-5-yl)-3,4-dihydro-2H-quinolin-5-yl]ethynyl]pyridine-2-carbonitrile

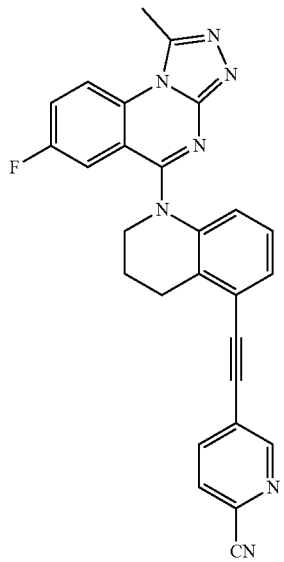 [SMILES: Cc1nnc2nc(N3CCCc4c(C#Cc5ccc(C#N)nc5)cccc43)c3cc(F)ccc3n12]

The title compound was synthesized as described in Example 211, except using 7-fluoro-5-(5-iodo-3,4-dihydro-2H-quinolin-1-yl)-1-methyl-[1,2,4]triazolo[4,3-a]quinazoline and 5-ethynylpyridine-2-carbonitrile.

Example 231: Synthesis of 4-[2-[1-(7-fluoro-1-methyl-[1,2,4]triazolo[4,3-a]quinazolin-5-yl)-3,4-dihydro-2H-quinolin-5-yl]ethynyl]-2-methyl-thiazole

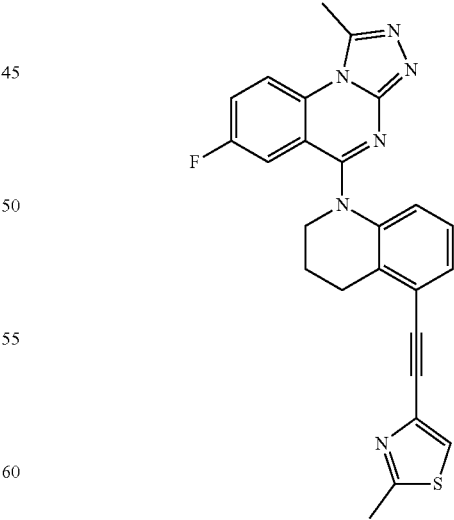

The title compound was synthesized as described in Example 211, except using 7-fluoro-5-(5-iodo-3,4-dihydro-2H-quinolin-1-yl)-1-methyl-[1,2,4]triazolo[4,3-a]quinazoline and 2-methyl-4-prop-1-ynyl-thiazole.

Example 232: Synthesis of 7-fluoro-1-methyl-5-[5-[2-(3-methylimidazol-4-yl)ethynyl]-3,4-dihydro-2H-quinolin-1-yl]-[1,2,4]triazolo[4,3-a]quinazoline

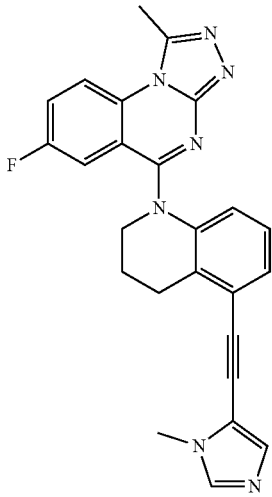 [SMILES: Cc1nnc2nc(N3CCCc4c(C#Cc5cncn5C)cccc43)c3cc(F)ccc3n12]

The title compound was synthesized as described in Example 211, except using 7-fluoro-5-(5-iodo-3,4-dihydro-2H-quinolin-1-yl)-1-methyl-[1,2,4]triazolo[4,3-a]quinazoline and 5-ethynyl-1-methyl-imidazole.

Example 233: Synthesis of 6-fluoro-1-methyl-5-[5-[2-(1-methylpyrazol-4-yl)ethynyl]-3,4-dihydro-2H-quinolin-1-yl]-[1,2,4]triazolo[4,3-a]quinazoline

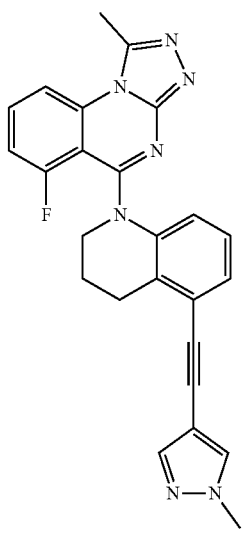 [SMILES: Cc1nnc2nc(N3CCCc4c(C#Cc5cnn(C)c5)cccc43)c3c(F)cccc3n12]

The title compound was synthesized in a similar manner to Example 1, using 5-(5-bromo-3,4-dihydro-2H-quinolin-1-yl)-6-fluoro-1-methyl-[1,2,4]triazolo[4,3-a]quinazoline and 4-ethynyl-1-methyl-pyrazole.

Example 234: Synthesis of [1-[2-[1-(7-fluoro-1-methyl-[1,2,4]triazolo[4,3-a]quinazolin-5-yl)-3,4-dihydro-2H-quinolin-5-yl]ethynyl]cyclopropyl]methanol

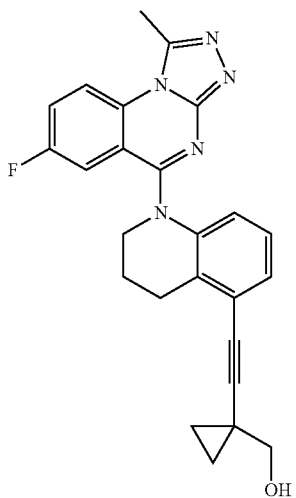 [SMILES: Cc1nnc2nc(N3CCCc4c(C#CC5(CO)CC5)cccc43)c3cc(F)ccc3n12]

The title compound was synthesized in a similar manner to Example 1, using 5-(5-bromo-3,4-dihydro-2H-quinolin-1-yl)-7-fluoro-1-methyl-[1,2,4]triazolo[4,3-a]quinazoline and (1-ethynylcyclopropyl)methanol.

Example 235: Synthesis of 4-[1-(7-fluoro-1-methyl-[1,2,4]triazolo[4,3-a]quinazolin-5-yl)-3,4-dihydro-2H-quinolin-5-yl]-2,2-dimethyl-but-3-yn-1-ol

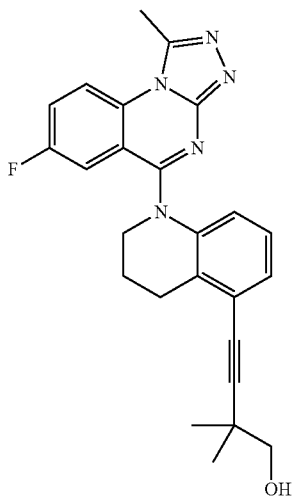 [SMILES: Cc1nnc2nc(N3CCCc4c(C#CC(C)(C)CO)cccc43)c3cc(F)ccc3n12]

The title compound was synthesized in a similar manner to Example 1, using 5-(5-bromo-3,4-dihydro-2H-quinolin-1-yl)-7-fluoro-1-methyl-[1,2,4]triazolo[4,3-a]quinazoline and 2,2-dimethylbut-3-yn-1-ol.

Example 236: Synthesis of 7-fluoro-1-methyl-5-[5-[2-(1-methylpyrazol-4-yl)ethynyl]-3,4-dihydro-2H-quinolin-1-yl]-[1,2,4]triazolo[4,3-a]quinazoline

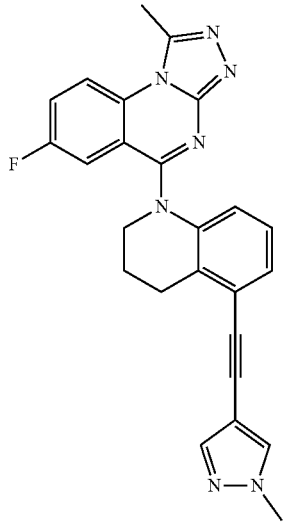 [SMILES: Cc1nnc2nc(N3CCCc4c(C#Cc5cnn(C)c5)cccc43)c3cc(F)ccc3n12]

The title compound was synthesized in a similar manner to Example 1, using 5-(5-bromo-3,4-dihydro-2H-quinolin-1-yl)-7-fluoro-1-methyl-[1,2,4]triazolo[4,3-a]quinazoline and 4-ethynyl-1-methyl-pyrazole.

Example 237: Synthesis of N-[3-[2-(3,3-difluorocyclobutyl)ethynyl]-5-fluoro-phenyl]-N-(2,2-difluoroethyl)-6,7-difluoro-1-methyl-[1,2,4]triazolo[4,3-a]quinazolin-5-amine

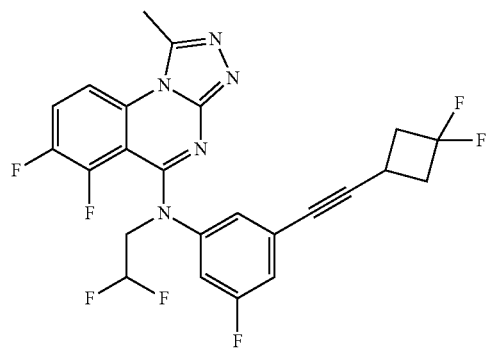 [SMILES: Cc1nnc2nc(N(CC(F)F)c3cc(F)cc(C#CC4CC(F)(F)C4)c3)c3c(F)c(F)ccc3n12]

The title compound was synthesized in a similar manner to Example 1.

Example 238: Synthesis of 1-[2-[3-[2,2-difluoroethyl-(6,7-difluoro-1-methyl-[1,2,4]triazolo[4,3-a]quinazolin-5-yl)amino]-5-fluoro-phenyl]ethynyl]cyclobutanol

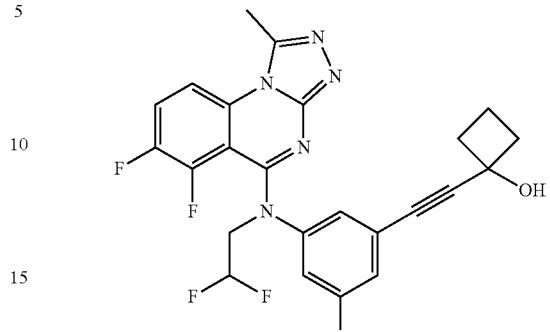

The title compound was synthesized in a similar manner to Example 1.

Example 239: Synthesis of 1-[3-[2,2-difluoroethyl-(6,7-difluoro-1-methyl-[1,2,4]triazolo[4,3-a]quinazolin-5-yl)amino]-5-fluoro-phenyl]pent-1-yn-3-ol

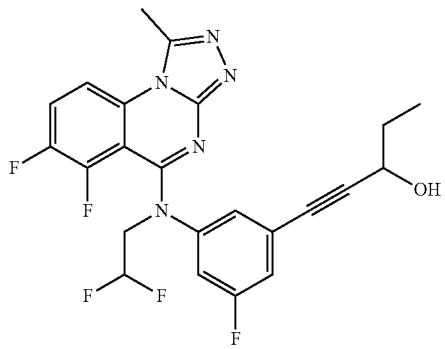 [SMILES: CCC(O)C#Cc1cc(F)cc(N(CC(F)F)c2nc3nnc(C)n3c3ccc(F)c(F)c23)c1]

The title compound was synthesized in a similar manner to Example 1.

Example 240: Synthesis of 4-[1-(6,7-difluoro-1-methyl-[1,2,4]triazolo[4,3-a]quinazolin-5-yl)-3,4-dihydro-2H-quinolin-5-yl]-2,2-dimethyl-but-3-ynenitrile

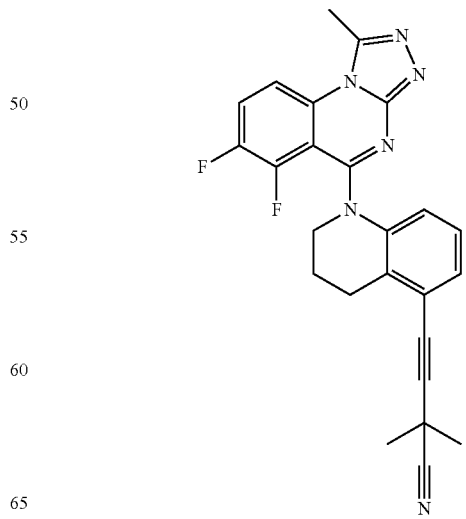

The title compound was synthesized in a similar manner to Example 1.

Example 241: Synthesis of 1-[3-[2,2-difluoroethyl-(6,7-difluoro-1-methyl-[1,2,4]triazolo[4,3-a]quinazolin-5-yl)amino]-5-fluoro-phenyl]-3-methyl-pent-1-yn-3-ol

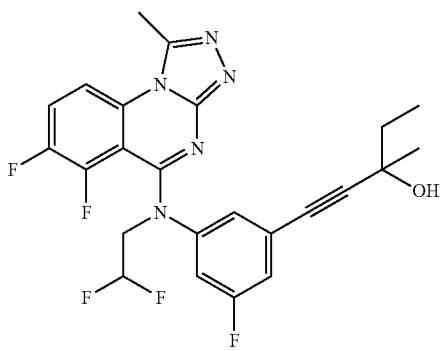 [SMILES: CCC(C)(O)C#Cc1cc(F)cc(N(CC(F)F)c2nc3nnc(C)n3c3ccc(F)c(F)c23)c1]

The title compound was synthesized in a similar manner to Example 1.

Example 242: Synthesis of 4-[1-(6,7-difluoro-[1,2,4]triazolo[4,3-a]quinazolin-5-yl)-3,4-dihydro-2H-quinolin-5-yl]-2,2-dimethyl-but-3-ynenitrile

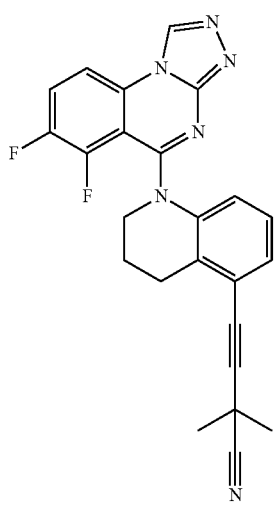 [SMILES: CC(C)(C#N)C#Cc1cccc2c1CCCN2c1nc2nncn2c2ccc(F)c(F)c12]

The title compound was synthesized in a similar manner to Example 1.

Example 243: Synthesis of 4-[1-(6-fluoro-[1,2,4]triazolo[4,3-a]quinazolin-5-yl)-3,4-dihydro-2H-quinolin-5-yl]-2,2-dimethyl-but-3-ynenitrile

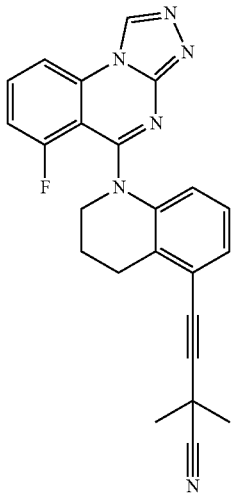 [SMILES: CC(C)(C#N)C#Cc1cccc2c1CCCN2c1nc2nncn2c2cccc(F)c12]

The title compound was synthesized in a similar manner to Example 1.

Example 244: Synthesis of 4-[1-(7-fluoro-1-methyl-[1,2,4]triazolo[4,3-a]quinazolin-5-yl)-3,4-dihydro-2H-quinolin-5-yl]-2,2-dimethyl-but-3-ynenitrile

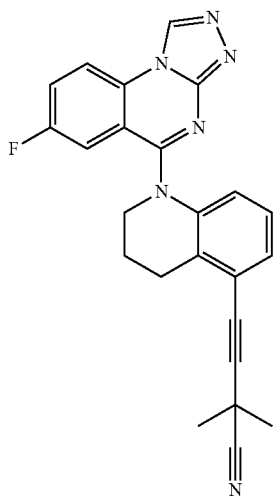

The title compound was synthesized in a similar manner to Example 1.

Example 245: Synthesis of 4-[3-[2,2-difluoroethyl-(7-fluoro-1-methyl-[1,2,4]triazolo[4,3-a]quinazolin-5-yl)amino]-5-fluoro-phenyl]-2,2-dimethyl-but-3-ynenitrile

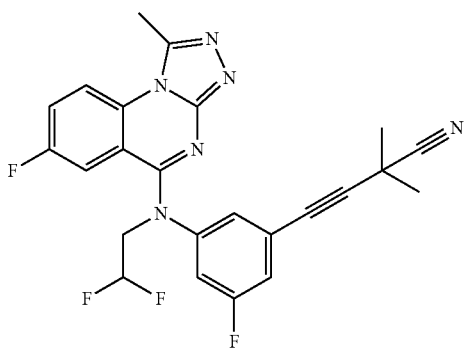 [SMILES: Cc1nnc2nc(N(CC(F)F)c3cc(F)cc(C#CC(C)(C)C#N)c3)c3cc(F)ccc3n12]

The title compound was synthesized in a similar manner to Example 1.

Example 246: Synthesis of 5-[5-(2-cyclobutylethynyl)-3,4-dihydro-2H-quinolin-1-yl]-6-fluoro-1-methyl-[1,2,4]triazolo[4,3-a]quinazoline

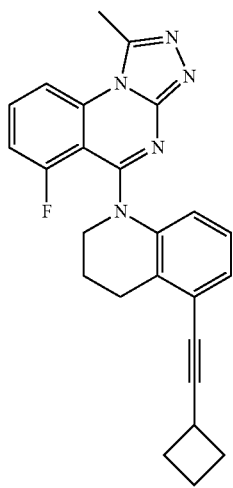 [SMILES: Cc1nnc2nc(N3CCCc4c(C#CC5CCC5)cccc43)c3c(F)cccc3n12]

The title compound was synthesized in a similar manner to Example 1.

Biological Activity
Measuring DGKα Activity

A 10 mM solution of the test compound in DMSO was further diluted with DMSO to ten levels of the concentration (0.0001 mM, 0.0003 mM, 0.001 mM, 0.003 mM, 0.01 mM, 0.03 mM, 0.1 mM, 0.3 mM, 1 mM, 3 mM), each of which was subjected to a 25-fold dilution with the assay buffer to obtain the drug solutions (4% DMSO solutions).

A drug solution of each concentration was added to each well to give a final volume of 20 μL. The kinase-inhibitory activity was evaluated using QSS Assist ADP-Glo™ Assay Kit (BTN-DGKα; Carna Biosciences, Inc., No. 12-403-20N).

The kinase activity was measured using ADP-Glo™ Kinase Assay (Promega Corporation). 10 μL of ADP-Glo™ Reagent (10 mM Mg added) provided by the kit was added to each well and incubated at 25° C. for 40 minutes. Then, 20 μL of Kinase Detection Reagent was added and incubated at 25° C. for 40 minutes. Luciferase activity of each well was measured using a microplate reader (EnVision, PerkinElmer, Inc.)

DGKα Biochemical Activity Assay

Alternatively, the enzymatic activity of human DGKα was monitored in a biochemical assay in the presence or absence of compounds and using micelles containing 18:1 Diacylglycerol (DAG), 16:0-18:1 PS (POPS) and Octylglucoside as substrate. DGKα activity led to conversion of DAG and ATP to Phosphatidic Acid (PA) and ADP. Levels of ADP were monitored by bioluminescence using the ADP-Glo Kinase Assay (Promega) and were indicative of DGKα activity.

Ten nanoliters of test compound dissolved in DMSO at various concentrations were dispensed into a 384-well low volume nonbinding service white plates (Corning #3824) using a Labcyte Echo instrument. Recombinant DGKα (Carna Biosciences) in assay buffer (5 μL in 50 mM MOPS [3-(N-morpholino) propanesulfonic acid], pH 7.2; 0.0025% Triton X-100; 1 mM dithiothreitol; 5 mM MgCl$_2$, 200 μM ATP) was added to the compound-containing plate and was incubated for 15 minutes at 25° C. A substrate solution (5 μL in 1.7 mM 1,2-dioleoyl-sn-glycerol [18:1 DAG], 13.5 mM 1-palmitoyl-2-oleoyl-sn-glycero-3-phospho-L-serine [16:0-18:1 PS](POPS), 2 μM CaCl$_2$, 100 mM Octylglucoside (OG), 1 mM DTT) (obtained from Carna Biosciences) diluted in DGK ALPHA assay buffer was then added to start the reaction. Final concentrations were 1 nM DGKα, 100 μM ATP, 1 μM calcium chloride, 0.85 mM 1,2-dioleoyl-sn-glycerol (18:1 DAG), 6.75 mM 1-palmitoyl-2-oleoyl-sn-glycero-3-phospho-L-serine (16:0-18:1 PS) (POPS), 1 μM CaCl$_2$, 50 mM Octylglucoside (OG) and 5 mM MgCl$_2$. The reaction mixture was incubated at 25° C. for 1 hour. ADP-Glo Reagent (10 μL, 10 mM Mg added) provided by the kit was added to each well and incubated at 25° C. for 40 minutes. Then, 20 μL of Kinase Detection Reagent was added and incubated at 25° C. for 40 minutes. Luciferase activity of each well was measured via luminescence on an Envision plate reader (PerkinElmer).

Data were normalized based on maximum inhibition (50 μM of kinase inhibitor CU3) and no inhibition (DMSO) controls. Least squares curve fittings were performed using a four-parameter variable slope nonlinear regression model. IC$_{50}$ was defined as the concentration of compound required to inhibit 50% of maximum activity. IC$_{50}$ values from multiple experiments were averaged by geometric mean and the standard deviation was calculated.

Exemplary biochemical data are shown in Table 2 below.

TABLE 2

| DGKα Biochemical Activity | |
|---|---|
| EXAMPLE | HTBS DGKa 1X ATP KM IC50 (nM) |
| 1 | 15.07 |
| 2 | 14.819 |
| 3 | 35.864 |
| 4 | 23.947 |
| 5 | 14.519 |
| 6 | 44.127 |
| 7 | 23.062 |
| 8 | 17.651 |
| 9 | 28.543 |
| 10 | 17.156 |

TABLE 2-continued

DGKα Biochemical Activity

| EXAMPLE | HTBS DGKa 1X ATP KM IC50 (nM) |
|---|---|
| 11 | 13.923 |
| 12 | 37.293 |
| 13 | 7.932 |
| 14 | 8.192 |
| 15 | 7.159 |
| 16 | 22.745 |
| 17 | 14.71 |
| 18 | 14.155 |
| 19 | 21.317 |
| 20 | 30.098 |
| 21 | 20.991 |
| 22 | 18.906 |
| 23 | 33.865 |
| 24 | 15.119 |
| 25 | 30.158 |
| 26 | 22.522 |
| 27 | 15.086 |
| 28 | 9.486 |
| 29 | 3.31 |
| 30 | 14.736 |
| 31 | 50.91 |
| 32 | 10.964 |
| 33 | 42.396 |
| 34 | 30.378 |
| 35 | 5.436 |
| 36 | 9.927 |
| 37 | 64.797 |
| 38 | 125.95 |
| 39 | 8.31 |
| 40 | 12.574 |
| 41 | 11.043 |
| 42 | 6.927 |
| 43 | 9.966 |
| 44 | 3.81 |
| 45 | 8.254 |
| 46 | 15.574 |
| 47 | 18.846 |
| 48 | 5.733 |
| 49 | 12.441 |
| 50 | 11.857 |
| 51 | 5.011 |
| 52 | 7.979 |
| 53 | 18.647 |
| 54 | 32.77 |
| 55 | 21.61 |
| 56 | 13.519 |
| 57 | 46.249 |
| 58 | 78.272 |
| 59 | 11.177 |
| 60 | 69.155 |
| 61 | 8.479 |
| 62 | 80.092 |
| 63 | 19.446 |
| 64 | 9.966 |
| 65 | 189.33 |
| 66 | 12.775 |
| 67 | 156.21 |
| 68 | 190.87 |
| 69 | 70.513 |
| 70 | 29.202 |
| 71 | 124.37 |
| 72 | 19.791 |
| 73 | 61.275 |
| 74 | 6.104 |
| 75 | 28.914 |
| 76 | 13.378 |
| 77 | 15.479 |
| 78 | 41.194 |
| 79 | 22.572 |
| 80 | 15.134 |
| 81 | 10.39 |
| 82 | 11.403 |
| 83 | 8.488 |
| 84 | 5.057 |
| 85 | 7.206 |
| 86 | 26.36 |
| 87 | 3.503 |
| 88 | 10.588 |
| 89 | 5.406 |
| 90 | 29.293 |
| 91 | 3.431 |
| 92 | 13.836 |
| 93 | 8.145 |
| 94 | 4.299 |
| 95 | 7.694 |
| 96 | 6.222 |
| 97 | 17.994 |
| 98 | 84.66 |
| 99 | 7.401 |
| 100 | 6.225 |
| 101 | 5.558 |
| 102 | 3.802 |
| 103 | 5.133 |
| 104 | 8.057 |
| 105 | 30.552 |
| 106 | 118.43 |
| 107 | 39.857 |
| 108 | 4.688 |
| 109 | 7.299 |
| 110 | 2.764 |
| 111 | 6.496 |
| 112 | 3.48 |
| 113 | 1.444 |
| 114 | 6.759 |
| 115 | 32.83 |
| 116 | 5.193 |
| 117 | 14.775 |
| 118 | 4.889 |
| 119 | 2.126 |
| 120 | 4.99 |
| 121 | 22.781 |
| 122 | 5.269 |
| 123 | 31.519 |
| 124 | 16.804 |
| 125 | 16.417 |
| 126 | 17.158 |
| 127 | 8.418 |
| 128 | 20.805 |
| 129 | 7.548 |
| 130 | 4.188 |
| 131 | 8.679 |
| 132 | 3.099 |
| 133 | 15.061 |
| 134 | 9.88 |
| 135 | 5.491 |
| 136 | 11.068 |
| 137 | 17.678 |
| 138 | 28.946 |
| 139 | 72.553 |
| 140 | 4.518 |
| 141 | 4.765 |
| 142 | 16.423 |
| 143 | 3.853 |
| 144 | 4.734 |
| 145 | 6.871 |
| 146 | 3.545 |
| 147 | 3.159 |
| 148 | 4.363 |
| 149 | 14.072 |
| 150 | 11.523 |
| 151 | 2.406 |
| 152 | 34.555 |
| 153 | 82.769 |
| 154 | 7.418 |
| 155 | 25.614 |
| 156 | 40.245 |
| 157 | 671.59 |
| 158 | 281.28 |
| 159 | 333.33 |
| 160 | 74.866 |

TABLE 2-continued

DGKα Biochemical Activity

| EXAMPLE | HTBS DGKa 1X ATP KM IC50 (nM) |
|---|---|
| 161 | 87.06 |
| 162 | 14.985 |
| 163 | 17.108 |
| 164 | 12.995 |
| 165 | 7.601 |
| 166 | 17.397 |
| 167 | 18.048 |
| 168 | 10.362 |
| 169 | 7.298 |
| 170 | 51.028 |
| 171 | 14.796 |
| 172 | 8.767 |
| 173 | 17.154 |
| 174 | 26.734 |
| 175 | 109.76 |
| 176 | 12.358 |
| 177 | 6.74 |
| 178 | 44.89 |
| 179 | 9.589 |
| 180 | 5.121 |
| 181 | 4.061 |
| 182 | 2.412 |
| 183 | 28.444 |
| 184 | 7.509 |
| 185 | 4.578 |
| 186 | 6.508 |
| 187 | 12.323 |
| 188 | 9.858 |
| 189 | 1.838 |
| 190 | 6.911 |
| 191 | 3.658 |
| 192 | 54.894 |
| 193 | 2.851 |
| 194 | 0.773 |
| 195 | 13.27 |
| 196 | 2.494 |
| 197 | 11.02 |
| 198 | 10.769 |
| 199 | 3.826 |
| 200 | 5.183 |
| 201 | 6.772 |
| 202 | 3.88 |
| 203 | 2.102 |
| 204 | 3.83 |
| 205 | 13.9 |
| 206 | 13.535 |
| 207 | 14.925 |
| 208 | 18.692 |
| 209 | 2.189 |
| 210 | 5.885 |
| 211 | 6.345 |
| 212 | 18.587 |
| 213 | 9.997 |
| 214 | 9.075 |
| 215 | 25.173 |
| 216 | 24.349 |
| 217 | 31.723 |
| 218 | 14.483 |
| 219 | 11.173 |
| 220 | 21.771 |
| 221 | 121.61 |
| 222 | 6.295 |
| 223 | 40.703 |
| 224 | 15.113 |
| 225 | 7.463 |
| 226 | 3.423 |
| 227 | 29.331 |
| 228 | 17.756 |
| 229 | 16.656 |
| 230 | 1.541 |
| 231 | 7.645 |
| 232 | 12.428 |
| 233 | 6.738 |
| 234 | 3.86 |
| 235 | 6.854 |
| 236 | 3.646 |
| 237 | 8.306 |
| 238 | 7.078 |
| 239 | 24.777 |
| 240 | 7.052 |
| 241 | 38.585 |
| 242 | 3.754 |
| 243 | 3.144 |
| 244 | 10.219 |
| 245 | 21.212 |
| 246 | 39.289 |

Jurkat NFκB-Luciferase Assay

The activity of compounds was tested in a cell based NFκB reporter assay. Jurkat cells that are stably expressing a luciferase reporter construct under the transcriptional control of a NFκB reporter element were activated with an anti-CD3 antibody and luciferase levels were measured with a bioluminescence readout. An increase in the levels of bioluminescence was indicative of enhanced T-cell activation following DGKα inhibition by the compound.

Flat-bottom polystyrene plates (384-well, tissue culture treated) were coated overnight at 4° C. with 20 ul/well of a solution of phosphate-buffered saline supplemented with 5 ug/ml anti-CD3 antibody (clone OKT3, Biolegend). The day after, the excess antibody was washed out five times with 100 ul/well of assay medium (RPMI supplemented with 10% fetal bovine serum) using a Biotek EL406 instrument and leaving 20 ul of residual volume in each well. Jurkat NFκB-luciferase cells (Promega #) were harvested and diluted to 1 million cells/ml in assay medium. Sixty nanoliters of test compound dissolved in DMSO at various concentrations were dispensed into 384-well v-bottom polypropylene plates (Greiner) using a Labcyte Echo instrument. Thirty microliters of medium containing the Jurkat NFκB-luciferase cells were then dispensed using a Biotek MicroFlo instrument in each well of the compound-containing plate. The medium/cell/compound mixture was mixed with a Bravo instrument and 20 ul/well of the mixture was transferred to the anti-CD3-coated plate. The assay mixture was then incubated for 2.5 hrs at 37° C. followed by equilibration at 25° C. for 30 min. Forty microliters of One-Glo Ex (Promega) was then added to the assay mixture and luciferase activity was read on a Envision plate reader 7 minutes later.

Bioluminescence data were normalized based on maximum enhancement (1 micromolar of compound) and on basal activation (DMSO) controls. Least squares curve fittings were performed using a four-parameter variable slope nonlinear regression model. $EC_{50}$ is defined as the concentration of compound required to produce 50% of maximum NFκB luciferase signal. $EC_{50}$ values from multiple experiments were averaged by geometric mean and the standard deviation was calculated.

Exemplary cell data are shown in Table 3 below.

TABLE 3

DGKα inhibition in Jurkat cells

| EXAMPLE | DGK NFKb Luciferase EC50 (nM) |
|---|---|
| 1 | 0.897 |
| 2 | 3.129 |

TABLE 3-continued

DGKα inhibition in Jurkat cells

| EXAMPLE | DGK NFKb Luciferase EC50 (nM) |
|---|---|
| 3 | 1.857 |
| 4 | 6.916 |
| 5 | 1.194 |
| 6 | 0.692 |
| 7 | 0.747 |
| 8 | 1.653 |
| 9 | 1.527 |
| 10 | 5.872 |
| 11 | 5.767 |
| 12 | 1.854 |
| 13 | 1.013 |
| 14 | 1.397 |
| 15 | 1.914 |
| 16 | 1.539 |
| 17 | 1.162 |
| 18 | 1.5 |
| 19 | 1.534 |
| 20 | 10.279 |
| 21 | 9.421 |
| 22 | 10.092 |
| 23 | 3.462 |
| 24 | 4.699 |
| 25 | 7.37 |
| 26 | 2.465 |
| 27 | 3.517 |
| 28 | 5.088 |
| 29 | 0.66 |
| 30 | 0.163 |
| 31 | 1.427 |
| 32 | 0.461 |
| 33 | 1.586 |
| 34 | 0.907 |
| 35 | 1.144 |
| 36 | 1.847 |
| 37 | 1.876 |
| 38 | 3.952 |
| 39 | 2.181 |
| 40 | 17.145 |
| 41 | 1.39 |
| 42 | 2.321 |
| 43 | 1.219 |
| 44 | 7.154 |
| 45 | 328.88 |
| 46 | 1.755 |
| 47 | 3.917 |
| 48 | 3.025 |
| 49 | 1.359 |
| 50 | 16.834 |
| 51 | 1.923 |
| 52 | 0.583 |
| 53 | 0.792 |
| 54 | 1.636 |
| 55 | 3.425 |
| 56 | 0.805 |
| 57 | 0.669 |
| 58 | 3.673 |
| 59 | 11.701 |
| 60 | 531.85 |
| 61 | 3.36 |
| 62 | 3.244 |
| 63 | 4.169 |
| 64 | 7.433 |
| 65 | 46.706 |
| 66 | 6.781 |
| 67 | 11.606 |
| 68 | 9.684 |
| 69 | 2.261 |
| 70 | 5.62 |
| 71 | 11.298 |
| 72 | 2.204 |
| 73 | 10.838 |
| 74 | 1.946 |
| 75 | 3.413 |
| 76 | 8.005 |
| 77 | 1.935 |
| 78 | 7.731 |
| 79 | 2.54 |
| 80 | 2.149 |
| 81 | 30.72 |
| 82 | 10.456 |
| 83 | 1.206 |
| 84 | 2.435 |
| 85 | 2.238 |
| 86 | 18.348 |
| 87 | 7.574 |
| 88 | 1.142 |
| 89 | 4.61 |
| 90 | 1.876 |
| 91 | 3.832 |
| 92 | 5.305 |
| 93 | 2.63 |
| 94 | 2.335 |
| 95 | 2.768 |
| 96 | 5.104 |
| 97 | 3.899 |
| 98 | 18.779 |
| 99 | 0.483 |
| 100 | 0.122 |
| 101 | 4.69 |
| 102 | 2.81 |
| 103 | 2.266 |
| 104 | 8.946 |
| 105 | 27.067 |
| 106 | 2.528 |
| 107 | 3.213 |
| 108 | 2.836 |
| 109 | 1.666 |
| 110 | 9.803 |
| 111 | 45.755 |
| 112 | 0.716 |
| 113 | 0.9 |
| 114 | 12.508 |
| 115 | 2.367 |
| 116 | 1.068 |
| 117 | 1.316 |
| 118 | 5.81 |
| 119 | 2.862 |
| 120 | 12.303 |
| 121 | 4.951 |
| 122 | 2.627 |
| 123 | 0.533 |
| 124 | 0.781 |
| 125 | 2.898 |
| 126 | 1.162 |
| 127 | 2.018 |
| 128 | 7.479 |
| 129 | 1.22 |
| 130 | 1.975 |
| 131 | 2.144 |
| 132 | 6.636 |
| 133 | 5.688 |
| 134 | 8.214 |
| 135 | 6.063 |
| 136 | 13.87 |
| 137 | 105.53 |
| 138 | 43.301 |
| 139 | 41.292 |
| 140 | 4.356 |
| 141 | 5.105 |
| 142 | 5.034 |
| 143 | 3.608 |
| 144 | 11.07 |
| 145 | 1.213 |
| 146 | 20.539 |
| 147 | 7.737 |
| 148 | 6.028 |
| 149 | 5.382 |
| 150 | 2.482 |
| 151 | 3.59 |
| 152 | 53.915 |

TABLE 3-continued

DGKα inhibition in Jurkat cells

| EXAMPLE | DGK NFKb Luciferase EC50 (nM) |
|---|---|
| 153 | 3.982 |
| 154 | 6.328 |
| 155 | 5.128 |
| 156 | 1.023 |
| 157 | 8.231 |
| 158 | 49.281 |
| 159 | 16.526 |
| 160 | 28.614 |
| 161 | 5.491 |
| 162 | 3.334 |
| 163 | 28.361 |
| 164 | 3.635 |
| 165 | 5.346 |
| 166 | 15.804 |
| 167 | 5.839 |
| 168 | 5.411 |
| 169 | 4.386 |
| 170 | 358.22 |
| 171 | 7.362 |
| 172 | 3.225 |
| 173 | 2.032 |
| 174 | 11.963 |
| 175 | 1.738 |
| 176 | 6.667 |
| 177 | 23.408 |
| 178 | 10.203 |
| 179 | 9.126 |
| 180 | 13.459 |
| 181 | 12.386 |
| 182 | 4.268 |
| 183 | 11.8 |
| 184 | 0.787 |
| 185 | 1.091 |
| 186 | 2.838 |
| 187 | 1.451 |
| 188 | 2.124 |
| 189 | 3.442 |
| 190 | 1.457 |
| 191 | 1.417 |
| 192 | 0.892 |
| 193 | 0.871 |
| 194 | 1.684 |
| 195 | 0.382 |
| 196 | 0.545 |
| 197 | 1.377 |
| 198 | 0.508 |
| 199 | 1.625 |
| 200 | 0.858 |
| 201 | 0.202 |
| 202 | 2.045 |
| 203 | 0.307 |
| 204 | 0.121 |
| 205 | 16.582 |
| 206 | 5.074 |
| 207 | 4.043 |
| 208 | 0.815 |
| 209 | 1.167 |
| 210 | 0.657 |
| 211 | 56.112 |
| 212 | 9.704 |
| 213 | 1.276 |
| 214 | 3.292 |
| 215 | 9.947 |
| 216 | 5.425 |
| 217 | 16.031 |
| 218 | 33.901 |
| 219 | 1.3 |
| 220 | 0.346 |
| 221 | 0.647 |
| 222 | 0.718 |
| 223 | 9.214 |
| 224 | 8.379 |
| 225 | 8.971 |
| 226 | 3.916 |
| 227 | 9.731 |
| 228 | 0.319 |
| 229 | 1.036 |
| 230 | 0.476 |
| 231 | 4.062 |
| 232 | 9.244 |
| 233 | 2.155 |
| 234 | 23.28 |
| 235 | 8.255 |
| 236 | 2.518 |
| 237 | 1.256 |
| 238 | 24.452 |
| 239 | 31.605 |
| 240 | 3.41 |
| 241 | 29.509 |
| 242 | 1.937 |
| 243 | 2.328 |
| 244 | 3.236 |
| 245 | 6.755 |
| 246 | 0.272 |

Although the foregoing invention has been described in some detail by way of illustration and Example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A compound of Formula (I):

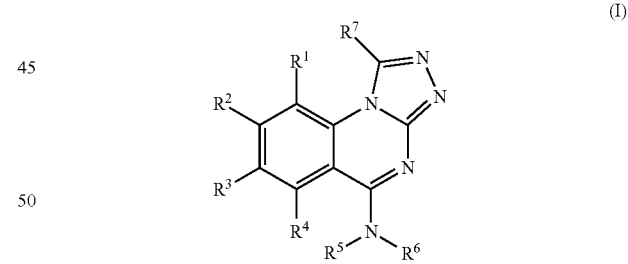

or a pharmaceutically acceptable salt thereof, wherein $R^1$ is hydrogen, $C_{1-6}$ alkyl, or halogen;

$R^2$ is hydrogen $C_{1-6}$ alkyl, or halogen;

$R^3$ is hydrogen, $C_{1-6}$ alkyl, halogen, or —CN;

$R^4$ is hydrogen, $C_{1-6}$ alkyl, or halogen;

is

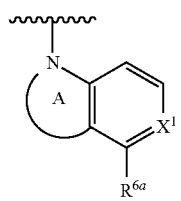

$X^1$ is N or CH;

Ring A is a 6 to 8 membered heterocycloalkyl optionally having one additional heteroatom N or O, wherein Ring A is optionally substituted with 1 or 2 $R^{6g}$, each $R^{6g}$ is independently $C_{1-6}$ alkyl, halogen, $C_{1-6}$ haloalkyl, —OH, or $C_{1-6}$ alkoxy;

$R^{6a}$ is $C_{2-6}$ alkynyl substituted with 1 or 2 $R^{6j}$;

each $R^{6j}$ is independently —C(O)N($R^{6j3}$)($R^{6j4}$), —N($R^{6j1}$)C(O)$R^{6j2}$, —N($R^{6j1}$)S(O)$_2$($R^{6j2}$), $C_{3-10}$ cycloalkyl substituted with 1 or 2 $R^{6p}$ which can be the same or different;

$R^{6j1}$ is hydrogen or $C_{1-6}$ alkyl;

$R^{6j2}$ is $C_{3-10}$ cycloalkyl substituted with $C_{1-6}$ haloalkyl, or heteroaryl substituted with 1 to 3 $R^{6j2a}$ which can be the same or different;

each $R^{6j2a}$ is independently $C_{1-6}$ alkyl or $C_{1-6}$ haloalkyl;

$R^{6j3}$ is hydrogen or $C_{1-6}$ alkyl;

$R^{6j4}$ is $C_{3-10}$ cycloalkyl substituted with $C_{1-6}$ haloalkyl;

or $R^{6j3}$ and $R^{6j4}$ together with the N to which they are attached form a 5 to 7 membered heterocycloalkyl optionally having one additional heteroatom N or O, the heterocycloalkyl is optionally substituted with 1 to 4 $R^{6j3a}$ which can be the same or different;

each $R^{6j3a}$ is independently halogen or $C_{1-6}$ alkyl;

each $R^{6p}$ is —N($R^{6p1}$)C(O)$R^{6p2}$ or heteroaryl substituted with $C_{1-6}$ alkyl;

$R^{6p1}$ is hydrogen or $C_{1-6}$ alkyl;

$R^{6p2}$ is $C_{3-10}$ cycloalkyl substituted with $C_{1-6}$ haloalkyl;

$R^7$ is hydrogen or $C_{1-6}$ alkyl; and each heteroaryl is a 5 to 6 membered ring having 1 to 2 heteroatoms each independently N or O.

2. The compound of claim 1, or a pharmaceutically acceptable salt thereof, wherein

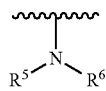

is

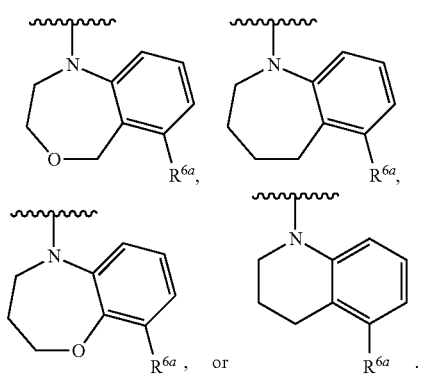

3. The compound of claim 1, or a pharmaceutically acceptable salt thereof, wherein

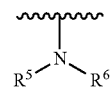

is

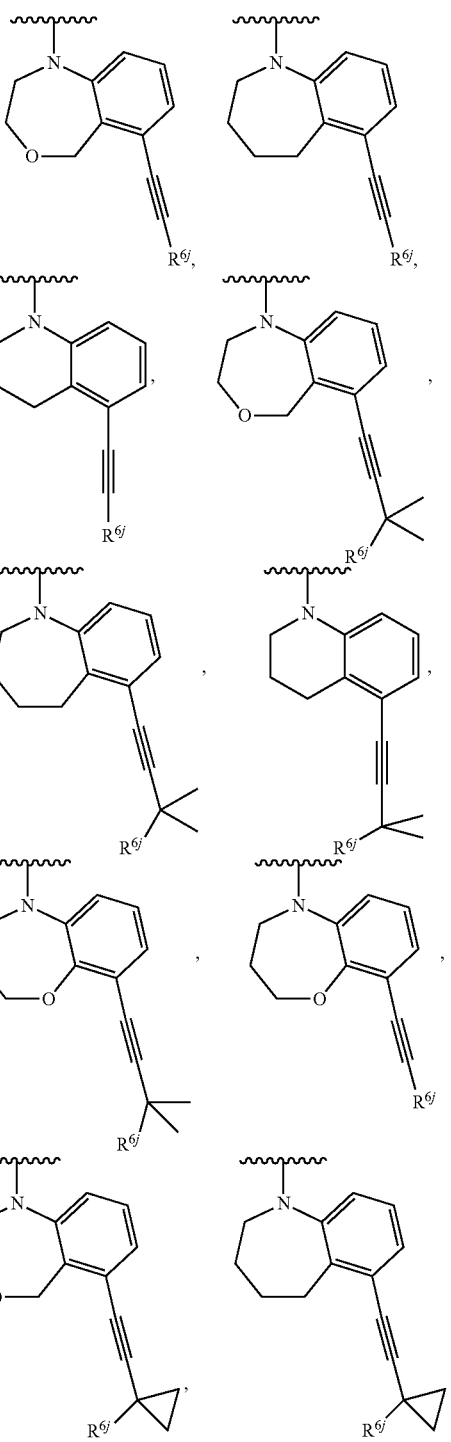

485

-continued

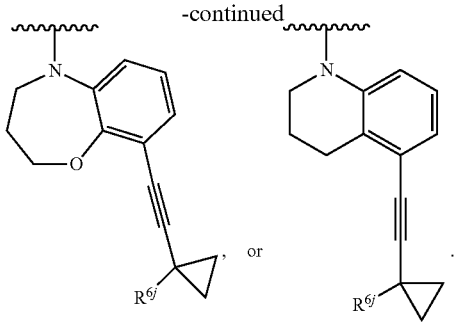

, or

486

-continued

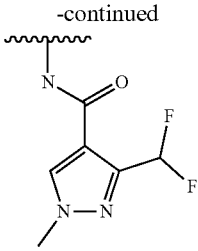

,

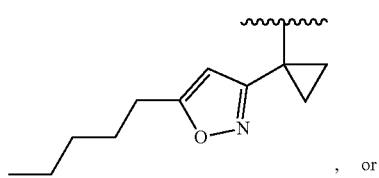

, or

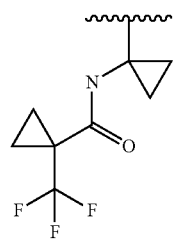

.

4. The compound of claim 1, or a pharmaceutically acceptable salt thereof, wherein $R^{6j}$ is —NHC(O)$R^{6j2}$, $R^{6j2}$ is cyclopropyl substituted with $C_{1-3}$ haloalkyl.

5. The compound of claim 1, or a pharmaceutically acceptable salt thereof, wherein $R^{6j}$ is —NHC(O)$R^{6j2}$; $R^{6j2}$ is 5 or 6 membered heteroaryl substituted 1 to 3 $R^{6j2a}$; and each $R^{6j2a}$ is independently $C_{1-3}$ alkyl or $C_{1-3}$ haloalkyl.

6. The compound of claim 1, or a pharmaceutically acceptable salt thereof, wherein $R^{6j}$ is —C(O)N($R^{6j3}$)($R^{6j4}$); $R^{6j3}$ is hydrogen; and $R^{6j4}$ is cyclopropyl substituted with $C_{1-3}$ haloalkyl.

7. The compound of claim 1, or a pharmaceutically acceptable salt thereof, wherein $R^{6j}$ is —C(O)N($R^{6j3}$)($R^{6j4}$); $R^{6j3}$ and $R^{6j4}$ together with the N to which they are attached form piperidinyl or morpholinyl, wherein the piperidinyl or morpholinyl is optionally substituted with 1 to 3 $R^{6j3a}$; each $R^{6j3a}$ is independently —F or $C_{1-3}$ alkyl.

8. The compound of claim 1, or a pharmaceutically acceptable salt thereof, wherein $R^{6j}$ is cyclopropyl substituted with —NHC(O)$R^{6p2}$, $R^{6p2}$ is cyclopropyl substituted with $C_{1-3}$ haloalkyl.

9. The compound of claim 1, or a pharmaceutically acceptable salt thereof, wherein $R^{6j}$ is cyclopropyl substituted with —NHC(O)$R^{6p2}$, $R^{6p2}$ is 5 to 6 membered heteroaryl having 1 to 2 heteroatoms each independently N or O, the heteroaryl is substituted with $C_{1-6}$ alkyl.

10. The compound of claim 1, or a pharmaceutically acceptable salt thereof, wherein each $R^{6j}$ is independently

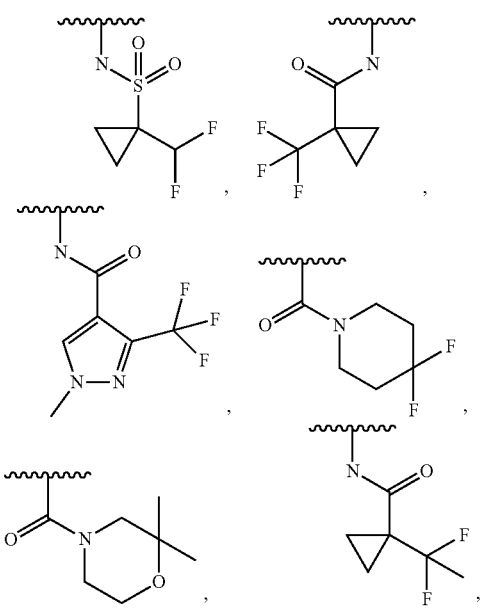

11. The compound of claim 1, or a pharmaceutically acceptable salt thereof, wherein $$R^5 \diagdown \underset{|}{N} \diagup R^6$$

is

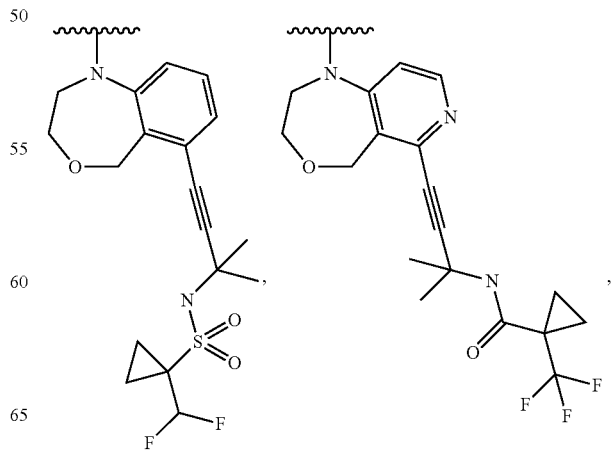

487
-continued
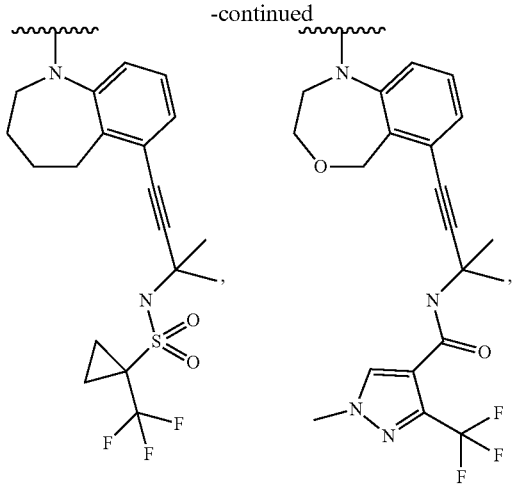
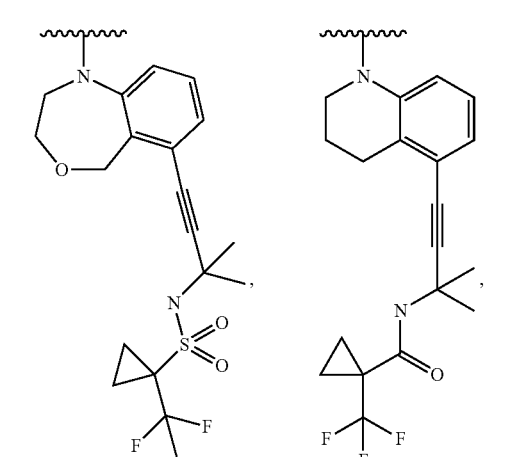
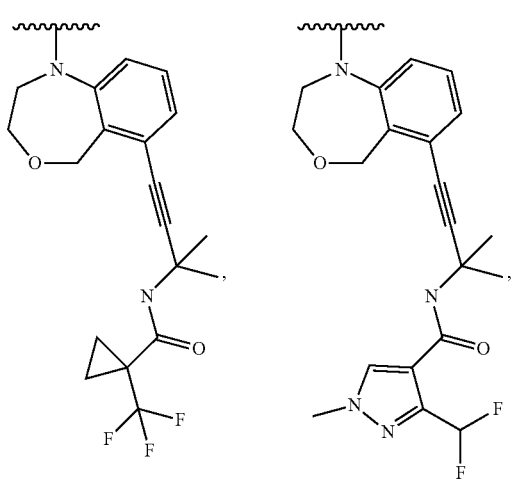
488
-continued
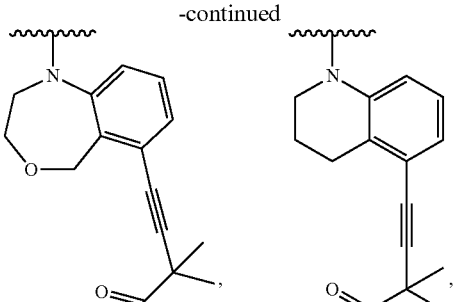
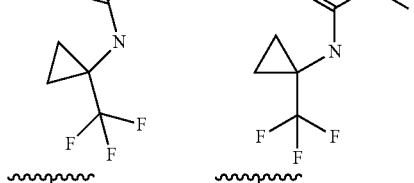
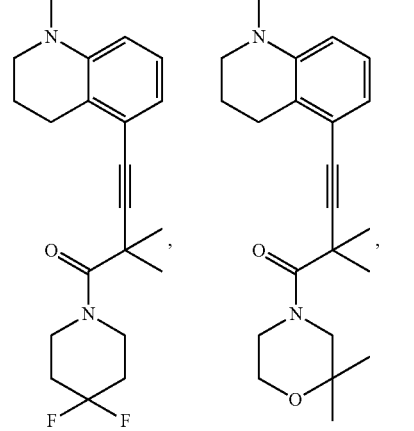
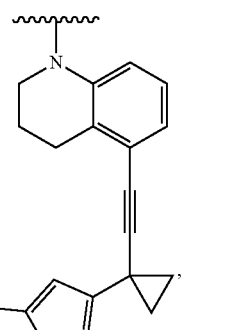
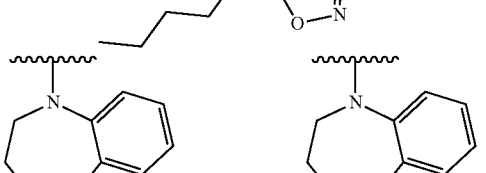
, or
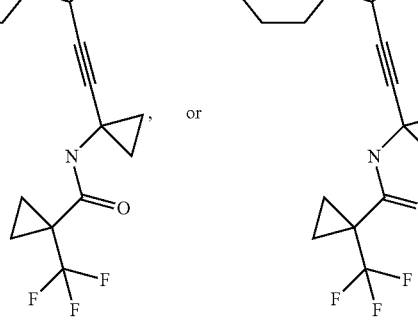

12. The compound of claim 1, or a pharmaceutically acceptable salt thereof, wherein R¹ is hydrogen, —CH₃, —F, or —Cl.

13. The compound of claim 1, or a pharmaceutically acceptable salt thereof, wherein R² is hydrogen, —F, or —Cl.

14. The compound of claim 1, or a pharmaceutically acceptable salt thereof, wherein R³ is hydrogen, —F, or —CN.

15. The compound of claim 1, or a pharmaceutically acceptable salt thereof, wherein R⁴ is hydrogen, —CH₃, —F, or —Cl.

16. The compound of claim 1, or a pharmaceutically acceptable salt thereof, wherein R⁷ is hydrogen.

17. A compound having a structure

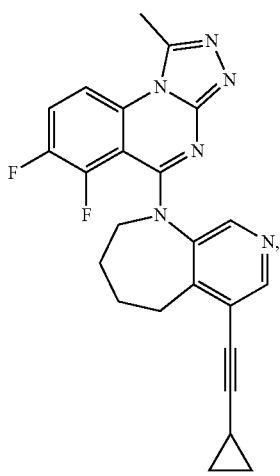

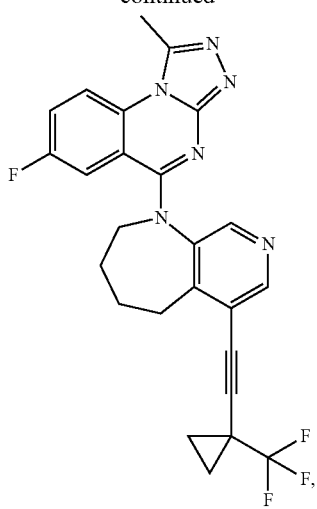

-continued

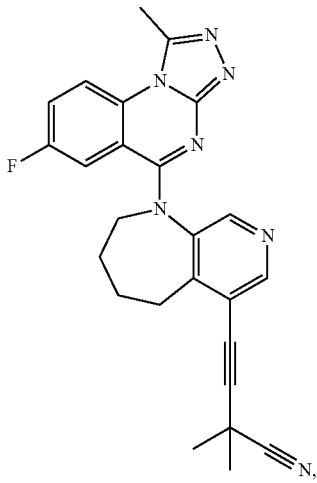

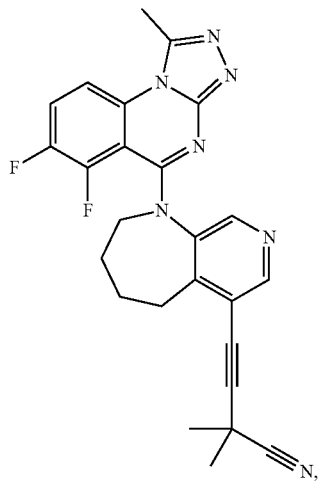

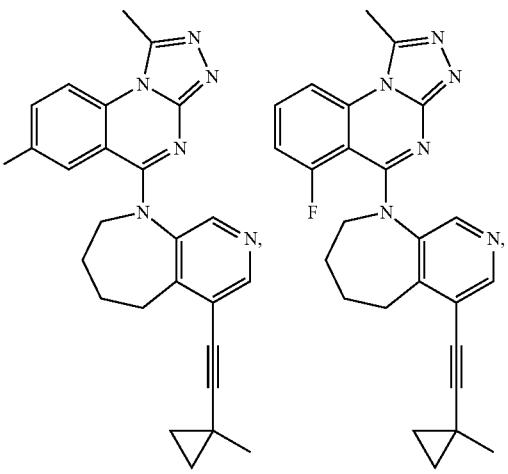

491
-continued
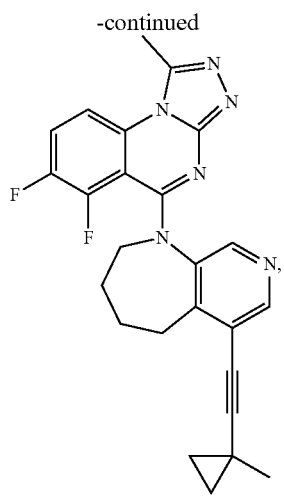
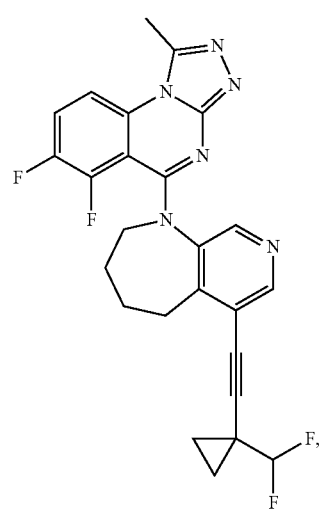
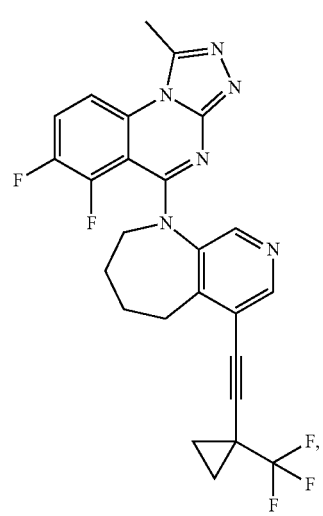
492
-continued
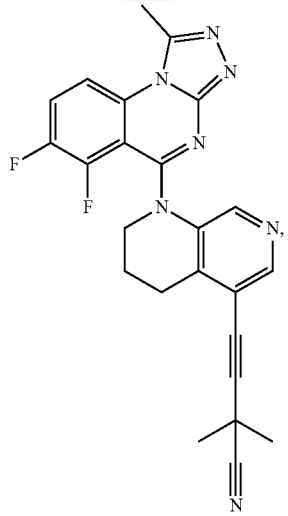
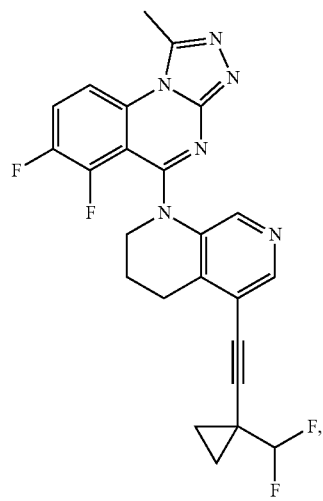
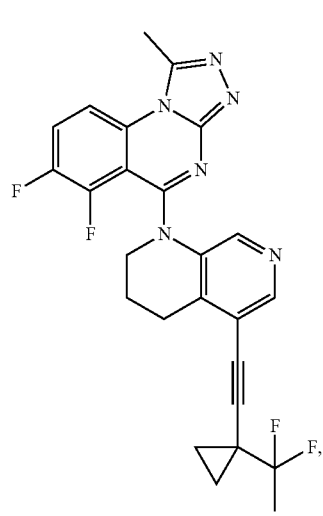

493
-continued
494
-continued
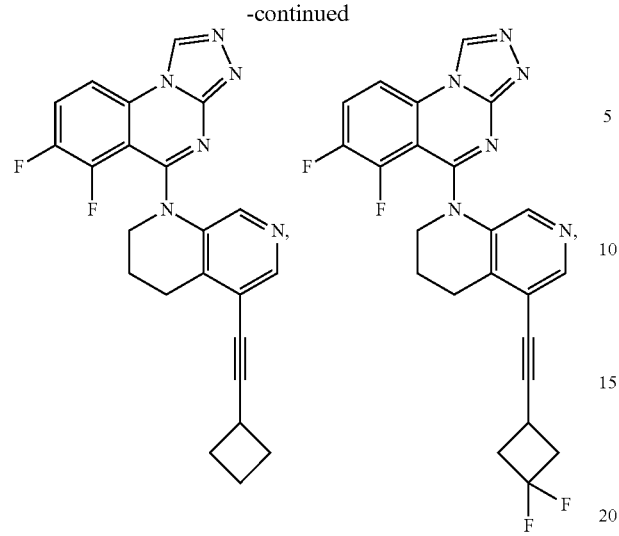
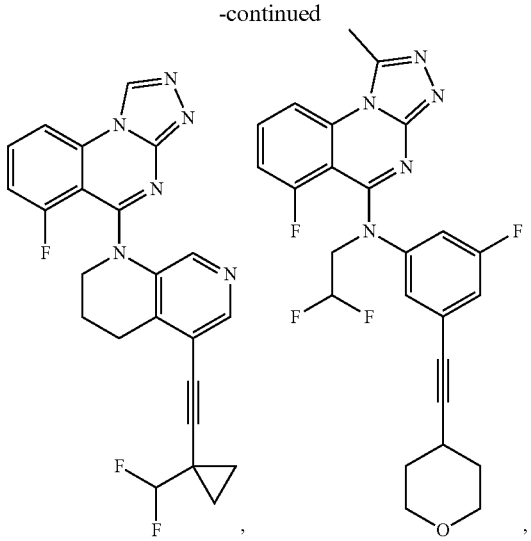
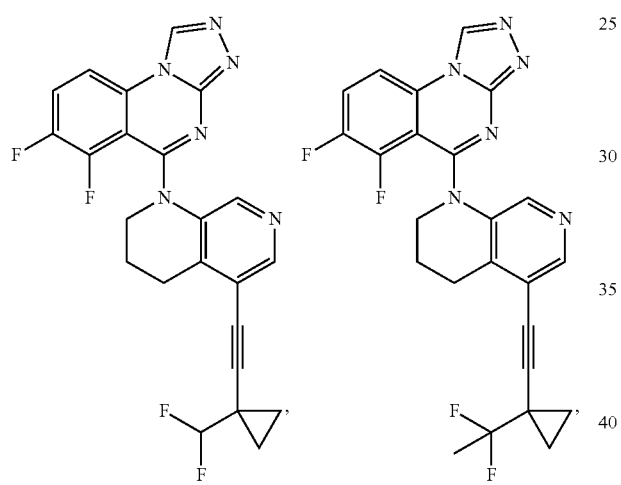
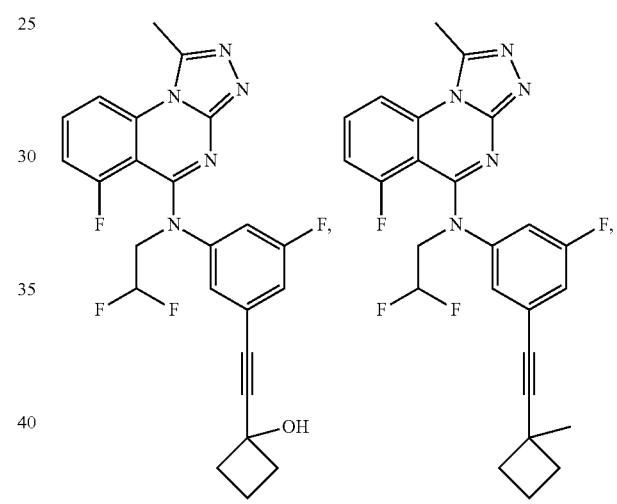
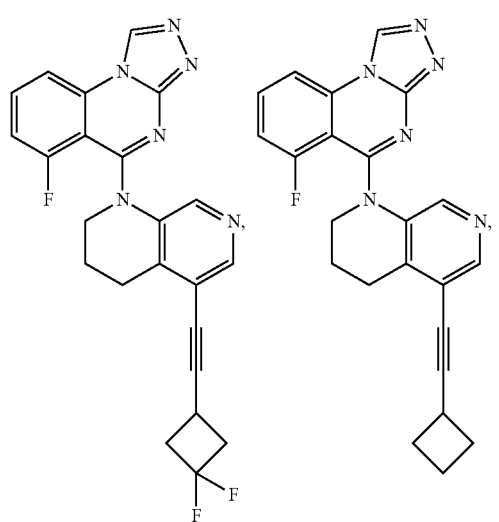
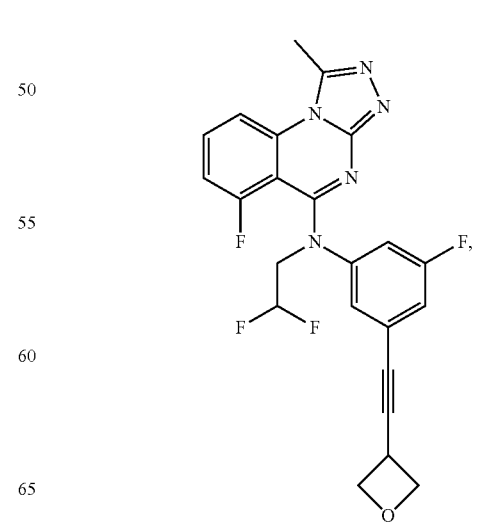

-continued
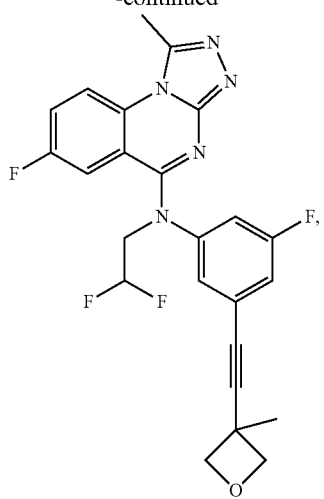
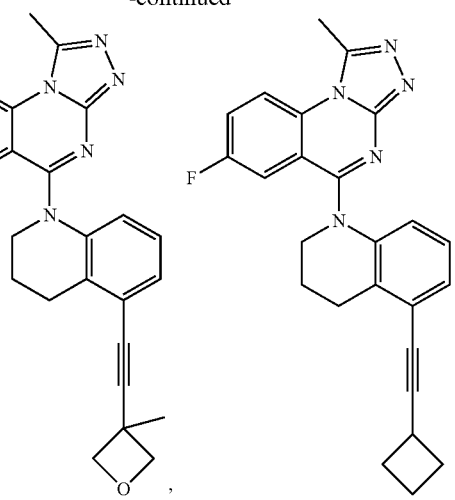
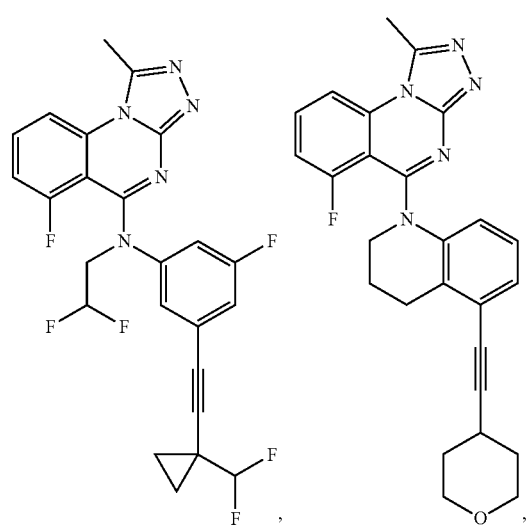
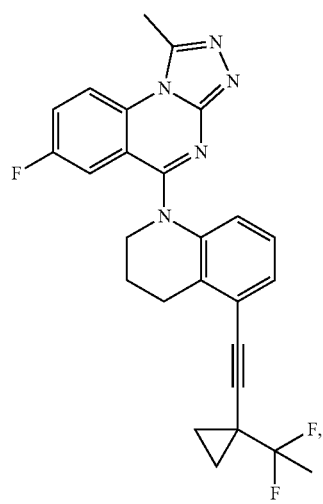
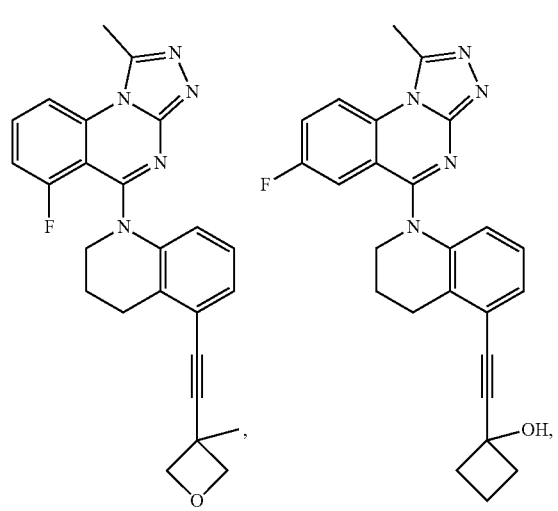
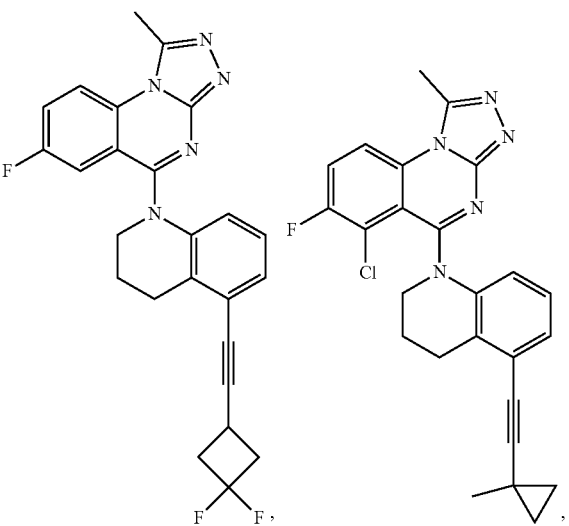

497
-continued
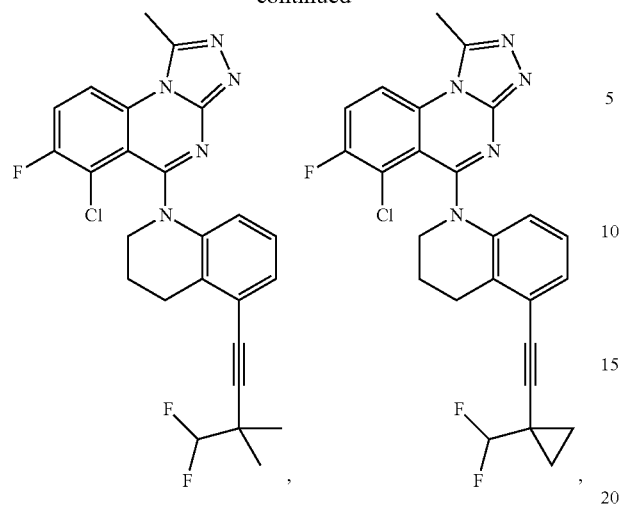
498
-continued
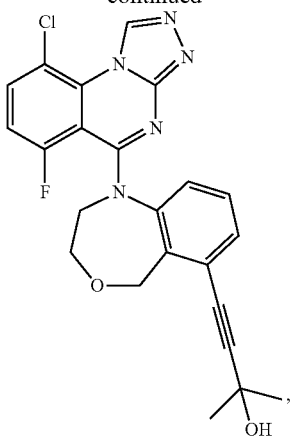
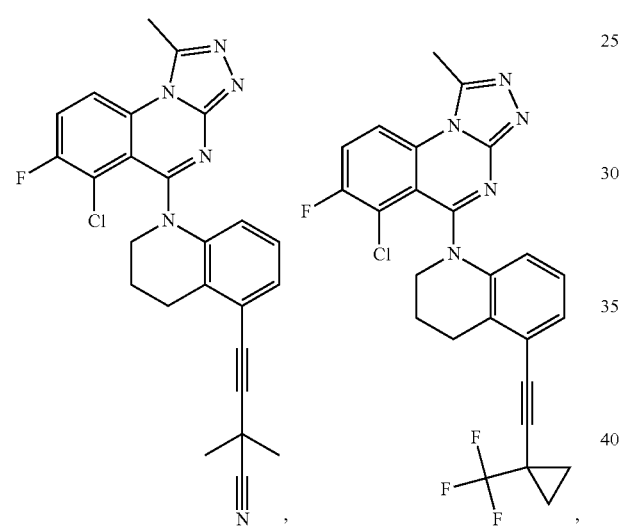
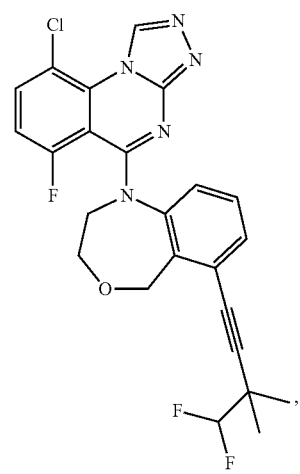
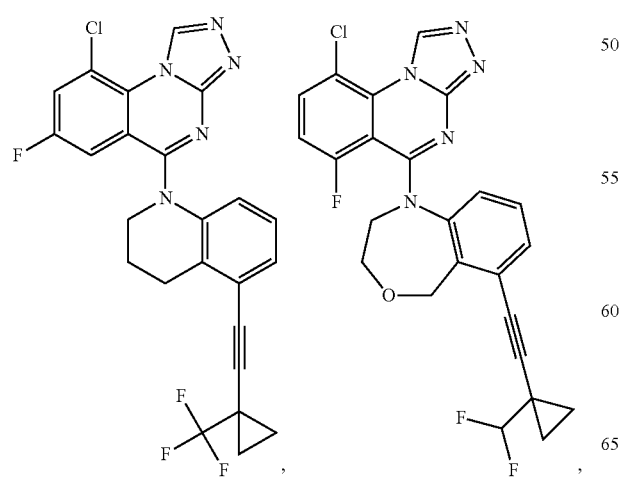
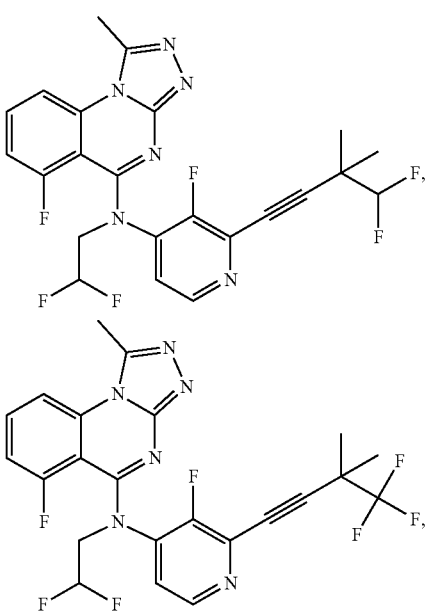

499
-continued
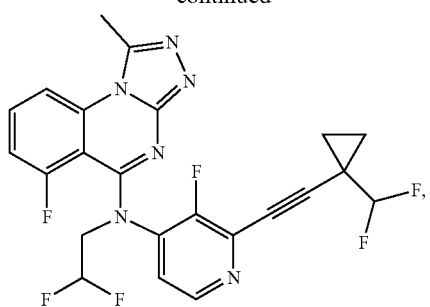
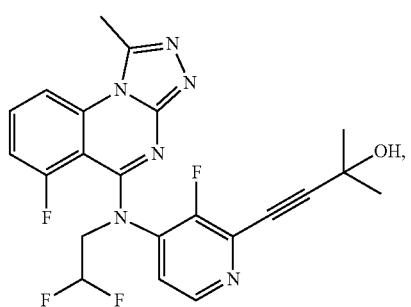
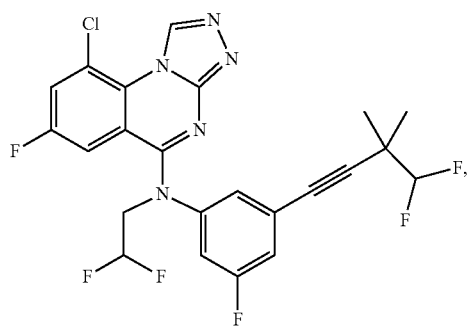
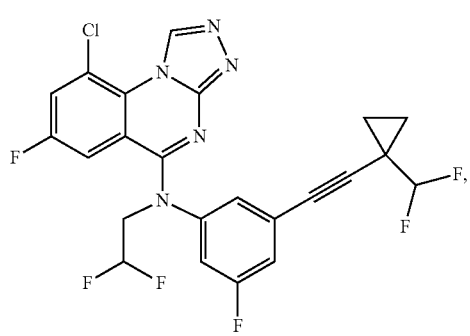
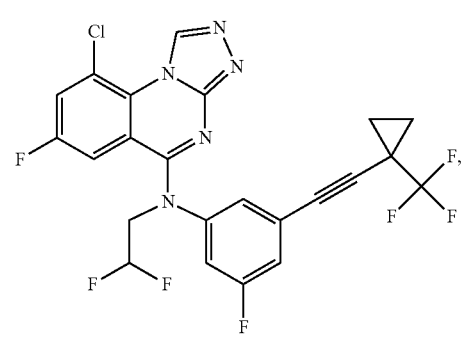
500
-continued
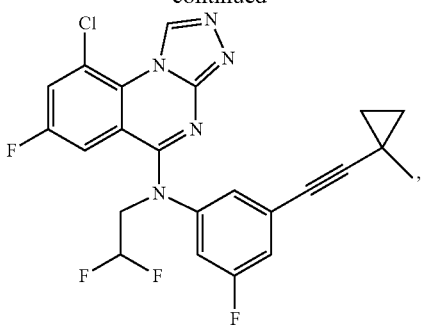
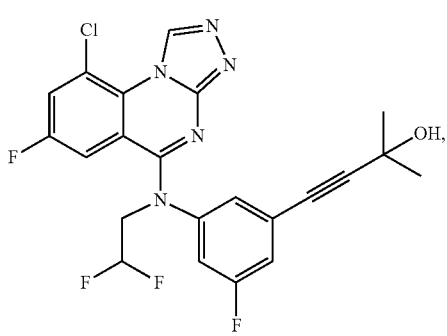
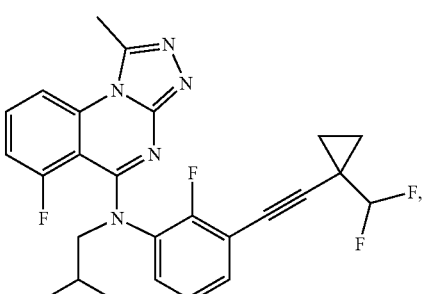
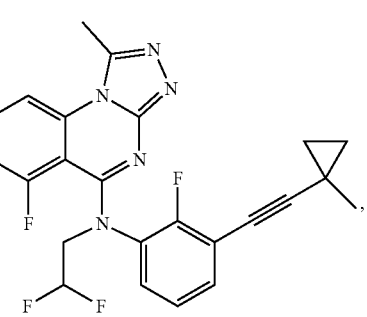
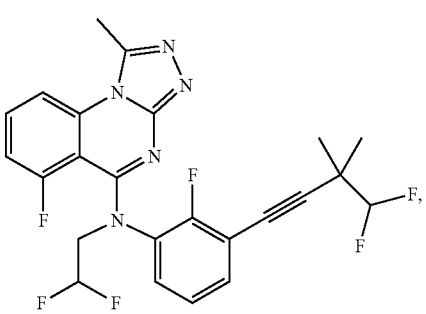

501
-continued
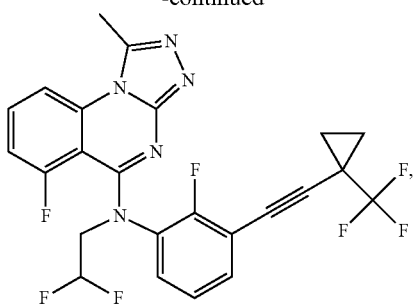
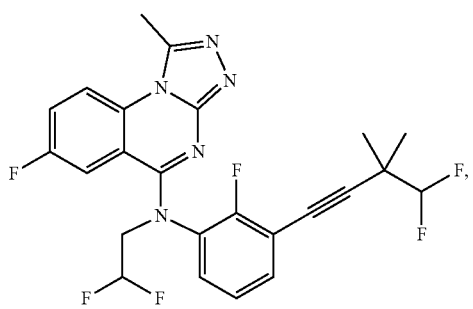
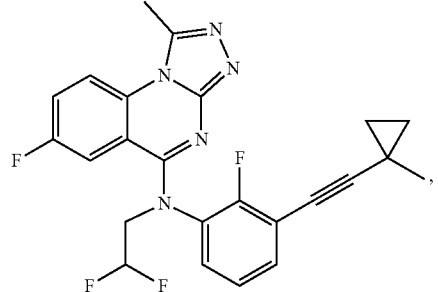
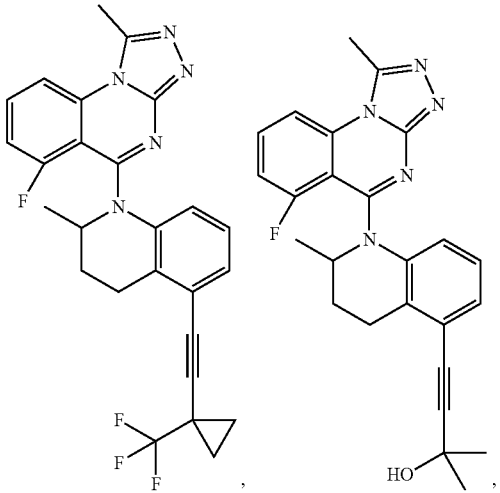
502
-continued
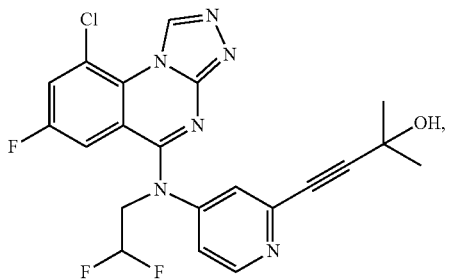
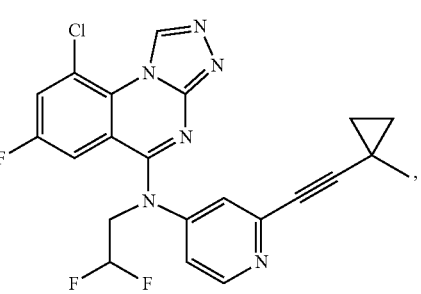
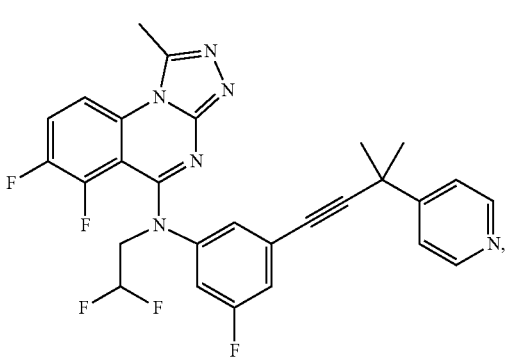
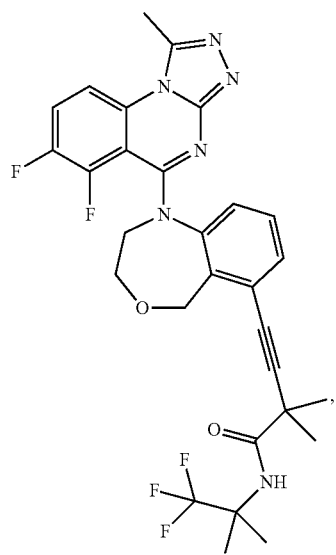

503 -continued
504 -continued
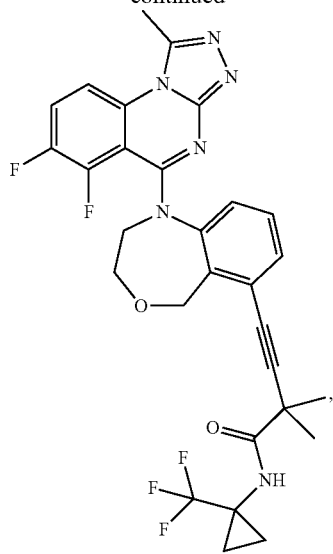
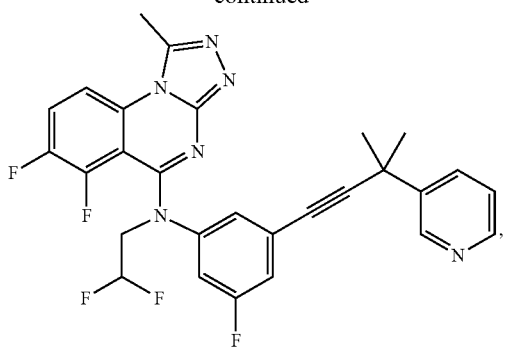
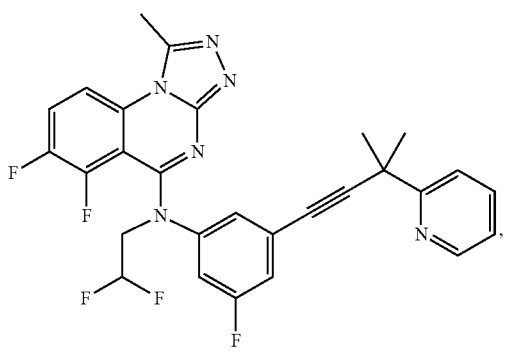
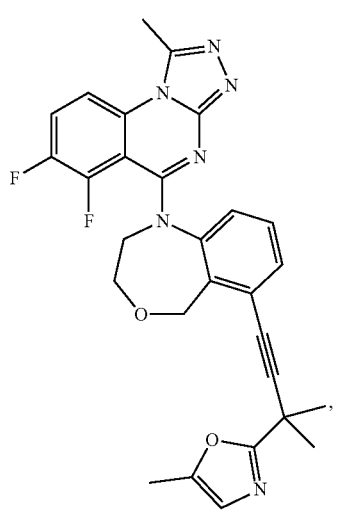
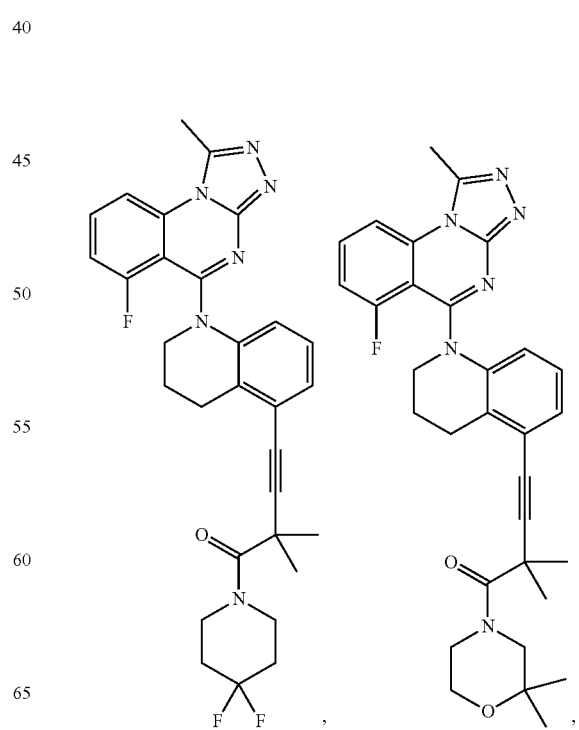

505
-continued
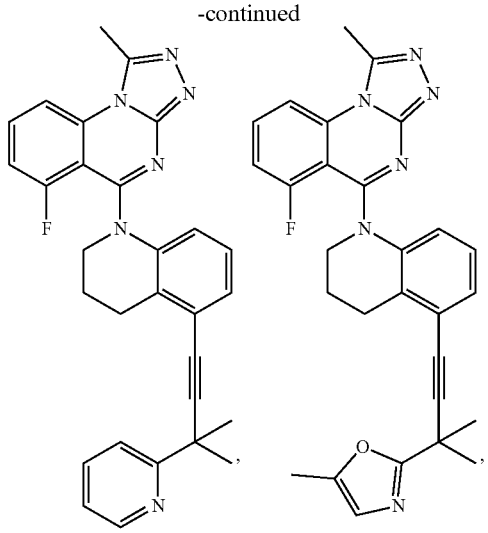
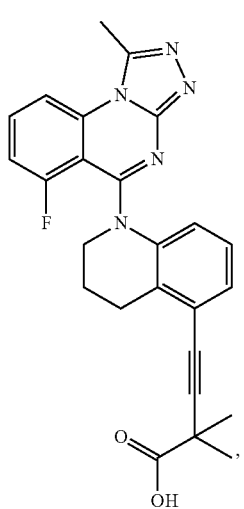
506
-continued
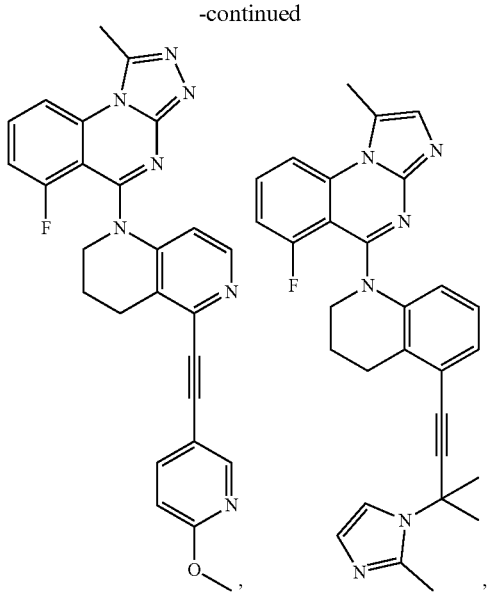
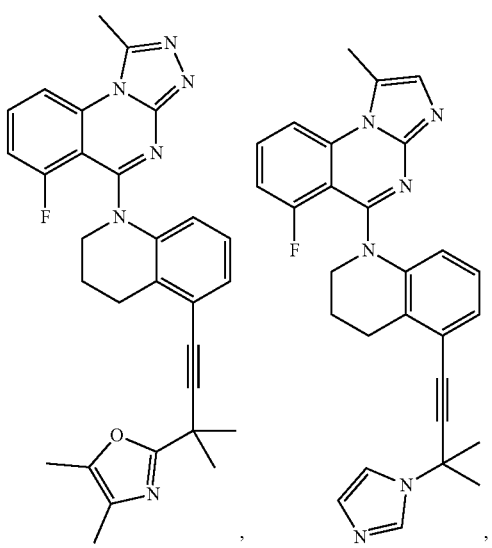
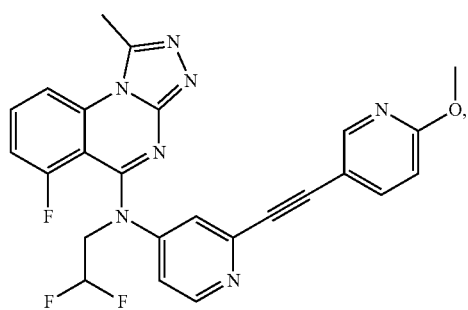
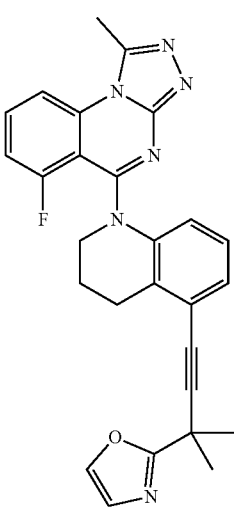

507
-continued
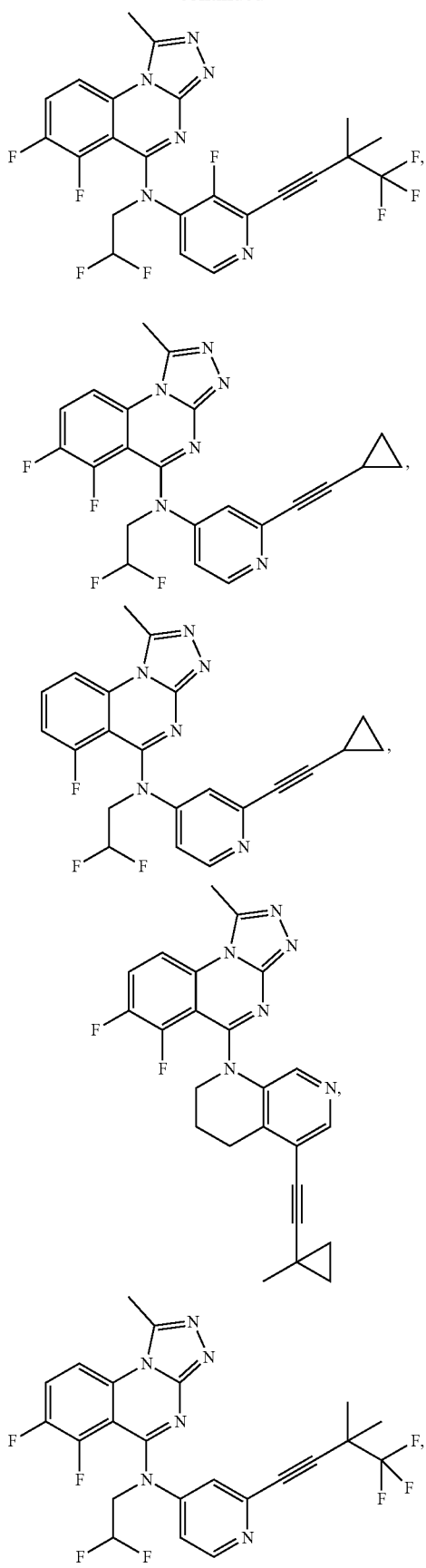
508
-continued
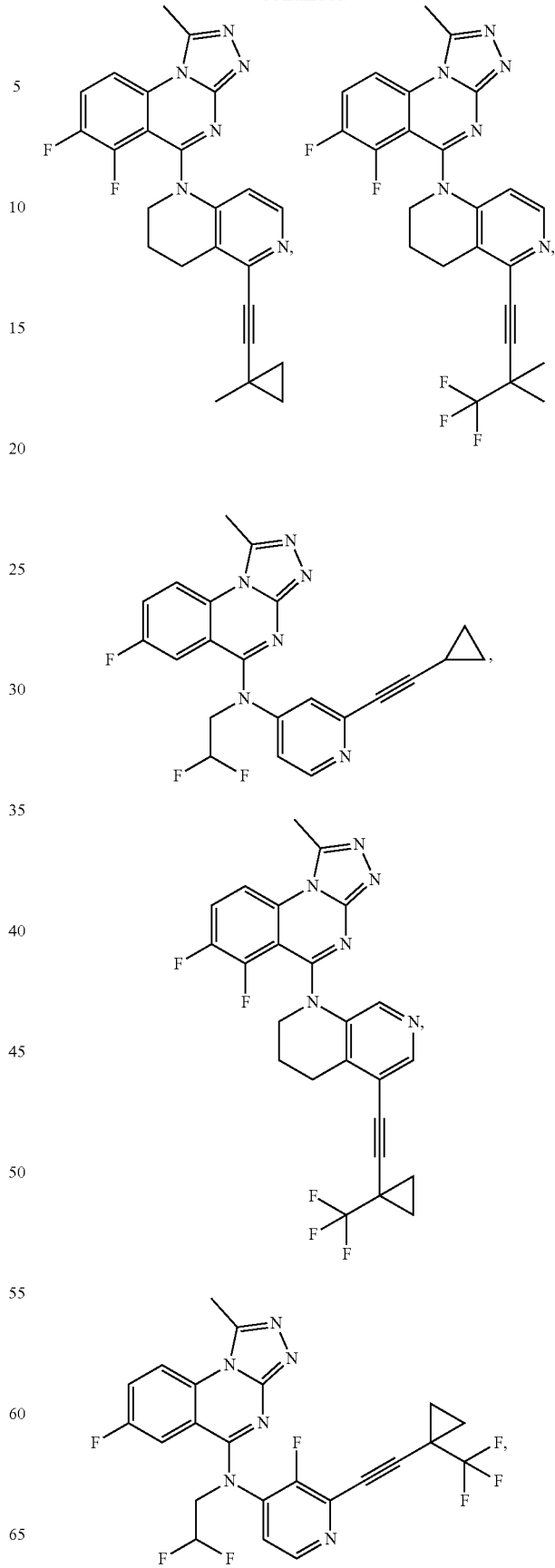

509
-continued
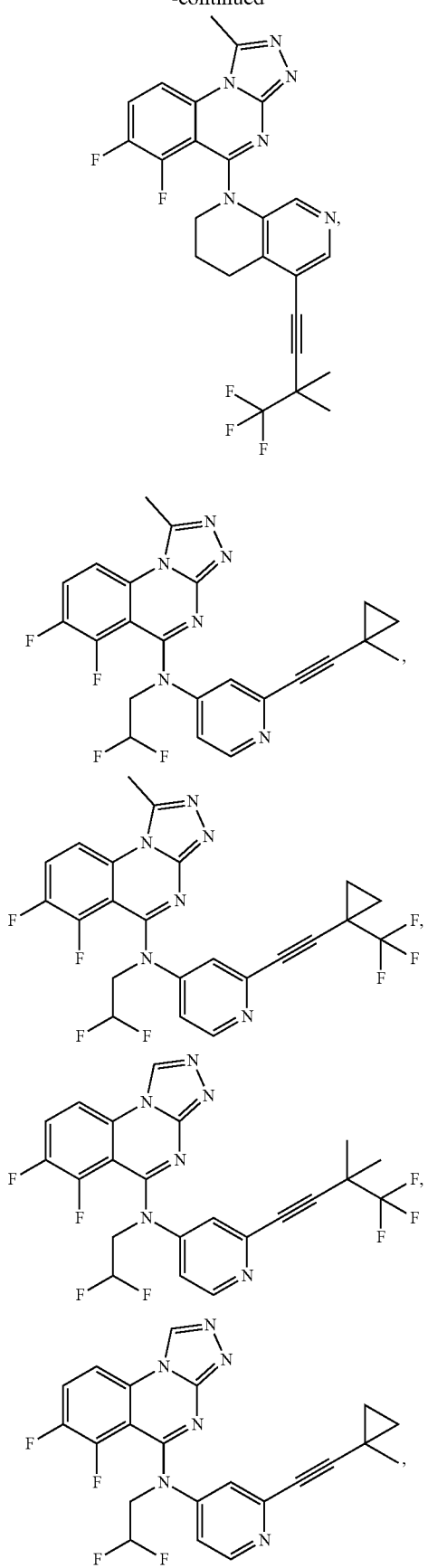
510
-continued
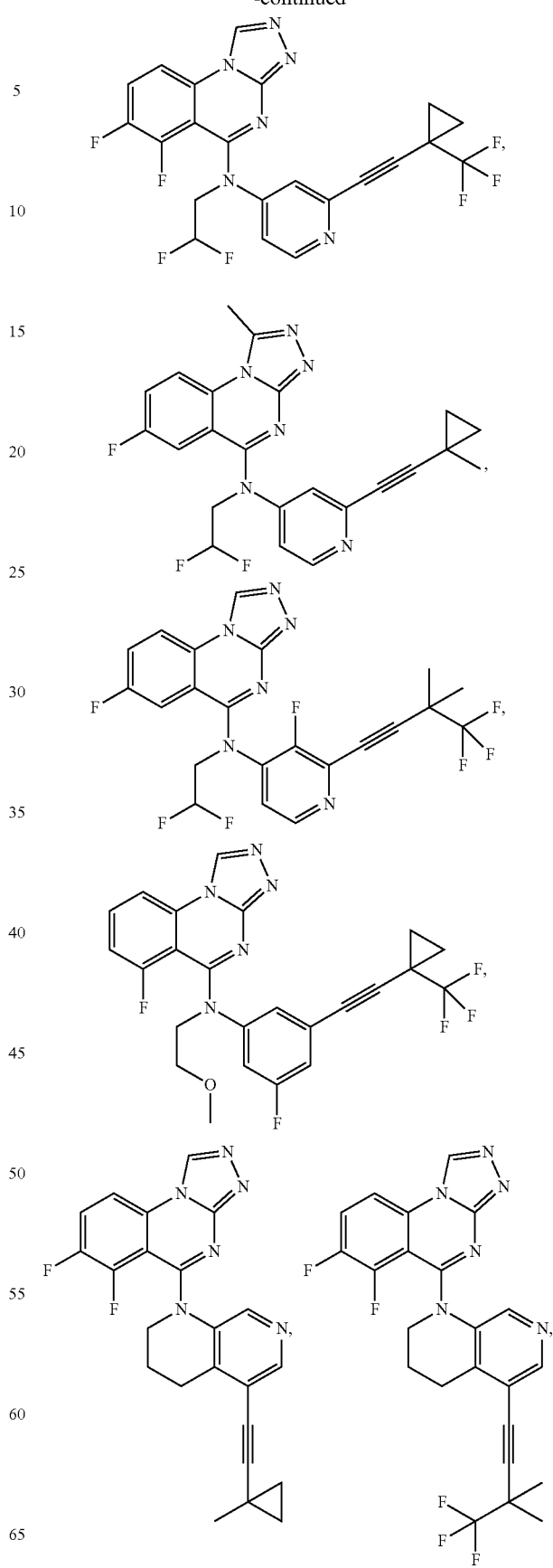

-continued
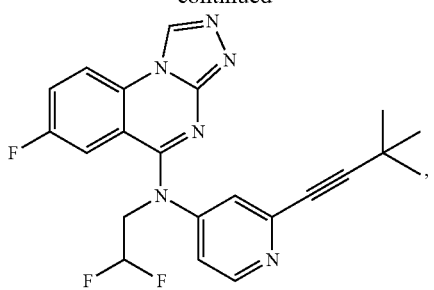
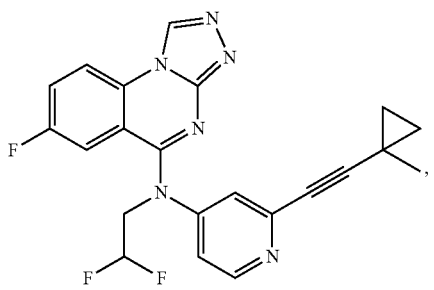
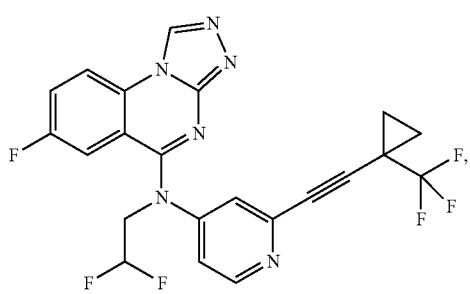
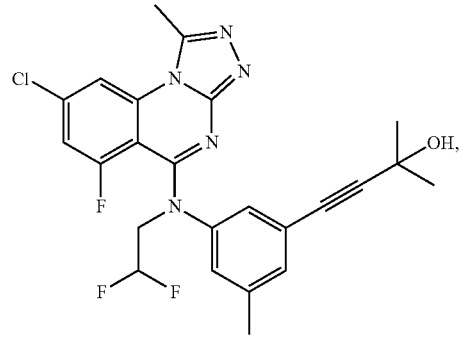
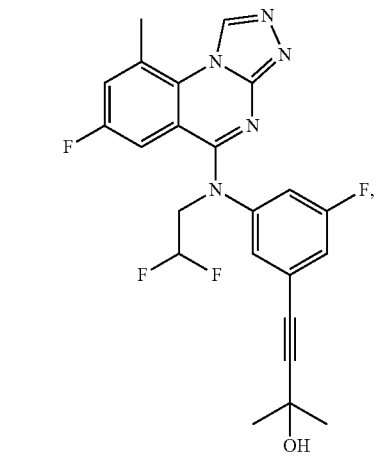
-continued
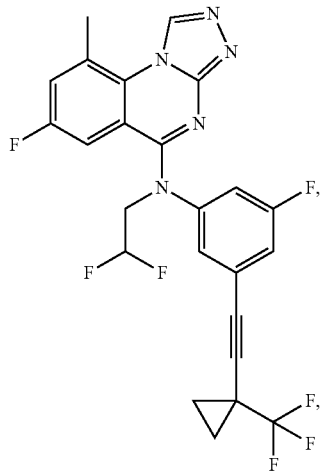
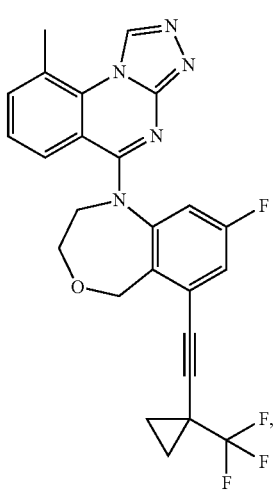
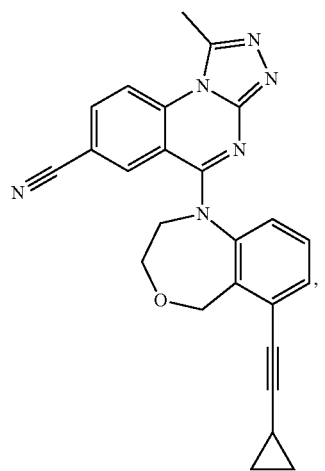

513
-continued
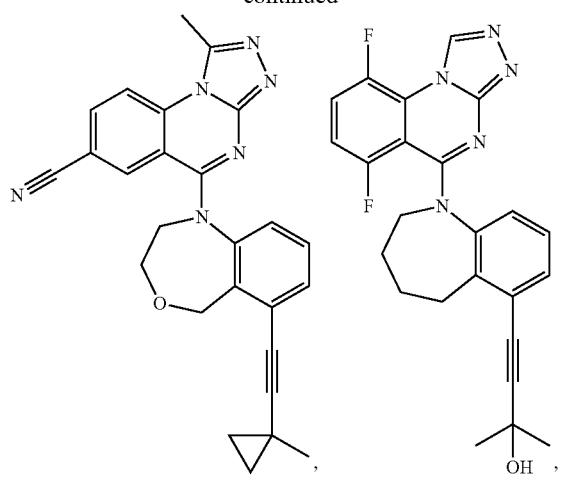
514
-continued
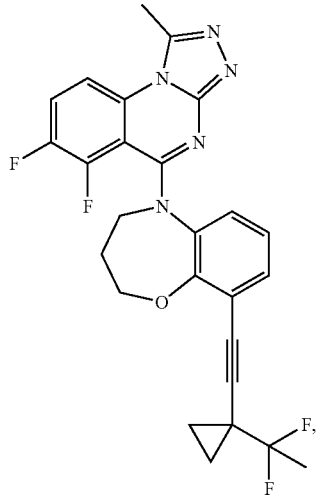
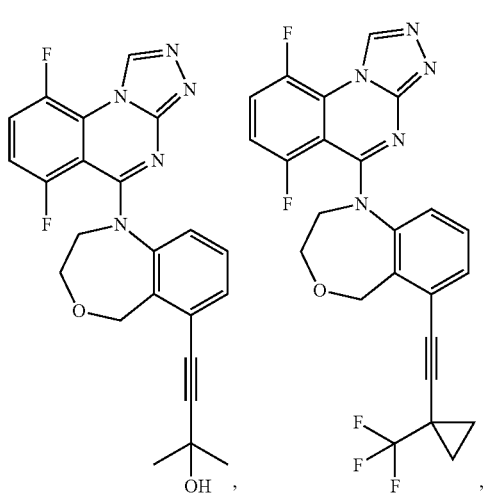
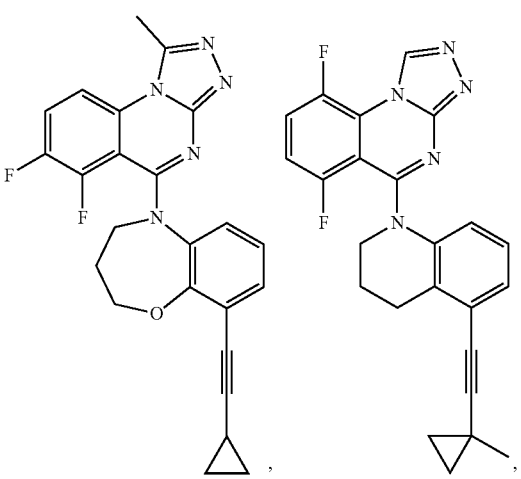
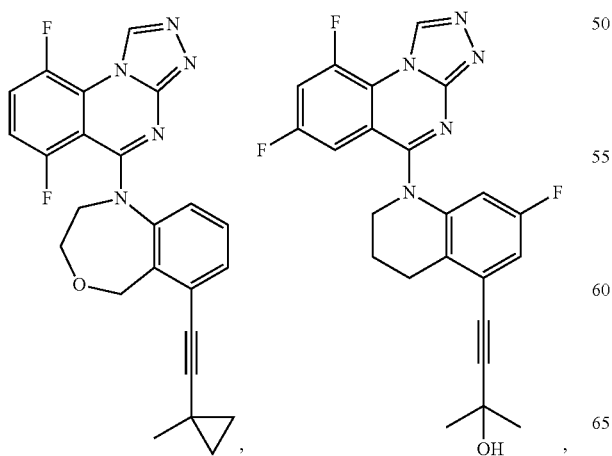
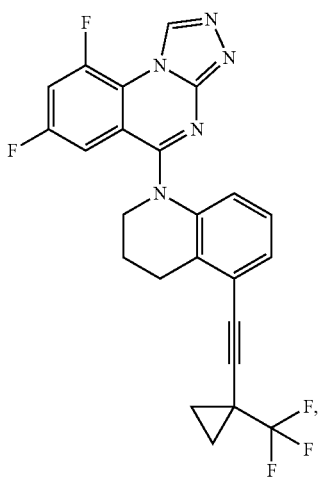

515
-continued
516
-continued
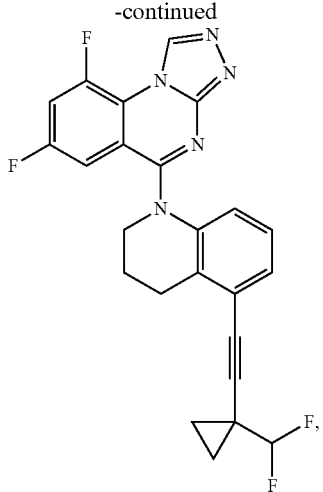
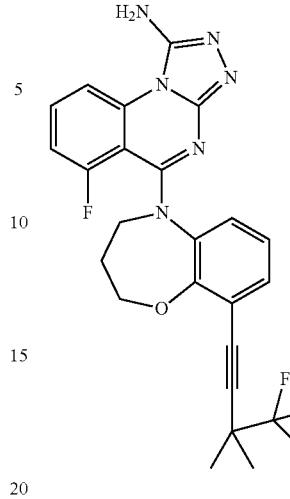
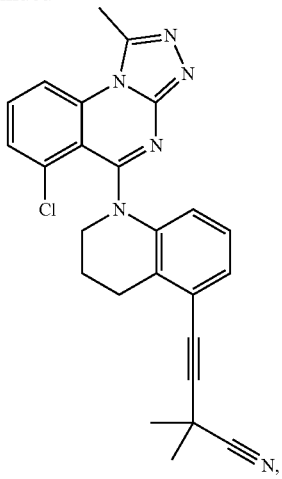
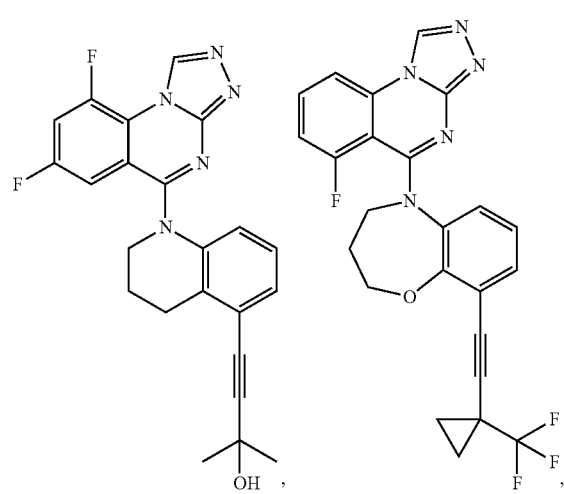
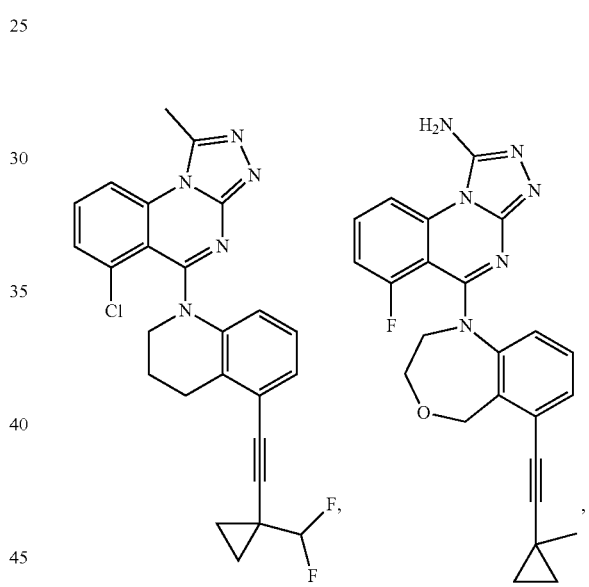
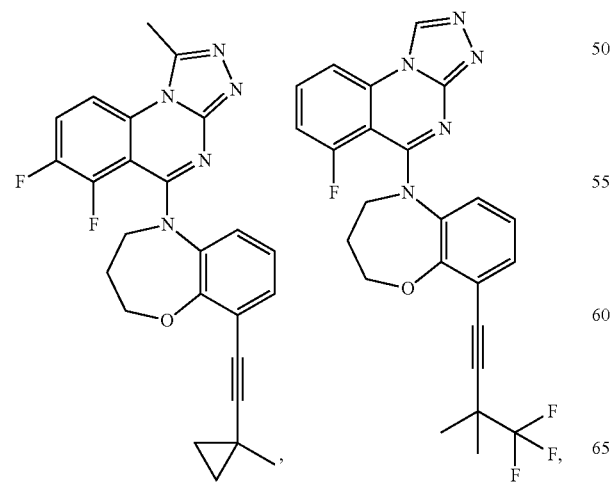
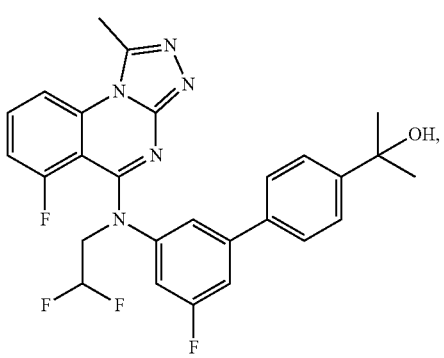

517
-continued
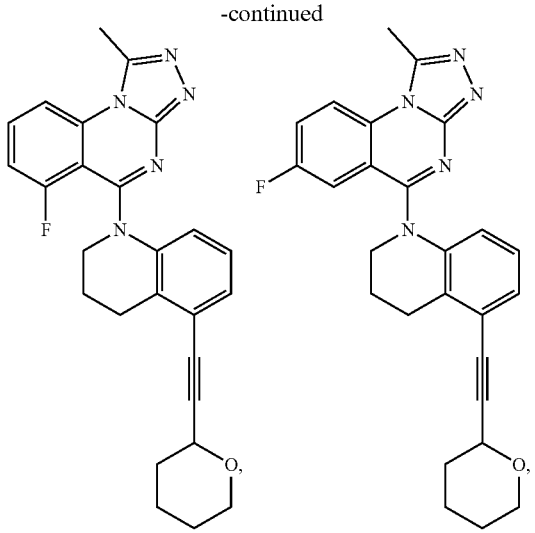
518
-continued
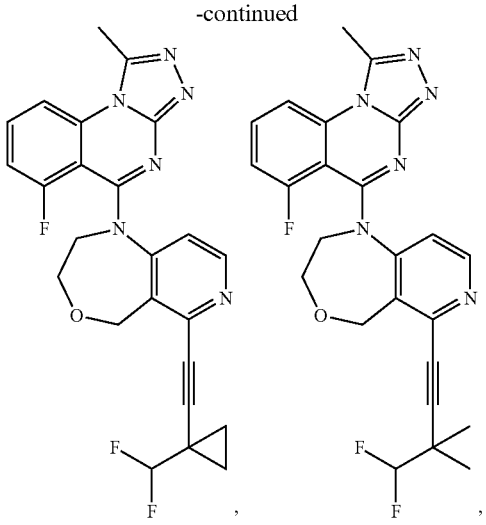

-continued
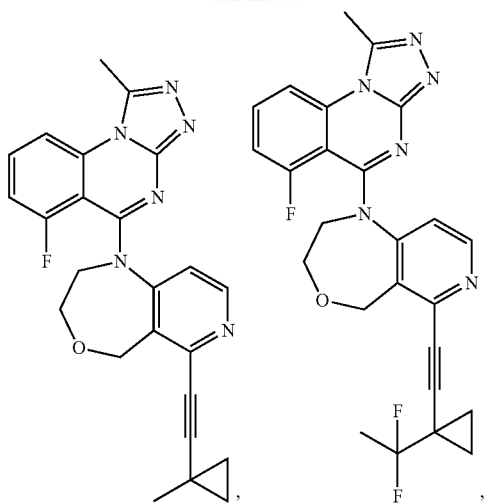
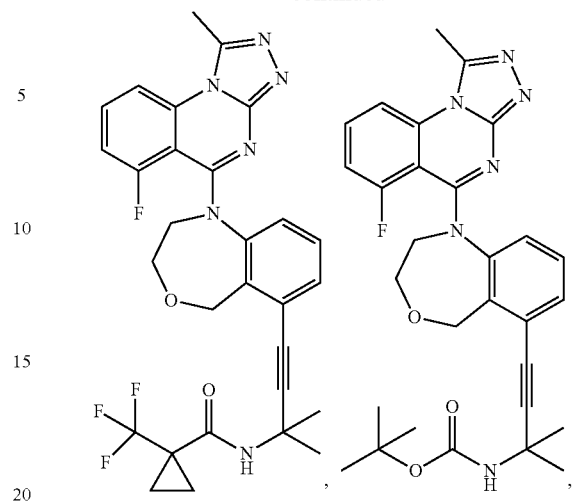
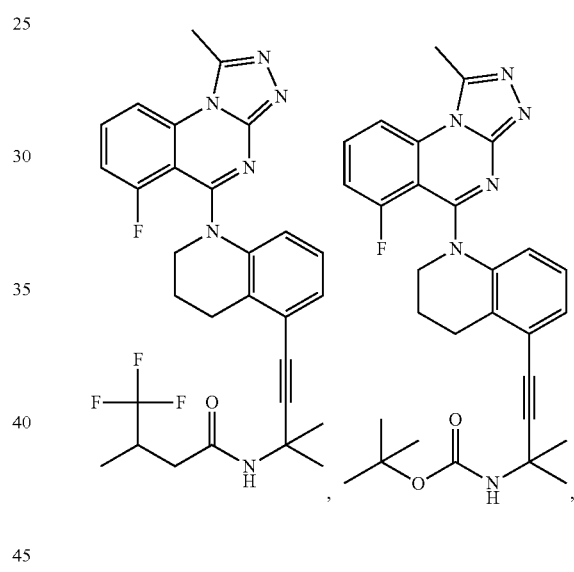
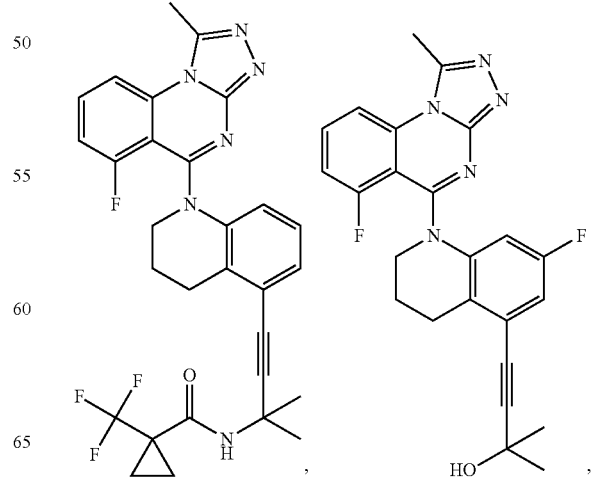

521
-continued
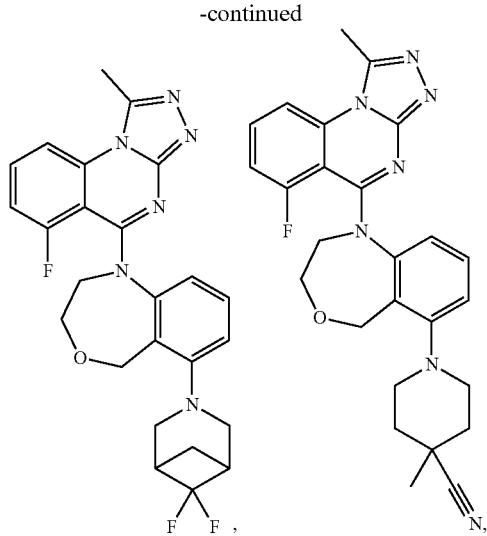
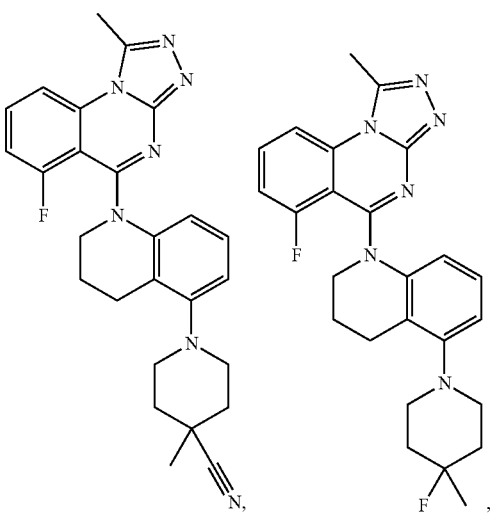
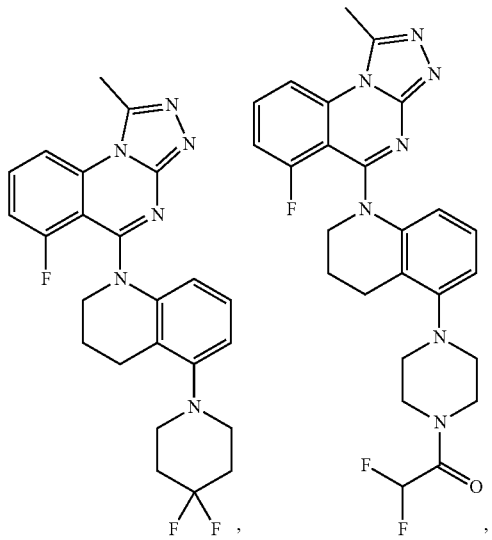
522
-continued
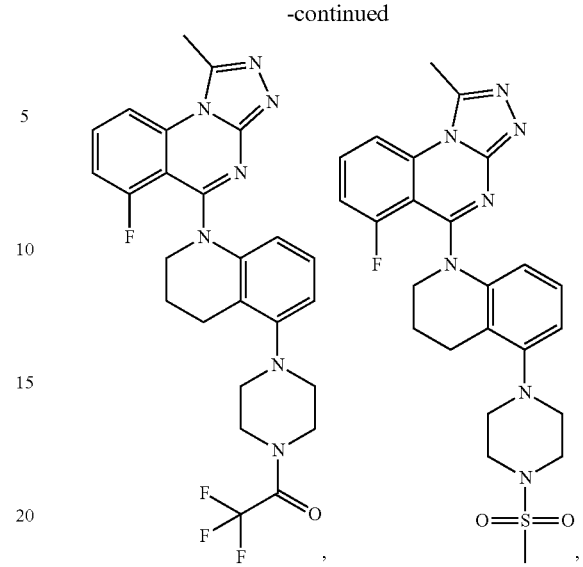
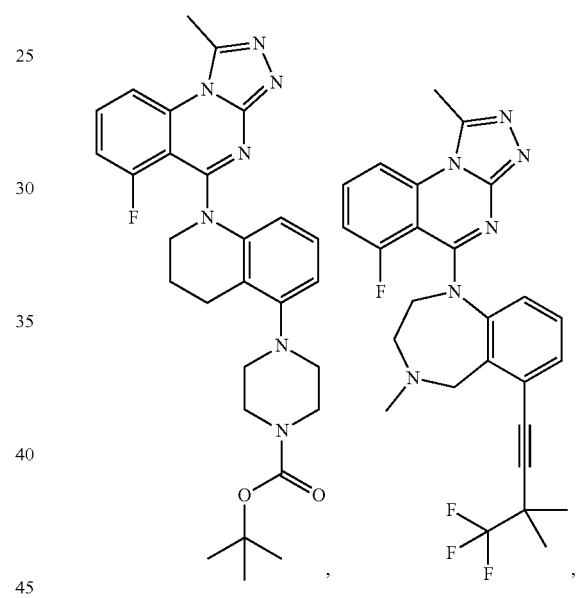
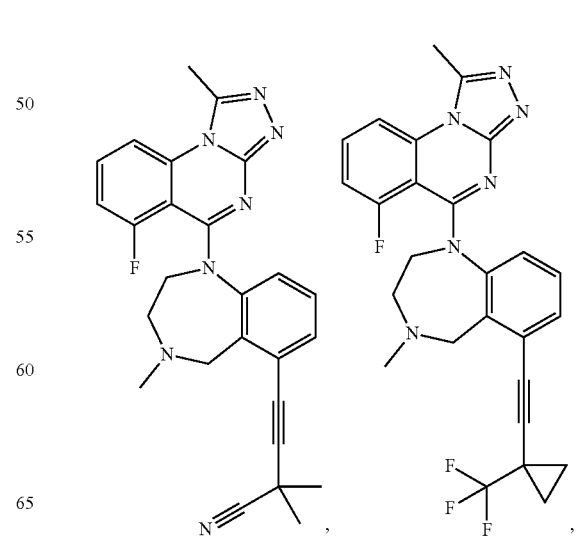

523
-continued
524
-continued
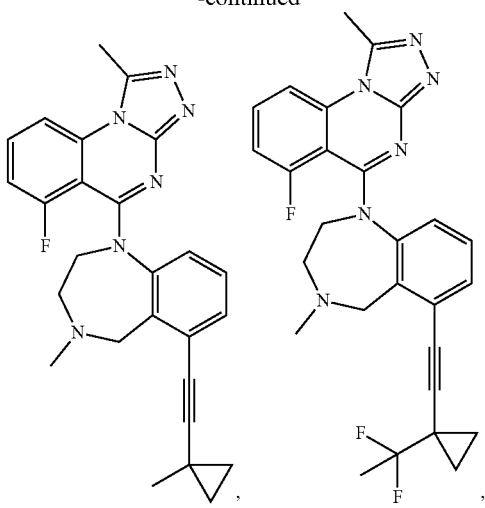
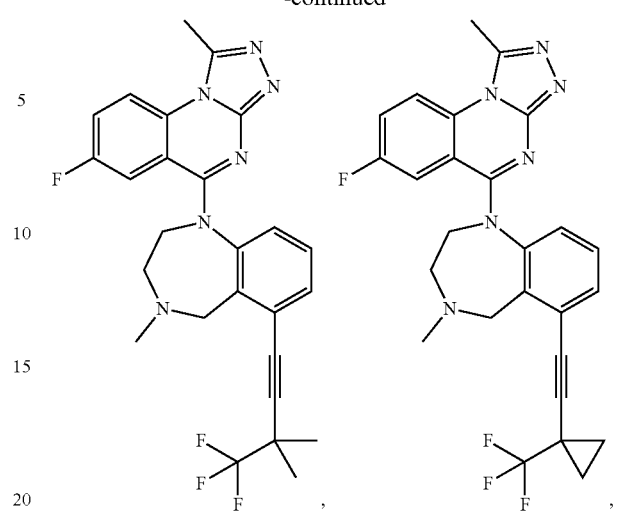
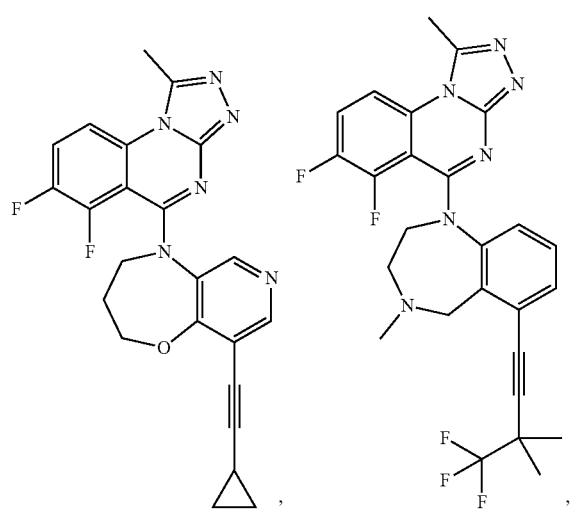
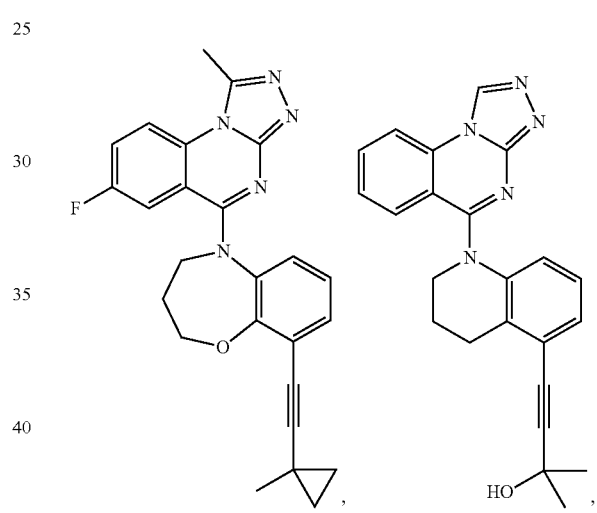
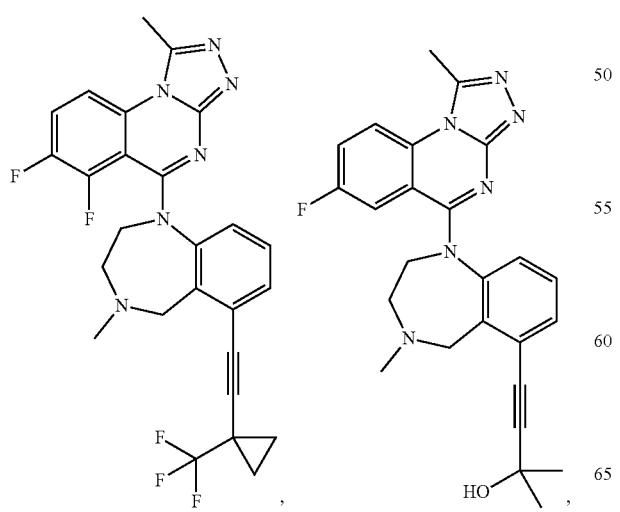
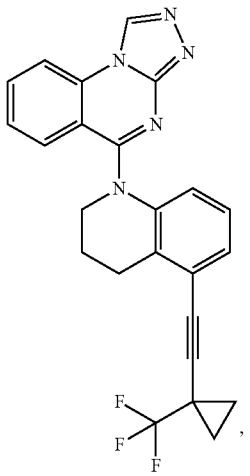

525
-continued
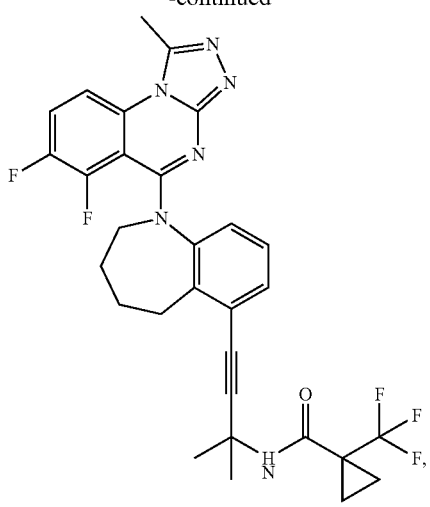
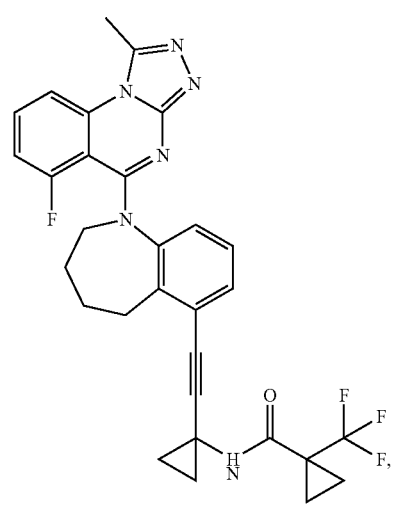
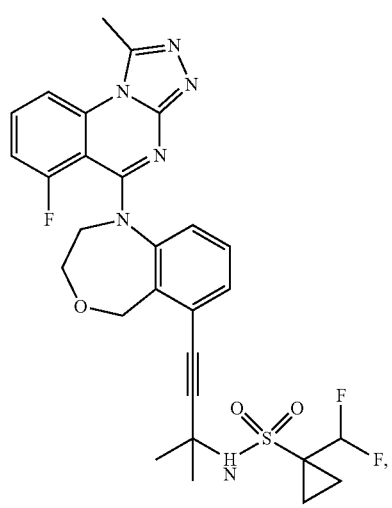
526
-continued
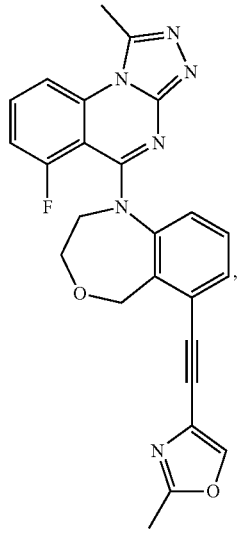
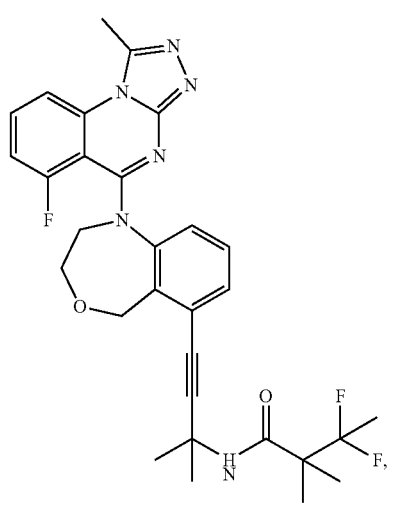
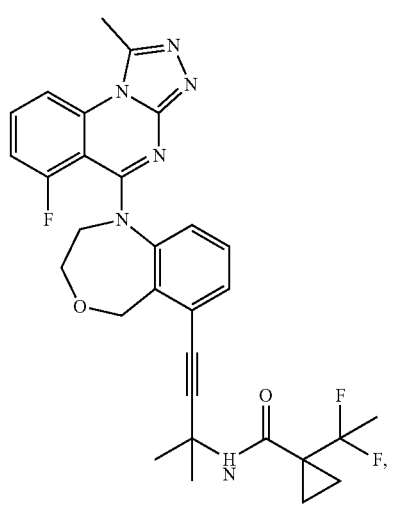

527
-continued
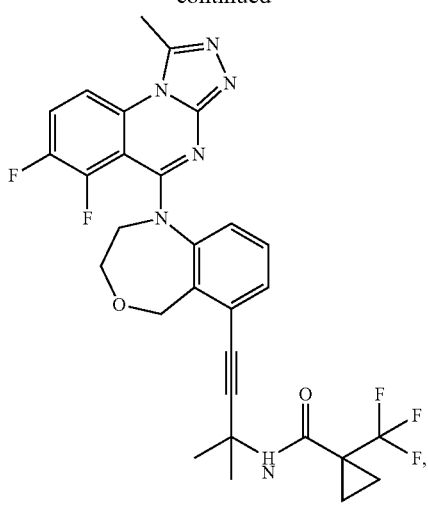
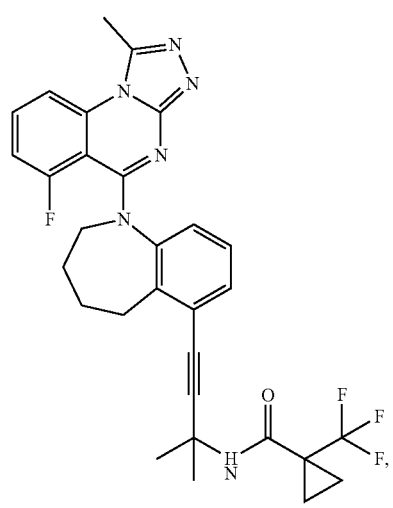
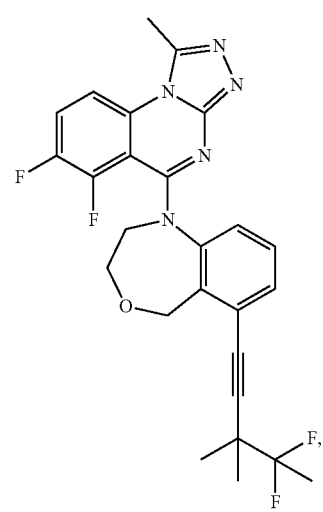
528
-continued
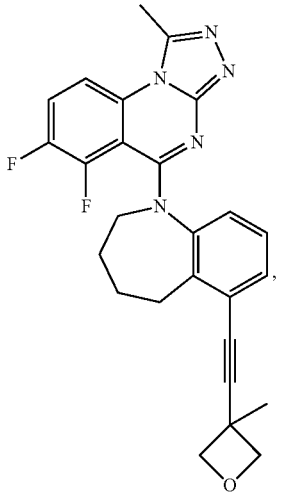
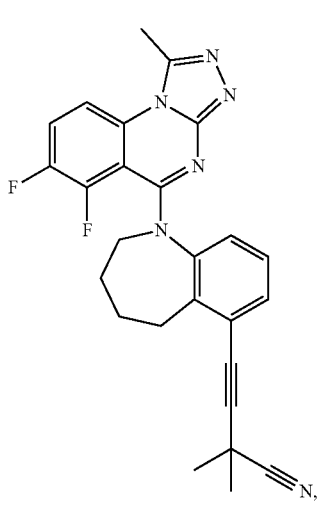
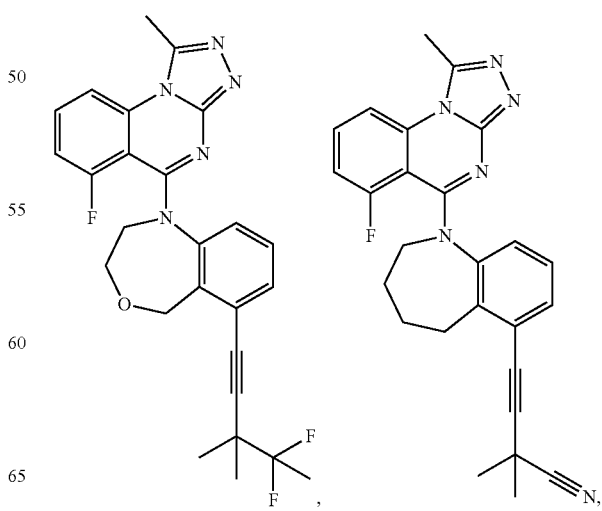

529
-continued
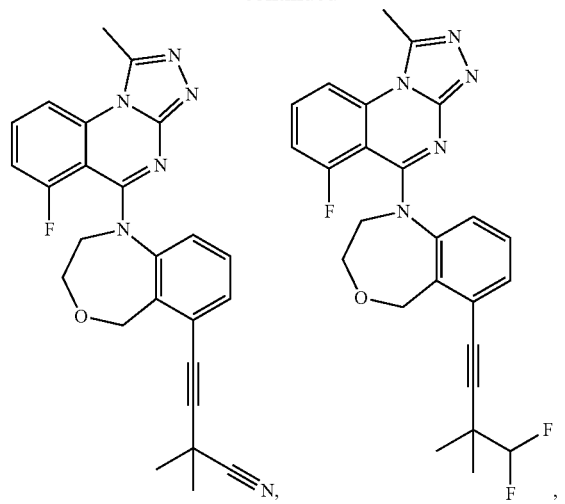
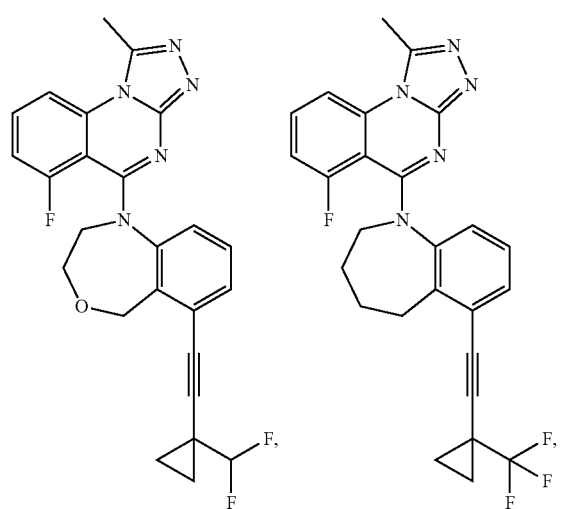
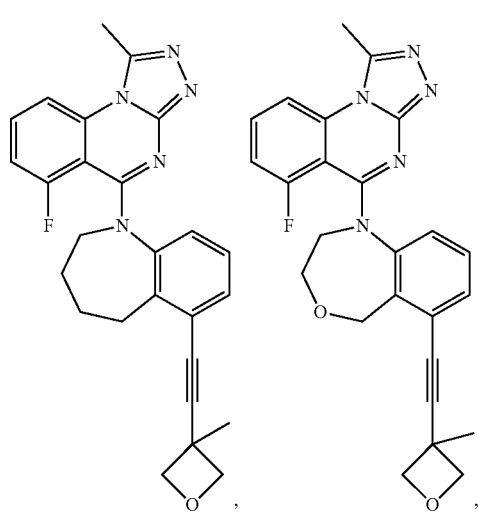
530
-continued
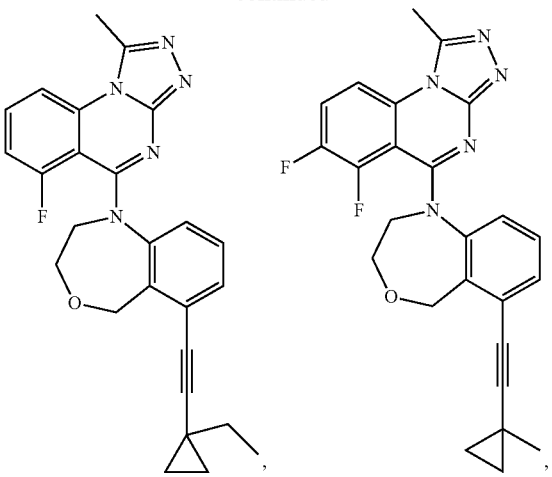
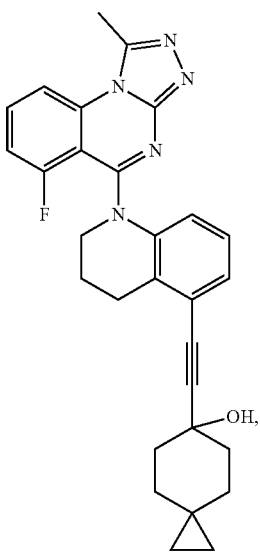
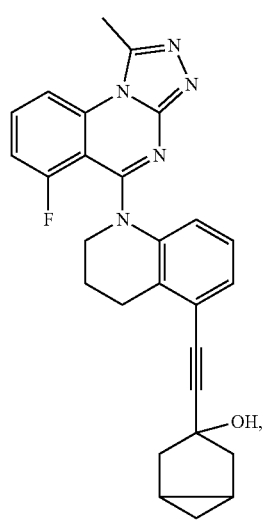

531
-continued
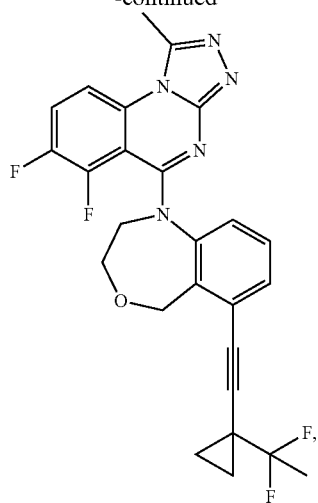
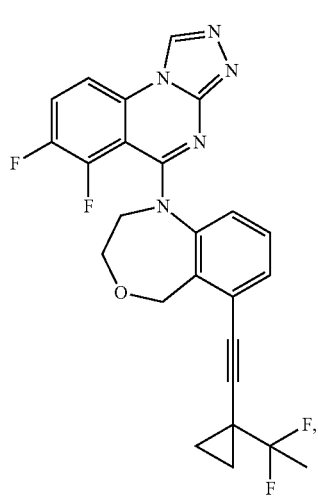
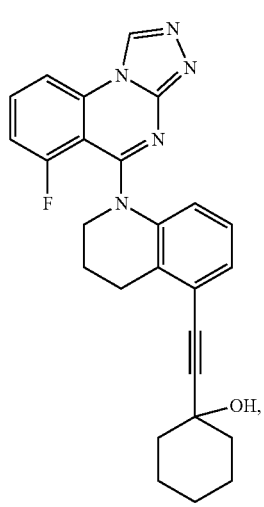
532
-continued
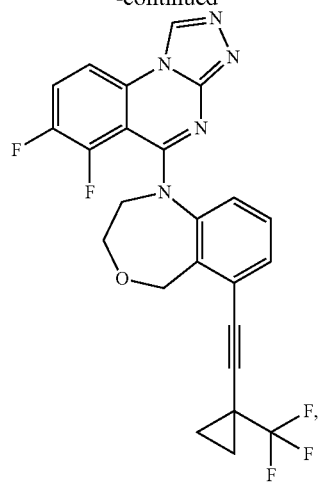
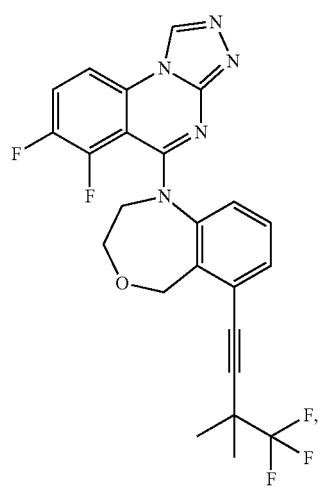
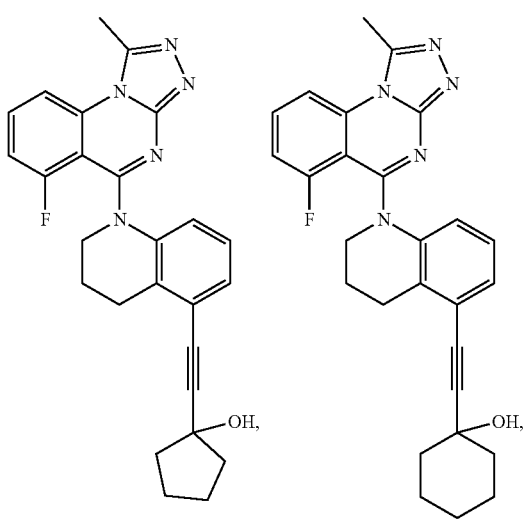

-continued
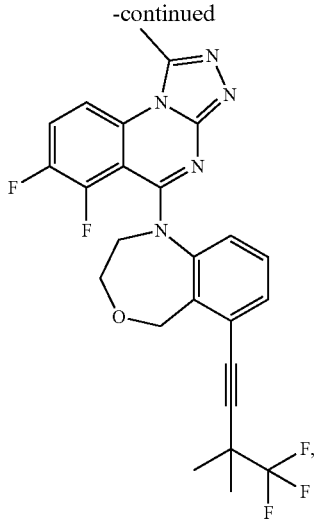
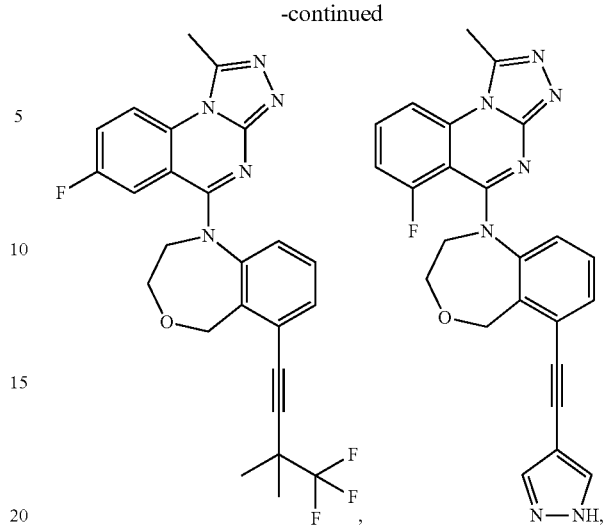
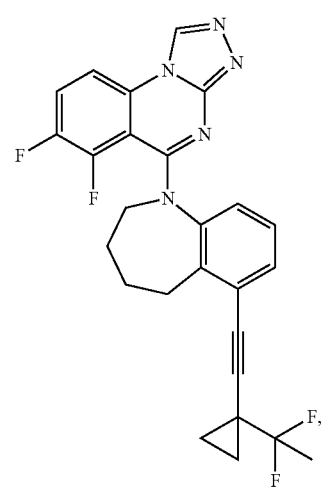
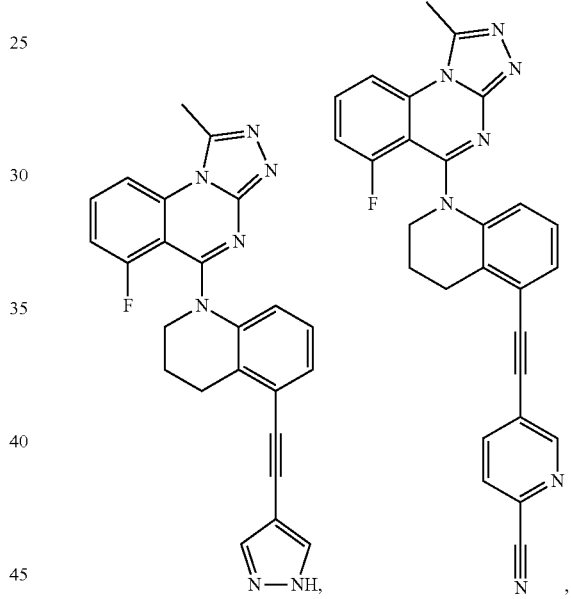
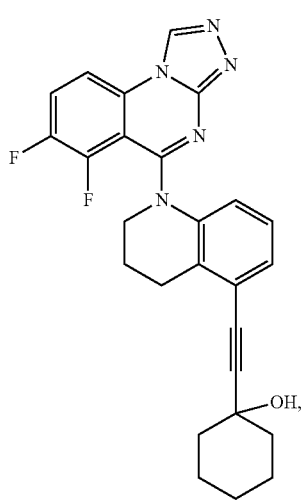
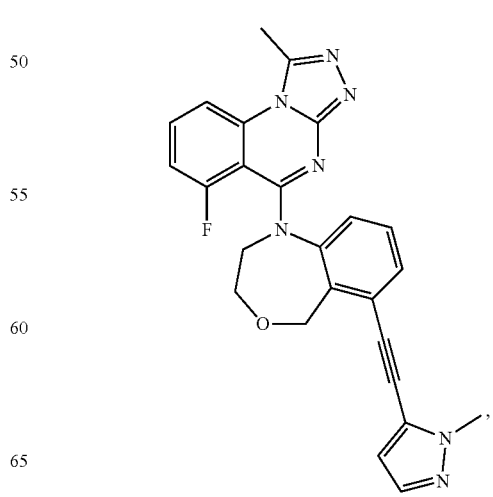

535
-continued
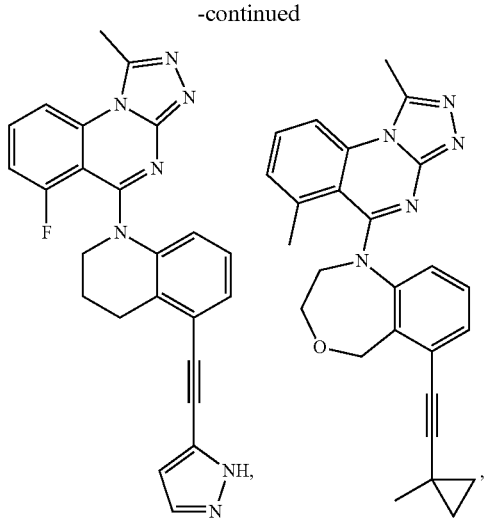
536
-continued
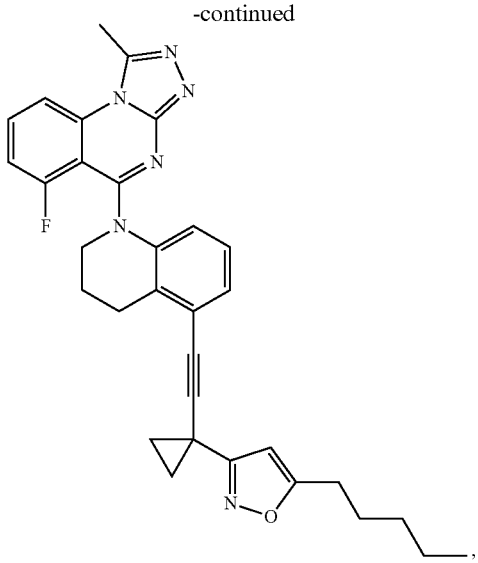
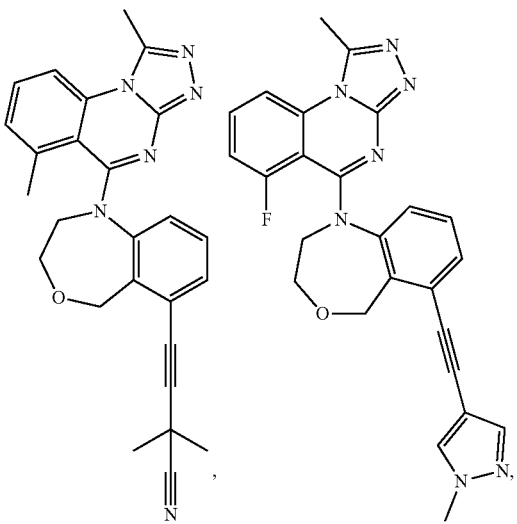
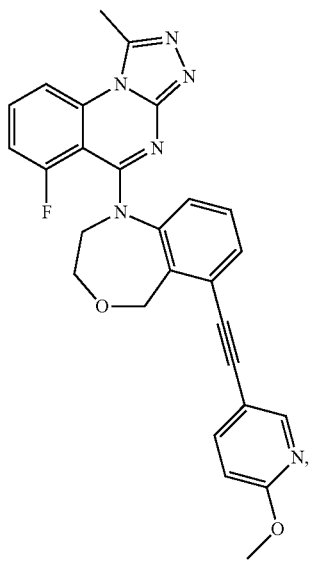 [SMILES: COc1ccc(C#Cc2cccc3c2COCCN3c2nc3nnc(C)n3c3cccc(F)c23)cn1]
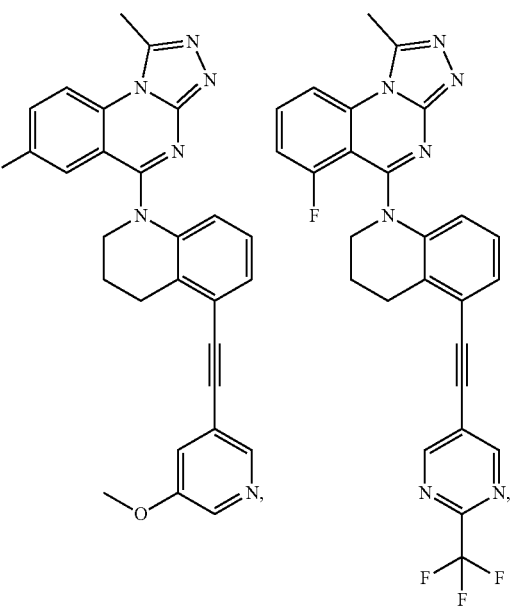
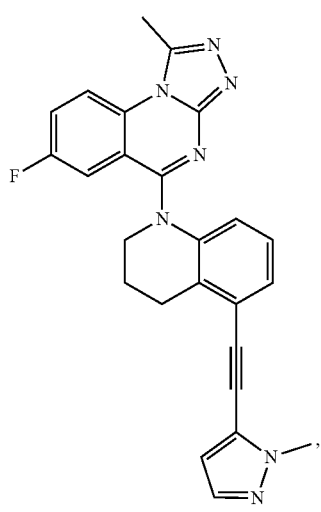

537
-continued
538
-continued
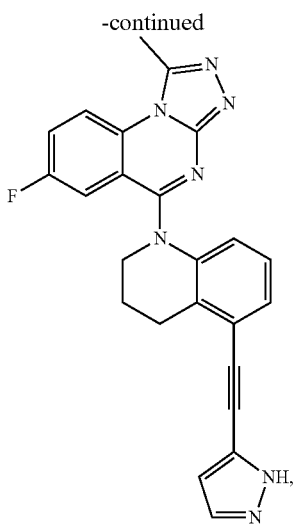
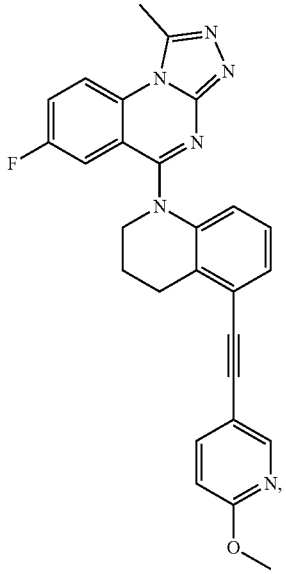
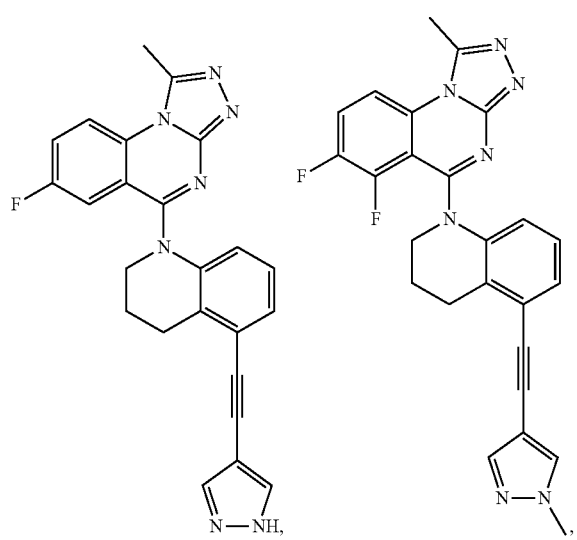
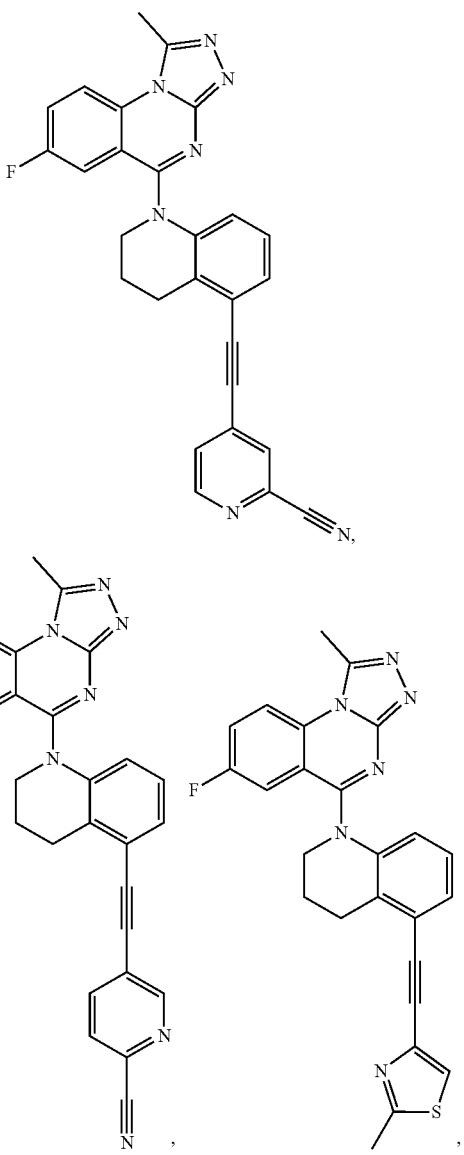

539
-continued
540
-continued
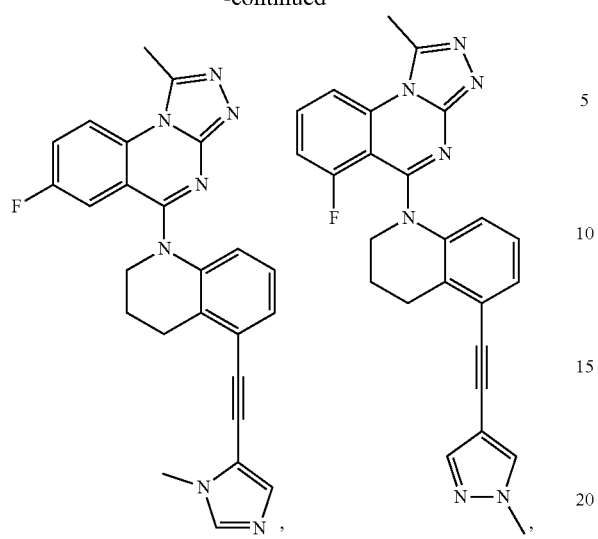
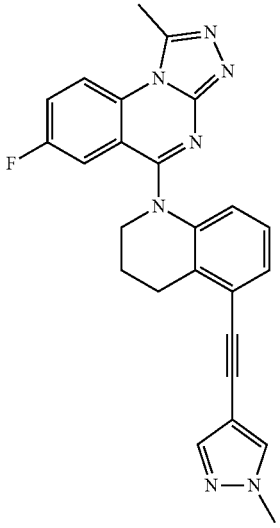

541
-continued

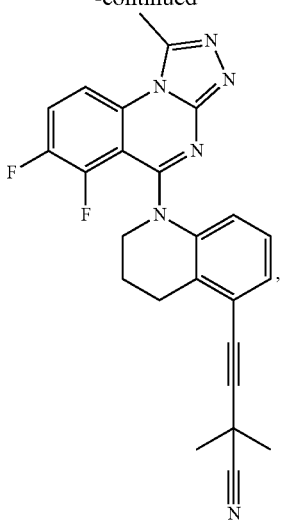

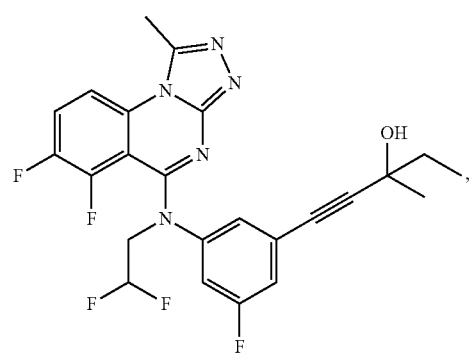

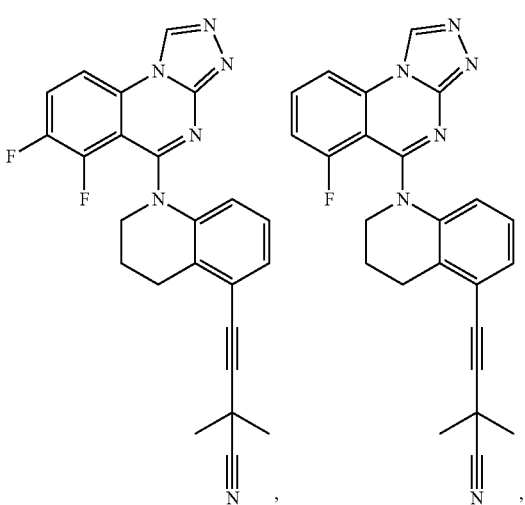

542
-continued

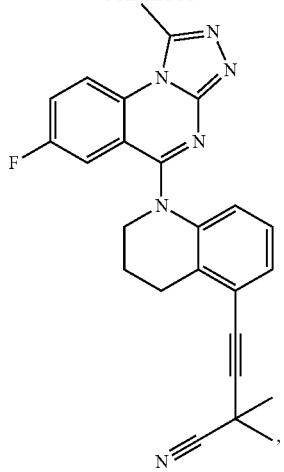

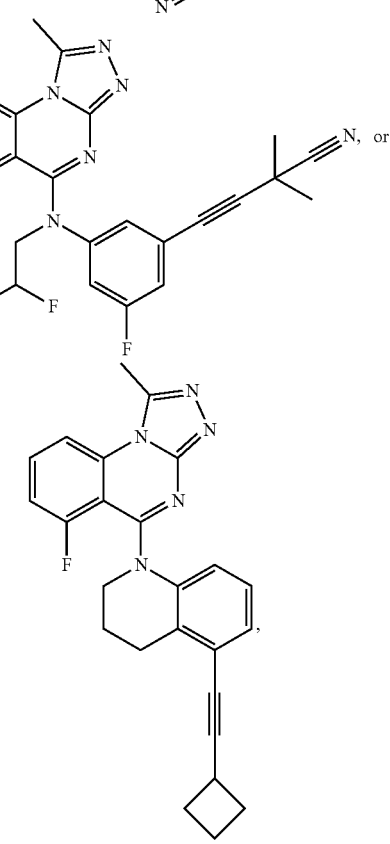

or a pharmaceutically acceptable salt thereof.

18. A pharmaceutical composition comprising a pharmaceutically effective amount of a compound of claim 1, or a pharmaceutically acceptable salt thereof, and a pharmaceutically acceptable carrier or excipient.

19. A pharmaceutical composition comprising a pharmaceutically effective amount of a compound of claim 17, or a pharmaceutically acceptable salt thereof, and a pharmaceutically acceptable carrier or excipient.

* * * * *